US010633426B2

(12) United States Patent
Brentjens et al.

(10) Patent No.: US 10,633,426 B2
(45) **Date of Patent: *Apr. 28, 2020**

(54) CHIMERIC ANTIGEN RECEPTORS TARGETING G-PROTEIN COUPLED RECEPTOR AND USES THEREOF

(71) Applicants: MEMORIAL SLOAN KETTERING CANCER CENTER, New York, NY (US); EUREKA THERAPEUTICS, INC., Emeryville, CA (US)

(72) Inventors: Renier J. Brentjens, New York, NY (US); Eric L. Smith, New York, NY (US); Cheng Liu, Emeryville, CA (US)

(73) Assignees: MEMORIAL SLOAN KETTERING CANCER CENTER, New York, NY (US); EUREKA THERAPEUTICS, INC., Emeryville, CA (US)

( * ) Notice: Subject to any disclaimer, the term of this patent is extended or adjusted under 35 U.S.C. 154(b) by 107 days.

This patent is subject to a terminal disclaimer.

(21) Appl. No.: 15/613,800

(22) Filed: Jun. 5, 2017

(65) Prior Publication Data

US 2018/0118803 A1 May 3, 2018

Related U.S. Application Data

(63) Continuation of application No. PCT/US2015/064102, filed on Dec. 4, 2015.

(60) Provisional application No. 62/088,286, filed on Dec. 5, 2014.

(51) Int. Cl.
*C07K 14/725* (2006.01)
*C07K 16/28* (2006.01)

(52) U.S. Cl.
CPC .......... *C07K 14/7051* (2013.01); *C07K 16/28* (2013.01); *C07K 2317/34* (2013.01); *C07K 2317/622* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 4,956,778 | A | 9/1990 | Naito |
| 5,091,513 | A | 2/1992 | Huston et al. |
| 5,132,405 | A | 7/1992 | Huston et al. |
| 5,399,346 | A | 3/1995 | Anderson et al. |
| 7,446,190 | B2 | 11/2008 | Sadelain et al. |
| 7,807,163 | B2 | 10/2010 | Law et al. |
| 8,389,282 | B2 | 3/2013 | Sadelain et al. |
| 10,098,951 | B2 | 10/2018 | Lu et al. |
| 10,464,988 | B2 | 11/2019 | Lu et al. |
| 2003/0207288 | A1 | 11/2003 | Lewin et al. |
| 2005/0019320 | A1 | 1/2005 | Sugaru et al. |
| 2005/0196754 | A1 | 9/2005 | Drmanac et al. |
| 2008/0057063 | A1 | 3/2008 | Rinkenberger et al. |
| 2011/0166330 | A1 | 7/2011 | Kobilka et al. |
| 2013/0130379 | A1 | 5/2013 | Adams et al. |
| 2014/0322183 | A1 | 10/2014 | Milone et al. |
| 2018/0118803 | A1 | 5/2018 | Brentjens et al. |
| 2019/0107537 | A1 | 4/2019 | Chaudhary |
| 2019/0112380 | A1 | 4/2019 | Chaudhary |
| 2019/0248865 | A1 | 8/2019 | Lu et al. |

FOREIGN PATENT DOCUMENTS

| | | | | |
|---|---|---|---|---|
| EP | 1 468 694 A1 | 10/2004 | | |
| RU | 2 526 517 C2 | 8/2014 | | |
| WO | WO 2004/072117 A2 | 8/2004 | | |
| WO | WO 2005/019258 A2 | 3/2005 | | |
| WO | WO 2009/039192 A2 | 3/2009 | | |
| WO | WO 2011/083088 A2 | 7/2011 | | |
| WO | WO 2012/009790 A1 | 1/2012 | | |
| WO | WO-2013033626 A2 * | 3/2013 | ....... | C07K 14/70503 |
| WO | WO 2014/087010 A1 | 6/2014 | | |
| WO | WO 2014/114800 A1 | 7/2014 | | |
| WO | WO 2014/127261 A1 | 8/2014 | | |
| WO | WO 2014/191128 A1 | 12/2014 | | |
| WO | WO 2015/142675 A2 | 9/2015 | | |
| WO | WO 2016/001810 A1 | 1/2016 | | |
| WO | WO 2016/014530 A1 | 1/2016 | | |

OTHER PUBLICATIONS

Lloyd et al (Protein Engineering, Design & Selection, 22:159-168, 2009).*

Edwards et al (J Mol Biol, 14;334(1):103-118, 2003).*

Mariuzza et al. (Annu. Rev. Biophys. Biophys. Chem., 16: 139-159, 1987).*

Cellular and Molecular Immunology (Eds. Abass et al.; 1991; W.B. Saunders: Philadelphia; p. 54).*

Lippincott-Schwartz (Current Protocols in Cell Biology, 16.0.1-16.0.2, 2002).*

U.S. Appl. No. 15/614,290, filed Jun. 5, 2017 (May 3, 2018).

U.S. Appl. No. 15/614,290, filed Sep. 20, 2018 Restriction Requirement.

Abdiche et al., "Probing the binding mechanism and affinity of tanezumab, a recombinant humanized anti-NGF monoclonal antibody, using a repertoire of biosensors," Protein Science 17:1326-1335 (2008).

Allen, "Ligand-Targeted Therapeutics in Anticancer Therapy," Nat. Rev. Cancer 2:750-763 (2002).

Altschul et al., "Gapped BLAST and PSI-BLAST: a new generation of protein database search programs," Nucleic Acids Res. 25(17):3389-3402 (1997).

(Continued)

*Primary Examiner* — Brad Duffy
(74) *Attorney, Agent, or Firm* — Baker Botts L.L.P.

(57) ABSTRACT

The presently disclosed subject matter provides for methods and compositions for treating multiple myeloma. It relates to chimeric antigen receptors (CARs) that specifically target a G-protein coupled receptor (e.g., a G-protein coupled receptor family C group 5 member D (GPRC5D)), and immunoresponsive cells comprising such CARs. The presently disclosed CARs targeting a G-protein coupled receptor (e.g., GPRC5D) have enhanced immune-activating properties, including anti-tumor activity.

49 Claims, 31 Drawing Sheets

Specification includes a Sequence Listing.

(56) References Cited

OTHER PUBLICATIONS

Altschul, et al., “Basic Local Alignment Search Tool,” J. Mol. Biol. 215:403-410 (1990).
Amon et al., “Monoclonal Antibodies for Immunotargeting of Drugs in Cancer Therapy,” in Monoclonal Antibodies and Cancer Therapy, Reisfeld et al. (eds.), pp. 243-256 (1985).
Azinovic et al., “Survival benefit associated with human anti-mouse antibody (HAMA) in patients with B-cell malignancies,” Cancer Immunol Immunother 55:1451-1458 (2006).
Baeuerle et al., “Bispecific T-cell Engaging Antibodies for Cancer Therapy,” Cancer Res., 69(12):4941-4944 (2009).
Bird et al., “Single-Chain Antigen-Binding Proteins,” Science 242(4877):423-426 (1988).
Brennan et al., “Preparation of Bispecific Antibodies by Chemical Recombination of Monoclonal Immunoglobulin G1 Fragments,” Science 229:81-83 (1985).
Brown et al., “Tolerance to Single, but not Multiple, Amino Acid Replacements in Antibody V-H CDR2: A Means of Minimizing B Cell Wastage from Somatic Hypermutation?” The Journal of Immunology, The American Association of Immunologists, 156:3285-3291 (1996).
Caron et al., “Engineered Humanized Dimeric Forms of IgG are More Effective Antibodies,” J Exp. Med 176:1191 -1195 (1992).
Chen et al., “Selection and Analysis of an Optimized Anti-VEGF Antibody: Crystal Structure of an Affinity-matured Fab in Complex with Antigen,” J. Mol. Biol. 293:865-881(1999).
Cuesta et al., “Multivalent antibodies: when design surpasses evolution,” Trends in Biotechnology 28(7):355-362 (2010).
Flatman et al., “Process analytics for purification of monoclonal antibodies,” J. Chromatogr. B 848:79-87 (2007).
Gershoni et al., “Epitope mapping—The first step in developing epitope-based vaccines,” Biod, Adis International Ltd., NZ, 21(3):145-156 (2007).
Glennie et al., “Preparation and performance of bispecific F(ab' gamma)2 antibody containing thioether-linked Fab' gamma fragments,” J. Immunol. 139:2367-2375 (1987).
Harris et al., “Crystallographic Structure of an Intact IgG1 Monoclonal Antibody,” Journal of Molecular Biology 275:861-872 (1998).
Hellstrom et al., “Antibodies for Drug Delivery,” in Controlled Drug Delivery (2nd Ed.), Robinson et al. (eds.), pp. 623-653 (1987).
International Search Report dated May 19, 2016 in International Application No. PCT/US15/64122.
Karpovsky et al., “Production of Target-Specific Effector Cells Using Hetero-Cross-Linked Aggregates Containing Anti-Target Cell and Anti-Fcy Receptor Antibodies,” J. Exp. Med. 160:1686-1701 (1984).
Klechevsky et al., “Antitumor activity of immunotoxins with T-cell receptor-like specificity against human melanoma xenografts,” Cancer Res 68(15):6360-6367 (2008).
Liu et al., “Heteroantibody duplexes target cells for lysis by cytotoxic T lymphocytes,” Proc. Natl. Acad. Sci. USA 82:8648-8652 (1985).
McCafferty et al., “Phage antibodies: filamentous phage displaying antibody variable domains,” Nature 348:552-554 (1990).
Meyers et al., “Optimal alignments in linear space,” Cabios 4(1):11-17 (1988).
Needleman et al., “A General Method Applicable to the Search for Similarities in the Amino Acid Sequence of Two Proteins,” J. Mol. Biol. 48:443-453 (1970).
Pastan et al., “Immunotoxins in cancer therapy,” Curr. Opin. Investig. Drugs 3(7):1089-1091 (2002).
Paulus, “Preparation and Biomedical Applications of Bispecific Antibodies,” Behring Ins. Mitt. 78:118-132 (1985).
Payne, “Progress in immunoconjugate cancer therapeutics,” Cancer Cell 3:207-212 (2003).
Persic et al., “An integrated vector system for the eukaryotic expression of antibodies or their fragments after selection from phage display libraries,” Gene 187:9-18 (1997).
Queen et al., “A humanized antibody that binds to the interleukin 2 receptor,” Proc Natl Acad Sci USA 86:10029-10033 (1989).
Riechmann et al., “Reshaping human antibodies for therapy,” Nature 332:323-327 (1988).
Ritter et al., “Serological Analysis of Human Anti-Human Antibody Responses in Colon Cancer Patients Treated with Repeated Doses of Humanized Monoclonal Antibody A33,” Cancer Res 61:6851-6859 (2001).
Roberts et al., “Vaccination with CD20 peptides induces a biologically active, specific immune response in mice,” Blood 99: 3748-3755 (2002).
Saito et al., “Drug delivery strategy utilizing conjugation via reversible disulfide linkages: role and site of cellular reducing activities,” Adv. Drug Deliv. Rev. 55:199-215 (2003).
Senter et al., “Selective activation of anticancer prodrugs by monoclonal antibody—enzyme conjugates,” Adv. Drug Deliv. Rev. 53:247-264 (2001).
Supplemental Partial European Search Report dated May 4, 2018 in Application No. EP 15865989.
Thorpe et al., “The Preparation and Cytotoxic Properties of Antibody-Toxin Conjugates,” Immunol. Rev., 62:119-158 (1982).
Thorpe, “Antibody Carriers of Cytotoxic Agents in Cancer Therapy: A Review,” in Monoclonal Antibodies ’84: Biological and Clinical Applications, Pinchera et al. (eds.), pp. 475-506 (1985).
Tjandra et al., “Development of human anti-murine antibody (HAMA) response in patients,” Immunol Cell Biol. 68:367-376 (1990).
Tomimatsu et al., “Production of Human Monoclonal Antibodies against FcεRIα by a Method Combining in-Vitro Immunization with Phage Display,” Biosci Biotechnol Biochem 73(7):1465-1469 (2009).
Trail et al., “Monoclonal antibody drug immunoconjugates for targeted treatment of cancer,” Cancer Immunol. Immunother. 52:328-337 (2003).
Ward et al., “Binding activities of a repertoire of single immunoglobulin variable domains secreted from *Escherichia coli*,” Nature 341:544-546 (1989).
Culture of Animal Cells: A Manual of Basic Technique and Specialized Applications, Sixth Edition, Freshney, 2010 (Table of Contents).
The Polymerase Chain Reaction. Mullis, 1994 (Foreword and Table of Contents).
Anderson, “Prospects for Human Gene Therapy,” Science 226(4673):401-409 (1984).
Atamaniuk et al., “Overexpression of G protein-coupled receptor 5D in the bone marrow is associated with poor prognosis in patients with multiple myeloma,” Euro J of Clin Invest 42(9):953-960 (2012).
Bam et al., “GPRC5D Is a Cell Surface Plasma Cell Marker Whose Expression Is High in Myeloma Cells and Reduced Following Coculture With Osteoclasts,” Blood 122:3099 (2013).
Bataille et al., “The phenotype of normal, reactive and malignant plasma cells. Identification of “many and multiple myelomas” and of new targets for myeloma therapy,” Haematologica 91:1234-1240 (2006).
Benton et al., “Screening Xgt Recombinant Clones by Hybridization to Single Plaques in situ,” Science 196(4286):180-182 (1977).
Bertilaccio et al., “Low-Dose Lenalidomide Improves CAR-Based Immunotherapy in CLL by Reverting T-Cell Defects In Vivo,” Blood 122:4171 (2013).
Blömer et al., “Highly Efficient and Sustained Gene Transfer in Adult Neurons with a Lentivirus Vector,” Journal of Virology 71(9):6641-6649 (1997).
Boyd et al., “The Clinical Impact and Molecular Biology of del(17p) in Multiple Myeloma Treated with Conventional or Thalidomide-Based Therapy,” Genes, Chromosomes & Cancer 50:765-774 (2011).
Bregni et al., “Human Peripheral Blood Hematopoietic Progenitors are Optimal Targets of Retroviral-Mediated Gene Transfer,” Blood 80(6):1418-1422 (1992).
Brentjens et al., “CD19-Targeted T Cells Rapidly Induce Molecular Remissions in Adults with Chemotherapy-Refractory Acute Lymphoblastic Leukemia,” Science Translational Medicine 5:177ra38 (2013).

(56) References Cited

OTHER PUBLICATIONS

Brentjens et al., "Eradication of systemic B-cell tumors by genetically targeted human T lymphocytes co-stimulated by CD80 and interleukin-15," Nature Medicine 9(3):279-286 (2003).
Brentjens et al., "Genetically Targeted T Cells Eradicate Systemic Acute Lymphoblastic Leukemia Xenografts," Clin Cancer Res 13(18):5426-5435 (2007).
Brentjens et al., "Safety and persistence of adoptively transferred autologous CD19-targeted T cells in patients with relapsed or chemotherapy refractory B-cell leukemias," Blood 118(18):4817-4828 (2011).
Brigham et al., "Rapid Communication: In vivo Transfection of Murine Lungs with a Functioning Prokaryotic Gene Using a Liposome Vehicle," Am. J. Med. Sci. 298(4):278-281 (1989).
Brocks et al., "A TNF receptor antagonistic scFv, which is not secreted in mammalian cells, is expressed as a soluble mono- and bivalent scFv derivative in insect cells," Immunotechnology 3:173-184 (1997).
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).
Cohen et al., "A GPRC5D is a promising marker for monitoring the tumor load and to target multiple myeloma cells," Hematology 18(6):348-351 (2013).
Cornetta et al., "Gene Transfer into Primates and Prospects for Gene Therapy in Humans," Progress in Nucleic Acid Research and Molecular Biology 36:311-322 (1987).
Danos et al., "Safe and efficient generation of recombinant retroviruses with amphotropic and ecotropic host ranges," PNAS USA 85:6460-6464 (1988).
Davila et al., "Efficacy and Toxicity Management of 19-28z CAR T Cell Therapy in B Cell Acute Lymphoblastic Leukemia," Science Translational Medicine 6:224ra25 (2014).
Dudley et al., "Adoptive Cell Therapy for Patients With Metastatic Melanoma: Evaluation of Intensive Myeloablative Chemoradiation Preparative Regimens," J Clin Oncol 26:5233-5239 (2008).
Dupont et al., "Artificial Antigen-Presenting Cells Transduced with Telomerase Efficiently Expand Epitope-Specific, Human Leukocyte Antigen-Restricted Cytotoxic T Cells," Cancer Res 65:5417-5427 (2005).
Eglitis et al., "Retroviral Vectors for Introduction of Genes into Mammalian Cells," BioTechniques 6(7):608-614 (1988).
Extended European Search Report dated Jul. 10, 2018 in Application No. EP 15865633.
Felgner et al., "Lipofection: A highly efficient, lipid-mediated DNA-transfection procedure," PNAS USA 84:7413-7417 (1987).
Fife et al., "Inhibition of T cell activation and autoimmune diabetes using a B cell surface—linked CTLA-4 agonist," J Clin Invest 116(8):2252-2261 (2006).
Friedmann, "Progress toward Human Gene Therapy," Science 244(4910):1275-1281 (1989).
Frigyesi et al., "Robust isolation of malignant plasma cells in multiple myeloma," Blood 123(9):1336-1340 (2014).
Gade et al., "Targeted Elimination of Prostate Cancer by Genetically Directed Human T Lymphocytes," Cancer Res 65(19):9080-9088 (2005).
Gahrton et al., "Allogeneic Bone Marrow Transplantation in Multiple Myeloma," N Engl J Med 325:1267-1273 (1991).
Giomarelli et al., "Inhibition of thrombin-induced platelet aggregation using human single-chain Fv antibodies specific for TREM-like transcript-I," Thromb Haemost 97:955-963 (2007).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia 1(2):123-127 (1999).
Grunstein et al., "Colony hybridization: A method for the isolation of cloned DNAs that contain a specific gene," PNAS USA 72(10):3961-3965 (1975).
Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).
Hollyman et al., "Manufacturing Validation of Biologically Functional T Cells Targeted to CD19 Antigen for Autologous Adoptive Cell Therapy," J Immunother 32:169-180 (2009).
Hughes et al., "Retroviral Gene Transfer to Primitive Normal and Leukemic Hematopoietic Cells Using Clinically Applicable Procedures," J. Clin. Invest. 89:1817-1824 (1992).
Hunder et al., "Treatment of Metastatic Melanoma with Autologous CD4+ T Cells against NY-ESO-1," N Engl J Med 358:2698-2703 (2008).
Huston et al., "Protein engineering of antibody binding sites: Recovery of specific activity in an anti-digoxin single-chain Fv analogue produced in *Escherichia coli*," PNAS USA, 85:5879-5883 (1988).
International Search Report dated Apr. 8, 2016 in International Application No. PCT/US15/64102.
Johnson, "Gene Therapy for Cystic Fibrosis," Chest 107:77S-83S (1995).
Kabat et al., Sequences of Proteins of Immunological Interest, 4$^{th}$ Edition, U. S. Department of Health and Human Services, National Institutes of Health (1987).
Kabat et al., Sequences of Proteins of Immunological Interest, vol. I, Fifth Edition, U.S. Department of Health and Human Services, NIH Publication No. 91-3242 (1991).
Kershaw et al., "Gene-Engineered T cells as a Superior Adjuvant Therapy for Metastatic Cancer," J Immunol 173:2143-2150 (2004).
Kido et al., "Use of a retroviral vector with an internal opsin promoter to direct gene expression to retinal photoreceptor cells," Current Eye Research 15:833-844 (1996).
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Le Gal La Salle et al., "An Adenovirus Vector for Gene Transfer into Neurons and Glia in the Brain," Science 259(5097):988-990 (1993).
Ledbetter et al., "Agonistic Activity of a CD40-Specific Single-Chain Fv Constructed from the Variable Regions of mAb G28-5," Crit. Rev Immun., 17:427-435 (1997).
Lyddane et al., "Cutting Edge: CD28 Controls Dominant Regulatory T Cell Activity during Active Immunization," J. Immunol. 176:3306-3310 (2006).
Maher et al., "Human T-lymphocyte cytotoxicity and proliferation directed by a single chimeric TCRζ/CD28 receptor," Nat. Biotechnol. 20:70-75 (2002).
Miller et al., "Improved Retroviral Vectors for Gene Transfer and Expression," Biotechniques 7(9):980-990 (1989).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Redesign of Retrovirus Packaging Cell Lines to Avoid Recombination Leading to Helper Virus Production," Mol. Cell. Biol. 6(8):2895-2902 (1986).
Miller, "Retrovirus Packaging Cells," Human Gene Therapy 1:5-14 (1990).
Miyoshi et al., "Stable and efficient gene transfer into the retina using an HIV-based lentiviral vector," PNAS USA 94:10319-10323 (1997).
Moen, "Directions in Gene Therapy," Blood Cells 17:407-416 (1991).
Moosmayer et al., "A single-chain TNF receptor antagonist is an effective inhibitor of TNF mediated cytotoxicity," Therapeutic Immunol 2:31-40 (1995).
Morgan et al., "Case Report of a Serious Adverse Event Following the Administration of T Cells Transduced with a Chimeric Antigen Receptor Recognizing *ERBB2*," Molecular Therapy 18(4):843-851 (2010).
Morgan et al., "Cancer Regression in Patients After Transfer of Genetically Engineered Lymphocytes," Science 314:126-129 (2006).

(56) References Cited

OTHER PUBLICATIONS

Naldini et al., "In Vivo Gene Delivery and Stable Transduction of Nondividing Cells by a Lentiviral Vector," Science 272(5259):263-267 (1996).
Ono et al., "Plasmid DNAs directly injected into mouse brain with lipofectin can be incorporated and expressed by brain cells," Neuroscience Letters, 117:259-263 (1990).
Panelli et al., "A Tumor-Infiltrating Lymphocyte from a Melanoma Metastasis with Decreased Expression of Melanoma Differentiation Antigens Recognizes MAGE-12," J Immunol 164:4382-4392 (2000).
Panelli et al., "Expansion of Tumor-T Cell Pairs from Fine Needle Aspirates of Melanoma Metastases," J Immunol 164:495-504 (2000).
Papanicolaou et al., "Rapid expansion of cytomegalovirus—specific cytotoxic T lymphocytes by artificial antigen-presenting cells expressing a single HLA allele," Blood 102:2498-2505 (2003).
Pegram et al., "Tumor-targeted T cells modified to secrete IL-12 eradicate systemic tumors without need for prior conditioning," Blood 119(18):4133-4141 (2012).
Peter et al., "scFv Single Chain Antibody Variable Fragment as Inverse Agonist of the β2-Adrenergic Receptor," J Biol. Chem 278(38):36740-36747 (2003).
Peter et al., "Protective effects of an anti-melanocortin-4 receptor scFv derivative in lipopolysaccharide-induced cachexia in rats," J Cachexia Sarcopenia Muscle 4:79-88 (2013).
Posthumus et al., "Analysis and Simulation of a Neutralizing Epitope of Transmissible Gastroenteritis Virus," J. Virology, 64(7):3304-3309 (1990).
Riviere et al., "Novel Strategies for Cancer Therapy: The Potential of Genetically Modified T Lymphocytes," Curr Hematol Rep 3:290-297 (2004).
Rosenberg et al., "Adoptive cell transfer: a clinical path to effective cancer immunotherapy," Nature Reviews Cancer 8:299-308 (2008).
Rosenberg et al., "Gene Transfer into Humans," N. Engl. J. Med 323(9):570-578 (1990).
Sadelain et al., "The basic principles of chimeric antigen receptor (CAR) design," Cancer Discovery 3(4):388-398 (2013).
Sadelain et al., "The promise and potential pitfalls of chimeric antigen receptors," Curr Opin Immunol 21:215-223 (2009).
Sadelain et al., "Targeting Tumours With Genetically Enhanced T Lymphocytes," Nat Rev Cancer 3:35-45 (2003).
Sambrook et al., Molecular Cloning: A Laboratory Manual, 2nd ed. Cold Spring Harbor Laboratory Press, New York (1989).
Sharp, "Gene Therapy," The Lancet 337:1277-1278 (1991).
Shaughnessy, Jr., et al., "A validated gene expression model of high-risk multiple myeloma is defined by deregulated expression of genes mapping to chromosome 1," Blood 109:2276-2284 (2007).
Shen et al., "Engineering Peptide Linkers for scFv Immunosensors," Anal. Chem. 80(6):1910-1917 (2008).
Shieh et al., "Transgenic Expression of Single-Chain Anti-CTLA-4 Fv on 13 Cells Protects Nonobese Diabetic Mice from Autoimmune Diabetes," J Immunol 183:2277-2285 (2009).
Siegel et al., "Cancer Statistics, 2013," CA Cancer J Clin 63:11-30 (2013).
Straubinger et al., "Liposomes as Carriers for Intracellular Delivery of Nucleic Acids," Methods in Enzymology, 101:512-527 (1983).
Stephan et al., "T cell-encoded CD80 and 4-1BBL induce auto- and transcostimulation, resulting in potent tumor rejection," Nat. Med 13(12):1440-1449 (2007).
Timmerman et al., "Functional reconstruction and synthetic mimicry of a conformational epitope using CLIPS™ technology," J. Mol. Recognit. 20:283-299 (2007).
Tolstoshev et al., "Gene expression using retroviral vectors," Current Opinion in Biotechnology 1:55-61 (1990).
Wahl et al., "Improved Radioimaging and Tumor Localization with Monoclonal F(ab')2," J. Nucl. Med. 24:316-325 (1983).
Wolff et al., "Direct Gene Transfer into Mouse Muscle in Vivo," Science 247(4949):1465-1468 (1990).
Wu et al., "Receptor-mediated Gene Delivery and Expression in Vivo," Journal of Biological Chemistry, 263(29):14621-14624 (1988).
Wu et al., "Targeting Genes: Delivery and Persistent Expression of a Foreign Gene Driven by Mammalian Regulatory Elements in Vivo," Journal of Biological Chemistry 264(29):16985-16987 (1989).
Xie et al., "Direct demonstration of MuSK involvement in acetylcholine receptor clustering through identification of agonist ScFv," Nat Biotech 15:768-771 (1997).
Xu et al., "Correction of the enzyme deficiency in hematopoietic cells of Gaucher patients using a clinically acceptable retroviral supernatant transduction protocol," Exp. Hemat. 22:223-230 (1994).
Zhao et al., "Characteristics of an scFV Antibody Fragment That Binds to Immunoglobulin G of Graves' Disease Patients and Inhibits Autoantibody-Mediated Thyroid-Stimulating Activity," Hybridoma 27(6):445-451 (2008).
Abbas et al., Cellular and Molecular Immunology, p. 54 (1991).
Clinical Immunology and Allergology: in 3 volumes / edited by L. Yeger; translated from German by S.S. Kirzon, A.P. Portnova, Editor Academician R.V.Petrov—[2nd edition, reworked and updated].—Moscow: Meditsina, 1990. 1:219-222 (with full English translation).
Hirano et al., "Novel reciprocal regulation of cAMP signaling and apoptosis by orphan G-protein-coupled receptor GPRC5A gene expression," Biochemical and Biophysical Research Communications 351:185-191 (2006).
Koyko, R. Immunology: Textbook for Post-Graduate Education of Physicians / R. Koyko, D. Sunshine, E. Benjamin; translated from English, Editor N.B. Serebryanaya. -Moscow: Akademiya; Saint-Petersburg: Philology Department of The S.-Petersburg State University, 2008, 1:37 (with full English translation).
Ozhegov, S.I. The Thesaurus of the Russian Language: 80,000 words and idioms / S.I. Ozhegov and N.Yu Shvedova; Russian Academy of Sciences, Institute of the Russian Language named after V.V. Vinogradov.—4th Edition, updated—Moscow: [A TEMP}, 2006. 1:375 (with full English translation).
Parkman, R., "Clonal analysis of murine graft-vs-host disease. I. Phenotypic and functional analysis of T lymphocyte clones," J. Immunol. 136:3543-3548 (1986).
Smith et al., "GPRC5D is a target for the immunotherapy of multiple myeloma with rationally designed CAR T cells," Sci Transl Med. 11:485, 14 pages (2019).
Search Report in Russian Application No. 2017123545 received by Applicant on Dec. 11, 2019.
Beckman et al., "Antibody constructs in cancer therapy: protein engineering strategies to improve exposure in solid tumors," Can. 109:170-179 (2007).
Cespedes et al., "Mouse models in oncogenesis and cancer therapy," Clin. Transl. Oncol. 8(5):318-329 (2006).
Dennis et al., "Cancer: Off by a Whisker," Nature 442:739-741 (2006).
Fujimori et al., "A Modeling Analysis of Monoclonal Antibody Percolation through Tumors: a Binding-Site Barrier," J. Nucl. Med. 31:1191-1198 (1990).
Huang et al., "Recombinant immunotherapeutics: current state and perspectives regarding the feasibility and market," Appl. Microbiol Biotechnol 87:401-410 (2010).
Kodama et al., "Anti-GPRC5D/CD3 Bispecific T-Cell—Redirecting Antibody for the Treatment of Multiple Myeloma," Mol. Cancer Ther. 18:1555-1564 (2010), Published Online first Jul. 3, 2019.
Rudnick et al., "Affinity and Avidity in Antibody-Based Tumor Targeting," Can. Biotherp. & Radiopharm 24(2):155-162 (2009).
Talmadge et al., "Murine Models to Evaluate Novel and Conventional Therapeutic Strategies for Cancer," Am. J. Pathol. 170(3):793-804 (2007).
Thurber et al., "Antibody tumor penetration: transport opposed by systemic and antigen-mediated clearance," Adv. Drug Deliv. Rev. 60:1421-1434 (2008).
Voskoglou-Nomikos et al., "Clinical Predictive Value of the in Vitro Cell Line, Human Xenograft, and Mouse Allograft Preclinical Cancer Models," Clin Can. Res. 9:4227-4239 (2003).

* cited by examiner

LTR, long terminal repeat promoter; SD, SA, splice donor and acceptor; Ψ, packaging element; black box, signal peptide; IRES, internal ribosomal entry site; GLuc, Gaussia luciferase; CD8, the human CD8 transmembrane domain

| Marker | %Gated |
|---|---|
| All | 100.00 |
| All | 100.00 |
| GPRC5D CAR+ | 85.06 |
| GPRC5D CAR+ | 0.00 |

Figure 6
5' LTR
SD
SA
GPRC5D scFv
CD8a TM
4-1BB
CD3ζ
3' LTR

IFNg, IL-6, TNFa, sCD40L, GM-CSF

| | Sample Name | Median, RED2-HLin |
|---|---|---|
| - - - - | B04 3T3-ET150 + ET150-5.fcs | 3216 |
| —— | A04 anti-M13 + APC mIgG.fcs | 10.9 |

| | Sample Name | Median, RED2-HLin |
|---|---|---|
| - - - - | B05 3T3-ET150 + ET150-8.fcs | 3113 |
| —— | A04 anti-M13 + APC mIgG.fcs | 10.9 |

| | Sample Name | Median, RED2-HLin |
|---|---|---|
| - - - - | B07 3T3-ET150 + ET150-18.fcs | 3176 |
| —— | A04 anti-M13 + APC mIgG.fcs | 10.9 |

CHIMERIC ANTIGEN RECEPTORS TARGETING G-PROTEIN COUPLED RECEPTOR AND USES THEREOF

CROSS-REFERENCE TO RELATED APPLICATIONS

This application is a Continuation of International Application Serial No. PCT/US2015/064102, filed Dec. 4, 2015, which claims priority to U.S. Provisional Patent Application Ser. No. 62/088,286, filed Dec. 5, 2014, the contents of each of which are incorporated by reference in their entirety, and to each of which priority is claimed.

SEQUENCE LISTING

The specification further incorporates by reference the Sequence Listing submitted herewith via EFS on Jun. 5, 2017. Pursuant to 37 C.F.R. § 1.52(e)(5), the Sequence Listing text file, identified as 0727340350CON_SL.txt, is 354,870 bytes and was created on Jun. 2, 2017. The Sequence Listing electronically filed herewith, does not extend beyond the scope of the specification and thus does not contain new matter.

INTRODUCTION

The presently disclosed subject matter provides for methods and compositions for treating cancer. It relates to chimeric antigen receptors (CARs) that specifically target a G-protein coupled receptor (e.g., a G-protein coupled receptor family C group 5 member D (GPRC5D)), immunoresponsive cells comprising such CARs, and methods of using such cells for treating cancer (e.g., multiple myeloma).

BACKGROUND OF THE INVENTION

Cell-based immunotherapy is a therapy with curative potential for the treatment of cancer. T cells and other immune cells may be modified to target tumor antigens through the introduction of genetic material coding for artificial or synthetic receptors for antigen, termed Chimeric Antigen Receptors (CARs), specific to selected antigens. Targeted T cell therapy using CARs has shown recent clinical success in treating hematologic malignancies.

Multiple myeloma (MM) is the second most common hematologic malignancy.[9] Approximately 25% of patients have high-risk cytogenetics, which portends a median survival of less then 2 years.[10,11] While recent strides have been made, regardless of cytogenetics, the disease is still considered incurable outside the immuno-therapeutic graft versus myeloma (GvM) effect of an allogeneic transplant. However, allogeneic transplants are limited by ineligibility and high rates of transplant-associated morbidity and mortality.[12] Similar to the GvM effect, a potentially curative T cell effect may be achieved with minimal toxicity through autologous adoptive T cell therapy.

Myeloma may be an ideal disease to test adoptive T cell therapy. First, as indicated above, allogeneic transplants demonstrate that the T cell can be a curative treatment, even with minimal or no concomitant chemotherapy such as after non-myeloablative transplants or post-transplantation donor lymphocyte infusions. Second, conditioning chemotherapy, possibly through the mechanism of depleting regulatory T cells (Tregs), enhances the efficacy of adoptive T cell therapy,[5,13] as such, the immediate post-autologous transplant period could be an optimal time to administer T cells, and myeloma is one of the few diseases where autologous stem cell transplantation is the standard of care. Third, the immunomodulatory drug lenalidomide may improve CAR based therapy, as has been shown in mice,[14] and lenalidomide is commonly used to treat MM. Fourth, adoptive T cell therapy works best in bone marrow predominant disease such as ALL,[7,8] when compared to solid tumors or extramedullary CLL,[5] and similar to ALL, myeloma is a disease of the bone marrow.

While there are various reasons to expect that adoptive T cell therapy may work well in MM, expanding adoptive T cell therapy to myeloma also poses unique challenges. Unlike other B-cell malignancies, CD19 expression is seen in only 2% of myeloma patients.[15] Furthermore, unlike CD19, the common extracellular immunophenotypic markers in myeloma (CD138, CD38, and CD56) are all co-expressed on other essential cell types, and we predict CARs to any of these targets would lead to unacceptable “off tumor, on target” toxicity[7] which can be fatal even in targets where antibodies are well tolerated, as was the case with a HER2 targeted CAR.[16] To address these challenges, we have identified extracellular targets with predicted high MM and limited essential normal tissue expression that may be optimal targets for adoptive T cell therapy of MM. Accordingly, there are needs for novel therapeutic strategies to design CARs targeting antigens that are highly expressed in MM cells and limited expression in normal tissues for treating multiple myeloma, which strategies capable of inducing potent tumor eradication with minimal toxicity and immunogenicity.

SUMMARY OF THE INVENTION

The presently disclosed subject matter generally provides chimeric antigen receptors (CARs) that specifically target a G-protein coupled receptor, immunoresponsive cells comprising such CARs, and uses of these CARs and immunoresponsive cells for treating multiple myeloma.

The presently disclosed subject matter provides CARs. In one non-limiting example, the CAR comprises an extracellular antigen-binding domain, a transmembrane domain and an intracellular domain, where the extracellular antigen-binding domain specifically binds to a G-protein coupled receptor. In certain embodiments, the G-protein coupled receptor is a G-protein coupled receptor family C group 5 member D (GPRC5D). In certain embodiments, the extracellular antigen-binding domain specifically binds to GPRC5D with a binding affinity ($K_D$) of from about $1\times10^{-9}$ M to about $3\times10^{-6}$ M. In certain embodiments, the extracellular antigen-binding domain is a single-chain variable fragment (scFv). In certain embodiments, the extracellular antigen-binding domain is a murine scFv. In certain embodiments, the extracellular antigen-binding domain is a human scFv. In certain embodiments, the extracellular antigen-binding domain is a Fab, which is optionally crosslinked. In certain embodiments, the extracellular binding domain is a $F(ab)_2$. In certain embodiments, any of the foregoing molecules can be comprised in a fusion protein with a heterologous sequence to form the extracellular antigen-binding domain.

In certain embodiments, the extracellular antigen-binding domain comprises a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS:1, 5, 9, 13, 17, 21, 25, 29, 33, 37, 41, 45, 49, 53, 57, 61, 65, 69, 73, 77, 81, 85, 89, 93, 302, 314, 326, 338, 350, 362, 374, and 386.

In certain embodiments, the extracellular antigen-binding domain comprises a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS:2, 6, 10, 14, 18, 22, 26, 30, 34, 38, 42, 46, 50, 54, 58, 62, 66, 70, 74, 78, 82, 86, 90, 94, 303, 315, 327, 339, 351, 363, 375, and 387.

In certain embodiments, the extracellular antigen-binding domain comprises (a) a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NO: 1, 5, 9, 13, 17, 21, 25, 29, 33, 37, 41, 45, 49, 53, 57, 61, 65, 69, 73, 77, 81, 85, 89, 93, 302, 314, 326, 338, 350, 362, 374, and 386; and (b) a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 303, 315, 327, 339, 351, 363, 375, and 387.

In certain embodiments, the extracellular antigen-binding domain comprises a heavy chain variable region comprising an amino acid sequence selected from the group consisting of SEQ ID NOS:1, 5, 9, 13, 17, 21, 25, 29, 33, 37, 41, 45, 49, 53, 57, 61, 65, 69, 73, 77, 81, 85, 89, 93, 302, 314, 326, 338, 350, 362, 374, and 386, and conservative modifications thereof.

In certain embodiments, the extracellular antigen-binding domain comprises a light chain variable region comprising an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 303, 315, 327, 339, 351, 363, 375, and 387, and conservative modifications thereof.

In certain embodiments, the extracellular antigen-binding domain comprises (a) a heavy chain variable region comprising an amino acid sequence selected from the group consisting of SEQ ID NOS:1, 5, 9, 13, 17, 21, 25, 29, 33, 37, 41, 45, 49, 53, 57, 61, 65, 69, 73, 77, 81, 85, 89, 93, 302, 314, 326, 338, 350, 362, 374, and 386, and conservative modifications thereof, and (b) a light chain variable region comprising an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 303, 315, 327, 339, 351, 363, 375, and 387, and conservative modifications thereof.

In certain embodiments, the extracellular antigen-binding domain comprises a heavy chain variable region comprising amino acids having a sequence selected from the group consisting of: SEQ ID NOS:1, 5, 9, 13, 17, 21, 25, 29, 33, 37, 41, 45, 49, 53, 57, 61, 65, 69, 73, 77, 81, 85, 89, 93, 302, 314, 326, 338, 350, 362, 374, and 386. In certain embodiments, the extracellular antigen-binding domain comprises a light chain variable region comprising amino acids having a sequence selected from the group consisting of: SEQ ID NOS:2, 6, 10, 14, 18, 22, 26, 30, 34, 38, 42, 46, 50, 54, 58, 62, 66, 70, 74, 78, 82, 86, 90, 94, 303, 315, 327, 339, 351, 363, 375, and 387. In certain embodiments, the extracellular antigen-binding domain comprises a heavy chain variable region comprising amino acids having the sequence set forth in SEQ ID NO:53. In certain embodiments, the extracellular antigen-binding domain comprises a heavy chain variable region comprising amino acids having the sequence set forth in SEQ ID NO:57. In certain embodiments, the extracellular antigen-binding domain comprises a heavy chain variable region comprising amino acids having the sequence set forth in SEQ ID NO:61. In certain embodiments, the extracellular antigen-binding domain comprises a heavy chain variable region comprising amino acids having the sequence set forth in SEQ ID NO:65. In certain embodiments, the extracellular antigen-binding domain comprises a heavy chain variable region comprising amino acids having the sequence set forth in SEQ ID NO:69. In certain embodiments, the extracellular antigen-binding domain comprises a light chain variable region comprising amino acids having the sequence set forth in SEQ ID NO:54. In certain embodiments, the extracellular antigen-binding domain comprises a light chain variable region comprising amino acids having the sequence set forth in SEQ ID NO:58. In certain embodiments, the extracellular antigen-binding domain comprises a light chain variable region comprising amino acids having the sequence set forth in SEQ ID NO:62. In certain embodiments, the extracellular antigen-binding domain comprises a light chain variable region comprising amino acids having the sequence set forth in SEQ ID NO:66. In certain embodiments, the extracellular antigen-binding domain comprises a light chain variable region comprising amino acids having the sequence set forth in SEQ ID NO:70. In certain embodiments, the extracellular antigen-binding domain comprises (a) a heavy chain variable region comprising amino acids having a sequence set forth in SEQ ID NO:1, and a light chain variable region comprising amino acids having a sequence set forth in SEQ ID NO:2; (b) a heavy chain variable region comprising amino acids having a sequence set forth in SEQ ID NO:5, and a light chain variable region comprising amino acids having a sequence set forth in SEQ ID NO:6; (c) a heavy chain variable region comprising amino acids having a sequence set forth in SEQ ID NO:9, and a light chain variable region comprising amino acids having a sequence set forth in SEQ ID NO:10; (d) a heavy chain variable region comprising amino acids having a sequence set forth in SEQ ID NO:13, and a light chain variable region comprising amino acids having a sequence set forth in SEQ ID NO:14; (e) a heavy chain variable region comprising amino acids having a sequence set forth in SEQ ID NO:17, and a light chain variable region comprising amino acids having a sequence set forth in SEQ ID NO:18; (f) a heavy chain variable region comprising amino acids having a sequence set forth in SEQ ID NO:21, and a light chain variable region comprising amino acids having a sequence set forth in SEQ ID NO:22; (g) a heavy chain variable region comprising amino acids having a sequence set forth in SEQ ID NO:25, and a light chain variable region comprising amino acids having a sequence set forth in SEQ ID NO:26; (h) a heavy chain variable region comprising amino acids having a sequence set forth in SEQ ID NO:29, and a light chain variable region comprising amino acids having a sequence set forth in SEQ ID NO:30; (i) a heavy chain variable region comprising amino acids having a sequence set forth in SEQ ID NO:33, and a light chain variable region comprising amino acids having a sequence set forth in SEQ ID NO:34; (j) a heavy chain variable region comprising amino acids having a sequence set forth in SEQ ID NO:37, and a light chain variable region comprising amino acids having a sequence set forth in SEQ ID NO:38; (k) a heavy chain variable region comprising amino acids having a sequence set forth in SEQ ID NO:41, and a light chain variable region comprising amino acids having a sequence set forth in SEQ ID NO:42; (l) a heavy chain variable region comprising amino acids having a sequence set forth in SEQ ID NO:45, and a light chain variable region comprising amino acids having a sequence set forth in SEQ ID NO:46; (m) a heavy chain variable region comprising amino acids having a sequence set forth in SEQ ID NO:49, and a light chain variable region comprising amino acids having a sequence set forth in SEQ ID NO:50; (n) a heavy chain variable region comprising amino acids having a sequence set forth in SEQ ID NO:53, and a light chain variable region comprising amino acids having a sequence set forth in SEQ ID NO:54; (o) a heavy chain variable region comprising amino acids having a sequence set forth in SEQ ID NO:57, and a light chain variable region comprising amino acids having a sequence set forth in SEQ ID NO:58; (p) a heavy chain variable region comprising amino acids having a sequence set forth in SEQ ID NO:61, and a light chain variable region comprising amino acids having a sequence set forth in SEQ ID NO:62; (q) a heavy chain variable region comprising amino acids having a sequence set forth in SEQ ID NO:65, and a light chain variable region comprising amino acids having a sequence set forth in SEQ ID NO:66; (r) a heavy chain variable region comprising amino acids having a sequence set forth in SEQ ID NO:69, and a light chain variable region comprising amino acids having a sequence set forth in SEQ ID NO:70; (s) a heavy chain variable region comprising amino acids having a sequence set forth in SEQ ID NO:73, and a light chain variable region comprising amino acids having a sequence set forth in SEQ ID NO:74; (t) a heavy chain variable region comprising amino acids having a sequence set forth in SEQ ID NO:77, and a light chain variable region comprising amino acids having a sequence set forth in SEQ ID NO:78; (u) a heavy chain variable region comprising amino acids having a sequence set forth in SEQ ID NO:81, and a light chain variable region comprising amino acids having a sequence set forth in SEQ ID NO:82; (v) a heavy chain variable region comprising amino acids having a sequence set forth in SEQ ID NO:85, and a light chain variable region comprising amino acids having a sequence set forth in SEQ ID NO:86; (w) a heavy chain variable region comprising amino acids having a sequence set forth in SEQ ID NO:89, and a light chain variable region comprising amino acids having a sequence set forth in SEQ ID NO:90; (x) a heavy chain variable region comprising amino acids having a sequence set forth in SEQ ID NO:93, and a light chain variable region comprising amino acids having a sequence set forth in SEQ ID NO:94, (y) a heavy chain variable region comprising amino acids having a sequence set forth in SEQ ID NO:302, and a light chain variable region comprising amino acids having a sequence set forth in SEQ ID NO:303; (z) a heavy chain variable region comprising amino acids having a sequence set forth in SEQ ID NO:314, and a light chain variable region comprising amino acids having a sequence set forth in SEQ ID NO:315; (aa) a heavy chain variable region comprising amino acids having a sequence set forth in SEQ ID NO:326, and a light chain variable region comprising amino acids having a sequence set forth in SEQ ID NO:327; (ab) a heavy chain variable region comprising amino acids having a sequence set forth in SEQ ID NO:338, and a light chain variable region comprising amino acids having a sequence set forth in SEQ ID NO:339; (ac) a heavy chain variable region comprising amino acids having a sequence set forth in SEQ ID NO:350, and a light chain variable region comprising amino acids having a sequence set forth in SEQ ID NO:351; (ad) a heavy chain variable region comprising amino acids having a sequence set forth in SEQ ID NO:362, and a light chain variable region comprising amino acids having a sequence set forth in SEQ ID NO:363; (ae) a heavy chain variable region comprising amino acids having a sequence set forth in SEQ ID NO:374, and a light chain variable region comprising amino acids having a sequence set forth in SEQ ID NO:375; or (af) a heavy chain variable region comprising amino acids having a sequence set forth in SEQ ID NO:386, and a light chain variable region comprising amino acids having a sequence set forth in SEQ ID NO:387. In certain embodiments, the extracellular antigen-binding domain comprises a heavy chain variable region comprising amino acids having the sequence set forth in SEQ ID NO:53; and a light chain variable region comprising amino acids having the sequence set forth in SEQ ID NO:54. In certain embodiments, the extracellular antigen-binding domain comprises a heavy chain variable region comprising amino acids having the sequence set forth in SEQ ID NO:57; and a light chain variable region comprising amino acids having the sequence set forth in SEQ ID NO:58. In certain embodiments, the extracellular antigen-binding domain comprises a heavy chain variable region comprising amino acids having the sequence set forth in SEQ ID NO:61; and a light chain variable region comprising amino acids having the sequence set forth in SEQ ID NO:62. In another embodiment, the extracellular antigen-binding domain comprises a heavy chain variable region comprising amino acids having the sequence set forth in SEQ ID NO:65; and a light chain variable region comprising amino acids having the sequence set forth in SEQ ID NO:66. In yet another embodiment, the extracellular antigen-binding domain comprises a heavy chain variable region comprising amino acids having the sequence set forth in SEQ ID NO:69; and a light chain variable region comprising amino acids having the sequence set forth in SEQ ID NO:70.

In certain embodiments, the extracellular antigen-binding domain comprises both of said heavy and light chains, optionally with a linker sequence, for example a linker peptide, between the heavy chain variable region and the light chain variable region. For example, in certain non-limiting embodiments, the extracellular antigen-binding domain comprises (i) a heavy chain variable region comprising amino acids having the sequence set forth in SEQ ID NO:57 and (ii) a light chain variable region comprising amino acids having the sequence set forth in SEQ ID NO:58, optionally with (iii) a linker sequence, for example a linker peptide, between the heavy chain variable region and the light chain variable region. In certain embodiments, the extracellular antigen-binding domain comprises (i) a heavy chain variable region comprising amino acids having the sequence set forth in SEQ ID NO:61 and (ii) a light chain variable region comprising amino acids having the sequence set forth in SEQ ID NO:62, optionally with (iii) a linker sequence, for example a linker peptide, between the heavy chain variable region and the light chain variable region. In certain embodiments, the extracellular antigen-binding domain comprises (i) a heavy chain variable region comprising amino acids having the sequence set forth in SEQ ID NO:53 and (ii) a light chain variable region comprising amino acids having the sequence set forth in SEQ ID NO:54, optionally with (iii) a linker sequence, for example a linker peptide, between the heavy chain variable region and the light chain variable region. In certain embodiments, the extracellular antigen-binding domain comprises (i) a heavy chain variable region comprising amino acids having the sequence set forth in SEQ ID NO:61 and (ii) a light chain variable region comprising amino acids having the sequence set forth in SEQ ID NO:62, optionally with (iii) a linker sequence, for example a linker peptide, between the heavy chain variable region and the light chain variable region. In certain embodiments, the extracellular antigen-binding domain comprises (i) a heavy chain variable region comprising amino acids having the sequence set forth in SEQ ID NO:65 and (ii) a light chain variable region comprising amino acids having the sequence set forth in SEQ ID NO:66, optionally with (iii) a linker sequence, for example a linker peptide, between the heavy chain variable region and the light chain variable region. In certain embodiments, the extracellular antigen-binding domain comprises (i) a heavy chain variable region comprising amino acids having the sequence set forth in SEQ ID NO:69 and (ii) a light chain variable region comprising amino acids having the sequence set forth in SEQ ID NO:70, optionally with (iii) a linker sequence, for example a linker peptide, between the heavy chain variable region and the light chain variable region.

In certain embodiments, the extracellular antigen-binding domain comprises (a) a heavy chain variable region CDR3 comprising an amino acid sequence selected from the group consisting of SEQ ID NOS: 126, 132, 138, 144, 150, 156, 162, 168, 174, 180, 186, 192, 198, 204, 210, 216, 222, 228, 234, 240, 246, 252, 258, 264, 306, 318, 330, 342, 354, 366, 378, and 390; and (b) a light chain variable region CDR3 comprising an amino acid sequence selected from the group consisting of SEQ ID NOS: 129, 135, 141, 147, 153, 159, 165, 171, 177, 183, 189, 195, 201, 207, 213, 219, 225, 231, 237, 243, 249, 255, 261, 267, 309, 321, 333, 345, 357, 369, 381, and 393.

In certain embodiments, the heavy chain variable region CDR2 comprises an amino acid sequence selected from the group consisting of SEQ ID NOs: 125, 131, 137, 143, 149, 155, 161, 167, 173, 179, 185, 191, 197, 203, 209, 215, 221, 227, 233, 239, 245, 251, 257, 263, 305, 317, 329, 341, 353, 365, 377, and 389, and conservative modifications thereof; and (b) the light chain variable region CDR2 comprises an amino acid sequence selected from the group consisting of SEQ ID NOS: 128, 134, 140, 146, 152, 158, 164, 170, 176, 182, 188, 194, 200, 206, 212, 218, 224, 230, 236, 242, 248, 254, 260, 266, 308, 320, 332, 344, 356, 368, 380, and 392, and conservative modifications thereof.

In certain embodiments, the heavy chain variable region CDR1 comprises an amino acid sequence selected from the group consisting of SEQ ID NOs: 124, 130, 136, 142, 148, 154, 160, 166, 172, 178, 184, 190, 196, 202, 208, 214, 220, 226, 232, 238, 244, 250, 256, 262, 304, 316, 328, 340, 352, 364, 376, and 388, and conservative modifications thereof; and (b) the light chain variable region CDR1 comprises an amino acid sequence selected from the group consisting of SEQ ID NOS: 127, 133, 139, 145, 151, 157, 163, 169, 175, 181, 187, 193, 199, 205, 211, 217, 223, 229, 235, 241, 247, 253, 259, 265, 307, 319, 331, 343, 355, 367, 379, and 391, and conservative modifications thereof.

In certain embodiments, the extracellular antigen-binding domain comprises: (a) a heavy chain variable region CDR1 comprising an amino acid sequence selected from the group consisting of SEQ ID NOS: 124, 130, 136, 142, 148, 154, 160, 166, 172, 178, 184, 190, 196, 202, 208, 214, 220, 226, 232, 238, 244, 250, 256, 262, 304, 316, 328, 340, 352, 364, 376, and 388; (b) a heavy chain variable region CDR2 comprising an amino acid sequence selected from the group consisting of SEQ ID NOs: 125, 131, 137, 143, 149, 155, 161, 167, 173, 179, 185, 191, 197, 203, 209, 215, 221, 227, 233, 239, 245, 251, 257, 263, 305, 317, 329, 341, 353, 365, 377, and 389; (c) a heavy chain variable region CDR3 comprising an amino acid sequence selected from the group consisting of SEQ ID NOS: 126, 132, 138, 144, 150, 156, 162, 168, 174, 180, 186, 192, 198, 204, 210, 216, 222, 228, 234, 240, 246, 252, 258, 264, 306, 318, 330, 342, 354, 366, 378, and 390; (d) a light chain variable region CDR1 comprising an amino acid sequence selected from the group consisting of SEQ ID NOs: 127, 133, 139, 145, 151, 157, 163, 169, 175, 181, 187, 193, 199, 205, 211, 217, 223, 229, 235, 241, 247, 253, 259, 265, 307, 319, 331, 343, 355, 367, 379, and 391; (e) a light chain variable region CDR2 comprising an amino acid sequence selected from the group consisting of SEQ ID NOs: 128, 134, 140, 146, 152, 158, 164, 170, 176, 182, 188, 194, 200, 206, 212, 218, 224, 230, 236, 242, 248, 254, 260, 266, 308, 320, 332, 344, 356, 368, 380, and 392; and (f) a light chain variable region CDR3 comprising an amino acid sequence selected from the group consisting of SEQ ID NOs: 129, 135, 141, 147, 153, 159, 165, 171, 177, 183, 189, 195, 201, 207, 213, 219, 225, 231, 237, 243, 249, 255, 261, 267, 309, 321, 333, 345, 357, 369, 381, and 393.

In certain embodiments, the extracellular antigen-binding domain comprises (a) a heavy chain variable region CDR1 comprising amino acids having the sequence set forth in SEQ ID NO: 124 or conservative modifications thereof; a heavy chain variable region CDR2 comprising amino acids having the sequence set forth in SEQ ID NO: 125 or conservative modifications thereof; and a heavy chain variable region CDR3 comprising amino acids having the sequence set forth in SEQ ID NO: 126 or conservative modifications thereof; (b) a heavy chain variable region CDR1 comprising amino acids having the sequence set forth in SEQ ID NO: 130 or conservative modifications thereof; a heavy chain variable region CDR2 comprising amino acids having the sequence set forth in SEQ ID NO: 131 or conservative modifications thereof; and a heavy chain variable region CDR3 comprising amino acids having the sequence set forth in SEQ ID NO: 132 or conservative modifications thereof; (c) a heavy chain variable region CDR1 comprising amino acids having the sequence set forth in SEQ ID NO: 136 or conservative modifications thereof; a heavy chain variable region CDR2 comprising amino acids having the sequence set forth in SEQ ID NO: 137 or conservative modifications thereof; and a heavy chain variable region CDR3 comprising amino acids having the sequence set forth in SEQ ID NO: 138 or conservative modifications thereof; (d) a heavy chain variable region CDR1 comprising amino acids having the sequence set forth in SEQ ID NO: 142 or conservative modifications thereof; a heavy chain variable region CDR2 comprising amino acids having the sequence set forth in SEQ ID NO: 143 or conservative modifications thereof; and a heavy chain variable region CDR3 comprising amino acids having the sequence set forth in SEQ ID NO: 144 or conservative modifications thereof; (e) a heavy chain variable region CDR1 comprising amino acids having the sequence set forth in SEQ ID NO: 148 or conservative modifications thereof; a heavy chain variable region CDR2 comprising amino acids having the sequence set forth in SEQ ID NO: 149 or conservative modifications thereof; and a heavy chain variable region CDR3 comprising amino acids having the sequence set forth in SEQ ID NO: 150 or conservative modifications thereof; (f) a heavy chain variable region CDR1 comprising amino acids having the sequence set forth in SEQ ID NO: 154 or conservative modifications thereof; a heavy chain variable region CDR2 comprising amino acids having the sequence set forth in SEQ ID NO: 155 or conservative modifications thereof; and a heavy chain variable region CDR3 comprising amino acids having the sequence set forth in SEQ ID NO: 156 or conservative modifications thereof; (g) a heavy chain variable region CDR1 comprising amino acids having the sequence set forth in SEQ ID NO: 160 or conservative modifications thereof; a heavy chain variable region CDR2 comprising amino acids having the sequence set forth in SEQ ID NO: 161 or conservative modifications thereof; and a heavy chain variable region CDR3 comprising amino acids having the sequence set forth in SEQ ID NO: 162 or conservative modifications thereof; (h) a heavy chain variable region CDR1 comprising amino acids having the sequence set forth in SEQ ID NO: 166 or conservative modifications thereof; a heavy chain variable region CDR2 comprising amino acids having the sequence set forth in SEQ ID NO: 167 or conservative modifications thereof; and a heavy chain variable region CDR3 comprising amino acids having the sequence set forth in SEQ ID NO: 168 or conservative modifications thereof; (i) a heavy chain variable region CDR1 comprising amino acids having the sequence set forth in SEQ ID NO: 172 or conservative modifications thereof; a heavy chain variable region CDR2 comprising amino acids having the sequence set forth in SEQ ID NO: 173 or conservative modifications thereof; and a heavy chain variable region CDR3 comprising amino acids having the sequence set forth in SEQ ID NO: 174 or conservative modifications thereof; (j) a heavy chain variable region CDR1 comprising amino acids having the sequence set forth in SEQ ID NO: 178 or conservative modifications thereof; a heavy chain variable region CDR2 comprising amino acids having the sequence set forth in SEQ ID NO: 179 or conservative modifications thereof; and a heavy chain variable region CDR3 comprising amino acids having the sequence set forth in SEQ ID NO: 180 or conservative modifications thereof; (k) a heavy chain variable region CDR1 comprising amino acids having the sequence set forth in SEQ ID NO: 184 or conservative modifications thereof; a heavy chain variable region CDR2 comprising amino acids having the sequence set forth in SEQ ID NO: 185 or conservative modifications thereof; and a heavy chain variable region CDR3 comprising amino acids having the sequence set forth in SEQ ID NO: 186 or conservative modifications thereof; (l) a heavy chain variable region CDR1 comprising amino acids having the sequence set forth in SEQ ID NO: 190 or conservative modifications thereof; a heavy chain variable region CDR2 comprising amino acids having the sequence set forth in SEQ ID NO: 191 or conservative modifications thereof; and a heavy chain variable region CDR3 comprising amino acids having the sequence set forth in SEQ ID NO: 192 or conservative modifications thereof; (m) a heavy chain variable region CDR1 comprising amino acids having the sequence set forth in SEQ ID NO: 196 or conservative modifications thereof; a heavy chain variable region CDR2 comprising amino acids having the sequence set forth in SEQ ID NO: 197 or conservative modifications thereof; and a heavy chain variable region CDR3 comprising amino acids having the sequence set forth in SEQ ID NO: 198 or conservative modifications thereof; (n) a heavy chain variable region CDR1 comprising amino acids having the sequence set forth in SEQ ID NO: 202 or conservative modifications thereof; a heavy chain variable region CDR2 comprising amino acids having the sequence set forth in SEQ ID NO: 203 or conservative modifications thereof; and a heavy chain variable region CDR3 comprising amino acids having the sequence set forth in SEQ ID NO: 204 or conservative modifications thereof; (o) a heavy chain variable region CDR1 comprising amino acids having the sequence set forth in SEQ ID NO: 208 or conservative modifications thereof; a heavy chain variable region CDR2 comprising amino acids having the sequence set forth in SEQ ID NO: 209 or conservative modifications thereof; and a heavy chain variable region CDR3 comprising amino acids having the sequence set forth in SEQ ID NO: 210 or conservative modifications thereof; (p) a heavy chain variable region CDR1 comprising amino acids having the sequence set forth in SEQ ID NO: 214 or conservative modifications thereof; a heavy chain variable region CDR2 comprising amino acids having the sequence set forth in SEQ ID NO: 215 or conservative modifications thereof; and a heavy chain variable region CDR3 comprising amino acids having the sequence set forth in SEQ ID NO: 216 or conservative modifications thereof; (q) a heavy chain variable region CDR1 comprising amino acids having the sequence set forth in SEQ ID NO: 220 or conservative modifications thereof; a heavy chain variable region CDR2 comprising amino acids having the sequence set forth in SEQ ID NO: 221 or conservative modifications thereof; and a heavy chain variable region CDR3 comprising amino acids having the sequence set forth in SEQ ID NO: 222 or conservative modifications thereof; (r) a heavy chain variable region CDR1 comprising amino acids having the sequence set forth in SEQ ID NO: 226 or conservative modifications thereof; a heavy chain variable region CDR2 comprising amino acids having the sequence set forth in SEQ ID NO: 227 or conservative modifications thereof; and a heavy chain variable region CDR3 comprising amino acids having the sequence set forth in SEQ ID NO: 228 or conservative modifications thereof; (s) a heavy chain variable region CDR1 comprising amino acids having the sequence set forth in SEQ ID NO: 232 or conservative modifications thereof; a heavy chain variable region CDR2 comprising amino acids having the sequence set forth in SEQ ID NO: 233 or conservative modifications thereof; and a heavy chain variable region CDR3 comprising amino acids having the sequence set forth in SEQ ID NO: 234 or conservative modifications thereof; (t) a heavy chain variable region CDR1 comprising amino acids having the sequence set forth in SEQ ID NO: 238 or conservative modifications thereof; a heavy chain variable region CDR2 comprising amino acids having the sequence set forth in SEQ ID NO: 239 or conservative modifications thereof; and a heavy chain variable region CDR3 comprising amino acids having the sequence set forth in SEQ ID NO: 240 or conservative modifications thereof; (u) a heavy chain variable region CDR1 comprising amino acids having the sequence set forth in SEQ ID NO: 244 or conservative modifications thereof; a heavy chain variable region CDR2 comprising amino acids having the sequence set forth in SEQ ID NO: 245 or conservative modifications thereof; and a heavy chain variable region CDR3 comprising amino acids having the sequence set forth in SEQ ID NO: 246 or conservative modifications thereof; (v) a heavy chain variable region CDR1 comprising amino acids having the sequence set forth in SEQ ID NO: 250 or conservative modifications thereof; a heavy chain variable region CDR2 comprising amino acids having the sequence set forth in SEQ ID NO: 251 or conservative modifications thereof; and a heavy chain variable region CDR3 comprising amino acids having the sequence set forth in SEQ ID NO: 252 or conservative modifications thereof; (w) a heavy chain variable region CDR1 comprising amino acids having the sequence set forth in SEQ ID NO: 256 or conservative modifications thereof; a heavy chain variable region CDR2 comprising amino acids having the sequence set forth in SEQ ID NO: 257 or conservative modifications thereof; and a heavy chain variable region CDR3 comprising amino acids having the sequence set forth in SEQ ID NO: 258 or conservative modifications thereof; (x) a heavy chain variable region CDR1 comprising amino acids having the sequence set forth in SEQ ID NO: 262 or conservative modifications thereof; a heavy chain variable region CDR2 comprising amino acids having the sequence set forth in SEQ ID NO: 263 or conservative modifications thereof; and a heavy chain variable region CDR3 comprising amino acids having the sequence set forth in SEQ ID NO: 264 or conservative modifications thereof; (y) a heavy chain variable region CDR1 comprising amino acids having the sequence set forth in SEQ ID NO: 304 or conservative modifications thereof; a heavy chain variable region CDR2 comprising amino acids having the sequence set forth in SEQ ID NO: 305 or conservative modifications thereof; and a heavy chain variable region CDR3 comprising amino acids having the sequence set forth in SEQ ID NO: 306 or conservative modifications thereof; (z) a heavy chain variable region CDR1 comprising amino acids having the sequence set forth in SEQ ID NO: 316 or conservative modifications thereof; a heavy chain variable region CDR2 comprising amino acids having the sequence set forth in SEQ ID NO: 317 or conservative modifications thereof; and a heavy chain variable region CDR3 comprising amino acids having the sequence set forth in SEQ ID NO: 318 or conservative modifications thereof; (aa) a heavy chain variable region CDR1 comprising amino acids having the sequence set forth in SEQ ID NO: 328 or conservative modifications thereof; a heavy chain variable region CDR2 comprising amino acids having the sequence set forth in SEQ ID NO: 329 or conservative modifications thereof; and a heavy chain variable region CDR3 comprising amino acids having the sequence set forth in SEQ ID NO: 330 or conservative modifications thereof; (ab) a heavy chain variable region CDR1 comprising amino acids having the sequence set forth in SEQ ID NO: 340 or conservative modifications thereof; a heavy chain variable region CDR2 comprising amino acids having the sequence set forth in SEQ ID NO: 341 or conservative modifications thereof; and a heavy chain variable region CDR3 comprising amino acids having the sequence set forth in SEQ ID NO: 342 or conservative modifications thereof; (ac) a heavy chain variable region CDR1 comprising amino acids having the sequence set forth in SEQ ID NO: 352 or conservative modifications thereof; a heavy chain variable region CDR2 comprising amino acids having the sequence set forth in SEQ ID NO: 353 or conservative modifications thereof; and a heavy chain variable region CDR3 comprising amino acids having the sequence set forth in SEQ ID NO: 354 or conservative modifications thereof; (ad) a heavy chain variable region CDR1 comprising amino acids having the sequence set forth in SEQ ID NO: 364 or conservative modifications thereof; a heavy chain variable region CDR2 comprising amino acids having the sequence set forth in SEQ ID NO: 365 or conservative modifications thereof; and a heavy chain variable region CDR3 comprising amino acids having the sequence set forth in SEQ ID NO: 366 or conservative modifications thereof; (ae) a heavy chain variable region CDR1 comprising amino acids having the sequence set forth in SEQ ID NO: 376 or conservative modifications thereof; a heavy chain variable region CDR2 comprising amino acids having the sequence set forth in SEQ ID NO: 377 or conservative modifications thereof; and a heavy chain variable region CDR3 comprising amino acids having the sequence set forth in SEQ ID NO: 378 or conservative modifications thereof; or (af) a heavy chain variable region CDR1 comprising amino acids having the sequence set forth in SEQ ID NO: 388 or conservative modifications thereof; a heavy chain variable region CDR2 comprising amino acids having the sequence set forth in SEQ ID NO: 389 or conservative modifications thereof; and a heavy chain variable region CDR3 comprising amino acids having the sequence set forth in SEQ ID NO: 390 or conservative modifications thereof. In certain embodiments, the extracellular antigen-binding domain comprises: a heavy chain variable region CDR1 comprising amino acids having the sequence set forth in SEQ ID NO: 202; a heavy chain variable region CDR2 comprising amino acids having the sequence set forth in SEQ ID NO: 203; and a heavy chain variable region CDR3 comprising amino acids having the sequence set forth in SEQ ID NO: 204. In certain embodiments, the extracellular antigen-binding domain comprises: a heavy chain variable region CDR1 comprising amino acids having the sequence set forth in SEQ ID NO: 208; a heavy chain variable region CDR2 comprising amino acids having the sequence set forth in SEQ ID NO: 209; and a heavy chain variable region CDR3 comprising amino acids having the sequence set forth in SEQ ID NO: 210. In another non-limiting embodiment, the extracellular antigen-binding domain comprises: a heavy chain variable region CDR1 comprising amino acids having the sequence set forth in SEQ ID NO: 214; a heavy chain variable region CDR2 comprising amino acids having the sequence set forth in SEQ ID NO: 215; and a heavy chain variable region CDR3 comprising amino acids having the sequence set forth in SEQ ID NO: 216. In yet another non-limiting embodiment, the extracellular antigen-binding domain comprises: a heavy chain variable region CDR1 comprising amino acids having the sequence set forth in SEQ ID NO: 220; a heavy chain variable region CDR2 comprising amino acids having the sequence set forth in SEQ ID NO: 221; and a heavy chain variable region CDR3 comprising amino acids having the sequence set forth in SEQ ID NO: 222. In another embodiment, the extracellular antigen-binding domain comprises: a heavy chain variable region CDR1 comprising amino acids having the sequence set forth in SEQ ID NO: 226; a heavy chain variable region CDR2 comprising amino acids having the sequence set forth in SEQ ID NO: 227; and a heavy chain variable region CDR3 comprising amino acids having the sequence set forth in SEQ ID NO: 228.

In certain embodiments, the extracellular antigen-binding domain comprises: (a) a light chain variable region CDR1 comprising amino acids having the sequence set forth in SEQ ID NO: 127 or conservative modifications thereof; a light chain variable region CDR2 comprising amino acids having the sequence set forth in SEQ ID NO:129 or conservative modifications thereof; and a light chain variable region CDR3 comprising amino acids having the sequence set forth in SEQ ID NO: 130 or conservative modifications thereof; (b) a light chain variable region CDR1 comprising amino acids having the sequence set forth in SEQ ID NO: 133 or conservative modifications thereof; a light chain variable region CDR2 comprising amino acids having the sequence set forth in SEQ ID NO:134 or conservative modifications thereof; and a light chain variable region CDR3 comprising SEQ ID NO: 135 or conservative modifications thereof; (c) a light chain variable region CDR1 comprising amino acids having the sequence set forth in SEQ ID NO: 139 or conservative modifications thereof; a light chain variable region CDR2 comprising amino acids having the sequence set forth in SEQ ID NO:140 or conservative modifications thereof; and a light chain variable region CDR3 comprising amino acids having the sequence set forth in SEQ ID NO: 141 or conservative modifications thereof; (d) a light chain variable region CDR1 comprising amino acids having the sequence set forth in SEQ ID NO: 145 or conservative modifications thereof; a light chain variable region CDR2 comprising SEQ ID NO:146 or conservative modifications thereof; and a light chain variable region CDR3 comprising amino acids having the sequence set forth in SEQ ID NO: 147 or conservative modifications thereof; (e) a light chain variable region CDR1 comprising amino acids having the sequence set forth in SEQ ID NO: 151 or conservative modifications thereof; a light chain variable region CDR2 comprising amino acids having the sequence set forth in SEQ ID NO:152 or conservative modifications thereof; and a light chain variable region CDR3 comprising amino acids having the sequence set forth in SEQ ID NO: 153 or conservative modifications thereof; (f) a light chain variable region CDR1 comprising amino acids having the sequence set forth in SEQ ID NO: 157 or conservative modifications thereof; a light chain variable region CDR2 comprising amino acids having the sequence set forth in SEQ ID NO:158 or conservative modifications thereof; and a light chain variable region CDR3 comprising amino acids having the sequence set forth in SEQ ID NO: 159 or conservative modifications thereof; (g) a light chain variable region CDR1 comprising amino acids having the sequence set forth in SEQ ID NO: 163 or conservative modifications thereof; a light chain variable region CDR2 comprising amino acids having the sequence set forth in SEQ ID NO:164 or conservative modifications thereof; and a light chain variable region CDR3 comprising amino acids having the sequence set forth in SEQ ID NO: 165 or conservative modifications thereof; (h) a light chain variable region CDR1 comprising amino acids having the sequence set forth in SEQ ID NO: 169 or conservative modifications thereof; a light chain variable region CDR2 comprising amino acids having the sequence set forth in SEQ ID NO:170 or conservative modifications thereof; and a light chain variable region CDR3 comprising SEQ ID NO: 171 or conservative modifications thereof; (i) a light chain variable region CDR1 comprising amino acids having the sequence set forth in SEQ ID NO: 175 or conservative modifications thereof; a light chain variable region CDR2 comprising amino acids having the sequence set forth in SEQ ID NO:176 or conservative modifications thereof; and a light chain variable region CDR3 comprising amino acids having the sequence set forth in SEQ ID NO: 177 or conservative modifications thereof; (j) a light chain variable region CDR1 comprising amino acids having the sequence set forth in SEQ ID NO: 181 or conservative modifications thereof; a light chain variable region CDR2 comprising amino acids having the sequence set forth in SEQ ID NO:182 or conservative modifications thereof; and a light chain variable region CDR3 comprising amino acids having the sequence set forth in SEQ ID NO: 183 or conservative modifications thereof; (k) a light chain variable region CDR1 comprising amino acids having the sequence set forth in SEQ ID NO: 187 or conservative modifications thereof; a light chain variable region CDR2 comprising amino acids having the sequence set forth in SEQ ID NO:188 or conservative modifications thereof; and a light chain variable region CDR3 comprising amino acids having the sequence set forth in SEQ ID NO: 189 or conservative modifications thereof; (l) a light chain variable region CDR1 comprising amino acids having the sequence set forth in SEQ ID NO: 193 or conservative modifications thereof; a light chain variable region CDR2 comprising amino acids having the sequence set forth in SEQ ID NO:194 or conservative modifications thereof; and a light chain variable region CDR3 comprising amino acids having the sequence set forth in SEQ ID NO: 195 or conservative modifications thereof; (m) a light chain variable region CDR1 comprising amino acids having the sequence set forth in SEQ ID NO: 199 or conservative modifications thereof; a light chain variable region CDR2 comprising amino acids having the sequence set forth in SEQ ID NO:200 or conservative modifications thereof; and a light chain variable region CDR3 comprising amino acids having the sequence set forth in SEQ ID NO: 201 or conservative modifications thereof; (n) a light chain variable region CDR1 comprising amino acids having the sequence set forth in SEQ ID NO: 205 or conservative modifications thereof; a light chain variable region CDR2 comprising amino acids having the sequence set forth in SEQ ID NO:206 or conservative modifications thereof; and a light chain variable region CDR3 comprising amino acids having the sequence set forth in SEQ ID NO: 207 or conservative modifications thereof; (o) a light chain variable region CDR1 comprising amino acids having the sequence set forth in SEQ ID NO: 211 or conservative modifications thereof; a light chain variable region CDR2 comprising amino acids having the sequence set forth in SEQ ID NO:212 or conservative modifications thereof; and a light chain variable region CDR3 comprising amino acids having the sequence set forth in SEQ ID NO: 213 or conservative modifications thereof; (p) a light chain variable region CDR1 comprising amino acids having the sequence set forth in SEQ ID NO: 217 or conservative modifications thereof; a light chain variable region CDR2 comprising amino acids having the sequence set forth in SEQ ID NO:218 or conservative modifications thereof; and a light chain variable region CDR3 comprising amino acids having the sequence set forth in SEQ ID NO: 219 or conservative modifications thereof; (q) a light chain variable region CDR1 comprising amino acids having the sequence set forth in SEQ ID NO: 223 or conservative modifications thereof; a light chain variable region CDR2 comprising amino acids having the sequence set forth in SEQ ID NO:224 or conservative modifications thereof; and a light chain variable region CDR3 comprising amino acids having the sequence set forth in SEQ ID NO: 225 or conservative modifications thereof; (r) a light chain variable region CDR1 comprising amino acids having the sequence set forth in SEQ ID NO: 229 or conservative modifications thereof; a light chain variable region CDR2 comprising amino acids having the sequence set forth in SEQ ID NO:230 or conservative modifications thereof; and a light chain variable region CDR3 comprising amino acids having the sequence set forth in SEQ ID NO: 231 or conservative modifications thereof; (s) a light chain variable region CDR1 comprising amino acids having the sequence set forth in SEQ ID NO: 235 or conservative modifications thereof; a light chain variable region CDR2 comprising amino acids having the sequence set forth in SEQ ID NO:236 or conservative modifications thereof; and a light chain variable region CDR3 comprising amino acids having the sequence set forth in SEQ ID NO: 237 or conservative modifications thereof; (t) a light chain variable region CDR1 comprising amino acids having the sequence set forth in SEQ ID NO: 241 or conservative modifications thereof; a light chain variable region CDR2 comprising amino acids having the sequence set forth in SEQ ID NO:242 or conservative modifications thereof; and a light chain variable region CDR3 comprising amino acids having the sequence set forth in SEQ ID NO: 243 or conservative modifications thereof; (u) a light chain variable region CDR1 comprising amino acids having the sequence set forth in SEQ ID NO: 247 or conservative modifications thereof; a light chain variable region CDR2 comprising amino acids having the sequence set forth in SEQ ID NO:248 or conservative modifications thereof; and a light chain variable region CDR3 comprising amino acids having the sequence set forth in SEQ ID NO: 249 or conservative modifications thereof; (v) a light chain variable region CDR1 comprising amino acids having the sequence set forth in SEQ ID NO: 253 or conservative modifications thereof; a light chain variable region CDR2 comprising amino acids having the sequence set forth in SEQ ID NO:254 or conservative modifications thereof; and a light chain variable region CDR3 comprising amino acids having the sequence set forth in SEQ ID NO: 255 or conservative modifications thereof; (w) a light chain variable region CDR1 comprising amino acids having the sequence set forth in SEQ ID NO: 259 or conservative modifications thereof; a light chain variable region CDR2 comprising amino acids having the sequence set forth in SEQ ID NO:260 or conservative modifications thereof; and a light chain variable region CDR3 comprising amino acids having the sequence set forth in SEQ ID NO: 261 or conservative modifications thereof; (x) a light chain variable region CDR1 comprising amino acids having the sequence set forth in SEQ ID NO: 265 or conservative modifications thereof; a light chain variable region CDR2 comprising amino acids having the sequence set forth in SEQ ID NO:266 or conservative modifications thereof; and a light chain variable region CDR3 comprising amino acids having the sequence set forth in SEQ ID NO: 267 or conservative modifications thereof; (y) a light chain variable region CDR1 comprising amino acids having the sequence set forth in SEQ ID NO: 307 or conservative modifications thereof; a light chain variable region CDR2 comprising amino acids having the sequence set forth in SEQ ID NO: 308 or conservative modifications thereof; and a light chain variable region CDR3 comprising amino acids having the sequence set forth in SEQ ID NO: 309 or conservative modifications thereof; (z) a light chain variable region CDR1 comprising amino acids having the sequence set forth in SEQ ID NO: 319 or conservative modifications thereof; a light chain variable region CDR2 comprising amino acids having the sequence set forth in SEQ ID NO:320 or conservative modifications thereof; and a light chain variable region CDR3 comprising amino acids having the sequence set forth in SEQ ID NO: 321 or conservative modifications thereof; (aa) a light chain variable region CDR1 comprising amino acids having the sequence set forth in SEQ ID NO: 331 or conservative modifications thereof; a light chain variable region CDR2 comprising amino acids having the sequence set forth in SEQ ID NO: 332 or conservative modifications thereof; and a light chain variable region CDR3 comprising amino acids having the sequence set forth in SEQ ID NO: 333 or conservative modifications thereof; (ab) a light chain variable region CDR1 comprising amino acids having the sequence set forth in SEQ ID NO: 343 or conservative modifications thereof; a light chain variable region CDR2 comprising amino acids having the sequence set forth in SEQ ID NO:344 or conservative modifications thereof; and a light chain variable region CDR3 comprising amino acids having the sequence set forth in SEQ ID NO: 345 or conservative modifications thereof; (ac) a light chain variable region CDR1 comprising amino acids having the sequence set forth in SEQ ID NO: 355 or conservative modifications thereof; a light chain variable region CDR2 comprising amino acids having the sequence set forth in SEQ ID NO: 356 or conservative modifications thereof; and a light chain variable region CDR3 comprising amino acids having the sequence set forth in SEQ ID NO: 357 or conservative modifications thereof; (ad) a light chain variable region CDR1 comprising amino acids having the sequence set forth in SEQ ID NO: 367 or conservative modifications thereof; a light chain variable region CDR2 comprising amino acids having the sequence set forth in SEQ ID NO: 368 or conservative modifications thereof; and a light chain variable region CDR3 comprising amino acids having the sequence set forth in SEQ ID NO: 369 or conservative modifications thereof; (ae) a light chain variable region CDR1 comprising amino acids having the sequence set forth in SEQ ID NO: 379 or conservative modifications thereof; a light chain variable region CDR2 comprising amino acids having the sequence set forth in SEQ ID NO: 380 or conservative modifications thereof; and a light chain variable region CDR3 comprising amino acids having the sequence set forth in SEQ ID NO: 381 or conservative modifications thereof; or (af) a light chain variable region CDR1 comprising amino acids having the sequence set forth in SEQ ID NO: 391 or conservative modifications thereof; a light chain variable region CDR2 comprising amino acids having the sequence set forth in SEQ ID NO: 392 or conservative modifications thereof; and a light chain variable region CDR3 comprising amino acids having the sequence set forth in SEQ ID NO: 393 or conservative modifications thereof. In certain embodiments, the extracellular antigen-binding domain comprises: a light chain variable region CDR1 comprising amino acids having the sequence set forth in SEQ ID NO: 205; a light chain variable region CDR2 comprising amino acids having the sequence set forth in SEQ ID NO:206; and a light chain variable region CDR3 comprising amino acids having the sequence set forth in SEQ ID NO: 207. In certain embodiments, the extracellular antigen-binding domain comprises: a light chain variable region CDR1 comprising amino acids having the sequence set forth in SEQ ID NO: 211; a light chain variable region CDR2 comprising amino acids having the sequence set forth in SEQ ID NO:212; and a light chain variable region CDR3 comprising amino acids having the sequence set forth in SEQ ID NO: 213. In certain embodiments, the extracellular antigen-binding domain comprises: a light chain variable region CDR1 comprising amino acids having the sequence set forth in SEQ ID NO: 217; a light chain variable region CDR2 comprising amino acids having the sequence set forth in SEQ ID NO:218; and a light chain variable region CDR3 comprising amino acids having the sequence set forth in SEQ ID NO: 219. In another non-limiting embodiment, the extracellular antigen-binding domain comprises: a light chain variable region CDR1 comprising amino acids having the sequence set forth in SEQ ID NO: 223; a light chain variable region CDR2 comprising amino acids having the sequence set forth in SEQ ID NO:224; and a light chain variable region CDR3 comprising amino acids having the sequence set forth in SEQ ID NO: 225. In yet another non-limiting embodiment, the extracellular antigen-binding domain comprises: a light chain variable region CDR1 comprising amino acids having the sequence set forth in SEQ ID NO: 229; a light chain variable region CDR2 comprising amino acids having the sequence set forth in SEQ ID NO:230; and a light chain variable region CDR3 comprising amino acids having the sequence set forth in SEQ ID NO: 231.

In certain embodiments, the extracellular antigen-binding domain comprises: (a) a heavy chain variable region CDR1 comprising amino acids having the sequence set forth in SEQ ID NO: 124; a heavy chain variable region CDR2 comprising amino acids having the sequence set forth in SEQ ID NO: 125; a heavy chain variable region CDR3 comprising amino acids having the sequence set forth in SEQ ID NO: 126; a light chain variable region CDR1 comprising amino acids having the sequence set forth in SEQ ID NO: 127; a light chain variable region CDR2 comprising amino acids having the sequence set forth in SEQ ID NO:128; and a light chain variable region CDR3 comprising amino acids having the sequence set forth in SEQ ID NO: 129; (b) a heavy chain variable region CDR1 comprising amino acids having the sequence set forth in SEQ ID NO: 130; a heavy chain variable region CDR2 comprising amino acids having the sequence set forth in SEQ ID NO: 131; a heavy chain variable region CDR3 comprising amino acids having the sequence set forth in SEQ ID NO: 132; a light chain variable region CDR1 comprising amino acids having the sequence set forth in SEQ ID NO: 133; a light chain variable region CDR2 comprising amino acids having the sequence set forth in SEQ ID NO:134; and a light chain variable region CDR3 comprising amino acids having the sequence set forth in SEQ ID NO: 135; (c) a heavy chain variable region CDR1 comprising amino acids having the sequence set forth in SEQ ID NO: 136; a heavy chain variable region CDR2 comprising amino acids having the sequence set forth in SEQ ID NO: 137; a heavy chain variable region CDR3 comprising amino acids having the sequence set forth in SEQ ID NO: 138; a light chain variable region CDR1 comprising amino acids having the sequence set forth in SEQ ID NO: 139; a light chain variable region CDR2 comprising amino acids having the sequence set forth in SEQ ID NO:140; and a light chain variable region CDR3 comprising amino acids having the sequence set forth in SEQ ID NO: 141; (d) a heavy chain variable region CDR1 comprising amino acids having the sequence set forth in SEQ ID NO: 142; a heavy chain variable region CDR2 comprising amino acids having the sequence set forth in SEQ ID NO: 143; a heavy chain variable region CDR3 comprising amino acids having the sequence set forth in SEQ ID NO: 144; a light chain variable region CDR1 comprising amino acids having the sequence set forth in SEQ ID NO: 145; a light chain variable region CDR2 comprising amino acids having the sequence set forth in SEQ ID NO:146; and a light chain variable region CDR3 comprising amino acids having the sequence set forth in SEQ ID NO: 147; (e) a heavy chain variable region CDR1 comprising amino acids having the sequence set forth in SEQ ID NO: 148; a heavy chain variable region CDR2 comprising amino acids having the sequence set forth in SEQ ID NO: 149; a heavy chain variable region CDR3 comprising amino acids having the sequence set forth in SEQ ID NO: 150; a light chain variable region CDR1 comprising amino acids having the sequence set forth in SEQ ID NO: 151; a light chain variable region CDR2 comprising amino acids having the sequence set forth in SEQ ID NO:152; and a light chain variable region CDR3 comprising amino acids having the sequence set forth in SEQ ID NO: 153; (f) a heavy chain variable region CDR1 comprising amino acids having the sequence set forth in SEQ ID NO: 154; a heavy chain variable region CDR2 comprising amino acids having the sequence set forth in SEQ ID NO: 155; a heavy chain variable region CDR3 comprising amino acids having the sequence set forth in SEQ ID NO: 156; a light chain variable region CDR1 comprising amino acids having the sequence set forth in SEQ ID NO: 157; a light chain variable region CDR2 comprising amino acids having the sequence set forth in SEQ ID NO:158; and a light chain variable region CDR3 comprising amino acids having the sequence set forth in SEQ ID NO: 159; (g) a heavy chain variable region CDR1 comprising amino acids having the sequence set forth in SEQ ID NO: 160; a heavy chain variable region CDR2 comprising amino acids having the sequence set forth in SEQ ID NO: 161; a heavy chain variable region CDR3 comprising amino acids having the sequence set forth in SEQ ID NO: 162; a light chain variable region CDR1 comprising amino acids having the sequence set forth in SEQ ID NO: 163; a light chain variable region CDR2 comprising amino acids having the sequence set forth in SEQ ID NO:164; and a light chain variable region CDR3 comprising amino acids having the sequence set forth in SEQ ID NO: 165; (h) a heavy chain variable region CDR1 comprising amino acids having the sequence set forth in SEQ ID NO: 166; a heavy chain variable region CDR2 comprising amino acids having the sequence set forth in SEQ ID NO: 167; a heavy chain variable region CDR3 comprising amino acids having the sequence set forth in SEQ ID NO: 168; a light chain variable region CDR1 comprising amino acids having the sequence set forth in SEQ ID NO: 169; a light chain variable region CDR2 comprising amino acids having the sequence set forth in SEQ ID NO:170; and a light chain variable region CDR3 comprising amino acids having the sequence set forth in SEQ ID NO: 171; (i) a heavy chain variable region CDR1 comprising amino acids having the sequence set forth in SEQ ID NO: 172; a heavy chain variable region CDR2 comprising amino acids having the sequence set forth in SEQ ID NO: 173; a heavy chain variable region CDR3 comprising amino acids having the sequence set forth in SEQ ID NO: 174; a light chain variable region CDR1 comprising amino acids having the sequence set forth in SEQ ID NO: 175; a light chain variable region CDR2 comprising amino acids having the sequence set forth in SEQ ID NO:176; and a light chain variable region CDR3 comprising amino acids having the sequence set forth in SEQ ID NO: 177; (j) a heavy chain variable region CDR1 comprising amino acids having the sequence set forth in SEQ ID NO: 178; a heavy chain variable region CDR2 comprising amino acids having the sequence set forth in SEQ ID NO: 179; a heavy chain variable region CDR3 comprising amino acids having the sequence set forth in SEQ ID NO: 180; a light chain variable region CDR1 comprising amino acids having the sequence set forth in SEQ ID NO: 181; a light chain variable region CDR2 comprising amino acids having the sequence set forth in SEQ ID NO:182; and a light chain variable region CDR3 comprising amino acids having the sequence set forth in SEQ ID NO: 183; (k) a heavy chain variable region CDR1 comprising amino acids having the sequence set forth in SEQ ID NO: 184; a heavy chain variable region CDR2 comprising amino acids having the sequence set forth in SEQ ID NO: 185; a heavy chain variable region CDR3 comprising amino acids having the sequence set forth in SEQ ID NO: 186; a light chain variable region CDR1 comprising amino acids having the sequence set forth in SEQ ID NO: 187; a light chain variable region CDR2 comprising amino acids having the sequence set forth in SEQ ID NO:188; and a light chain variable region CDR3 comprising amino acids having the sequence set forth in SEQ ID NO: 189; (l) a heavy chain variable region CDR1 comprising amino acids having the sequence set forth in SEQ ID NO: 190; a heavy chain variable region CDR2 comprising amino acids having the sequence set forth in SEQ ID NO: 191; a heavy chain variable region CDR3 comprising amino acids having the sequence set forth in SEQ ID NO: 192; a light chain variable region CDR1 comprising amino acids having the sequence set forth in SEQ ID NO: 193; a light chain variable region CDR2 comprising amino acids having the sequence set forth in SEQ ID NO:194; and a light chain variable region CDR3 comprising amino acids having the sequence set forth in SEQ ID NO: 195; (m) a heavy chain variable region CDR1 comprising amino acids having the sequence set forth in SEQ ID NO: 196; a heavy chain variable region CDR2 comprising amino acids having the sequence set forth in SEQ ID NO: 197; a heavy chain variable region CDR3 comprising amino acids having the sequence set forth in SEQ ID NO: 198; a light chain variable region CDR1 comprising amino acids having the sequence set forth in SEQ ID NO: 199; a light chain variable region CDR2 comprising amino acids having the sequence set forth in SEQ ID NO:200; and a light chain variable region CDR3 comprising amino acids having the sequence set forth in SEQ ID NO: 201; (n) a heavy chain variable region CDR1 comprising amino acids having the sequence set forth in SEQ ID NO: 202; a heavy chain variable region CDR2 comprising amino acids having the sequence set forth in SEQ ID NO: 203; a heavy chain variable region CDR3 comprising amino acids having the sequence set forth in SEQ ID NO: 204; a light chain variable region CDR1 comprising amino acids having the sequence set forth in SEQ ID NO: 205; a light chain variable region CDR2 comprising amino acids having the sequence set forth in SEQ ID NO:206; and a light chain variable region CDR3 comprising amino acids having the sequence set forth in SEQ ID NO: 207; (o) a heavy chain variable region CDR1 comprising amino acids having the sequence set forth in SEQ ID NO: 208; a heavy chain variable region CDR2 comprising amino acids having the sequence set forth in SEQ ID NO: 209; a heavy chain variable region CDR3 comprising amino acids having the sequence set forth in SEQ ID NO: 210; a light chain variable region CDR1 comprising amino acids having the sequence set forth in SEQ ID NO: 211; a light chain variable region CDR2 comprising amino acids having the sequence set forth in SEQ ID NO:212; and a light chain variable region CDR3 comprising amino acids having the sequence set forth in SEQ ID NO: 213; (p) a heavy chain variable region CDR1 comprising amino acids having the sequence set forth in SEQ ID NO: 214; a heavy chain variable region CDR2 comprising amino acids having the sequence set forth in SEQ ID NO: 215; a heavy chain variable region CDR3 comprising amino acids having the sequence set forth in SEQ ID NO: 216; a light chain variable region CDR1 comprising amino acids having the sequence set forth in SEQ ID NO: 217; a light chain variable region CDR2 comprising amino acids having the sequence set forth in SEQ ID NO:218; and a light chain variable region CDR3 comprising amino acids having the sequence set forth in SEQ ID NO: 219; (q) a heavy chain variable region CDR1 comprising amino acids having the sequence set forth in SEQ ID NO: 220; a heavy chain variable region CDR2 comprising amino acids having the sequence set forth in SEQ ID NO: 221; a heavy chain variable region CDR3 comprising amino acids having the sequence set forth in SEQ ID NO: 222; a light chain variable region CDR1 comprising amino acids having the sequence set forth in SEQ ID NO: 223; a light chain variable region CDR2 comprising amino acids having the sequence set forth in SEQ ID NO:224; and a light chain variable region CDR3 comprising amino acids having the sequence set forth in SEQ ID NO: 225; (r) a heavy chain variable region CDR1 comprising amino acids having the sequence set forth in SEQ ID NO: 226; a heavy chain variable region CDR2 comprising amino acids having the sequence set forth in SEQ ID NO: 227; a heavy chain variable region CDR3 comprising amino acids having the sequence set forth in SEQ ID NO: 228; a light chain variable region CDR1 comprising amino acids having the sequence set forth in SEQ ID NO: 229; a light chain variable region CDR2 comprising amino acids having the sequence set forth in SEQ ID NO:230; and a light chain variable region CDR3 comprising amino acids having the sequence set forth in SEQ ID NO: 231; (s) a heavy chain variable region CDR1 comprising amino acids having the sequence set forth in SEQ ID NO: 232; a heavy chain variable region CDR2 comprising amino acids having the sequence set forth in SEQ ID NO: 233; a heavy chain variable region CDR3 comprising amino acids having the sequence set forth in SEQ ID NO: 234; a light chain variable region CDR1 comprising amino acids having the sequence set forth in SEQ ID NO: 235; a light chain variable region CDR2 comprising amino acids having the sequence set forth in SEQ ID NO:236; and a light chain variable region CDR3 comprising amino acids having the sequence set forth in SEQ ID NO: 237; (t) a heavy chain variable region CDR1 comprising amino acids having the sequence set forth in SEQ ID NO: 238; a heavy chain variable region CDR2 comprising amino acids having the sequence set forth in SEQ ID NO: 239; a heavy chain variable region CDR3 comprising amino acids having the sequence set forth in SEQ ID NO: 240; a light chain variable region CDR1 comprising amino acids having the sequence set forth in SEQ ID NO: 241; a light chain variable region CDR2 comprising amino acids having the sequence set forth in SEQ ID NO:242; and a light chain variable region CDR3 comprising amino acids having the sequence set forth in SEQ ID NO: 243; (u) a heavy chain variable region CDR1 comprising amino acids having the sequence set forth in SEQ ID NO: 244; a heavy chain variable region CDR2 comprising amino acids having the sequence set forth in SEQ ID NO: 245; a heavy chain variable region CDR3 comprising amino acids having the sequence set forth in SEQ ID NO: 246; a light chain variable region CDR1 comprising amino acids having the sequence set forth in SEQ ID NO: 247; a light chain variable region CDR2 comprising amino acids having the sequence set forth in SEQ ID NO:248; and a light chain variable region CDR3 comprising amino acids having the sequence set forth in SEQ ID NO: 249; (v) a heavy chain variable region CDR1 comprising amino acids having the sequence set forth in SEQ ID NO: 250; a heavy chain variable region CDR2 comprising amino acids having the sequence set forth in SEQ ID NO: 251; a heavy chain variable region CDR3 comprising amino acids having the sequence set forth in SEQ ID NO: 252; a light chain variable region CDR1 comprising amino acids having the sequence set forth in SEQ ID NO: 253; a light chain variable region CDR2 comprising amino acids having the sequence set forth in SEQ ID NO:254; and a light chain variable region CDR3 comprising amino acids having the sequence set forth in SEQ ID NO: 255; (w) a heavy chain variable region CDR1 comprising amino acids having the sequence set forth in SEQ ID NO: 256; a heavy chain variable region CDR2 comprising amino acids having the sequence set forth in SEQ ID NO: 257; a heavy chain variable region CDR3 comprising amino acids having the sequence set forth in SEQ ID NO: 258; a light chain variable region CDR1 comprising amino acids having the sequence set forth in SEQ ID NO: 259; a light chain variable region CDR2 comprising amino acids having the sequence set forth in SEQ ID NO:260; and a light chain variable region CDR3 comprising amino acids having the sequence set forth in SEQ ID NO: 261; (x) a heavy chain variable region CDR1 comprising amino acids having the sequence set forth in SEQ ID NO: 262; a heavy chain variable region CDR2 comprising amino acids having the sequence set forth in SEQ ID NO: 263; a heavy chain variable region CDR3 comprising amino acids having the sequence set forth in SEQ ID NO: 264; a light chain variable region CDR1 comprising amino acids having the sequence set forth in SEQ ID NO: 265; a light chain variable region CDR2 comprising amino acids having the sequence set forth in SEQ ID NO:266; and a light chain variable region CDR3 comprising amino acids having the sequence set forth in SEQ ID NO: 267; (y) a heavy chain variable region CDR1 comprising amino acids having the sequence set forth in SEQ ID NO: 304; a heavy chain variable region CDR2 comprising amino acids having the sequence set forth in SEQ ID NO: 305; a heavy chain variable region CDR3 comprising amino acids having the sequence set forth in SEQ ID NO: 306; a light chain variable region CDR1 comprising amino acids having the sequence set forth in SEQ ID NO: 307; a light chain variable region CDR2 comprising amino acids having the sequence set forth in SEQ ID NO: 308; and a light chain variable region CDR3 comprising amino acids having the sequence set forth in SEQ ID NO: 309; (z) a heavy chain variable region CDR1 comprising amino acids having the sequence set forth in SEQ ID NO: 316; a heavy chain variable region CDR2 comprising amino acids having the sequence set forth in SEQ ID NO: 317; a heavy chain variable region CDR3 comprising amino acids having the sequence set forth in SEQ ID NO: 318; a light chain variable region CDR1 comprising amino acids having the sequence set forth in SEQ ID NO: 319; a light chain variable region CDR2 comprising amino acids having the sequence set forth in SEQ ID NO: 320; and a light chain variable region CDR3 comprising amino acids having the sequence set forth in SEQ ID NO: 321; (aa) a heavy chain variable region CDR1 comprising amino acids having the sequence set forth in SEQ ID NO: 328; a heavy chain variable region CDR2 comprising amino acids having the sequence set forth in SEQ ID NO: 329; a heavy chain variable region CDR3 comprising amino acids having the sequence set forth in SEQ ID NO: 330; a light chain variable region CDR1 comprising amino acids having the sequence set forth in SEQ ID NO: 331; a light chain variable region CDR2 comprising amino acids having the sequence set forth in SEQ ID NO: 332; and a light chain variable region CDR3 comprising amino acids having the sequence set forth in SEQ ID NO: 333; (ab) a heavy chain variable region CDR1 comprising amino acids having the sequence set forth in SEQ ID NO: 340; a heavy chain variable region CDR2 comprising amino acids having the sequence set forth in SEQ ID NO: 341; a heavy chain variable region CDR3 comprising amino acids having the sequence set forth in SEQ ID NO: 342; a light chain variable region CDR1 comprising amino acids having the sequence set forth in SEQ ID NO: 343; a light chain variable region CDR2 comprising amino acids having the sequence set forth in SEQ ID NO: 344; and a light chain variable region CDR3 comprising amino acids having the sequence set forth in SEQ ID NO: 345; (ac) a heavy chain variable region CDR1 comprising amino acids having the sequence set forth in SEQ ID NO: 352; a heavy chain variable region CDR2 comprising amino acids having the sequence set forth in SEQ ID NO: 353; a heavy chain variable region CDR3 comprising amino acids having the sequence set forth in SEQ ID NO: 354; a light chain variable region CDR1 comprising amino acids having the sequence set forth in SEQ ID NO: 355; a light chain variable region CDR2 comprising amino acids having the sequence set forth in SEQ ID NO: 356; and a light chain variable region CDR3 comprising amino acids having the sequence set forth in SEQ ID NO: 357; (ad) a heavy chain variable region CDR1 comprising amino acids having the sequence set forth in SEQ ID NO: 364; a heavy chain variable region CDR2 comprising amino acids having the sequence set forth in SEQ ID NO: 365; a heavy chain variable region CDR3 comprising amino acids having the sequence set forth in SEQ ID NO: 366; a light chain variable region CDR1 comprising amino acids having the sequence set forth in SEQ ID NO: 367; a light chain variable region CDR2 comprising amino acids having the sequence set forth in SEQ ID NO: 368; and a light chain variable region CDR3 comprising amino acids having the sequence set forth in SEQ ID NO: 369; (ae) a heavy chain variable region CDR1 comprising amino acids having the sequence set forth in SEQ ID NO: 376; a heavy chain variable region CDR2 comprising amino acids having the sequence set forth in SEQ ID NO: 377; a heavy chain variable region CDR3 comprising amino acids having the sequence set forth in SEQ ID NO: 378; a light chain variable region CDR1 comprising amino acids having the sequence set forth in SEQ ID NO: 379; a light chain variable region CDR2 comprising amino acids having the sequence set forth in SEQ ID NO: 380; and a light chain variable region CDR3 comprising amino acids having the sequence set forth in SEQ ID NO: 381; or (af) a heavy chain variable region CDR1 comprising amino acids having the sequence set forth in SEQ ID NO: 388; a heavy chain variable region CDR2 comprising amino acids having the sequence set forth in SEQ ID NO: 389; a heavy chain variable region CDR3 comprising amino acids having the sequence set forth in SEQ ID NO: 390; a light chain variable region CDR1 comprising amino acids having the sequence set forth in SEQ ID NO: 391; a light chain variable region CDR2 comprising amino acids having the sequence set forth in SEQ ID NO: 392; and a light chain variable region CDR3 comprising amino acids having the sequence set forth in SEQ ID NO: 393. In certain embodiments, the extracellular antigen-binding domain comprises: a heavy chain variable region CDR1 comprising amino acids having the sequence set forth in SEQ ID NO: 202; a heavy chain variable region CDR2 comprising amino acids having the sequence set forth in SEQ ID NO: 203; a heavy chain variable region CDR3 comprising amino acids having the sequence set forth in SEQ ID NO: 204; a light chain variable region CDR1 comprising amino acids having the sequence set forth in SEQ ID NO: 205; a light chain variable region CDR2 comprising amino acids having the sequence set forth in SEQ ID NO:206; and a light chain variable region CDR3 comprising amino acids having the sequence set forth in SEQ ID NO: 207. In certain embodiments, the extracellular antigen-binding domain comprises: a heavy chain variable region CDR1 comprising amino acids having the sequence set forth in SEQ ID NO: 208; a heavy chain variable region CDR2 comprising amino acids having the sequence set forth in SEQ ID NO: 209; a heavy chain variable region CDR3 comprising amino acids having the sequence set forth in SEQ ID NO: 210; a light chain variable region CDR1 comprising amino acids having the sequence set forth in SEQ ID NO: 211; a light chain variable region CDR2 comprising amino acids having the sequence set forth in SEQ ID NO:212; and a light chain variable region CDR3 comprising amino acids having the sequence set forth in SEQ ID NO: 213. In certain embodiments, the extracellular antigen-binding domain comprises: a heavy chain variable region CDR1 comprising amino acids having the sequence set forth in SEQ ID NO: 214; a heavy chain variable region CDR2 comprising amino acids having the sequence set forth in SEQ ID NO: 215; a heavy chain variable region CDR3 comprising amino acids having the sequence set forth in SEQ ID NO: 216; a light chain variable region CDR1 comprising amino acids having the sequence set forth in SEQ ID NO: 217; a light chain variable region CDR2 comprising amino acids having the sequence set forth in SEQ ID NO:218; and a light chain variable region CDR3 comprising amino acids having the sequence set forth in SEQ ID NO: 219. In another non-limiting embodiment, the extracellular antigen-binding domain comprises: a heavy chain variable region CDR1 comprising amino acids having the sequence set forth in SEQ ID NO: 220; a heavy chain variable region CDR2 comprising amino acids having the sequence set forth in SEQ ID NO: 221; a heavy chain variable region CDR3 comprising amino acids having the sequence set forth in SEQ ID NO: 222; a light chain variable region CDR1 comprising amino acids having the sequence set forth in SEQ ID NO: 223; a light chain variable region CDR2 comprising amino acids having the sequence set forth in SEQ ID NO:224; and a light chain variable region CDR3 comprising amino acids having the sequence set forth in SEQ ID NO: 225. In yet another non-limiting embodiment, the extracellular antigen-binding domain comprises: a heavy chain variable region CDR1 comprising amino acids having the sequence set forth in SEQ ID NO: 226; a heavy chain variable region CDR2 comprising amino acids having the sequence set forth in SEQ ID NO: 227; a heavy chain variable region CDR3 comprising amino acids having the sequence set forth in SEQ ID NO: 228; a light chain variable region CDR1 comprising amino acids having the sequence set forth in SEQ ID NO: 229; a light chain variable region CDR2 comprising amino acids having the sequence set forth in SEQ ID NO:230; and a light chain variable region CDR3 comprising amino acids having the sequence set forth in SEQ ID NO: 231. In certain embodiments, the human scFv comprises a heavy chain variable region, a light chain variable region, a linker peptide between the heavy chain variable region and the light chain variable region, and an His-tag and an HA-tag. In certain embodiments, the amino acid sequence of the His-tag and HA-tag comprises the amino acid sequence of SEQ ID NO:275, which is provided below:

```
                                        [SEQ ID NO: 275]
TSGQAGQHHHHHHGAYPYDVPDYAS
```

The nucleotide sequence encoding SEQ ID NO: 275 is SEQ ID NO: 276, which is provided below:

```
                                        [SEQ ID NO: 276]
ACTAGTGGCCAGGCCGGCCAGCACCATCACCATCACCATGGCGCATAC

CCGTACGACGTTCCGGACTACGCTTCT
```

In certain embodiments, the GPRC5D comprises the amino acid sequence set forth in SEQ ID NO:97. In certain embodiments, the extracellular antigen-binding domain binds to one, two, three or four epitope region selected from the group consisting of an epitope region in N-terminal region comprising amino acids 1-27 of SEQ ID NO:97, an epitope region in ECL1 region comprising amino acids 85-93 of SEQ ID NO:97, an epitope region in ECL2 region comprising amino acids 145-167 of SEQ ID NO:97, and an epitope region in ECL3 region comprising amino acids 226-239 of SEQ ID NO:97. In certain embodiments, the extracellular antigen-binding domain binds to an epitope region comprising amino acids 16-23 of SEQ ID NO:97. In certain embodiments, the extracellular antigen-binding domain binds to an epitope region comprising amino acids 15-23 of SEQ ID NO:97. In certain embodiments, the extracellular antigen-binding domain binds to an epitope region comprising amino acids 16-25 of SEQ ID NO:97. In certain embodiments, the extracellular antigen-binding domain binds to an epitope region comprising amino acids 10-17 of SEQ ID NO:97. In certain embodiments, the extracellular antigen-binding domain binds to an epitope region comprising amino acids 5-17 of SEQ ID NO:97. In certain embodiments, the extracellular antigen-binding domain binds to an epitope region comprising amino acids 85-95 of SEQ ID NO:97. In certain embodiments, the extracellular antigen-binding domain binds to an epitope region comprising amino acids 157-164 of SEQ ID NO:97. In certain embodiments, the extracellular antigen-binding domain binds to an epitope region comprising amino acids 157-167 of SEQ ID NO:97. In certain embodiments, the extracellular antigen-binding domain binds to an epitope region comprising amino acids 230-237 of SEQ ID NO:97. In certain embodiments, the extracellular antigen-binding domain binds to an epitope region comprising amino acids 229-237 of SEQ ID NO:97. In certain embodiments, the extracellular antigen-binding domain binds to an epitope region comprising amino acids 230-243 of SEQ ID NO:97. In certain embodiments, the extracellular antigen-binding domain binds to an epitope region comprising amino acids 227-237 of SEQ ID NO:97.

In certain embodiments, the extracellular antigen-binding domain binds to one, two, or three epitope region selected from the group consisting of an epitope region comprising amino acids 16-25 of SEQ ID NO:97, an epitope region comprising amino acids 157-164 of SEQ ID NO:97, and an epitope region comprising amino acids 229-237 of SEQ ID NO:97. For example, the extracellular antigen-binding domain comprises a heavy chain variable region comprising amino acids having the sequence set forth in SEQ ID NO:57 and a light chain variable region comprising amino acids having the sequence set forth in SEQ ID NO:58. For example, the extracellular antigen-binding domain comprises a $V_H$ CDR1 comprising amino acids having the sequence set forth in SEQ ID NO: 208, a $V_H$ CDR2 comprising amino acids having the sequence set forth in SEQ ID NO: 209, a $V_H$ CDR3 comprising amino acids having the sequence set forth in SEQ ID NO: 210, a $V_L$ CDR1 comprising amino acids having the sequence set forth in SEQ ID NO: 211, a $V_L$ CDR2 comprising amino acids having the sequence set forth in SEQ ID NO: 212, and a $V_L$ CDR3 comprising amino acids having the sequence set forth in SEQ ID NO: 213.

In certain embodiments, the extracellular antigen-binding domain binds to one, two, or three epitope region selected from the group consisting of an epitope region comprising amino acids 5-17 of SEQ ID NO:97, an epitope region comprising amino acids 85-95 of SEQ ID NO:97, and an epitope region comprising amino acids 157-164 of SEQ ID NO:97. For example, the extracellular antigen-binding domain comprises a heavy chain variable region comprising amino acids having the sequence set forth in SEQ ID NO:61 and a light chain variable region comprising amino acids having the sequence set forth in SEQ ID NO:62. For example, the extracellular antigen-binding domain comprises a $V_H$ CDR1 comprising amino acids having the sequence set forth in SEQ ID NO: 214, a $V_H$ CDR2 comprising amino acids having the sequence set forth in SEQ ID NO: 215, a $V_H$ CDR3 comprising amino acids having the sequence set forth in SEQ ID NO: 216, a $V_L$ CDR1 comprising amino acids having the sequence set forth in SEQ ID NO: 217, a $V_L$ CDR2 comprising amino acids having the sequence set forth in SEQ ID NO: 218 and a $V_L$ CDR3 comprising amino acids having the sequence set forth in SEQ ID NO: 219.

In certain embodiments, the extracellular antigen-binding domain binds to one or two epitope region selected from the group consisting of an epitope region comprising amino acids 15-23 of SEQ ID NO:97, and an epitope region comprising amino acids 230-243 of SEQ ID NO:97. For example, the extracellular antigen-binding domain comprises a heavy chain variable region comprising amino acids having the sequence set forth in SEQ ID NO:65 and a light chain variable region comprising amino acids having the sequence set forth in SEQ ID NO:66. For example, the extracellular antigen-binding domain comprises a $V_H$ CDR1 comprising amino acids having the sequence set forth in SEQ ID NO: 220, a $V_H$ CDR2 comprising amino acids having the sequence set forth in SEQ ID NO: 221, a $V_H$ CDR3 comprising amino acids having the sequence set forth in SEQ ID NO: 222, a $V_L$ CDR1 comprising amino acids having the sequence set forth in SEQ ID NO: 223, a $V_L$ CDR2 comprising amino acids having the sequence set forth in SEQ ID NO: 224, and a $V_L$ CDR3 comprising amino acids having the sequence set forth in SEQ ID NO: 225.

In certain embodiments, the extracellular antigen-binding domain binds to one, two, or three epitope region selected from the group consisting of an epitope region comprising amino acids 10-17 of SEQ ID NO:97, an epitope region comprising amino acids 157-167 of SEQ ID NO:97, and an epitope region comprising amino acids 227-237 of SEQ ID NO:97. For example, the extracellular antigen-binding domain comprises a heavy chain variable region comprising amino acids having the sequence set forth in SEQ ID NO:69 and a light chain variable region comprising amino acids having the sequence set forth in SEQ ID NO:70. For example, the extracellular antigen-binding domain comprises a $V_H$ CDR1 comprising amino acids having the sequence set forth in SEQ ID NO: 226, a $V_H$ CDR2 comprising amino acids having the sequence set forth in SEQ ID NO: 227, a $V_H$ CDR3 comprising amino acids having the sequence set forth in SEQ ID NO: 228, a $V_L$ CDR1 comprising amino acids having the sequence set forth in SEQ ID NO: 229, a $V_L$ CDR2 comprising amino acids having the sequence set forth in SEQ ID NO: 230, and a $V_L$ CDR3 comprising amino acids having the sequence set forth in SEQ ID NO: 231.

In accordance with the presently disclosed subject matter, the extracellular antigen-binding domain is covalently joined to a transmembrane domain. The extracellular antigen-binding domain can comprise a signal peptide that is covalently joined to the 5' terminus of the extracellular antigen-binding domain. In certain embodiments, the transmembrane domain of the CAR comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof. In certain embodiments, the transmembrane domain comprises a CD8 polypeptide. In certain embodiments, the transmembrane domain comprises a CD28 polypeptide.

In accordance with the presently disclosed subject matter, the intracellular domain comprises a CD3ζ polypeptide. In certain embodiments, the intracellular domain further comprises at least one signaling region. In certain embodiments, the at least one signaling region comprises a CD28 polypeptide, a 4-1BB polypeptide, an OX40 polypeptide, an ICOS polypeptide, a DAP-10 polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof. In certain embodiments, the signaling region is a co-stimulatory signaling region. In certain embodiments, the co-stimulatory signaling region comprises a CD28 polypeptide, a 4-1BB polypeptide, an OX40 polypeptide, an ICOS polypeptide, a DAP-10 polypeptide, or a combination thereof. In certain embodiments, the at least one co-stimulatory signaling region comprises a CD28 polypeptide. In certain embodiments, the at least one co-stimulatory signaling region comprises a 4-1BB polypeptide. In certain embodiments, the transmembrane domain comprises a CD28 polypeptide, the intracellular domain comprises a CD3ζ polypeptide, and the co-stimulatory signaling domain comprises a CD28 polypeptide.

In certain embodiments, the CAR is recombinantly expressed. The CAR can be expressed from a vector. In certain embodiments, the vector is a γ-retroviral rector.

The presently disclosed subject matter also provides isolated immunoresponsive cells comprising the above-described CARs. In certain embodiments, the isolated immunoresponsive cell is transduced with the CAR, for example, the CAR is constitutively expressed on the surface of the immunoresponsive cell. In certain embodiments, the isolated immunoresponsive cell is further transduced with at least one co-stimulatory ligand such that the immunoresponsive cell expresses the at least one co-stimulatory ligand. In certain embodiments, the at least one co-stimulatory ligand is selected from the group consisting of 4-1BBL, CD80, CD86, CD70, OX40L, CD48, TNFRSF14, and combinations thereof. In certain embodiments, the isolated immunoresponsive cell is further transduced with at least one cytokine such that the immunoresponsive cell secrets the at least one cytokine. In certain embodiments, the at least cytokine is selected from the group consisting of IL-2, IL-3, IL-6, IL-7, IL-11, IL-12, IL-15, IL-17, IL-21, and combinations thereof. In some embodiments, the isolated immunoresponsive cell is selected from the group consisting of a T cell, a Natural Killer (NK) cell, a cytotoxic T lymphocyte (CTL), a regulatory T cell, a human embryonic stem cell, a lymphoid progenitor cell, a T cell-precursor cell, and a pluripotent stem cell from which lymphoid cells may be differentiated. In certain embodiments, the immunoresponsive cell is a T cell.

The presently disclosed subject matter further provides nucleic acid molecules encoding the presently disclosed CARs, vectors comprising the nucleic acid molecules, and host cells expressing such nucleic acid molecules. In certain embodiments, the nucleic acid molecule comprises nucleic acids having the sequence set forth in SEQ ID NO:397. In certain embodiments, the nucleic acid molecule comprises nucleic acids having the sequence set forth in SEQ ID NO:398. In certain embodiments, the nucleic acid molecule comprises nucleic acids having the sequence set forth in SEQ ID NO:399. In certain embodiments, the nucleic acid molecule comprises nucleic acids having the sequence set forth in SEQ ID NO:400. In certain embodiments, the nucleic acid molecule comprises nucleic acids having the sequence set forth in SEQ ID NO:401. In certain embodiments, the nucleic acid molecule comprises nucleic acids having the sequence set forth in SEQ ID NO:402. In certain embodiments, the nucleic acid molecule comprises nucleic acids having the sequence set forth in SEQ ID NO:403. In certain embodiments, the nucleic acid molecule comprises nucleic acids having the sequence set forth in SEQ ID NO:406. In certain embodiments, the nucleic acid molecule comprises nucleic acids having the sequence set forth in SEQ ID NO:407. In certain embodiments, the nucleic acid molecule comprises nucleic acids having the sequence set forth in SEQ ID NO:408. In certain embodiments, the vector is a γ-retroviral vector. In certain embodiments, the host cell is a T cell.

Furthermore, the presently disclosed subject matter provides methods of using the above-described immunoresponsive cell for reducing tumor burden in a subject. For example, the presently disclosed subject matter provides methods of treating reducing tumor burden in a subject, where the method comprises administering an effective amount of the presently disclosed immunoresponsive cell to the subject, thereby inducing tumor cell death in the subject. In certain embodiments, the method reduces the number of the number of tumor cells. In another embodiment, the method reduces tumor size. In yet another embodiment, the method eradicates the tumor in the subject. In certain embodiments, the subject is a human. In certain embodiments, the immunoresponsive cell is a T cell. In certain embodiments, the tumor is multiple myeloma or Waldenstrom's Macroglobulinemia. In certain embodiments, the tumor is multiple myeloma.

Furthermore, the presently disclosed subject matter provides methods of using the above-described immunoresponsive cell for increasing or lengthening survival of a subject having neoplasia. For example, the presently disclosed subject matter provides methods of increasing or lengthening survival of a subject having neoplasia, where the method comprises administering an effective amount of the presently disclosed immunoresponsive cell to the subject, thereby increasing or lengthening survival of the subject. In certain embodiments, the neoplasia is multiple myeloma or Waldenstrom's Macroglobulinemia. In certain embodiments, the neoplasia is multiple myeloma. In certain embodiments, the method reduces or eradicates tumor burden in the subject.

The presently disclosed subject matter also provides methods for producing an immunoresponsive cell that binds to a G-protein coupled receptor. In one non-limiting example, the method comprises introducing into the immunoresponsive cell a nucleic acid sequence that encodes a chimeric antigen receptor (CAR), which comprises an extracellular antigen-binding domain, a transmembrane domain and an intracellular domain, wherein the extracellular antigen-binding domain specifically binds to a G-protein coupled receptor. In certain embodiments, the G-protein coupled receptor is a G-protein coupled receptor family C group 5 member D (GPRC5D). In a specific non-limiting embodiment, the extracellular antigen-binding domain is an scFv.

The presently disclosed subject matter further provides pharmaceutical compositions comprising an effective amount of the presently disclosed immunoresponsive cells and a pharmaceutically acceptable excipient. In certain embodiments, the pharmaceutical compositions are for treating a neoplasia. In certain embodiments, the neoplasia is multiple myeloma or Waldenstrom's Macroglobulinemia. In certain embodiments, the neoplasia is multiple myeloma.

The presently disclosed subject matter further provides kits for treating a neoplasia, comprising the presently disclosed immunoresponsive cells. In certain embodiments, the kit further include written instructions for using the immunoresponsive cell for treating a neoplasia. In certain embodiments, the neoplasia is multiple myeloma or Waldenstrom's Macroglobulinemia. In certain embodiments, the neoplasia is multiple myeloma.

BRIEF DESCRIPTION OF THE FIGURES

The following Detailed Description, given by way of example, but not intended to limit the invention to specific embodiments described, may be understood in conjunction with the accompanying drawings.

Combinatorial peptides are synthesized on a proprietary minicard and chemically converted into spatially defined CLIPS constructs (right).

Figure 16:
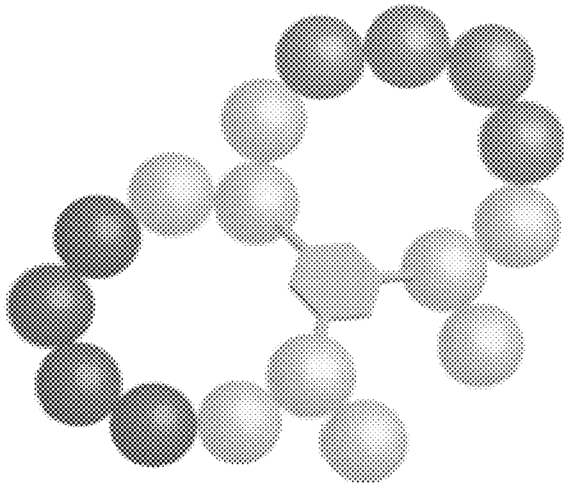

FIG. 16 depicts T3 looped CLIPSTM construct.

FIGS. 17A-17D illustrates heat map technology. (A) Table of combined peptides, with two sub-sequences indicated as "Loop 1" and "Loop 2". (B) Data from A displayed as a matrix. (C) Color bar indication of the heat map representation. (D) Heat map visualization of data from A.

Figure 18:
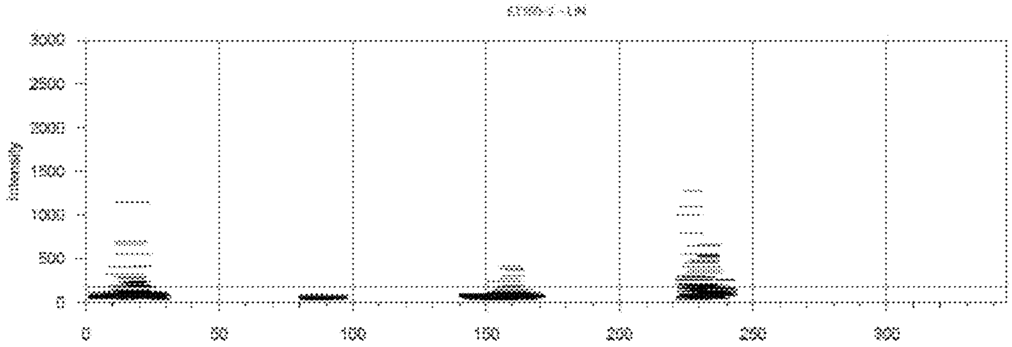

FIG. 18 shows intensity profiles recorded for ET150-2. Lines are drawn from the starting residue to the ending residue of a single peptide on the height at which the signal for that peptide is recorded.

Figure 19:
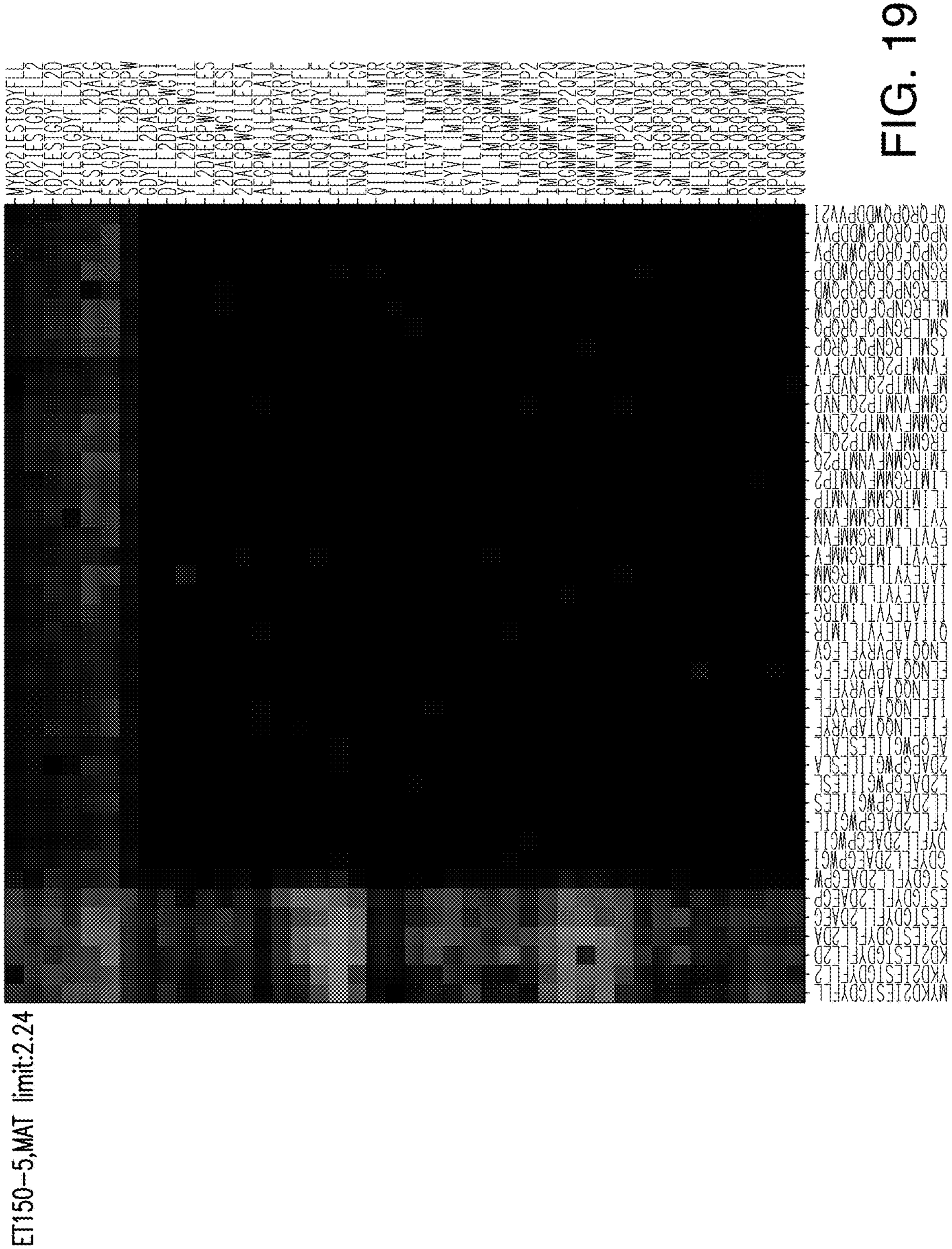

FIG. 19 shows heatmap analysis of data recorded for ET150-5 under high stringency conditions.

Figure 20:
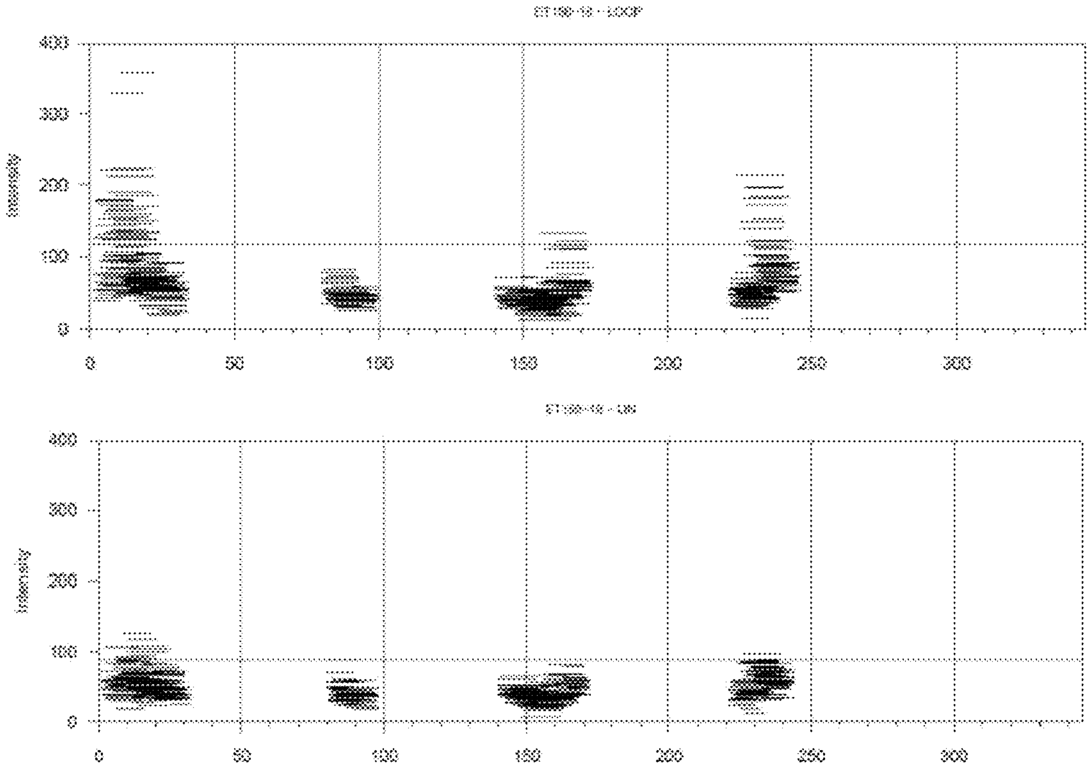

FIG. 20 shows intensity profiles recorded for ET150-18.

Figure 21:
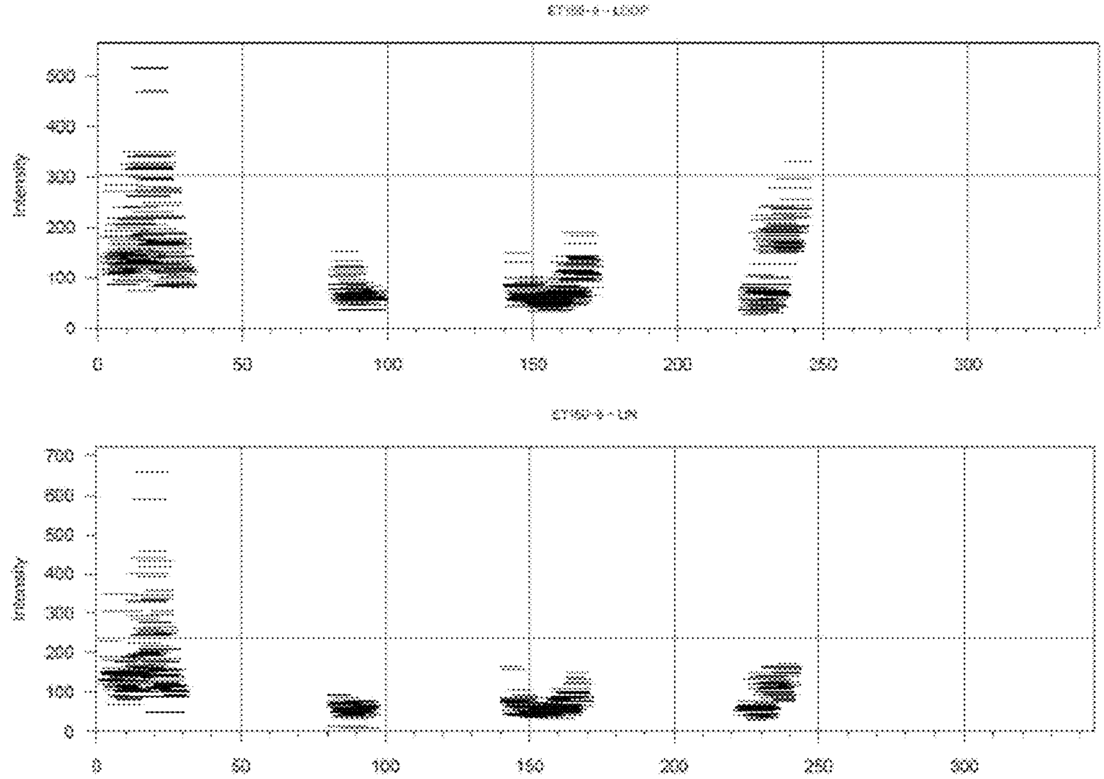

FIG. 21 shows intensity profiles recorded for ET150-8.

Figure 22:
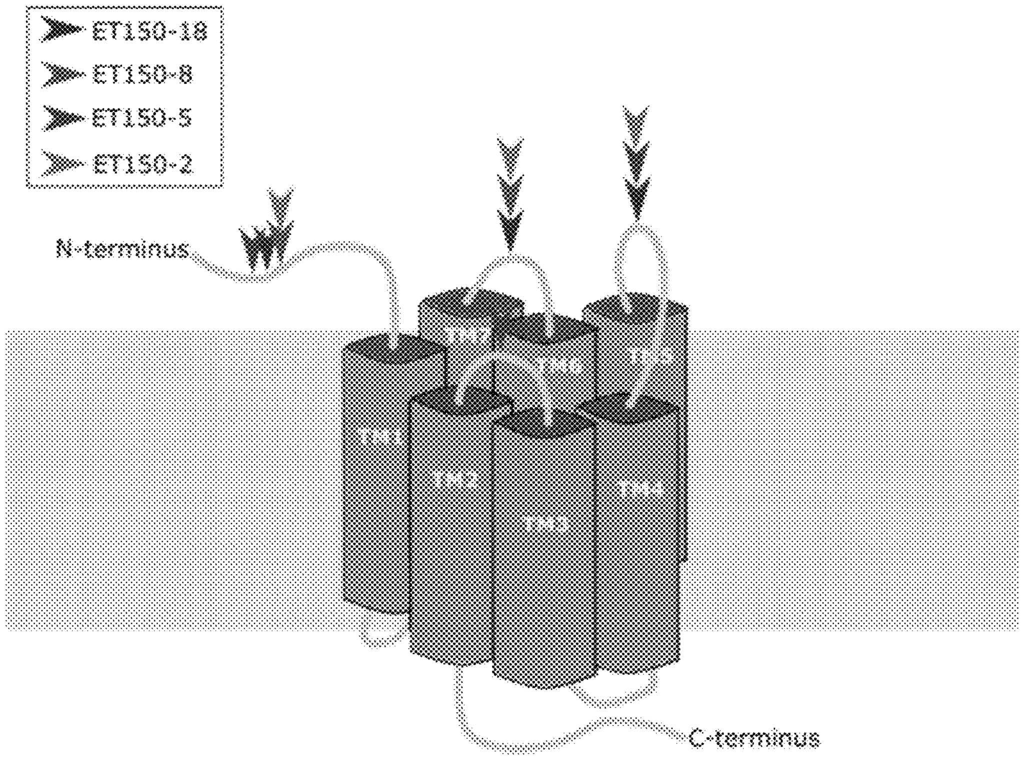

FIG. 22 depicts schematic drawing of GPCR containing seven transmembrane helices (TM) and 3 extracellular regions (ECLs). With colored arrows binding sites for each antibody is depicted.

Figure 23:
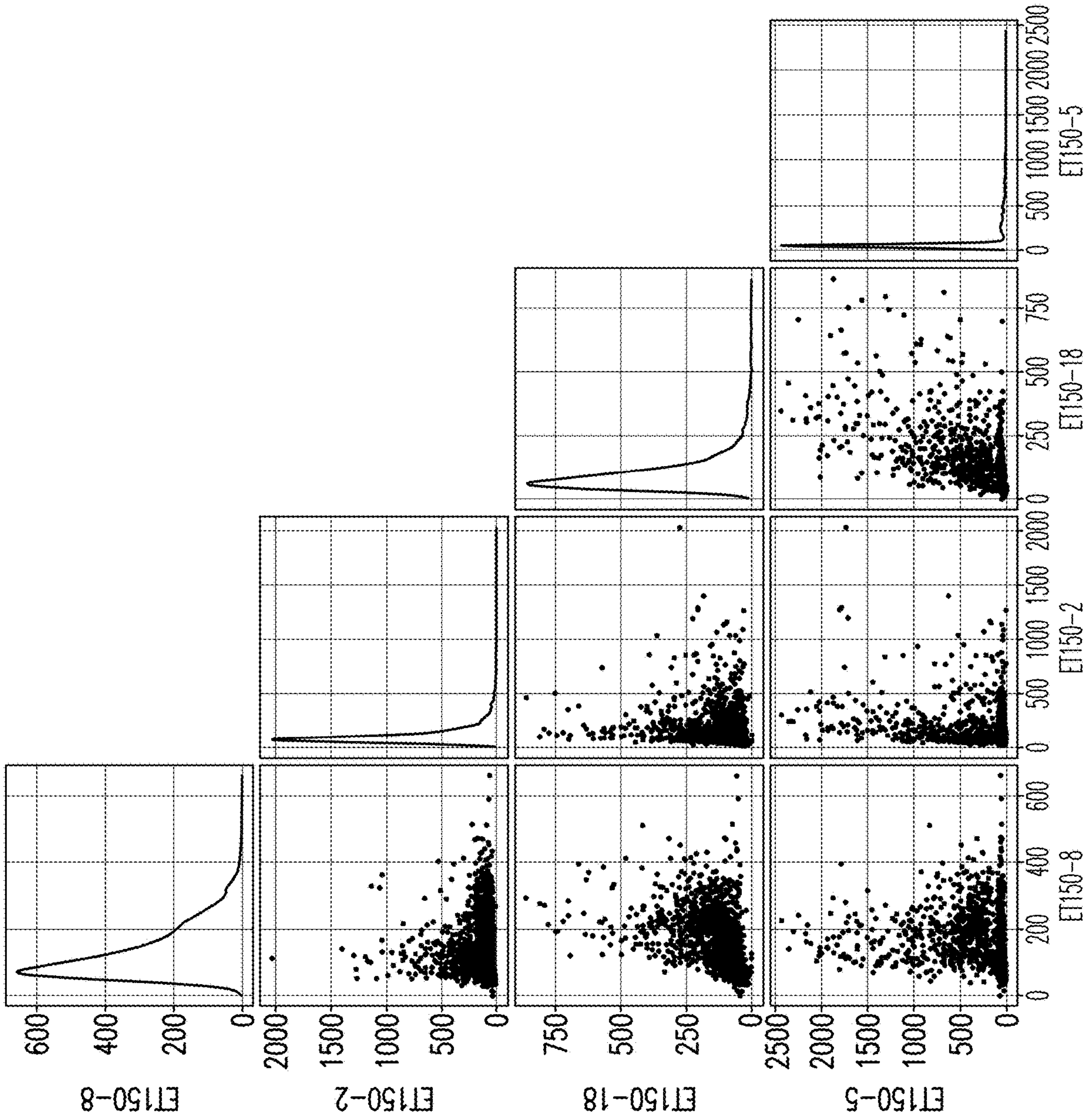

FIG. 23 depicts scatterplot analysis of all data recorded for each sample. On the diagonal is the statistical data distribution.

Figure 24:
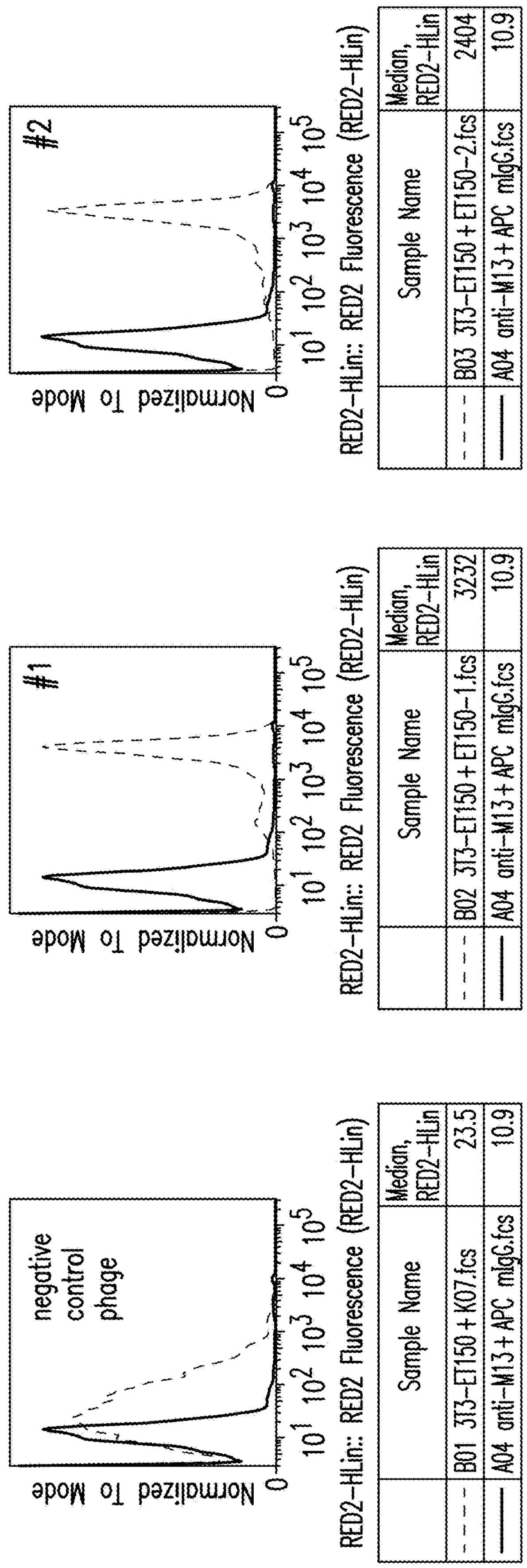
Figure 24:
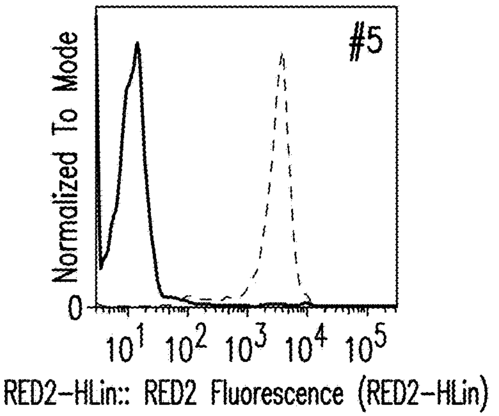
Figure 24:
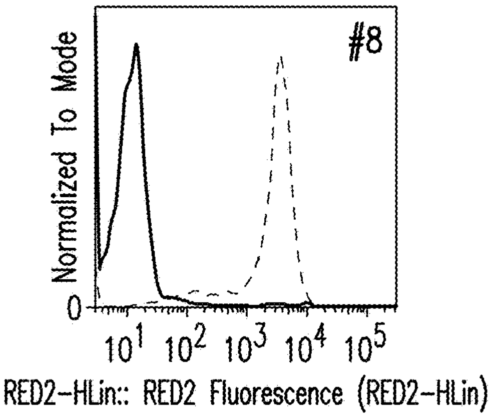
Figure 24:
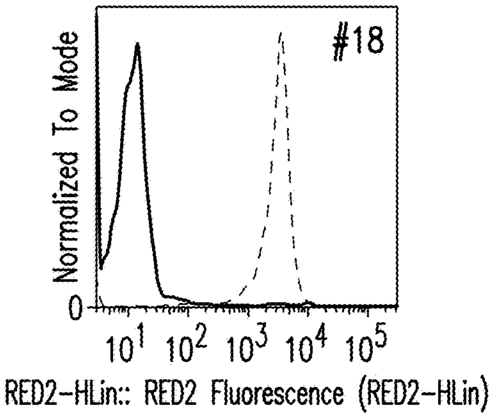

FIG. 24 depicts FACS analysis of anti-GPRC5D antibodies.

Figure 25:
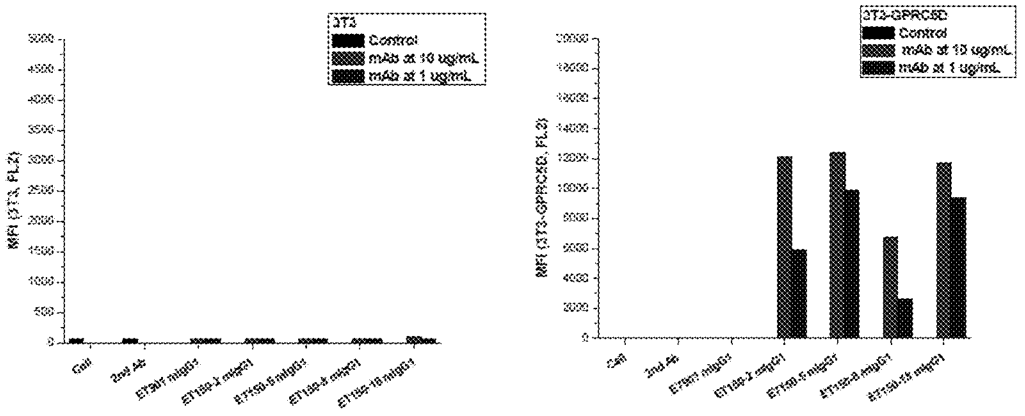

FIG. 25 depicts FACS analysis of anti-GPRC5D antibodies.

Figure 26:
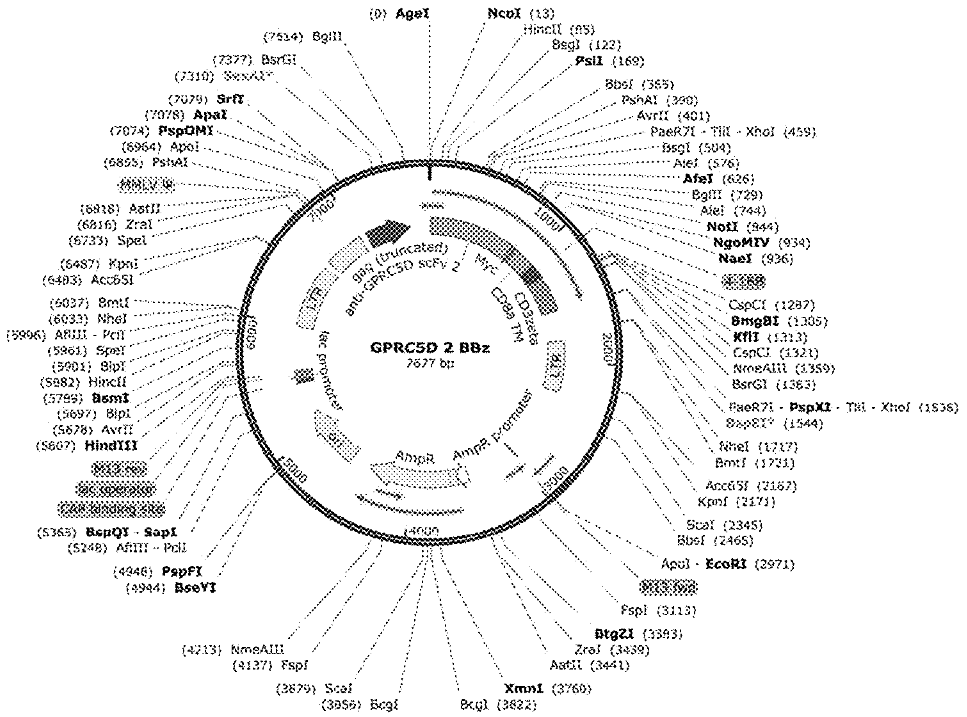

FIG. 26 depicts a nucleic acid molecule that encodes a GPRC5D-targeted CAR in accordance with one non-limiting embodiment of the presently disclosed subject matter.

Figure 27:
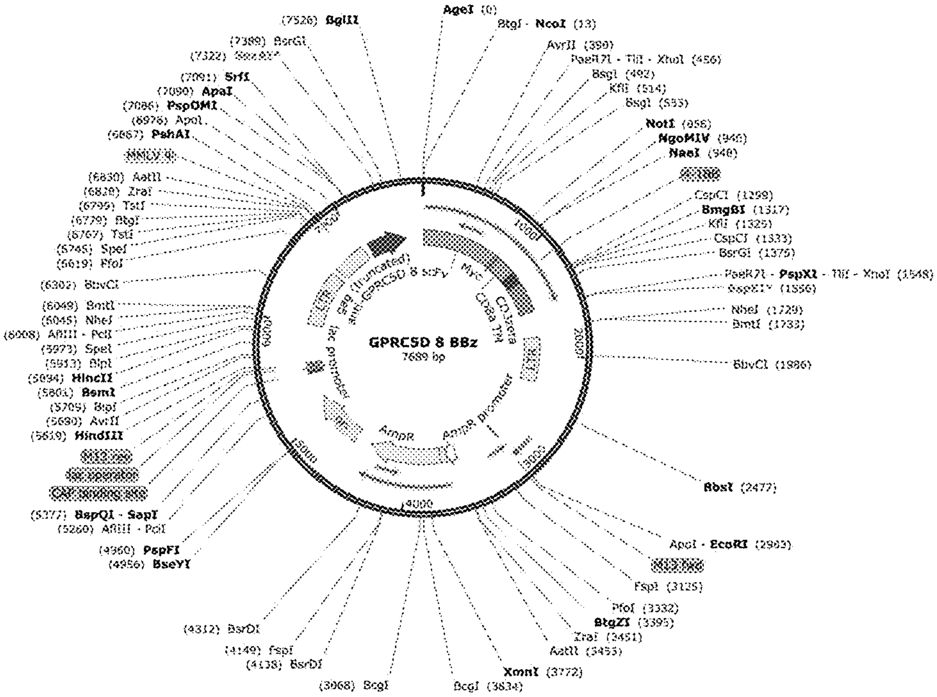

FIG. 27 depicts a nucleic acid molecule that encodes a GPRC5D-targeted CAR in accordance with one non-limiting embodiment of the presently disclosed subject matter.

DETAILED DESCRIPTION OF THE INVENTION

The presently disclosed subject matter generally provides chimeric antigen receptors (CARs) targeting a G-protein coupled receptor (e.g., a G-protein coupled receptor family C group 5 member D (GPRC5D)). In one non-limiting example, the CAR comprises an extracellular antigen-binding domain, a transmembrane domain and an intracellular domain, where the extracellular antigen-binding domain specifically binds to a G-protein coupled receptor. The presently disclosed subject matter also provides immunoresponsive cells (e.g., T cell, a Natural Killer (NK) cell, a cytotoxic T lymphocyte (CTL), a regulatory T cell, a human embryonic stem cell, a lymphoid progenitor cell, a T cell-precursor cell, and a pluripotent stem cell from which lymphoid cells may be differentiated) expressing the CARs targeting a G-protein coupled receptor, and methods of using such immunoresponsive cells for treating cancer, e.g., multiple myeloma.

I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells expressing similar or different phenotypes.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fe fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::VL heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. In certain embodiments, the linker is a G4S linker.

In a non-limiting example, the linker comprises amino acids having the sequence set forth in SEQ ID NO:897 as provided below.

[SEQ ID NO: 284]

GGGGSGGGGSGGGGS.

In certain embodiments, the nucleic acid sequence encoding the amino acid sequence of SEQ ID NO:284 is set forth in SEQ ID NO:285, which is provided below:

[SEQ ID NO: 285]
GGTGGAGGTGGATCAGGTGGAGGTGGATCTGGTGGAGGTGGATCT.

In another non-limiting example, the linker comprises amino acids having the sequence set forth in SEQ ID NO:98 as provided below.

[SEQ ID NO: 98]
SRGGGGSGGGGSGGGGSLEMA

In certain embodiments, the nucleic acid sequence encoding the amino acid sequence of SEQ ID NO:98 is set forth in SEQ ID NO:99, which is provided below:

[SEQ ID NO: 99]
tctagaggtggtggtggtagcggcggcggcggctctggtggtggtggatc cctcgagatggcc Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chern 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "$F(ab')_2$" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "expression vector" refers to a recombinant nucleic acid sequence, i.e. recombinant DNA molecule, containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. (1991) Sequences of Proteins of Immunological Interest, Fifth Edition, U.S. Department of Health and Human Services, NIH Publication No. 91-3242).

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between e-3 and e-100 indicating a closely related sequence.

As used herein, the term "analog" refers to a structurally related polypeptide or nucleic acid molecule having the function of a reference polypeptide or nucleic acid molecule.

As used herein, the term "ligand" refers to a molecule that binds to a receptor. In particular, the ligand binds a receptor on another cell, allowing for cell-to-cell recognition and/or interaction.

As used herein, the term "disease" refers to any condition or disorder that damages or interferes with the normal function of a cell, tissue, or organ. Examples of diseases include neoplasia or pathogen infection of cell.

As used herein, the term "effective amount" refers to an amount sufficient to have a therapeutic effect. In certain embodiments, an "effective amount" is an amount sufficient to arrest, ameliorate, or inhibit the continued proliferation, growth, or metastasis (e.g., invasion, or migration) of a neoplasia.

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "immunoresponsive cell" refers to a cell that functions in an immune response or a progenitor, or progeny thereof.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "isolated cell" refers to a cell that is separated from the molecular and/or cellular components that naturally accompany the cell.

As used herein, the term "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "secreted" is meant a polypeptide that is released from a cell via the secretory pathway through the endoplasmic reticulum, Golgi apparatus, and as a vesicle that transiently fuses at the cell plasma membrane, releasing the proteins outside of the cell.

As used herein, the term "specifically binds" or "specifically binds to" or "specifically target" is meant a polypeptide or fragment thereof that recognizes and binds a biological molecule of interest (e.g., a polypeptide), but which does not substantially recognize and bind other molecules in a sample, for example, a biological sample, which naturally includes a polypeptide of the invention.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

II. G-Protein Coupled Receptor

G protein-coupled receptors ("GPRs"), also known as seven-transmembrane domain receptors, 7TM receptors, heptahelical receptors, serpentine receptor, and G protein-linked receptors, constitute a large protein family of receptors that sense molecules outside the cell and activate inside signal transduction pathways and, ultimately, cellular responses. GPCRs can be categorized into six classes based on sequence homology and functional similarity: Class A (Rhodopsin-like), Class B (Secretin receptor family), Class C (Metabotropic glutamate/pheromone), Class D (Fungal mating pheromone receptors), Class E (Cyclic AMP receptors), and Class F (Frizzled/Smoothened). In certain embodiments, the GRPs are Class C GRPs. In certain non-limiting embodiments, the Class C GRP is a G-protein coupled receptor family C group 5 member D.

Figure 2:
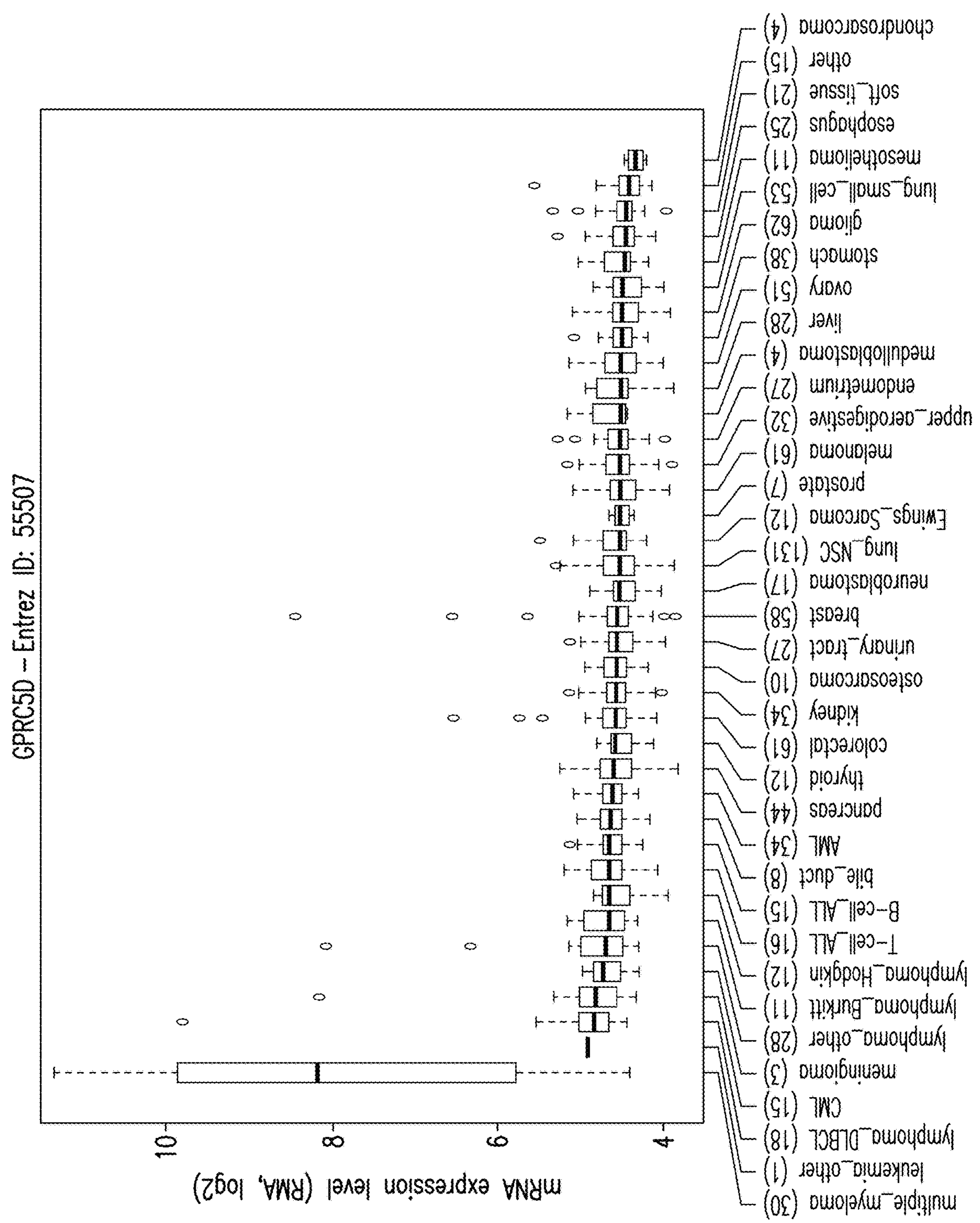
FIG. 2 depicts the human GPRC5D expression in normal tissues and human cancer cell lines.
Figure 2:
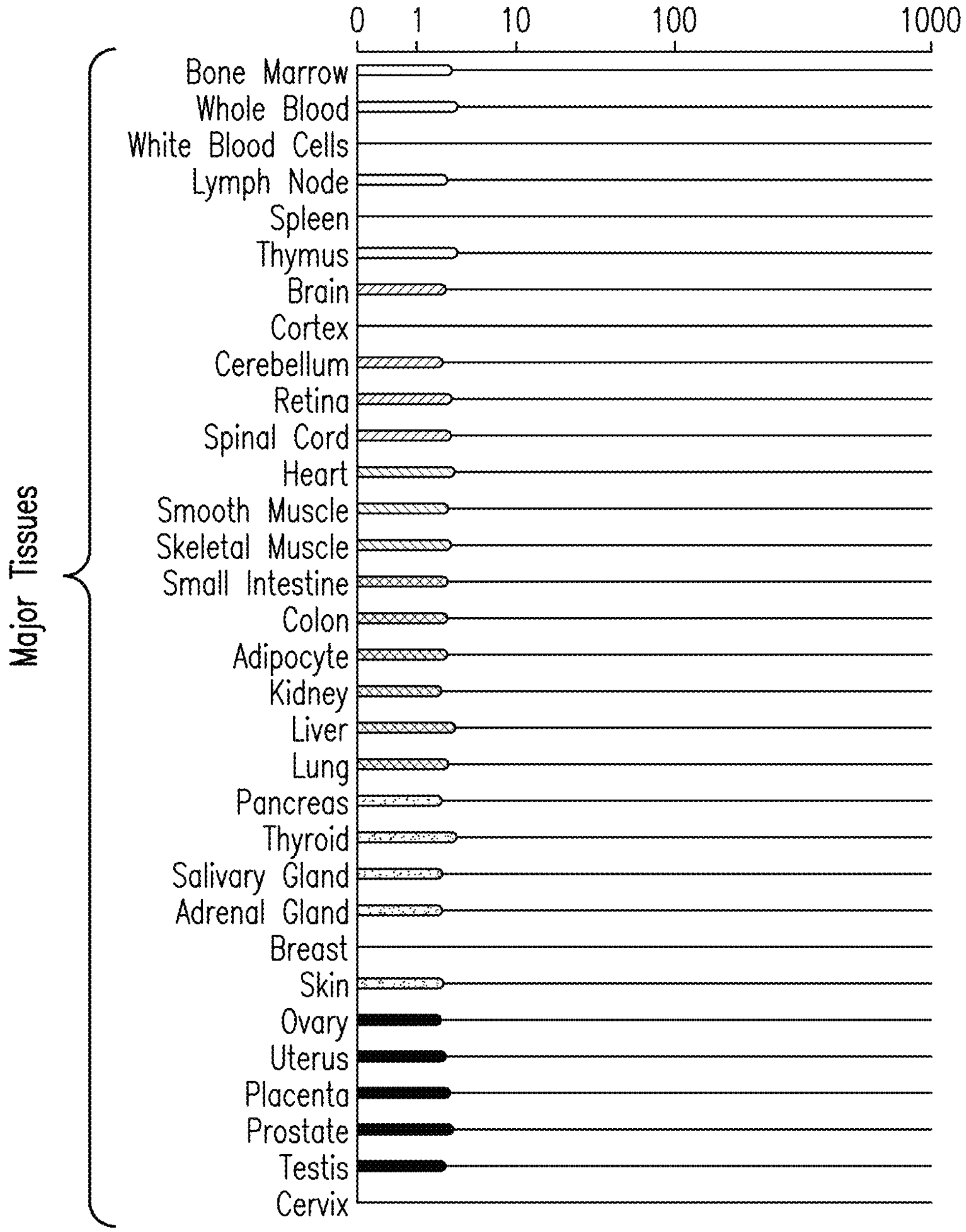
Figure 2:
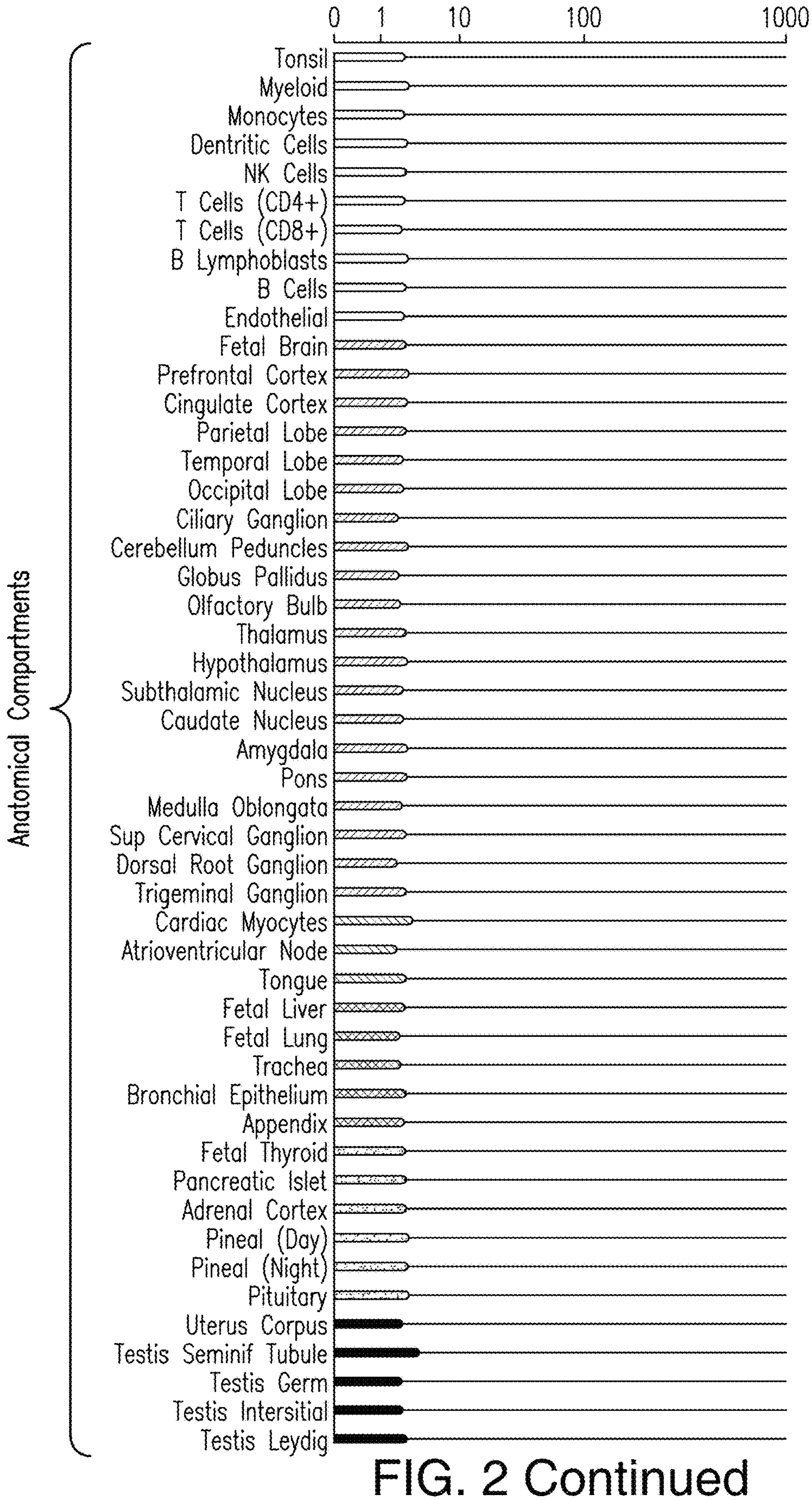

G-protein coupled receptor family C group 5 member D (GPRC5D) is an orphan receptor with no known ligand or function in humans. It is a member of a family of retinoic acid-inducible G-protein-coupled receptors. It is overexpressed in multiple myeloma (MM) cells and is not expressed or expressed in a significantly lower level in any other cell type, benign or malignant, as shown in FIG. 2. Several groups have identified this gene as highly differentially expressed by gene expression profiling of primary MM cells when compared to normal tissue[1] or other hematologic malignancies.[2-4] It has been shown that higher mRNA expression correlates with worse overall survival.[1] Surface staining of Bone marrow aspirates from patients with MM demonstrate plasma cell specific staining.[4] To the knowledge of the inventors, this is the first time GPRC5D has been targeted by any therapeutic. Additionally, to the knowledge of the inventors, this is the first time a CAR targeting any G-protein coupled receptor has been generated.

In certain non-limiting embodiments, GPRC5D is human GPRC5D having the amino acid sequence set forth in SEQ ID NO:97, or fragments thereof.

SEQ ID NO:97 is provided below:

```
                                        [SEQ ID NO: 97]
MYKDCIESTGDYFLLCDAEGPWGIILESLAILGIVVTILLLLAFLFLMRK

IQDCSQWNVLPTQLLFLLSVLGLFGLAFAFIIELNQQTAPVRYFLFGVLF

ALCFSCLLAHASNLVKLVRGCVSFSWTTILCIAIGCSLLQIIIATEYVTL

IMTRGMMFVNMTPCQLNVDFVVLLVYVLFLMALTFFVSKATFCGPCENWK

QHGRLIFITVLFSIIIWVVWISMLLRGNPQFQRQPQWDDPVVCIALVTNA

WVFLLLYIVPELCILYRSCRQECPLQGNACPVTAYQHSFQVENQELSRAR

DSDGAEEDVALTSYGTPIQPQTVDPTQECFIPQAKLSPQQDAGGV
```

The N-terminal region of human GPRC5D has amino acids 1-27 of SEQ ID NO:97. The extracellular loop 1 (ECL1) region of human GPRC5D has amino acids 85-93 of SEQ ID NO:97. The extracellular loop 2 (ECL2) region of human GPRC5D has amino acids 145-167 of SEQ ID NO:97. The extracellular loop 3 (ECL3) region of human GPRC5D has amino acids 226-239 of SEQ ID NO:97.

III. Chimeric Antigen Receptor (CAR)

Chimeric antigen receptors (CARs) are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARs. "First generation" CARs are typically composed of an extracellular antigen binding domain (e.g., a single-chain variable fragments (scFv)) fused to a transmembrane domain, fused to cytoplasmic/intracellular domain of the T cell receptor chain. "First generation" CARs typically have the intracellular domain from the CD3ζ-chain, which is the primary transmitter of signals from endogenous TCRs. "First generation" CARs can provide de novo antigen recognition and cause activation of both $CD4^+$ and $CD8^+$ T cells through their CD3ζ chain signaling domain in a single fusion molecule, independent of HLA-mediated antigen presentation. "Second generation" CARs add intracellular domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (CD3ζ). Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL). "Third generation" CARs comprise those that provide multiple co-stimulation (e.g., CD28 and 4-1BB) and activation (CD3ζ).

In accordance with the presently disclosed subject matter, the CARs comprise an extracellular antigen-binding domain, a transmembrane domain and an intracellular domain, where the extracellular antigen-binding domain binds to a G-protein coupled receptor. In certain embodiments, the G-protein coupled receptor is a GPRC5D. In a specific non-limiting embodiment, the extracellular antigen-binding domain is a scFv. In a specific non-limiting embodiment, the extracellular antigen-binding domain is a Fab, which is optionally crosslinked. In a specific non-limiting embodiment, the extracellular binding domain is a $F(ab)_2$. In a specific non-limiting embodiment, any of the foregoing molecules may be comprised in a fusion protein with a heterologous sequence to form the extracellular antigen-binding domain.

In certain non-limiting embodiments, the extracellular antigen-binding domain of a presently disclosed CAR has a high binding specificity as well as high binding affinity to the G-protein coupled receptor (e.g., GPRC5D). For example, in such embodiments, the extracellular antigen-binding domain of the CAR (embodied, for example, in a scFv or an analog thereof) binds to GPRC5D with a dissociation constant ($K_D$) of about $3\times10^{-6}$ M or less. In certain embodiments, the $K_D$ is about $1\times10^{-6}$ M or less, about $1\times10^{-7}$ M or less, about $1\times10^{-8}$ M or less, or about $1\times10^{-9}$ M or less, about $1\times10^{-10}$ M or less, or about $1\times10^{-11}$ M or less. In certain embodiments, the $K_D$ is about $1\times10^{-8}$M or less. In certain embodiments, the $K_D$ is from about $1\times10^{-11}$M to about $3\times10^{-6}$ M, such as from about $1\times10^{-11}$M to about $1\times10^{-10}$ M, from about $1\times10^{-10}$ M to about $1\times10^{-9}$ M, from about $1\times10^{-9}$M to about $1\times10^{-8}$ M, from about $1\times10^{-8}$M to about $1\times10^{-7}$ M, or from about $1\times10^{-7}$M to about $1\times10^{-6}$ M, or from about $1\times10^{-6}$M to about $3\times10^{-6}$ M. In certain embodiments, the $K_D$ is from about $1\times10^{-9}$ M to about $1\times10^{-8}$ M. In certain embodiments, the $K_D$ is from about $1\times10^{-9}$ M to about $1.5\times10^{-9}$ M. In certain embodiments, the $K_D$ is about $1.2\times10^{-9}$M. In certain embodiments, the $K_D$ is from about $4\times10^{-9}$M to about $5\times10^{-9}$ M. In certain embodiments, the $K_D$ is about $5\times10^{-9}$ M. In certain embodiments, the $K_D$ is about $4.8\times10^{-9}$ M. In certain embodiments, the $K_D$ is from about $8\times10^{-9}$M to about $9\times10^{-9}$ M. In certain embodiments, the $K_D$ is about $8\times10^{-9}$M. In certain embodiments, the $K_D$ is about $8.1\times10^{-9}$M Binding of the extracellular antigen-binding domain (embodiment, for example, in an scFv or an analog thereof) of a presently disclosed CAR to a G-protein coupled receptor (e.g., GPRC5D) can be confirmed by, for example, enzyme-linked immunosorbent assay (ELISA), radioimmunoassay (MA), FACS analysis, bioassay (e.g., growth inhibition), or Western Blot assay. Each of these assays generally detect the presence of protein-antibody complexes of particular interest by employing a labeled reagent (e.g., an antibody, or a scFv) specific for the complex of interest. For example, the scFv can be radioactively labeled and used in a radioimmunoassay (MA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the GPRC5D-targeted extracellular antigen-binding domain is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet). In certain embodiments, the GPRC5D-targeted human scFv is labeled with GFP.

In certain embodiments, the extracellular antigen-binding domain of a presently disclosed CAR comprises a single-chain variable fragment (scFv). In one specific embodiment, the extracellular antigen-binding domain of a presently disclosed CAR comprises a human scFv that specifically binds to human GPRC5D. In another specific embodiment, the extracellular antigen-binding domain of a presently disclosed CAR comprises a murine scFv that specifically binds to human GPRC5D. In certain embodiments, the scFv are identified by screening scFv phage library with cells (e.g., 3T3 cells) that express GPRC5D.

Extracellular Antigen-Binding Domain of A CAR

In certain embodiments, the extracellular antigen-binding domain (e.g., scFv) comprises a heavy chain variable region comprising amino acids having a sequence selected from the group consisting of: SEQ ID NOS:1, 5, 9, 13, 17, 21, 25, 29, 33, 37, 41, 45, 49, 53, 57, 61, 65, 69, 73, 77, 81, 85, 89, and 93. The nucleic acid sequences encoding the amino acid sequence of SEQ ID NOS:1, 5, 9, 13, 17, 21, 25, 29, 33, 37, 41, 45, 49, 53, 57, 61, 65, 69, 73, 77, 81, 85, 89, and 93 are 3, 7, 11, 15, 19, 23, 27, 31, 35, 39, 43, 47, 51, 55, 59, 63, 67, 71, 75, 79, 83, 87, 91, and 95, respectively. In some embodiments, the extracellular antigen-binding domain (e.g., scFv) comprises a light chain variable region comprising amino acids having a sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, and 94. The nucleic acid sequences encoding the amino acid sequence of SEQ ID NOS: 2, 6, 10, 14, 18, 22, 26, 30, 34, 38, 42, 46, 50, 54, 58, 62, 66, 70, 74, 78, 82, 86, 90, and 94 are 4, 8, 12, 16, 20, 24, 28, 32, 36, 40, 44, 48, 52, 56, 60, 64, 68, 72, 76, 80, 84, 88, 92, and 96, respectively. The sequences of SEQ ID NOS:1-96 are described in the following Tables 1-24.

In certain embodiments, the extracellular antigen-binding domain (e.g., scFv) comprises heavy and light chain variable regions comprising amino acid sequences that are homologous to the amino acid sequences described herein and as disclosed in Tables 1-24. For example, and not by way of limitation, the extracellular antigen-binding domain (e.g., scFv) comprises a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 302, 314, 326, 338, 350, 362, 374, and 386.

In certain embodiments, the extracellular antigen-binding domain (e.g., scFv) comprises a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 303, 315, 327, 339, 351, 363, 375, and 387.

In certain embodiments, the extracellular antigen-binding domain (e.g., scFv) comprises (a) a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 302, 314, 326, 338, 350, 362, 374, and 386; and (b) a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 303, 315, 327, 339, 351, 363, 375, and 387.

The presently disclosed subject matter further provides extracellular antigen-binding domains (e.g., scFv) that comprise heavy chain variable region and light chain variable region CDRs, e.g., CDR1s, CDR2s and CDR3s, as disclosed herein in Tables 1-24. The CDR regions are delineated using the Kabat system (Kabat, E. A., et al. (1991) Sequences of Proteins of Immunological Interest, Fifth Edition, U.S. Department of Health and Human Services, NIH Publication No. 91-3242). The presently disclosed subject matter further provides extracellular antigen-binding domains (e.g., scFv) that comprise conservative modifications of the antibody sequences disclosed herein. For example, and not by way of limitation, an extracellular antigen-binding domains (e.g., scFv) of the presently disclosed subject matter comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences disclosed herein, or conservative modifications thereof, and wherein the extracellular antigen-binding domains retain the desired functional properties.

In certain embodiments, the presently disclosed subject matter provides an extracellular antigen-binding domain (e.g., scFv) comprising a heavy chain variable region, wherein the heavy chain variable region comprises: (a) a CDR1 comprising an amino acid sequence selected from the group consisting of SEQ ID NOS: 124, 130, 136, 142, 148, 154, 160, 166, 172, 178, 184, 190, 196, 202, 208, 214, 220, 226, 232, 238, 244, 250, 256, 262, 304, 316, 328, 340, 352, 364, 376, and 388, and conservative modifications thereof; (b) a CDR2 comprising an amino acid sequence selected from the group consisting of SEQ ID NOS: 125, 131, 137, 143, 149, 155, 161, 167, 173, 179, 185, 191, 197, 203, 209, 215, 221, 227, 233, 239, 245, 251, 257, 263, 305, 317, 329, 341, 353, 365, 377, and 389, and conservative modifications thereof; and (c) a CDR3 comprising an amino acid sequence selected from the group consisting of SEQ ID NOS: 126, 132, 138, 144, 150, 156, 162, 168, 174, 180, 186, 192, 198, 204, 210, 216, 222, 228, 234, 240, 246, 252, 258, 264, 306, 318, 330, 342, 354, 366, 378, and 390, and conservative modifications thereof.

In certain embodiments, the extracellular antigen-binding domain (e.g., scFv) comprises a light chain variable region, wherein the light chain variable region comprises: (a) a CDR1 comprising an amino acid sequence selected from the group consisting of SEQ ID NOS: 127, 133, 139, 145, 151, 157, 163, 169, 175, 181, 187, 193, 199, 205, 211, 217, 223, 229, 235, 241, 247, 253, 259, 265, 307, 319, 331, 343, 355, 367, 379, and 391, and conservative modifications thereof; (b) a CDR2 comprising an amino acid sequence selected from the group consisting of SEQ ID NOS: 128, 134, 140, 146, 152, 158, 164, 170, 176, 182, 188, 194, 200, 206, 212, 218, 224, 230, 236, 242, 248, 254, 260, 266, 308, 320, 332, 344, 356, 368, 380, and 392, and conservative modifications thereof and (c) a CDR3 comprising an amino acid sequence selected from the group consisting of SEQ ID NOS: 129, 135, 141, 147, 153, 159, 165, 171, 177, 183, 189, 195, 201, 207, 213, 219, 225, 231, 237, 243, 249, 255, 261, 267, 309, 321, 333, 345, 357, 369, 381, and 393, and conservative modifications thereof.

The presently disclosed subject matter provides an extracellular antigen-binding domain (e.g., scFv) comprising a heavy chain variable region comprising CDR1, CDR2, and CDR3 sequences and a light chain variable region comprising CDR1, CDR2, and CDR3 sequences, wherein: (a) the heavy chain variable region CDR3 comprises an amino acid sequence selected from the group consisting of SEQ ID NOs: 126, 132, 138, 144, 150, 156, 162, 168, 174, 180, 186, 192, 198, 204, 210, 216, 222, 228, 234, 240, 246, 252, 258, 264, 306, 318, 330, 342, 354, 366, 378, and 390, and conservative modifications thereof and (b) the light chain variable region CDR3 comprises an amino acid sequence selected from the group consisting of SEQ ID NOS: 129, 135, 141, 147, 153, 159, 165, 171, 177, 183, 189, 195, 201, 207, 213, 219, 225, 231, 237, 243, 249, 255, 261, 267, 309, 321, 333, 345, 357, 369, 381, and 393, and conservative modifications thereof wherein the extracellular antigen-binding domain specifically binds to a GPRC5D polypeptide (e.g., a human GPRC5D polypeptide). In certain embodiments, the heavy chain variable region CDR2 comprises an amino acid sequence selected from the group consisting of SEQ ID NOs: 125, 131, 137, 143, 149, 155, 161, 167, 173, 179, 185, 191, 197, 203, 209, 215, 221, 227, 233, 239, 245, 251, 257, 263, 305, 317, 329, 341, 353, 365, 377, and 389, and conservative modifications thereof; and (b) the light chain variable region CDR2 comprises an amino acid sequence selected from the group consisting of SEQ ID NOS: 128, 134, 140, 146, 152, 158, 164, 170, 176, 182, 188, 194, 200, 206, 212, 218, 224, 230, 236, 242, 248, 254, 260, 266, 308, 320, 332, 344, 356, 368, 380, and 392, and conservative modifications thereof; wherein the extracellular antigen-binding domain specifically binds to a GPRC5D polypeptide (e.g., a human GPRC5D polypeptide). In certain embodiments, the heavy chain variable region CDR1 comprises an amino acid sequence selected from the group consisting of SEQ ID NOs: 124, 130, 136, 142, 148, 154, 160, 166, 172, 178, 184, 190, 196, 202, 208, 214, 220, 226, 232, 238, 244, 250, 256, 262, 304, 316, 328, 340, 352, 364, 376, and 388, and conservative modifications thereof; and (b) the light chain variable region CDR1 comprises an amino acid sequence selected from the group consisting of SEQ ID NOS: 127, 133, 139, 145, 151, 157, 163, 169, 175, 181, 187, 193, 199, 205, 211, 217, 223, 229, 235, 241, 247, 253, 259, 265, 307, 319, 331, 343, 355, 367, 379, and 391, and conservative modifications thereof; wherein the extracellular antigen-binding domain specifically binds to a GPRC5D polypeptide (e.g., a human GPRC5D polypeptide).

In certain embodiments, the extracellular antigen-binding domain is a scFv, which comprises the amino acid sequence of SEQ ID NO: 100 and specifically binds to a GPRC5D polypeptide (e.g., a GPRC5D polypeptide having the amino acid sequence SEQ ID NO:97, or fragments thereof), which scFv is designated as ET150-153 scFv (also referred to as "ET150-3 scFv").

In certain embodiments, the extracellular antigen-binding domain is a scFv, which comprises a heavy chain variable region comprising amino acids having the sequence set forth in SEQ ID NO:1 and a light chain variable region comprising amino acids having the sequence set forth in SEQ ID NO:2, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 1. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:1, as shown in Table 1. In certain embodiments, the extracellular antigen-binding domain comprises a $V_H$ comprising amino acids having the sequence set forth in SEQ ID NO:1, as shown in Table 1. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:2, as shown in Table 1. In certain embodiments, the extracellular antigen-binding domain comprises a $V_L$ comprising amino acids having the sequence set forth in SEQ ID NO:2, as shown in Table 1. In certain embodiments, the extracellular antigen-binding domain comprises a $V_H$ comprising amino acids having the sequence set forth in SEQ ID NO:1 and a $V_L$ comprising amino acids having the sequence set forth in SEQ ID NO:2, as shown in Table 1. In certain embodiments, the extracellular antigen-binding domain comprises a $V_H$ CDR1 comprising amino acids having the sequence set forth in SEQ ID NO:124 or conservative modifications thereof, a $V_H$ CDR2 comprising amino acids having the sequence set forth in SEQ ID NO:125 or conservative modifications thereof, and a $V_H$ CDR3 comprising amino acids having the sequence set forth in SEQ ID NO:126 or conservative modifications thereof, as shown in Table 1. In certain embodiments, the extracellular antigen-binding domain comprises a $V_L$ CDR1 comprising amino acids having the sequence set forth in SEQ ID NO:127 or conservative modifications thereof, a $V_L$ CDR2 comprising amino acids having the sequence set forth in SEQ ID NO:128 or conservative modifications thereof, and a $V_L$ CDR3 comprising amino acids having the sequence set forth in SEQ ID NO:129 or conservative modifications thereof, as shown in Table 1. In certain embodiments, the extracellular antigen-binding domain comprises a $V_H$ CDR1 comprising amino acids having the sequence set forth in SEQ ID NO:124 or conservative modifications thereof, a $V_H$ CDR2 comprising amino acids having the sequence set forth in SEQ ID NO:125 or conservative modifications thereof, a $V_H$ CDR3 comprising amino acids having the sequence set forth in SEQ ID NO:126 or conservative modifications thereof, a $V_L$ CDR1 comprising amino acids having the sequence set forth in SEQ ID NO:127 or conservative modifications thereof, a $V_L$ CDR2 comprising amino acids having the sequence set forth in SEQ ID NO:128 or conservative modifications thereof, and a $V_L$ CDR3 comprising amino acids having the sequence set forth in SEQ ID NO:129 or conservative modifications thereof, as shown in Table 1. In certain embodiments, the extracellular antigen-binding domain comprises a $V_H$ CDR1 comprising amino acids having the sequence set forth in SEQ ID NO:124, a $V_H$ CDR2 comprising amino acids having the sequence set forth in SEQ ID NO:125, a $V_H$ CDR3 comprising amino acids having the sequence set forth in SEQ ID NO:126, a $V_L$ CDR1 comprising amino acids having the sequence set forth in SEQ ID NO:127, a $V_L$ CDR2 comprising amino acids having the sequence set forth in SEQ ID NO:128, and a $V_L$ CDR3 comprising amino acids having the sequence set forth in SEQ ID NO:129.

TABLE 1

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFTSYY [SEQ ID NO: 124] | GYTFTSYY [SEQ ID NO: 125] | ARGMYRSLLFYDP [SEQ ID NO: 126] |
| $V_L$ | RSNVGNYY [SEQ ID NO: 127] | DNN [SEQ ID NO: 128] | GTWDGSLSAHV [SEQ ID NO: 129] |
| Full $V_H$ | QVQLVQSGSELKKPGASVRVSCTASGYTFTSYYMHWVRQAPGQ GLEWMGVINPNAGSTRYAQKFQGRVTMSTDTSTSTAYMDLSSL RSEDTAVYYCARGMYRSLLFYDPWGQGTLVTVSS [SEQ ID NO: 1] | | |
| DNA | Caggtgcagctggtgcagtctgggtctgagttgaagaagcctggggcctcagtcagagtctcctgcac ggcttctggatacaccttcaccagttactatatgcactgggtgcgacaggcccctggacaagggcttga gtggatgggagtaatcaaccctaatgctggcagcacaagatacgcacagaaattccagggcagagtca ccatgagcactgacacgtccacgagcacagcctacatggacctgagcagtctgagatctgaggacac ggccgtgtattactgtgcgcgcggtatgtaccgttctctgctgttctacgatccgtggggtcaaggtactct ggtgaccgtctcctca [SEQ ID NO: 3] | | |
| Full $V_L$ | QSVLTQPPSVSAAPGQKVTIPCSGSRSNVGNYYVSWYQQLPGTA PKLLIYDNNKRPSGIPDRFSGSKSGTSATLGITGLQTGDEADYFCG TWDGSLSAHVFGTGTKVTVLG [SEQ ID NO: 2] | | |
| DNA | Cagtctgtgttgacgcagccgccctcagtgtctgcggccccaggacagaaggtcaccatcccctgctc tggaagccgttccaacgttgggaattattatgtgtcctggtaccagcaactcccaggaacagcccccaa actcctcatttatgacaataataagcgaccctcagggattcctgaccgattctctggctccaagtctggca cgtcagccaccctgggcatcaccggactccagactggggacgaggccgattatttctgcggaacatgg gatggcagcctgagtgcccatgtatcggaactgggaccaaggtcaccgtcctaggt [SEQ ID NO: 4] | | |

TABLE 1-continued

| | |
|---|---|
| scFv | QSVLTQPPSVSAAPGQKVTIPCSGSRSNVGNYYVSWYQQLPGTA PKLLIYDNNKRPSGIPDRFSGSKSGTSATLGITGLQTGDEADYFCG TWDGSLSAHVFGTGTKVTVLGSRGGGGSGGGGSGGGGSLEMAQ VQLVQSGSELKKPGASVRVSCTASGYTFTSYYMHWVRQAPGQG LEWMGVINPNAGSTRYAQKFQGRVTMSTDTSTSTAYMDLSSLRS EDTAVYYCARGMYRSLLFYDPWGQGTLVTVSS [SEQ ID NO: 100] |

In certain embodiments, the extracellular antigen-binding domain is a scFv, which comprises the amino acid sequence of SEQ ID NO: 101 and specifically binds to a GPRC5D polypeptide (e.g., a GPRC5D polypeptide having the amino acid sequence SEQ ID NO:97, or fragments thereof), which scFv is designated as ET150-166 scFv (also referred to as "ET150-16 scFv").

In certain embodiments, the extracellular antigen-binding domain is a scFv, which comprises a heavy chain variable region comprising amino acids having the sequence set forth in SEQ ID NO:5 and a light chain variable region comprising amino acids having the sequence set forth in SEQ ID NO:6, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 2. In certain embodiments, the extracellular antigen-binding domain is a human scFv. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:5, as shown in Table 2. In certain embodiments, the extracellular antigen-binding domain comprises a $V_H$ comprising amino acids having the sequence set forth in SEQ ID NO:5, as shown in Table 2. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:6, as shown in Table 2. In certain embodiments, the extracellular antigen-binding domain comprises a $V_L$ comprising amino acids having the sequence set forth in SEQ ID NO:6, as shown in Table 2. In certain embodiments, the extracellular antigen-binding domain comprises a $V_H$ comprising amino acids having the sequence set forth in SEQ ID NO:5 and a $V_L$ comprising amino acids having the sequence set forth in SEQ ID NO:6, as shown in Table 2. In certain embodiments, the extracellular antigen-binding domain comprises a $V_H$ CDR1 comprising amino acids having the sequence set forth in SEQ ID NO:130 or conservative modifications thereof, a $V_H$ CDR2 comprising amino acids having the sequence set forth in SEQ ID NO:131 or conservative modifications thereof, and a $V_H$ CDR3 comprising amino acids having the sequence set forth in SEQ ID NO:132 or conservative modifications thereof, as shown in Table 2. In certain embodiments, the extracellular antigen-binding domain comprises a $V_L$ CDR1 comprising amino acids having the sequence set forth in SEQ ID NO:133 or conservative modifications thereof, a $V_L$ CDR2 comprising amino acids having the sequence set forth in SEQ ID NO:134 or conservative modifications thereof, and a $V_L$ CDR3 comprising amino acids having the sequence set forth in SEQ ID NO:135 or conservative modifications thereof, as shown in Table 2. In certain embodiments, the extracellular antigen-binding domain comprises a $V_H$ CDR1 comprising amino acids having the sequence set forth in SEQ ID NO:130 or conservative modifications thereof, a $V_H$ CDR2 comprising amino acids having the sequence set forth in SEQ ID NO:131 or conservative modifications thereof, a $V_H$ CDR3 comprising amino acids having the sequence set forth in SEQ ID NO:132 or conservative modifications thereof, a $V_L$ CDR1 comprising amino acids having the sequence set forth in SEQ ID NO:133 or conservative modifications thereof, a $V_L$ CDR2 comprising amino acids having the sequence set forth in SEQ ID NO:134 or conservative modifications thereof, and a $V_L$ CDR3 comprising amino acids having the sequence set forth in SEQ ID NO:135 or conservative modifications thereof, as shown in Table 2. In certain embodiments, the extracellular antigen-binding domain comprises a $V_H$ CDR1 comprising amino acids having the sequence set forth in SEQ ID NO:130, a $V_H$ CDR2 comprising amino acids having the sequence set forth in SEQ ID NO:131, a $V_H$ CDR3 comprising amino acids having the sequence set forth in SEQ ID NO:132, a $V_L$ CDR1 comprising amino acids having the sequence set forth in SEQ ID NO:133, a $V_L$ CDR2 comprising amino acids having the sequence set forth in SEQ ID NO:134, and a $V_L$ CDR3 comprising amino acids having the sequence set forth in SEQ ID NO:135.

TABLE 2

| | | | |
|---|---|---|---|
| Antigen | A GPRC5D polypeptide having the amino acid sequence of SEQ ID NO: 97 | | |
| CDRs | 1 | 2 | 3 |
| $V_H$ | GFTFSNYA [SEQ ID NO: 130] | ISGSGNT [SEQ ID NO: 131] | ARGSVRYTDI [SEQ ID NO: 132] |
| $V_L$ | SGAIAGAY [SEQ ID NO: 133] | DDN [SEQ ID NO: 134] | QSYDYDSSNVL [SEQ ID NO: 135] |
| Full $V_H$ | EVQLVESGGGLVQPGGSLRLSCAASGFTFSNYAMSWVRQAPGK GLEWVSAISGSGNTYYADSVKGRFTISRDNSKNTLYLQMNSLRA EDTAVYYCARGSVRYTDIWGQGTLVTVSS [SEQ ID NO: 5] | | |

TABLE 2-continued

```
DNA      Gaggtgcagctggtggagtctgggggaggcttggtacagcctggggggtccctgagactctcctgtg
         cagcctctggattcacctttagcaactatgccatgagttgggtccgccaggctccagggaagggactgg
         agtgggtctcagctattagtggtagtggtaacacatactacgcagactccgtgaagggccggttcaccat
         ctccagagacaattccaagaacacgctgtatctgcaaatgaacagcctgagagccgaggacacggcc
         gtatattactgtgcgcgcggttctgttcgttacactgatatctggggtcaaggtactctggtgaccgtctcct
         ca [SEQ ID NO: 7]

Full V_L NFMLTQPHSVSESPGKTVSISCTRTSGAIAGAYVQWFQQRPGSAP
         TTVIYDDNKRPSGVPDRFSGSIDKSSNSASLTISGLKTEDEADYYC
         QSYDYDSSNVLFGGGTKLTVLG [SEQ ID NO: 6]

DNA      Aattttatgctgactcagccccactcagtgtcggagtctccggggaagacggtaagcatctcctgcacc
         cgcaccagtggcgccattgccggcgcctatgtgcagtggttccagcagcgcccgggcagtgccccca
         ccactgtgatctatgacgataacaaaagaccctctggggtccctgatcggttctctgggtccatcgacaa
         gtcctccaactctgcctccctcaccatctctggactgaagactgaggacgaggctgactattattgtcagt
         cttatgattatgatagcagcaatgtgctattcggcggagggaccaagctgaccgtcctaggt [SEQ
         ID NO: 8]

scFv     NFMLTQPHSVSESPGKTVSISCTRTSGAIAGAYVQWFQQRPGSAP
         TTVIYDDNKRPSGVPDRFSGSIDKSSNSASLTISGLKTEDEADYYC
         QSYDYDSSNVLFGGGTKLTVLGSRGGGGSGGGGSGGGGSLEMA
         EVQLVESGGGLVQPGGSLRLSCAASGFTFSNYAMSWVRQAPGK
         GLEWVSAISGSGNTYYADSVKGRFTISRDNSKNTLYLQMNSLRA
         EDTAVYYCARGSVRYTDIWGQGTLVTVSS [SEQ ID NO: 101]
```

In certain embodiments, the extracellular antigen-binding domain is a scFv, which comprises the amino acid sequence of SEQ ID NO: 102 and specifically binds to a GPRC5D polypeptide (e.g., a GPRC5D polypeptide having the amino acid sequence SEQ ID NO:97, or fragments thereof), which scFv is designated as ET150-170 scFv (also referred to as "ET150-20 scFv").

In certain embodiments, the extracellular antigen-binding domain is a scFv, which comprises a heavy chain variable region comprising amino acids having the sequence set forth in SEQ ID NO:9 and a light chain variable region comprising amino acids having the sequence set forth in SEQ ID NO:10, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 3. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:9, as shown in Table 3. In certain embodiments, the extracellular antigen-binding domain comprises a $V_H$ comprising amino acids having the sequence set forth in SEQ ID NO:9, as shown in Table 3. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:10, as shown in Table 3. In certain embodiments, the extracellular antigen-binding domain comprises a $V_L$ comprising amino acids having the sequence set forth in SEQ ID NO:10, as shown in Table 3. In certain embodiments, the extracellular antigen-binding domain comprises a $V_H$ comprising amino acids having the sequence set forth in SEQ ID NO:9 and a $V_L$ comprising amino acids having the sequence set forth in SEQ ID NO:10, as shown in Table 3. In certain embodiments, the extracellular antigen-binding domain comprises a $V_H$ CDR1 comprising amino acids having the sequence set forth in SEQ ID NO:136 or conservative modifications thereof, a $V_H$ CDR2 comprising amino acids having the sequence set forth in SEQ ID NO:137 or conservative modifications thereof, and a $V_H$ CDR3 comprising amino acids having the sequence set forth in SEQ ID NO:138 or conservative modifications thereof, as shown in Table 3. In certain embodiments, the extracellular antigen-binding domain comprises a $V_L$ CDR1 comprising amino acids having the sequence set forth in SEQ ID NO:139 or conservative modifications thereof, a $V_L$ CDR2 comprising amino acids having the sequence set forth in SEQ ID NO:140 or conservative modifications thereof, and a $V_L$ CDR3 comprising amino acids having the sequence set forth in SEQ ID NO:141 or conservative modifications thereof, as shown in Table 3. In certain embodiments, the extracellular antigen-binding domain comprises a $V_H$ CDR1 comprising amino acids having the sequence set forth in SEQ ID NO:136 or conservative modifications thereof, a $V_H$ CDR2 comprising amino acids having the sequence set forth in SEQ ID NO:137 or conservative modifications thereof, a $V_H$ CDR3 comprising amino acids having the sequence set forth in SEQ ID NO:138 or conservative modifications thereof, a $V_L$ CDR1 comprising amino acids having the sequence set forth in SEQ ID NO:139 or conservative modifications thereof, a $V_L$ CDR2 comprising amino acids having the sequence set forth in SEQ ID NO:140 or conservative modifications thereof, and a $V_L$ CDR3 comprising amino acids having the sequence set forth in SEQ ID NO:141 or conservative modifications thereof, as shown in Table 3. In certain embodiments, the extracellular antigen-binding domain comprises a $V_H$ CDR1 comprising amino acids having the sequence set forth in SEQ ID NO:136, a $V_H$ CDR2 comprising amino acids having the sequence set forth in SEQ ID NO:137, a $V_H$ CDR3 comprising amino acids having the sequence set forth in SEQ ID NO:138, a $V_L$ CDR1 comprising amino acids having the sequence set forth in SEQ ID NO:139, a $V_L$ CDR2 comprising amino acids having the sequence set forth in SEQ ID NO:140, and a $V_L$ CDR3 comprising amino acids having the sequence set forth in SEQ ID NO:141.

TABLE 3

| | | | |
|---|---|---|---|
| Antigen | A GPRC5D polypeptide having the amino acid sequence of SEQ ID NO: 97 | | |
| CDRs | 1 | 2 | 3 |
| $V_H$ | GFTFNNYW [SEQ ID NO: 136] | IKQDGSEK [SEQ ID NO: 137] | ARSMSTAV [SEQ ID NO: 138] |
| $V_L$ | QSISSY [SEQ ID NO: 139] | AAS [SEQ ID NO: 140] | QQSYSVPYT [SEQ ID NO: 141] |
| Full $V_H$ | EVQLVQSGGGLVQPGGSLRLSCATSGFTFNNYWMSWVRQAPGK<br>GLEWVANIKQDGSEKYYADSVRGRFTISRDNAKNSLSLQLNNLRA<br>EDTAVYYCARSMSTAWGYDEWGQGTLVTVSS [SEQ ID NO: 9] | | |
| DNA | Gaggtgcagctggtgcagtctgggggaggcttggtccagcctggggggtccctgagactctcctgtgc<br>aacctctggattcacctttaataactattggatgagttgggtccgccaggctccagggaaggggctggagt<br>gggtggccaacataaagcaagatggaagtgagaaatactacgcggactctgtgaggggccgattcacc<br>atctccagagacaacgccaagaactcactgtctctgcaattgaacaacctgagagccgaggacacggcc<br>gtgtattactgtgcgcgctctatgtctactgcttggggttacgatgaatggggtcaaggtactctggtgacc<br>gtctcctca [SEQ ID NO: 11] | | |
| Full $V_L$ | DIQLTQSPSSLSASVGDRVTITCRASQSISSYLNWYQQKPGKAPKL<br>LIYAASSLQSGVPSRFSGSGSGTDFTLTISSLQPADFATYYCQQSYS<br>VPYTFGQGTKLEIKR [SEQ ID NO: 10] | | |
| DNA | Gacatccagttgacccagtctccatcctccctgtctgcatctgtcggagacagagtcaccatcacttgccg<br>ggcaagtcagagcattagcagctatttaaattggtatcaacagaaaccagggaaagcccctaagctcctg<br>atctatgctgcatccagtttgcaaagtggggtcccatcaaggttcagtggcagtggatctgggacagatttc<br>actctcaccatcagcagtctgcaacctgcagattttgcaacttactactgtcaacagagttacagtgtcccgt<br>acacttttggccaggggaccaagctggagatcaaacgt [SEQ ID NO: 12] | | |
| scFv | DIQLTQSPSSLSASVGDRVTITCRASQSISSYLNWYQQKPGKAPKL<br>LIYAASSLQSGVPSRFSGSGSGTDFTLTISSLQPADFATYYCQQSYS<br>VPYTFGQGTKLEIKRSRGGGGSGGGGSGGGGSLEMAEVQLVQSG<br>GGLVQPGGSLRLSCATSGFTFNNYWMSWVRQAPGKGLEWVANI<br>KQDGSEKYYADSVRGRFTISRDNAKNSLSLQLNNLRAEDTAVYY<br>CARSMSTAWGYDEWGQGTLVTVSS [SEQ ID NO: 102] | | |

In certain embodiments, the extracellular antigen-binding domain is a scFv, which comprises the amino acid sequence of SEQ ID NO: 103 and specifically binds to a GPRC5D polypeptide (e.g., a GPRC5D polypeptide having the amino acid sequence SEQ ID NO:97, or fragments thereof), which scFv is designated as ET150-171 scFv (also referred to as "ET150-21 scFv").

In certain embodiments, the extracellular antigen-binding domain is a scFv, which comprises a heavy chain variable region comprising amino acids having the sequence set forth in SEQ ID NO:13 and a light chain variable region comprising amino acids having the sequence set forth in SEQ ID NO:14, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 4. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:13, as shown in Table 4. In certain embodiments, the extracellular antigen-binding domain comprises a $V_H$ comprising amino acids having the sequence set forth in SEQ ID NO:13, as shown in Table 4. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:14, as shown in Table 4. In certain embodiments, the extracellular antigen-binding domain comprises a $V_L$ comprising amino acids having the sequence set forth in SEQ ID NO:14, as shown in Table 4. In certain embodiments, the extracellular antigen-binding domain comprises a $V_H$ comprising amino acids having the sequence set forth in SEQ ID NO:13 and a $V_L$ comprising amino acids having the sequence set forth in SEQ ID NO:14, as shown in Table 4. In certain embodiments, the extracellular antigen-binding domain comprises a $V_H$ CDR1 comprising amino acids having the sequence set forth in SEQ ID NO:142 or conservative modifications thereof, a $V_H$ CDR2 comprising amino acids having the sequence set forth in SEQ ID NO:143 or conservative modifications thereof, and a $V_H$ CDR3 comprising amino acids having the sequence set forth in SEQ ID NO:144 or conservative modifications thereof, as shown in Table 4. In certain embodiments, the extracellular antigen-binding domain comprises a $V_L$ CDR1 comprising amino acids having the sequence set forth in SEQ ID NO:145 or conservative modifications thereof, a $V_L$ CDR2 comprising amino acids having the sequence set forth in SEQ ID NO:146 or conservative modifications thereof, and a $V_L$ CDR3 comprising amino acids having the sequence set forth in SEQ ID NO:147 or conservative modifications thereof, as shown in Table 4. In certain embodiments, the extracellular antigen-binding domain comprises a $V_H$ CDR1 comprising amino acids having the sequence set forth in SEQ ID NO:142 or conservative modifications thereof, a $V_H$ CDR2 comprising amino acids having the sequence set forth in SEQ ID NO:143 or conservative modifications thereof, a $V_H$ CDR3 comprising amino acids having the sequence set forth in SEQ ID NO:144 or conservative modifications thereof, a $V_L$ CDR1 comprising amino acids having the sequence set forth in SEQ ID NO:145 or conservative modifications thereof, a $V_L$ CDR2 comprising amino acids having the sequence set forth in SEQ ID NO:146 or conservative modifications thereof, and a $V_L$ CDR3 comprising amino acids having the sequence set forth in SEQ ID NO:147 or conservative modifications thereof, as shown in Table 4. In certain embodiments, the extracellular antigen-binding domain comprises a $V_H$ CDR1 comprising amino acids having the sequence set forth in SEQ ID NO:142, a $V_H$ CDR2 comprising amino acids having the sequence set forth in SEQ ID NO:143, a $V_H$ CDR3 comprising amino acids having the sequence set forth in SEQ ID NO:144, a $V_L$ CDR1 comprising amino acids having the sequence set forth in SEQ ID NO:145, a $V_L$ CDR2 comprising amino acids having the sequence set forth in SEQ ID NO:146, and a $V_L$ CDR3 comprising amino acids having the sequence set forth in SEQ ID NO:147.

In certain embodiments, the extracellular antigen-binding domain is a scFv, which comprises a heavy chain variable region comprising amino acids having the sequence set forth in SEQ ID NO:17 and a light chain variable region comprising amino acids having the sequence set forth in SEQ ID NO:18, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 5. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:17, as shown in Table 5. In certain embodiments, the extracellular

TABLE 4

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFTSYY [SEQ ID NO: 142] | INPSGGST [SEQ ID NO: 143] | ARGSSRWGGWTGDY [SEQ ID NO: 144] |
| $V_L$ | SSDVGGYNF [SEQ ID NO: 145] | DVS [SEQ ID NO: 146] | SSYTSTRTVIFAGGTKVTVL [SEQ ID NO: 147] |
| Full $V_H$ | QVQLVQSGAEVKKPGASVKVSCKASGYTFTSYYMHWVRQAPG QGLEWMGIINPSGGSTRYAQKFQGRVTMTRDTSTSTVYMELSSL RSEDTAVYYCARGSSRWGGWTGDYWGQGTLVTVSS [SEQ ID NO: 13] | | |
| DNA | Caggtgcagctggtgcagtctggggctgaggtgaagaagcctggggcctcagtgaaggtttcctgca aggcatctggatacaccttcaccagctactatatgcactgggtgcgacaggcccctggacaagggcttg agtggatgggaataatcaaccctagtggtggtagcacaaggtacgcacagaagttccagggcagagtc accatgaccagggacacgtcaacgagcacagtctacatggagctgagcagcctgagatctgaggaca cggccgtgtattactgtgcgcgcggttcttctcgctggggtggttggactggtgattactggggtcaaggt actctggtgaccgtctcctca [SEQ ID NO: 15] | | |
| Full $V_L$ | QSALTQPASVSGSPGQSITISCTGTSSDVGGYNFVSWYQQHPGKA PKVMIYDVSKRPSGISNRFSGSKSGNTASLTISGLQVEDEAEYYCS SYTSTRTVIFAGGTKVTVLG [SEQ ID NO: 14] | | |
| DNA | Caatctgccctgactcagcctgcctccgtgtctgggtctcctggacagtcgatcaccatctcctgcactg gaaccagcagtgacgttggtggttataactttgtctcctggtaccaacagcacccaggcaaagcccccca aagtcatgatttatgatgtcagtaageggccctcagggatttctaatcgcttctctggctccaagtctggca acacggcctccctgaccatctctgggctccaggttgaggacgaggctgaatattactgcagctcatatac aagcactagaactgtgatattcgccggagggaccaaggtcaccgtcctaggt [SEQ ID NO: 16] | | |
| scFv | QSALTQPASVSGSPGQSITISCTGTSSDVGGYNFVSWYQQHPGKA PKVMIYDVSKRPSGISNRFSGSKSGNTASLTISGLQVEDEAEYYCS SYTSTRTVIFAGGTKVTVLG SRGGGGSGGGGSGGGGSLEMAQVQLVQSGAEVKKPGASVKVSC KASGYTFTSYYMHWVRQAPGQGLEWMGIINPSGGSTRYAQKFQ GRVTMTRDTSTSTVYMELSSLRSEDTAVYYCARGSSRWGGWTG DYWGQGTLVTVSS [SEQ ID NO: 103] | | |

In certain embodiments, the extracellular antigen-binding domain is a scFv, which comprises the amino acid sequence of SEQ ID NO: 104 and specifically binds to a GPRC5D polypeptide (e.g., a GPRC5D polypeptide having the amino acid sequence SEQ ID NO:97, or fragments thereof), which scFv is designated as ET150-175 scFv (also referred to as "ET150-25 scFv").

antigen-binding domain comprises a $V_H$ comprising amino acids having the sequence set forth in SEQ ID NO:17, as shown in Table 5. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:18, as shown in Table 5. In certain embodiments, the extracellular antigen-binding domain comprises a $V_L$ comprising amino acids having the sequence set forth in SEQ ID NO:18, as shown in Table 5. In certain embodiments, the extracellular antigen-binding domain comprises a $V_H$ comprising amino acids having the sequence set forth in SEQ ID NO:17 and a $V_L$ comprising amino acids having the sequence set forth in SEQ ID NO:18, as shown in Table 5. In certain embodiments, the extracellular antigen-binding domain comprises a $V_H$ CDR1 comprising amino acids having the sequence set forth in SEQ ID NO:148 or conservative modifications thereof, a $V_H$ CDR2 comprising amino acids having the sequence set forth in SEQ ID NO:149 or conservative modifications thereof, and a $V_H$ CDR3 comprising amino acids having the sequence set forth in0 SEQ ID NO:150 or conservative modifications thereof, as shown in Table 5. In certain embodiments, the extracellular antigen-binding domain comprises a $V_L$ CDR1 comprising amino acids having the sequence set forth in SEQ ID NO:151 or conservative modifications thereof, a $V_L$ CDR2 comprising amino acids having the sequence set forth in SEQ ID NO:152 or conservative modifications thereof, and a $V_L$ CDR3 comprising amino acids having the sequence set forth in SEQ ID NO:153 or conservative modifications thereof, as shown in Table 5. In certain embodiments, the extracellular antigen-binding domain comprises a $V_H$ CDR1 comprising amino acids having the sequence set forth in SEQ ID NO:148 or conservative modifications thereof, a $V_H$ CDR2 comprising amino acids having the sequence set forth in SEQ ID NO:149 or conservative modifications thereof, a $V_H$ CDR3 comprising amino acids having the sequence set forth in SEQ ID NO:150 or conservative modifications thereof, a $V_L$ CDR1 comprising amino acids having the sequence set forth in SEQ ID NO:151 or conservative modifications thereof, a $V_L$ CDR2 comprising amino acids having the sequence set forth in SEQ ID NO:152 or conservative modifications thereof, and a $V_L$ CDR3 comprising amino acids having the sequence set forth in SEQ ID NO:153 or conservative modifications thereof, as shown in Table 5. In certain embodiments, the extracellular antigen-binding domain comprises a $V_H$ CDR1 comprising amino acids having the sequence set forth in SEQ ID NO:148, a $V_H$ CDR2 comprising amino acids having the sequence set forth in SEQ ID NO:149, a $V_H$ CDR3 comprising amino acids having the sequence set forth in SEQ ID NO:150, a $V_L$ CDR1 comprising amino acids having the sequence set forth in SEQ ID NO:151, a $V_L$ CDR2 comprising amino acids having the sequence set forth in SEQ ID NO:152, and a $V_L$ CDR3 comprising amino acids having the sequence set forth in SEQ ID NO:153.

TABLE 5

| Antigen | A GPRC5D polypeptide having the amino acid sequence of SEQ ID NO: 97 | | |
|---|---|---|---|
| CDRs | 1 | 2 | 3 |
| $V_H$ | GSTFSSYA [SEQ ID NO: 148] | ISGRGRST [SEQ ID NO: 149] | ARYYKSKDH [SEQ ID NO: 150] |
| $V_L$ | RSNIGTNY [SEQ ID NO: 151] | RNH [SEQ ID NO: 152] | AAWDDNLSGVV [SEQ ID NO: 153] |
| Full $V_H$ | EVQLVETGGGLVQPGGSLRLSCAASGSTFSSYAMSWVRQAPGKG LEWVSAISGRGRSTYYADSVKGRFTISRDNSKNTLYLQMNSLRA EDTAVYYCARYYKSSKDHWGQGTLVTVSS [SEQ ID NO: 17] | | |
| DNA | Gaggtgcagctggtggagactgggggaggcttggtacagcctggggggtccctgagactctcctgtg cagcctctggatccacctttagcagctatgccatgagctgggtccgccaggctccagggaaggggctg gagtgggtctcagctattagtggtcgtggtcgtagcacatactacgcagactccgtgaagggccggttc accatctccagagacaattccaagaacacgctgtatctgcaaatgaacagcctgagagccgaggacac ggccgtatattactgtgcgcgctactacaaatcttctaaagatcattggggtcaaggtactctggtgaccg tctcctca [SEQ ID NO: 19] | | |
| Full $V_L$ | QSVLTQPPSLSGAPGQRVTISCSGSRSNIGTNYVSWXQQLPGTAP KLLIYRNHQWPSGVPDRFTGSKSGTSASLAISGLRSEDEADYYCA AWDDNLSGVVFGGGTKLTVLG [SEQ ID NO: 18] | | |
| DNA | Cagtctgtgttgacgcagccgccctcactgtctggggccccagggcagagggtcaccatctcttgttcc ggaagcaggtccaacatcggaactaattatgtatcctggnaccagcaactcccaggaacggcccccaa actcctcatctataggaatcatcagtggccctcaggggtccctgaccgattcactggctccaagtctggc acctcagcctccctggccatcagtgggctccggtccgaggatgaggctgattactactgtgcagcatgg gatgacaatttgagtggtgtggtgttcggcggagggaccaagctgaccgtcctaggt [SEQ ID NO: 20] | | |
| scFv | QSVLTQPPSLSGAPGQRVTISCSGSRSNIGTNYVSWXQQLPGTAP KLLIYRNHQWPSGVPDRFTGSKSGTSASLAISGLRSEDEADYYCA AWDDNLSGVVFGGGTKLTVLGSRGGGGSGGGGSGGGGSLEMA EVQLVETGGGLVQPGGSLRLSCAASGSTFSSYAMSWVRQAPGKG LEWVSAISGRGRSTYYADSVKGRFTISRDNSKNTLYLQMNSLRA EDTAVYYCARYYKSSKDHWGQGTLVTVSS [SEQ ID NO: 104] | | |

In certain embodiments, the extracellular antigen-binding domain is a scFv, which comprises the amino acid sequence of SEQ ID NO: 105 and specifically binds to a GPRC5D polypeptide (e.g., a GPRC5D polypeptide having the amino acid sequence SEQ ID NO:97, or fragments thereof), which scFv is designated as ET150-154 scFv (also referred to as "ET150-4 scFv").

In certain embodiments, the extracellular antigen-binding domain is a scFv, which comprises a heavy chain variable region comprising amino acids having the sequence set forth in SEQ ID NO:21 and a light chain variable region comprising amino acids having the sequence set forth in SEQ ID NO:22, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 6. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:21, as shown in Table 6. In certain embodiments, the extracellular antigen-binding domain comprises a $V_H$ comprising amino acids having the sequence set forth in SEQ ID NO:21, as shown in Table 6. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:22, as shown in Table 6. In certain embodiments, the extracellular antigen-binding domain comprises a $V_L$ comprising amino acids having the sequence set forth in SEQ ID NO:22, as shown in Table 6. In certain embodiments, the extracellular antigen-binding domain comprises a $V_H$ comprising amino acids having the sequence set forth in SEQ ID NO:21 and a $V_L$ comprising amino acids having the sequence set forth in SEQ ID NO:22, as shown in Table 6. In certain embodiments, the extracellular antigen-binding domain comprises a $V_H$ CDR1 comprising amino acids having the sequence set forth in SEQ ID NO:154 or conservative modifications thereof, a $V_H$ CDR2 comprising amino acids having the sequence set forth in SEQ ID NO:155 or conservative modifications thereof, and a $V_H$ CDR3 comprising amino acids having the sequence set forth in SEQ ID NO:156 or conservative modifications thereof, as shown in Table 6. In certain embodiments, the extracellular antigen-binding domain comprises a $V_L$ CDR1 comprising amino acids having the sequence set forth in SEQ ID NO:157 or conservative modifications thereof, a $V_L$ CDR2 comprising amino acids having the sequence set forth in SEQ ID NO:158 or conservative modifications thereof, and a $V_L$ CDR3 comprising amino acids having the sequence set forth in SEQ ID NO:159 or conservative modifications thereof, as shown in Table 6. In certain embodiments, the extracellular antigen-binding domain comprises a $V_H$ CDR1 comprising amino acids having the sequence set forth in SEQ ID NO:154 or conservative modifications thereof, a $V_H$ CDR2 comprising amino acids having the sequence set forth in SEQ ID NO:155 or conservative modifications thereof, a $V_H$ CDR3 comprising amino acids having the sequence set forth in SEQ ID NO:156 or conservative modifications thereof, a $V_L$ CDR1 comprising amino acids having the sequence set forth in SEQ ID NO:157 or conservative modifications thereof, a $V_L$ CDR2 comprising amino acids having the sequence set forth in SEQ ID NO:158 or conservative modifications thereof, and a $V_L$ CDR3 comprising amino acids having the sequence set forth in SEQ ID NO:159 or conservative modifications thereof, as shown in Table 6. In certain embodiments, the extracellular antigen-binding domain comprises a $V_H$ CDR1 comprising amino acids having the sequence set forth in SEQ ID NO:154, a $V_H$ CDR2 comprising amino acids having the sequence set forth in SEQ ID NO:155, a $V_H$ CDR3 comprising amino acids having the sequence set forth in SEQ ID NO:156, a $V_L$ CDR1 comprising amino acids having the sequence set forth in SEQ ID NO:157, a $V_L$ CDR2 comprising amino acids having the sequence set forth in SEQ ID NO:158, and a $V_L$ CDR3 comprising amino acids having the sequence set forth in SEQ ID NO:159.

TABLE 6

| | | | |
|---|---|---|---|
| Antigen | A GPRC5D polypeptide having the amino acid sequence of SEQ ID NO: 97 | | |
| CDRs | 1 | 2 | 3 |
| $V_H$ | AYTFTDYY [SEQ ID NO: 154] | INPKSGRT [SEQ ID NO: 155] | ARVYGYSRWSGFDL [SEQ ID NO: 156] |
| $V_L$ | SSNIGSNY [SEQ ID NO: 157] | RNN [SEQ ID NO: 158] | AAWDDSLSGYV [SEQ ID NO: 159] |
| Full $V_H$ | QVQLVQSGAEVQRPGASVRVSCKAIAYTFTDYYIHWVRQAPGQ GPEWMGWINPKSGRTQYAPKFQDRVTLARETPISTASMELRGLT SDDTAVYYCARVYGYSRWSGFDLWGQGTLVTVSS [SEQ ID NO: 21] | | |
| DNA | Caggtccagctggtgcagtctggggctgaggtgcagaggcctggggcctcagtgagggtctcctgca aggctattgcgtacaccttcaccgactactatatccactgggtgcgacaggcccctggacaagggcctg agtggatggggtggatcaaccctaaaagtggtcgcacacagtatgcaccgaagtttcaagacagggtc accctggccagggagacgcccatcagcacagcctccatggagctgcgcggactgacatctgacgac acggccgtgtattactgtgcgcgcgtttacggttactctcgttggtctggtttcgatctgtggggtcaaggt actctggtgaccgtctcctca [SEQ ID NO: 23] | | |
| Full $V_L$ | QAVLTQPPSASGTPGQRVTISCSGSSSNIGSNYVYWYQQLPGTAP KLLIYRNNQRPSGVPDRFSGSKSGTSASLAISGLRSEDEADYYCA AWDDSLSGYVFGTGTKVTVLG [SEQ ID NO: 22] | | |
| DNA | Caggctgtgctgactcagccaccctcagcgtctgggacccccgggcagagggtcaccatctcttgttct ggaagcagctccaacatcggaagtaattatgtatactggtaccagcagctcccaggaacggcccccaa actcctcatctataggaataatcagcggccctcaggggtccctgaccgattctctggctccaagtctggc | | |

TABLE 6-continued

| | |
|---|---|
| | acctcagcctccctggccatcagtgggctccggtccgaggatgaggctgattattactgtgcagcatgg gatgacagcctgagtggttatgtcttcggaactgggaccaaggtcaccgtcctaggt [SEQ ID NO: 24] |
| scFv | QAVLTQPPSASGTPGQRVTISCSGSSSNIGSNYVYWYQQLPGTAP KLLIYRNNQRPSGVPDRFSGSKSGTSASLAISGLRSEDEADYYCA AWDDSLSGYVFGTGTKVTVLGSRGGGGSGGGGSGGGGSLEMAQ VQLVQSGAEVQRPGASVRVSCKAIAYTFTDYYIHWVRQAPGQGP EWMGWINPKSGRTQYAPKFQDRVTLARETPISTASMELRGLTSD DTAVYYCARVYGYSRWSGFDLWGQGTLVTVSS [SEQ ID NO: 105] |

In certain embodiments, the extracellular antigen-binding domain is a scFv, which comprises the amino acid sequence of SEQ ID NO: 106 and specifically binds to a GPRC5D polypeptide (e.g., a GPRC5D polypeptide having the amino acid sequence SEQ ID NO:97, or fragments thereof), which scFv is designated as ET150-156 scFv (also referred to as "ET150-6 scFv").

In certain embodiments, the extracellular antigen-binding domain is a scFv, which comprises a heavy chain variable region comprising amino acids having the sequence set forth in SEQ ID NO:25 and a light chain variable region comprising amino acids having the sequence set forth in SEQ ID NO:26, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 7. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:25, as shown in Table 7. In certain embodiments, the extracellular antigen-binding domain comprises a $V_H$ comprising amino acids having the sequence set forth in SEQ ID NO:25, as shown in Table 7. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:26, as shown in Table 7. In certain embodiments, the extracellular antigen-binding domain comprises a $V_L$ comprising amino acids having the sequence set forth in SEQ ID NO:26, as shown in Table 7. In certain embodiments, the extracellular antigen-binding domain comprises a $V_H$ comprising amino acids having the sequence set forth in SEQ ID NO:25 and a $V_L$ comprising amino acids having the sequence set forth in SEQ ID NO:26, as shown in Table 7. In certain embodiments, the extracellular antigen-binding domain comprises a $V_H$ CDR1 comprising amino acids having the sequence set forth in SEQ ID NO:160 or conservative modifications thereof, a $V_H$ CDR2 comprising amino acids having the sequence set forth in SEQ ID NO:161 or conservative modifications thereof, and a $V_H$ CDR3 comprising amino acids having the sequence set forth in SEQ ID NO:162 or conservative modifications thereof, as shown in Table 7. In certain embodiments, the extracellular antigen-binding domain comprises a $V_L$ CDR1 comprising amino acids having the sequence set forth in SEQ ID NO:163 or conservative modifications thereof, a $V_L$ CDR2 comprising amino acids having the sequence set forth in SEQ ID NO:164 or conservative modifications thereof, and a $V_L$ CDR3 comprising amino acids having the sequence set forth in SEQ ID NO:165 or conservative modifications thereof, as shown in Table 7. In certain embodiments, the extracellular antigen-binding domain comprises a $V_H$ CDR1 comprising amino acids having the sequence set forth in SEQ ID NO:160 or conservative modifications thereof, a $V_H$ CDR2 comprising amino acids having the sequence set forth in SEQ ID NO:161 or conservative modifications thereof, a $V_H$ CDR3 comprising amino acids having the sequence set forth in SEQ ID NO:162 or conservative modifications thereof, a $V_L$ CDR1 comprising amino acids having the sequence set forth in SEQ ID NO:163 or conservative modifications thereof, a $V_L$ CDR2 comprising amino acids having the sequence set forth in SEQ ID NO:164 or conservative modifications thereof, and a $V_L$ CDR3 comprising amino acids having the sequence set forth in SEQ ID NO:165 or conservative modifications thereof, as shown in Table 7. In certain embodiments, the extracellular antigen-binding domain comprises a $V_H$ CDR1 comprising amino acids having the sequence set forth in SEQ ID NO:160, a $V_H$ CDR2 comprising amino acids having the sequence set forth in SEQ ID NO:161, a $V_H$ CDR3 comprising amino acids having the sequence set forth in SEQ ID NO:162, a $V_L$ CDR1 comprising amino acids having the sequence set forth in SEQ ID NO:163, a $V_L$ CDR2 comprising amino acids having the sequence set forth in SEQ ID NO:164, and a $V_L$ CDR3 comprising amino acids having the sequence set forth in SEQ ID NO:165.

TABLE 7

| Antigen | A GPRC5D polypeptide having the amino acid sequence of SEQ ID NO: 97 | | |
|---|---|---|---|
| CDRs | 1 | 2 | 3 |
| $V_H$ | GYTFTTYY [SEQ ID NO: 160] | INPNGGGT [SEQ ID NO: 161] | ARGHKVYKSHPTGGYDR [SEQ ID NO: 162] |

TABLE 7-continued

| | | | |
|---|---|---|---|
| $V_L$ | SRDVGGYNY [SEQ ID NO: 163] | EVS [SEQ ID NO: 164] | SSYTSSSTLD [SEQ ID NO: 165] |
| Full $V_H$ | QVQLVQSGAEVKQPGASVKVSCQASGYTFTTYYMHWVRQAPGQ GLEWMGIINPNGGGTFYAQKFQDRVTMTRDTSTGTVYMELSSLRS DDTAVYYCARGHKVYKSHPTGGYDRWGQGTLVTVSS [SEQ ID NO: 25] | | |
| DNA | Caggtgcagctggtgcaatctggggctgaggtgaagcagcctggggcctcagtgaaggtttcctgccag gcatctggatacaccttcaccacttattatatgcactgggtgcgacaggcccctggacaagggcttgagtg gatgggaataatcaaccctaatggtggtggcacattctacgcacagaagttccaggacagagtcaccatg accagggacacgtccacgggcacagtctacatggaactgagcagcctgagatctgacgacactgccgtg tattactgtgcgcgcggtcataaagtttacaaatctcatccgactggtggttacgatcgttggggtcaaggta ctctggtgaccgtctcctca [SEQ ID NO: 27] | | |
| Full $V_L$ | QSALTQPASVSGSPGQSITISCTGTSRDVGGYNYVSWYQQYPGKAP KLMIYEVSKRPSGVSNRFSGSKSGNTASLTISGLQAEDEADYYCSS YTSSSTLDFGTGTKVTVLG [SEQ ID NO: 26] | | |
| DNA | Caatctgccctgactcagcctgcctccgtgtctgggtctcctggacagtcgatcaccatctcctgcactgga accagccgtgacgttggtggttataactatgtctcctggtaccaacagtacccaggcaaagcccccaaact catgatttatgaggtcagtaagcggccctcaggggtttctaatcgcttctctggctccaagtctggcaacacg gcctccctgaccatctctgggctccaggctgaggacgaggctgattattactgcagctcatataccagtagc agcactttagacttcggaactgggaccaaggtcaccgtcctaggt [SEQ ID NO: 28] | | |
| scFv | QSALTQPASVSGSPGQSITISCTGTSRDVGGYNYVSWYQQYPGKAP KLMIYEVSKRPSGVSNRFSGSKSGNTASLTISGLQAEDEADYYCSS YTSSSTLDFGTGTKVTVLGSRGGGGSGGGGSGGGGSLEMAQVQL VQSGAEVKQPGASVKVSCQASGYTFTTYYMHWVRQAPGQGLEW MGIINPNGGGTFYAQKFQDRVTMTRDTSTGTVYMELSSLRSDDTA VYYCARGHKVYKSHPTGGYDRWGQGTLVTVSS [SEQ ID NO: 106] | | |

In certain embodiments, the extracellular antigen-binding domain is a scFv, which comprises the amino acid sequence of SEQ ID NO: 107 and specifically binds to a GPRC5D polypeptide (e.g., a GPRC5D polypeptide having the amino acid sequence SEQ ID NO:97, or fragments thereof), which scFv is designated as ET150-157 scFv (also referred to as "ET150-7 scFv").

In certain embodiments, the extracellular antigen-binding domain is a scFv, which comprises a heavy chain variable region comprising amino acids having the sequence set forth in SEQ ID NO:29 and a light chain variable region comprising amino acids having the sequence set forth in SEQ ID NO:30, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 8. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:29, as shown in Table 8. In certain embodiments, the extracellular antigen-binding domain comprises a $V_H$ comprising amino acids having the sequence set forth in SEQ ID NO:29, as shown in Table 8. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:30, as shown in Table 8. In certain embodiments, the extracellular antigen-binding domain comprises a $V_L$ comprising amino acids having the sequence set forth in SEQ ID NO:30, as shown in Table 8. In certain embodiments, the extracellular antigen-binding domain comprises a $V_H$ comprising amino acids having the sequence set forth in SEQ ID NO:29 and a $V_L$ comprising amino acids having the sequence set forth in SEQ ID NO:30, as shown in Table 8. In certain embodiments, the extracellular antigen-binding domain comprises a $V_H$ CDR1 comprising amino acids having the sequence set forth in SEQ ID NO:166 or conservative modifications thereof, a $V_H$ CDR2 comprising amino acids having the sequence set forth in SEQ ID NO:167 or conservative modifications thereof, and a $V_H$ CDR3 comprising amino acids having the sequence set forth in SEQ ID NO:168 or conservative modifications thereof, as shown in Table 8. In certain embodiments, the extracellular antigen-binding domain comprises a $V_L$ CDR1 comprising amino acids having the sequence set forth in SEQ ID NO:169 or conservative modifications thereof, a $V_L$ CDR2 comprising amino acids having the sequence set forth in SEQ ID NO:170 or conservative modifications thereof, and a $V_L$ CDR3 comprising amino acids having the sequence set forth in SEQ ID NO:171 or conservative modifications thereof, as shown in Table 8. In certain embodiments, the extracellular antigen-binding domain comprises a $V_H$ CDR1 comprising amino acids having the sequence set forth in SEQ ID NO:166 or conservative modifications thereof, a $V_H$ CDR2 comprising amino acids having the sequence set forth in SEQ ID NO:167 or conservative modifications thereof, a $V_H$ CDR3 comprising amino acids having the sequence set forth in SEQ ID NO:168 or conservative modifications thereof, a $V_L$ CDR1 comprising amino acids having the sequence set forth in SEQ ID NO:169 or conservative modifications thereof, a $V_L$ CDR2 comprising amino acids having the sequence set forth in SEQ ID NO:170 or conservative modifications thereof, and a $V_L$ CDR3 comprising amino acids having the sequence set forth in SEQ ID NO:171 or conservative modifications thereof, as shown in Table 8. In certain embodiments, the extracellular antigen-binding domain comprises a $V_H$ CDR1 comprising amino acids having the sequence set forth in SEQ ID NO:166, a $V_H$ CDR2 comprising amino acids having the sequence set forth in SEQ ID NO:167, a $V_H$ CDR3 comprising amino acids having the sequence set forth in SEQ ID NO:168, a $V_L$ CDR1 comprising amino acids having the sequence set forth in SEQ ID NO:169, a $V_L$ CDR2 comprising amino acids having the sequence set forth in SEQ ID NO:170, and a $V_L$ CDR3 comprising amino acids having the sequence set forth in SEQ ID NO:171.

TABLE 8

| | | | |
|---|---|---|---|
| Antigen | A GPRC5D polypeptide having the amino acid sequence of SEQ ID NO: 97 | | |
| CDRs | 1 | 2 | 3 |
| $V_H$ | GGTFSSYA [SEQ ID NO: 166] | IIPIFGTA [SEQ ID NO: 167] | ARSHVAWSLLDY [SEQ ID NO: 168] |
| $V_L$ | SSNIGSNY [SEQ ID NO: 169] | RNN [SEQ ID NO: 170] | AAWDDSLSGVV [SEQ ID NO: 171] |
| Full $V_H$ | EVQLVQSGAEVKKPGSSVKVSCKASGGTFSSYAISWVRQAPGQG LEWMGGIIPIFGTAKYAQKFQGRVTITADESTSTAYMELSSLRSED TAVYYCARSHVAWSLLDYWGQGTLVTVSS [SEQ ID NO: 29] | | |
| DNA | Gaggtccagctggtgcagtctggggctgaggtgaagaagcctgggtcctcggtgaaggtctcctgca aggatctggaggcaccttcagcagctatgctatcagctgggtgcgacaggcccctggacaagggctt gagtggatgggagggattatccctatctttggtacagcaaaatatgcacagaagttccagggcagagtc acgattaccgcggacgaatccacgagcacagcctacatggagctgagcagcctgagatctgaggaca cggccgtgtattactgtgcgcgctctcatgttgcttggtctctgctggattactggggtcaaggtactctgg tgaccgtctcctca [SEQ ID NO: 31] | | |
| Full $V_L$ | SYELTQPPSASGTPGQRVTISCSGSSSNIGSNYVSWYQQLPGTAPK LLIYRNNQRPSGVPDRFSGSKSGTSASLAISGLRSEDEADYYCAA WDDSLSGVVFGGGTKLTVLG [SEQ ID NO: 30] | | |
| DNA | Tcctatgagctgactcagccaccctcagcgtctgggacccccgggcagagggtcaccatctcttgttct ggaagcagctccaacatcggaagtaattatgtatcctggtaccagcagctcccaggaacggcccccaa actcctcatctataggaataatcagcggccctcaggggtccctgaccgattctctggctccaagtctggc acctcagcctccctggccatcagtgggctccggtccgaggatgaggctgattattactgtgcagcatgg gatgacagcctgagtggtgtggtattcggcggagggaccaagctgaccgtcctaggt [SEQ ID NO: 32] | | |
| scFv | SYELTQPPSASGTPGQRVTISCSGSSSNIGSNYVSWYQQLPGTAPK LLIYRNNQRPSGVPDRFSGSKSGTSASLAISGLRSEDEADYYCAA WDDSLSGVVFGGGTKLTVLGSRGGGGSGGGGSGGGGSLEMAEV QLVQSGAEVKKPGSSVKVSCKASGGTFSSYAISWVRQAPGQGLE WMGGIIPIFGTAKYAQKFQGRVTITADESTSTAYMELSSLRSEDT AVYYCARSHVAWSLLDYWGQGTLVTVSS [SEQ ID NO: 107] | | |

In certain embodiments, the extracellular antigen-binding domain is a scFv, which comprises the amino acid sequence of SEQ ID NO: 108 and specifically binds to a GPRC5D polypeptide (e.g., a GPRC5D polypeptide having the amino acid sequence SEQ ID NO:97, or fragments thereof), which scFv is designated as ET150-159 scFv (also referred to as "ET150-9 scFv").

In certain embodiments, the extracellular antigen-binding domain is a scFv, which comprises a heavy chain variable region comprising amino acids having the sequence set forth in SEQ ID NO:33 and a light chain variable region comprising amino acids having the sequence set forth in SEQ ID NO:34, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 9. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:33, as shown in Table 9. In certain embodiments, the extracellular antigen-binding domain comprises a $V_H$ comprising amino acids having the sequence set forth in SEQ ID NO:33, as shown in Table 9. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:34, as shown in Table 9. In certain embodiments, the extracellular antigen-binding domain comprises a $V_L$ comprising amino acids having the sequence set forth in SEQ ID NO:34, as shown in Table 9. In certain embodiments, the extracellular antigen-binding domain comprises a $V_H$ comprising amino acids having the sequence set forth in SEQ ID NO:33 and a $V_L$ comprising amino acids having the sequence set forth in SEQ ID NO:34, as shown in Table 9. In certain embodiments, the extracellular antigen-binding domain comprises a $V_H$ CDR1 comprising amino acids having the sequence set forth in SEQ ID NO:172 or conservative modifications thereof, a $V_H$ CDR2 comprising amino acids having the sequence set forth in SEQ ID NO:173 or conservative modifications thereof, and a V<sub>H</sub> CDR3 comprising amino acids having the sequence set forth in SEQ ID NO:174 or conservative modifications thereof, as shown in Table 9. In certain embodiments, the extracellular antigen-binding domain comprises a V<sub>L</sub> CDR1 comprising amino acids having the sequence set forth in SEQ ID NO:175 or conservative modifications thereof, a V<sub>L</sub> CDR2 comprising amino acids having the sequence set forth in SEQ ID NO:176 or conservative modifications thereof, and a V<sub>L</sub> CDR3 comprising amino acids having the sequence set forth in SEQ ID NO:177 or conservative modifications thereof, as shown in Table 9. In certain embodiments, the extracellular antigen-binding domain comprises a V<sub>H</sub> CDR1 comprising amino acids having the sequence set forth in SEQ ID NO:172 or conservative modifications thereof, a V<sub>H</sub> CDR2 comprising amino acids having the sequence set forth in SEQ ID NO:173 or conservative modifications thereof, a V<sub>H</sub> CDR3 comprising amino acids having the sequence set forth in SEQ ID NO:174 or conservative modifications thereof, a V<sub>L</sub> CDR1 comprising amino acids having the sequence set forth in SEQ ID NO:175 or conservative modifications thereof, a V<sub>L</sub> CDR2 comprising amino acids having the sequence set forth in SEQ ID NO:176 or conservative modifications thereof, and a V<sub>L</sub> CDR3 comprising amino acids having the sequence set forth in SEQ ID NO:177 or conservative modifications thereof, as shown in Table 9. In certain embodiments, the extracellular antigen-binding domain comprises a V<sub>H</sub> CDR1 comprising amino acids having the sequence set forth in SEQ ID NO:172, a V<sub>H</sub> CDR2 comprising amino acids having the sequence set forth in SEQ ID NO:173, a V<sub>H</sub> CDR3 comprising amino acids having the sequence set forth in SEQ ID NO:174 a V<sub>L</sub> CDR1 comprising amino acids having the sequence set forth in SEQ ID NO:175, a V<sub>L</sub> CDR2 comprising amino acids having the sequence set forth in SEQ ID NO:176, and a V<sub>L</sub> CDR3 comprising amino acids having the sequence set forth in SEQ ID NO:177.

TABLE 9

Antigen A GPRC5D polypeptide having the amino acid sequence of SEQ ID NO: 97

| CDRs | 1 | 2 | 3 |
|---|---|---|---|
| V<sub>H</sub> | GGTFSSYA [SEQ ID NO: 172] | MNPNSGNT [SEQ ID NO: 173] | ARYQSYKGSQSDS [SEQ ID NO: 174] |
| V<sub>L</sub> | SSNIGSNY [SEQ ID NO: 175] | RNN [SEQ ID NO: 176] | AAWDDSLSGWV [SEQ ID NO: 177] |
| Full V<sub>H</sub> | QVQLVQSGAEVKKPGSSVKVSCKASGGTFSSYAISWVRQAPGQG LEWMGWMNPNSGNTGYAQKFQGRVTMTRNTSISTAYMELSSLR SEDTAVYYCARYQSYKGSQSDSWGQGTLVTVSS [SEQ ID NO: 33] | | |
| DNA | Caggtgcagctggtgcagtctggggctgaggtgaagaagcctgggtcctcagtgaaggtctcctgca aggcttctggaggcaccttcagcagctatgctatcagctgggtgcgacaggcccctggacaagggctt gagtggatgggatggatgaaccctaacagtggtaacacaggctatgcacagaagttccagggcagag tcaccatgaccaggaacacctccataagcacagcctacatggagctgagcagcctgagatctgaggac acggccgtgtattactgtgcgcgctaccagtatacaaaggttctcagtctgattcttggggtcaaggtact ctggtgaccgtctcctca [SEQ ID NO: 35] | | |
| Full V<sub>L</sub> | QSVLTQPPSASGTPGQRVTISCSGSSSNIGSNYVYWYQQLPGTAP KLLIYRNNQRPSGVPDRFSGSKSGTSASLAISGLRSEDEADYYCA AWDDSLSGWVFGGGTKLTVLG [SEQ ID NO: 34] | | |
| DNA | Cagtctgtgttgacgcagccacccctcagcgtctgggaccccgggcagagggtcaccatctcttgttct ggaagcagctccaacatcggaagtaattatgtatactggtaccagcagctcccaggaacggcccccaa actcctcatctataggaataatcagcggccctcaggggtccctgaccgattctctggctccaagtctggc acctcagcctccctggccatcagtgggctccggtccgaggatgaggctgattattactgtgcagcatgg gatgacagcctgagtggttgggtgttcggcggagggaccaagctgaccgtcctaggt [SEQ ID NO: 36] | | |
| scFv | QSVLTQPPSASGTPGQRVTISCSGSSSNIGSNYVYWYQQLPGTAP KLLIYRNNQRPSGVPDRFSGSKSGTSASLAISGLRSEDEADYYCA AWDDSLSGWVFGGGTKLTVLGSRGGGGSGGGGSGGGGSLEMA QVQLVQSGAEVKKPGSSVKVSCKASGGTFSSYAISWVRQAPGQG LEWMGWMNPNSGNTGYAQKFQGRVTMTRNTSISTAYMELSSLR SEDTAVYYCARYQSYKGSQSDSWGQGTLVTVSS [SEQ ID NO: 108] | | |

In certain embodiments, the extracellular antigen-binding domain is a scFv, which comprises the amino acid sequence of SEQ ID NO: 109 and specifically binds to a GPRC5D polypeptide (e.g., a GPRC5D polypeptide having the amino acid sequence SEQ ID NO:97, or fragments thereof), which scFv is designated as ET150-160 scFv (also referred to as "ET150-10 scFv").

In certain embodiments, the extracellular antigen-binding domain is a scFv, which comprises a heavy chain variable region comprising amino acids having the sequence set forth in SEQ ID NO:37 and a light chain variable region comprising amino acids having the sequence set forth in SEQ ID NO:38, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with V<sub>H</sub> and V<sub>L</sub> regions or CDRs selected from Table 10. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:37, as shown in Table 10. In certain embodiments, the extracellular antigen-binding domain comprises a $V_H$ comprising amino acids having the sequence set forth in SEQ ID NO:37, as shown in Table 10. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:38, as shown in Table 10. In certain embodiments, the extracellular antigen-binding domain comprises a $V_L$ comprising amino acids having the sequence set forth in SEQ ID NO:38, as shown in Table 10. In certain embodiments, the extracellular antigen-binding domain comprises a $V_H$ comprising amino acids having the sequence set forth in SEQ ID NO:37 and a $V_L$ comprising amino acids having the sequence set forth in SEQ ID NO:38, as shown in Table 10. In certain embodiments, the extracellular antigen-binding domain comprises a $V_H$ CDR1 comprising amino acids having the sequence set forth in SEQ ID NO:178 or conservative modifications thereof, a $V_H$ CDR2 comprising amino acids having the sequence set forth in SEQ ID NO:179 or conservative modifications thereof, and a $V_H$ CDR3 comprising amino acids having the sequence set forth in SEQ ID NO:180 or conservative modifications thereof, as shown in Table 10. In certain embodiments, the extracellular antigen-binding domain comprises a $V_L$ CDR1 comprising amino acids having the sequence set forth in SEQ ID NO:181 or conservative modifications thereof, a $V_L$ CDR2 comprising amino acids having the sequence set forth in SEQ ID NO:182 or conservative modifications thereof, and a $V_L$ CDR3 comprising amino acids having the sequence set forth in SEQ ID NO:183 or conservative modifications thereof, as shown in Table 10. In certain embodiments, the extracellular antigen-binding domain comprises a $V_H$ CDR1 comprising amino acids having the sequence set forth in SEQ ID NO:178 or conservative modifications thereof, a $V_H$ CDR2 comprising amino acids having the sequence set forth in SEQ ID NO:179 or conservative modifications thereof, a $V_H$ CDR3 comprising amino acids having the sequence set forth in SEQ ID NO:180 or conservative modifications thereof, a $V_L$ CDR1 comprising amino acids having the sequence set forth in SEQ ID NO:181 or conservative modifications thereof, a $V_L$ CDR2 comprising amino acids having the sequence set forth in SEQ ID NO:182 or conservative modifications thereof, and a $V_L$ CDR3 comprising amino acids having the sequence set forth in SEQ ID NO:183 or conservative modifications thereof, as shown in Table 10. In certain embodiments, the extracellular antigen-binding domain comprises a $V_H$ CDR1 comprising amino acids having the sequence set forth in SEQ ID NO:178, a $V_H$ CDR2 comprising amino acids having the sequence set forth in SEQ ID NO:179, a $V_H$ CDR3 comprising amino acids having the sequence set forth in SEQ ID NO:180, a $V_L$ CDR1 comprising amino acids having the sequence set forth in SEQ ID NO:181, a $V_L$ CDR2 comprising amino acids having the sequence set forth in SEQ ID NO:182, and a $V_L$ CDR3 comprising amino acids having the sequence set forth in SEQ ID NO:183.

TABLE 10

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFTSYY[SEQ ID NO: 178] | INPSGGST [SEQ ID NO: 179] | ARGGSKKWSGEKWRRENFDY [SEQ ID NO: 180] |
| $V_L$ | SSDVGGYNY [SEQ ID NO: 181] | DVS [SEQ ID NO: 182] | SSYTRSSTEV [SEQ ID NO: 183] |
| Full $V_H$ | EVQLVQSGAEVKKPGASVKVSCKASGYTFTSYYMHWVRQAPGQ<br>GLEWMGIINPSGGSTSYAQKFQGRVTMTRDTSTSTVYMELSSLRS<br>EDTAVYYCARGGSKKWSGEKWRRENFDYWGQGTLVTVSS [SEQ ID NO: 37] | | |
| DNA | Gaggtccagctggtacagtctggggctgaggtgaagaagcctggggcctcagtgaaggtttcctgcaa<br>ggcatctggatacaccttcaccagctactatatgcactgggtgcgacaggcccctggacaagggcttga<br>gtggatgggaataatcaaccctagtggtggtagcacaagctacgcacagaagttccagggcagagtcac<br>catgaccagggacacgtccacgagcacagtctacatggagctgagcagcctgagatctgaggacacg<br>gccgtgtattactgtgcgcgcggtggttctaaaaaatggtctggtgaaaaatggcgtcgtgaaaacttcga<br>ttactggggtcaaggtactctggtgaccgtctcctca [SEQ ID NO: 39] | | |
| Full $V_L$ | QSALTQPASVSGSPGQSITISCTGTSSDVGGYNYVSWYQQHPGKA<br>PKLMIYDVSKRPSGVSNRFSGSKSGNTASLTISGLQAEDEADYYCS<br>SYTRSSTEVFGGGTKLTVLG [SEQ ID NO: 38] | | |
| DNA | Caatctgccctgactcagcctgcctccgtgtctgggtctcctggacagtcgatcaccatctcctgcactgg<br>aaccagcagtgacgttggtggttataactatgtctcctggtaccaacagcacccaggcaaagcccccaaa<br>ctcatgatttatgatgtcagtaagcggccctcaggggtttctaatcgcttctctggctccaagtctggcaaca<br>cggcctccctgaccatctctgggctccaggctgaggacgaggctgattattactgcagctcatatacaag<br>aagcagcactgaggtattcggcggagggaccaagctgaccgtcctaggt [SEQ ID NO: 40] | | |
| scFv | QSALTQPASVSGSPGQSITISCTGTSSDVGGYNYVSWYQQHPGKA<br>PKLMIYDVSKRPSGVSNRFSGSKSGNTASLTISGLQAEDEADYYCS<br>SYTRSSTEVFGGGTKLTVLGSRGGGGSGGGGSGGGGSLEMAEVQ<br>LVQSGAEVKKPGASVKVSCKASGYTFTSYYMHWVRQAPGQGLE<br>WMGIINPSGGSTSYAQKFQGRVTMTRDTSTSTVYMELSSLRSEDT<br>AVYYCARGGSKKWSGEKWRRENFDYWGQGTLVTVSS [SEQ ID NO: 109] | | |

In certain embodiments, the extracellular antigen-binding domain is a scFv, which comprises the amino acid sequence of SEQ ID NO: 110 and specifically binds to a GPRC5D polypeptide (e.g., a GPRC5D polypeptide having the amino acid sequence SEQ ID NO:97, or fragments thereof), which scFv is designated as ET150-161 scFv (also referred to as "ET150-11 scFv").

In certain embodiments, the extracellular antigen-binding domain is a scFv, which comprises a heavy chain variable region comprising amino acids having the sequence set forth in SEQ ID NO:41 and a light chain variable region comprising amino acids having the sequence set forth in SEQ ID NO:42, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 11. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:41, as shown in Table 11. In certain embodiments, the extracellular antigen-binding domain comprises a $V_H$ comprising amino acids having the sequence set forth in SEQ ID NO:41, as shown in Table 11. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:42, as shown in Table 11. In certain embodiments, the extracellular antigen-binding domain comprises a $V_L$ comprising amino acids having the sequence set forth in SEQ ID NO:42, as shown in Table 11. In certain embodiments, the extracellular antigen-binding domain comprises a $V_H$ comprising amino acids having the sequence set forth in SEQ ID NO:41 and a $V_L$ comprising amino acids having the sequence set forth in SEQ ID NO:42, as shown in Table 11. In certain embodiments, the extracellular antigen-binding domain comprises a $V_H$ CDR1 comprising amino acids having the sequence set forth in SEQ ID NO:184 or conservative modifications thereof, a $V_H$ CDR2 comprising amino acids having the sequence set forth in SEQ ID NO: 185 or conservative modifications thereof, and a $V_H$ CDR3 comprising amino acids having the sequence set forth in SEQ ID NO: 186 or conservative modifications thereof, as shown in Table 11. In certain embodiments, the extracellular antigen-binding domain comprises a $V_L$ CDR1 comprising amino acids having the sequence set forth in SEQ ID NO: 187 or conservative modifications thereof, a $V_L$ CDR2 comprising amino acids having the sequence set forth in SEQ ID NO: 188 or conservative modifications thereof, and a $V_L$ CDR3 comprising amino acids having the sequence set forth in SEQ ID NO: 189 or conservative modifications thereof, as shown in Table 11. In certain embodiments, the extracellular antigen-binding domain comprises a $V_H$ CDR1 comprising amino acids having the sequence set forth in SEQ ID NO: 184 or conservative modifications thereof, a $V_H$ CDR2 comprising amino acids having the sequence set forth in SEQ ID NO: 185 or conservative modifications thereof, a $V_H$ CDR3 comprising amino acids having the sequence set forth in SEQ ID NO: 186 or conservative modifications thereof, a $V_L$ CDR1 comprising amino acids having the sequence set forth in SEQ ID NO: 187 or conservative modifications thereof, a $V_L$ CDR2 comprising amino acids having the sequence set forth in SEQ ID NO: 188 or conservative modifications thereof, and a $V_L$ CDR3 comprising amino acids having the sequence set forth in SEQ ID NO: 189 or conservative modifications thereof, as shown in Table 11. In certain embodiments, the extracellular antigen-binding domain comprises a $V_H$ CDR1 comprising amino acids having the sequence set forth in SEQ ID NO: 184, a $V_H$ CDR2 comprising amino acids having the sequence set forth in SEQ ID NO: 185, a $V_H$ CDR3 comprising amino acids having the sequence set forth in SEQ ID NO: 186, a $V_L$ CDR1 comprising amino acids having the sequence set forth in SEQ ID NO: 187, a $V_L$ CDR2 comprising amino acids having the sequence set forth in SEQ ID NO: 188, and a $V_L$ CDR3 comprising amino acids having the sequence set forth in SEQ ID NO: 189.

TABLE 11

| | | | |
|---|---|---|---|
| Antigen | A GPRC5D polypeptide having the amino acid sequence of SEQ ID NO: 97 | | |
| CDRs | 1 | 2 | 3 |
| $V_H$ | EYTFTRHI [SEQ ID NO: 184] | INPGNGNT [SEQ ID NO: 185] | ARLPDQ [SEQ ID NO: 186] |
| $V_L$ | SSNIGSNT [SEQ ID NO: 187] | RNN [SEQ ID NO: 188] | AAWDDSLSGL [SEQ ID NO: 189] |
| Full $V_H$ | QMQLVQSGAEVKKPGASVKVSCKASEYTFTRHILHWVRQAPGQ SLEWMGWINPGNGNTKYSQKFQVRVTFTRDTSASTVYMELSSLR SEDTAVYYCARLPDQWGQGTLVTVSS [SEQ ID NO: 41] | | |
| DNA | Cagatgcagctggtgcagtctggggctgaggtgaagaagcctggggcctcagtgaaggtttcctgcaa ggatctgaatacaccttcactaggcatattctacattgggtgcgccaggctcccggacaaagccttgagt ggatgggatggatcaacccaggcaatggtaatacaaaatattcacagaagttccaggtcagagtcacctt taccagggacacatccgcgagcacagtctatatggagctgagcagcctgagatctgaagacacggcc gtgtattactgtgcgcgcctgccggatcagtggggtcaaggtactctggtgaccgtctcctca [SEQ ID NO: 43] | | |

TABLE 11-continued

| | |
|---|---|
| Full $V_L$ | SYVLTQPPSASGTPGQRVTISCSGSSSNIGSNTVNWYQQLPGTAPK LLIYRNNQRPSGVPDRFSGSKSGTSASLAISGLRSEDEADYYCAA WDDSLSGLFGTGTKVTVLG [SEQ ID NO: 42] |
| DNA | Tcctatgtgctgactcagccaccctcagcgtctgggacccccgggcagagggtcaccatctcttgttct ggaagcagctccaacatcggaagtaatactgtaaactggtaccagcagctcccaggaacggcccccaaactcctcatctataggaataatcagcggccctcaggggtccctgaccgattctctggctccaagtctggcacctcagcctccctggccatcagtgggctccggtccgaggatgaggctgattattactgtgcagcatg ggatgacagcctgagtggtctcttcggaactgggaccaaggtcaccgtcctaggt [SEQ ID NO: 44] |
| scFv | SYVLTQPPSASGTPGQRVTISCSGSSSNIGSNTVNWYQQLPGTAPK LLIYRNNQRPSGVPDRFSGSKSGTSASLAISGLRSEDEADYYCAA WDDSLSGLFGTGTKVTVLGSRGGGGSGGGGSGGGGSLEMAQMQ LVQSGAEVKKPGASVKVSCKASEYTFTRHILHWVRQAPGQSLEW MGWINPGNGNTKYSQKFQVRVTFTRDTSASTVYMELSSLRSEDT AVYYCARLPDQWGQGTLVTVSS [SEQ ID NO: 110] |

In certain embodiments, the extracellular antigen-binding domain is a scFv, which comprises the amino acid sequence of SEQ ID NO: 111 and specifically binds to a GPRC5D polypeptide (e.g., a GPRC5D polypeptide having the amino acid sequence SEQ ID NO:97, or fragments thereof), which scFv is designated as ET150-162 scFv (also referred to as "ET150-12 scFv").

In certain embodiments, the extracellular antigen-binding domain is a scFv, which comprises a heavy chain variable region comprising amino acids having the sequence set forth in SEQ ID NO:45 and a light chain variable region comprising amino acids having the sequence set forth in SEQ ID NO:46, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 12. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:45, as shown in Table 12. In certain embodiments, the extracellular antigen-binding domain comprises a $V_H$ comprising amino acids having the sequence set forth in SEQ ID NO:45, as shown in Table 12. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:46, as shown in Table 12. In certain embodiments, the extracellular antigen-binding domain comprises a $V_L$ comprising amino acids having the sequence set forth in SEQ ID NO:46, as shown in Table 12. In certain embodiments, the extracellular antigen-binding domain comprises a $V_H$ comprising amino acids having the sequence set forth in SEQ ID NO:45 and a $V_L$ comprising amino acids having the sequence set forth in SEQ ID NO:46, as shown in Table 12. In certain embodiments, the extracellular antigen-binding domain comprises a $V_H$ CDR1 comprising amino acids having the sequence set forth in SEQ ID NO:190 or conservative modifications thereof, a $V_H$ CDR2 comprising amino acids having the sequence set forth in SEQ ID NO: 191 or conservative modifications thereof, and a $V_H$ CDR3 comprising amino acids having the sequence set forth in SEQ ID NO: 192 or conservative modifications thereof, as shown in Table 12. In certain embodiments, the extracellular antigen-binding domain comprises a $V_L$ CDR1 comprising amino acids having the sequence set forth in SEQ ID NO: 193 or conservative modifications thereof, a $V_L$ CDR2 comprising amino acids having the sequence set forth in SEQ ID NO: 194 or conservative modifications thereof, and a $V_L$ CDR3 comprising amino acids having the sequence set forth in SEQ ID NO: 195 or conservative modifications thereof, as shown in Table 12. In certain embodiments, the extracellular antigen-binding domain comprises a $V_H$ CDR1 comprising amino acids having the sequence set forth in SEQ ID NO: 190 or conservative modifications thereof, a $V_H$ CDR2 comprising amino acids having the sequence set forth in SEQ ID NO: 191 or conservative modifications thereof, a $V_H$ CDR3 comprising amino acids having the sequence set forth in SEQ ID NO: 192 or conservative modifications thereof, a $V_L$ CDR1 comprising amino acids having the sequence set forth in SEQ ID NO: 193 or conservative modifications thereof, a $V_L$ CDR2 comprising amino acids having the sequence set forth in SEQ ID NO: 194 or conservative modifications thereof, and a $V_L$ CDR3 comprising amino acids having the sequence set forth in SEQ ID NO: 195 or conservative modifications thereof, as shown in Table 12. In certain embodiments, the extracellular antigen-binding domain comprises a $V_H$ CDR1 comprising amino acids having the sequence set forth in SEQ ID NO: 190, a $V_H$ CDR2 comprising amino acids having the sequence set forth in SEQ ID NO: 191, a $V_H$ CDR3 comprising amino acids having the sequence set forth in SEQ ID NO: 192, a $V_L$ CDR1 comprising amino acids having the sequence set forth in SEQ ID NO: 193, a $V_L$ CDR2 comprising amino acids having the sequence set forth in SEQ ID NO: 194, and a $V_L$ CDR3 comprising amino acids having the sequence set forth in SEQ ID NO: 195.

TABLE 12

| | | | |
|---|---|---|---|
| Antigen | A GPRC5D polypeptide having the amino acid sequence of SEQ ID NO: 97 | | |
| CDRs | 1 | 2 | 3 |
| $V_H$ | GFTFGDYG [SEQ ID NO: 190] | INWNGGST [SEQ ID NO: 191] | ARSKQDY [SEQ ID NO: 192] |
| $V_L$ | SRDAGGYNY [SEQ ID NO: 193] | EVT [SEQ ID NO: 194] | SSYGGSNNFRV [SEQ ID NO: 195] |
| Full $V_H$ | EVQLVESGGGVVRPGGSLRLSCAASGFTFGDYGMSWVRQAPGK GLEWVSGINWNGGSTGYADSVKGRFTISRDNAKNSLYLQMNSLR AEDTAVYYCARSKQDYWGQGTLVTVSS [SEQ ID NO: 45] | | |
| DNA | Gaggtgcagctggtggagtctgggggaggtgtggtacggcctggggggtccctgagactctcctgtg cagcctctggattcacctttggtgattatggcatgagctgggtccgccaagctccagggaaggggctgg agtgggtctctggtattaattggaatggtggtagcacaggttatgcagactctgtgaagggccgattcacc atctccagagacaacgccaagaactccctgtatctgcaaatgaacagtctgagagccgaggacacggc cgtatattactgtgcgcgctctaaacaggattactggggtcaaggtactctggtgaccgtctcctca [SEQ ID NO: 47] | | |
| Full $V_L$ | QSALTQPPSASGSPGQSVTISCTGTSRDAGGYNYFSWYQQHPGKA PKLLIYEVTKRPSGVPDRFSGSKSGKTASLTVSGLQADDEAVYYC SSYGGSNNFRVFGGGTKLTVLG [SEQ ID NO: 46] | | |
| DNA | Cagtctgccctgactcagcctccctccgcgtccgggtctcctggacagtcagtcaccatctcctgcactg gaaccagcagggacgctggtggttataattatttctcctggtaccaacaacacccaggcaaagcccccca aactcctgatttatgaggtcactaagcggccctcaggggtccctgatcgcttctctggctccaagtctggc aagacggcctccctgaccgtctctgggctccaggctgacgatgaggctgtatattactgcagctcatatg gaggcagcaacaactttcgggtgttcggcggagggaccaagctgaccgtcctaggt [SEQ ID NO: 48] | | |
| scFv | QSALTQPPSASGSPGQSVTISCTGTSRDAGGYNYFSWYQQHPGKA PKLLIYEVTKRPSGVPDRFSGSKSGKTASLTVSGLQADDEAVYYC SSYGGSNNFRVFGGGTKLTVLGSRGGGGSGGGGSGGGGSLEMA EVQLVESGGGVVRPGGSLRLSCAASGFTFGDYGMSWVRQAPGK GLEWVSGINWNGGSTGYADSVKGRFTISRDNAKNSLYLQMNSLR AEDTAVYYCARSKQDYWGQGTLVTVSS [SEQ ID NO: 111] | | |

In certain embodiments, the extracellular antigen-binding domain is a scFv, which comprises the amino acid sequence of SEQ ID NO: 112 and specifically binds to a GPRC5D polypeptide (e.g., a GPRC5D polypeptide having the amino acid sequence SEQ ID NO:97, or fragments thereof), which scFv is designated as ET150-163 scFv (also referred to as "ET150-13 scFv").

In certain embodiments, the extracellular antigen-binding domain is a scFv, which comprises a heavy chain variable region comprising amino acids having the sequence set forth in SEQ ID NO:49 and a light chain variable region comprising amino acids having the sequence set forth in SEQ ID NO:50, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 13. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:49, as shown in Table 13. In certain embodiments, the extracellular antigen-binding domain comprises a $V_H$ comprising amino acids having the sequence set forth in SEQ ID NO:49, as shown in Table 13. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:50, as shown in Table 13. In certain embodiments, the extracellular antigen-binding domain comprises a $V_L$ comprising amino acids having the sequence set forth in SEQ ID NO:50, as shown in Table 13. In certain embodiments, the extracellular antigen-binding domain comprises a $V_H$ comprising amino acids having the sequence set forth in SEQ ID NO:49 and a $V_L$ comprising amino acids having the sequence set forth in SEQ ID NO:50, as shown in Table 13. In certain embodiments, the extracellular antigen-binding domain comprises a $V_H$ CDR1 comprising amino acids having the sequence set forth in SEQ ID NO:196 or conservative modifications thereof, a $V_H$ CDR2 comprising amino acids having the sequence set forth in SEQ ID NO: 197 or conservative modifications thereof, and a $V_H$ CDR3 comprising amino acids having the sequence set forth in SEQ ID NO: 198 or conservative modifications thereof, as shown in Table 13. In certain embodiments, the extracellular antigen-binding domain comprises a $V_L$ CDR1 comprising amino acids having the sequence set forth in SEQ ID NO: 199 or conservative modifications thereof, a $V_L$ CDR2 comprising amino acids having the sequence set forth in SEQ ID NO:200 or conservative modifications thereof, and a $V_L$ CDR3 comprising amino acids having the sequence set forth in SEQ ID NO:201 or conservative modifications thereof, as shown in Table 13. In certain embodiments, the extracellular antigen-binding domain comprises a $V_H$ CDR1 comprising amino acids having the sequence set forth in SEQ ID NO: 196 or conservative modifications thereof, a $V_H$ CDR2 comprising amino acids having the sequence set forth in SEQ ID NO: 197 or conservative modifications thereof, a $V_H$ CDR3 comprising amino acids having the sequence set forth in SEQ ID NO: 198 or conservative modifications thereof, a $V_L$ CDR1 comprising amino acids having the sequence set forth in SEQ ID NO: 199 or conservative modifications thereof, a $V_L$ CDR2 comprising amino acids having the sequence set forth in SEQ ID NO:200 or conservative modifications thereof, and a $V_L$ CDR3 comprising amino acids having the sequence set forth in SEQ ID NO:201 or conservative modifications thereof, as shown in Table 13. In certain embodiments, the extracellular antigen-binding domain comprises a $V_H$ CDR1 comprising amino acids having the sequence set forth in SEQ ID NO: 196, a $V_H$ CDR2 comprising amino acids having the sequence set forth in SEQ ID NO: 197, a $V_H$ CDR3 comprising amino acids having the sequence set forth in SEQ ID NO: 198 a $V_L$ CDR1 comprising amino acids having the sequence set forth in SEQ ID NO: 199, a $V_L$ CDR2 comprising amino acids having the sequence set forth in SEQ ID NO:200, and a $V_L$ CDR3 comprising amino acids having the sequence set forth in SEQ ID NO:201.

In certain embodiments, the extracellular antigen-binding domain comprises a heavy chain variable region comprising amino acids having the sequence set forth in SEQ ID NO:53 and a light chain variable region comprising amino acids having the sequence set forth in SEQ ID NO:54, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 14. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:53, as shown in Table 14. In certain embodiments, the extracellular antigen-binding domain comprises a $V_H$ comprising amino acids having the sequence set forth in SEQ ID NO:53, as shown in Table 14. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:54, as shown in Table 14. In certain embodiments, the extracellular antigen-binding domain

TABLE 13

| | | | |
|---|---|---|---|
| Antigen | A GPRC5D polypeptide having the amino acid sequence of SEQ ID NO: 97 | | |
| CDRs | 1 | 2 | 3 |
| $V_H$ | GFSFSGTA[SEQ ID NO: 196] | ISSTGRST [SEQ ID NO: 197] | ARVSFDY [SEQ ID NO: 198] |
| $V_L$ | SSNIGAGYD [SEQ ID NO: 199] | GNS [SEQ ID NO: 200] | QSYDSSLSGSYV [SEQ ID NO: 201] |
| Full $V_H$ | EVQLVETGGNLVQPGASLRLSCAASGFSFSGTAMHWVRQAPGK GLEWVSTISSTGRSTYYRDSVKGRFTISRDNSKNTLYLQMNSLRG EDTAVYYCARVSFDYWGQGTLVTVSS [SEQ ID NO: 49] | | |
| DNA | Gaggtgcagctggtggagactgggggaaacttggtacagccgggggcgtccctgagactctcctgtg cagcctctggattcagctttagtggcactgccatgcactgggtccgccaggctccagggaaggggctg gaatgggtctcgactattagtagtactgggcgtagcacatactacagagactccgtgaagggccggttc accatctccagagacaattccaagaacacgctgtatctgcaaatgaacagcctgagaggcgaggacac ggccgtatattactgtgcgcgcgtttctttcgattactggggtcaaggtactctggtgaccgtctcctca [SEQ ID NO: 51] | | |
| Full $V_L$ | QSVVTQPPSVSGAPGQRVTISCTGSSSNIGAGYDVHWYQQLPGTA PKLLIYGNSNRPSGVPDRFSGSKSGTSASLAITGLQAEDEADYYC QSYDSSLSGSYVFGTGTKLTVLG [SEQ ID NO: 50] | | |
| DNA | Cagtctgtcgtgacgcagccgccctcagtgtctggggccccagggcagagggtcaccatctcctgca ctgggagcagctccaacatcggggcaggttatgatgtacactggtaccagcagatccaggaacagcc cccaaactcctcatctatggtaacagcaatcggccctcaggggtccctgaccgattctctggctccaagt ctggcacctcagcctccctggccatcactgggctccaggctgaggatgaggctgattattactgccagt cctatgacagcagcctgagtggctcctacgtatcggaactgggaccaagctgaccgtcctaggt [SEQ ID NO: 52] | | |
| scFv | QSVVTQPPSVSGAPGQRVTISCTGSSSNIGAGYDVHWYQQLPGTA PKLLIYGNSNRPSGVPDRFSGSKSGTSASLAITGLQAEDEADYYC QSYDSSLSGSYVFGTGTKLTVLGSRGGGGSGGGGSGGGGSLEMA EVQLVETGGNLVQPGASLRLSCAASGFSFSGTAMHWVRQAPGK GLEWVSTISSTGRSTYYRDSVKGRFTISRDNSKNTLYLQMNSLRG EDTAVYYCARVSFDYWGQGTLVTVSS [SEQ ID NO: 112] | | |

In certain embodiments, the extracellular antigen-binding domain is a scFv, which comprises the amino acid sequence of SEQ ID NO: 113 and specifically binds to a GPRC5D polypeptide (e.g., a GPRC5D polypeptide having the amino acid sequence SEQ ID NO:97, or fragments thereof), which scFv is designated as ET150-151 scFv (also referred to as "ET150-1 scFv").

comprises a $V_L$ comprising amino acids having the sequence set forth in SEQ ID NO:54, as shown in Table 14. In certain embodiments, the extracellular antigen-binding domain comprises a $V_H$ comprising amino acids having the sequence set forth in SEQ ID NO:53 and a $V_L$ comprising amino acids having the sequence set forth in SEQ ID NO:54, as shown in Table 14. In certain embodiments, the extracellular antigen-binding domain comprises a $V_H$ CDR1 comprising amino acids having the sequence set forth in SEQ ID NO:202 or conservative modifications thereof, a $V_H$ CDR2 comprising amino acids having the sequence set forth in SEQ ID NO:203 or conservative modifications thereof, and a $V_H$ CDR3 comprising amino acids having the sequence set forth in SEQ ID NO: 204 or conservative modifications thereof, as shown in Table 14. In certain embodiments, the extracellular antigen-binding domain comprises a $V_L$ CDR1 conservative modifications thereof, a $V_L$ CDR2 comprising amino acids having the sequence set forth in SEQ ID NO: 206 or conservative modifications thereof, and a $V_L$ CDR3 comprising amino acids having the sequence set forth in SEQ ID NO: 207 or conservative modifications thereof, as shown in Table 14. In certain embodiments, the extracellular antigen-binding domain comprises a $V_H$ CDR1 comprising amino acids having the sequence set forth in SEQ ID NO: 202, a $V_H$ CDR2 comprising amino acids having the sequence set forth in SEQ ID NO: 203, a $V_H$ CDR3 comprising amino acids having the sequence set forth in SEQ ID NO: 204, a $V_L$ CDR1 comprising amino acids having the sequence set forth in SEQ ID NO: 205, a $V_L$ CDR2 comprising amino acids having the sequence set forth in SEQ ID NO: 206, and a $V_L$ CDR3 comprising amino acids having the sequence set forth in SEQ ID NO: 207.

TABLE 14

| Antigen | A GPRC5D polypeptide having the amino acid sequence of SEQ ID NO: 97 | | |
|---|---|---|---|
| CDRs | 1 | 2 | 3 |
| $V_H$ | GFTFSSYA [SEQ ID NO: 202] | ISGRGRST [SEQ ID NO: 203] | ARYYHAGAFDL [SEQ ID NO: 204] |
| $V_L$ | SSDVGGYNY [SEQ ID NO: 205] | DVS [SEQ ID NO: 206] | SSYTSSSTLV [SEQ ID NO: 207] |
| Full $V_H$ | EVQLVESGGAFVQPGGSLRLSCAASGFTFSSYAMTWVRQAPGKG LEWVSTISGRGRSTFYADSVKGRFTISRDNSKNTLYLQMNSLRAE DTAVYYCARYYHAGAFDLWGQGTLVTVSS [SEQ ID NO: 53] | | |
| DNA | Gaggtgcagctggtggagtctgggggagcctttgtacagcctggggggtecctgagactctcctgtgc agcctctggattcacctttagcagctatgccatgacctgggtccgccaggctccagggaagggcctgga atgggtctcgactattagtggtcgtggtcgtagcacattctacgcagactccgtgaagggccggtttacca tctccagagacaattccaagaacacgctatatctgcaaatgaacagtctgagagccgaggacacggcc gtatattactgtgcgcgctactaccatgctggtgctttcgatctgtggggtcaaggtactctggtgaccgtc tcctca [SEQ ID NO: 55] | | |
| Full $V_L$ | QSVVTQPASVSGSPGQSITISCTGTSSDVGGYNYVSWYQQHPGKA PKLMIYDVSKRPSGVSNRFSGSKSGNTASLTISGLQAEDEADYYC SSYTSSSTLVFGGGTKLTVLG [SEQ ID NO: 54] | | |
| DNA | Cagtctgtcgtgacgcagcctgcctccgtgtctgggtctcctggacagtcgatcaccatctcctgcactg gaaccagcagtgacgttggtggttataactatgtctcctggtaccaacagcacccaggcaaagcccca aactcatgatttatgatgtcagtaagcggccctcaggggtttctaatcgcttctctggctccaagtctggca acacggcctccctgaccatctctgggctccaggctgaggacgaggctgattattactgcagctcatatac aagcagcagcactttggtattcggcggagggaccaagctgaccgtcctaggt [SEQ ID NO: 56] | | |
| scFv | QSVVTQPASVSGSPGQSITISCTGTSSDVGGYNYVSWYQQHPGKA PKLMIYDVSKRPSGVSNRFSGSKSGNTASLTISGLQAEDEADYYC SSYTSSSTLVFGGGTKLTVLGSRGGGGSGGGGSGGGGSLEMAEV QLVESGGAFVQPGGSLRLSCAASGFTFSSYAMTWVRQAPGKGLE WVSTISGRGRSTFYADSVKGRFTISRDNSKNTLYLQMNSLRAEDT AVYYCARYYHAGAFDLWGQGTLVTVSS [SEQ ID NO: 113] | | |

comprising amino acids having the sequence set forth in SEQ ID NO: 205 or conservative modifications thereof, a $V_L$ CDR2 comprising amino acids having the sequence set forth in SEQ ID NO: 206 or conservative modifications thereof, and a $V_L$ CDR3 comprising amino acids having the sequence set forth in SEQ ID NO: 207 or conservative modifications thereof, as shown in Table 14. In certain embodiments, the extracellular antigen-binding domain comprises a $V_H$ CDR1 comprising amino acids having the sequence set forth in SEQ ID NO: 202 or conservative modifications thereof, a $V_H$ CDR2 comprising amino acids having the sequence set forth in SEQ ID NO: 203 or conservative modifications thereof, a $V_H$ CDR3 comprising amino acids having the sequence set forth in SEQ ID NO: 204 or conservative modifications thereof, a $V_L$ CDR1 comprising amino acids having the sequence set forth in SEQ ID NO: 205 or In certain embodiments, the extracellular antigen-binding domain is a scFv, which comprises the amino acid sequence of SEQ ID NO: 114 and specifically binds to a GPRC5D polypeptide (e.g., a GPRC5D polypeptide having the amino acid sequence SEQ ID NO:97, or fragments thereof), which scFv is designated as ET150-152 scFv (also referred to as "ET150-2 scFv").

In certain embodiments, the extracellular antigen-binding domain is a scFv, which comprises a heavy chain variable region comprising amino acids having the sequence set forth in SEQ ID NO:57 and a light chain variable region comprising amino acids having the sequence set forth in SEQ ID NO:58, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 15. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:57, as shown in Table 15. In certain embodiments, the extracellular antigen-binding domain comprises a $V_H$ comprising amino acids having the sequence set forth in SEQ ID NO:57, as shown in Table 15. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:58, as shown in Table 15. In certain embodiments, the extracellular antigen-binding domain comprises a $V_L$ comprising amino acids having the sequence set forth in SEQ ID NO:58, as shown in Table 15. In certain embodiments, the extracellular antigen-binding domain comprises a $V_H$ comprising amino acids having the sequence set forth in SEQ ID NO:57 and a $V_L$ comprising amino acids having the sequence set forth in SEQ ID NO:58, as shown in Table 15. In certain embodiments, the extracellular antigen-binding domain comprises a $V_H$ CDR1 comprising amino acids having the sequence set forth in SEQ ID NO:208 or conservative modifications thereof, a $V_H$ CDR2 comprising amino acids having the sequence set forth in SEQ ID NO: 209 or conservative modifications thereof, and a $V_H$ CDR3 comprising amino acids having the sequence set forth in SEQ ID NO: 210 or conservative modifications thereof, as shown in Table 15. In certain embodiments, the extracellular antigen-binding domain comprises a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof, as shown in Table 15. In certain embodiments, the extracellular antigen-binding domain comprises a $V_H$ CDR1 comprising amino acids having the sequence set forth in SEQ ID NO: 208 or conservative modifications thereof, a $V_H$ CDR2 comprising amino acids having the sequence set forth in SEQ ID NO: 209 or conservative modifications thereof, a $V_H$ CDR3 comprising amino acids having the sequence set forth in SEQ ID NO: 210 or conservative modifications thereof, a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof, as shown in Table 15. In certain embodiments, the extracellular antigen-binding domain comprises a $V_H$ CDR1 comprising amino acids having the sequence set forth in SEQ ID NO: 208, a $V_H$ CDR2 comprising amino acids having the sequence set forth in SEQ ID NO: 209, a $V_H$ CDR3 comprising amino acids having the sequence set forth in SEQ ID NO: 210, a $V_L$ CDR1 comprising amino acids having the sequence set forth in SEQ ID NO: 211, a $V_L$ CDR2 comprising amino acids having the sequence set forth in SEQ ID NO: 212, and a $V_L$ CDR3 comprising amino acids having the sequence set forth in SEQ ID NO: 213.

TABLE 15

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFNRYA [SEQ ID NO: 208] | ISAYNGNS [SEQ ID NO: 209] | ARMAYDS [SEQ ID NO: 210] |
| $V_L$ | SNDVGAYKY [SEQ ID NO: 211] | DVF [SEQ ID NO: 212] | FSLTSSNTYV [SEQ ID NO: 213] |
| Full $V_H$ | QMQLVQSGAEVKKPGASVKVSCKASGYTFNRYAITWVRQAPGQ<br>GLEWMGWISAYNGNSHYAQKLQGRVTMTTDTSTGTAYMELRRL<br>RSDDTAVYYCARMAYDSWGQGTLVTVSS [SEQ ID NO: 57] | | |
| DNA | Cagatgcagctggtgcagtctggagctgaggtgaagaagcctggggcctcagtgaaggtctcctgcaa<br>ggatctggttacacctttaacagatatgctatcacctgggtgcgacaggcccctggacaaggccttgagt<br>ggatgggatggatcagcgcttacaatggtaattcacactatgcacagaagctccagggcagagtcaccat<br>gaccacagacacatccacgggcacagcctatatggagctgaggaggctgagatctgacgacacggcc<br>gtgtattactgtgcgcgcatggcttacgattatggggtcaaggtactctggtgaccgtctcctca [SEQ ID NO: 59] | | |
| Full $V_L$ | QSVLTQPASVSGSPGQSLTISCTGTSNDVGAYKYVSWYQQYPGKA<br>PKLILYDVFKRPSGVSNRFSGSKSDNTASLTISGLQAEDEADYYCF<br>SLTSSNTYVFGTGTKVTVLG [SEQ ID NO: 58] | | |
| DNA | Cagtctgtgttgacgcagcctgcctccgtgtctgggtctcctggacagtcgctcaccatctcctgcactgg<br>aaccagcaatgacgttggtgatataagtatgtctcctggtatcaacagtacccaggcaaagcccccaaac<br>tcatactttatgatgtattaagcggccctcaggggtctctaatcgcttctctggctccaagtctgacaacac<br>ggcctccctgaccatctctgggctccaggctgaggacgaggctgattattactgatctcacttacaagca<br>gtaacacttatgtcttcggaactgggaccaaggtcaccgtcctaggt [SEQ ID NO: 60] | | |
| scFv | QSVLTQPASVSGSPGQSLTISCTGTSNDVGAYKYVSWYQQYPGKA<br>PKLILYDVFKRPSGVSNRFSGSKSDNTASLTISGLQAEDEADYYCF | | |

TABLE 15-continued

| |
|---|
| SLTSSNTYVFGTGTKVTVLGSRGGGGSGGGGSGGGGSLEMAQMQ LVQSGAEVKKPGASVKVSCKASGYTFNRYAITWVRQAPGQGLEW MGWISAYNGNSHYAQKLQGRVTMTTDTSTGTAYMELRRLRSDD TAVYYCARMAYDSWGQGTLVTVSS [SEQ ID NO: 114] |

In certain embodiments, the extracellular antigen-binding domain is a scFv, which comprises the amino acid sequence of SEQ ID NO: 115 and specifically binds to a GPRC5D polypeptide (e.g., a GPRC5D polypeptide having the amino acid sequence SEQ ID NO:97, or fragments thereof), which scFv is designated as ET150-155 scFv (also referred to as "ET150-5 scFv").

In certain embodiments, the extracellular antigen-binding domain is a scFV, which comprises a heavy chain variable region comprising amino acids having the sequence set forth in SEQ ID NO:61 and a light chain variable region comprising amino acids having the sequence set forth in SEQ ID NO:62, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 16. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:61, as shown in Table 16. In certain embodiments, the extracellular antigen-binding domain comprises a $V_H$ comprising amino acids having the sequence set forth in SEQ ID NO:61, as shown in Table 16. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:62, as shown in Table 16. In certain embodiments, the extracellular antigen-binding domain comprises a $V_L$ comprising amino acids having the sequence set forth in SEQ ID NO:62, as shown in Table 16. In certain embodiments, the extracellular antigen-binding domain comprises a $V_H$ comprising amino acids having the sequence set forth in SEQ ID NO:61 and a $V_L$ comprising amino acids having the sequence set forth in SEQ ID NO:62, as shown in Table 16. In certain embodiments certain embodiments, the extracellular antigen-binding domain comprises a $V_H$ CDR1 comprising amino acids having the sequence set forth in SEQ ID NO:214 or conservative modifications thereof, a $V_H$ CDR2 comprising amino acids having the sequence set forth in SEQ ID NO: 215 or conservative modifications thereof, and a $V_H$ CDR3 comprising amino acids having the sequence set forth in SEQ ID NO: 216 or conservative modifications thereof, as shown in Table 16. In certain embodiments, the extracellular antigen-binding domain comprises a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof, as shown in Table 16. In certain embodiments, the extracellular antigen-binding domain comprises a $V_H$ CDR1 comprising amino acids having the sequence set forth in SEQ ID NO: 214 or conservative modifications thereof, a $V_H$ CDR2 comprising amino acids having the sequence set forth in SEQ ID NO: 215 or conservative modifications thereof, a $V_H$ CDR3 comprising amino acids having the sequence set forth in SEQ ID NO: 216 or conservative modifications thereof, a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof, as shown in Table 16. In certain embodiments, the extracellular antigen-binding domain comprises a $V_H$ CDR1 comprising amino acids having the sequence set forth in SEQ ID NO: 214, a $V_H$ CDR2 comprising amino acids having the sequence set forth in SEQ ID NO: 215, a $V_H$ CDR3 comprising amino acids having the sequence set forth in SEQ ID NO: 216, a $V_L$ CDR1 comprising amino acids having the sequence set forth in SEQ ID NO: 217, a $V_L$ CDR2 comprising amino acids having the sequence set forth in SEQ ID NO: 218 and a $V_L$ CDR3 comprising amino acids having the sequence set forth in SEQ ID NO: 219.

TABLE 16

| Antigen | A GPRC5D polypeptide having the amino acid sequence of SEQ ID NO: 97 | | |
|---|---|---|---|
| CDRs | 1 | 2 | 3 |
| $V_H$ | GFTFSDYY [SEQ ID NO: 214] | ISSSGSTI [SEQ ID NO: 215] | ARGYGKAYDQ [SEQ ID NO: 216] |
| $V_L$ | RSNVGGNY [SEQ ID NO: 217] | RSN [SEQ ID NO: 218] | ATWDDSLSGFV [SEQ ID NO: 219] |
| Full $V_H$ | EVQLVESGGGLVKPGGSLRLSCAASGFTFSDYYMSWIRQAPGKG LEWVSYISSSGSTIYYADSVKGRFTISRDNAKNSLYLQMNSLRAE DTAVYYCARGYGKAYDQWGQGTLVTVSS [SEQ ID NO: 61] | | |

TABLE 16-continued

| | |
|---|---|
| DNA | Gaggtgcagctggtggagtctgggggaggcttggtcaagcctggagggtccctgagactctcctgtg cagcctctggattcaccttcagtgactactacatgagctggatccgccaggctccagggaaggggctg gagtgggtttcatacattagtagtagtggtagtaccatatactacgcagactctgtgaagggccgattcac catctccagggacaacgccaagaactcactgtatctgcaaatgaacagcctgagagccgaggacacg gccgtatattactgtgcgcgcggttacggtaaagcttacgatcagtggggtcaaggtactctggtgaccg tctcctca [SEQ ID NO: 63] |
| Full $V_L$ | QSVLTQPPSASGTPGQRVTISCSGSRSNVGGNYVFWYQQVPGATP KLLIYRSNQRPSGVPDRFAGSKSGSSASLAISGLRSEDEADYYCAT WDDSLSGFVFGTGTKVTVLG [SEQ ID NO: 62] |
| DNA | Cagtctgtgttgactcagccaccctcagcgtctgggacccccggacagagggtcaccatctcttgttct ggaagcaggtccaacgtaggaggtaattatgtattttggtaccagcaagtccccggagcgacccccaa actcctcatctataggagtaatcagcggccctcggggtccctgaccgattcgctggctccaagtctgg ctcctcagcctccctggccatcagtggactccggtccgaggatgaggctgattattactgtgcaacatgg gatgacagcctgagtggttttgtcttcggaactgggaccaaggtcaccgtcctaggt [SEQ ID NO: 64] |
| scFv | QSVLTQPPSASGTPGQRVTISCSGSRSNVGGNYVFWYQQVPGATP KLLIYRSNQRPSGVPDRFAGSKSGSSASLAISGLRSEDEADYYCAT WDDSLSGFVFGTGTKVTVLGSRGGGGSGGGGSGGGGSLEMAEV QLVESGGGLVKPGGSLRLSCAASGFTFSDYYMSWIRQAPGKGLE WVSYISSSGSTIYYADSVKGRFTISRDNAKNSLYLQMNSLRAEDT AVYYCARGYGKAYDQWGQGTLVTVSS [SEQ ID NO: 115] |

In certain embodiments, the extracellular antigen-binding domain is a scFv, which comprises the amino acid sequence of SEQ ID NO: 116 and specifically binds to a GPRC5D polypeptide (e.g., a GPRC5D polypeptide having the amino acid sequence SEQ ID NO:97, or fragments thereof), which scFv is designated as ET150-158 scFv (also referred to as "ET150-8 scFv").

In certain embodiments, the extracellular antigen-binding domain is a scFv, which comprises a heavy chain variable region comprising amino acids having the sequence set forth in SEQ ID NO:65 and a light chain variable region comprising amino acids having the sequence set forth in SEQ ID NO:66, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 17. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:65, as shown in Table 17. In certain embodiments, the extracellular antigen-binding domain comprises a $V_H$ comprising amino acids having the sequence set forth in SEQ ID NO:65, as shown in Table 17. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:66, as shown in Table 17. In certain embodiments, the extracellular antigen-binding domain comprises a $V_L$ comprising amino acids having the sequence set forth in SEQ ID NO:66, as shown in Table 17. In certain embodiments, the extracellular antigen-binding domain comprises a $V_H$ comprising amino acids having the sequence set forth in SEQ ID NO:65 and a $V_L$ comprising amino acids having the sequence set forth in SEQ ID NO:66, as shown in Table 17. In certain embodiments, the extracellular antigen-binding domain comprises a $V_H$ CDR1 comprising amino acids having the sequence set forth in SEQ ID NO:220 or conservative modifications thereof, a $V_H$ CDR2 comprising amino acids having the sequence set forth in SEQ ID NO: 221 or conservative modifications thereof, and a $V_H$ CDR3 comprising amino acids having the sequence set forth in SEQ ID NO: 222 or conservative modifications thereof, as shown in Table 17. In certain embodiments, the extracellular antigen-binding domain comprises a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof, as shown in Table 17. In certain embodiments, the extracellular antigen-binding domain comprises a $V_H$ CDR1 comprising amino acids having the sequence set forth in SEQ ID NO: 220 or conservative modifications thereof, a $V_H$ CDR2 comprising amino acids having the sequence set forth in SEQ ID NO: 221 or conservative modifications thereof, a $V_H$ CDR3 comprising amino acids having the sequence set forth in SEQ ID NO: 222 or conservative modifications thereof, a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof, as shown in Table 17. In certain embodiments, the extracellular antigen-binding domain comprises a $V_H$ CDR1 comprising amino acids having the sequence set forth in SEQ ID NO: 220, a $V_H$ CDR2 comprising amino acids having the sequence set forth in SEQ ID NO: 221, a $V_H$ CDR3 comprising amino acids having the sequence set forth in SEQ ID NO: 222, a $V_L$ CDR1 comprising amino acids having the sequence set forth in SEQ ID NO: 223, a $V_L$ CDR2 comprising amino acids having the sequence set forth in SEQ ID NO: 224, and a $V_L$ CDR3 comprising amino acids having the sequence set forth in SEQ ID NO: 225.

TABLE 17

| | | | |
|---|---|---|---|
| Antigen | A GPRC5D polypeptide having the amino acid sequence of SEQ ID NO: 97 | | |
| CDRs | 1 | 2 | 3 |
| $V_H$ | GFTFRSHS [SEQ ID NO: 220] | ISSDSTYT [SEQ ID NO: 221] | ARSGGQWKYYDY [SEQ ID NO: 222] |
| $V_L$ | SLRSYY [SEQ ID NO: 223] | GKN [SEQ ID NO: 224] | NSRDSSGNPPVV [SEQ ID NO: 225] |
| Full $V_H$ | QVQLVESGGGLVHPGGSLRLSCAASGFTFRSHSMNWVRQAPGKG LEWVSSISSDSTYTYYADSVKGRFTISRDNAKNSLYLQMNSLRAE DTAVYYCARSGGQWKYYDYWGQGTLVTVSS [SEQ ID NO: 65] | | |
| DNA | Caggtgcagctggtggagtctgggggaggcctggtccaccctgggggtccctgagactctcctgtgc agcctctggattcaccttcagaagccatagcatgaactgggtccgccaggctccagggaaggggctgg agtgggtctcatccattagtagtgatagtacttacacatactacgcagactcagtgaagggccgattcacc atctccagagacaacgccaagaactcactgtatctgcaaatgaacagcctgagagccgaggacacggc cgtatattactgtgcgcgctctggtggtcagtggaaatactacgattactggggtcaaggtactctggtgac cgtctcctca [SEQ ID NO: 67] | | |
| Full $V_L$ | SSELTQDPAVSVALGQTVRITCQGDSLRSYYASWYQQKPGQAPVL VIYGKNNRPSGIPDRFSGSSSGNTASLTITGAQAEDEADYYCNSRD SSGNPPVVFGGGTKLTVLG [SEQ ID NO: 66] | | |
| DNA | Tcttctgagctgactcaggaccctgctgtgtctgtggccttgggacagacagtcaggatcacatgccaag gagacagcctcagaagctattatgcaagctggtaccagcagaagccaggacaggcccctgtacttgtca tctatggtaaaaacaaccggccctcagggatcccagaccgattctctggctccagctcaggaaacacag cttccttgaccatcactggggctcaggcggaagatgaggctgactattactgtaactcccgggacagcag tggtaacccccctgtggtattcggcggagggaccaagctgaccgtcctaggt [SEQ ID NO: 68] | | |
| scFv | SSELTQDPAVSVALGQTVRITCQGDSLRSYYASWYQQKPGQAPVL VIYGKNNRPSGIPDRFSGSSSGNTASLTITGAQAEDEADYYCNSRD SSGNPPVVFGGGTKLTVLGSRGGGGSGGGGSGGGGSLEMAQVQL VESGGGLVHPGGSLRLSCAASGFTFRSHSMNWVRQAPGKGLEWV SSISSDSTYTYYADSVKGRFTISRDNAKNSLYLQMNSLRAEDTAV YYCARSGGQWKYYDYWGQGTLVTVSS [SEQ ID NO: 116] | | |

In certain embodiments, the extracellular antigen-binding domain is a scFv, which comprises the amino acid sequence of SEQ ID NO: 117 and specifically binds to a GPRC5D polypeptide (e.g., a GPRC5D polypeptide having the amino acid sequence SEQ ID NO:97, or fragments thereof), which scFv is designated as ET150-168 scFv (also referred to as "ET150-18 scFv").

In certain embodiments, the extracellular antigen-binding domain is a scFv, which comprises a heavy chain variable region comprising amino acids having the sequence set forth in SEQ ID NO:69 and a light chain variable region comprising amino acids having the sequence set forth in SEQ ID NO:70, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 18. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:69, as shown in Table 18. In certain embodiments, the extracellular antigen-binding domain comprises a $V_H$ comprising amino acids having the sequence set forth in SEQ ID NO:69, as shown in Table 18. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:70, as shown in Table 18. In certain embodiments, the extracellular antigen-binding domain comprises a $V_L$ comprising amino acids having the sequence set forth in SEQ ID NO:70, as shown in Table 18. In certain embodiments, the extracellular antigen-binding domain comprises a $V_H$ comprising amino acids having the sequence set forth in SEQ ID NO:69 and a $V_L$ comprising amino acids having the sequence set forth in SEQ ID NO:70, as shown in Table 18. In certain embodiments, the extracellular antigen-binding domain comprises a $V_H$ CDR1 comprising amino acids having the sequence set forth in SEQ ID NO:226 or conservative modifications thereof, a $V_H$ CDR2 comprising amino acids having the sequence set forth in SEQ ID NO: 227 or conservative modifications thereof, and a $V_H$ CDR3 comprising amino acids having the sequence set forth in SEQ ID NO: 228 or conservative modifications thereof, as shown in Table 18. In certain embodiments, the extracellular antigen-binding domain comprises a $V_L$ CDR1 comprising amino acids having the sequence set forth in SEQ ID NO: 229 or conservative modifications thereof, a $V_L$ CDR2 comprising amino acids having the sequence set forth in SEQ ID NO: 230 or conservative modifications thereof, and a $V_L$ CDR3 comprising amino acids having the sequence set forth in SEQ ID NO: 231 or conservative modifications thereof, as shown in Table 18. In certain embodiments, the extracellular antigen-binding domain comprises a $V_H$ CDR1 comprising amino acids having the sequence set forth in SEQ ID NO: 226 or conservative modifications thereof, a $V_H$ CDR2 comprising amino acids having the sequence set forth in SEQ ID NO: 227 or conservative modifications thereof, a $V_H$ CDR3 comprising amino acids having the sequence set forth in SEQ ID NO: 228 or conservative modifications thereof, a $V_L$ CDR1 comprising amino acids having the sequence set forth in SEQ ID NO: 229 or conservative modifications thereof, a $V_L$ CDR2 comprising amino acids having the sequence set forth in SEQ ID NO: 230 or conservative modifications thereof, and a $V_L$ CDR3 comprising amino acids having the sequence set forth in SEQ ID NO: 231 or conservative modifications thereof, as shown in Table 18. In certain embodiments, the extracellular antigen-binding domain comprises a $V_H$ CDR1 comprising amino acids having the sequence set forth in SEQ ID NO: 226, a $V_H$ CDR2 comprising amino acids having the sequence set forth in SEQ ID NO: 227, a $V_H$ CDR3 comprising amino acids having the sequence set forth in SEQ ID NO: 228, a $V_L$ CDR1 comprising amino acids having the sequence set forth in SEQ ID NO: 229, a $V_L$ CDR2 comprising amino acids having the sequence set forth in SEQ ID NO: 230, and a $V_L$ CDR3 comprising amino acids having the sequence set forth in SEQ ID NO: 231.

scFv is designated as ET150-164 scFv (also referred to as "ET150-14 scFv").

In certain embodiments, the extracellular antigen-binding domain is a scFv, which comprises a heavy chain variable region comprising amino acids having the sequence set forth in SEQ ID NO:73 and a light chain variable region comprising amino acids having the sequence set forth in SEQ ID NO:74, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 19. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:73, as shown in Table 19. In certain embodiments, the extracellular antigen-binding domain comprises a $V_H$ comprising amino acids having the sequence set forth in SEQ ID NO:73, as shown in Table 19. In certain embodiments, the extracellular

TABLE 18

| Antigen | A GPRC5D polypeptide having the amino acid sequence of SEQ ID NO: 97 | | |
|---|---|---|---|
| CDRs | 1 | 2 | 3 |
| $V_H$ | GFTFSNYA [SEQ ID NO: 226] | INGRGSST [SEQ ID NO: 227] | ARYISRGLGDS [SEQ ID NO: 228] |
| $V_L$ | NSNIERNY[SEQ ID NO: 229] | DND [SEQ ID NO: 230] | GTWDSSLRGWV [SEQ ID NO: 231] |
| Full $V_H$ | EVQLVESGGGLIQPGGSLRLSCAASGFTFSNYAMNWVRQAPGKG<br>LEWVSTINGRGSSTIYADSVKGRFTISRDNSKNTLYLQMNSLRAED<br>TATYYCARYISRGLGDSWGQGTLVTV [SEQ ID NO: 69] | | |
| DNA | Gaggtgcagctggtggagtccgggggaggcttgatacagcctggggggtccctgagactctcctgtgc<br>agcctctggattcacctttagcaactatgccatgaactgggtccgccaggctccagggaaggggctgga<br>gtgggtctcaactattaatggtcgtggtagtagtacaatctacgcagactccgtgaagggccggttcacca<br>tctccagagacaattccaagaacacgctgtatctgcaaatgaacagcctgagagccgaggacacagcca<br>cgtattactgtgcgcgctacatctctcgtggtctgggtgattcttggggtcaaggtactctggtgaccgtctc<br>ctca [SEQ ID NO: 71] | | |
| Full $V_L$ | QSVVTQPPSMSAAPGQQVTISCSGGNSNIERNYVSWYLQLPGTAP<br>KLVIFDNDRRPSGIPDRFSGSKSGTSATLGITGLQTGDEADYYCGT<br>WDSSLRGWVFGGGTKLTVLG [SEQ ID NO: 70] | | |
| DNA | Cagtctgtcgtgacgcagccgccctcaatgtctgcggccccaggacagcaagtcaccatctcctgctct<br>ggaggcaactccaacattgagagaaattatgtatcctggtacctccagctccctggaacagcccccaaac<br>tcgtcatttttgacaatgataggcgaccctcagggattcctgaccgattctctggctccaagtctggcacgt<br>cagccaccctgggcatcaccggactccagactggggacgaggccgattattactgcggaacatgggat<br>agcagcctgagaggttgggtgttcggcggagggaccaagctgaccgtcctaggt [SEQ ID<br>NO: 72] | | |
| scFv | QSVVTQPPSMSAAPGQQVTISCSGGNSNIERNYVSWYLQLPGTAP<br>KLVIFDNDRRPSGIPDRFSGSKSGTSATLGITGLQTGDEADYYCGT<br>WDSSLRGWVFGGGTKLTVLGSRGGGGSGGGGSGGGGSLEMAEV<br>QLVESGGGLIQPGGSLRLSCAASGFTFSNYAMNWVRQAPGKGLE<br>WVSTINGRGSSTIYADSVKGRFTISRDNSKNTLYLQMNSLRAEDT<br>ATYYCARYISRGLGDSWGQGTLVTV [SEQ ID NO: 117] | | |

In certain embodiments, the extracellular antigen-binding domain is a scFv, which comprises the amino acid sequence of SEQ ID NO: 118 and specifically binds to a GPRC5D polypeptide (e.g., a GPRC5D polypeptide having the amino acid sequence SEQ ID NO:97, or fragments thereof), which antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:74, as shown in Table 19. In certain embodiments, the extracellular antigen-binding domain comprises a $V_L$ comprising amino acids having the sequence set forth in SEQ ID NO:74, as shown in Table 19. In certain embodiments, the extracellular antigen-binding domain comprises a $V_H$ comprising amino acids having the sequence set forth in SEQ ID NO:73 and a $V_L$ comprising amino acids having the sequence set forth in SEQ ID NO:74, as shown in Table 19. In certain embodiments, the extracellular antigen-binding domain comprises a $V_H$ CDR1 comprising amino acids having the sequence set forth in SEQ ID NO:232 or conservative modifications thereof, a $V_H$ CDR2 comprising amino acids having the sequence set forth in SEQ ID NO: 233 or conservative modifications thereof, and a $V_H$ CDR3 comprising amino acids having the sequence set forth in SEQ ID NO: 234 or conservative modifications thereof, as shown in Table 19. In certain embodiments, the extracellular antigen-binding domain comprises a $V_L$ CDR1 comprising amino acids having the sequence set forth in SEQ ID NO: 235 or conservative modifications thereof, a $V_L$ CDR2 comprising amino acids having the sequence set forth in SEQ ID NO: 236 or conservative modifications thereof, and a $V_L$ CDR3 comprising amino acids having the sequence set forth in SEQ ID NO: 237 or conservative modifications thereof, as shown in Table 19. In certain embodiments, the extracellular antigen-binding domain comprises a $V_H$ CDR1 comprising amino acids having the sequence set forth in SEQ ID NO: 232 or conservative modifications thereof, a $V_H$ CDR2 comprising amino acids having the sequence set forth in SEQ ID NO: 233 or conservative modifications thereof, a $V_H$ CDR3 comprising amino acids having the sequence set forth in SEQ ID NO: 234 or conservative modifications thereof, a $V_L$ CDR1 comprising amino acids having the sequence set forth in SEQ ID NO: 235 or conservative modifications thereof, a $V_L$ CDR2 comprising amino acids having the sequence set forth in SEQ ID NO: 236 or conservative modifications thereof, and a $V_L$ CDR3 comprising amino acids having the sequence set forth in SEQ ID NO: 237 or conservative modifications thereof, as shown in Table 19. In certain embodiments, the extracellular antigen-binding domain comprises a $V_H$ CDR1 comprising amino acids having the sequence set forth in SEQ ID NO: 232, a $V_H$ CDR2 comprising amino acids having the sequence set forth in SEQ ID NO: 233, a $V_H$ CDR3 comprising amino acids having the sequence set forth in SEQ ID NO: 234, a $V_L$ CDR1 comprising amino acids having the sequence set forth in SEQ ID NO: 235, a $V_L$ CDR2 comprising amino acids having the sequence set forth in SEQ ID NO: 236, and a $V_L$ CDR3 comprising amino acids having the sequence set forth in SEQ ID NO: 237.

TABLE 19

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFTSYY [SEQ ID NO: 232] | INPSGGST [SEQ ID NO: 233 | ARAGMGMDT [SEQ ID NO: 234] |
| $V_L$ | SSDVGGYNY [SEQ ID NO: 235] | EVS [SEQ ID NO: 236] | SSYAGSNTLV [SEQ ID NO: 237] |
| Full $V_H$ | QMQLVQSGAEVKKPGASVKVSCKASGYTFTSYYMHWVRQAPG QGLEWMGIINPSGGSTSYAQKFQGRVTMTRDTSTSTVYMELSSL RSEDTAVYYCARAGMGMDTWGQGTLVTVSS [SEQ ID NO: 73] | | |
| DNA | Cagatgcagctggtgcagtctggggctgaggtgaagaagcctggggcctcagtgaaggtttcctgca aggcatctggatacaccttcaccagctactatatgcactgggtgcgacaggcccctggacaagggcttg agtggatgggaataatcaaccctagtggtggtagcacaagctacgcacagaagttccagggcagagtc accatgaccagggacacgtccacgagcacagtctacatggagctgagcagcctgagatctgaggaca cggccgtgtattactgtgcgcgcgctggtatgggtatggatacttggggtcaaggtactctggtgaccgt ctcctca [SEQ ID NO: 75] | | |
| Full $V_L$ | QSALTQPPSASGSPGQSVTISCTGTSSDVGGYNYVSWYQQHPGK APKLMIYEVSKRPSGVPDRFSGSKSGNTASLTVSGLQAEDEADYY CSSYAGSNTLVFGGGTKLTVLG [SEQ ID NO: 74] | | |
| DNA | Cagtctgccctgactcagcctccctccgcgtccgggtctcctggacagtcagtcaccatctcctgcact ggaaccagcagtgacgttggtggttataactatgtctcctggtaccaacagcacccaggcaaagccccc aaactcatgatttatgaggtcagtaagcggccctcaggggtccctgatcgcttctctggctccaagtctgg caacacggcctccctgaccgtctctgggctccaggctgaggatgaggctgattattactgcagctcatat gcaggcagcaacaccttggtgttcggcggagggaccaagctgaccgtcctaggt [SEQ ID NO: 76] | | |
| scFv | QSALTQPPSASGSPGQSVTISCTGTSSDVGGYNYVSWYQQHPGK APKLMIYEVSKRPSGVPDRFSGSKSGNTASLTVSGLQAEDEADYY CSSYAGSNTLVFGGGTKLTVLGSRGGGGSGGGGSGGGGSLEMA QMQLVQSGAEVKKPGASVKVSCKASGYTFTSYYMHWVRQAPG QGLEWMGIINPSGGSTSYAQKFQGRVTMTRDTSTSTVYMELSSL RSEDTAVYYCARAGMGMDTWGQGTLVTVSS [SEQ ID NO: 118] | | |

In certain embodiments, the extracellular antigen-binding domain is a scFv, which comprises the amino acid sequence of SEQ ID NO: 119 and specifically binds to a GPRC5D polypeptide (e.g., a GPRC5D polypeptide having the amino acid sequence SEQ ID NO:97, or fragments thereof), which scFv is designated as ET150-165 scFv (also referred to as "ET150-15 scFv").

In certain embodiments, the extracellular antigen-binding domain is a scFv, which comprises a heavy chain variable region comprising amino acids having the sequence set forth in SEQ ID NO:77 and a light chain variable region comprising amino acids having the sequence set forth in SEQ ID NO:78, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 20. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:77, as shown in Table 20. In certain embodiments, the extracellular antigen-binding domain comprises a $V_H$ comprising amino acids having the sequence set forth in SEQ ID NO:77, as shown in Table 20. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:78, as shown in Table 20. In certain embodiments, the extracellular antigen-binding domain comprises a $V_L$ comprising amino acids having the sequence set forth in SEQ ID NO:78, as shown in Table 20. In certain embodiments, the extracellular antigen-binding domain comprises a $V_H$ comprising amino acids having the sequence set forth in SEQ ID NO:77 and a $V_L$ comprising amino acids having the sequence set forth in SEQ ID NO:78, as shown in Table 20. In certain embodiments, the extracellular antigen-binding domain comprises a $V_H$ CDR1 comprising amino acids having the sequence set forth in SEQ ID NO:238 or conservative modifications thereof, a $V_H$ CDR2 comprising amino acids having the sequence set forth in SEQ ID NO: 239 or conservative modifications thereof, and a $V_H$ CDR3 comprising amino acids having the sequence set forth in SEQ ID NO: 240 or conservative modifications thereof, as shown in Table 20. In certain embodiments, the extracellular antigen-binding domain comprises a $V_L$ CDR1 comprising amino acids having the sequence set forth in SEQ ID NO: 241 or conservative modifications thereof, a $V_L$ CDR2 comprising amino acids having the sequence set forth in SEQ ID NO: 242 or conservative modifications thereof, and a $V_L$ CDR3 comprising amino acids having the sequence set forth in SEQ ID NO: 243 or conservative modifications thereof, as shown in Table 20. In certain embodiments, the extracellular antigen-binding domain comprises a $V_H$ CDR1 comprising amino acids having the sequence set forth in SEQ ID NO: 238 or conservative modifications thereof, a $V_H$ CDR2 comprising amino acids having the sequence set forth in SEQ ID NO: 239 or conservative modifications thereof, a $V_H$ CDR3 comprising amino acids having the sequence set forth in SEQ ID NO: 240 or conservative modifications thereof, a $V_L$ CDR1 comprising amino acids having the sequence set forth in SEQ ID NO: 241 or conservative modifications thereof, a $V_L$ CDR2 comprising amino acids having the sequence set forth in SEQ ID NO: 242 or conservative modifications thereof, and a $V_L$ CDR3 comprising amino acids having the sequence set forth in SEQ ID NO: 243 or conservative modifications thereof, as shown in Table 20. In certain embodiments, the extracellular antigen-binding domain comprises a $V_H$ CDR1 comprising amino acids having the sequence set forth in SEQ ID NO: 238, a $V_H$ CDR2 comprising amino acids having the sequence set forth in SEQ ID NO: 239, a $V_H$ CDR3 comprising amino acids having the sequence set forth in SEQ ID NO: 240, a $V_L$ CDR1 comprising amino acids having the sequence set forth in SEQ ID NO: 241, a $V_L$ CDR2 comprising amino acids having the sequence set forth in SEQ ID NO: 242, and a $V_L$ CDR3 comprising amino acids having the sequence set forth in SEQ ID NO: 243.

TABLE 20

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFTAYS [SEQ ID NO: 238] | INPSSGGA [SEQ ID NO: 239] | ARNVGGQADD [SEQ ID NO: 240] |
| $V_L$ | SSDIGGYNY [SEQ ID NO: 241] | EVN [SEQ ID NO: 242] | ASFAGRKTLV [SEQ ID NO: 243] |
| Full $V_H$ | QVQLVQSGAEVKKPGASVKVSCRASGYTFTAYSLHWVRQAPGQ GLEWMGWINPSSGGAVYAQKFQGRVTMTRDTSISTAYMELSGL RSDDTAVYYCARNVGGQADDWGQGTLVTVSS [SEQ ID NO: 77] | | |
| DNA | Caggtgcagctggtgcagtctggggctgaggtgaagaagcctggggcctcagtgaaggtctcctgca gggatctggatacaccttcaccgcctactattacactgggtgcgacaggcccctggacaagggcttg agtggatgggatggatcaaccctagcagtggtggcgcagtttatgcacagaaatttcagggtagggtca ccatgaccagggacacgtccatcagcacagcctacatggagctgagtggcctgagatctgacgacac ggccgtgtattactgtgcgcgcaacgttggtggtcaggctgatgactggggtcaaggtactctggtgac cgtctcctca [SEQ ID NO: 79] | | |
| Full $V_L$ | QSALTQPPSASGSPGQSVTISCTGTSSDIGGYNYVSWYQQHPGKA PKLMIYEVNKRPSGVPDRFSGSKSGNTASLTVSGLQAEDEADYY CASFAGRKTLVFGGGTKLTVLG [SEQ ID NO: 78] | | |

TABLE 20-continued

| | |
|---|---|
| DNA | Caatctgccctgactcagcctccctccgcgtccgggtctcctggacagtcagtcaccatctcctgcactg<br>gaaccagcagtgacattggtggttataactatgtctcctggtaccaacagcacccaggcaaagccccca<br>aactcatgatttatgaggtcaataagcggccctcaggggtccctgatcgcttctcgggctccaagtctgg<br>caacacggcctccctgaccgtctctgggctccaggctgaggatgaggctgattattactgcgcctcattt<br>gcgggcaggaagacattggtcttcggcggagggaccaagctgaccgtcctaggt [SEQ ID<br>NO: 80] |
| scFv | QSALTQPPSASGSPGQSVTISCTGTSSDIGGYNYVSWYQQHPGKA<br>PKLMIYEVNKRPSGVPDRFSGSKSGNTASLTVSGLQAEDEADYY<br>CASFAGRKTLVFGGGTKLTVLGSRGGGGSGGGGSGGGGSLEMA<br>QVQLVQSGAEVKKPGASVKVSCRASGYTFTAYSLHWVRQAPGQ<br>GLEWMGWINPSSGGAVYAQKFQGRVTMTRDTSISTAYMELSGL<br>RSDDTAVYYCARNVGGQADDWGQGTLVTVSS [SEQ ID NO: 119] |

In certain embodiments, the extracellular antigen-binding domain is a scFv, which comprises the amino acid sequence of SEQ ID NO: 120 and specifically binds to a GPRC5D polypeptide (e.g., a GPRC5D polypeptide having the amino acid sequence SEQ ID NO:97, or fragments thereof), which scFv is designated as ET150-167 scFv (also referred to as "ET150-17 scFv").

In certain embodiments, the extracellular antigen-binding domain is a scFv, which comprises a heavy chain variable region comprising amino acids having the sequence set forth in SEQ ID NO:81 and a light chain variable region comprising amino acids having the sequence set forth in SEQ ID NO:82, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 21. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:81, as shown in Table 21. In certain embodiments, the extracellular antigen-binding domain comprises a $V_H$ comprising amino acids having the sequence set forth in SEQ ID NO:81, as shown in Table 21. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:82, as shown in Table 21. In certain embodiments, the extracellular antigen-binding domain comprises a $V_L$ comprising amino acids having the sequence set forth in SEQ ID NO:82, as shown in Table 21. In certain embodiments, the extracellular antigen-binding domain comprises a $V_H$ comprising amino acids having the sequence set forth in SEQ ID NO:81 and a $V_L$ comprising amino acids having the sequence set forth in SEQ ID NO:82, as shown in Table 21. In certain embodiments, the extracellular antigen-binding domain comprises a $V_H$ CDR1 comprising amino acids having the sequence set forth in SEQ ID NO:244 or conservative modifications thereof, a $V_H$ CDR2 comprising amino acids having the sequence set forth in SEQ ID NO: 245 or conservative modifications thereof, and a $V_H$ CDR3 comprising amino acids having the sequence set forth in SEQ ID NO: 246 or conservative modifications thereof, as shown in Table 21. In certain embodiments, the extracellular antigen-binding domain comprises a $V_L$ CDR1 comprising amino acids having the sequence set forth in SEQ ID NO: 247 or conservative modifications thereof, a $V_L$ CDR2 comprising amino acids having the sequence set forth in SEQ ID NO: 248 or conservative modifications thereof, and a $V_L$ CDR3 comprising amino acids having the sequence set forth in SEQ ID NO: 249 or conservative modifications thereof, as shown in Table 21. In certain embodiments, the extracellular antigen-binding domain comprises a $V_H$ CDR1 comprising amino acids having the sequence set forth in SEQ ID NO: 244 or conservative modifications thereof, a $V_H$ CDR2 comprising amino acids having the sequence set forth in SEQ ID NO: 245 or conservative modifications thereof, a $V_H$ CDR3 comprising amino acids having the sequence set forth in SEQ ID NO: 246 or conservative modifications thereof, a $V_L$ CDR1 comprising amino acids having the sequence set forth in SEQ ID NO: 247 or conservative modifications thereof, a $V_L$ CDR2 comprising amino acids having the sequence set forth in SEQ ID NO: 248 or conservative modifications thereof, and a $V_L$ CDR3 comprising amino acids having the sequence set forth in SEQ ID NO: 249 or conservative modifications thereof, as shown in Table 21. In certain embodiments, the extracellular antigen-binding domain comprises a $V_H$ CDR1 comprising amino acids having the sequence set forth in SEQ ID NO: 244, a $V_H$ CDR2 comprising amino acids having the sequence set forth in SEQ ID NO: 245, a $V_H$ CDR3 comprising amino acids having the sequence set forth in SEQ ID NO: 246, a $V_L$ CDR1 comprising amino acids having the sequence set forth in SEQ ID NO: 247, a $V_L$ CDR2 comprising amino acids having the sequence set forth in SEQ ID NO: 248, and a $V_L$ CDR3 comprising amino acids having the sequence set forth in SEQ ID NO: 249.

TABLE 21

Antigen A GPRC5D polypeptide having the amino acid sequence of SEQ ID NO: 97

| CDRs | 1 | 2 | 3 |
|---|---|---|---|
| $V_H$ | GYTFTAYS [SEQ ID NO: 244] | INPSSGGA [SEQ ID NO: 245] | ARNVGGHADD [SEQ ID NO: 246] |

TABLE 21-continued

| | | | |
|---|---|---|---|
| $V_L$ | STDIGGYNY [SEQ ID NO: 247] | EVN [SEQ ID NO: 248] | ASFAGRKTLV [SEQ ID NO: 249] |
| Full $V_H$ | QVQLVQSGAEVKKPGASVKVSCRASGYTFTAYSLHWVRQAPGQ GLEWMGWINPSSGGAVYAQKFQGRVTMTRDTSISTAYMELSGL RSDDTAVYYCARNVGGHADDWGQGTLVTVSS [SEQ ID NO: 81] | | |
| DNA | Caggtgcagctggtgcagtctggggctgaggtgaaaaagcctggggcctcagtgaaagtctcctgca gggatctggatacaccttcaccgcctactattacactgggtgcgacaggcccctggacaagggcttg agtggatgggatggatcaaccctagcagtggtggcgcagtttatgcacagaaatttcagggtagggtca ccatgaccagggacacgtccatcagcacagcctacatggagctgagtggcctgagatctgacgacac ggccgtgtattactgtgcgcgcaacgttggtggtcacgctgatgactggggtcaaggtactctggtgac cgtctcctca [SEQ ID NO: 83] | | |
| Full $V_L$ | QSALTQPPSASGSPGQSVTISCTGTSTDIGGYNYVSWYQHHPSKA PKLMIYEVNKRPSGVPDRFSGSKSGNTASLTVSGLQAEDEADYY CASFAGRKTLVFGGGTKLTVLG [SEQ ID NO: 82] | | |
| DNA | Caatctgccctgactcagcctccctccgcgtccgggtctcctggacagtcagtcaccatctcctgcactg gaaccagcactgacattggtggttataactatgtctcctggtaccaacaccacccaagcaaagcccca aactcatgatttatgaggtcaataagcggccctcaggggtccctgatcgcttctcgggctccaagtctgg caacacggcctccctgaccgtctctgggctccaggctgaggatgaggctgattattactgcgcctcattt gcgggcaggaagacattggtcttcggcggagggaccaagctgaccgtcctaggt [SEQ ID NO: 84] | | |
| scFv | QSALTQPPSASGSPGQSVTISCTGTSTDIGGYNYVSWYQHHPSKA PKLMIYEVNKRPSGVPDRFSGSKSGNTASLTVSGLQAEDEADYY CASFAGRKTLVFGGGTKLTVLGSRGGGGSGGGGSGGGGSLEMA QVQLVQSGAEVKKPGASVKVSCRASGYTFTAYSLHWVRQAPGQ GLEWMGWINPSSGGAVYAQKFQGRVTMTRDTSISTAYMELSGL RSDDTAVYYCARNVGGHADDWGQGTLVTVSS [SEQ ID NO: 120] | | |

In certain embodiments, the extracellular antigen-binding domain is a scFv, which comprises the amino acid sequence of SEQ ID NO: 121 and specifically binds to a GPRC5D polypeptide (e.g., a GPRC5D polypeptide having the amino acid sequence SEQ ID NO:97, or fragments thereof), which scFv is designated as ET150-169 scFv (also referred to as "ET150-19 scFv").

In certain embodiments, the extracellular antigen-binding domain is a scFv, which comprises a heavy chain variable region comprising amino acids having the sequence set forth in SEQ ID NO:85 and a light chain variable region comprising amino acids having the sequence set forth in SEQ ID NO:86, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 22. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:85, as shown in Table 22. In certain embodiments, the extracellular antigen-binding domain comprises a $V_H$ comprising amino acids having the sequence set forth in SEQ ID NO:85, as shown in Table 22. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:86, as shown in Table 22. In certain embodiments, the extracellular antigen-binding domain comprises a $V_L$ comprising amino acids having the sequence set forth in SEQ ID NO:86, as shown in Table 22. In certain embodiments, the extracellular antigen-binding domain comprises a $V_H$ comprising amino acids having the sequence set forth in SEQ ID NO:85 and a $V_L$ comprising amino acids having the sequence set forth in SEQ ID NO:86, as shown in Table 22. In certain embodiments, the extracellular antigen-binding domain comprises a $V_H$ CDR1 comprising amino acids having the sequence set forth in SEQ ID NO:250 or conservative modifications thereof, a $V_H$ CDR2 comprising amino acids having the sequence set forth in SEQ ID NO: 251 or conservative modifications thereof, and a $V_H$ CDR3 comprising amino acids having the sequence set forth in SEQ ID NO: 252 or conservative modifications thereof, as shown in Table 22. In certain embodiments, the extracellular antigen-binding domain comprises a $V_L$ CDR1 comprising amino acids having the sequence set forth in SEQ ID NO: 253 or conservative modifications thereof, a $V_L$ CDR2 comprising amino acids having the sequence set forth in SEQ ID NO: 254 or conservative modifications thereof, and a $V_L$ CDR3 comprising amino acids having the sequence set forth in SEQ ID NO: 255 or conservative modifications thereof, as shown in Table 22. In certain embodiments, the extracellular antigen-binding domain comprises a $V_H$ CDR1 comprising amino acids having the sequence set forth in SEQ ID NO: 250 or conservative modifications thereof, a $V_H$ CDR2 comprising amino acids having the sequence set forth in SEQ ID NO: 251 or conservative modifications thereof, a $V_H$ CDR3 comprising amino acids having the sequence set forth in SEQ ID NO: 252 or conservative modifications thereof, a $V_L$ CDR1 comprising amino acids having the sequence set forth in SEQ ID NO: 253 or conservative modifications thereof, a $V_L$ CDR2 comprising amino acids having the sequence set forth in SEQ ID NO: 254 or conservative modifications thereof, and a $V_L$ CDR3 comprising amino acids having the sequence set forth in SEQ ID NO: 255 or conservative modifications thereof, as shown in Table 22. In certain embodiments, the extracellular antigen-binding domain comprises a $V_H$ CDR1 comprising amino acids having the sequence set forth in SEQ ID NO: 250, a $V_H$ CDR2 comprising amino acids having the sequence set forth in SEQ ID NO: 251, a $V_H$ CDR3 comprising amino acids having the sequence set forth in SEQ ID NO: 252, a $V_L$ CDR1 comprising amino acids having the sequence set forth in SEQ ID NO: 253, a $V_L$ CDR2 comprising amino acids having the sequence set forth in SEQ ID NO: 254, and a $V_L$ CDR3 comprising amino acids having the sequence set forth in SEQ ID NO: 255.

forth in SEQ ID NO:98. In certain embodiments, the extracellular antigen-binding domain is a scFv-Fc fusion protein or full length human IgG with $V_H$ and $V_L$ regions or CDRs selected from Table 23. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:89, as shown in Table 23. In certain embodiments, the extracellular

TABLE 22

| | | | |
|---|---|---|---|
| Antigen | A GPRC5D polypeptide having the amino acid sequence of SEQ ID NO: 97 | | |
| CDRs | 1 | 2 | 3 |
| $V_H$ | GFTFNTYG [SEQ ID NO: 250] | ISANNGHT [SEQ ID NO: 251] | ARGGYHHQMQRYYKATSVYSDY [SEQ ID NO: 252] |
| $V_L$ | SSNIGNNY [SEQ ID NO: 253] | DNN [SEQ ID NO: 254] | GTWDSSLSGVV [SEQ ID NO: 255] |
| Full $V_H$ | QVQLVQSGGEVKKPGASVKVSCKASGFTFNTYGISWVRQAPGQGLEWMGWISANNGHTKSAQRFQDRVAMATDTSTSTAYMELRSLKFDDTAVYYCARGGYHHQMQRYYKATSVYSDYWGQGTLVTVSS [SEQ ID NO: 85] | | |
| DNA | Caggtccagctggtgcagtctggaggtgaggtgaagaagcctggggcctcagtgaaggtctcctgcaaggatctggtttcacctttaacacctatggcatcagttgggtgcgacaggcccctggacaagggcttgagtggatgggatggatcagcgctaacaatggtcacacaaagtctgcacagaggttccaggacagagtcgccatggccacagacacatccacgagcacggcctacatggagctgaggagcctgaaatttgacgacacggccgtgtattactgtgcgcgcggtggttaccatcatcagatgcagcggtactacaaagctacttctgtttactctgattactggggtcaaggtactctggtgaccgtctcctca [SEQ ID NO: 87] | | |
| Full $V_L$ | QSVVTQPPSVSAAPGQKVTISCSGSSSNIGNNYVSWYQQLPGTAPKLLIYDNNKRPSGIPDRFSGSKSGTSATLGITGLQTGDEADYYCGTWDSSLSGVVFGGGTKLTVLG [SEQ ID NO: 86] | | |
| DNA | Cagtctgtcgtgacgcagccgccctcagtgtctgcggccccaggacagaaggtcaccatctcctgctctggaagcagctccaacattgggaataattatgtatcctggtaccagcaactcccaggaacagcccccaaactcctcatttatgacaataataagcgaccctcagggattcctgaccgattctctggctccaagtctggcacgtctgccaccctgggcatcaccggactccagactggggacgaggccgattattactgcggaacatgggatagcagcctgagtggtgtggtattcggcggagggaccaagctgaccgtcctaggt [SEQ ID NO: 88] | | |
| scFv | QSVVTQPPSVSAAPGQKVTISCSGSSSNIGNNYVSWYQQLPGTAPKLLIYDNNKRPSGIPDRFSGSKSGTSATLGITGLQTGDEADYYCGTWDSSLSGVVFGGGTKLTVLGSRGGGGSGGGGSGGGGSLEMAQVQLVQSGGEVKKPGASVKVSCKASGFTFNTYGISWVRQAPGQGLEWMGWISANNGHTKSAQRFQDRVAMATDTSTSTAYMELRSLKFDDTAVYYCARGGYHHQMQRYYKATSVYSDYWGQGTLVTVSS [SEQ ID NO: 121] | | |

In certain embodiments, the extracellular antigen-binding domain is a scFv, which comprises the amino acid sequence of SEQ ID NO: 122 and specifically binds to a GPRC5D polypeptide (e.g., a GPRC5D polypeptide having the amino acid sequence SEQ ID NO:97, or fragments thereof), which scFv is designated as ET150-172 scFv (also referred to as "ET150-22 scFv").

In certain embodiments, the extracellular antigen-binding domain is a scFv, which comprises a heavy chain variable region comprising amino acids having the sequence set forth in SEQ ID NO:89 and a light chain variable region comprising amino acids having the sequence set forth in SEQ ID NO:90, optionally with (iii) a linker sequence, for example a linker peptide, between the heavy chain variable region and the light chain variable region. In certain embodiments, the linker comprises amino acids having the sequence set antigen-binding domain comprises a $V_H$ comprising amino acids having the sequence set forth in SEQ ID NO:89, as shown in Table 23. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:90, as shown in Table 23. In certain embodiments, the extracellular antigen-binding domain comprises a $V_L$ comprising amino acids having the sequence set forth in SEQ ID NO:90, as shown in Table 23. In certain embodiments, the extracellular antigen-binding domain comprises a $V_H$ comprising amino acids having the sequence set forth in SEQ ID NO:89 and a $V_L$ comprising amino acids having the sequence set forth in SEQ ID NO:90, as shown in Table 23. In certain embodiments, the extracellular antigen-binding domain comprises a $V_H$ CDR1 comprising amino acids having the sequence set forth in SEQ ID NO:256 or conservative modifications thereof, a $V_H$ CDR2 comprising amino acids having the sequence set forth in SEQ ID NO: 257 or conservative modifications thereof, and a $V_H$ CDR3 comprising amino acids having the sequence set forth in SEQ ID NO: 258 or conservative modifications thereof, as shown in Table 23. In certain embodiments, the extracellular antigen-binding domain comprises a $V_L$ CDR1 comprising amino acids having the sequence set forth in SEQ ID NO: 259 or conservative modifications thereof, a $V_L$ CDR2 comprising amino acids having the sequence set forth in SEQ ID NO: 260 or conservative modifications thereof, and a $V_L$ CDR3 comprising amino acids having the sequence set forth in SEQ ID NO: 261 or conservative modifications thereof, as shown in Table 23. In certain embodiments, the extracellular antigen-binding domain comprises a $V_H$ CDR1 comprising amino acids having the sequence set forth in SEQ ID NO: 256 or conservative modifications thereof, a $V_H$ CDR2 comprising amino acids having the sequence set forth in SEQ ID NO: 257 or conservative modifications thereof, a $V_H$ CDR3 comprising amino acids having the sequence set forth in SEQ ID NO: 258 or conservative modifications thereof, a $V_L$ CDR1 comprising amino acids having the sequence set forth in SEQ ID NO: 259 or conservative modifications thereof, a $V_L$ CDR2 comprising amino acids having the sequence set forth in SEQ ID NO: 260 or conservative modifications thereof, and a $V_L$ CDR3 comprising amino acids having the sequence set forth in SEQ ID NO: 261 or conservative modifications thereof, as shown in Table 23. In certain embodiments, the extracellular antigen-binding domain comprises a $V_H$ CDR1 comprising amino acids having the sequence set forth in SEQ ID NO: 256, a $V_H$ CDR2 comprising amino acids having the sequence set forth in SEQ ID NO: 257, a $V_H$ CDR3 comprising amino acids having the sequence set forth in SEQ ID NO: 258, a $V_L$ CDR1 comprising amino acids having the sequence set forth in SEQ ID NO: 259, a $V_L$ CDR2 comprising amino acids having the sequence set forth in SEQ ID NO: 260, and a $V_L$ CDR3 comprising amino acids having the sequence set forth in SEQ ID NO: 261.

TABLE 23

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFTSYY [SEQ ID NO: 256] | INPSGGSS [SEQ ID NO: 257] | ARAGMGMDT [SEQ ID NO: 258] |
| $V_L$ | SSDVGGYNY [SEQ ID NO: 259] | EVS [SEQ ID NO: 260] | SSYAGSNTLV [SEQ ID NO: 261] |
| Full $V_H$ | QMQLVQSGAEVKKPGASVKVSCKASGYTFTSYYMHWVRQAPG<br>QGLEWMGIINPSGGSSSYAQKFQGRVTMTRDTSTSTVYMELSSL<br>RSEDTAVYYCARAGMGMDTWGQGTLVTVSS [SEQ ID NO: 89] | | |
| DNA | Cagatgcagctggtgcagtctggggctgaggtgaagaagcctggggcctcagtgaaggtttcctgca<br>aggcatctggatacaccttcaccagctactatatgcactgggtgcgacaggcccctggacaagggcttg<br>agtggatgggaataatcaaccctagtggtggtagctcaagctacgcacagaagttccagggcagagtc<br>accatgaccagggacacgtccacgagcacagtctacatggagctgagcagcctgagatctgaggaca<br>cggccgtgtattactgtgcgcgcgctggtatgggtatggatacttggggtcaaggtactctggtgaccgt<br>ctcctca [SEQ ID NO: 91] | | |
| Full $V_L$ | QSALTQPPSASGSPGQSVTISCTGTSSDVGGYNYVSWYQQHPGK<br>APKLMIYEVSKRPSGVPDRFSGSKSGNTASLTVSGLQAEDEADYY<br>CSSYAGSNTLVFGGGTKLTVLG [SEQ ID NO: 90] | | |
| DNA | Cagtctgccctgactcagcctccctccgcgtccgggtctcctggacagtcagtcaccatctcctgcact<br>ggaaccagcagtgacgttggtggttataactatgtctcctggtaccaacagcacccaggcaaagccccc<br>aaactcatgatttatgaggtcagtaagcggccctcaggggtccctgatcgcttctctggctccaagtctgg<br>caacacggcctccctgaccgtctctgggctccaggctgaggatgaggctgattattactgcagctcatat<br>gcaggcagcaacaccttggtgtteggeggagggaccaagctgaccgtcctaggt [SEQ ID NO: 92] | | |
| scFv | QSALTQPPSASGSPGQSVTISCTGTSSDVGGYNYVSWYQQHPGK<br>APKLMIYEVSKRPSGVPDRFSGSKSGNTASLTVSGLQAEDEADYY<br>CSSYAGSNTLVFGGGTKLTVLGSRGGGGSGGGGSGGGGSLEMA<br>QMQLVQSGAEVKKPGASVKVSCKASGYTFTSYYMHWVRQAPG<br>QGLEWMGIINPSGGSSSYAQKFQGRVTMTRDTSTSTVYMELSSL<br>RSEDTAVYYCARAGMGMDTWGQGTLVTVSS [SEQ ID NO: 122] | | |

In certain embodiments, the extracellular antigen-binding domain is a scFv, which comprises the amino acid sequence of SEQ ID NO: 123 and specifically binds to a GPRC5D polypeptide (e.g., a GPRC5D polypeptide having the amino acid sequence SEQ ID NO:97, or fragments thereof), which scFv is designated as ET150-173 scFv (also referred to as "ET150-23 scFv").

In certain embodiments, the extracellular antigen-binding domain is a scFv, which comprises a heavy chain variable region comprising amino acids having the sequence set forth in SEQ ID NO:93 and a light chain variable region comprising amino acids having the sequence set forth in SEQ ID NO:94, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 24. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:93, as shown in Table 24. In certain embodiments, the extracellular antigen-binding domain comprises a $V_H$ comprising amino acids having the sequence set forth in SEQ ID NO:93, as shown in Table 24. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:94, as shown in Table 24. In certain embodiments, the extracellular antigen-binding domain comprises a $V_L$ comprising amino acids having the sequence set forth in SEQ ID NO:94, as shown in Table 24. In certain embodiments, the extracellular antigen-binding domain comprises a $V_H$ comprising amino acids having the sequence set forth in SEQ ID NO:93 and a $V_L$ comprising amino acids having the sequence set forth in SEQ ID NO:94, as shown in Table 24. In certain embodiments, the extracellular antigen-binding domain comprises a $V_H$ CDR1 comprising amino acids having the sequence set forth in SEQ ID NO:262 or conservative modifications thereof, a $V_H$ CDR2 comprising amino acids having the sequence set forth in SEQ ID NO: 263 or conservative modifications thereof, and a $V_H$ CDR3 comprising amino acids having the sequence set forth in SEQ ID NO: 264 or conservative modifications thereof, as shown in Table 24. In certain embodiments, the extracellular antigen-binding domain comprises a $V_L$ CDR1 comprising amino acids having the sequence set forth in SEQ ID NO: 265 or conservative modifications thereof, a $V_L$ CDR2 comprising amino acids having the sequence set forth in SEQ ID NO: 266 or conservative modifications thereof, and a $V_L$ CDR3 comprising amino acids having the sequence set forth in SEQ ID NO: 267 or conservative modifications thereof, as shown in Table 24. In certain embodiments, the extracellular antigen-binding domain comprises a $V_H$ CDR1 comprising amino acids having the sequence set forth in SEQ ID NO: 262 or conservative modifications thereof, a $V_H$ CDR2 comprising amino acids having the sequence set forth in SEQ ID NO: 263 or conservative modifications thereof, a $V_H$ CDR3 comprising amino acids having the sequence set forth in SEQ ID NO: 264 or conservative modifications thereof, a $V_L$ CDR1 comprising amino acids having the sequence set forth in SEQ ID NO: 265 or conservative modifications thereof, a $V_L$ CDR2 comprising amino acids having the sequence set forth in SEQ ID NO: 266 or conservative modifications thereof, and a $V_L$ CDR3 comprising amino acids having the sequence set forth in SEQ ID NO: 267 or conservative modifications thereof, as shown in Table 24. In certain embodiments, the extracellular antigen-binding domain comprises a $V_H$ CDR1 comprising amino acids having the sequence set forth in SEQ ID NO: 262, a $V_H$ CDR2 comprising amino acids having the sequence set forth in SEQ ID NO: 263, a $V_H$ CDR3 comprising amino acids having the sequence set forth in SEQ ID NO: 264, a $V_L$ CDR1 comprising amino acids having the sequence set forth in SEQ ID NO: 265 f, a $V_L$ CDR2 comprising amino acids having the sequence set forth in SEQ ID NO: 266, and a $V_L$ CDR3 comprising amino acids having the sequence set forth in SEQ ID NO: 267.

TABLE 24

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFTSYY [SEQ ID NO: 262] | INPSGGST [SEQ ID NO: 263] | ARDVISGFDS [SEQ ID NO: 264] |
| $V_L$ | SSDVGGYNY [SEQ ID NO: 265] | GVS [SEQ ID NO: 266] | SSYAGVNNLM [SEQ ID NO: 267] |
| Full $V_H$ | QVQLVQSGAEVKKPGASVKVSCKASGYTFTSYYMHWVRQAPGQ GLEWMGIINPSGGSTSYAQKFQGRVTMTRDTSTSTVYMELSSLRS EDTAVYYCARDVISGFDSWGQGTLVTVSS [SEQ ID NO: 93] | | |
| DNA | Caggtgcagctggtgcaatctggggctgaggtgaagaagcctggggcctcagtgaaggtttcctgcaa ggcatctggatacaccttcaccagctactatatgcactgggtgcgacaggcccctggacaagggcttga gtggatgggaataatcaaccctagtggtggtagcacaagctacgcacagaagttccagggcagagtcac catgaccagggacacgtccacgagcacagtctacatggagctgagcagcctgagatctgaggacactg ccgtgtattactgtgcgcgcgacgttatctctggtttcgattcttggggtcaaggtactctggtgaccgtctc ctca [SEQ ID NO: 95] | | |
| Full $V_L$ | QSALTQPASVSGSPGQSITISCTGTSSDVGGYNYVSWYQQSPGKAP RLMIYGVSKRPSGVPDRFSGSKSGNTASLTVSGLQAEDEADYYCS SYAGVNNLMEGGGTKLTVLG [SEQ ID NO: 94] | | |

TABLE 24-continued

| | |
|---|---|
| DNA | Cagtctgccctgactcagcctgcctccgtgtctgggtctcctggacagtcgatcaccatctcctgcactgg<br>aaccagcagtgacgttggtggttataactatgtctcctggtaccaacaatccccaggcaaagcccccaga<br>ctcatgatttatggggtcagtaagcggccctctggggtccctgatcgcttctctggctccaagtctggcaac<br>acggcctccctgaccgtctctgggctccaggctgaagatgaggctgattattactgcagctcatatgcagg<br>cgtcaacaatttaatgttcggcggagggaccaagctgaccgtcctaggt [SEQ ID NO: 96] |
| scFv | QSALTQPASVSGSPGQSITISCTGTSSDVGGYNYVSWYQQSPGKAP<br>RLMIYGVSKRPSGVPDRFSGSKSGNTASLTVSGLQAEDEADYYCS<br>SYAGVNNLMEGGGTKLTVLGSRGGGGSGGGGSGGGGSLEMAQV<br>QLVQSGAEVKKPGASVKVSCKASGYTFTSYYMHWVRQAPGQGL<br>EWMGIINPSGGSTSYAQKFQGRVTMTRDTSTSTVYMELSSLRSED<br>TAVYYCARDVISGFDSWGQGTLVTVSS [SEQ ID NO: 123] |

In certain embodiments, the extracellular antigen-binding domain is a scFv, which comprises the amino acid sequence of SEQ ID NO: 301 and specifically binds to a GPRC5D polypeptide (e.g., a GPRC5D polypeptide having the amino acid sequence SEQ ID NO:97, or fragments thereof), which scFv is designated as ET150-024 scFv (also referred to as "ET150-174 scFv").

In certain embodiments, the extracellular antigen-binding domain is a scFv, which comprises a heavy chain variable region comprising amino acids having the sequence set forth in SEQ ID NO:302 and a light chain variable region comprising amino acids having the sequence set forth in SEQ ID NO:303, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 25. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:302, as shown in Table 25. In certain embodiments, the extracellular antigen-binding domain comprises a $V_H$ comprising amino acids having the sequence set forth in SEQ ID NO:302, as shown in Table 25. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:303, as shown in Table 25. In certain embodiments, the extracellular antigen-binding domain comprises a $V_L$ comprising amino acids having the sequence set forth in SEQ ID NO:303, as shown in Table 25. In certain embodiments, the extracellular antigen-binding domain comprises a $V_H$ comprising amino acids having the sequence set forth in SEQ ID NO:302 and a $V_L$ comprising amino acids having the sequence set forth in SEQ ID NO:303, as shown in Table 25. In certain embodiments, the extracellular antigen-binding domain comprises a $V_H$ CDR1 comprising amino acids having the sequence set forth in SEQ ID NO:304 or conservative modifications thereof, a $V_H$ CDR2 comprising amino acids having the sequence set forth in SEQ ID NO:305 or conservative modifications thereof, and a $V_H$ CDR3 comprising amino acids having the sequence set forth in SEQ ID NO:306 or conservative modifications thereof, as shown in Table 25. In certain embodiments, the extracellular antigen-binding domain comprises a $V_L$ CDR1 comprising amino acids having the sequence set forth in SEQ ID NO:307 or conservative modifications thereof, a $V_L$ CDR2 comprising amino acids having the sequence set forth in SEQ ID NO:308 or conservative modifications thereof, and a $V_L$ CDR3 comprising amino acids having the sequence set forth in SEQ ID NO:309 or conservative modifications thereof, as shown in Table 25. In certain embodiments, the extracellular antigen-binding domain comprises a $V_H$ CDR1 comprising amino acids having the sequence set forth in SEQ ID NO: 304 or conservative modifications thereof, a $V_H$ CDR2 comprising amino acids having the sequence set forth in SEQ ID NO: 305 or conservative modifications thereof, a $V_H$ CDR3 comprising amino acids having the sequence set forth in SEQ ID NO: 306 or conservative modifications thereof, a $V_L$ CDR1 comprising amino acids having the sequence set forth in SEQ ID NO: 307 or conservative modifications thereof, a $V_L$ CDR2 comprising amino acids having the sequence set forth in SEQ ID NO: 308 or conservative modifications thereof, and a $V_L$ CDR3 comprising amino acids having the sequence set forth in SEQ ID NO: 309 or conservative modifications thereof, as shown in Table 25. In certain embodiments, the extracellular antigen-binding domain comprises a $V_H$ CDR1 comprising amino acids having the sequence set forth in SEQ ID NO: 304, a $V_H$ CDR2 comprising amino acids having the sequence set forth in SEQ ID NO: 305, a $V_H$ CDR3 comprising amino acids having the sequence set forth in SEQ ID NO: 306, a $V_L$ CDR1 comprising amino acids having the sequence set forth in SEQ ID NO: 307, a $V_L$ CDR2 comprising amino acids having the sequence set forth in SEQ ID NO: 308, and a $V_L$ CDR3 comprising amino acids having the sequence set forth in SEQ ID NO: 309.

TABLE 25

| | | | |
|---|---|---|---|
| Antigen | A GPRC5D polypeptide having the amino acid sequence of SEQ ID NO: 97 | | |
| CDRs | 1 | 2 | 3 |
| $V_H$ | GFTFGDYG [SEQ ID NO: 304] | INWNGGST [SEQ ID NO: 305] | ARSKQGY [SEQ ID NO: 306] |
| $V_L$ | SRDAGGYNY [SEQ ID NO: 307] | EVT [SEQ ID NO: 308] | SSYGGSNNFRV [SEQ ID NO: 309] |
| Full $V_H$ | EVQLVESGGGVVRPGGSLRLSCAASGFTFGDYGMSWVRQAPGK GLEWVSGINWNGGSTGYADSVKGRFTISRDNAKNSLYLQMNSL RAEDTAVYYCARSKQDYWGQGTLVTVSS [SEQ ID NO: 302] | | |
| DNA | GAGGTGCAGCTGGTGGAGTCTGGGGGAGGTGTGGTACGGCCT GGGGGGTCCCTGAGACTCTCCTGTGCAGCCTCTGGATTCACCT TTGGTGATTATGGCATGAGCTGGGTCCGCCAAGCTCCAGGGAA GGGGCTGGAGTGGGTCTCTGGTATTAATTGGAATGGTGGTAGC ACAGGTTATGCAGACTCTGTGAAGGGCCGATTCACCATCTCCA GAGACAACGCCAAGAACTCCCTGTATCTGCAAATGAACAGTC TGAGAGCCGAGGACACGGCCGTATATTACTGTGCGCGCTCTAA ACAGGATTACTGGGGTCAAGGTACTCTGGTGACCGTCTCCTCA [SEQ ID NO: 310] | | |
| Full $V_L$ | MKKTAIAIAVALAGFATVAQAAELQSALTQPPSASGSPGQSVTIS CTGTSRDAGGYNYFSWYQQHPGKAPKLLIYEVTKRPSGVPDRFS GSKSGKTASLTVSGLQADDEAVYYCSSYGGSNNFRVFGGGTKLT VLG [SEQ ID NO: 302] | | |
| DNA | ATGAAAAAGACAGCTATCGCGATTGCAGTGGCACTGGCTGGT TTCGCTACCGTGGCCCAGGCGGCCGAGCTCCAGTCTGCCCTGA CTCAGCCTCCCTCCGCGTCCGGGTCTCCTGGACAGTCAGTCAC CATCTCCTGCACTGGAACCAGCAGGGACGCTGGTGGTTATAAT TATTTCTCCTGGTACCAACAACACCCAGGCAAAGCCCCCAAAC TCCTGATTTATGAGGTCACTAAGCGGCCCTCAGGGGTCCCTGA TCGCTTCTCTGGCTCCAAGTCTGGCAAGACGGCCTCCCTGACC GTCTCTGGGCTCCAGGCTGACGATGAGGCTGTATATTACTGCA GCTCATATGGAGGCAGCAACAACTTTCGGGTGTTCGGCGGAG GGACCAAGCTGACCGTCCTAGGT [SEQ ID NO: 311] | | |
| scFv | MKKTAIAIAVALAGFATVAQAAELQSALTQPPSASGSPGQSVTIS CTGTSRDAGGYNYFSWYQQHPGKAPKLLIYEVTKRPSGVPDRFS GSKSGKTASLTVSGLQADDEAVYYCSSYGGSNNFRVFGGGTKLT VLGSRGGGGSGGGGSGGGGSLEMAEVQLVESGGGVVRPGGSLR LSCAASGFTFGDYGMSWVRQAPGKGLEWVSGINWNGGSTGYA DSVKGRFTISRDNAKNSLYLQMNSLRAEDTAVYYCARSKQDYW GQGTLVTVSS [SEQ ID NO: 301] | | |
| DNA | ATGAAAAAGACAGCTATCGCGATTGCAGTGGCACTGGCTGGT TTCGCTACCGTGGCCCAGGCGGCCGAGCTCCAGTCTGCCCTGA CTCAGCCTCCCTCCGCGTCCGGGTCTCCTGGACAGTCAGTCAC CATCTCCTGCACTGGAACCAGCAGGGACGCTGGTGGTTATAAT TATTTCTCCTGGTACCAACAACACCCAGGCAAAGCCCCCAAAC TCCTGATTTATGAGGTCACTAAGCGGCCCTCAGGGGTCCCTGA TCGCTTCTCTGGCTCCAAGTCTGGCAAGACGGCCTCCCTGACC GTCTCTGGGCTCCAGGCTGACGATGAGGCTGTATATTACTGCA GCTCATATGGAGGCAGCAACAACTTTCGGGTGTTCGGCGGAG GGACCAAGCTGACCGTCCTAGGTTCTAGAGGTGGTGGTGGTA GCGGCGGCGGCGGCTCTGGTGGTGGTGGATCCCTCGAGATGG CCGAGGTGCAGCTGGTGGAGTCTGGGGGAGGTGTGGTACGGC CTGGGGGGTCCCTGAGACTCTCCTGTGCAGCCTCTGGATTCAC CTTTGGTGATTATGGCATGAGCTGGGTCCGCCAAGCTCCAGGG AAGGGGCTGGAGTGGGTCTCTGGTATTAATTGGAATGGTGGTA GCACAGGTTATGCAGACTCTGTGAAGGGCCGATTCACCATCTC CAGAGACAACGCCAAGAACTCCCTGTATCTGCAAATGAACAG TCTGAGAGCCGAGGACACGGCCGTATATTACTGTGCGCGCTCT AAACAGGATTACTGGGGTCAAGGTACTCTGGTGACCGTCTCCT CA [SEQ ID NO: 312] | | |

In certain embodiments, the extracellular antigen-binding domain is a scFv, which comprises the amino acid sequence of SEQ ID NO: 313 and specifically binds to a GPRC5D polypeptide (e.g., a GPRC5D polypeptide having the amino acid sequence SEQ ID NO:97, or fragments thereof), which scFv is designated as ET150-026 scFv (also referred to as "ET150-176 scFv").

In certain embodiments, the extracellular antigen-binding domain is a scFv, which comprises a heavy chain variable region comprising amino acids having the sequence set forth in SEQ ID NO:314 and a light chain variable region comprising amino acids having the sequence set forth in SEQ ID NO:315, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 26. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:314 as shown in Table 26. In certain embodiments, the extracellular antigen-binding domain comprises a $V_H$ comprising amino acids having the sequence set forth in SEQ ID NO:314, as shown in Table 26. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:315, as shown in Table 26. In certain embodiments, the extracellular antigen-binding domain comprises a $V_L$ comprising amino acids having the sequence set forth in SEQ ID NO:315, as shown in Table 26. In certain embodiments, the extracellular antigen-binding domain comprises a $V_H$ comprising amino acids having the sequence set forth in SEQ ID NO:314 and a $V_L$ comprising amino acids having the sequence set forth in SEQ ID NO:315 as shown in Table 26. In certain embodiments, the extracellular antigen-binding domain comprises a $V_H$ CDR1 comprising amino acids having the sequence set forth in SEQ ID NO:316 or conservative modifications thereof, a $V_H$ CDR2 comprising amino acids having the sequence set forth in SEQ ID NO:317 or conservative modifications thereof, and a $V_H$ CDR3 comprising amino acids having the sequence set forth in SEQ ID NO:318 or conservative modifications thereof, as shown in Table 26. In certain embodiments, the extracellular antigen-binding domain comprises a $V_L$ CDR1 comprising amino acids having the sequence set forth in SEQ ID NO:319 or conservative modifications thereof, a $V_L$ CDR2 comprising amino acids having the sequence set forth in SEQ ID NO:320 or conservative modifications thereof, and a $V_L$ CDR3 comprising amino acids having the sequence set forth in SEQ ID NO:321 or conservative modifications thereof, as shown in Table 26. In certain embodiments, the extracellular antigen-binding domain comprises a $V_H$ CDR1 comprising amino acids having the sequence set forth in SEQ ID NO: 316 or conservative modifications thereof, a $V_H$ CDR2 comprising amino acids having the sequence set forth in SEQ ID NO: 317 or conservative modifications thereof, a $V_H$ CDR3 comprising amino acids having the sequence set forth in SEQ ID NO: 318 or conservative modifications thereof, a $V_L$ CDR1 comprising amino acids having the sequence set forth in SEQ ID NO: 319 or conservative modifications thereof, a $V_L$ CDR2 comprising amino acids having the sequence set forth in SEQ ID NO: 320 or conservative modifications thereof, and a $V_L$ CDR3 comprising amino acids having the sequence set forth in SEQ ID NO: 321 or conservative modifications thereof, as shown in Table 26. In certain embodiments, the extracellular antigen-binding domain comprises a $V_H$ CDR1 comprising amino acids having the sequence set forth in SEQ ID NO: 316, a $V_H$ CDR2 comprising amino acids having the sequence set forth in SEQ ID NO: 317, a $V_H$ CDR3 comprising amino acids having the sequence set forth in SEQ ID NO: 318, a $V_L$ CDR1 comprising amino acids having the sequence set forth in SEQ ID NO: 319, a $V_L$ CDR2 comprising amino acids having the sequence set forth in SEQ ID NO: 320, and a $V_L$ CDR3 comprising amino acids having the sequence set forth in SEQ ID NO: 321.

TABLE 26

| | | | |
|---|---|---|---|
| Antigen | A GPRC5D polypeptide having the amino acid sequence of SEQ ID NO: 97 | | |
| CDRs | 1 | 2 | 3 |
| $V_H$ | GFTFSNYA [SEQ ID NO: 316] | ITNSGRST [SEQ ID NO: 317] | ARVTHRRYGSTFDS [SEQ ID NO: 318] |
| $V_L$ | SSNIGSNT [SEQ ID NO: 319] | SNN [SEQ ID NO: 320] | AAWDDSVNGYV [SEQ ID NO: 321] |
| Full $V_H$ | QLQLQESGGGSVQPGGSLRLSCAASGFTFSNYAMSWVRQAPGK GLEWVSAITNSGRSTYYADSVKGRFTISRDNSKNTLSLQMSSLRA EDTAVYYCARVTHRRYGSTFDSRGQGTLVTVSS [SEQ ID NO: 314] | | |
| DNA | CAGCTGCAGCTGCAGGAGTCGGGGGGAGGCTCGGTACAGCCG GGGGGGTCTCTGAGACTGTCCTGTGCAGCCTCTGGATTCACCT TTAGCAACTATGCCATGAGCTGGGTCCGCCAGGCTCCAGGGA AGGGGCTGGAGTGGGTCTCAGCTATCACTAATAGTGGTCGTAG TACATACTACGCAGACTCCGTGAAGGGCCGGTTCACCATCTCC AGAGACAATTCCAAGAACACGCTGTCTTTGCAAATGAGCAGC CTGAGAGCCGAAGACACGGCCGTGTATTACTGTGCGCGCGTTA CTCATCGTCGTTACGGTTCTACTTTCGATTCTCGGGGTCAAGGT ACTCTGGTGACCGTCTCCTCA ACTAGTGGCCAGGCCGGCCAGC [SEQ ID NO: 322] | | |
| Full $V_L$ | MKKTAIAIAVALAGFATVAQAAELSYELTQPPSASGTPGQRVSIS CSGSSSNIGSNTVNWYQQFPGTAPKLLIHSNNQRPSGVPDRFSGS KSGTSASLAISGPQSEDEADYYCAAWDDSVNGYVFGTGTKVTVL G [SEQ ID NO: 315] | | |

TABLE 26-continued

| | |
|---|---|
| DNA | ATGAAAAAGACAGCTATCGCGATTGCAGTGGCACTGGCTGGT<br>TTCGCTACCGTGGCCCAGGCGGCCGAGCTCTCCTATGAGCTGA<br>CTCAGCCACCCTCAGCGTCTGGGACCCCCGGGCAGAGGGTCA<br>GCATCTCTTGTTCTGGAAGCAGCTCCAACATCGGGAGTAATAC<br>TGTAAACTGGTACCAACAGTTCCCCGGAACGGCCCCCAAACTC<br>CTCATCCATAGTAATAATCAGCGGCCCTCAGGGGTCCCTGACC<br>GATTCTCTGGCTCCAAGTCTGGCACCTCAGCCTCCCTGGCCAT<br>CAGTGGGCCCCAGTCTGAGGATGAGGCTGATTATTACTGTGCA<br>GCTTGGGATGACAGTGTGAATGGTTATGTCTTCGGAACTGGGA<br>CCAAGGTCACCGTCCTAGGT [SEQ ID NO: 323] |
| scFv | MKKTAIAIAVALAGFATVAQAAELSYELTQPPSASGTPGQRVSIS<br>CSGSSSNIGSNTVNWYQQFPGTAPKLLIHSNNQRPSGVPDRFSGS<br>KSGTSASLAISGPQSEDEADYYCAAWDDSVNGYVFGTGTKVTVL<br>GSRGGGGSGGGGSGGGGSLEMAQLQLQESGGGSVQPGGSLRLS<br>CAASGFTFSNYAMSWVRQAPGKGLEWVSAITNSGRSTYYADSV<br>KGRFTISRDNSKNTLSLQMSSLRAEDTAVYYCARVTHRRYGSTF<br>DSRGQGTLVTVSS [SEQ ID NO: 313] |
| DNA | ATGAAAAAGACAGCTATCGCGATTGCAGTGGCACTGGCTGGT<br>TTCGCTACCGTGGCCCAGGCGGCCGAGCTCTCCTATGAGCTGA<br>CTCAGCCACCCTCAGCGTCTGGGACCCCCGGGCAGAGGGTCA<br>GCATCTCTTGTTCTGGAAGCAGCTCCAACATCGGGAGTAATAC<br>TGTAAACTGGTACCAACAGTTCCCCGGAACGGCCCCCAAACTC<br>CTCATCCATAGTAATAATCAGCGGCCCTCAGGGGTCCCTGACC<br>GATTCTCTGGCTCCAAGTCTGGCACCTCAGCCTCCCTGGCCAT<br>CAGTGGGCCCCAGTCTGAGGATGAGGCTGATTATTACTGTGCA<br>GCTTGGGATGACAGTGTGAATGGTTATGTCTTCGGAACTGGGA<br>CCAAGGTCACCGTCCTAGGTTCTAGAGGTGGTGGTGGTAGCGG<br>CGGCGGCGGCTCTGGTGGTGGTGGATCCCTCGAGATGGCCCA<br>GCTGCAGCTGCAGGAGTCGGGGGGAGGCTCGGTACAGCCGGG<br>GGGGTCTCTGAGACTGTCCTGTGCAGCCTCTGGATTCACCTTT<br>AGCAACTATGCCATGAGCTGGGTCCGCCAGGCTCCAGGGAAG<br>GGGCTGGAGTGGGTCTCAGCTATCACTAATAGTGGTCGTAGTA<br>CATACTACGCAGACTCCGTGAAGGGCCGGTTCACCATCTCCAG<br>AGACAATTCCAAGAACACGCTGTCTTTGCAAATGAGCAGCCTG<br>AGAGCCGAAGACACGGCCGTGTATTACTGTGCGCGCGTTACTC<br>ATCGTCGTTACGGTTCTACTTTCGATTCTCGGGGTCAAGGTACT<br>CTGGTGACCGTCTCCTCA [SEQ ID NO: 324] |

In certain embodiments, the extracellular antigen-binding domain is a scFv, which comprises the amino acid sequence of SEQ ID NO: 325 and specifically binds to a GPRC5D polypeptide (e.g., a GPRC5D polypeptide having the amino acid sequence SEQ ID NO:97, or fragments thereof), which scFv is designated as ET150-028 scFv (also referred to as "ET150-178 scFv").

In certain embodiments, the extracellular antigen-binding domain is a scFv, which comprises a heavy chain variable region comprising amino acids having the sequence set forth in SEQ ID NO:326 and a light chain variable region comprising amino acids having the sequence set forth in SEQ ID NO:327, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 27. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:325 as shown in Table 27. In certain embodiments, the extracellular antigen-binding domain comprises a $V_H$ comprising amino acids having the sequence set forth in SEQ ID NO:325, as shown in Table 27. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:326, as shown in Table 27. In certain embodiments, the extracellular antigen-binding domain comprises a $V_L$ comprising amino acids having the sequence set forth in SEQ ID NO:326, as shown in Table 27. In certain embodiments, the extracellular antigen-binding domain comprises a $V_H$ comprising amino acids having the sequence set forth in SEQ ID NO:325 and a $V_L$ comprising amino acids having the sequence set forth in SEQ ID NO:327 as shown in Table 27. In certain embodiments, the extracellular antigen-binding domain comprises a $V_H$ CDR1 comprising amino acids having the sequence set forth in SEQ ID NO:328 or conservative modifications thereof, a $V_H$ CDR2 comprising amino acids having the sequence set forth in SEQ ID NO:329 or conservative modifications thereof, and a $V_H$ CDR3 comprising amino acids having the sequence set forth in SEQ ID NO:330 or conservative modifications thereof, as shown in Table 27. In certain embodiments, the extracellular antigen-binding domain comprises a $V_L$ CDR1 comprising amino acids having the sequence set forth in SEQ ID NO:331 or conservative modifications thereof, a $V_L$ CDR2 comprising amino acids having the sequence set forth in SEQ ID NO:332 or conservative modifications thereof, and a $V_L$ CDR3 comprising amino acids having the sequence set forth in SEQ ID NO:333 or conservative modifications thereof, as shown in Table 27. In certain embodiments, the extracellular antigen-binding domain comprises a $V_H$ CDR1 comprising amino acids having the sequence set forth in SEQ ID NO: 328 or conservative modifications thereof, a $V_H$ CDR2 comprising amino acids having the sequence set forth in SEQ ID NO: 329 or conservative modifications thereof, a $V_H$ CDR3 comprising amino acids having the sequence set forth in SEQ ID NO: 330 or conservative modifications thereof, a $V_L$ CDR1 comprising amino acids having the sequence set forth in SEQ ID NO: 331 or conservative modifications thereof, a $V_L$ CDR2 comprising amino acids having the sequence set forth in SEQ ID NO: 332 or conservative modifications thereof, and a $V_L$ CDR3 comprising amino acids having the sequence set forth in SEQ ID NO: 333 or conservative modifications thereof, as shown in Table 27. In certain embodiments, the extracellular antigen-binding domain comprises a $V_H$ CDR1 comprising amino acids having the sequence set forth in SEQ ID NO: 328, a $V_H$ CDR2 comprising amino acids having the sequence set forth in SEQ ID NO: 329, a $V_H$ CDR3 comprising amino acids having the sequence set forth in SEQ ID NO: 330, a $V_L$ CDR1 comprising amino acids having the sequence set forth in SEQ ID NO: 331, a $V_L$ CDR2 comprising amino acids having the sequence set forth in SEQ ID NO: 332, and a $V_L$ CDR3 comprising amino acids having the sequence set forth in SEQ ID NO: 333.

TABLE 27

| | | | |
|---|---|---|---|
| Antigen | A GPRC5D polypeptide having the amino acid sequence of SEQ ID NO: 97 | | |
| CDRs | 1 | 2 | 3 |
| $V_H$ | GGTFRSYA [SEQ ID NO: 328] | IIPMLDIT [SEQ ID NO: 329] | ARTYSRSPFHMEDF [SEQ ID NO: 330] |
| $V_L$ | SSNIGGNT [SEQ ID NO: 331] | RNN [SEQ ID NO: 332] | AAWDASRQGV [SEQ ID NO: 333] |
| Full $V_H$ | QVQLVQSGAEVKKPGSSVKVSCKASGGTFRSYAITWVRQAPGQ GLEWMGRIIPMLDITNYAQKFQGRVTITADKSTSTAYMELSSLRS EDTAVYYCARTYSRSPFHMEDFWGQGTLVTVSS [SEQ ID NO: 326] | | |
| DNA | CAGGTGCAGCTGGTGCAGTCTGGGGCTGAGGTGAAGAAGCCT GGGTCCTCGGTGAAGGTCTCCTGCAAGGCTTCTGGAGGCACCT TCCGCAGCTATGCTATCACCTGGGTGCGACAGGCCCCTGGACA AGGGCTTGAGTGGATGGGAAGGATCATCCCTATGCTTGATATA ACAAACTACGCACAGAAGTTCCAGGGCAGAGTCACGATTACC GCGGACAAATCCACGAGCACAGCCTACATGGAGCTGAGCAGC CTGAGATCTGAGGACACGGCCGTGTATTACTGTGCGCGCACTT ACTCTCGTTCTCCGTTCCATATGGAAGATTTCTGGGGTCAAGG TACTCTGGTGACCGTCTCCTCA [SEQ ID NO: 334] | | |
| Full $V_L$ | MKKTAIAIAVALAGFATVAQAAELQPVLTQPPSASGTPGQRVTIS CSGSSSNIGGNTVSWYQQVPGTAPRLLIFRNNQRPPGVPDRFSGS KSGTSASLAISGLRSEDEADYYCAAWDASRQGVFGGGTKLTVLG [SEQ ID NO: 327] | | |
| DNA | ATGAAAAAGACAGCTATCGCGATTGCAGTGGCACTGGCTGGT TTCGCTACCGTGGCCCAGGCGGCCGAGCTCCAGCCTGTGCTGA CTCAGCCACCCTCAGCGTCTGGGACCCCCGGGCAGAGGGTCA CCATCTCTTGTTCTGGAAGCAGCTCCAATATCGGAGGTAACAC TGTCAGCTGGTACCAGCAGGTCCCAGGAACGGCCCCCAGACT CCTCATTTTTAGGAATAATCAACGGCCCCCAGGGGTCCCTGAC CGATTCTCTGGCTCCAAGTCTGGCACCTCAGCCTCCCTGGCCA TCAGTGGGCTCCGGTCTGAGGATGAGGCTGATTATTACTGTGC AGCATGGGACGCCAGTCGACAAGGGGTGTTCGGCGGAGGGAC CAAGCTGACCGTCCTAGGT [SEQ ID NO: 335] | | |
| scFv | MKKTAIAIAVALAGFATVAQAAELQPVLTQPPSASGTPGQRVTIS CSGSSSNIGGNTVSWYQQVPGTAPRLLIFRNNQRPPGVPDRFSGS KSGTSASLAISGLRSEDEADYYCAAWDASRQGVFGGGTKLTVLG SRGGGGSGGGGSGGGGSLEMAQVQLVQSGAEVKKPGSSVKVSC KASGGTFRSYAITWVRQAPGQGLEWMGRIIPMLDITNYAQKFQG RVTITADKSTSTAYMELSSLRSEDTAVYYCARTYSRSPFHMEDF WGQGTLVTVSS [SEQ ID NO: 325] | | |
| DNA | ATGAAAAAGACAGCTATCGCGATTGCAGTGGCACTGGCTGGT TTCGCTACCGTGGCCCAGGCGGCCGAGCTCCAGCCTGTGCTGA CTCAGCCACCCTCAGCGTCTGGGACCCCCGGGCAGAGGGTCA CCATCTCTTGTTCTGGAAGCAGCTCCAATATCGGAGGTAACAC TGTCAGCTGGTACCAGCAGGTCCCAGGAACGGCCCCCAGACT CCTCATTTTTAGGAATAATCAACGGCCCCCAGGGGTCCCTGAC CGATTCTCTGGCTCCAAGTCTGGCACCTCAGCCTCCCTGGCCA TCAGTGGGCTCCGGTCTGAGGATGAGGCTGATTATTACTGTGC AGCATGGGACGCCAGTCGACAAGGGGTGTTCGGCGGAGGGAC CAAGCTGACCGTCCTAGGTTCTAGAGGTGGTGGTGGTAGCGGC GGCGGCGGCTCTGGTGGTGGTGGATCCCTCGAGATGGCCCAG GTGCAGCTGGTGCAGTCTGGGGCTGAGGTGAAGAAGCCTGGG | | |

TABLE 27-continued

| |
|---|
| TCCTCGGTGAAGGTCTCCTGCAAGGCTTCTGGAGGCACCTTCC GCAGCTATGCTATCACCTGGGTGCGACAGGCCCCTGGACAAG GGCTTGAGTGGATGGGAAGGATCATCCCTATGCTTGATATAAC AAACTACGCACAGAAGTTCCAGGGCAGAGTCACGATTACCGC GGACAAATCCACGAGCACAGCCTACATGGAGCTGAGCAGCCT GAGATCTGAGGACACGGCCGTGTATTACTGTGCGCGCACTTAC TCTCGTTCTCCGTTCCATATGGAAGATTTCTGGGGTCAAGGTA CTCTGGTGACCGTCTCCTCA [SEQ ID NO: 336] |

In certain embodiments, the extracellular antigen-binding domain is a scFv, which comprises the amino acid sequence of SEQ ID NO: 337 and specifically binds to a GPRC5D polypeptide (e.g., a GPRC5D polypeptide having the amino acid sequence SEQ ID NO:97, or fragments thereof), which scFv is designated as ET150-029 scFv (also referred to as "ET150-179 scFv").

In certain embodiments, the extracellular antigen-binding domain is a scFv, which comprises a heavy chain variable region comprising amino acids having the sequence set forth in SEQ ID NO:338 and a light chain variable region comprising amino acids having the sequence set forth in SEQ ID NO:339, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 28. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:338 as shown in Table 28. In certain embodiments, the extracellular antigen-binding domain comprises a $V_H$ comprising amino acids having the sequence set forth in SEQ ID NO:338, as shown in Table 28. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:339, as shown in Table 28. In certain embodiments, the extracellular antigen-binding domain comprises a $V_L$ comprising amino acids having the sequence set forth in SEQ ID NO:339, as shown in Table 28. In certain embodiments, the extracellular antigen-binding domain comprises a $V_H$ comprising amino acids having the sequence set forth in SEQ ID NO:338 and a $V_L$ comprising amino acids having the sequence set forth in SEQ ID NO:339 as shown in Table 28. In certain embodiments, the extracellular antigen-binding domain comprises a $V_H$ CDR1 comprising amino acids having the sequence set forth in SEQ ID NO:340 or conservative modifications thereof, a $V_H$ CDR2 comprising amino acids having the sequence set forth in SEQ ID NO:341 or conservative modifications thereof, and a $V_H$ CDR3 comprising amino acids having the sequence set forth in SEQ ID NO:342 or conservative modifications thereof, as shown in Table 28. In certain embodiments, the extracellular antigen-binding domain comprises a $V_L$ CDR1 comprising amino acids having the sequence set forth in SEQ ID NO:343 or conservative modifications thereof, a $V_L$ CDR2 comprising amino acids having the sequence set forth in SEQ ID NO:344 or conservative modifications thereof, and a $V_L$ CDR3 comprising amino acids having the sequence set forth in SEQ ID NO:345 or conservative modifications thereof, as shown in Table 28. In certain embodiments, the extracellular antigen-binding domain comprises a $V_H$ CDR1 comprising amino acids having the sequence set forth in SEQ ID NO: 340 or conservative modifications thereof, a $V_H$ CDR2 comprising amino acids having the sequence set forth in SEQ ID NO: 341 or conservative modifications thereof, a $V_H$ CDR3 comprising amino acids having the sequence set forth in SEQ ID NO: 342 or conservative modifications thereof, a $V_L$ CDR1 comprising amino acids having the sequence set forth in SEQ ID NO: 343 or conservative modifications thereof, a $V_L$ CDR2 comprising amino acids having the sequence set forth in SEQ ID NO: 344 or conservative modifications thereof, and a $V_L$ CDR3 comprising amino acids having the sequence set forth in SEQ ID NO: 345 or conservative modifications thereof, as shown in Table 28. In certain embodiments, the extracellular antigen-binding domain comprises a $V_H$ CDR1 comprising amino acids having the sequence set forth in SEQ ID NO: 340, a $V_H$ CDR2 comprising amino acids having the sequence set forth in SEQ ID NO: 341, a $V_H$ CDR3 comprising amino acids having the sequence set forth in SEQ ID NO: 342, a $V_L$ CDR1 comprising amino acids having the sequence set forth in SEQ ID NO: 343, a $V_L$ CDR2 comprising amino acids having the sequence set forth in SEQ ID NO: 344, and a $V_L$ CDR3 comprising amino acids having the sequence set forth in SEQ ID NO: 345.

TABLE 28

| Antigen | A GPRC5D polypeptide having the amino acid sequence of SEQ ID NO: 97 | | |
|---|---|---|---|
| CDRs | 1 | 2 | 3 |
| $V_H$ | GFTFSSYA[SEQ ID NO: 340] | ISGSGGST [SEQ ID NO: 341] | ARKYQDV [SEQ ID NO: 342] |
| $V_L$ | SSNIGSNT[SEQ ID NO: 343] | RNN [SEQ ID NO: 344] | AAWDDSLSGRV [SEQ ID NO: 345] |

TABLE 28-continued

| | |
|---|---|
| Full $V_H$ | EVQLVESGGGLVQPGGSLRLSCAASGFTFSSYAMSWVRQAPGKG LEWVSAISGSGGSTYYADSVKGRFTISRDNAKNTLYLQMNSLRA EDTAVYYCARKYQDVWGQGTLVTVSS [SEQ ID NO: 338] |
| DNA | GAGGTGCAGCTGGTGGAGTCTGGGGGAGGCTTGGTACAGCCT GGGGGGTCCCTGAGACTCTCCTGTGCAGCCTCTGGATTCACCT TTAGCAGCTATGCCATGAGCTGGGTCCGCCAGGCTCCAGGGA AGGGGCTGGAGTGGGTCTCAGCTATTAGTGGTAGTGGTGGTA GCACATACTACGCAGACTCCGTGAAGGGCCGGTTCACCATCTC CAGAGACAATGCCAAGAACACGCTGTATCTGCAAATGAACAG CCTGAGAGCCGAGGACACGGCCGTATATTACTGTGCGCGCAA ATACCAGGATGTTTGGGGTCAAGGTACTCTGGTGACCGTCTCC TCA [SEQ ID NO: 346] |
| Full $V_L$ | MKKTAIAIAVALAGFATVAQAAELQSVLTQPPSASGTPGQRVTIS CSGSSSNIGSNTVNWYQQLPGTAPKLLIYRNNQRPSGVPDRFSGS KSGTSASLAISGLRSEDEADYYCAAWDDSLSGRVFGGGTKLTVL G [SEQ ID NO: 339] |
| DNA | ATGAAAAAGACAGCTATCGCGATTGCAGTGGCACTGGCTGGT TTCGCTACCGTGGCCCAGGCGGCCGAGCTCCAGTCTGTGCTGA CGCAGCCGCCCTCAGCGTCTGGGACCCCCGGGCAGAGGGTCA CCATCTCTTGTTCTGGAAGCAGCTCCAACATCGGAAGTAATAC TGTAAACTGGTACCAGCAGCTCCCAGGAACGGCCCCCAAACT CCTCATCTATAGGAATAATCAGCGGCCCTCAGGGGTCCCTGAC CGATTCTCTGGCTCCAAGTCTGGCACCTCAGCCTCCCTGGCCA TCAGTGGGCTCCGGTCCGAGGATGAGGCTGATTATTACTGTGC AGCATGGGATGACAGCCTGAGTGGTAGGGTGTTCGGCGGAGG GACCAAGCTGACCGTCCTAGGT [SEQ ID NO: 347] |
| scFv | MKKTAIAIAVALAGFATVAQAAELQSVLTQPPSASGTPGQRVTIS CSGSSSNIGSNTVNWYQQLPGTAPKLLIYRNNQRPSGVPDRFSGS KSGTSASLAISGLRSEDEADYYCAAWDDSLSGRVFGGGTKLTVL GSRGGGGSGGGGSGGGGSLEMAEVQLVESGGGLVQPGGSLRLS CAASGFTFSSYAMSWVRQAPGKGLEWVSAISGSGGSTYYADSVK GRFTISRDNAKNTLYLQMNSLRAEDTAVYYCARKYQDVWGQGT LVTVSS [SEQ ID NO: 337] |
| DNA | ATGAAAAAGACAGCTATCGCGATTGCAGTGGCACTGGCTGGT TTCGCTACCGTGGCCCAGGCGGCCGAGCTCCAGTCTGTGCTGA CGCAGCCGCCCTCAGCGTCTGGGACCCCCGGGCAGAGGGTCA CCATCTCTTGTTCTGGAAGCAGCTCCAACATCGGAAGTAATAC TGTAAACTGGTACCAGCAGCTCCCAGGAACGGCCCCCAAACT CCTCATCTATAGGAATAATCAGCGGCCCTCAGGGGTCCCTGAC CGATTCTCTGGCTCCAAGTCTGGCACCTCAGCCTCCCTGGCCA TCAGTGGGCTCCGGTCCGAGGATGAGGCTGATTATTACTGTGC AGCATGGGATGACAGCCTGAGTGGTAGGGTGTTCGGCGGAGG GACCAAGCTGACCGTCCTAGGTTCTAGAGGTGGTGGTGGTAGC GGCGGCGGCGGCTCTGGTGGTGGTGGATCCCTCGAGATGGCC GAGGTGCAGCTGGTGGAGTCTGGGGGAGGCTTGGTACAGCCT GGGGGGTCCCTGAGACTCTCCTGTGCAGCCTCTGGATTCACCT TTAGCAGCTATGCCATGAGCTGGGTCCGCCAGGCTCCAGGGA AGGGGCTGGAGTGGGTCTCAGCTATTAGTGGTAGTGGTGGTA GCACATACTACGCAGACTCCGTGAAGGGCCGGTTCACCATCTC CAGAGACAATGCCAAGAACACGCTGTATCTGCAAATGAACAG CCTGAGAGCCGAGGACACGGCCGTATATTACTGTGCGCGCAA ATACCAGGATGTTTGGGGTCAAGGTACTCTGGTGACCGTCTCC TCA [SEQ ID NO: 348] |

In certain embodiments, the extracellular antigen-binding domain is a scFv, which comprises the amino acid sequence of SEQ ID NO: 349 and specifically binds to a GPRC5D polypeptide (e.g., a GPRC5D polypeptide having the amino acid sequence SEQ ID NO:97, or fragments thereof), which scFv is designated as ET150-030 scFv (also referred to as "ET150-180 scFv").

In certain embodiments, the extracellular antigen-binding domain is a scFv, which comprises a heavy chain variable region comprising amino acids having the sequence set forth in SEQ ID NO:350 and a light chain variable region comprising amino acids having the sequence set forth in SEQ ID NO:351, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 29. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:350 as shown in Table 29. In certain embodiments, the extracellular antigen-binding domain comprises a $V_H$ comprising amino acids having the sequence set forth in SEQ ID NO:350, as shown in Table 29. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:351, as shown in Table 29. In certain embodiments, the extracellular antigen-binding domain comprises a $V_L$ comprising amino acids having the sequence set forth in SEQ ID NO:351, as shown in Table 29. In certain embodiments, the extracellular antigen-binding domain comprises a $V_H$ comprising amino acids having the sequence set forth in SEQ ID NO:350 and a $V_L$ comprising amino acids having the sequence set forth in SEQ ID NO:351 as shown in Table 29. In certain embodiments, the extracellular antigen-binding domain comprises a $V_H$ CDR1 comprising amino acids having the sequence set forth in SEQ ID NO:352 or conservative modifications thereof, a $V_H$ CDR2 comprising amino acids having the sequence set forth in SEQ ID NO:353 or conservative modifications thereof, and a $V_H$ CDR3 comprising amino acids having the sequence set forth in SEQ ID NO:354 or conservative modifications thereof, as shown in Table 29. In certain embodiments, the extracellular antigen-binding domain comprises a $V_L$ CDR1 comprising amino acids having the sequence set forth in SEQ ID NO:355 or conservative modifications thereof, a $V_L$ CDR2 comprising amino acids having the sequence set forth in SEQ ID NO:356 or conservative modifications thereof, and a $V_L$ CDR3 comprising amino acids having the sequence set forth in SEQ ID NO:357 or conservative modifications thereof, as shown in Table 29. In certain embodiments, the extracellular antigen-binding domain comprises a $V_H$ CDR1 comprising amino acids having the sequence set forth in SEQ ID NO: 352 or conservative modifications thereof, a $V_H$ CDR2 comprising amino acids having the sequence set forth in SEQ ID NO: 353 or conservative modifications thereof, a $V_H$ CDR3 comprising amino acids having the sequence set forth in SEQ ID NO: 354 or conservative modifications thereof, a $V_L$ CDR1 comprising amino acids having the sequence set forth in SEQ ID NO: 355 or conservative modifications thereof, a $V_L$ CDR2 comprising amino acids having the sequence set forth in SEQ ID NO: 356 or conservative modifications thereof, and a $V_L$ CDR3 comprising amino acids having the sequence set forth in SEQ ID NO: 357 or conservative modifications thereof, as shown in Table 29. In certain embodiments, the extracellular antigen-binding domain comprises a $V_H$ CDR1 comprising amino acids having the sequence set forth in SEQ ID NO: 352, a $V_H$ CDR2 comprising amino acids having the sequence set forth in SEQ ID NO: 353, a $V_H$ CDR3 comprising amino acids having the sequence set forth in SEQ ID NO: 354, a $V_L$ CDR1 comprising amino acids having the sequence set forth in SEQ ID NO: 355, a $V_L$ CDR2 comprising amino acids having the sequence set forth in SEQ ID NO: 356, and a $V_L$ CDR3 comprising amino acids having the sequence set forth in SEQ ID NO: 357.

TABLE 29

| | | | |
|---|---|---|---|
| Antigen | A GPRC5D polypeptide having the amino acid sequence of SEQ ID NO: 97 | | |
| CDRs | 1 | 2 | 3 |
| $V_H$ | GFSFSGTA [SEQ ID NO: 352] | ISSTGRST [SEQ ID NO: 353] | ARPVSSMTLSIQSDG [SEQ ID NO: 354] |
| $V_L$ | SSNIGAGYD [SEQ ID NO: 355] | GNS [SEQ ID NO: 356] | QSYDSSLRGYV [SEQ ID NO: 357] |
| Full $V_H$ | QVQLVQSGGGVVQPGRSLRLSCAASGFSFSGTAMHWVRQAPGKGLEWVSTISSTGRSTYYRDSVKGRFTISRDNSKNTLYLQMNSLRGEDTAVYYCARPVSSMTLSIQSDGWGQGTLVTVSS [SEQ ID NO: 350] | | |
| DNA | CAGGTGCAGCTGGTGCAGTCTGGGGGAGGCGTGGTCCAGCCTGGGAGGTCCCTGAGACTCTCCTGTGCAGCCTCTGGATTCAGCTTTAGTGGCACTGCCATGCACTGGGTCCGCCAGGCTCCAGGGAAGGGGCTGGAATGGGTCTCGACTATTAGTAGTACTGGGCGTAGCACATACTACAGAGACTCCGTGAAGGGCCGGTTCACCATCTCCAGAGACAATTCCAAGAACACGCTGTATCTGCAAATGAACAGCCTGAGAGGCGAGGACACGGCCGTATATTACTGTGCGCGCCCGGTTTCTTCTATGACTCTGTCTATCCAGTCTGATGGTTGGGGTCAAGGTACTCTGGTGACCGTCTCCTCA [SEQ ID NO: 358] | | |
| Full $V_L$ | MKKTAIAIAVALAGFATVAQAAELQSVLTQPPSVSGAPGQRVTISCTGSSSNIGAGYDVHWYQQLPGRAPKLLIYGNSNRPSGVPDRFSGSKSGTSASLAITGLQAEDEADYYCQSYDSSLRGYVFGTGTKVTVLG [SEQ ID NO: 351] | | |
| DNA | ATGAAAAAGACAGCTATCGCGATTGCAGTGGCACTGGCTGGTTTCGCTACCGTGGCCCAGGCGGCCGAGCTCCAGTCTGTGTTGACGCAGCCGCCCTCAGTGTCTGGGGCCCCAGGGCAGAGGGTCACCATCTCCTGCACTGGGAGCAGCTCCAACATCGGGGCAGGTTATGATGTACACTGGTACCAGCAGCTTCCAGGAAGAGCCCCCAAACTCCTCATCTATGGTAACAGCAATCGGCCCTCAGGGGTCCCTGACCGATTCTCTGGCTCCAAGTCTGGCACCTCAGCCTCCCTGGCCATCACTGGGCTCCAGGCTGAGGATGAGGCTGATTATTACTGCCAGTCCTATGACAGCAGCCTGAGAGGTTATGTCTTCGGAACTGGGACCAAGGTCACCGTCCTAGGT [SEQ ID NO: 359] | | |
| scFv | MKKTAIAIAVALAGFATVAQAAELQSVLTQPPSVSGAPGQRVTISCTGSSSNIGAGYDVHWYQQLPGRAPKLLIYGNSNRPSGVPDRF | | |

TABLE 29-continued

| | |
|---|---|
| | SGSKSGTSASLAITGLQAEDEADYYCQSYDSSLRGYVFGTGTKV<br>TVLGSRGGGGSGGGGSGGGGSLEMAQVQLVQSGGGVVQPGRS<br>LRLSCAASGFSFSGTAMHWVRQAPGKGLEWVSTISSTGRSTYYR<br>DSVKGRFTISRDNSKNTLYLQMNSLRGEDTAVYYCARPVSSMT<br>LSIQSDGWGQGTLVTVSS [SEQ ID NO: 349] |
| DNA | ATGAAAAAGACAGCTATCGCGATTGCAGTGGCACTGGCTGGT<br>TTCGCTACCGTGGCCCAGGCGGCCGAGCTCCAGTCTGTGTTG<br>ACGCAGCCGCCCTCAGTGTCTGGGGCCCCAGGGCAGAGGGTC<br>ACCATCTCCTGCACTGGGAGCAGCTCCAACATCGGGGCAGGT<br>TATGATGTACACTGGTACCAGCAGCTTCCAGGAAGAGCCCCC<br>AAACTCCTCATCTATGGTAACAGCAATCGGCCCTCAGGGGTC<br>CCTGACCGATTCTCTGGCTCCAAGTCTGGCACCTCAGCCTCCC<br>TGGCCATCACTGGGCTCCAGGCTGAGGATGAGGCTGATTATT<br>ACTGCCAGTCCTATGACAGCAGCCTGAGAGGTTATGTCTTCG<br>GAACTGGGACCAAGGTCACCGTCCTAGGTTCTAGAGGTGGTG<br>GTGGTAGCGGCGGCGGCGGCTCTGGTGGTGGTGGATCCCTCG<br>AGATGGCCCAGGTGCAGCTGGTGCAGTCTGGGGGAGGCGTG<br>GTCCAGCCTGGGAGGTCCCTGAGACTCTCCTGTGCAGCCTCT<br>GGATTCAGCTTTAGTGGCACTGCCATGCACTGGGTCCGCCAG<br>GCTCCAGGGAAGGGGCTGGAATGGGTCTCGACTATTAGTAGT<br>ACTGGGCGTAGCACATACTACAGAGACTCCGTGAAGGGCCGG<br>TTCACCATCTCCAGAGACAATTCCAAGAACACGCTGTATCTG<br>CAAATGAACAGCCTGAGAGGCGAGGACACGGCCGTATATTA<br>CTGTGCGCGCCCGGTTTCTTCTATGACTCTGTCTATCCAGTCT<br>GATGGTTGGGGTCAAGGTACTCTGGTGACCGTCTCCTCA [SEQ<br>ID NO: 360] |

In certain embodiments, the extracellular antigen-binding domain is a scFv, which comprises the amino acid sequence of SEQ ID NO: 361 and specifically binds to a GPRC5D polypeptide (e.g., a GPRC5D polypeptide having the amino acid sequence SEQ ID NO:97, or fragments thereof), which scFv is designated as ET150-031 scFv (also referred to as "ET150-181 scFv").

In certain embodiments, the extracellular antigen-binding domain is a scFv, which comprises a heavy chain variable region comprising amino acids having the sequence set forth in SEQ ID NO:362 and a light chain variable region comprising amino acids having the sequence set forth in SEQ ID NO:363, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 30. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:362 as shown in Table 30. In certain embodiments, the extracellular antigen-binding domain comprises a $V_H$ comprising amino acids having the sequence set forth in SEQ ID NO:362, as shown in Table 30. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:363, as shown in Table 30. In certain embodiments, the extracellular antigen-binding domain comprises a $V_L$ comprising amino acids having the sequence set forth in SEQ ID NO:363, as shown in Table 30. In certain embodiments, the extracellular antigen-binding domain comprises a $V_H$ comprising amino acids having the sequence set forth in SEQ ID NO:362 and a $V_L$ comprising amino acids having the sequence set forth in SEQ ID NO:363 as shown in Table 30. In certain embodiments, the extracellular antigen-binding domain comprises a $V_H$ CDR1 comprising amino acids having the sequence set forth in SEQ ID NO:364 or conservative modifications thereof, a $V_H$ CDR2 comprising amino acids having the sequence set forth in SEQ ID NO:365 or conservative modifications thereof, and a $V_H$ CDR3 comprising amino acids having the sequence set forth in SEQ ID NO:366 or conservative modifications thereof, as shown in Table 30. In certain embodiments, the extracellular antigen-binding domain comprises a $V_L$ CDR1 comprising amino acids having the sequence set forth in SEQ ID NO:367 or conservative modifications thereof, a $V_L$ CDR2 comprising amino acids having the sequence set forth in SEQ ID NO:368 or conservative modifications thereof, and a $V_L$ CDR3 comprising amino acids having the sequence set forth in SEQ ID NO:369 or conservative modifications thereof, as shown in Table 30. In certain embodiments, the extracellular antigen-binding domain comprises a $V_H$ CDR1 comprising amino acids having the sequence set forth in SEQ ID NO: 364 or conservative modifications thereof, a $V_H$ CDR2 comprising amino acids having the sequence set forth in SEQ ID NO: 365 or conservative modifications thereof, a $V_H$ CDR3 comprising amino acids having the sequence set forth in SEQ ID NO: 366 or conservative modifications thereof, a $V_L$ CDR1 comprising amino acids having the sequence set forth in SEQ ID NO: 367 or conservative modifications thereof, a $V_L$ CDR2 comprising amino acids having the sequence set forth in SEQ ID NO: 368 or conservative modifications thereof, and a $V_L$ CDR3 comprising amino acids having the sequence set forth in SEQ ID NO: 369 or conservative modifications thereof, as shown in Table 30. In certain embodiments, the extracellular antigen-binding domain comprises a $V_H$ CDR1 comprising amino acids having the sequence set forth in SEQ ID NO: 364, a $V_H$ CDR2 comprising amino acids having the sequence set forth in SEQ ID NO: 365, a $V_H$ CDR3 comprising amino acids having the sequence set forth in SEQ ID NO: 366, a $V_L$ CDR1 comprising amino acids having the sequence set forth in SEQ ID NO: 367, a $V_L$ CDR2 comprising amino acids having the sequence set forth in SEQ ID NO: 368, and a $V_L$ CDR3 comprising amino acids having the sequence set forth in SEQ ID NO: 369.

TABLE 30

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFTSYY [SEQ ID NO: 364] | INPSGGST [SEQ ID NO: 365] | ARGQKYHSQYSRGGTGGGMTQDM [SEQ ID NO: 366] |
| $V_L$ | SSNIGNNY [SEQ ID NO: 367] | DNN [SEQ ID NO: 368] | GTWDSSLRNWV [SEQ ID NO: 369] |
| Full $V_H$ | QMQLVQSGAEVKKPGASVKVSCKASGYTFTSYYMHWVRQAPG QGLEWMGIINPSGGSTSYAQKFQGRVTMTRDTSTSTVYMELSSL RSEDTAVYYCARGQKYHSQYSRGGTGGGMTQDMWGQGTLVTV SS [SEQ ID NO: 362] | | |
| DNA | CAGATGCAGCTGGTGCAGTCTGGGGCTGAGGTGAAGAAGCCT GGGGCCTCAGTGAAGGTTTCCTGCAAGGCATCTGGATACACCT TCACCAGCTACTATATGCACTGGGTGCGACAGGCCCCTGGACA AGGGCTTGAGTGGATGGGAATAATCAACCCTAGTGGTGGTAG CACAAGCTACGCACAAAAGTTCCAGGGCAGAGTCACCATGAC CAGGGACACGTCCACGAGCACAGTCTACATGGAGCTGAGCAG CCTGAGATCTGAGGACACGGCCGTGTATTACTGTGCGCGCGGT CAGAAATACCATTCTCAGTACTCTCGTGGTGGTACTGGTGGTG GTATGACTCAGGATATGTGGGGTCAAGGTACTCTGGTGACCGT CTCCTCA [SEQ ID NO: 370] | | |
| Full $V_L$ | MKKTAIAIAVALAGFATVAQAAELQSVVTQPPSVSAAPGQRVTIS CSGGSSNIGNNYVSWFQQLPRTAPKLLIYDNNKRPSGIPDRFSGSK SGTSAALDITVLQTGDEADYYCGTWDSSLRNWVFGGGTKLTVL G [SEQ ID NO: 363] | | |
| DNA | ATGAAAAAGACAGCTATCGCGATTGCAGTGGCACTGGCTGGT TTCGCTACCGTGGCCCAGGCGGCCGAGCTCCAGTCTGTCGTGA CGCAGCCGCCCTCTGTGTCTGCGGCCCCAGGACAGAGGGTCAC CATCTCCTGCTCTGGAGGTAGTTCCAACATTGGGAATAATTAT GTTTCCTGGTTCCAACAACTCCCACGAACAGCCCCCAAACTCC TCATTTATGACAATAATAAGCGACCCTCAGGGATTCCTGACCG ATTCTCTGGCTCCAAGTCTGGCACGTCAGCCGCCCTGGACATC ACCGTTCTCCAGACTGGGGACGAGGCCGATTATTACTGCGGAA CTTGGGATAGCAGCCTGAGAAATTGGGTGTTCGGCGGAGGGA CCAAGCTGACCGTCCTAGGT [SEQ ID NO: 371] | | |
| scFv | MKKTAIAIAVALAGFATVAQAAELQSVVTQPPSVSAAPGQRVTIS CSGGSSNIGNNYVSWFQQLPRTAPKLLIYDNNKRPSGIPDRFSGSK SGTSAALDITVLQTGDEADYYCGTWDSSLRNWVFGGGTKLTVL GSRGGGGSGGGGSGGGGSLEMAQMQLVQSGAEVKKPGASVKV SCKASGYTFTSYYMHWVRQAPGQGLEWMGIINPSGGSTSYAQKF QGRVTMTRDTSTSTVYMELSSLRSEDTAVYYCARGQKYHSQYS RGGTGGGMTQDMWGQGTLVTVSS [SEQ ID NO: 361] | | |
| DNA | ATGAAAAAGACAGCTATCGCGATTGCAGTGGCACTGGCTGGT TTCGCTACCGTGGCCCAGGCGGCCGAGCTCCAGTCTGTCGTGA CGCAGCCGCCCTCTGTGTCTGCGGCCCCAGGACAGAGGGTCAC CATCTCCTGCTCTGGAGGTAGTTCCAACATTGGGAATAATTAT GTTTCCTGGTTCCAACAACTCCCACGAACAGCCCCCAAACTCC TCATTTATGACAATAATAAGCGACCCTCAGGGATTCCTGACCG ATTCTCTGGCTCCAAGTCTGGCACGTCAGCCGCCCTGGACATC ACCGTTCTCCAGACTGGGGACGAGGCCGATTATTACTGCGGAA CTTGGGATAGCAGCCTGAGAAATTGGGTGTTCGGCGGAGGGA CCAAGCTGACCGTCCTAGGTTCTAGAGGTGGTGGTGGTAGCGG CGGCGGCGGCTCTGGTGGTGGTGGATCCCTCGAGATGGCCCA GATGCAGCTGGTGCAGTCTGGGGCTGAGGTGAAGAAGCCTGG GGCCTCAGTGAAGGTTTCCTGCAAGGCATCTGGATACACCTTC ACCAGCTACTATATGCACTGGGTGCGACAGGCCCCTGGACAA GGGCTTGAGTGGATGGGAATAATCAACCCTAGTGGTGGTAGC ACAAGCTACGCACAAAAGTTCCAGGGCAGAGTCACCATGACC AGGGACACGTCCACGAGCACAGTCTACATGGAGCTGAGCAGC CTGAGATCTGAGGACACGGCCGTGTATTACTGTGCGCGCGGTC AGAAATACCATTCTCAGTACTCTCGTGGTGGTACTGGTGGTGG TATGACTCAGGATATGTGGGGTCAAGGTACTCTGGTGACCGTC TCCTCA [SEQ ID NO: 372] | | |

In certain embodiments, the extracellular antigen-binding domain is a scFv, which comprises the amino acid sequence of SEQ ID NO: 373 and specifically binds to a GPRC5D polypeptide (e.g., a GPRC5D polypeptide having the amino acid sequence SEQ ID NO:97, or fragments thereof), which scFv is designated as ET150-032 scFv (also referred to as "ET150-182 scFv").

In certain embodiments, the extracellular antigen-binding domain is a scFv, which comprises a heavy chain variable region comprising amino acids having the sequence set forth in SEQ ID NO:374 and a light chain variable region comprising amino acids having the sequence set forth in SEQ ID NO:375, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 31. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:374 as shown in Table 31. In certain embodiments, the extracellular antigen-binding domain comprises a $V_H$ comprising amino acids having the sequence set forth in SEQ ID NO:374, as shown in Table 31. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:375, as shown in Table 31. In certain embodiments, the extracellular antigen-binding domain comprises a $V_L$ comprising amino acids having the sequence set forth in SEQ ID NO:375, as shown in Table 31. In certain embodiments, the extracellular antigen-binding domain comprises a $V_H$ comprising amino acids having the sequence set forth in SEQ ID NO:374 and a $V_L$ comprising amino acids having the sequence set forth in SEQ ID NO:375 as shown in Table 31. In certain embodiments, the extracellular antigen-binding domain comprises a $V_H$ CDR1 comprising amino acids having the sequence set forth in SEQ ID NO:376 or conservative modifications thereof, a $V_H$ CDR2 comprising amino acids having the sequence set forth in SEQ ID NO:377 or conservative modifications thereof, and a $V_H$ CDR3 comprising amino acids having the sequence set forth in SEQ ID NO:378 or conservative modifications thereof, as shown in Table 31. In certain embodiments, the extracellular antigen-binding domain comprises a $V_L$ CDR1 comprising amino acids having the sequence set forth in SEQ ID NO:379 or conservative modifications thereof, a $V_L$ CDR2 comprising amino acids having the sequence set forth in SEQ ID NO:380 or conservative modifications thereof, and a $V_L$ CDR3 comprising amino acids having the sequence set forth in SEQ ID NO:381 or conservative modifications thereof, as shown in Table 31. In certain embodiments, the extracellular antigen-binding domain comprises a $V_H$ CDR1 comprising amino acids having the sequence set forth in SEQ ID NO: 376 or conservative modifications thereof, a $V_H$ CDR2 comprising amino acids having the sequence set forth in SEQ ID NO: 377 or conservative modifications thereof, a $V_H$ CDR3 comprising amino acids having the sequence set forth in SEQ ID NO: 378 or conservative modifications thereof, a $V_L$ CDR1 comprising amino acids having the sequence set forth in SEQ ID NO: 379 or conservative modifications thereof, a $V_L$ CDR2 comprising amino acids having the sequence set forth in SEQ ID NO: 380 or conservative modifications thereof, and a $V_L$ CDR3 comprising amino acids having the sequence set forth in SEQ ID NO: 381 or conservative modifications thereof, as shown in Table 31. In certain embodiments, the extracellular antigen-binding domain comprises a $V_H$ CDR1 comprising amino acids having the sequence set forth in SEQ ID NO: 376, a $V_H$ CDR2 comprising amino acids having the sequence set forth in SEQ ID NO: 377, a $V_H$ CDR3 comprising amino acids having the sequence set forth in SEQ ID NO: 378, a $V_L$ CDR1 comprising amino acids having the sequence set forth in SEQ ID NO: 379, a $V_L$ CDR2 comprising amino acids having the sequence set forth in SEQ ID NO: 380, and a $V_L$ CDR3 comprising amino acids having the sequence set forth in SEQ ID NO: 381.

TABLE 31

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFSRYY [SEQ ID NO: 376] | MNPNSGNT [SEQ ID NO: 377] | ARGRYHVIDY [SEQ ID NO: 378] |
| $V_L$ | SSDVGGYNH [SEQ ID NO: 379] | EVT [SEQ ID NO: 380] | SSYAGSAHWV [SEQ ID NO: 381] |
| Full $V_H$ | EVQLVQSGAEVKKPGASVKVSCKASGYTFSRYYIHWVRQAPGQ GLEWMGWMNPNSGNTGYAQKFQGRVTMTRNTSISTAYMELSSL RSEDTAVYYCARGRYHVIDYWGQGTLVTVSS [SEQ ID NO: 374] | | |
| DNA | GAGGTCCAGCTGGTGCAGTCTGGGGCTGAGGTGAAGAAGCCT GGGGCCTCAGTGAAGGTTTCCTGCAAGGCATCTGGATACACCT TCAGCAGGTACTATATACACTGGGTGCGACAGGCCCCTGGAC AAGGGCTTGAGTGGATGGGATGGATGAACCCTAACAGTGGTA ACACAGGCTATGCACAGAAGTTCCAGGGCAGAGTCACCATGA CCAGGAACACCTCCATAAGCACAGCCTACATGGAGCTGAGCA GCCTGAGATCTGAGGACACGGCCGTGTATTACTGTGCGCGCGG TCGTTACCATGTTATCGATTACTGGGGTCAAGGTACTCTGGTG ACCGTCTCCTCA [SEQ ID NO: 382] | | |

TABLE 31-continued

| | |
|---|---|
| Full $V_L$ | MKKTAIAIAVALAGFATVAQAAELQSVLTQPPSASGSPGQSLTIS<br>CTGTSSDVGGYNHVSWYQQYPGKAPKLMIYEVTKRPSGVPDRFS<br>GSKSGNTASLTVSGLQAEDEADYYCSSYAGSAHWVFGGGTKLT<br>VLG [SEQ ID NO: 375] |
| DNA | ATGAAAAAGACAGCTATCGCGATTGCAGTGGCACTGGCTGGT<br>TTCGCTACCGTGGCCCAGGCGGCCGAGCTCCAGTCTGTGTTGA<br>CTCAGCCACCCTCCGCGTCCGGGTCTCCTGGACAGTCACTCAC<br>CATCTCCTGCACTGGAACCAGCAGTGACGTTGGTGGTTATAAC<br>CATGTCTCCTGGTACCAACAGTACCCAGGCAAAGCCCCCAAAC<br>TCATGATTTATGAGGTCACTAAGCGGCCCTCAGGGGTCCCTGA<br>TCGCTTCTCTGGCTCCAAGTCTGGCAACACGGCCTCCCTGACC<br>GTCTCTGGGCTCCAGGCTGAGGATGAGGCTGATTATTACTGCA<br>GCTCATATGCAGGCAGCGCCCATTGGGTGTTCGGCGGAGGGA<br>CCAAGCTGACCGTCCTAGGT [SEQ ID NO: 383] |
| scFv | MKKTAIAIAVALAGFATVAQAAELQSVLTQPPSASGSPGQSLTIS<br>CTGTSSDVGGYNHVSWYQQYPGKAPKLMIYEVTKRPSGVPDRFS<br>GSKSGNTASLTVSGLQAEDEADYYCSSYAGSAHWVFGGGTKLT<br>VLGSRGGGGSGGGGSGGGGSLEMAEVQLVQSGAEVKKPGASVK<br>VSCKASGYTFSRYYIHWVRQAPGQGLEWMGWMNPNSGNTGYA<br>QKFQGRVTMTRNTSISTAYMELSSLRSEDTAVYYCARGRYHVID<br>YWGQGTLVTVSS [SEQ ID NO: 373] |
| DNA | ATGAAAAAGACAGCTATCGCGATTGCAGTGGCACTGGCTGGT<br>TTCGCTACCGTGGCCCAGGCGGCCGAGCTCCAGTCTGTGTTGA<br>CTCAGCCACCCTCCGCGTCCGGGTCTCCTGGACAGTCACTCAC<br>CATCTCCTGCACTGGAACCAGCAGTGACGTTGGTGGTTATAAC<br>CATGTCTCCTGGTACCAACAGTACCCAGGCAAAGCCCCCAAAC<br>TCATGATTTATGAGGTCACTAAGCGGCCCTCAGGGGTCCCTGA<br>TCGCTTCTCTGGCTCCAAGTCTGGCAACACGGCCTCCCTGACC<br>GTCTCTGGGCTCCAGGCTGAGGATGAGGCTGATTATTACTGCA<br>GCTCATATGCAGGCAGCGCCCATTGGGTGTTCGGCGGAGGGA<br>CCAAGCTGACCGTCCTAGGTTCTAGAGGTGGTGGTGGTAGCGG<br>CGGCGGCGGCTCTGGTGGTGGTGGATCCCTCGAGATGGCCGA<br>GGTCCAGCTGGTGCAGTCTGGGGCTGAGGTGAAGAAGCCTGG<br>GGCCTCAGTGAAGGTTTCCTGCAAGGCATCTGGATACACCTTC<br>AGCAGGTACTATATACACTGGGTGCGACAGGCCCCTGGACAA<br>GGGCTTGAGTGGATGGGATGGATGAACCCTAACAGTGGTAAC<br>ACAGGCTATGCACAGAAGTTCCAGGGCAGAGTCACCATGACC<br>AGGAACACCTCCATAAGCACAGCCTACATGGAGCTGAGCAGC<br>CTGAGATCTGAGGACACGGCCGTGTATTACTGTGCGCGCGGTC<br>GTTACCATGTTATCGATTACTGGGGTCAAGGTACTCTGGTGAC<br>CGTCTCCTCA [SEQ ID NO: 384] |

In certain embodiments, the extracellular antigen-binding domain is a scFv, which comprises the amino acid sequence of SEQ ID NO: 385 and specifically binds to a GPRC5D polypeptide (e.g., a GPRC5D polypeptide having the amino acid sequence SEQ ID NO:97, or fragments thereof), which scFv is designated as ET150-033 scFv (also referred to as "ET150-183 scFv").

In certain embodiments, the extracellular antigen-binding domain is a scFv, which comprises a heavy chain variable region comprising amino acids having the sequence set forth in SEQ ID NO:386 and a light chain variable region comprising amino acids having the sequence set forth in SEQ ID NO:387, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv-Fc fusion protein or full length human IgG with $V_H$ and $V_L$ regions or CDRs selected from Table 32. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:386 as shown in Table 32. In certain embodiments, the extracellular antigen-binding domain comprises a $V_H$ comprising amino acids having the sequence set forth in SEQ ID NO:386, as shown in Table 32. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:387, as shown in Table 32. In certain embodiments, the extracellular antigen-binding domain comprises a $V_L$ comprising amino acids having the sequence set forth in SEQ ID NO:387, as shown in Table 32. In certain embodiments, the extracellular antigen-binding domain comprises a $V_H$ comprising amino acids having the sequence set forth in SEQ ID NO:386 and a $V_L$ comprising amino acids having the sequence set forth in SEQ ID NO:387 as shown in Table 32. In certain embodiments, the extracellular antigen-binding domain comprises a $V_H$ CDR1 comprising amino acids having the sequence set forth in SEQ ID NO:388 or conservative modifications thereof, a $V_H$ CDR2 comprising amino acids having the sequence set forth in SEQ ID NO:389 or conservative modifications thereof, and a $V_H$ CDR3 comprising amino acids having the sequence set forth in SEQ ID NO:390 or conservative modifications thereof, as shown in Table 32. In certain embodiments, the extracellular antigen-binding domain comprises a $V_L$ CDR1 comprising amino acids having the sequence set forth in SEQ ID NO:391 or conservative modifications thereof, a $V_L$ CDR2 comprising amino acids having the sequence set forth in SEQ ID NO:392 or conservative modifications thereof, and a $V_L$ CDR3 comprising amino acids having the sequence set forth in SEQ ID NO:393 or conservative modifications thereof, as shown in Table 32. In certain embodiments, the extracellular antigen-binding domain comprises a $V_H$ CDR1 comprising amino acids having the sequence set forth in SEQ ID NO: 388 or conservative modifications thereof, a $V_H$ CDR2 comprising amino acids having the sequence set forth in SEQ ID NO: 389 or conservative modifications thereof, a $V_H$ CDR3 comprising amino acids having the sequence set forth in SEQ ID NO: 390 or conservative modifications thereof, a $V_L$ CDR1 comprising amino acids having the sequence set forth in SEQ ID NO: 391 or conservative modifications thereof, a $V_L$ CDR2 comprising amino acids having the sequence set forth in SEQ ID NO: 392 or conservative modifications thereof, and a $V_L$ CDR3 comprising amino acids having the sequence set forth in SEQ ID NO: 393 or conservative modifications thereof, as shown in Table 32. In certain embodiments, the extracellular antigen-binding domain comprises a $V_H$ CDR1 comprising amino acids having the sequence set forth in SEQ ID NO: 388, a $V_H$ CDR2 comprising amino acids having the sequence set forth in SEQ ID NO: 389, a $V_H$ CDR3 comprising amino acids having the sequence set forth in SEQ ID NO: 390, a $V_L$ CDR1 comprising amino acids having the sequence set forth in SEQ ID NO: 391, a $V_L$ CDR2 comprising amino acids having the sequence set forth in SEQ ID NO: 392, and a $V_L$ CDR3 comprising amino acids having the sequence set forth in SEQ ID NO: 393.

TABLE 32

| | | | |
|---|---|---|---|
| Antigen | A GPRC5D polypeptide having the amino acid sequence of SEQ ID NO: 97 | | |
| CDRs | 1 | 2 | 3 |
| $V_H$ | GYTFNTYY [SEQ ID NO: 388] | INPNNGGT [SEQ ID NO: 389] | ARSYDY [SEQ ID NO: 390] |
| $V_L$ | SSNIGSNY [SEQ ID NO: 391] | RNN [SEQ ID NO: 392] | AAWDDSLSGRV [SEQ ID NO: 393] |
| Full $V_H$ | QLQLVQSGAEVKKPGSSVKVSCKASGYTFNTYYLHWVRQAPGQ GLEWMGRINPNNGGTNYAQKFQGRVTMTRDTSINTAYMELSRL RSDDTAVYYCARSYDYWGQGTLVTVSS [SEQ ID NO: 386] | | |
| DNA | CAGCTGCAGCTGGTGCAATCTGGGGCTGAGGTGAAGAAGCCT GGGTCCTCGGTGAAGGTCTCCTGCAAGGCTTCTGGATACACCT TCAACACCTACTATCTGCACTGGGTACGACAGGCCCCTGGACA AGGGCTTGAGTGGATGGGACGGATCAACCCTAACAATGGTGG CACAAACTATGCACAGAAGTTTCAGGGCAGGGTCACCATGAC CAGGGACACGTCCATCAACACAGCCTACATGGAGCTGAGCAG GCTGAGATCTGACGACACGGCCGTGTATTACTGTGCGCGCTCT TACGATTACTGGGGTCAAGGTACTCTGGTGACCGTCTCCTCA [SEQ ID NO: 394] | | |
| Full $V_L$ | MKKTAIAIAVALAGFATVAQAAELQAVLTQPPSASGTPGQRVTIS CSGSSSNIGSNYVYWYQQLPGTAPKLLIYRNNQRPSGVPDRFSGS KSGTSASLAISGLRSEDEADYYCAAWDDSLSGRVFGTGTKVTVL G [SEQ ID NO: 387] | | |
| DNA | ATGAAAAAGACAGCTATCGCGATTGCAGTGGCACTGGCTGGT TTCGCTACCGTGGCCCAGGCGGCCGAGCTCCAGGCTGTGCTGA CTCAGCCACCCTCAGCGTCTGGGACCCCCGGGCAGAGGGTCA CCATCTCTTGTTCTGGAAGCAGCTCCAACATCGGAAGTAATTA TGTATACTGGTACCAGCAGCTCCCAGGAACGGCCCCCAAACTC CTCATCTATAGGAATAATCAGCGGCCCTCAGGGGTCCCTGACC GATTCTCTGGCTCCAAGTCTGGCACCTCAGCCTCCCTGGCCAT CAGTGGGCTCCGGTCCGAGGATGAGGCTGATTATTACTGTGCA GCATGGGATGACAGCCTGAGTGGTCGGGTCTTCGGAACTGGG ACCAAGGTCACCGTCCTAGGT [SEQ ID NO: 395] | | |
| scFv | MKKTAIAIAVALAGFATVAQAAELQAVLTQPPSASGTPGQRVTIS CSGSSSNIGSNYVYWYQQLPGTAPKLLIYRNNQRPSGVPDRFSGS KSGTSASLAISGLRSEDEADYYCAAWDDSLSGRVFGTGTKVTVL GSRGGGGSGGGGSGGGGSLEMAQLQLVQSGAEVKKPGSSVKVS CKASGYTFNTYYLHWVRQAPGQGLEWMGRINPNNGGTNYAQK FQGRVTMTRDTSINTAYMELSRLRSDDTAVYYCARSYDYWGQG TLVTVSS [SEQ ID NO: 385] | | |
| DNA | ATGAAAAAGACAGCTATCGCGATTGCAGTGGCACTGGCTGGT TTCGCTACCGTGGCCCAGGCGGCCGAGCTCCAGGCTGTGCTGA CTCAGCCACCCTCAGCGTCTGGGACCCCCGGGCAGAGGGTCA CCATCTCTTGTTCTGGAAGCAGCTCCAACATCGGAAGTAATTA TGTATACTGGTACCAGCAGCTCCCAGGAACGGCCCCCAAACTC CTCATCTATAGGAATAATCAGCGGCCCTCAGGGGTCCCTGACC GATTCTCTGGCTCCAAGTCTGGCACCTCAGCCTCCCTGGCCAT CAGTGGGCTCCGGTCCGAGGATGAGGCTGATTATTACTGTGCA | | |

TABLE 32-continued

| |
|---|
| GCATGGGATGACAGCCTGAGTGGTCGGGTCTTCGGAACTGGG<br>ACCAAGGTCACCGTCCTAGGTTCTAGAGGTGGTGGTGGTAGCG<br>GCGGCGGCGGCTCTGGTGGTGGTGGATCCCTCGAGATGGCCC<br>AGCTGCAGCTGGTGCAATCTGGGGCTGAGGTGAAGAAGCCTG<br>GGTCCTCGGTGAAGGTCTCCTGCAAGGCTTCTGGATACACCTT<br>CAACACCTACTATCTGCACTGGGTACGACAGGCCCCTGGACAA<br>GGGCTTGAGTGGATGGGACGGATCAACCCTAACAATGGTGGC<br>ACAAACTATGCACAGAAGTTTCAGGGCAGGGTCACCATGACC<br>AGGGACACGTCCATCAACACAGCCTACATGGAGCTGAGCAGG<br>CTGAGATCTGACGACACGGCCGTGTATTACTGTGCGCGCTCTT<br>ACGATTACTGGGGTCAAGGTACTCTGGTGACCGTCTCCTCA<br>[SEQ ID NO: 396] |

An extracellular antigen-binding domain (e.g., scFv) comprising $V_H$ and/or $V_L$ regions having high (i.e., 80% or greater) homology to the $V_H$ and $V_L$ regions of the sequences set forth above, can be obtained by mutagenesis (e.g., site-directed or PCR-mediated mutagenesis), followed by testing of the encoded altered scFv for retained function (i.e., the binding affinity) using the binding assays described herein. In certain embodiments, a $V_H$ sequence having at least 9 about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homology contains substitutions (e.g., conservative substitutions to generate conservative modifications of a sequence), insertions or deletions relative to the reference sequence, but an extracellular antigen-binding domain (e.g., scFv) comprising that sequence retains the ability to bind to a GPRC5D polypeptide. In certain embodiments, a $V_L$ sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous contains substitutions (e.g., conservative substitutions), insertions or deletions relative to the reference sequence, but an extracellular antigen-binding domain (e.g., scFv) comprising that sequence retains the ability to bind to a GPRC5D polypeptide. In certain embodiments, a total of about 1 to about 10 amino acids have been substituted, inserted and/or deleted in the disclosed sequences. For example, and not by way of limitation, a $V_H$ sequence or a $V_L$ sequence, can have up to about one, up to about two, up to about three, up to about four, up to about five, up to about six, up to about seven, up to about eight, up to about nine or up to about ten amino acid residues that are modified and/or substituted. Non-limiting examples of conservative modifications are provided below, e.g., within Table 33.

As used herein, the term "conservative sequence modifications" refers to amino acid modifications that do not significantly affect or alter the binding characteristics of the presently disclosed CAR (e.g., the extracellular antigen-binding domain) comprising the amino acid sequence. Such conservative modifications include amino acid substitutions, additions and deletions. Modifications can be introduced into the human scFv of the presently disclosed subject matter by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (l) above) using the functional assays described herein. In certain embodiments, no more than one, no more than two, no more than three, no more than four, no more than five residues within a specified sequence or a CDR region are altered. Exemplary conservative amino acid substitutions are shown in Table 33.

TABLE 33

| Original Residue | Exemplary conservative amino acid Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

In certain non-limiting embodiments, an extracellular antigen-binding domain of the CAR can comprise a linker connecting the heavy chain variable region and light chain variable region of the extracellular antigen-binding domain. As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). Non-limiting examples of peptide linkers are disclosed in Shen et al., Anal. Chem. 80(6):1910-1917 (2008) and WO 2014/087010.

In one non-limiting example, the linker is a G4S linker that comprises amino acids having the sequence set forth in SEQ ID NO:98. In certain embodiments, the nucleotide sequence encoding the amino acid sequence of SEQ ID NO:98 is set forth in SEQ ID NO:99. In one non-limiting example, the linker comprises amino acids having the sequence set forth in SEQ ID NO:284. In certain embodiments, the nucleotide sequence encoding the amino acid sequence of SEQ ID NO:307 is set forth in SEQ ID NO:285.

In certain embodiments, the linker comprises amino acids having the sequence set forth in SEQ ID NO:286 as provided below.

[SEQ ID NO: 286]
GGGGS.

In certain embodiments, the linker comprises amino acids having the sequence set forth in SEQ ID NO:287 as provided below.

[SEQ ID NO: 287]
SGGSGGS.

In certain embodiments, the linker comprises amino acids having the sequence set forth in SEQ ID NO:288 as provided below.

[SEQ ID NO: 288]
GGGGSGGGS.

In certain embodiments, the linker comprises amino acids having the sequence set forth in SEQ ID NO:289 as provided below.

[SEQ ID NO: 289]
GGGGSGGGGS.

In certain embodiments, the linker comprises amino acids having the sequence set forth in SEQ ID NO:290 as provided below.

[SEQ ID NO: 290]
GGGGSGGGGSGGGGGGGS.

In certain embodiments, the linker comprises amino acids having the sequence set forth in SEQ ID NO:291 as provided below.

[SEQ ID NO: 291]
GGGGSGGGGSGGGGSGGGGS.

In certain embodiments, the linker comprises amino acids having the sequence set forth in SEQ ID NO:292 as provided below.

[SEQ ID NO: 292]
GGGGSGGGGSGGGGSGGGGSGGGGS.

In certain embodiments, the linker comprises amino acids having the sequence set forth in SEQ ID NO:293 as provided below.

[SEQ ID NO: 293]
GGGGSGGGGSGGGGSGGGGSGGGGSGGGGS.

In certain embodiments, the linker comprises amino acids having the sequence set forth in SEQ ID NO:294 as provided below.

[SEQ ID NO: 294]
GGGGSGGGGSGGGGSGGGGSGGGGSGGGGSGGGGS.

In certain embodiments, the linker comprises amino acids having the sequence set forth in SEQ ID NO:295 as provided below.

[SEQ ID NO: 295]
EPKSCDKTHTCPPCP.

In certain embodiments, the linker comprises amino acids having the sequence set forth in SEQ ID NO:296 as provided below.

[SEQ ID NO: 296]
GGGGSGGGSEPKSCDKTHTCPPCP.

In certain embodiments, the linker comprises amino acids having the sequence set forth in SEQ ID NO:297 as provided below.

[SEQ ID NO: 297]
ELKTPLGDTTHTCPRCPEPKSCDTPPPCPRCPEPKSCDTPPPCPRCPEPK
SCDTPPPCPRCP.

In certain embodiments, the linker comprises amino acids having the sequence set forth in SEQ ID NO:298 as provided below.

[SEQ ID NO: 298]
GSGSGS.

In certain embodiments, the linker comprises amino acids having the sequence set forth in SEQ ID NO:299 as provided below.

[SEQ ID NO: 299]
AAA.

In addition, the extracellular antigen-binding domain can comprise a leader or a signal peptide that directs the nascent protein into the endoplasmic reticulum. Signal peptide or leader can be essential if the CAR is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway. In non-limiting examples, the signal peptide is covalently joined to the 5' terminus of the extracellular antigen-binding domain. In certain embodiments, the signal peptide comprises a CD8 polypeptide comprising amino acids having the sequence set forth in SEQ ID NO:268 as provided below.

[SEQ ID NO: 268]
MALPVTALLLPLALLLHAAR

The nucleotide sequence encoding the amino acid sequence of SEQ ID NO:268 is set forth in SEQ ID NO:269, which is provided below:

[SEQ ID NO: 269]

ATGGCTCTCCCAGTGACTGCCCTACTGCTTCCCCTAGCGCTTCTCCTGCA

TGCAGCTCGT

In certain embodiments, the signal peptide comprises amino acids having the sequence set forth in SEQ ID NO:282 as provided below.

[SEQ ID NO: 282]

METDTLLLWVLLLWVPGSTG

The nucleotide sequence encoding the amino acid sequence of SEQ ID NO:282 is set forth in SEQ ID NO:283, which is provided below:

[SEQ ID NO: 283]

ATGGAAACCGACACCCTGCTGCTGTGGGTGCTGCTGCTGTGGGTGCCAGG

ATCCACAGGA

In certain embodiments, the human scFv comprises a heavy chain variable region, a light chain variable region, a linker peptide between the heavy chain variable region and the light chain variable region, and an His-tag and an HA-tag. In certain embodiments, the amino acid sequence of the His-tag and HA-tag comprises the amino acid sequence of SEQ ID NO:409, which is provided below:

[SEQ ID NO: 409]

TSGQAGQHHHHHHGAYPYDVPDYAS

The nucleotide sequence encoding SEQ ID NO: 409 is SEQ ID NO: 410, which is provided below:

[SEQ ID NO: 410]

ACTAGTGGCCAGGCCGGCCAGCACCATCACCATCACCATGGCGCATACCC

GTACGACGTTCCGGACTACGCTTCT

In certain embodiments, the extracellular antigen-binding domain binds to a human GPRC5D polypeptide comprising the amino acid sequence set forth in SEQ ID NO: 97. In certain embodiments, the extracellular antigen-binding domain binds to one, two, three or four of N-terminal region (amino acids 1-27 of SEQ ID NO:97), ECL1 region (amino acids 85-93 of SEQ ID NO:97), ECL2 region (amino acids 145-167 of SEQ ID NO:97), and ECL3 region (amino acids 226-239 of SEQ ID NO:97). In certain embodiments, the extracellular antigen-binding domain binds to an epitope region in the N-terminal region, including, but not limited to, an epitope region comprising amino acids 16-23 of SEQ ID NO:97, and an epitope region comprising amino acids 10-17 of SEQ ID NO:97. In certain embodiments, the epitope region in the N-terminal region comprises amino acids 15-23 of SEQ ID NO:97. In certain embodiments, the epitope region in the N-terminal region comprises amino acids 16-25 of SEQ ID NO:97. In certain embodiments, the epitope region in the N-terminal region comprises amino acids 10-17 of SEQ ID NO:97. In certain embodiments, the epitope region in the N-terminal region comprises amino acids 5-17 of SEQ ID NO:97.

In certain embodiments, the extracellular antigen-binding domain binds to an epitope region in the ECL1 region, including, but not limited to, an epitope region comprising amino acids 85-95 of SEQ ID NO:97.

In certain embodiments, the extracellular antigen-binding domain binds to an epitope region in the ECL2 region, including, but not limited to, an epitope region comprising amino acids 157-164 of SEQ ID NO:97. In certain embodiments, the epitope region in the ECL2 region comprises amino acids 157-164 of SEQ ID NO:97. In certain embodiments, the epitope region in the ECL2 region comprises amino acids 157-167 of SEQ ID NO:97.

In certain embodiments, the extracellular antigen-binding domain binds to an epitope region in the ECL3 region, including, but not limited to, an epitope region comprising amino acids 230-237 of SEQ ID NO:97. In certain embodiments, the epitope region in the ECL3 region comprises amino acids 229-237 of SEQ ID NO:97. In certain embodiments, the epitope region in the ECL3 region comprises amino acids 230-243 of SEQ ID NO:97. In certain embodiments, the epitope region in the ECL3 region comprises amino acids 227-237 of SEQ ID NO:97.

In certain embodiments, the extracellular antigen-binding domain binds to one, two, or three epitope region selected from the group consisting of an epitope region comprising amino acids 16-25 of SEQ ID NO:97, an epitope region comprising amino acids 157-164 of SEQ ID NO:97, and an epitope region comprising amino acids 229-237 of SEQ ID NO:97. For example, the extracellular antigen-binding domain comprises a heavy chain variable region comprising amino acids having the sequence set forth in SEQ ID NO:57 and a light chain variable region comprising amino acids having the sequence set forth in SEQ ID NO:58, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv. In certain embodiments, the extracellular antigen-binding domain is a scFv-Fc fusion protein or full length human IgG with $V_H$ and $V_L$ regions or CDRs selected from Table 15. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:57. In certain embodiments, the extracellular antigen-binding domain comprises a $V_H$ comprising amino acids having the sequence set forth in SEQ ID NO:57. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:58. In certain embodiments, the extracellular antigen-binding domain comprises a $V_L$ comprising amino acids having the sequence set forth in SEQ ID NO:58. In certain embodiments, the extracellular antigen-binding domain comprises a $V_H$ comprising amino acids having the sequence set forth in SEQ ID NO:57 and a $V_L$ comprising amino acids having the sequence set forth in SEQ ID NO:58. In certain embodiments, the extracellular antigen-binding domain comprises a $V_H$ CDR1 comprising amino acids having the sequence set forth in SEQ ID NO:208 or conservative modifications thereof, a $V_H$ CDR2 comprising amino acids having the sequence set forth in SEQ ID NO: 209 or conservative modifications thereof, and a $V_H$ CDR3 comprising amino acids having the sequence set forth in SEQ ID NO: 210 or conservative modifications thereof. In certain embodiments, the extracellular antigen-binding domain comprises a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof. In certain embodiments, the extracellular antigen-binding domain comprises a $V_H$ CDR1 comprising amino acids having the sequence set forth in SEQ ID NO: 208 or conservative modifications thereof, a $V_H$ CDR2 comprising amino acids having the sequence set forth in SEQ ID NO: 209 or conservative modifications thereof, a $V_H$ CDR3 comprising amino acids having the sequence set forth in SEQ ID NO: 210 or conservative modifications thereof, a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof. In certain embodiments, the extracellular antigen-binding domain comprises a $V_H$ CDR1 comprising amino acids having the sequence set forth in SEQ ID NO: 208, a $V_H$ CDR2 comprising amino acids having the sequence set forth in SEQ ID NO: 209, a $V_H$ CDR3 comprising amino acids having the sequence set forth in SEQ ID NO: 210, a $V_L$ CDR1 comprising amino acids having the sequence set forth in SEQ ID NO: 211, a $V_L$ CDR2 comprising amino acids having the sequence set forth in SEQ ID NO: 212, and a $V_L$ CDR3 comprising amino acids having the sequence set forth in SEQ ID NO: 213. In certain embodiments, the extracellular antigen-binding domain is ET150-2 scFv (or ET150-152 scFv).

In certain embodiments, the extracellular antigen-binding domain binds to one, two, or three epitope region selected from the group consisting of an epitope region comprising amino acids 5-17 of SEQ ID NO:97, an epitope region comprising amino acids 85-95 of SEQ ID NO:97, and an epitope region comprising amino acids 157-164 of SEQ ID NO:97. For example, the extracellular antigen-binding domain comprises a heavy chain variable region comprising amino acids having the sequence set forth in SEQ ID NO:61 and a light chain variable region comprising amino acids having the sequence set forth in SEQ ID NO:62, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv. In certain embodiments, the extracellular antigen-binding domain is a scFv-Fc fusion protein or full length human IgG with $V_H$ and $V_L$ regions or CDRs selected from Table 16. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:61. In certain embodiments, the extracellular antigen-binding domain comprises a $V_H$ comprising amino acids having the sequence set forth in SEQ ID NO:61. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:62. In certain embodiments, the extracellular antigen-binding domain comprises a $V_L$ comprising amino acids having the sequence set forth in SEQ ID NO:62. In certain embodiments, the extracellular antigen-binding domain comprises a $V_H$ comprising amino acids having the sequence set forth in SEQ ID NO:61 and a $V_L$ comprising amino acids having the sequence set forth in SEQ ID NO:62. In certain embodiments certain embodiments, the extracellular antigen-binding domain comprises a $V_H$ CDR1 comprising amino acids having the sequence set forth in SEQ ID NO:214 or conservative modifications thereof, a $V_H$ CDR2 comprising amino acids having the sequence set forth in SEQ ID NO: 215 or conservative modifications thereof, and a $V_H$ CDR3 comprising amino acids having the sequence set forth in SEQ ID NO: 216 or conservative modifications thereof. In certain embodiments, the extracellular antigen-binding domain comprises a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof. In certain embodiments, the extracellular antigen-binding domain comprises a $V_H$ CDR1 comprising amino acids having the sequence set forth in SEQ ID NO: 214 or conservative modifications thereof, a $V_H$ CDR2 comprising amino acids having the sequence set forth in SEQ ID NO: 215 or conservative modifications thereof, a $V_H$ CDR3 comprising amino acids having the sequence set forth in SEQ ID NO: 216 or conservative modifications thereof, a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof. In certain embodiments, the extracellular antigen-binding domain comprises a $V_H$ CDR1 comprising amino acids having the sequence set forth in SEQ ID NO: 214, a $V_H$ CDR2 comprising amino acids having the sequence set forth in SEQ ID NO: 215, a $V_H$ CDR3 comprising amino acids having the sequence set forth in SEQ ID NO: 216, a $V_L$ CDR1 comprising amino acids having the sequence set forth in SEQ ID NO: 217, a $V_L$ CDR2 comprising amino acids having the sequence set forth in SEQ ID NO: 218 and a $V_L$ CDR3 comprising amino acids having the sequence set forth in SEQ ID NO: 219. In certain embodiments, the extracellular antigen-binding domain is ET150-155 scFv (or ET150-5 scFv).

In certain embodiments, the extracellular antigen-binding domain binds to one or two epitope region selected from the group consisting of an epitope region comprising amino acids 15-23 of SEQ ID NO:97, and an epitope region comprising amino acids 230-243 of SEQ ID NO:97. For example, the extracellular antigen-binding domain comprises a heavy chain variable region comprising amino acids having the sequence set forth in SEQ ID NO:65 and a light chain variable region comprising amino acids having the sequence set forth in SEQ ID NO:66, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv. In certain embodiments, the extracellular antigen-binding domain is a scFv-Fc fusion protein or full length human IgG with $V_H$ and $V_L$ regions or CDRs selected from Table 17. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:65. In certain embodiments, the extracellular antigen-binding domain comprises a $V_H$ comprising amino acids having the sequence set forth in SEQ ID NO:65. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:66, as shown in Table 17. In certain embodiments, the extracellular antigen-binding domain comprises a $V_L$ comprising amino acids having the sequence set forth in SEQ ID NO:66. In certain embodiments, the extracellular antigen-binding domain comprises a $V_H$ comprising amino acids having the sequence set forth in SEQ ID NO:65 and a $V_L$ comprising amino acids having the sequence set forth in SEQ ID NO:66. In certain embodiments, the extracellular antigen-binding domain comprises a $V_H$ CDR1 comprising amino acids having the sequence set forth in SEQ ID NO:220 or conservative modifications thereof, a $V_H$ CDR2 comprising amino acids having the sequence set forth in SEQ ID NO: 221 or conservative modifications thereof, and a $V_H$ CDR3 comprising amino acids having the sequence set forth in SEQ ID NO: 222 or conservative modifications thereof. In certain embodiments, the extracellular antigen-binding domain comprises a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof. In certain embodiments, the extracellular antigen-binding domain comprises a $V_H$ CDR1 comprising amino acids having the sequence set forth in SEQ ID NO: 220 or conservative modifications thereof, a $V_H$ CDR2 comprising amino acids having the sequence set forth in SEQ ID NO: 221 or conservative modifications thereof, a $V_H$ CDR3 comprising amino acids having the sequence set forth in SEQ ID NO: 222 or conservative modifications thereof, a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof. In certain embodiments, the extracellular antigen-binding domain comprises a $V_H$ CDR1 comprising amino acids having the sequence set forth in SEQ ID NO: 220, a $V_H$ CDR2 comprising amino acids having the sequence set forth in SEQ ID NO: 221, a $V_H$ CDR3 comprising amino acids having the sequence set forth in SEQ ID NO: 222, a $V_L$ CDR1 comprising amino acids having the sequence set forth in SEQ ID NO: 223, a $V_L$ CDR2 comprising amino acids having the sequence set forth in SEQ ID NO: 224, and a $V_L$ CDR3 comprising amino acids having the sequence set forth in SEQ ID NO: 225. In certain embodiments, the extracellular antigen-binding domain is ET150-8 scFv (or ET150-158 scFv).

In certain embodiments, the extracellular antigen-binding domain binds to one, two, or three epitope region selected from the group consisting of an epitope region comprising amino acids 10-17 of SEQ ID NO:97, an epitope region comprising amino acids 157-167 of SEQ ID NO:97, and an epitope region comprising amino acids 227-237 of SEQ ID NO:97. For example, the extracellular antigen-binding domain comprises a heavy chain variable region comprising amino acids having the sequence set forth in SEQ ID NO:69 and a light chain variable region comprising amino acids having the sequence set forth in SEQ ID NO:70, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the extracellular antigen-binding domain is a scFv. In certain embodiments, the extracellular antigen-binding domain is a scFv-Fc fusion protein or full length human IgG with $V_H$ and $V_L$ regions or CDRs selected from Table 18. In certain embodiments, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:69. In certain embodiments, the extracellular antigen-binding domain comprises a $V_H$ comprising amino acids having the sequence set forth in SEQ ID NO:69. In certain embodiments, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the amino acid sequence set forth in SEQ ID NO:70. In certain embodiments, the extracellular antigen-binding domain comprises a $V_L$ comprising amino acids having the sequence set forth in SEQ ID NO:70. In certain embodiments, the extracellular antigen-binding domain comprises a $V_H$ comprising amino acids having the sequence set forth in SEQ ID NO:69 and a $V_L$ comprising amino acids having the sequence set forth in SEQ ID NO:70. In certain embodiments, the extracellular antigen-binding domain comprises a $V_H$ CDR1 comprising amino acids having the sequence set forth in SEQ ID NO:226 or conservative modifications thereof, a $V_H$ CDR2 comprising amino acids having the sequence set forth in SEQ ID NO: 227 or conservative modifications thereof, and a $V_H$ CDR3 comprising amino acids having the sequence set forth in SEQ ID NO: 228 or conservative modifications thereof. In certain embodiments, the extracellular antigen-binding domain comprises a $V_L$ CDR1 comprising amino acids having the sequence set forth in SEQ ID NO: 229 or conservative modifications thereof, a $V_L$ CDR2 comprising amino acids having the sequence set forth in SEQ ID NO: 230 or conservative modifications thereof, and a $V_L$ CDR3 comprising amino acids having the sequence set forth in SEQ ID NO: 231 or conservative modifications thereof. In certain embodiments, the extracellular antigen-binding domain comprises a $V_H$ CDR1 comprising amino acids having the sequence set forth in SEQ ID NO: 226 or conservative modifications thereof, a $V_H$ CDR2 comprising amino acids having the sequence set forth in SEQ ID NO: 227 or conservative modifications thereof, a $V_H$ CDR3 comprising amino acids having the sequence set forth in SEQ ID NO: 228 or conservative modifications thereof, a $V_L$ CDR1 comprising amino acids having the sequence set forth in SEQ ID NO: 229 or conservative modifications thereof, a $V_L$ CDR2 comprising amino acids having the sequence set forth in SEQ ID NO: 230 or conservative modifications thereof, and a $V_L$ CDR3 comprising amino acids having the sequence set forth in SEQ ID NO: 231 or conservative modifications thereof. In certain embodiments, the extracellular antigen-binding domain comprises a $V_H$ CDR1 comprising amino acids having the sequence set forth in SEQ ID NO: 226, a $V_H$ CDR2 comprising amino acids having the sequence set forth in SEQ ID NO: 227, a $V_H$ CDR3 comprising amino acids having the sequence set forth in SEQ ID NO: 228, a $V_L$ CDR1 comprising amino acids having the sequence set forth in SEQ ID NO: 229, a $V_L$ CDR2 comprising amino acids having the sequence set forth in SEQ ID NO: 230, and a $V_L$ CDR3 comprising amino acids having the sequence set forth in SEQ ID NO: 231. In certain embodiments, the extracellular antigen-binding domain is ET150-18 scFv (or ET150-168 scFv).

Transmembrane Domain of a CAR

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof.

In certain embodiments, the transmembrane domain of a presently disclosed CAR comprises a CD28 polypeptide. The CD28 polypeptide can have an amino acid sequence that is at least about 85%, about 90%, about 95%, about 96%, about 97%, about 98%, about 99% or 100% homologous to the sequence having a NCBI Reference No: P10747 or NP_006130 (SEQ ID No: 270), or fragments thereof, and/or may optionally comprise up to one or up to two or up to three conservative amino acid substitutions. In non-limiting embodiments, the CD28 polypeptide can have an amino acid sequence that is a consecutive portion of SEQ ID NO:270 which is at least 20, or at least 30, or at least 40, or at least 50, and up to 220 amino acids in length. Alternatively or additionally, in non-limiting various embodiments, the CD28 polypeptide has an amino acid sequence of amino acids 1 to 220, 1 to 50, 50 to 100, 100 to 150, 150 to 200, or 200 to 220 of SEQ ID NO: 270. In certain embodiments, the CAR of the presently disclosed comprises a transmembrane domain comprising a CD28 polypeptide, and an intracellular domain comprising a co-stimulatory signaling region that comprises a CD28 polypeptide. In certain embodiments, the CD28 polypeptide comprised in the transmembrane domain and the intracellular domain has an amino acid sequence of amino acids 114 to 220 of SEQ ID NO:270.

SEQ ID NO:270 is provided below:

```
                                                          [SEQ ID NO: 270]
  1 MLRLLLALNL FPSIQVTGNK ILVKQSPMLV AYDNAVNLSC KYSYNLFSRE FRASLHKGLD

 61 SAVEVCVVYG NYSQQLQVYS KTGFNCDGKL GNESVTFYLQ NLYVNQTDIY FCKIEVMYPP

121 PYLDNEKSNG TIIHVKGKHL CPSPLFPGPS KPFWVLVVVG GVLACYSLLV TVAFIIFWVR

181 SKRSRLLHSD YMNMTPRRPG PTRKHYQPYA PPRDFAAYRS
```

In accordance with the presently disclosed subject matter, a "CD28 nucleic acid molecule" refers to a polynucleotide encoding a CD28 polypeptide. In certain embodiments, the CD28 nucleic acid molecule encoding the CD28 polypeptide comprised in the transmembrane domain and the intracellular domain (e.g., the co-stimulatory signaling region) of the presently disclosed CAR (amino acids 114 to 220 of SEQ ID NO:270) comprises nucleic acids having the sequence set forth in SEQ ID NO:271 as provided below.

```
                                            [SEQ ID NO: 271]
ATTGAAGTTATGTATCCTCCTCCTTACCTAGACAATGAGAAGAGCAATGG

AACCATTATCCATGTGAAAGGGAAACACCTTTGTCCAAGTCCCCTATTTC

CCGGACCTTCTAAGCCCTTTTGGGTGCTGGTGGTGGTTGGTGGAGTCCTG

GCTTGCTATAGCTTGCTAGTAACAGTGGCCTTTATTATTTTCTGGGTGAG

GAGTAAGAGGAGCAGGCTCCTGCACAGTGACTACATGAACATGACTCCCC

GCCGCCCCGGGCCCACCCGCAAGCATTACCAGCCCTATGCCCCACCACGC

GACTTCGCAGCCTATCGCTCC
```

In certain embodiments, the transmembrane domain of a presently disclosed CAR comprises a CD8 polypeptide. The CD8 polypeptide can have an amino acid sequence that is at least about 85%, about 90%, about 95%, about 96%, about 97%, about 98%, about 99% or 100% homologous to the sequence having a NCBI Reference No: AAH25715 (SEQ ID No: 404), or fragments thereof, and/or may optionally comprise up to one or up to two or up to three conservative amino acid substitutions. In non-limiting embodiments, the CD8 polypeptide can have an amino acid sequence that is a consecutive portion of SEQ ID NO: 404 which is at least 20, or at least 30, or at least 40, or at least 50, or at least 70, or at least 100, or at least 150, or at least 200 and up to 235 amino acids in length. Alternatively or additionally, in non-limiting various embodiments, the CD28 polypeptide has an amino acid sequence of amino acids 1 to 235, 1 to 50, 50 to 100, 100 to 150, 150 to 200, 130 to 210, or 200 to 235 of SEQ ID NO: 404. In certain embodiments, the CD8 polypeptide comprised in the transmembrane domain has an amino acid sequence of amino acids 137 to 207 of SEQ ID NO: 404.

SEQ ID NO: 226 is provided below:

```
                                                    [SEQ ID NO: 404]
  1MALPVTALLL PLALLLHAAR PSQFRVSPLD RTWNLGETVE LKCQVLLSNP TSGCSWLFQP

 61RGAAASPTFL LYLSQNKPKA AEGLDTQRFS GKRLGDTFVL TLSDFRRENE GCYFCSALSN

121SIMYFSHFVP VFLPAKPTTT PAPRPPTPAP TIASQPLSLR PEACRPAAGG AVHTRGLDFA

181CDIYIWAPLA GTCGVLLLSL VITLYCNHRN RRRVCKCPRP VVKSGDKPSL SARYV.
```

In accordance with the presently disclosed subject matter, a "CD8 nucleic acid molecule" refers to a polynucleotide encoding a CD8 polypeptide. In certain embodiments, the CD8 nucleic acid molecule encoding the CD8 polypeptide comprised in the transmembrane domain of the presently disclosed CAR (amino acids 137 to 207 of SEQ ID NO: 404) comprises nucleic acids having the sequence set forth in SEQ ID NO: 405 as provided below.

```
                                         [SEQ ID NO: 227]
CCCACCACGACGCCAGCGCCGCGACCACCAACCCCGGCGCCCACGATCGC

GTCGCAGCCCCTGTCCCTGCGCCCAGAGGCGTGCCGGCCAGCGGCGGGGG

GCGCAGTGCACACGAGGGGGCTGGACTTCGCCTGTGATATCTACATCTGG

GCGCCCCTGGCCGGGACTTGTGGGGTCCTTCTCCTGTCACTGGTTATCAC

CCTTTACTGCAAC
```

In certain non-limiting embodiments, a CAR can also comprise a spacer region that links the extracellular antigen-binding domain to the transmembrane domain. The spacer region can be flexible enough to allow the antigen binding domain to orient in different directions to facilitate antigen recognition. The spacer region can be the hinge region from IgG1, or the $CH_2CH_3$ region of immunoglobulin and portions of CD3.

Intracellular Domain of a CAR

In certain non-limiting embodiments, an intracellular domain of the CAR can comprise a CD3ζ polypeptide, which can activate or stimulate a cell (e.g., a cell of the lymphoid lineage, e.g., a T cell). CD3ζ comprises three ITAMs, and transmits an activation signal to the cell (e.g., a cell of the lymphoid lineage, e.g., a T cell) after antigen is bound. The CD3ζ polypeptide can have an amino acid sequence that is at least about 85%, about 90%, about 95%, about 96%, about 97%, about 98%, about 99% or about 100% homologous to the sequence set forth in SEQ ID NO:272, or fragments thereof, and/or may optionally comprise up to one or up to two or up to three conservative amino acid substitutions. In non-limiting embodiments, the CD3ζ polypeptide can have an amino acid sequence that is a consecutive portion of SEQ ID NO:272 which is at least 20, or at least 30, or at least 40, or at least 50, and up to 163 amino acids in length. Alternatively or additionally, in non-limiting various embodiments, the CD3ζ polypeptide has an amino acid sequence of amino acids 1 to 163, 1 to 50, 50 to 100, 100 to 150, or 150 to 163 of SEQ ID NO: 272. In certain embodiments, the CD3ζ polypeptide comprised in the intracellular domain of a presently disclosed CAR has an amino acid sequence of amino acids 52 to 163 of SEQ ID NO: 272.

SEQ ID NO: 272 is provided below:

```
                                                    [SEQ ID NO: 272]
  1MKWKALFTAA ILQAQLPITE AQSFGLLDPK LCYLLDGILF IYGVILTALF LRVKFSRSAD

 61APAYQQGQNQ LYNELNLGRR EEYDVLDKRR GRDPEMGGKP RRKNPQEGLY NELQKDKMAE

121AYSEIGMKGE RRRGKGHDGL YQGLSTATKD TYDALHMQAL PPR
```

In accordance with the presently disclosed subject matter, a "CD3ζ nucleic acid molecule" refers to a polynucleotide encoding a CD3ζ polypeptide. In certain embodiments, the CD3ζ nucleic acid molecule encoding the CD3ζ polypeptide comprised in the intracellular domain of a presently disclosed CARs (amino acids 52 to 163 of SEQ ID NO: 272) comprises nucleic acids having the sequence set forth in SEQ ID NO: 273 as provided below.

```
                                         [SEQ ID NO: 273]
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAA
```

In certain non-limiting embodiments, an intracellular domain of the CAR further comprises at least one signaling region. The at least one signaling region can include a CD28 polypeptide, a 4-1BB polypeptide, an OX40 polypeptide, an ICOS polypeptide, a DAP-10 polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof.

In certain embodiments, the signaling region is a co-stimulatory signaling region. In certain embodiments, the co-stimulatory region comprises at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a DAP-10 polypeptide, or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands, include, but are not limited to CD80, CD86, CD70, OX40L, 4-1BBL, CD48, TNFRSF14, and PD-L1. As one example, a 4-1BB ligand (i.e., 4-1BBL) may bind to 4-1BB (also known as "CD137") for providing an intracellular signal that in combination with a CAR signal induces an effector cell function of the $CAR^+$ T cell. CARs comprising an intracellular domain that comprises a co-stimulatory signaling region comprising 4-1BB, ICOS or DAP-10 are disclosed in U.S. Pat. No. 7,446,190 (e.g., the nucleotide sequence encoding 4-1BB is set forth in SEQ ID NO:15, the nucleotide sequence encoding ICOS is set forth in SEQ ID NO:16, and the nucleotide sequence encoding DAP-10 is set forth in SEQ ID NO:17 in U.S. Pat. No. 7,446,190), which is herein incorporated by reference in its entirety. In certain embodiments, the intracellular domain of the CAR comprises a co-stimulatory signaling region that comprises a CD28 polypeptide. In certain embodiments, the intracellular domain of the CAR comprises a co-stimulatory signaling region that comprises two co-stimulatory molecules:CD28 and 4-1BB or CD28 and OX40.

4-1BB can act as a tumor necrosis factor (TNF) ligand and have stimulatory activity. The 4-1BB polypeptide can have an amino acid sequence that is at least about 85%, about 90%, about 95%, about 96%, about 97%, about 98%, about 99% or 100% homologous to the sequence having a NCBI Reference No: P41273 or NP_001552 (SEQ ID NO: 274) or fragments thereof, and/or may optionally comprise up to one or up to two or up to three conservative amino acid substitutions. In certain embodiments, the 4-1BB polypeptide comprised in the intracellular domain of a presently disclosed CAR has an amino acid sequence of amino acids 214 to 255 of SEQ ID NO: 274. SEQ ID NO: 274 is provided below:

```
                                                  [SEQ ID NO: 274]
  1MGNSCYNIVA TLLLVLNFER TRSLQDPCSN CPAGTFCDNN RNQICSPCPP NSFSSAGGQR

 61TCDICRQCKG VFRTRKECSS TSNAECDCTP GFHCLGAGCS MCEQDCKQGQ ELTKKGCKDC

121CFGTFNDQKR GICRPWTNCS LDGKSVLVNG TKERDVVCGP SPADLSPGAS SVTPPAPARE

181PGHSPQIISF FLALTSTALL FLLFFLTLRF SVVKRGRKKL LYIFKQPFMR PVQTTQEEDG

241CSCRFPEEEE GGCEL
```

In accordance with the presently disclosed subject matter, a "4-1BB nucleic acid molecule" refers to a polynucleotide encoding a 4-1BB polypeptide. In certain embodiments, the 4-1BB nucleic acid molecule encoding the 4-1BB polypeptide comprised in the intracellular domain of a presently disclosed CARs (amino acids 214 to 255 of SEQ ID NO: 274) comprises nucleic acids having the sequence set forth in SEQ ID NO: 300 as provided below.

[SEQ ID NO: 300]
aaacggggcagaaagaagctcctgtatatattcaaacaaccatttatgag accagtacaaactactcaagaggaagatggctgtagctgccgatttccag aagaagaagaaggaggatgtgaactg An OX40 polypeptide can have an amino acid sequence that is at least about 85%, about 90%, about 95%, about 96%, about 97%, about 98%, about 99% or 100% homologous to the sequence having a NCBI Reference No: P43489 or NP_003318 (SEQ ID NO: 275), or fragments thereof, and/or may optionally comprise up to one or up to two or up to three conservative amino acid substitutions.

SEQ ID NO: 275 is provided below:

[SEQ ID NO: 275]
1MCVGARRLGR GPCAALLLLG LGLSTVTGLH CVGDTYPSND RCCHECRPGN GMVSRCSRSQ

61NTVCRPCGPG FYNDVVSSKP CKPCTWCNLR SGSERKQLCT ATQDTVCRCR AGTQPLDSYK

121PGVDCAPCPP GHFSPGDNQA CKPWTNCTLA GKHTLQPASN SSDAICEDRD PPATQPQETQ

181GPPARPITVQ PTEAWPRTSQ GPSTRPVEVP GGRAVAAILG LGLVLGLLGP LAILLALYLL

241RRDQRLPPDA HKPPGGGSFR TPIQEEQADA HSTLAKI

In accordance with the presently disclosed subject matter, an "OX40 nucleic acid molecule" refers to a polynucleotide encoding an OX40 polypeptide.

An ICOS polypeptide can have an amino acid sequence that is at least about 85%, about 90%, about 95%, about 96%, about 97%, about 98%, about 99% or 100% homologous to the sequence having a NCBI Reference No: NP_036224 (SEQ ID NO: 276) or fragments thereof, and/or may optionally comprise up to one or up to two or up to three conservative amino acid substitutions.

SEQ ID NO: 276 is provided below:

[SEQ ID NO: 276]
1MKSGLWYFFL FCLRIKVLTG EINGSANYEM FIFHNGGVQI LCKYPDIVQQ FKMQLLKGGQ

61ILCDLTKTKG SGNTVSIKSL KFCHSQLSNN SVSFFLYNLD HSHANYYFCN LSIFDPPPFK

121VTLTGGYLHI YESQLCCQLK FWLPIGCAAF VVVCILGCIL ICWLTKKKYS SSVHDPNGEY

181MFMRAVNTAK KSRLTDVTL

In accordance with the presently disclosed subject matter, an "ICOS nucleic acid molecule" refers to a polynucleotide encoding an ICOS polypeptide.

CTLA-4 is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion, enhanced the endogenous anti-tumor response albeit, in the clinical setting, with significant unforeseen toxicities.

CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif able to bind PI3K, PP2A and SHP-2 and one proline-rich motif able to bind SH3 containing proteins. One role of CTLA-4 in inhibiting T cell responses seem to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

In accordance with the presently disclosed subject matter, a CTLA-4 polypeptide can have an amino acid sequence that is at least about 85%, about 90%, about 95%, about 96%, about 97%, about 98%, about 99% or about 100% homologous to UniProtKB/Swiss-Prot Ref. No.: P16410.3 (SEQ ID NO: 277) (homology herein may be determined using standard software such as BLAST or FASTA) or fragments thereof, and/or may optionally comprise up to one or up to two or up to three conservative amino acid substitutions.

SEQ ID NO: 277 is provided below:

```
                                                [SEQ ID NO: 277 ]
  1MACLGFQRHK AQLNLATRTW PCTLLFFLLF IPVFCKAMHV AQPAVVLASS RGIASFVCEY

 61ASPGKATEVR VTVLRQADSQ VTEVCAATYM MGNELTFLDD SICTGTSSGN QVNLTIQGLR

121AMDTGLYICK VELMYPPPYY LGIGNGTQIY VIDPEPCPDS DFLLWILAAV SSGLFFYSFL

181LTAVSLSKML KKRSPLTTGV YVKMPPTEPE CEKQFQPYFI PIN
```

In accordance with the presently disclosed subject matter, a "CTLA-4 nucleic acid molecule" refers to a polynucleotide encoding a CTLA-4 polypeptide.

PD-1 is a negative immune regulator of activated T cells upon engagement with its corresponding ligands PD-L1 and PD-L2 expressed on endogenous macrophages and dendritic cells. PD-1 is a type I membrane protein of 268 amino acids. PD-1 has two ligands, PD-L1 and PD-L2, which are members of the B7 family. The protein's structure comprises an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, that PD-1 negatively regulates TCR signals. SHP-I and SHP-2 phosphatases bind to the cytoplasmic tail of PD-1 upon ligand binding. Upregulation of PD-L1 is one mechanism tumor cells may evade the host immune system. In pre-clinical and clinical trials, PD-1 blockade by antagonistic antibodies induced anti-tumor responses mediated through the host endogenous immune system.

In accordance with the presently disclosed subject matter, a PD-1 polypeptide can have an amino acid sequence that is at least about 85%, about 90%, about 95%, about 96%, about 97%, about 98%, about 99% or about 100% homologous to NCBI Reference No: NP_005009.2 (SEQ ID NO: 278) or fragments thereof, and/or may optionally comprise up to one or up to two or up to three conservative amino acid substitutions.

SEQ ID NO: 278 is provided below:

```
                                                     [SEQ ID NO: 278 ]
  1MQIPQAPWPV VWAVLQLGWR PGWFLDSPDR PWNPPTFSPA LLVVTEGDNA TFTCSFSNTS

 61ESFVLNWYRM SPSNQTDKLA AFPEDRSQPG QDCRFRVTQL PNGRDFHMSV VRARRNDSGT

121YLCGAISLAP KAQIKESLRA ELRVTERRAE VPTAHPSPSP RPAGQFQTLV VGVVGGLLGS

181LVLLVWVLAV ICSRAARGTI GARRTGQPLK EDPSAVPVFS VDYGELDFQW REKTPEPPVP

241CVPEQTEYAT IVFPSGMGTS SPARRGSADG PRSAQPLRPE DGHCSWPL
```

In accordance with the presently disclosed subject matter, a "PD-1 nucleic acid molecule" refers to a polynucleotide encoding a PD-1 polypeptide.

Lymphocyte-activation protein 3 (LAG-3) is a negative immune regulator of immune cells. LAG-3 belongs to the immunoglobulin (lg) superfamily and contains 4 extracellular Ig-like domains. The LAG3 gene contains 8 exons. The sequence data, exon/intron organization, and chromosomal localization all indicate a close relationship of LAG3 to CD4. LAG3 has also been designated CD223 (cluster of differentiation 223).

In accordance with the the presently disclosed subject matter, a LAG-3 polypeptide can have an amino acid sequence that is at least about 85%, about 90%, about 95%, about 96%, about 97%, about 98%, about 99% or about 100% homologous to UniProtKB/Swiss-Prot Ref. No.: P18627.5 (SEQ ID NO: 279) or fragments thereof, and/or may optionally comprise up to one or up to two or up to three conservative amino acid substitutions.

SEQ ID NO: 279 is provided below:

```
                                                     [SEQ ID NO: 279 ]
  1MWEAQFLGLL FLQPLWVAPV KPLQPGAEVP VVWAQEGAPA QLPCSPTIPL QDLSLLRRAG

 61VTWQHQPDSG PPAAAPGHPL APGPHPAAPS SWGPRPRRYT VLSVGPGGLR SGRLPLQPRV

121QLDERGRQRG DFSLWLRPAR RADAGEYRAA VHLRDRALSC RLRLRLGQAS MTASPPGSLR

181ASDWVILNCS FSRPDRPASV HWFRNRGQGR VPVRESPHHH LAESFLFLPQ VSPMDSGPWG

241CILTYRDGFN VSIMYNLTVL GLEPPTPLTV YAGAGSRVGL PCRLPAGVGT RSFLTAKWTP

301PGGGPDLLVT GDNGDFTLRL EDVSQAQAGT YTCHIHLQEQ QLNATVTLAI ITVTPKSFGS

361PGSLGKLLCE VTPVSGQERF VWSSLDTPSQ RSFSGPWLEA QEAQLLSQPW QCQLYQGERL

421LGAAVYFTEL SSPGAQRSGR APGALPAGHL LLFLILGVLS LLLLVTGAFG FHLWRRQWRP

481RRFSALEQGI HPPQAQSKIE ELEQEPEPEP EPEPEPEPEP EPEQL
```

In accordance with the presently disclosed subject matter, a "LAG-3 nucleic acid molecule" refers to a polynucleotide encoding a LAG-3 polypeptide.

Natural Killer Cell Receptor 2B4 (2B4) mediates non-MHC restricted cell killing on NK cells and subsets of T cells. To date, the function of 2B4 is still under investigation, with the 2B4-S isoform believed to be an activating receptor, and the 2B4-L isoform believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

In accordance with the presently disclosed subject matter, a 2B4 polypeptide can have an amino acid sequence that is at least about 85%, about 90%, about 95%, about 96%, about 97%, about 98%, about 99% or about 100% homologous to UniProtKB/Swiss-Prot Ref. No.: Q9BZW8.2 (SEQ ID NO: 280) or fragments thereof, and/or may optionally comprise up to one or up to two or up to three conservative amino acid substitutions.

SEQ ID NO: 280 is provided below:

```
                                                     [SEQ ID NO: 280 ]
  1MLGQVVTLIL LLLLKVYQGK GCQGSADHVV SISGVPLQLQ PNSIQTKVDS IAWKKLLPSQ

 61NGFHHILKWE NGSLPSNTSN DRFSFIVKNL SLLIKAAQQQ DSGLYCLEVT SISGKVQTAT

121FQVFVFESLL PDKVEKPRLQ GQGKILDRGR CQVALSCLVS RDGNVSYAWY RGSKLIQTAG

181NLTYLDEEVD INGTHTYTCN VSNPVSWESH TLNLTQDCQN AHQEFRFWPF LVIIVILSAL

241FLGTLACFCV WRRKRKEKQS ETSPKEFLTI YEDVKDLKTR RNHEQEQTFP GGGSTIYSMI
```

-continued

301 QSQSSAPTSQ EPAYTLYSLI QPSRKSGSRK RNHSPSFNST IYEVIGKSQP KAQNPARLSR

361 KELENFDVYS

In accordance with the presently disclosed subject matter, a "2B4 nucleic acid molecule" refers to a polynucleotide encoding a 2B4 polypeptide.

B- and T-lymphocyte attenuator (BTLA) expression is induced during activation of T cells, and BTLA remains expressed on Th1 cells but not Th2 cells. Like PD1 and CTLA4, BTLA interacts with a B7 homolog, B7H4. However, unlike PD-1 and CTLA-4, BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human $CD8^+$ cancer-specific T cells. BTLA has also been designated as CD272 (cluster of differentiation 272).

In accordance with the presently disclosed subject matter, a BTLA polypeptide can have an amino acid sequence that is at least about 85%, about 90%, about 95%, about 96%, about 97%, about 98%, about 99% or about 100% homologous to UniProtKB/Swiss-Prot Ref. No.: Q7Z6A9.3 (SEQ ID NO: 281) or fragments thereof, and/or may optionally comprise up to one or up to two or up to three conservative amino acid substitutions.

SEQ ID NO: 281 is provided below:

[SEQ ID NO: 281 ]

1 MKTLPAMLGT GKLFWVFFLI PYLDIWNIHG KESCDVQLYI KRQSEHSILA GDPFELECPV

61 KYCANRPHVT WCKLNGTTCV KLEDRQTSWK EEKNISFFIL HFEPVLPNDN GSYRCSANFQ

121 SNLIESHSTT LYVTDVKSAS ERPSKDEMAS RPWLLYRLLP LGGLPLLITT CFCLFCCLRR

181 HQGKQNELSD TAGREINLVD AHLKSEQTEA STRQNSQVLL SETGIYDNDP DLCFRMQEGS

241 EVYSNPCLEE NKPGIVYASL NHSVIGPNSR LARNVKEAPT EYASICVRS

In accordance with the presently disclosed subject matter, a "BTLA nucleic acid molecule" refers to a polynucleotide encoding a BTLA polypeptide.

Figure 1:
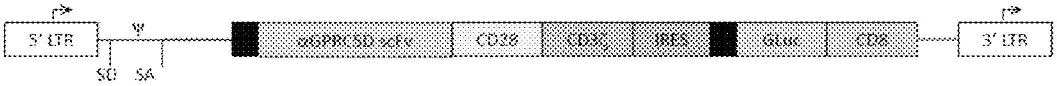
FIG. 1 shows a chimeric antigen receptor targeting a G-protein coupled receptor in accordance with one non-limiting embodiment of the presently disclosed subject matter.

In certain embodiments, the CAR comprises an extracellular antigen-binding region that specifically binds to a G-protein coupled receptor (e.g., GPRC5D), a transmembrane domain comprising a CD28 polypeptide, and an intracellular domain comprising a CD3ζ polypeptide and a co-stimulatory signaling region that comprises a CD28 polypeptide, as shown in FIG. 1. As shown in FIG. 1, the CAR also comprises a signal peptide or a leader covalently joined to the 5' terminus of the extracellular antigen-binding domain. In certain embodiments, the signal peptide comprises amino acids having the sequence set forth in SEQ ID NO:282.

Figure 6:
FIG. 6 shows a chimeric antigen receptor targeting GPRC5D in accordance with one non-limiting embodiment of the presently disclosed subject matter.
Figure 7:
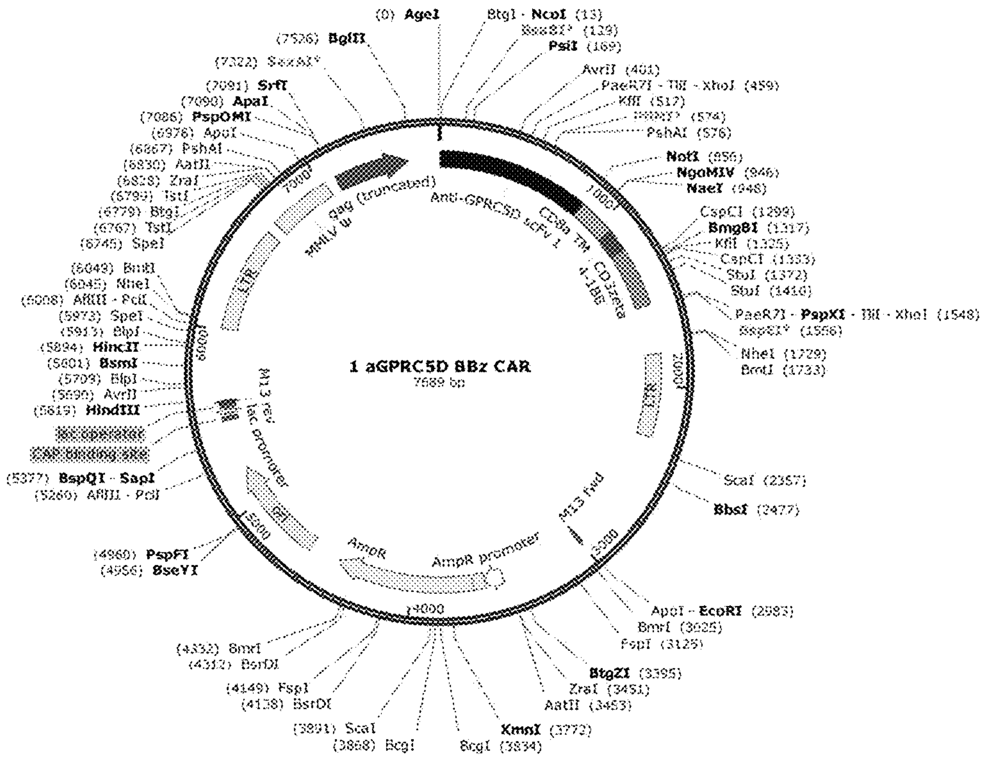
FIG. 7 depicts a nucleic acid molecule that encodes a GPRC5D-targeted CAR in accordance with one non-limiting embodiment of the presently disclosed subject matter.
Figure 8:
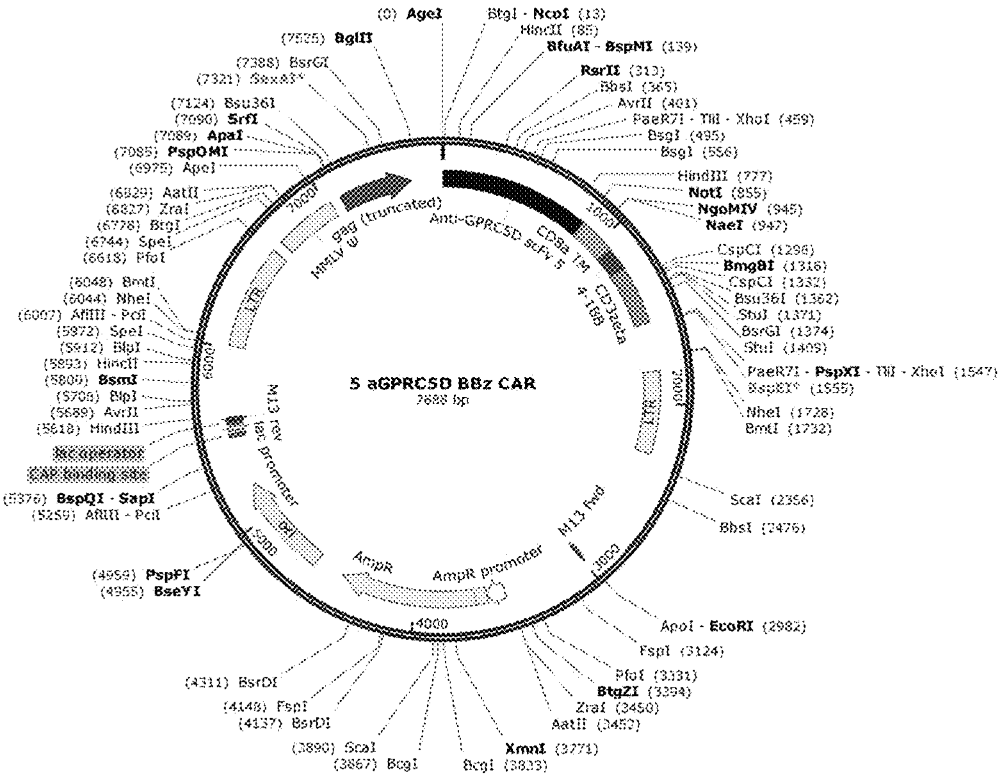
FIG. 8 depicts a nucleic acid molecule that encodes a GPRC5D-targeted CAR in accordance with one non-limiting embodiment of the presently disclosed subject matter.
Figure 9:
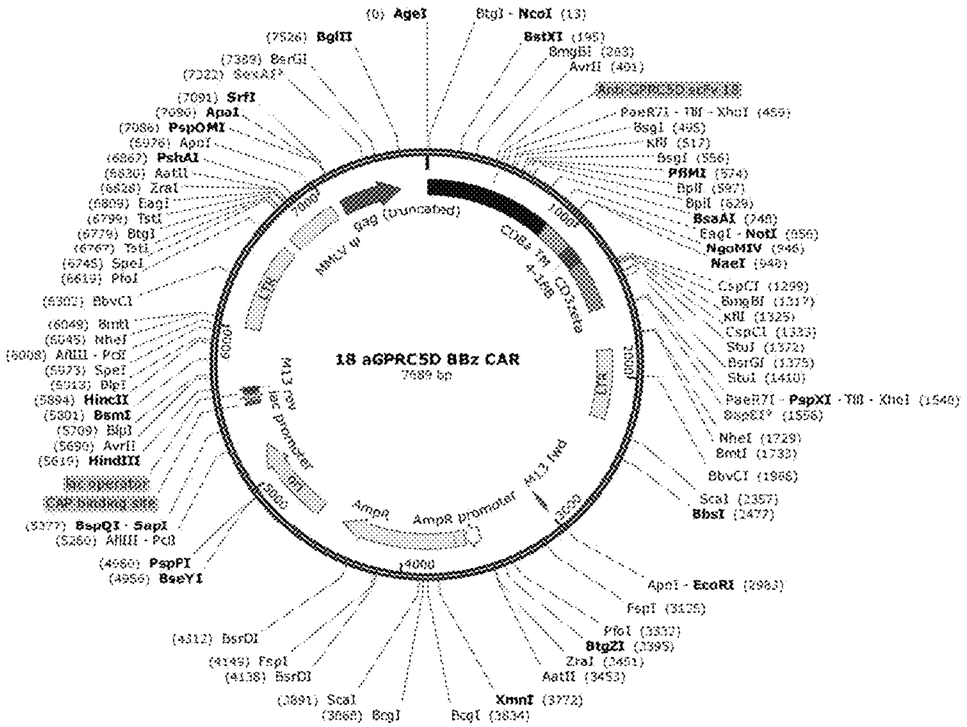
FIG. 9 depicts a nucleic acid molecule that encodes a GPRC5D-targeted CAR in accordance with one non-limiting embodiment of the presently disclosed subject matter.

In certain embodiments, the CAR comprises an extracellular antigen-binding region that specifically binds to a G-protein coupled receptor (e.g., GPRC5D), a transmembrane domain comprising a CD8 polypeptide, and an intracellular domain comprising a CD3ζ polypeptide and a co-stimulatory signaling region that comprises a 4-1BB polypeptide, as shown in FIG. 6. As shown in FIG. 6, the CAR also comprises a signal peptide or a leader covalently joined to the 5' terminus of the extracellular antigen-binding domain. In certain embodiments, the signal peptide comprises amino acids having the sequence set forth in SEQ ID NO:282.

In some embodiments, the CAR of the presently disclosed subject matter can further comprise an inducible promoter, for expressing nucleic acid sequences in human cells. Promoters for use in expressing CAR genes can be a constitutive promoter, such as ubiquitin C (UbiC) promoter.

The presently disclosed subject matter also provides isolated nucleic acid molecule encoding the CAR targeting a G-protein coupled receptor (e.g., GPRC5D) described herein or a functional portion thereof. In certain embodiments, the isolated nucleic acid molecule encodes a presently disclosed CAR targeting a G-protein coupled receptor (e.g., GPRC5D) comprising an scFv that specifically binds to human GPRC5D, a transmembrane domain comprising a CD28 polypeptide, and an intracellular domain comprising a CD3ζ polypeptide and a co-stimulatory signaling region comprising a CD28 polypeptide. In certain embodiments, the scFv is a human scFv. In certain embodiments, the scFv is a murine scFv. In one specific non-limiting example, the isolated nucleic acid molecule comprises nucleic acids having the sequence set forth in SEQ ID NO:397 provided below:

[SEQ ID NO: 397 ]

cagtctgtgttgacgcagcctgcctccgtgtctgggtctcctggacagtc gctcaccatctcctgcactggaaccagcaatgacgttggtgcttataagt atgtctcctggtatcaacagtacccaggcaaagcccccaaactcatactt tatgatgtctttaagcggccctcaggggtctctaatcgcttctctggctc caagtctgacaacacggcctccctgaccatctctgggctccaggctgagg acgaggctgattattactgcttctcacttacaagcagtaacacttatgtc ttcggaactgggaccaaggtcaccgtcctaggttctagaggtggtggtgg tagcggcggcggcggctctggtggtggtggatccctcgagatggcccaga tgcagctggtgcagtctggagctgaggtgaagaagcctggggcctcagtg aaggtctcctgcaaggcttctggttacacctttaacagatatgctatcac ctgggtgcgacaggcccctggacaaggccttgagtggatgggatggatca gcgcttacaatggtaattcacactatgcacagaagctccagggcagagtc accatgaccacagacacatccacgggcacagcctatatggagctgaggag gctgagatctgacgacacggccgtgtattactgtgcgcgcatggcttacg -continued attcttggggtcaaggtactctggtgaccgtctcctcagcggccgcaatt gaagttatgtatcctcctccttacctagacaatgagaagagcaatggaac cattatccatgtgaaagggaaacacctttgtccaagtcccctatttcccg gaccttctaagcccttttgggtgctggtggtggttggtggagtcctggct tgctatagcttgctagtaacagtggcctttattattttctgggtgaggag taagaggagcaggctcctgcacagtgactacatgaacatgactccccgcc gccccgggcccacccgcaagcattaccagccctatgccccaccacgcgac ttcgcagcctatcgctccagagtgaagttcagcaggagcgcagacgcccc cgcgtaccagcagggccagaaccagctctataacgagctcaatctaggac gaagagaggagtacgatgttttggacaagagacgtggccgggaccctgag atgggggggaaagccgagaaggaagaaccctcaggaaggcctgtacaatga actgcagaaagataagatggcggaggcctacagtgagattgggatgaaag gcgagcgccggaggggcaaggggcacgatggcctttaccagggtctcagt acagccaccaaggacacctacgacgcccttcacatgcaggccctgccccc tcgc In one specific non-limiting example, the isolated nucleic acid molecule comprises nucleic acids having the sequence set forth in SEQ ID NO:398 provided below:

[SEQ ID NO: 398 ]

cagtctgtgttgactcagccaccctcagcgtctgggacccccggacagag ggtcaccatctcttgttctggaagcaggtccaacgtaggaggtaattatg tattttggtaccagcaagtccccggagcgacccccaaactcctcatctat aggagtaatcagcggccctcggggggtccctgaccgattcgctggctccaa gtctggctcctcagcctccctggccatcagtggactccggtccgaggatg aggctgattattactgtgcaacatgggatgacagcctgagtggttttgtc ttcggaactgggaccaaggtcaccgtcctaggttctagaggtggtggtgg tagcggcggcggcggctctggtggtggtggatccctcgagatggccgagg tgcagctggtggagtctgggggaggcttggtcaagcctggagggtccctg agactctcctgtgcagcctctggattcaccttcagtgactactacatgag ctggatccgccaggctccagggaaggggctggagtgggtttcatacatta gtagtagtggtagtaccatatactacgcagactctgtgaagggccgattc accatctccagggacaacgccaagaactcactgtatctgcaaatgaacag cctgagagccgaggacacggccgtatattactgtgcgcgcggttacggta aagcttacgatcagtggggtcaaggtactctggtgaccgtctcctcagcg gccgcaattgaagttatgtatcctcctccttacctagacaatgagaagag caatggaaccattatccatgtgaaagggaaacacctttgtccaagtcccc tatttcccggaccttctaagcccttttgggtgctggtggtggttggtgga gtcctggcttgctatagcttgctagtaacagtggcctttattattttctg ggtgaggagtaagaggagcaggctcctgcacagtgactacatgaacatga ctccccgccgccccgggcccacccgcaagcattaccagccctatgcccca ccacgcgacttcgcagcctatcgctccagagtgaagttcagcaggagcgc -continued agacgcccccgcgtaccagcagggccagaaccagctctataacgagctca atctaggacgaagagaggagtacgatgttttggacaagagacgtggccgg gaccctgagatgggggggaaagccgagaaggaagaaccctcaggaaggcct gtacaatgaactgcagaaagataagatggcggaggcctacagtgagattg ggatgaaaggcgagcgccggaggggcaaggggcacgatggcctttaccag ggtctcagtacagccaccaaggacacctacgacgcccttcacatgcaggc cctgccccctcgc In one specific non-limiting example, the isolated nucleic acid molecule comprises nucleic acids having the sequence set forth in SEQ ID NO:399 provided below:

[SEQ ID NO: 399]

Tcttctgagctgactcaggaccctgctgtgtctgtggccttgggacagac agtcaggatcacatgccaaggagacagcctcagaagctattatgcaagct ggtaccagcagaagccaggacaggcccctgtacttgtcatctatggtaaa aacaaccggccctcagggatcccagaccgattctctggctccagctcagg aaacacagcttccttgaccatcactggggctcaggcggaagatgaggctg actattactgtaactcccgggacagcagtggtaacccccctgtggtattc ggcggagggaccaagctgaccgtcctaggttctagaggtggtggtggtag cggcggcggcggctctggtggtggtggatccctcgagatggccCaggtgc agctggtggagtctgggggaggcctggtccaccctggggggtccctgaga ctctcctgtgcagcctctggattcaccttcagaagccatagcatgaactg ggtccgccaggctccagggaaggggctggagtgggtctcatccattagta gtgatagtacttacacatactacgcagactcagtgaagggccgattcacc atctccagagacaacgccaagaactcactgtatctgcaaatgaacagcct gagagccgaggacacggccgtatattactgtgcgcgctctggtggtcagt ggaaatactacgattactggggtcaaggtactctggtgaccgtctcctca gcggccgcaattgaagttatgtatcctcctccttacctagacaatgagaa gagcaatggaaccattatccatgtgaaagggaaacacctttgtccaagtc ccctatttcccggaccttctaagcccttttgggtgctggtggtggttggt ggagtcctggcttgctatagcttgctagtaacagtggcctttattatttt ctgggtgaggagtaagaggagcaggctcctgcacagtgactacatgaaca tgactccccgccgccccgggcccacccgcaagcattaccagccctatgcc ccaccacgcgacttcgcagcctatcgctccagagtgaagttcagcaggag cgcagacgcccccgcgtaccagcagggccagaaccagctctataacgagc tcaatctaggacgaagagaggagtacgatgttttggacaagagacgtggc cgggaccctgagatgggggggaaagccgagaaggaagaaccctcaggaagg cctgtacaatgaactgcagaaagataagatggcggaggcctacagtgaga ttgggatgaaaggcgagcgccggaggggcaaggggcacgatggcctttac cagggtctcagtacagccaccaaggacacctacgacgcccttcacatgca ggccctgccccctcgc In one specific non-limiting example, the isolated nucleic acid molecule comprises nucleic acids having the sequence set forth in SEQ ID NO:400 provided below:

[SEQ ID NO: 400]
cagtctgtcgtgacgcagccgccctcaatgtctgcggccccaggacagca agtcaccatctcctgctctggaggcaactccaacattgagagaaattatg tatcctggtacctccagctccctggaacagcccccaaactcgtcattttt gacaatgataggcgaccctcagggattcctgaccgattctctggctccaa gtctggcacgtcagccaccctgggcatcaccggactccagactggggacg aggccgattattactgcggaacatgggatagcagcctgagaggttgggtg ttcggcggagggaccaagctgaccgtcctaggttctagaggtggtggtgg tagcggcggcggcggctctggtggtggtggatccctcgagatggccgagg tgcagctggtggagtccgggggaggcttgatacagcctggggggtccctg agactctcctgtgcagcctctggattcacctttagcaactatgccatgaa ctgggtccgccaggctccagggaaggggctggagtgggtctcaactatta atggtcgtggtagtagtacaatctacgcagactccgtgaagggccggttc accatctccagagacaattccaagaacacgctgtatctgcaaatgaacag cctgagagccgaggacacagccacgtattactgtgcgcgctacatctctc gtggtctgggtgattcttggggtcaaggtactctggtgaccgtctcctca gcggccgcaattgaagttatgtatcctcctccttacctagacaatgagaa gagcaatggaaccattatccatgtgaaagggaaacacctttgtccaagtc ccctatttcccggaccttctaagcccttttgggtgctggtggtggttggt ggagtcctggcttgctatagcttgctagtaacagtggcctttattatttt ctgggtgaggagtaagaggagcaggctcctgcacagtgactacatgaaca tgactccccgccgccccgggcccacccgcaagcattaccagccctatgcc ccaccacgcgacttcgcagcctatcgctccagagtgaagttcagcaggag cgcagacgcccccgcgtaccagcagggccagaaccagctctataacgagc tcaatctaggacgaagagaggagtacgatgttttggacaagagacgtggc cgggaccctgagatgggggaaagccgagaaggaagaaccctcaggaagg cctgtacaatgaactgcagaaagataagatggcggaggcctacagtgaga ttgggatgaaaggcgagcgccggaggggcaaggggcacgatggcctttac cagggtctcagtacagccaccaaggacacctacgacgcccttcacatgca ggccctgccccctcgc In one specific non-limiting example, the isolated nucleic acid molecule comprises nucleic acids having the sequence set forth in SEQ ID NO:401 provided below:

[SEQ ID NO: 401]
CCGGTGCCGCCACCATGGAAACCGACACCCTGCTGCTGTGGGTGCTGCTG

CTGTGGGTGCCAGGATCCACAGGACAGTCTGTCGTGACGCAGCCTGCCTC

CGTGTCTGGGTCTCCTGGACAGTCGATCACCATCTCCTGCACTGGAACCA

GCAGTGACGTTGGTGGTTATAACTATGTCTCCTGGTACCAACAGCACCCA

GGCAAAGCCCCCAAACTCATGATTTATGATGTCAGTAAGCGGCCCTCAGG

-continued

GGTTTCTAATCGCTTCTCTGGCTCCAAGTCTGGCAACACGGCCTCCCTGA

CCATCTCTGGGCTCCAGGCTGAGGACGAGGCTGATTATTACTGCAGCTCA

TATACAAGCAGCAGCACTTTGGTATTCGGCGGAGGGACCAAGCTGACCGT

CCTAGGTTCTAGAGGTGGTGGTGGTAGCGGCGGCGGCGGCTCTGGTGGTG

GTGGATCCCTCGAGATGGCCGAGGTGCAGCTGGTGGAGTCTGGGGGAGCC

TTTGTACAGCCTGGGGGGTCCCTGAGACTCTCCTGTGCAGCCTCTGGATT

CACCTTTAGCAGCTATGCCATGACCTGGGTCCGCCAGGCTCCAGGGAAGG

GCCTGGAATGGGTCTCGACTATTAGTGGTCGTGGTCGTAGCACATTCTAC

GCAGACTCCGTGAAGGGCCGGTTTACCATCTCCAGAGACAATTCCAAGAA

CACGCTATATCTGCAAATGAACAGTCTGAGAGCCGAGGACACGGCCGTAT

ATTACTGTGCGCGCTACTACCATGCTGGTGCTTTCGATCTGTGGGGTCAA

GGTACTCTGGTGACCGTCTCCTCAGAACAAAAACTCATCTCAGAAGAGGA

TCTGGCggccgcacccaccacgacgccagcgccgcgaccaccaacccccgg cgcccacgatcgcgtcgcagcccctgtccctgcgcccagaggcgtgccgg ccagcggcgggggggcgcagtgcacacgagggggctggacttcgcctgtga tatctacatctgggcgcccctggccgggacttgtggggtccttctcctgt cactggttatcaccctttactgcaacaaacggggcagaaagaagctcctg tatatattcaaacaaccatttatgagaccagtacaaactactcaagagga agatggctgtagctgccgatttccagaagaagaagaaggaggatgtgaac tgagagtgaagttcagcaggagcgcagagcccccgcgtaccagcagggc cagaaccagctctataacgagctcaatctaggacgaagagaggagtacga tgttttggacaagagacgtggccgggaccctgagatgggggaaagccga gaaggaagaaccctcaggaaggcctgtacaatgaactgcagaaagataag atggcggaggcctacagtgagattgggatgaaaggcgagcgccggagggg caaggggcacgatggcctttaccagggtctcagtacagccaccaaggaca cctacgacgcccttcacatgcaggccctgccccctcgctaacagccactc gaggatccggattagtccaatttgttaaagacaggatatcagtggtccag gctctagttttgactcaacaatatcaccagctgaagcctatagagtacga gccatagataaaataaaagattttatttagtctccagaaaaaggggggaa tgaaagaccccacctgtaggtttggcaagctagcttaagtaacgccattt tgcaaggcatggaaaaatacataactgagaatagagaagttcagatcaag gtcaggaacagatggaacagctgaatatgggccaaacaggatatctgtgg taagcagttcctgccccggctcagggccaagaacagatggaacagctgaa tatgggccaaacaggatatctgtggtaagcagttcctgccccggctcagg gccaagaacagatggtccccagatgcggtccagccctcagcagtttctag agaaccatcagatgtttccagggtgccccaaggacctgaaatgaccctgt gccttatttgaactaaccaatcagttcgcttctcgcttctgttcgcgcgc ttctgctccccgagctcaataaaagagcccacaacccctcactcggggcg ccagtcctccgattgactgagtcgcccgggtacccgtgtatccaataaac cctcttgcagttgcatccgacttgtggtctcgctgttccttgggagggtc tcctctgagtgattgactacccgtcagcgggggtctttcacacatgcagc -continued atgtatcaaaattaatttggtttttttcttaagtatttacattaaatgg
ccatagtacttaaagttacattggcttccttgaaataaacatggagtatt
cagaatgtgtcataaatatttctaattttaagatagtatctccattggct
ttctactttttctttttattttttttgtcctctgtcttccatttgttgtt
gttgttgtttgtttgtttgtttgttggttggttggttaatttttttttaa
agatcctacactatagttcaagctagactattagctactctgtaacccag
ggtgaccttgaagtcatgggtagcctgctgttttagccttcccacatcta
agattacaggtatgagctatcatttttggtatattgattgattgattgat
tgatgtgtgtgtgtgtgattgtgtttgtgtgtgtgactgtgaaaatgtgt
gtatgggtgtgtgtgaatgtgtgtatgtatgtgtgtgtgtgagtgtgtgt
gtgtgtgtgtgcatgtgtgtgtgtgtgactgtgtctatgtgtatgactgt
gtgtgtgtgtgtgtgtgtgtgtgtgtgtgtgtgtgtgtgtgtgttgtgaa
aaaatattctatggtagtgagagccaacgctccggctcaggtgtcaggtt
ggtttttgagacagagtctttcacttagcttggAATTCACTGGCCGTCGT
TTTACAACGTCGTGACTGGGAAAACCCTGGCGTTACCCAACTTAATCGCC
TTGCAGCACATCCCCCTTTCGCCAGCTGGCGTAATAGCGAAGAGGCCCGC
ACCGATCGCCCTTCCCAACAGTTGCGCAGCCTGAATGGCGAATGGCGCCT
GATGCGGTATTTTCTCCTTACGCATCTGTGCGGTATTTCACACCGCATAT
GGTGCACTCTCAGTACAATCTGCTCTGATGCCGCATAGTTAAGCCAGCCC
CGACACCCGCCAACACCCGCTGACGCGCCCTGACGGGCTTGTCTGCTCCC
GGCATCCGCTTACAGACAAGCTGTGACCGTCTCCGGGAGCTGCATGTGTC
AGAGGTTTTCACCGTCATCACCGAAACGCGCGATGACGAAAGGGCCTCGT
GATACGCCTATTTTTATAGGTTAATGTCATGATAATAATGGTTTCTTAGA
CGTCAGGTGGCACTTTTCGGGGAAATGTGCGCGGAACCCCTATTTGTTTA
TTTTTCTAAATACATTCAAATATGTATCCGCTCATGAGACAATAACCCTG
ATAAATGCTTCAATAATATTGAAAAAGGAAGAGTATGAGTATTCAACATT
TCCGTGTCGCCCTTATTCCCTTTTTTGCGGCATTTTGCCTTCCTGTTTTT
GCTCACCCAGAAACGCTGGTGAAAGTAAAAGATGCTGAAGATCAGTTGGG
TGCACGAGTGGGTTACATCGAACTGGATCTCAACAGCGGTAAGATCCTTG
AGAGTTTTCGCCCCGAAGAACGTTTTCCAATGATGAGCACTTTTAAAGTT
CTGCTATGTGGCGCGGTATTATCCCGTATTGACGCCGGGCAAGAGCAACT
CGGTCGCCGCATACACTATTCTCAGAATGACTTGGTTGAGTACTCACCAG
TCACAGAAAAGCATCTTACGGATGGCATGACAGTAAGAGAATTATGCAGT
GCTGCCATAACCATGAGTGATAACACTGCGGCCAACTTACTTCTGACAAC
GATCGGAGGACCGAAGGAGCTAACCGCTTTTTTGCACAACATGGGGGATC
ATGTAACTCGCCTTGATCGTTGGGAACCGGAGCTGAATGAAGCCATACCA
AACGACGAGCGTGACACCACGATGCCTGTAGCAATGGCAACAACGTTGCG
CAAACTATTAACTGGCGAACTACTTACTCTAGCTTCCCGGCAACAATTAA
TAGACTGGATGGAGGCGGATAAAGTTGCAGGACCACTTCTGCGCTCGGCC
CTTCCGGCTGGCTGGTTTATTGCTGATAAATCTGGAGCCGGTGAGCGTGG -continued GTCTCGCGGTATCATTGCAGCACTGGGGCCAGATGGTAAGCCCTCCCGTA
TCGTAGTTATCTACACGACGGGGAGTCAGGCAACTATGGATGAACGAAAT
AGACAGATCGCTGAGATAGGTGCCTCACTGATTAAGCATTGGTAACTGTC
AGACCAAGTTTACTCATATATACTTTAGATTGATTTAAAACTTCATTTTT
AATTTAAAAGGATCTAGGTGAAGATCCTTTTTGATAATCTCATGACCAAA
ATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCT
TGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGAT
ACCAAATACTGTCCTTCTAGTGTAGCCGTAGTTAGGCCACCACTTCAAGA
ACTCTGTAGCACCGCCTACATACCTCGCTCTGCTAATCCTGTTACCAGTG
GCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCA
CACAGCCCAGCTTGGAGCGAACGACCTACACCGAACTGAGATACCTACAG
CGTGAGCATTGAGAAAGCGCCACGCTTCCCGAAGGGAGAAAGGCGGACAG
GTATCCGGTAAGCGGCAGGGTCGGAACAGGAGAGCGCACGAGGGAGCTTC
CAGGGGGAAACGCCTGGTATCTTTATAGTCCTGTCGGGTTTCGCCACCTC
TGACTTGAGCGTCGATTTTTGTGATGCTCGTCAGGGGGGCGGAGCCTATG
GAAAAACGCCAGCAACGCGGCCTTTTTACGGTTCCTGGCCTTTTGCTGGC
CTTTTGCTCACATGTTCTTTCCTGCGTTATCCCCTGATTCTGTGGATAAC
CGTATTACCGCCTTTGAGTGAGCTGATACCGCTCGCCGCAGCCGAACGAC
CGAGCGCAGCGAGTCAGTGAGCGAGGAAGCGGAAGAGCGCCCAATACGCA
AACCGCCTCTCCCCGCGCGTTGGCCGATTCATTAATGCAGCTGGCACGAC
AGGTTTCCCGACTGGAAAGCGGGCAGTGAGCGCAACGCAATTAATGTGAG
TTAGCTCACTCATTAGGCACCCCAGGCTTTACACTTTATGCTTCCGGCTC
GTATGTTGTGTGGAATTGTGAGCGGATAACAATTTCACACAGGAAACAGC
TATGACCATGATTACGCCAAGCTTTGCTCTTAGGAGTTTCCTAATACATC
CCAAACTCAAATATATAAAGCATTTGACTTGTTCTATGCCCTAGGGGGCG
GGGGGAAGCTAAGCCAGCTTTTTTTAACATTTAAAATGTTAATTCCATTT
TAAATGCACAGATGTTTTTATTTCATAAGGGTTTCAATGTGCATGAATGC
TGCAATATTCCTGTTACCAAAGCTAGTATAAATAAAAATAGATAAACGTG
GAAATTACTTAGAGTTTCTGTCATTAACGTTTCCTTCCTCAGTTGACAAC
ATAAATGCGCTGCTGAGCAAGCCAGTTTGCATCTGTCAGGATCAATTTCC
CATTATGCCAGTCATATTAATTACTAGTCAATTAGTTGATTTTTATTTTT
GACATATACATGTGAATGAAAGACCCCACCTGTAGGTTTGGCAAGCTAGC
TTAAGTAACGCCATTTTGCAAGGCATGGAAAAATACATAACTGAGAATAG
AAAAGTTCAGATCAAGGTCAGGAACAGATGGAACAGCTGAATATGGGCCA
AACAGGATATCTGTGGTAAGCAGTTCCTGCCCCGGCTCAGGGCCAAGAAC
AGATGGAACAGCTGAATATGGGCCAAACAGGATATCTGTGGTAAGCAGTT
CCTGCCCCGGCTCAGGGCCAAGAACAGATGGTCCCCAGATGCGGTCCAGC
CCTCAGCAGTTTCTAGAGAACCATCAGATGTTTCCAGGGTGCCCCAAGGA -continued

CCTGAAATGACCCTGTGCCTTATTTGAACTAACCAATCAGTTCGCTTCTC

GCTTCTGTTCGCGCGCTTATGCTCCCCGAGCTCAATAAAAGAGCCCACAA

CCCCTCACTCGGGGCGCCAGTCCTCCGATTGACTGAGTCGCCCGGGTACC

CGTGTATCCAATAAACCCTCTTGCAGTTGCATCCGACTTGTGGTCTCGCT

GTTCCTTGGGAGGGTCTCCTCTGAGTGATTGACTACCCGTCAGCGGGGGT

CTTTCATTTGGGGGCTCGTCCGGGATCGGGAGACCCCTGCCCAGGGACCA

CCGACCCACCACCGGGAGGTAAGCTGGCCAGCAACTTATCTGTGTCTGTC

CGATTGTCTAGTGTCTATGACTGATTTTATGCGCCTGCGTCGGTACTAGT

TAGCTAACTAGCTCTGTATCTGGCGGACCCGTGGTGGAACTGACGAGTTC

GGAACACCCGGCCGCAACCCTGGGAGACGTCCCAGGGACTTCGGGGGCCG

TTTTTGTGGCCCGACCTGAGTCCTAAAATCCCGATCGTTTAGGACTCTTT

GGTGCACCCCCCTTAGAGGAGGGATATGTGGTTCTGGTAGGAGACGAGAA

CCTAAAACAGTTCCCGCCTCCGTCTGAATTTTTGCTTTCGGTTTGGGACC

GAAGCCGCGCCGCGCGTCTTGTCTGCTGCAGCATCGTTCTGTGTTGTCTC

TGTCTGACTGTGTTTCTGTATTTGTCTGAAAATATGGGCCCGGGCTAGAC

TGTTACCACTCCCTTAAGTTTGACCTTAGGTCACTGGAAAGATGTCGAGC

GGATCGCTCACAACCAGTCGGTAGATGTCAAGAAGAGACGTTGGGTTACC

TTCTGCTCTGCAGAATGGCCAACCTTTAACGTCGGATGGCCGCGAGACGG

CACCTTTAACCGAGACCTCATCACCCAGGTTAAGATCAAGGTCTTTTCAC

CTGGCCCGCATGGACACCCAGACCAGGTCCCCTACATCGTGACCTGGGAA

GCCTTGGCTTTTGACCCCCCTCCCTGGGTCAAGCCCTTTGTACACCCTAA

GCCTCCGCCTCCTCTTCCTCCATCCGCCCCGTCTCTCCCCCTTGAACCTC

CTCGTTCGACCCCGCCTCGATCCTCCCTTTATCCAGCCCTCACTCCTTCT

CTAGGCGCCCCCATATGGCCATATGAGATCTTATATGGGGCACCCCCGCC

CCTTGTAAACTTCCCTGACCCTGACATGACAAGAGTTACTAACAGCCCCT

CTCTCCAAGCTCACTTACAGGCTCTCTACTTAGTCCAGCACGAAGTCTGG

AGACCTCTGGCGGCAGCCTACCAAGAACAACTGGACCGA

In one specific non-limiting example, the isolated nucleic acid molecule comprises nucleic acids having the sequence set forth in SEQ ID NO:402 provided below:

[SEQ ID NO: 402]

CCGGTGCCGCCACCATGGAAACCGACACCCTGCTGCTGTGGGTGCTGCTG

CTGTGGGTGCCAGGATCCACAGGACAGTCTGTGTTGACTCAGCCACCCTC

AGCGTCTGGGACCCCCGGACAGAGGGTCACCATCTCTTGTTCTGGAAGCA

GGTCCAACGTAGGAGGTAATTATGTATTTTGGTACCAGCAAGTCCCCGGA

GCGACCCCCAAACTCCTCATCTATAGGAGTAATCAGCGGCCCTCGGGGGT

CCCTGACCGATTCGCTGGCTCCAAGTCTGGCTCCTCAGCCTCCCTGGCCA

TCAGTGGACTCCGGTCCGAGGATGAGGCTGATTATTACTGTGCAACATGG

GATGACAGCCTGAGTGGTTTTGTCTTCGGAACTGGGACCAAGGTCACCGT

CCTAGGTTCTAGAGGTGGTGGTGGTAGCGGCGGCGGCGGCTCTGGTGGTG

GTGGATCCCTCGAGATGGCCGAGGTGCAGCTGGTGGAGTCTGGGGGAGGC

-continued

TTGGTCAAGCCTGGAGGGTCCCTGAGACTCTCCTGTGCAGCCTCTGGATT

CACCTTCAGTGACTACTACATGAGCTGGATCCGCCAGGCTCCAGGGAAGG

GGCTGGAGTGGGTTTCATACATTAGTAGTAGTGGTAGTACCATATACTAC

GCAGACTCTGTGAAGGGCCGATTCACCATCTCCCAGGGACAACGCCAAGA

ACTCACTGTATCTGCAAATGAACAGCCTGAGAGCCGAGGACACGGCCGTA

TATTACTGTGCGCGCGGGTTACGGTAAAGCTTACGATCAGTGGGGTCAAG

GTACTCTGGTGACCGTCTCCTCAGAACAAAAACTCATCTCAGAAGAGGAT

CTGGCggccgcacccaccacgacgccagcgccgcgaccaccaaccccggc gcccacgatcgcgtcgcagcccctgtccctgcgcccagaggcgtgccggc cagcggcggggggcgcagtgcacacgagggggctggacttcgcctgtgat atctacatctgggcgcccctggccgggacttgtggggtccttctcctgtc actggttatcaccctttactgcaacaaacggggcagaaagaagctcctgt atatattcaaacaaccatttatgagaccagtacaaactactcaagaggaa gatggctgtagctgccgatttccagaagaagaagaaggaggatgtgaact gagagtgaagttcagcaggagcgcagagcccccgcgtaccagcagggcc agaaccagctctataacgagctcaatctaggacgaagagaggagtacgat gttttggacaagagacgtggccgggaccctgagatgggggaaagccgag aaggaagaaccctcaggaaggcctgtacaatgaactgcagaaagataaga tggcggaggcctacagtgagattgggatgaaaggcgagcgccggaggggc aaggggcacgatggcctttaccagggtctcagtacagccaccaaggacac ctacgacgcccttcacatgcaggccctgccccctcgctaacagccactcg aggatccggattagtccaatttgttaaagacaggatatcagtggtccagg ctctagttttgactcaacaatatcaccagctgaagcctatagagtacgag ccatagataaaataaaagattttatttagtctccagaaaaaggggggaat gaaagaccccacctgtaggtttggcaagctagcttaagtaacgccatttt gcaaggcatggaaaaatacataactgagaatagagaagttcagatcaagg tcaggaacagatggaacagctgaatatgggccaaacaggatatctgtggt aagcagttcctgccccggctcagggccaagaacagatggaacagctgaat atgggccaaacaggatatctgtggtaagcagttcctgccccggctcaggg ccaagaacagatggtccccagatgcggtccagccctcagcagtttctaga gaaccatcagatgtttccagggtgccccaaggacctgaaatgaccctgtg ccttatttgaactaaccaatcagttcgcttctcgcttctgttcgcgcgct tctgctccccgagctcaataaaagagcccacaacccctcactcggggcgc cagtcctccgattgactgagtcgcccgggtacccgtgtatccaataaacc ctcttgcagttgcatccgacttgtggtctcgctgttccttgggagggtct cctctgagtgattgactacccgtcagcgggggtctttcacacatgcagca tgtatcaaaattaatttggtttttttttcttaagtatttacattaaatggc catagtacttaaagttacattggcttccttgaaataaacatggagtattc agaatgtgtcataaatatttctaattttaagatagtatctccattggctt tctacttttttcttttattttttttttgtcctctgtcttccatttgttgttg -continued ttgttgtttgtttgtttgtttgttggttggttggttaattttttttttaaa
gatcctacactatagttcaagctagactattagctactctgtaacccagg
gtgaccttgaagtcatgggtagcctgctgttttagccttcccacatctaa
gattacaggtatgagctatcatttttggtatattgattgattgattgatt
gatgtgtgtgtgtgtgattgtgtttgtgtgtgtgactgtgaaaatgtgtg
tatgggtgtgtgtgaatgtgtgtatgtatgtgtgtgtgtgagtgtgtgtg
tgtgtgtgtgcatgtgtgtgtgtgtgactgtgtctatgtgtatgactgtg
tgtgtgtgtgtgtgtgtgtgtgtgtgtgtgtgtgtgtgtgtgtgttgtgaaa
aaatattctatggtagtgagagccaacgctccggctcaggtgtcaggttg
gtttttgagacagagtctttcacttagcttggAATTCACTGGCCGTCGTT
TTACAACGTCGTGACTGGGAAAACCCTGGCGTTACCCAACTTAATCGCCT
TGCAGCACATCCCCCTTTCGCCAGCTGGCGTAATAGCGAAGAGGCCCGCA
CCGATCGCCCTTCCCAACAGTTGCGCAGCCTGAATGGCGAATGGCGCCTG
ATGCGGTATTTTCTCCTTACGCATCTGTGCGGTATTTCACACCGCATATG
GTGCACTCTCAGTACAATCTGCTCTGATGCCGCATAGTTAAGCCAGCCCC
GACACCCGCCAACACCCGCTGACGCGCCCTGACGGGCTTGTCTGCTCCCG
GCATCCGCTTACAGACAAGCTGTGACCGTCTCCGGGAGCTGCATGTGTCA
GAGGTTTTCACCGTCATCACCGAAACGCGCGATGACGAAAGGGCCTCGTG
ATACGCCTATTTTTATAGGTTAATGTCATGATAATAATGGTTTCTTAGAC
GTCAGGTGGCACTTTTCGGGGAAATGTGCGCGGAACCCCTATTTGTTTAT
TTTTCTAAATACATTCAAATATGTATCCGCTCATGAGACAATAACCCTGA
TAAATGCTTCAATAATATTGAAAAAGGAAGAGTATGAGTATTCAACATTT
CCGTGTCGCCCTTATTCCCTTTTTTGCGGCATTTTGCCTTCCTGTTTTTG
CTCACCCAGAAACGCTGGTGAAAGTAAAAGATGCTGAAGATCAGTTGGGT
GCACGAGTGGGTTACATCGAACTGGATCTCAACAGCGGTAAGATCCTTGA
GAGTTTTCGCCCCGAAGAACGTTTTCCAATGATGAGCACTTTTAAAGTTC
TGCTATGTGGCGCGGTATTATCCCGTATTGACGCCGGGCAAGAGCAACTC
GGTCGCCGCATACACTATTCTCAGAATGACTTGGTTGAGTACTCACCAGT
CACAGAAAAGCATCTTACGGATGGCATGACAGTAAGAGAATTATGCAGTG
CTGCCATAACCATGAGTGATAACACTGCGGCCAACTTACTTCTGACAACG
ATCGGAGGACCGAAGGAGCTAACCGCTTTTTTGCACAACATGGGGGATCA
TGTAACTCGCCTTGATCGTTGGGAACCGGAGCTGAATGAAGCCATACCAA
ACGACGAGCGTGACACCACGATGCCTGTAGCAATGGCAACAACGTTGCGC
AAACTATTAACTGGCGAACTACTTACTCTAGCTTCCCGGCAACAATTAAT
AGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGG
TCTCGCGGTATCATTGCAGCACTGGGGCCAGATGGTAAGCCCTCCCGTAT
CGTAGTTATCTACACGACGGGGAGTCAGGCAACTATGGATGAACGAAATA
GACAGATCGCTGAGATAGGTGCCTCACTGATTAAGCATTGGTAACTGTCA
GACCAAGTTTACTCATATATACTTTAGATTGATTTAAAACTTCATTTTTA
ATTTAAAAGGATCTAGGTGAAGATCCTTTTTGATAATCTCATGACCAAAA -continued TCCCTTAACGTGAGTTTTCGTTCCACTGAGCGTCAGACCCCGTAGAAAAG
ATCAAAGGATCTTCTTGAGATCCTTTTTTTCTGCGCGTAATCTGCTGCTT
GCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAA
CTCTGTAGCACCGCCTACATACCTCGCTCTGCTAATCCTGTTACCAGTGG
CTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCAC
ACAGCCCAGCTTGGAGCGAACGACCTACACCGAACTGAGATACCTACAGC
GTGAGCATTGAGAAAGCGCCACGCTTCCCGAAGGGAGAAAGGCGGACAGG
TATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCT
GACTTGAGCGTCGATTTTTGTGATGCTCGTCAGGGGGGCGGAGCCTATGG
AAAAACGCCAGCAACGCGGCCTTTTTACGGTTCCTGGCCTTTTGCTGGCC
TTTTGCTCACATGTTCTTTCCTGCGTTATCCCCTGATTCTGTGGATAACC
GTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAA
ACCGCCTCTCCCCGCGCGTTGGCCGATTCATTAATGCAGCTGGCACGACA
GGTTTCCCGACTGGAAAGCGGGCAGTGAGCGCAACGCAATTAATGTGAGT
TAGCTCACTCATTAGGCACCCCAGGCTTTACACTTTATGCTTCCGGCTCG
TATGTTGTGTGGAATTGTGAGCGGATAACAATTTCACACAGGAAACAGCT
ATGACCATGATTACGCCAAGCTTTGCTCTTAGGAGTTTCCTAATACATCC
CAAACTCAAATATATAAAGCATTTGACTTGTTCTATGCCCTAGGGGGCGG
GGGGAAGCTAAGCCAGCTTTTTTTAACATTTAAAATGTTAATTCCATTTT
AAATGCACAGATGTTTTTATTTCATAAGGGTTTCAATGTGCATGAATGCT
GCAATATTCCTGTTACCAAAGCTAGTATAAATAAAAATAGATAAACGTGG
AAATTACTTAGAGTTTCTGTCATTAACGTTTCCTTCCTCAGTTGACAACA
TAAATGCGCTGCTGAGCAAGCCAGTTTGCATCTGTCAGGATCAATTTCCC
ATTATGCCAGTCATATTAATTACTAGTCAATTAGTTGATTTTTATTTTTG
ACATATACATGTGAATGAAAGACCCCACCTGTAGGTTTGGCAAGCTAGCT
TAAGTAACGCCATTTTGCAAGGCATGGAAAAATACATAACTGAGAATAGA
AAAGTTCAGATCAAGGTCAGGAACAGATGGAACAGCTGAATATGGGCCAA
ACAGGATATCTGTGGTAAGCAGTTCCTGCCCCGGCTCAGGGCCAAGAACA
GATGGAACAGCTGAATATGGGCCAAACAGGATATCTGTGGTAAGCAGTTC
CTGCCCCGGCTCAGGGCCAAGAACAGATGGTCCCCAGATGCGGTCCAGCC
CTCAGCAGTTTCTAGAGAACCATCAGATGTTTCCAGGGTGCCCCAAGGAC
CTGAAATGACCCTGTGCCTTATTTGAACTAACCAATCAGTTCGCTTCTCG
CTTCTGTTCGCGCGCTTATGCTCCCCGAGCTCAATAAAAGAGCCCACAAC
CCCTCACTCGGGGCGCCAGTCCTCCGATTGACTGAGTCGCCCGGGTACCC
GTGTATCCAATAAACCCTCTTGCAGTTGCATCCGACTTGTGGTCTCGCTG -continued TTCCTTGGGAGGGTCTCCTCTGAGTGATTGACTACCCGTCAGCGGGGGTC
TTTCATTTGGGGGCTCGTCCGGGATCGGGAGACCCCTGCCCAGGGACCAC
CGACCCACCACCGGGAGGTAAGCTGGCCAGCAACTTATCTGTGTCTGTCC
GATTGTCTAGTGTCTATGACTGATTTTATGCGCCTGCGTCGGTACTAGTT
AGCTAACTAGCTCTGTATCTGGCGGACCCGTGGTGGAACTGACGAGTTCG
GAACACCCGGCCGCAACCCTGGGAGACGTCCCAGGGACTTCGGGGGCCGT
TTTTGTGGCCCGACCTGAGTCCTAAAATCCCGATCGTTTAGGACTCTTTG
GTGCACCCCCCTTAGAGGAGGGATATGTGGTTCTGGTAGGAGACGAGAAC
CTAAAACAGTTCCCGCCTCCGTCTGAATTTTTGCTTTCGGTTTGGGACCG
AAGCCGCGCCGCGCGTCTTGTCTGCTGCAGCATCGTTCTGTGTTGTCTCT
GTCTGACTGTGTTTCTGTATTTGTCTGAAAATATGGGCCCGGGCTAGACT
GTTACCACTCCCTTAAGTTTGACCTTAGGTCACTGGAAAGATGTCGAGCG
GATCGCTCACAACCAGTCGGTAGATGTCAAGAAGAGACGTTGGGTTACCT
TCTGCTCTGCAGAATGGCCAACCTTTAACGTCGGATGGCCGCGAGACGGC
ACCTTTAACCGAGACCTCATCACCCAGGTTAAGATCAAGGTCTTTTCACC
TGGCCCGCATGGACACCCAGACCAGGTCCCCTACATCGTGACCTGGGAAG
CCTTGGCTTTTGACCCCCCTCCCTGGGTCAAGCCCTTTGTACACCCTAAG
CCTCCGCCTCCTCTTCCTCCATCCGCCCCGTCTCTCCCCCTTGAACCTCC
TCGTTCGACCCCGCCTCGATCCTCCCTTTATCCAGCCCTCACTCCTTCTC
TAGGCGCCCCCATATGGCCATATGAGATCTTATATGGGCACCCCCGCCC
CTTGTAAACTTCCCTGACCCTGACATGACAAGAGTTACTAACAGCCCCTC
TCTCCAAGCTCACTTACAGGCTCTCTACTTAGTCCAGCACGAAGTCTGGA
GACCTCTGGCGGCAGCCTACCAAGAACAACTGGACCGA In one specific non-limiting example, the isolated nucleic acid molecule comprises nucleic acids having the sequence set forth in SEQ ID NO:403 provided below:

[SEQ ID NO: 403]

CCGGTGCCGCCACCATGGAAACCGACACCCTGCTGCTGTGGGTGCTGCTG
CTGTGGGTGCCAGGATCCACAGGACAGTCTGTCGTGACGCAGCCGCCCTC
AATGTCTGCGGCCCCAGGACAGCAAGTCACCATCTCCTGCTCTGGAGGCA
ACTCCAACATTGAGAGAAATTATGTATCCTGGTACCTCCAGCTCCCTGGA
ACAGCCCCCAAACTCGTCATTTTTGACAATGATAGGCGACCCTCAGGGAT
TCCTGACCGATTCTCTGGCTCCAAGTCTGGCACGTCAGCCACCCTGGGCA
TCACCGGACTCCAGACTGGGGACGAGGCCGATTATTACTGCGGAACATGG
GATAGCAGCCTGAGAGGTTGGGTGTTCGGCGGAGGGACCAAGCTGACCGT
CCTAGGTTCTAGAGGTGGTGGTGGTAGCGGCGGCGGCGGCTCTGGTGGTG
GTGGATCCCTCGAGATGGCCGAGGTGCAGCTGGTGGAGTCCGGGGGAGGC
TTGATACAGCCTGGGGGGTCCCTGAGACTCTCCTGTGCAGCCTCTGGATT
CACCTTTAGCAACTATGCCATGAACTGGGTCCGCCAGGCTCCAGGGAAGG
GGCTGGAGTGGGTCTCAACTATTAATGGTCGTGGTAGTAGTACAATCTAC
GCAGACTCCGTGAAGGGCCGGTTCACCATCTCCAGAGACAATTCCAAGAA

-continued

CACGCTGTATCTGCAAATGAACAGCCTGAGAGCCGAGGACACAGCCACGT
ATTACTGTGCGCGCTACATCTCTCGTGGTCTGGGTGATTCTTGGGGTCAA
GGTACTCTGGTGACCGTCTCCTCAGAACAAAAACTCATCTCAGAGGAGGA
TCTGGCggccgcacccaccacgacgccagcgccgcgaccaccaaccccgg
cgcccacgatcgcgtcgcagcccctgtccctgcgcccagaggcgtgccgg
ccagcggcgggggcgcagtgcacacgagggggctggacttcgcctgtga
tatctacatctgggcgcccctggccgggacttgtggggtccttctcctgt
cactggttatcaccctttactgcaacaaacggggcagaaagaagctcctg
tatatattcaaacaaccatttatgagaccagtacaaactactcaagagga
agatggctgtagctgccgatttccagaagaagaagaaggaggatgtgaac
tgagagtgaagttcagcaggagcgcagagcccccgcgtaccagcagggc
cagaaccagctctataacgagctcaatctaggacgaagagaggagtacga
tgttttggacaagagacgtggccgggaccctgagatgggggaaagccga
gaaggaagaaccctcaggaaggcctgtacaatgaactgcagaaagataag
atggcggaggcctacagtgagattgggatgaaaggcgagcgccggagggg
caaggggcacgatggcctttaccagggtctcagtacagccaccaaggaca
cctacgacgcccttcacatgcaggccctgccccctcgctaacagccactc
gaggatccggattagtccaatttgttaaagacaggatatcagtggtccag
gctctagttttgactcaacaatatcaccagctgaagcctatagagtacga
gccatagataaaataaaagattttatttagtctccagaaaaaggggggaa
tgaaagaccccacctgtaggtttggcaagctagcttaagtaacgccattt
tgcaaggcatggaaaaatacataactgagaatagagaagttcagatcaag
gtcaggaacagatggaacagctgaatatgggccaaacaggatatctgtgg
taagcagttcctgccccggctcagggccaagaacagatggaacagctgaa
tatgggccaaacaggatatctgtggtaagcagttcctgccccggctcagg
gccaagaacagatggtccccagatgcggtccagccctcagcagtttctag
agaaccatcagatgtttccagggtgccccaaggacctgaaatgaccctgt
gccttatttgaactaaccaatcagttcgcttctcgcttctgttcgcgcgc
ttctgctccccgagctcaataaaagagcccacaacccctcactcggggcg
ccagtcctccgattgactgagtcgcccgggtacccgtgtatccaataaac
cctcttgcagttgcatccgacttgtggtctcgctgttccttgggagggtc
tcctctgagtgattgactacccgtcagcgggggtctttcacacatgcagc
atgtatcaaaattaatttggtttttttcttaagtatttacattaaatgg
ccatagtacttaaagttacattggcttccttgaaataaacatggagtatt
cagaatgtgtcataaatatttctaattttaagatagtatctccattggct
ttctactttttctttatttttttttgtcctctgtcttccatttgttgtt
gttgttgtttgtttgtttgtttgttggttggttggttaatttttttttaa
agatcctacactatagttcaagctagactattagctactctgtaacccag
ggtgaccttgaagtcatgggtagcctgctgttttagccttcccacatcta
agattacaggtatgagctatcatttttggtatattgattgattgattgat
tgatgtgtgtgtgtgtgattgtgtttgtgtgtgtgactgtgaaaatgtgt -continued gtatgggtgtgtgtgaatgtgtgtatgtatgtgtgtgtgtgagtgtgtgt
gtgtgtgtgtgcatgtgtgtgtgtgtgactgtgtctatgtgtatgactgt
gtgtgtgtgtgtgtgtgtgtgtgtgtgtgtgtgtgtgtgtgtgttgtgaa
aaaatattctatggtagtgagagccaacgctccggctcaggtgtcaggtt
ggtttttgagacagagtctttcacttagcttggAATTCACTGGCCGTCGT
TTTACAACGTCGTGACTGGGAAAACCCTGGCGTTACCCAACTTAATCGCC
TTGCAGCACATCCCCCTTTCGCCAGCTGGCGTAATAGCGAAGAGGCCCGC
ACCGATCGCCCTTCCCAACAGTTGCGCAGCCTGAATGGCGAATGGCGCCT
GATGCGGTATTTTCTCCTTACGCATCTGTGCGGTATTTCACACCGCATAT
GGTGCACTCTCAGTACAATCTGCTCTGATGCCGCATAGTTAAGCCAGCCC
CGACACCCGCCAACACCCGCTGACGCGCCCTGACGGGCTTGTCTGCTCCC
GGCATCCGCTTACAGACAAGCTGTGACCGTCTCCGGGAGCTGCATGTGTC
AGAGGTTTTCACCGTCATCACCGAAACGCGCGATGACGAAAGGGCCTCGT
GATACGCCTATTTTTATAGGTTAATGTCATGATAATAATGGTTTCTTAGA
CGTCAGGTGGCACTTTTCGGGGAAATGTGCGCGGAACCCCTATTTGTTTA
TTTTTCTAAATACATTCAAATATGTATCCGCTCATGAGACAATAACCCTG
ATAAATGCTTCAATAATATTGAAAAAGGAAGAGTATGAGTATTCAACATT
TCCGTGTCGCCCTTATTCCCTTTTTTGCGGCATTTTGCCTTCCTGTTTTT
GCTCACCCAGAAACGCTGGTGAAAGTAAAAGATGCTGAAGATCAGTTGGG
TGCACGAGTGGGTTACATCGAACTGGATCTCAACAGCGGTAAGATCCTTG
AGAGTTTTCGCCCCGAAGAACGTTTTCCAATGATGAGCACTTTTAAAGTT
CTGCTATGTGGCGCGGTATTATCCCGTATTGACGCCGGGCAAGAGCAACT
CGGTCGCCGCATACACTATTCTCAGAATGACTTGGTTGAGTACTCACCAG
TCACAGAAAAGCATCTTACGGATGGCATGACAGTAAGAGAATTATGCAGT
GCTGCCATAACCATGAGTGATAACACTGCGGCCAACTTACTTCTGACAAC
GATCGGAGGACCGAAGGAGCTAACCGCTTTTTTGCACAACATGGGGGATC
ATGTAACTCGCCTTGATCGTTGGGAACCGGAGCTGAATGAAGCCATACCA
AACGACGAGCGTGACACCACGATGCCTGTAGCAATGGCAACAACGTTGCG
CAAACTATTAACTGGCGAACTACTTACTCTAGCTTCCCGGCAACAATTAA
TAGACTGGATGGAGGCGGATAAAGTTGCAGGACCACTTCTGCGCTCGGCC
CTTCCGGCTGGCTGGTTTATTGCTGATAAATCTGGAGCCGGTGAGCGTGG
GTCTCGCGGTATCATTGCAGCACTGGGGCCAGATGGTAAGCCCTCCCGTA
TCGTAGTTATCTACACGACGGGGAGTCAGGCAACTATGGATGAACGAAAT
AGACAGATCGCTGAGATAGGTGCCTCACTGATTAAGCATTGGTAACTGTC
AGACCAAGTTTACTCATATATACTTTAGATTGATTTAAAACTTCATTTTT
AATTTAAAAGGATCTAGGTGAAGATCCTTTTTGATAATCTCATGACCAAA
ATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCT
TGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGAT -continued ACCAAATACTGTCCTTCTAGTGTAGCCGTAGTTAGGCCACCACTTCAAGA
ACTCTGTAGCACCGCCTACATACCTCGCTCTGCTAATCCTGTTACCAGTG
GCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCA
CACAGCCCAGCTTGGAGCGAACGACCTACACCGAACTGAGATACCTACAG
CGTGAGCATTGAGAAAGCGCCACGCTTCCCGAAGGGAGAAAGGCGGACAG
GTATCCGGTAAGCGGCAGGGTCGGAACAGGAGAGCGCACGAGGGAGCTTC
CAGGGGGAAACGCCTGGTATCTTTATAGTCCTGTCGGGTTTCGCCACCTC
TGACTTGAGCGTCGATTTTTGTGATGCTCGTCAGGGGGGCGGAGCCTATG
GAAAAACGCCAGCAACGCGGCCTTTTTACGGTTCCTGGCCTTTTGCTGGC
CTTTTGCTCACATGTTCTTTCCTGCGTTATCCCCTGATTCTGTGGATAAC
CGTATTACCGCCTTTGAGTGAGCTGATACCGCTCGCCGCAGCCGAACGAC
CGAGCGCAGCGAGTCAGTGAGCGAGGAAGCGGAAGAGCGCCCAATACGCA
AACCGCCTCTCCCCGCGCGTTGGCCGATTCATTAATGCAGCTGGCACGAC
AGGTTTCCCGACTGGAAAGCGGGCAGTGAGCGCAACGCAATTAATGTGAG
TTAGCTCACTCATTAGGCACCCCAGGCTTTACACTTTATGCTTCCGGCTC
GTATGTTGTGTGGAATTGTGAGCGGATAACAATTTCACACAGGAAACAGC
TATGACCATGATTACGCCAAGCTTTGCTCTTAGGAGTTTCCTAATACATC
CCAAACTCAAATATATAAAGCATTTGACTTGTTCTATGCCCTAGGGGGCG
GGGGGAAGCTAAGCCAGCTTTTTTTAACATTTAAAATGTTAATTCCATTT
TAAATGCACAGATGTTTTTATTTCATAAGGGTTTCAATGTGCATGAATGC
TGCAATATTCCTGTTACCAAAGCTAGTATAAATAAAAATAGATAAACGTG
GAAATTACTTAGAGTTTCTGTCATTAACGTTTCCTTCCTCAGTTGACAAC
ATAAATGCGCTGCTGAGCAAGCCAGTTTGCATCTGTCAGGATCAATTTCC
CATTATGCCAGTCATATTAATTACTAGTCAATTAGTTGATTTTTATTTTT
GACATATACATGTGAATGAAAGACCCCACCTGTAGGTTTGGCAAGCTAGC
TTAAGTAACGCCATTTTGCAAGGCATGGAAAAATACATAACTGAGAATAG
AAAAGTTCAGATCAAGGTCAGGAACAGATGGAACAGCTGAATATGGGCCA
AACAGGATATCTGTGGTAAGCAGTTCCTGCCCCGGCTCAGGGCCAAGAAC
AGATGGAACAGCTGAATATGGGCCAAACAGGATATCTGTGGTAAGCAGTT
CCTGCCCCGGCTCAGGGCCAAGAACAGATGGTCCCCAGATGCGGTCCAGC
CCTCAGCAGTTTCTAGAGAACCATCAGATGTTTCCAGGGTGCCCCAAGGA
CCTGAAATGACCCTGTGCCTTATTTGAACTAACCAATCAGTTCGCTTCTC
GCTTCTGTTCGCGCGCTTATGCTCCCCGAGCTCAATAAAAGAGCCCACAA
CCCCTCACTCGGGGCGCCAGTCCTCCGATTGACTGAGTCGCCCGGGTACC
CGTGTATCCAATAAACCCTCTTGCAGTTGCATCCGACTTGTGGTCTCGCT
GTTCCTTGGGAGGGTCTCCTCTGAGTGATTGACTACCCGTCAGCGGGGGT
CTTTCATTTGGGGGCTCGTCCGGGATCGGGAGACCCCTGCCCAGGGACCA
CCGACCCACCACCGGGAGGTAAGCTGGCCAGCAACTTATCTGTGTCTGTC
CGATTGTCTAGTGTCTATGACTGATTTTATGCGCCTGCGTCGGTACTAGT
TAGCTAACTAGCTCTGTATCTGGCGGACCCGTGGTGGAACTGACGAGTTC -continued

GGAACACCCGGCCGCAACCCTGGGAGACGTCCCAGGGACTTCGGGGGCCG

TTTTTGTGGCCCGACCTGAGTCCTAAAATCCCGATCGTTTAGGACTCTTT

GGTGCACCCCCCTTAGAGGAGGGATATGTGGTTCTGGTAGGAGACGAGAA

CCTAAAACAGTTCCCGCCTCCGTCTGAATTTTTGCTTTCGGTTTGGGACC

GAAGCCGCGCCGCGCGTCTTGTCTGCTGCAGCATCGTTCTGTGTTGTCTC

TGTCTGACTGTGTTTCTGTATTTGTCTGAAAATATGGGCCCGGGCTAGAC

TGTTACCACTCCCTTAAGTTTGACCTTAGGTCACTGGAAAGATGTCGAGC

GGATCGCTCACAACCAGTCGGTAGATGTCAAGAAGAGACGTTGGGTTACC

TTCTGCTCTGCAGAATGGCCAACCTTTAACGTCGGATGGCCGCGAGACGG

CACCTTTAACCGAGACCTCATCACCCAGGTTAAGATCAAGGTCTTTTCAC

CTGGCCCGCATGGACACCCAGACCAGGTCCCCTACATCGTGACCTGGGAA

GCCTTGGCTTTTGACCCCCCTCCCTGGGTCAAGCCCTTTGTACACCCTAA

GCCTCCGCCTCCTCTTCCTCCATCCGCCCCGTCTCTCCCCCTTGAACCTC

CTCGTTCGACCCCGCCTCGATCCTCCCTTTATCCAGCCCTCACTCCTTCT

CTAGGCGCCCCCATATGGCCATATGAGATCTTATATGGGGCACCCCCGCC

CCTTGTAAACTTCCCTGACCCTGACATGACAAGAGTTACTAACAGCCCCT

CTCTCCAAGCTCACTTACAGGCTCTCTACTTAGTCCAGCACGAAGTCTGG

AGACCTCTGGCGGCAGCCTACCAAGAACAACTGGACCGA

In one specific non-limiting example, the isolated nucleic acid molecule comprises nucleic acids having the sequence set forth in SEQ ID NO:406 provided below:

[SEQ ID NO: 406]

atggaaaccgacaccctgctgctgtgggtgctgctgctgtgggtgccagg atccacaggacagtctgtcgtgacgcagcctgcctccgtgtctgggtctc ctggacagtcgatcaccatctcctgcactggaaccagcagtgacgttggt ggttataactatgtctcctggtaccaacagcacccaggcaaagcccccaa actcatgatttatgatgtcagtaagcggccctcaggggtttctaatcgct tctctggctccaagtctggcaacacggcctccctgaccatctctgggctc caggctgaggacgaggctgattattactgcagctcatatacaagcagcag cactttggtattcggcggagggaccaagctgaccgtcctaggttctagag gtggtggtggtagcggcggcggcggctctggtggtggtggatccctcgag atggccgaggtgcagctggtggagtctgggggagcctttgtacagcctgg ggggtccctgagactctcctgtgcagcctctggattcacctttagcagct atgccatgacctgggtccgccaggctccagggaagggcctggaatgggtc tcgactattagtggtcgtggtcgtagcacattctacgcagactccgtgaa gggccggtttaccatctccagagacaattccaagaacacgctatatctgc aaatgaacagtctgagagccgaggacacggccgtatattactgtgcgcgc tactaccatgctggtgctttcgatctgtggggtcaaggtactctggtgac cgtctcctcagaacaaaaactcatctcagaagaggatctggcggccgcaa ttgaagttatgtatcctcctccttacctagacaatgagaagagcaatgga accattatccatgtgaaagggaaacacctttgtccaagtcccctatttcc -continued cggaccttctaagcccttttgggtgctggtggtggttggtggagtcctgg cttgctatagcttgctagtaacagtggcctttattattttctgggtgagg agtaagaggagcaggctcctgcacagtgactacatgaacatgactccccg ccgccccgggcccacccgcaagcattaccagccctatgccccaccacgcg acttcgcagcctatcgctccagagtgaagttcagcaggagcgcagacgcc cccgcgtaccagcagggccagaaccagctctataacgagctcaatctagg acgaagagaggagtacgatgttttggacaagagacgtggccgggaccctg agatgggggaaagccgagaaggaagaaccctcaggaaggcctgtacaat gaactgcagaaagataagatggcggaggcctacagtgagattgggatgaa aggcgagcgccggaggggcaaggggcacgatggcctttaccagggtctca gtacagccaccaaggacacctacgacgcccttcacatgcaggccctgccc cctcgctaa In one specific non-limiting example, the isolated nucleic acid molecule comprises nucleic acids having the sequence set forth in SEQ ID NO:407 provided below:

[SEQ ID NO: 407]

CCGGTGCCGCCACcatggaaaccgacaccctgctgctgtgggtgctgctg ctgtgggtgccaggatccacaggacagtctgtgttgacgcagcctgcctc cgtgtctgggtctcctggacagtcgctcaccatctcctgcactggaacca gcaatgacgttggtgcttataagtatgtctcctggtatcaacagtaccca ggcaaagcccccaaactcatactttatgatgtctttaagcggccctcagg ggtctctaatcgcttctctggctccaagtctgacaacacggcctccctga ccatctctgggctccaggctgaggacgaggctgattattactgcttctca cttacaagcagtaacacttatgtcttcggaactgggaccaaggtcaccgt cctaggttctagaggtggtggtggtagcggcggcggcggctctggtggtg gtggatccctcgagatggcccagatgcagctggtgcagtctggagctgag gtgaagaagcctggggcctcagtgaaggtctcctgcaaggcttctggtta cacctttaacagatatgctatcacctgggtgcgacaggcccctggacaag gccttgagtggatgggatggatcagcgcttacaatggtaattcacactat gcacagaagctccagggcagagtcaccatgaccacagacacatccacggg cacagcctatatggagctgaggaggctgagatctgacgacacggccgtgt attactgtgcgcgcatggcttacgattcttggggtcaaggtactctggtg accgtctcctcagaacaaaaactcatctcagaagaggatctggcggccgc acccaccacgacgccagcgccgcgaccaccaaccccggcgcccacgatcg cgtcgcagcccctgtccctgcgcccagaggcgtgccggccagcggcgggg ggcgcagtgcacacgagggggctggacttcgcctgtgatatctacatctg ggcgcccctggccgggacttgtggggtccttctcctgtcactggttatca ccctttactgcaacaaacggggcagaaagaagctcctgtatatattcaaa caaccatttatgagaccagtacaaactactcaagaggaagatggctgtag ctgccgatttccagaagaagaagaaggaggatgtgaactgagagtgaagt tcagcaggagcgcagaCGcccccgcgtaccagcagggccagaaccagctc tataacgagctcaatctaggacgaagagaggagtacgatgttttggacaa gagacgtggccgggaccctgagatgggggaaagccgagaaggaagaacc ctcaggaaggcctgtacaatgaactgcagaaagataagatggcggaggcc tacagtgagattgggatgaaaggcgagcgccggaggggcaaggggcacga tggcctttaccagggtctcagtacagccaccaaggacacctacgacgccc ttcacatgcaggccctgccccctcgctaacagccactcgaggatccggat tagtccaatttgttaaagacaggatatcagtggtccaggctctagttttg actcaacaatatcaccagctgaagcctatagagtacgagccatagataaa ataaaagattttatttagtctccagaaaaaggggggaatgaaagacccca cctgtaggtttggcaagctagcttaagtaacgccattttgcaaggcatgg aaaaatacataactgagaatagagaagttcagatcaaggtcaggaacaga tggaacagctgaatatgggccaaacaggatatctgtggtaagcagttcct gccccggctcagggccaagaacagatggaacagctgaatatgggccaaac aggatatctgtggtaagcagttcctgccccggctcagggccaagaacaga tggtccccagatgcggtccagccctcagcagtttctagagaaccatcaga tgtttccagggtgccccaaggacctgaaatgaccctgtgccttatttgaa ctaaccaatcagttcgcttctcgcttctgttcgcgcgcttctgctccccg agctcaataaaagagcccacaacccctcactcggggcgccagtcctccga ttgactgagtcgcccgggtacccgtgtatccaataaaccctcttgcagtt gcatccgacttgtggtctcgctgttccttgggagggtctcctctgagtga ttgactacccgtcagcgggggtctttcacacatgcagcatgtatcaaaat taatttggtttttttttcttaagtatttacattaaatggccatagtactta aagttacattggcttccttgaaataaacatggagtattcagaatgtgtca taaatatttctaattttaagatagtatctccattggctttctacttttc ttttattttttttttgtcctctgtcttccatttgttgttgttgttgtttgt ttgtttgtttgttggttggttggttaatttttttttaaagatcctacact atagttcaagctagactattagctactctgtaacccagggtgaccttgaa gtcatgggtagcctgctgttttagccttcccacatctaagattacaggta tgagctatcatttttggtatattgattgattgattgattgatgtgtgtgt gtgtgattgtgtttgtgtgtgtgactgtgaaaatgtgtgtatgggtgtgt gtgaatgtgtgtatgtatgtgtgtgtgtgagtgtgtgtgtgtgtgtgtgc atgtgtgtgtgtgtgactgtgtctatgtgtatgactgtgtgtgtgtgtgt gtgtgtgtgtgtgtgtgtgtgtgtgtgtgtgttgtgaaaaaatattctat ggtagtgagagccaacgctccggctcaggtgtcaggttggtttttgagac agagtctttcacttagcttggAATTCACTGGCCGTCGTTTTACAACGTCG

TGACTGGGAAAACCCTGGCGTTACCCAACTTAATCGCCTTGCAGCACATC

CCCCTTTCGCCAGCTGGCGTAATAGCGAAGAGGCCCGCACCGATCGCCCT

TCCCAACAGTTGCGCAGCCTGAATGGCGAATGGCGCCTGATGCGGTATTT

TCTCCTTACGCATCTGTGCGGTATTTCACACCGCATATGGTGCACTCTCA

GTACAATCTGCTCTGATGCCGCATAGTTAAGCCAGCCCCGACACCCGCCA

ACACCCGCTGACGCGCCCTGACGGGCTTGTCTGCTCCCGGCATCCGCTTA

CAGACAAGCTGTGACCGTCTCCGGGAGCTGCATGTGTCAGAGGTTTTCAC

CGTCATCACCGAAACGCGCGATGACGAAAGGGCCTCGTGATACGCCTATT

TTTATAGGTTAATGTCATGATAATAATGGTTTCTTAGACGTCAGGTGGCA

CTTTTCGGGGAAATGTGCGCGGAACCCCTATTTGTTTATTTTTCTAAATA

CATTCAAATATGTATCCGCTCATGAGACAATAACCCTGATAAATGCTTCA

ATAATATTGAAAAAGGAAGAGTATGAGTATTCAACATTTCCGTGTCGCCC

TTATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGGG

TTACATCGAACTGGATCTCAACAGCGGTAAGATCCTTGAGAGTTTTCGCC

CCGAAGAACGTTTTCCAATGATGAGCACTTTTAAAGTTCTGCTATGTGGC

GCGGTATTATCCCGTATTGACGCCGGGCAAGAGCAACTCGGTCGCCGCAT

ACACTATTCTCAGAATGACTTGGTTGAGTACTCACCAGTCACAGAAAAGC

ATCTTACGGATGGCATGACAGTAAGAGAATTATGCAGTGCTGCCATAACC

ATGAGTGATAACACTGCGGCCAACTTACTTCTGACAACGATCGGAGGACC

GAAGGAGCTAACCGCTTTTTTGCACAACATGGGGGATCATGTAACTCGCC

TTGATCGTTGGGAACCGGAGCTGAATGAAGCCATACCAAACGACGAGCGT

GACACCACGATGCCTGTAGCAATGGCAACAACGTTGCGCAAACTATTAAC

TGGCGAACTACTTACTCTAGCTTCCCGGCAACAATTAATAGACTGGATGG

AGGCGGATAAAGTTGCAGGACCACTTCTGCGCTCGGCCCTTCCGGCTGGC

TGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCT

ACACGACGGGGAGTCAGGCAACTATGGATGAACGAAATAGACAGATCGCT

GAGATAGGTGCCTCACTGATTAAGCATTGGTAACTGTCAGACCAAGTTTA

CTCATATATACTTTAGATTGATTTAAAACTTCATTTTTAATTTAAAAGGA

TCTAGGTGAAGATCCTTTTTGATAATCTCATGACCAAAATCCCTTAACGT

GAGTTTTCGTTCCACTGAGCGTCAGACCCCGTAGAAAAGATCAAAGGATC

TTCTTGAGATCCTTTTTTTCTGCGCGTAATCTGCTGCTTGCAAACAAAAA

AACCACCGCTACCAGCGGTGGTTTGTTTGCCGGATCAAGAGCTACCAACT

CTTTTTCCGAAGGTAACTGGCTTCAGCAGAGCGCAGATACCAAATACTGT

CCTTCTAGTGTAGCCGTAGTTAGGCCACCACTTCAAGAACTCTGTAGCAC

CGCCTACATACCTCGCTCTGCTAATCCTGTTACCAGTGGCTGCTGCCAGT

GGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCT

TGGAGCGAACGACCTACACCGAACTGAGATACCTACAGCGTGAGCATTGA

GAAAGCGCCACGCTTCCCGAAGGGAGAAAGGCGGACAGGTATCCGGTAAG

CGGCAGGGTCGGAACAGGAGAGCGCACGAGGGAGCTTCCAGGGGGAAACG

CCTGGTATCTTTATAGTCCTGTCGGGTTTCGCCACCTCTGACTTGAGCGT

CGATTTTTGTGATGCTCGTCAGGGGGGCGGAGCCTATGGAAAAACGCCAG

CAACGCGGCCTTTTTACGGTTCCTGGCCTTTTGCTGGCCTTTTGCTCACA

TGTTCTTTCCTGCGTTATCCCCTGATTCTGTGGATAACCGTATTACCGCC

-continued

TTTGAGTGAGCTGATACCGCTCGCCGCAGCCGAACGACCGAGCGCAGCGA

GTCAGTGAGCGAGGAAGCGGAAGAGCGCCCAATACGCAAACCGCCTCTCC

CCGCGCGTTGGCCGATTCATTAATGCAGCTGGCACGACAGGTTTCCCGAC

TGGAAAGCGGGCAGTGAGCGCAACGCAATTAATGTGAGTTAGCTCACTCA

TTAGGCACCCCAGGCTTTACACTTTATGCTTCCGGCTCGTATGTTGTGTG

GAATTGTGAGCGGATAACAATTTCACACAGGAAACAGCTATGACCATGAT

TACGCCAAGCTTTGCTCTTAGGAGTTTCCTAATACATCCCAAACTCAAAT

ATATAAAGCATTTGACTTGTTCTATGCCCTAGGGGGCGGGGGGAAGCTAA

GCCAGCTTTTTTTAACATTTAAAATGTTAATTCCATTTTAAATGCACAGA

TGTTTTTATTTCATAAGGGTTTCAATGTGCATGAATGCTGCAATATTCCT

GTTACCAAAGCTAGTATAAATAAAAATAGATAAACGTGGAAATTACTTAG

AGTTTCTGTCATTAACGTTTCCTTCCTCAGTTGACAACATAAATGCGCTG

CTGAGCAAGCCAGTTTGCATCTGTCAGGATCAATTTCCCATTATGCCAGT

CATATTAATTACTAGTCAATTAGTTGATTTTTATTTTTGACATATACATG

TGAATGAAAGACCCCACCTGTAGGTTTGGCAAGCTAGCTTAAGTAACGCC

ATTTTGCAAGGCATGGAAAAATACATAACTGAGAATAGAAAAGTTCAGAT

CAAGGTCAGGAACAGATGGAACAGCTGAATATGGGCCAAACAGGATATCT

GTGGTAAGCAGTTCCTGCCCCGGCTCAGGGCCAAGAACAGATGGAACAGC

TGAATATGGGCCAAACAGGATATCTGTGGTAAGCAGTTCCTGCCCCGGCT

CAGGGCCAAGAACAGATGGTCCCCAGATGCGGTCCAGCCCTCAGCAGTTT

CTAGAGAACCATCAGATGTTTCCAGGGTGCCCCAAGGACCTGAAATGACC

CTGTGCCTTATTTGAACTAACCAATCAGTTCGCTTCTCGCTTCTGTTCGC

GCGCTTATGCTCCCCGAGCTCAATAAAAGAGCCCACAACCCCTCACTCGG

GGCGCCAGTCCTCCGATTGACTGAGTCGCCCGGGTACCCGTGTATCCAAT

AAACCCTCTTGCAGTTGCATCCGACTTGTGGTCTCGCTGTTCCTTGGGAG

GGTCTCCTCTGAGTGATTGACTACCCGTCAGCGGGGGTCTTTCATTTGGG

GGCTCGTCCGGGATCGGGAGACCCCTGCCCAGGGACCACCGACCCACCAC

CGGGAGGTAAGCTGGCCAGCAACTTATCTGTGTCTGTCCGATTGTCTAGT

GTCTATGACTGATTTTATGCGCCTGCGTCGGTACTAGTTAGCTAACTAGC

TCTGTATCTGGCGGACCCGTGGTGGAACTGACGAGTTCGGAACACCCGGC

CGCAACCCTGGGAGACGTCCCAGGGACTTCGGGGGCCGTTTTTGTGGCCC

GACCTGAGTCCTAAAATCCCGATCGTTTAGGACTCTTTGGTGCACCCCCC

TTAGAGGAGGGATATGTGGTTCTGGTAGGAGACGAGAACCTAAAACAGTT

CCCGCCTCCGTCTGAATTTTTGCTTTCGGTTTGGGACCGAAGCCGCGCCG

CGCGTCTTGTCTGCTGCAGCATCGTTCTGTGTTGTCTCTGTCTGACTGTG

TTTCTGTATTTGTCTGAAAATATGGGCCCGGGCTAGACTGTTACCACTCC

CTTAAGTTTGACCTTAGGTCACTGGAAAGATGTCGAGCGGATCGCTCACA

ACCAGTCGGTAGATGTCAAGAAGAGACGTTGGGTTACCTTCTGCTCTGCA

GAATGGCCAACCTTTAACGTCGGATGGCCGCGAGACGGCACCTTTAACCG

AGACCTCATCACCCAGGTTAAGATCAAGGTCTTTTCACCTGGCCCGCATG

-continued

GACACCCAGACCAGGTCCCCTACATCGTGACCTGGGAAGCCTTGGCTTTT

GACCCCCCTCCCTGGGTCAAGCCCTTTGTACACCCTAAGCCTCCGCCTCC

TCTTCCTCCATCCGCCCCGTCTCTCCCCCTTGAACCTCCTCGTTCGACCC

CGCCTCGATCCTCCCTTTATCCAGCCCTCACTCCTTCTCTAGGCGCCCCC

ATATGGCCATATGAGATCTTATATGGGGCACCCCCGCCCCTTGTAAACTT

CCCTGACCCTGACATGACAAGAGTTACTAACAGCCCCTCTCTCCAAGCTC

ACTTACAGGCTCTCTACTTAGTCCAGCACGAAGTCTGGAGACCTCTGGCG

GCAGCCTACCAAGAACAACTGGACCGA

In one specific non-limiting example, the isolated nucleic acid molecule comprises nucleic acids having the sequence set forth in SEQ ID NO:408 provided below:

[SEQ ID NO: 408]

CCGGTGCCGCCACcatggaaaccgacaccctgctgctgtgggtgctgctg ctgtgggtgccaggatccacaggatcttctgagctgactcaggaccctgc tgtgtctgtggccttgggacagacagtcaggatcacatgccaaggagaca gcctcagaagctattatgcaagctggtaccagcagaagccaggacaggcc cctgtacttgtcatctatggtaaaaacaaccggccctcagggatcccaga ccgattctctggctccagctcaggaaacacagcttccttgaccatcactg gggctcaggcggaagatgaggctgactattactgtaactcccgggacagc agtggtaaccccccctgtggtattcggcggagggaccaagctgaccgtcct aggttctagaggtggtggtggtagcggcggcggcggctctggtggtggtg gatccctcgagatggcccaggtgcagctggtggagtctgggggaggcctg gtccacccctggggggtccctgagactctcctgtgcagcctctggattcac cttcagaagccatagcatgaactgggtccgccaggctccagggaaggggc tggagtgggtctcatccattagtagtgatagtacttacacatactacgca gactcagtgaagggccgattcaccatctccagagacaacgccaagaactc actgtatctgcaaatgaacagcctgagagccgaggacacggccgtatatt actgtgcgcgctctggtggtcagtggaaatactacgattactggggtcaa ggtactctggtgaccgtctcctcagaacaaaaactcatctcagaagagga tctggcggccgcacccaccacgacgccagcgccgcgaccaccaaccccgg cgcccacgatcgcgtcgcagcccctgtccctgcgcccagaggcgtgccgg ccagcggcggggggcgcagtgcacacgagggggctggacttcgcctgtga tatctacatctgggcgcccctggccgggacttgtggggtccttctcctgt cactggttatcaccctttactgcaacaaacggggcagaaagaagctcctg tatatattcaaacaaccatttatgagaccagtacaaactactcaagagga agatggctgtagctgccgatttccagaagaagaagaaggaggatgtgaac tgagagtgaagttcagcaggagcgcagaCGcccccgcgtaccagcagggc cagaaccagctctataacgagctcaatctaggacgaagagaggagtacga tgttttggacaagagacgtggccgggaccctgagatggggggaaagccga gaaggaagaaccctcaggaaggcctgtacaatgaactgcagaaagataag atggcggaggcctacagtgagattgggatgaaaggcgagcgccggagggg -continued caaggggcacgatggcctttaccagggtctcagtacagccaccaaggaca cctacgacgcccttcacatgcaggccctgccccctcgctaacagccactc gaggatccggattagtccaatttgttaaagacaggatatcagtggtccag gctctagttttgactcaacaatatcaccagctgaagcctatagagtacga gccatagataaaataaaagattttatttagtctccagaaaaaggggggaa tgaaagaccccacctgtaggtttggcaagctagcttaagtaacgccattt tgcaaggcatggaaaaatacataactgagaatagagaagttcagatcaag gtcaggaacagatggaacagctgaatatgggccaaacaggatatctgtgg taagcagttcctgccccggctcagggccaagaacagatggaacagctgaa tatgggccaaacaggatatctgtggtaagcagttcctgccccggctcagg gccaagaacagatggtccccagatgcggtccagccctcagcagtttctag agaaccatcagatgtttccagggtgccccaaggacctgaaatgaccctgt gccttatttgaactaaccaatcagttcgcttctcgcttctgttcgcgcgc ttctgctccccgagctcaataaaagagcccacaacccctcactcggggcg ccagtcctccgattgactgagtcgcccgggtacccgtgtatccaataaac cctcttgcagttgcatccgacttgtggtctcgctgttccttgggagggtc tcctctgagtgattgactacccgtcagcgggggtctttcacacatgcagc atgtatcaaaattaatttggtttttttttcttaagtatttacattaaatgg ccatagtacttaaagttacattggcttccttgaaataaacatggagtatt cagaatgtgtcataaatatttctaattttaagatagtatctccattggct ttctactttttcttttatttttttttgtcctctgtcttccatttgttgtt gttgttgtttgtttgtttgtttgttggttggttggttaatttttttttaa agatcctacactatagttcaagctagactattagctactctgtaacccag ggtgaccttgaagtcatgggtagcctgctgttttagccttcccacatcta agattacaggtatgagctatcatttttggtatattgattgattgattgat tgatgtgtgtgtgtgtgattgtgtttgtgtgtgtgactgtgaaaatgtgt gtatgggtgtgtgtgaatgtgtgtatgtatgtgtgtgtgtgagtgtgtgt gtgtgtgtgtgcatgtgtgtgtgtgtgactgtgtctatgtgtatgactgt gtgtgtgtgtgtgtgtgtgtgtgtgtgtgtgtgtgtgtgtgtgttgtgaa aaaatattctatggtagtgagagccaacgctccggctcaggtgtcaggtt ggtttttgagacagagtctttcacttagcttggAATTCACTGGCCGTCGT

TTTACAACGTCGTGACTGGGAAAACCCTGGCGTTACCCAACTTAATCGCC

TTGCAGCACATCCCCCTTTCGCCAGCTGGCGTAATAGCGAAGAGGCCCGC

ACCGATCGCCCTTCCCAACAGTTGCGCAGCCTGAATGGCGAATGGCGCCT

GATGCGGTATTTTCTCCTTACGCATCTGTGCGGTATTTCACACCGCATAT

GGTGCACTCTCAGTACAATCTGCTCTGATGCCGCATAGTTAAGCCAGCCC

CGACACCCGCCAACACCCGCTGACGCGCCCTGACGGGCTTGTCTGCTCCC

GGCATCCGCTTACAGACAAGCTGTGACCGTCTCCGGGAGCTGCATGTGTC

AGAGGTTTTCACCGTCATCACCGAAACGCGCGATGACGAAAGGGCCTCGT

GATACGCCTATTTTTATAGGTTAATGTCATGATAATAATGGTTTCTTAGA

CGTCAGGTGGCACTTTTCGGGGAAATGTGCGCGGAACCCCTATTTGTTTA

-continued

TTTTTCTAAATACATTCAAATATGTATCCGCTCATGAGACAATAACCCTG

ATAAATGCTTCAATAATATTGAAAAAGGAAGAGTATGAGTATTCAACATT

TCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGG

TGCACGAGTGGGTTACATCGAACTGGATCTCAACAGCGGTAAGATCCTTG

AGAGTTTTCGCCCCGAAGAACGTTTTCCAATGATGAGCACTTTTAAAGTT

CTGCTATGTGGCGCGGTATTATCCCGTATTGACGCCGGGCAAGAGCAACT

CGGTCGCCGCATACACTATTCTCAGAATGACTTGGTTGAGTACTCACCAG

TCACAGAAAAGCATCTTACGGATGGCATGACAGTAAGAGAATTATGCAGT

GCTGCCATAACCATGAGTGATAACACTGCGGCCAACTTACTTCTGACAAC

GATCGGAGGACCGAAGGAGCTAACCGCTTTTTTGCACAACATGGGGGATC

ATGTAACTCGCCTTGATCGTTGGGAACCGGAGCTGAATGAAGCCATACCA

AACGACGAGCGTGACACCACGATGCCTGTAGCAATGGCAACAACGTTGCG

CAAACTATTAACTGGCGAACTACTTACTCTAGCTTCCCGGCAACAATTAA

TAGACTGGATGGAGGCGGATAAAGTTGCAGGACCACTTCTGCGCTCGGCC

CTTCCGGCTGGCTGGTTTATTGCTGATAAATCTGGAGCCGGTGAGCGTGG

GTCTCGCGGTATCATTGCAGCACTGGGGCCAGATGGTAAGCCCTCCCGTA

TCGTAGTTATCTACACGACGGGGAGTCAGGCAACTATGGATGAACGAAAT

AGACAGATCGCTGAGATAGGTGCCTCACTGATTAAGCATTGGTAACTGTC

AGACCAAGTTTACTCATATATACTTTAGATTGATTTAAAACTTCATTTTT

AATTTAAAAGGATCTAGGTGAAGATCCTTTTTGATAATCTCATGACCAAA

ATCCCTTAACGTGAGTTTTCGTTCCACTGAGCGTCAGACCCCGTAGAAAA

GATCAAAGGATCTTCTTGAGATCCTTTTTTTCTGCGCGTAATCTGCTGCT

TGCAAACAAAAAAACCACCGCTACCAGCGGTGGTTTGTTTGCCGGATCAA

GAGCTACCAACTCTTTTTCCGAAGGTAACTGGCTTCAGCAGAGCGCAGAT

ACCAAATACTGTCCTTCTAGTGTAGCCGTAGTTAGGCCACCACTTCAAGA

ACTCTGTAGCACCGCCTACATACCTCGCTCTGCTAATCCTGTTACCAGTG

GCTGCTGCCAGTGGCGATAAGTCGTGTCTTACCGGGTTGGACTCAAGACG

ATAGTTACCGGATAAGGCGCAGCGGTCGGGCTGAACGGGGGGTTCGTGCA

CACAGCCCAGCTTGGAGCGAACGACCTACACCGAACTGAGATACCTACAG

CGTGAGCATTGAGAAAGCGCCACGCTTCCCGAAGGGAGAAAGGCGGACAG

GTATCCGGTAAGCGGCAGGGTCGGAACAGGAGAGCGCACGAGGGAGCTTC

CAGGGGGAAACGCCTGGTATCTTTATAGTCCTGTCGGGTTTCGCCACCTC

TGACTTGAGCGTCGATTTTTGTGATGCTCGTCAGGGGGGCGGAGCCTATG

GAAAAACGCCAGCAACGCGGCCTTTTTACGGTTCCTGGCCTTTTGCTGGC

CTTTTGCTCACATGTTCTTTCCTGCGTTATCCCCTGATTCTGTGGATAAC

CGTATTACCGCCTTTGAGTGAGCTGATACCGCTCGCCGCAGCCGAACGAC

CGAGCGCAGCGAGTCAGTGAGCGAGGAAGCGGAAGAGCGCCCAATACGCA

AACCGCCTCTCCCCGCGCGTTGGCCGATTCATTAATGCAGCTGGCACGAC

AGGTTTCCCGACTGGAAAGCGGGCAGTGAGCGCAACGCAATTAATGTGAG

-continued

```
TTAGCTCACTCATTAGGCACCCCAGGCTTTACACTTTATGCTTCCGGCTC

GTATGTTGTGTGGAATTGTGAGCGGATAACAATTTCACACAGGAAACAGC

TATGACCATGATTACGCCAAGCTTTGCTCTTAGGAGTTTCCTAATACATC

CCAAACTCAAATATATAAAGCATTTGACTTGTTCTATGCCCTAGGGGGCG

GGGGGAAGCTAAGCCAGCTTTTTTTAACATTTAAAATGTTAATTCCATTT

TAAATGCACAGATGTTTTTATTTCATAAGGGTTTCAATGTGCATGAATGC

TGCAATATTCCTGTTACCAAAGCTAGTATAAATAAAAATAGATAAACGTG

GAAATTACTTAGAGTTTCTGTCATTAACGTTTCCTTCCTCAGTTGACAAC

ATAAATGCGCTGCTGAGCAAGCCAGTTTGCATCTGTCAGGATCAATTTCC

CATTATGCCAGTCATATTAATTACTAGTCAATTAGTTGATTTTTATTTTT

GACATATACATGTGAATGAAAGACCCCACCTGTAGGTTTGGCAAGCTAGC

TTAAGTAACGCCATTTTGCAAGGCATGGAAAAATACATAACTGAGAATAG

AAAAGTTCAGATCAAGGTCAGGAACAGATGGAACAGCTGAATATGGGCCA

AACAGGATATCTGTGGTAAGCAGTTCCTGCCCCGGCTCAGGGCCAAGAAC

AGATGGAACAGCTGAATATGGGCCAAACAGGATATCTGTGGTAAGCAGTT

CCTGCCCCGGCTCAGGGCCAAGAACAGATGGTCCCCAGATGCGGTCCAGC

CCTCAGCAGTTTCTAGAGAACCATCAGATGTTTCCAGGGTGCCCCAAGGA

CCTGAAATGACCCTGTGCCTTATTTGAACTAACCAATCAGTTCGCTTCTC

GCTTCTGTTCGCGCGCTTATGCTCCCCGAGCTCAATAAAAGAGCCCACAA

CCCCTCACTCGGGGCGCCAGTCCTCCGATTGACTGAGTCGCCCGGGTACC

CGTGTATCCAATAAACCCTCTTGCAGTTGCATCCGACTTGTGGTCTCGCT

GTTCCTTGGGAGGGTCTCCTCTGAGTGATTGACTACCCGTCAGCGGGGGT

CTTTCATTTGGGGGCTCGTCCGGGATCGGGAGACCCCTGCCCAGGGACCA

CCGACCCACCACCGGGAGGTAAGCTGGCCAGCAACTTATCTGTGTCTGTC

CGATTGTCTAGTGTCTATGACTGATTTTATGCGCCTGCGTCGGTACTAGT

TAGCTAACTAGCTCTGTATCTGGCGGACCCGTGGTGGAACTGACGAGTTC

GGAACACCCGGCCGCAACCCTGGGAGACGTCCCAGGGACTTCGGGGGCCG

TTTTTGTGGCCCGACCTGAGTCCTAAAATCCCGATCGTTTAGGACTCTTT

GGTGCACCCCCCTTAGAGGAGGGATATGTGGTTCTGGTAGGAGACGAGAA

CCTAAAACAGTTCCCGCCTCCGTCTGAATTTTTGCTTTCGGTTTGGGACC

GAAGCCGCGCCGCGCGTCTTGTCTGCTGCAGCATCGTTCTGTGTTGTCTC

TGTCTGACTGTGTTTCTGTATTTGTCTGAAAATATGGGCCCGGGCTAGAC

TGTTACCACTCCCTTAAGTTTGACCTTAGGTCACTGGAAAGATGTCGAGC

GGATCGCTCACAACCAGTCGGTAGATGTCAAGAAGAGACGTTGGGTTACC

TTCTGCTCTGCAGAATGGCCAACCTTTAACGTCGGATGGCCGCGAGACGG

CACCTTTAACCGAGACCTCATCACCCAGGTTAAGATCAAGGTCTTTTCAC

CTGGCCCGCATGGACACCCAGACCAGGTCCCCTACATCGTGACCTGGGAA

GCCTTGGCTTTTGACCCCCCTCCCTGGGTCAAGCCCTTTGTACACCCTAA

GCCTCCGCCTCCTCTTCCTCCATCCGCCCCGTCTCTCCCCCTTGAACCTC

CTCGTTCGACCCCGCCTCGATCCTCCCTTTATCCAGCCCTCACTCCTTCT

CTAGGCGCCCCCATATGGCCATATGAGATCTTATATGGGGCACCCCCGCC
```

-continued

```
CCTTGTAAACTTCCCTGACCCTGACATGACAAGAGTTACTAACAGCCCCT

CTCTCCAAGCTCACTTACAGGCTCTCTACTTAGTCCAGCACGAAGTCTGG

AGACCTCTGGCGGCAGCCTACCAAGAACAACTGGACCGA
```

The isolated nucleic acid molecule having the nucleotide sequence of SEQ ID NO:406 encodes a GPRC5D-targeted CAR (designated as GRPC5D 28z CAR1) comprising a human scFv that comprises a heavy chain variable region comprising amino acids having the sequence set forth in SEQ ID NO:53, a light chain variable region comprising amino acids having the sequence set forth in SEQ ID NO:54, and a linker having an amino acid sequence of SEQ ID NO:98 positioned between the heavy chain variable region and the light chain variable region, a transmembrane domain comprising a CD28 polypeptide, and an intracellular domain comprising a CD3ζ polypeptide comprising amino acids 52 to 163 of SEQ ID NO: 272, and a co-stimulatory signaling region comprising a CD28 polypeptide, wherein the CD28 region comprising the transmembrane domain and the co-stimulatory signaling region comprises amino acids 114 to 220 of SEQ ID NO:270.

The isolated nucleic acid molecule having the nucleotide sequence of SEQ ID NO:397 encodes a GPRC5D-targeted CAR (designated as GRPC5D 28z CAR2) comprising a human scFv that comprises a heavy chain variable region comprising amino acids having the sequence set forth in SEQ ID NO:57, a light chain variable region comprising amino acids having the sequence set forth in SEQ ID NO:58, and a linker having an amino acid sequence of SEQ ID NO:98 positioned between the heavy chain variable region and the light chain variable region, a transmembrane domain comprising a CD28 polypeptide, and an intracellular domain comprising a CD3ζ polypeptide comprising amino acids 52 to 163 of SEQ ID NO: 272, and a co-stimulatory signaling region comprising a CD28 polypeptide, wherein the CD28 region comprising the transmembrane domain and the co-stimulatory signaling region comprises amino acids 114 to 220 of SEQ ID NO:270.

The isolated nucleic acid molecule having the nucleotide sequence of SEQ ID NO:398 encodes a GPRC5D-targeted CAR (designated as GRPC5D 28z CAR5) comprising a human scFv that comprises a heavy chain variable region comprising amino acids having the sequence set forth in SEQ ID NO:61, a light chain variable region comprising amino acids having the sequence set forth in SEQ ID NO:62, and a linker having an amino acid sequence of SEQ ID NO:98 positioned between the heavy chain variable region and the light chain variable region, a transmembrane domain comprising a CD28 polypeptide, and an intracellular domain comprising a CD3ζ polypeptide comprising amino acids 52 to 163 of SEQ ID NO: 272, and a co-stimulatory signaling region comprising a CD28 polypeptide, wherein the CD28 region comprising the transmembrane domain and the co-stimulatory signaling region comprises amino acids 114 to 220 of SEQ ID NO:270.

The isolated nucleic acid molecule having the nucleotide sequence of SEQ ID NO:399 encodes a GPRC5D-targeted CAR (designated as GRPC5D 28z CAR8) comprising a human scFv that comprises a heavy chain variable region comprising amino acids having the sequence set forth in SEQ ID NO:65, a light chain variable region comprising amino acids having the sequence set forth in SEQ ID NO:66, and a linker having an amino acid sequence of SEQ ID NO:98 positioned between the heavy chain variable region and the light chain variable region, a transmembrane domain comprising a CD28 polypeptide, and an intracellular domain comprising a CD3ζ polypeptide comprising amino acids 52 to 163 of SEQ ID NO: 272 and a co-stimulatory signaling region comprising a CD28 polypeptide, wherein the CD28 region comprising the transmembrane domain and the co-stimulatory signaling region comprises amino acids 114 to 220 of SEQ ID NO:270.

The isolated nucleic acid molecule having the nucleotide sequence of SEQ ID NO:400 encodes a GPRC5D-targeted CAR (designated as GRPC5D 28z CAR18) comprising a human scFv that comprises a heavy chain variable region comprising amino acids having the sequence set forth in SEQ ID NO:69, a light chain variable region comprising amino acids having the sequence set forth in SEQ ID NO:70, and a linker having an amino acid sequence of SEQ ID NO:98 positioned between the heavy chain variable region and the light chain variable region, a transmembrane domain comprising a CD28 polypeptide, and an intracellular domain comprising a CD3ζ polypeptide comprising amino acids 52 to 163 of SEQ ID NO: 272, and a co-stimulatory signaling region comprising a CD28 polypeptide, wherein the CD28 region comprising the transmembrane domain and the co-stimulatory signaling region comprises amino acids 114 to 220 of SEQ ID NO:270.

The isolated nucleic acid molecule having the nucleotide sequence of SEQ ID NO:401 encodes a GPRC5D-targeted CAR (designated as GRPC5D BBz CAR1) comprising a human scFv that comprises a heavy chain variable region comprising amino acids having the sequence set forth in SEQ ID NO: 53, a light chain variable region comprising amino acids having the sequence set forth in SEQ ID NO: 54, and a linker having an amino acid sequence of SEQ ID NO:98 positioned between the heavy chain variable region and the light chain variable region, a transmembrane domain comprising a CD8 polypeptide having 137 to 207 of SEQ ID NO: 404, and an intracellular domain comprising a CD3ζ polypeptide comprising amino acids 52 to 163 of SEQ ID NO: 272, and a co-stimulatory signaling region comprising a 4-1BB polypeptide having amino acids 214-255 of SEQ ID NO: 274. Nucleotide sequences 6-856 of SEQ ID NO: 401 encodes the human scFv. Nucleotide sequences 864-1076 of SEQ ID NO: 401 encodes the CD8 polypeptide comprised in the transmembrane domain. Nucleotide sequences 1077-1202 of SEQ ID NO: 401 encodes the 4-1BB polypeptide comprised in the intracellular domain. Nucleotide sequences 1203-1541 of SEQ ID NO: 401 encodes the CD3ζ polypeptide comprised in the intracellular domain. Other portions of SEQ ID NO: 401 are shown in Table 34.

TABLE 34

| Portions | nucleotide Sequence positions of SEQ ID NO: 401 | number of nucleotides |
|---|---|---|
| LTR | 1821 . . . 2290 | 470 |
| M13 fwd | 2989 . . . 3005 | 17 |
| AmpR promoter | 3480 . . . 3584 | 105 |
| AmpR | 3585 . . . 4445 | 861 |
| ori | 4616 . . . 5204 | 589 |
| CAP binding site | 5492 . . . 5513 | 22 |
| lac promoter | 5528 . . . 5558 | 31 |
| lac operator | 5566 . . . 5582 | 17 |
| M13 rev | 5590 . . . 5606 | 17 |
| LTR | 6015 . . . 6608 | 594 |
| MMLV Psi | 6671 . . . 7028 | 358 |
| gag (truncated) | 7093 . . . 7509 | 417 |

The isolated nucleic acid molecule having the nucleotide sequence of SEQ ID NO:407 encodes a GPRC5D-targeted CAR (designated as GRPC5D BBz CAR2) comprising a human scFv that comprises a heavy chain variable region comprising amino acids having the sequence set forth in SEQ ID NO: 57, a light chain variable region comprising amino acids having the sequence set forth in SEQ ID NO:58, and a linker having an amino acid sequence of SEQ ID NO:98 positioned between the heavy chain variable region and the light chain variable region, a transmembrane domain comprising a CD8 polypeptide having 137 to 207 of SEQ ID NO: 404, and an intracellular domain comprising a CD3ζ polypeptide comprising amino acids 52 to 163 of SEQ ID NO: 272, and a co-stimulatory signaling region comprising a 4-1BB polypeptide having amino acids 214-255 of SEQ ID NO: 274. Nucleotide sequences 5-855 of SEQ ID NO: 402 encodes the human scFv. Nucleotide sequences 15-812 of SEQ ID NO: 407 encodes the human scFv. Nucleotide sequences 852-1064 of SEQ ID NO: 407 encodes the CD8 polypeptide comprised in the transmembrane domain. Nucleotide sequences 1065-1190 of SEQ ID NO: 407 encodes the 4-1BB polypeptide comprised in the intracellular domain. Nucleotide sequences 1191-1529 of SEQ ID NO: 407 encodes the CD3ζ polypeptide comprised in the intracellular domain. Other portions of SEQ ID NO: 407 are shown in Table 41.

TABLE 41

| Portions | nucleotide Sequence positions of SEQ ID NO: 407 | number of nucleotides |
|---|---|---|
| Myc | 813 . . . 842 | 30 |
| LTR | 1809 . . . 2278 | 470 |
| M13 fwd | 2977 . . . 2993 | 17 |
| AmpR promoter | 3468 . . . 3572 | 105 |
| AmpR | 3573 . . . 4433 | 861 |
| ori | 4604 . . . 5192 | 589 |
| CAP binding site | 5480 . . . 5501 | 22 |
| lac promoter | 5516 . . . 5546 | 31 |
| lac operator | 5554 . . . 5570 | 17 |
| M13 rev | 5578 . . . 5594 | 17 |
| LTR | 6003 . . . 6596 | 594 |
| MMLV Psi | 6659 . . . 7016 | 358 |
| gag (truncated) | 7081 . . . 7497 | 417 |

The isolated nucleic acid molecule having the nucleotide sequence of SEQ ID NO:402 encodes a GPRC5D-targeted CAR (designated as GRPC5D BBz CAR5) comprising a human scFv that comprises a heavy chain variable region comprising amino acids having the sequence set forth in SEQ ID NO: 61, a light chain variable region comprising amino acids having the sequence set forth in SEQ ID NO:62, and a linker having an amino acid sequence of SEQ ID NO:98 positioned between the heavy chain variable region and the light chain variable region, a transmembrane domain comprising a CD8 polypeptide having 137 to 207 of SEQ ID NO: 404, and an intracellular domain comprising a CD3ζ polypeptide comprising amino acids 52 to 163 of SEQ ID NO: 272, and a co-stimulatory signaling region comprising a 4-1BB polypeptide having amino acids 214-255 of SEQ ID NO: 274. Nucleotide sequences 5-855 of SEQ ID NO: 402 encodes the human scFv. Nucleotide sequences 863-1075 of SEQ ID NO: 402 encodes the CD8 polypeptide comprised in the transmembrane domain. Nucleotide sequences 1076-1201 of SEQ ID NO: 402 encodes the 4-1BB polypeptide comprised in the intracellular domain. Nucleotide sequences 1202-1540 of SEQ ID NO: 402 encodes the CD3ζ polypeptide comprised in the intracellular domain. Other portions of SEQ ID NO: 402 are shown in Table 35.

TABLE 35

| Portions | nucleotide Sequence positions of SEQ ID NO: 402 | number of nucleotides |
|---|---|---|
| LTR | 1820 . . . 2289 | 470 |
| M13 fwd | 2988 . . . 3004 | 17 |
| AmpR promoter | 3479 . . . 3583 | 105 |
| AmpR | 3584 . . . 4444 | 861 |
| ori | 4615 . . . 5203 | 589 |
| CAP binding site | 5491 . . . 5512 | 22 |
| lac promoter | 5527 . . . 5557 | 31 |
| lac operator | 5565 . . . 5581 | 17 |
| M13 rev | 5589 . . . 5605 | 17 |
| LTR | 6014 . . . 6607 | 594 |
| MMLV Psi | 6670 . . . 7027 | 358 |
| gag (truncated) | 7092 . . . 7508 | 417 |

The isolated nucleic acid molecule having the nucleotide sequence of SEQ ID NO:408 encodes a GPRC5D-targeted CAR (designated as GRPC5D BBz CAR8) comprising a human scFv that comprises a heavy chain variable region comprising amino acids having the sequence set forth in SEQ ID NO: 65, a light chain variable region comprising amino acids having the sequence set forth in SEQ ID NO: 66, and a linker having an amino acid sequence of SEQ ID NO:98 positioned between the heavy chain variable region and the light chain variable region, a transmembrane domain comprising a CD8 polypeptide having 137 to 207 of SEQ ID NO: 404, and an intracellular domain comprising a CD3ζ polypeptide comprising amino acids 52 to 163 of SEQ ID NO: 272, and a co-stimulatory signaling region comprising a 4-1BB polypeptide having amino acids 214-255 of SEQ ID NO: 274. Nucleotide sequences 15-824 of SEQ ID NO: 408 encodes the human scFv. Nucleotide sequences 864-1076 of SEQ ID NO: 408 encodes the CD8 polypeptide comprised in the transmembrane domain. Nucleotide sequences 1077-1202 of SEQ ID NO: 408 encodes the 4-1BB polypeptide comprised in the intracellular domain. Nucleotide sequences 1203-1541 of SEQ ID NO: 408 encodes the CD3ζ polypeptide comprised in the intracellular domain. Other portions of SEQ ID NO: 408 are shown in Table 42.

TABLE 42

| Portions | nucleotide Sequence positions of SEQ ID NO: 408 | number of nucleotides |
|---|---|---|
| Myc | 825 . . . 854 | 30 |
| LTR | 1821 . . . 2290 | 470 |
| M13 fwd | 2989 . . . 3005 | 17 |
| AmpR promoter | 3480 . . . 3584 | 105 |
| AmpR | 3585 . . . 4445 | 861 |
| ori | 4616 . . . 5204 | 589 |
| CAP binding site | 5492 . . . 5513 | 22 |
| lac promoter | 5528 . . . 5558 | 31 |
| lac operator | 5566 . . . 5582 | 17 |
| M13 rev | 5590 . . . 5606 | 17 |
| LTR | 6015 . . . 6608 | 594 |
| MMLV Psi | 6671 . . . 7028 | 358 |
| gag (truncated) | 7093 . . . 7509 | 417 |

The isolated nucleic acid molecule having the nucleotide sequence of SEQ ID NO:403 encodes a GPRC5D-targeted CAR (designated as GRPC5D BBz CAR18) comprising a human scFv that comprises a heavy chain variable region comprising amino acids having the sequence set forth in SEQ ID NO: 69, a light chain variable region comprising amino acids having the sequence set forth in SEQ ID NO: 70, and a linker having an amino acid sequence of SEQ ID NO:98 positioned between the heavy chain variable region and the light chain variable region, a transmembrane domain comprising a CD8 polypeptide having 137 to 207 of SEQ ID NO: 404, and an intracellular domain comprising a CD3ζ polypeptide comprising amino acids 52 to 163 of SEQ ID NO: 272, and a co-stimulatory signaling region comprising a 4-1BB polypeptide having amino acids 214-255 of SEQ ID NO: 274. Nucleotide sequences 6-856 of SEQ ID NO: 403 encodes the human scFv. Nucleotide sequences 864-1076 of SEQ ID NO: 403 encodes the CD8 polypeptide comprised in the transmembrane domain. Nucleotide sequences 1077-1202 of SEQ ID NO: 403 encodes the 4-1BB polypeptide comprised in the intracellular domain. Nucleotide sequences 1203-1541 of SEQ ID NO: 403 encodes the CD3ζ polypeptide comprised in the intracellular domain. Other portions of SEQ ID NO: 403 are shown in Table 36.

TABLE 36

| Portions | nucleotide Sequence positions of SEQ ID NO: 403 | number of nucleotides |
|---|---|---|
| LTR | 1821 . . . 2290 | 470 |
| M13 fwd | 2989 . . . 3005 | 17 |
| AmpR promoter | 3480 . . . 3584 | 105 |
| AmpR | 3585 . . . 4445 | 861 |
| ori | 4616 . . . 5204 | 589 |
| CAP binding site | 5492 . . . 5513 | 22 |
| lac promoter | 5528 . . . 5558 | 31 |
| lac operator | 566 . . . 5582 | 17 |
| M13 rev | 5590 . . . 5606 | 17 |
| LTR | 6015 . . . 6608 | 594 |
| MMLV Psi | 6671 . . . 7028 | 358 |
| gag (truncated) | 7093 . . . 7509 | 417 |

In certain embodiments, the isolated nucleic acid molecule encodes a functional portion of a presently disclosed CAR targeting a G-protein coupled receptor (e.g., GPRC5D). As used herein, the term "functional portion" refers to any portion, part or fragment of a presently disclosed CAR targeting a G-protein coupled receptor (e.g., GPRC5D), which portion, part or fragment retains the biological activity of the CAR targeting a G-protein coupled receptor (e.g., GPRC5D) (the parent CAR). For example, functional portions encompass the portions, parts or fragments of a presently disclosed CAR targeting a G-protein coupled receptor (e.g., GPRC5D) that retains the ability to recognize a target cell, to treat a disease, e.g., multiple myeloma, to a similar, same, or even a higher extent as the parent CAR. In certain embodiments, an isolated nucleic acid molecule encoding a functional portion of a presently disclosed CAR targeting a G-protein coupled receptor (e.g., GPRC5D) can encode a protein comprising, e.g., about 10%, 20%, 25%, 30%, 35%, 40%, 45%, 50%, 55%, 60%, 65%, 70%, 75%, 80%, 85%, 90%, and 95%, or more of the parent CAR.

III. Immunoresponsive Cells

The presently disclosed subject matter provides immunoresponsive cells expressing a CAR that comprises an extracellular antigen-binding domain, a transmembrane domain and an intracellular domain, where the extracellular antigen-binding domain specifically binds to a G-protein coupled receptor (e.g., GPRC5D), as described above. The immunoresponsive cells can be transduced with a presently disclosed CAR such that the cells express the CAR. The presently disclosed subject matter also provides methods of using such cells for the treatment of a tumor, e.g., multiple myeloma (MM). The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of immunoresponsive cells of the lymphoid lineage include T cells, Natural Killer (NK) cells, cytotoxic T lymphocytes (CTLs), regulatory T cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells), Regulatory T cells (also known as suppressor T cells), Natural killer T cells, Mucosal associated invariant T cells, and γδ T cells. In certain embodiments, the CAR-expressing T cells express Foxp3 to achieve and maintain a T regulatory phenotype. Natural killer (NK) cells can be lymphocytes that are part of cell-mediated immunity and act during the innate immune response. NK cells do not require prior activation in order to perform their cytotoxic effect on target cells. Cytotoxic T cells (CTL or killer T cells) are a subset of T lymphocytes capable of inducing the death of infected somatic or tumor cells.

The immunoresponsive cells of the presently disclosed subject matter can express an extracellular antigen-binding domain (e.g., an scFV, a Fab that is optionally crosslinked, or a $F(ab)_2$) that specifically binds to a G-protein coupled receptor (e.g., GPRC5D), for the treatment of multiple myeloma. Such immunoresponsive cells can be administered to a subject (e.g., a human subject) in need thereof for the treatment of multiple myeloma. In certain embodiments, the immunoresponsive cell is a T cell. The T cell can be a $CD4^+$ T cell or a $CD8^+$ T cell. In certain embodiments, the T cell is a $CD4^+$ T cell. In certain embodiments, the T cell is a $CD8^+$ T cell.

A presently disclosed immunoresponsive cell can be further transduced with at least one co-stimulatory ligand, such that the immunoresponsive cell co-expresses or is induced to co-express the CAR targeting a G-protein coupled receptor (e.g., GPRC5D) and the at least one co-stimulatory ligand. The interaction between the CAR targeting a G-protein coupled receptor (e.g., GPRC5D) and at least one co-stimulatory ligand provides a non-antigen-specific signal important for full activation of an immunoresponsive cell (e.g., T cell). Co-stimulatory ligands include, but are not limited to, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, without limitation, nerve growth factor (NGF), CD40L (CD40L)/CD154, CD137L/4-1BBL, TNF-α, CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, but are not limited to, CD80 and CD86, both ligands for CD28, PD-L1/(B7-H1) that ligands for PD-1. In some embodiments, the at least one co-stimulatory ligand is selected from the group consisting of 4-1BBL, CD80, CD86, CD70, OX40L, CD48, TNFRSF14, PD-L1, and combinations thereof. In certain embodiments, the immunoresponsive cell is transduced with one co-stimulatory ligand that is 4-1BBL. In certain embodiments, the immunoresponsive cell is transduced with two co-stimulatory ligands that are 4-1BBL and CD80. CARs transduced with at least one co-stimulatory ligand are described in U.S. Pat. No. 8,389,282, which is incorporated by reference in its entirety.

Furthermore, a presently disclosed immunoresponsive cell can be further transduced with at least one cytokine, such that the immunoresponsive cell secretes the at least one cytokine as well as expresses the CAR targeting a G-protein coupled receptor (e.g., GPRC5D). In certain embodiments, the at least one cytokine is selected from the group consisting of IL-2, IL-3, IL-6, IL-7, IL-11, IL-12, IL-15, IL-17, and IL-21. In certain embodiments, the cytokine is IL-12.

The G-protein coupled receptor (e.g., GPRC5D)-specific or -targeted human lymphocytes that can be used in peripheral donor lymphocytes, e.g., those disclosed in Sadelain, M., et al. 2003 *Nat Rev Cancer* 3:35-45 (disclosing peripheral donor lymphocytes genetically modified to express CARs), in Morgan, R. A., et al. 2006 *Science* 314:126-129 (disclosing peripheral donor lymphocytes genetically modified to express a full-length tumor antigen-recognizing T cell receptor complex comprising the α and β heterodimer), in Panelli, M. C., et al. 2000 *J Immunol* 164:495-504; Panelli, M. C., et al. 2000 *J Immunol* 164:4382-4392 (disclosing lymphocyte cultures derived from tumor infiltrating lymphocytes (TILs) in tumor biopsies), and in Dupont, J., et al. 2005 *Cancer Res* 65:5417-5427; Papanicolaou, G. A., et al. 2003 *Blood* 102:2498-2505 (disclosing selectively in vitro-expanded antigen-specific peripheral blood leukocytes employing artificial antigen-presenting cells (AAPCs) or pulsed dendritic cells). The immunoresponsive cells (e.g., T cells) can be autologous, non-autologous (e.g., allogeneic), or derived in vitro from engineered progenitor or stem cells.

In certain embodiments, a presently disclosed immunoresponsive cell (e.g., T cell) expresses from about 1 to about 4, from about 2 to about 4, from about 3 to about 4, from about 1 to about 2, from about 1 to about 3, or from about 2 to about 3 vector copy numbers/cell of a presently disclosed CAR targeting a G-protein coupled receptor (e.g., GPRC5D).

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. Monoclonal antibodies are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

IV. Vectors

Genetic modification of immunoresponsive cells (e.g., T cells, CTL cells, NK cells) can be accomplished by transducing a substantially homogeneous cell composition with a recombinant DNA or RNA construct. The vector can be a retroviral vector (e.g., gamma retroviral), which is employed for the introduction of the DNA or RNA construct into the host cell genome. For example, a polynucleotide encoding the G-protein coupled receptor (e.g., GPRC5D-specific CAR can be cloned into a retroviral vector and expression can be driven from its endogenous promoter, from the retroviral long terminal repeat, or from an alternative internal promoter.

Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide G-protein coupled receptor (e.g., GPRC5D-specific CAR expressing cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Transducing viral vectors can be used to express a co-stimulatory ligand (e.g., 4-1BBL and IL-12) in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263 267, 1996; and Miyoshi et al., Proc. Natl. Acad. Sci. U.S.A. 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

In certain non-limiting embodiments, the vector expressing a presently disclosed G-protein coupled receptor (e.g., GPRC5D)-targeted CAR is a retroviral vector, e.g., a 293galv9 retroviral vector.

Non-viral approaches can also be employed for the expression of a protein in cell. For example, a nucleic acid molecule can be introduced into a cell by administering the nucleic acid in the presence of lipofection (Feigner et al., Proc. Nat'l. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1 a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

V. Polypeptides and Analogs and Polynucleotides

Also included in the presently disclosed subject matter are extracellular antigen-binding domains that specifically binds to a G-protein coupled receptor (e.g., GPRC5D) (e.g., an scFv, a Fab, or a $(Fab)_2$), CD3ζ, CD8, CD28, etc. polypeptides or fragments thereof, and polynucleotides encoding thereof that are modified in ways that enhance their anti-tumor activity when expressed in an immunoresponsive cell. The presently disclosed subject matter provides methods for optimizing an amino acid sequence or a nucleic acid sequence by producing an alteration in the sequence. Such alterations may comprise certain mutations, deletions, insertions, or post-translational modifications. The presently disclosed subject matter further comprises analogs of any naturally-occurring polypeptide of the presently disclosed subject matter. Analogs can differ from a naturally-occurring polypeptide of the presently disclosed subject matter by amino acid sequence differences, by post-translational modifications, or by both. Analogs of the presently disclosed subject matter can generally exhibit at least about 85%, about 90%, about 91%, about 92%, about 93%, about 94%, about 95%, about 96%, about 97%, about 98%, about 99% or more identity with all or part of a naturally-occurring amino, acid sequence of the presently disclosed subject matter. The length of sequence comparison is at least 5, 10, 15, 20, 25, 50, 75, 100 or more amino acid residues. Again, in an exemplary approach to determining the degree of identity, a BLAST program may be used, with a probability score between $e^{-3}$ and $e^{-100}$ indicating a closely related sequence. Modifications comprise in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the presently disclosed subject matter by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amina acids, e.g., D-amino acids or non-naturally occurring or synthetic amino acids, e.g., beta (β) or gamma (γ) amino acids.

In addition to full-length polypeptides, the presently disclosed subject matter also provides fragments of any one of the polypeptides or peptide domains of the presently disclosed subject matter. A fragment can be at least 5, 10, 13, or 15 amino acids. In certain embodiments, a fragment is at least 20 contiguous amino acids, at least 30 contiguous amino acids, or at least 50 contiguous amino acids. In certain embodiments, a fragment is at least 60 to 80, 100, 200, 300 or more contiguous amino acids. Fragments of the presently disclosed subject matter can be generated by methods known to those of ordinary skill in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the presently disclosed subject matter. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. The protein analogs can be relatively resistant to in vivo degradation, resulting in a more prolonged therapeutic effect upon administration. Assays for measuring functional activity include, but are not limited to, those described in the Examples below.

In accordance with the presently disclosed subject matter, the polynucleotides encoding an extracellular antigen-binding domain that specifically binds to a G-protein coupled receptor (e.g., GPRC5D) (e.g., an scFV, a Fab, or a $(Fab)_2$), CD3ζ, CD8, CD28) can be modified by codon optimization. Codon optimization can alter both naturally occurring and recombinant gene sequences to achieve the highest possible levels of productivity in any given expression system. Factors that are involved in different stages of protein expression include codon adaptability, mRNA structure, and various cis-elements in transcription and translation. Any suitable codon optimization methods or technologies that are known to ones skilled in the art can be used to modify the polynucleotids of the presently disclosed subject matter, including, but not limited to, OPTIMUMGENE™, Encor optimization, and Blue Heron.

VI. Administration

G-protein coupled receptor (e.g., GPRC5D)-specific CARs and immunoresponsive cells expressing thereof of the presently disclosed subject matter can be provided systemically or directly to a subject for treating or preventing a neoplasia. In certain embodiments, the G-protein coupled receptor (e.g., GPRC5D)-specific CARs and immunoresponsive cells expressing thereof are directly injected into an organ of interest (e.g., an organ affected by a neoplasia). Alternatively or additionally, the G-protein coupled receptor (e.g., GPRC5D)-specific CARs and immunoresponsive cells expressing thereof are provided indirectly to the organ of interest, for example, by administration into the circulatory system (e.g., the tumor vasculature). Expansion and differentiation agents can be provided prior to, during or after administration of cells and compositions to increase production of T cells in vitro or in vivo.

G-protein coupled receptor (e.g., GPRC5D)-specific CARs and immunoresponsive cells expressing thereof of the presently disclosed subject matter can be administered in any physiologically acceptable vehicle, normally intravascularly, although they may also be introduced into bone or other convenient site where the cells may find an appropriate site for regeneration and differentiation (e.g., thymus). Usually, at least $1\times10^5$ cells can be administered, eventually reaching $1\times10^{10}$ or more. A cell population comprising immunoresponsive cells expressing a G-protein coupled receptor (e.g., GPRC5D)-specific CAR can comprise a purified population of cells. Those skilled in the art can readily determine the percentage of immunoresponsive cells in a cell population using various well-known methods, such as fluorescence activated cell sorting (FACS). The ranges of purity in cell populations comprising genetically modified immunoresponsive cells expressing a G-protein coupled receptor (e.g., GPRC5D)-specific CAR can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art (e.g., a decrease in purity may require an increase in dosage). The immunoresponsive cells can be introduced by injection, catheter, or the like. If desired, factors can also be included, including, but not limited to, interleukins, e.g. IL-2, IL-3, IL 6, IL-11, IL-7, IL-12, IL-15, IL-21, as well as the other interleukins, the colony stimulating factors, such as G-, M- and GM-CSF, interferons, e.g., γ-interferon.

Compositions of the presently disclosed subject matter comprise pharmaceutical compositions comprising immunoresponsive cells expressing a G-protein coupled receptor (e.g., GPRC5D)-specific CAR and a pharmaceutically acceptable carrier. Administration can be autologous or non-autologous. For example, immunoresponsive cells expressing a G-protein coupled receptor (e.g., GPRC5D)-specific CAR and compositions comprising thereof can be obtained from one subject, and administered to the same subject or a different, compatible subject. Peripheral blood derived T cells of the presently disclosed subject matter or their progeny (e.g., in vivo, ex vivo or in vitro derived) can be administered via localized injection, including catheter administration, systemic injection, localized injection, intravenous injection, or parenteral administration. When administering a pharmaceutical composition of the presently disclosed subject matter (e.g., a pharmaceutical composition comprising immunoresponsive cells expressing a G-protein coupled receptor (e.g., GPRC5D)-specific CAR), it can be formulated in a unit dosage injectable form (solution, suspension, emulsion).

VII. Formulations

Immunoresponsive cells expressing a generally G-protein coupled receptor (e.g., GPRC5D)-specific CAR and compositions comprising thereof of the presently disclosed subject matter can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions comprising immunoresponsive cells expressing a generally G-protein coupled receptor (e.g., GPRC5D)-specific CAR of the presently disclosed subject matter in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the present invention, however, any vehicle, diluent, or additive used would have to be compatible with the immunoresponsive cells expressing a generally G-protein coupled receptor (e.g., GPRC5D)-specific CAR of the presently disclosed subject matter.

The compositions can be isotonic, i.e., they can have the same osmotic pressure as blood and lacrimal fluid. The desired isotonicity of the compositions of the presently disclosed subject matter may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the immunoresponsive cells as describe in the presently disclosed subject matter. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the immunoresponsive cells of the presently disclosed subject matter is the quantity of cells necessary to achieve an optimal effect. The quantity of cells to be administered will vary for the subject being treated. In certain embodiments, from about $10^4$ to about $10^{10}$, from about $10^5$ to about $10^9$, or from about $10^6$ to about $10^8$ immunoresponsive cells of the presently disclosed subject matter are administered to a subject. More effective cells may be administered in even smaller numbers. In some embodiments, at least about $1\times10^8$, about $2\times10^8$, about $3\times10^8$, about $4\times10^8$, and about $5\times10^8$ immunoresponsive cells of the presently disclosed subject matter are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the presently disclosed subject matter. Typically, any additives (in addition to the active cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

VIII. Methods of Treatment

Tumor Microenvironment.

Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory $CD4^+$ T cells (Tregs), myeloid derived suppressor cells (MDSCs), tumor associated macrophages (TAMs), immune suppressive cytokines including IL-10 and TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred CAR modified T cells upon encounter with targeted tumor cells.

Challenges in Tumor Immunology.

Effective tumor immunity requires recognition of tumor antigens and unopposed tumor elimination by immune effector cells. Tumor antigens must contain peptide epitopes that are presented by the tumor and can be recognized by specific cytotoxic T lymphocytes (CTLs). The primed CTLs must expand to a sufficient number and migrate to tumor sites, wherein they mature into effectors to perform their functions, which are enhanced by helper T cells and dampened by Tregs and inhibitory macrophages.

Targeted T Cell Therapy with Engineered T Lymphocytes.

T cell engineering is a groundbreaking strategy to potentially resolve many previously observed shortcomings of earlier immunotherapeutic approaches. Within the past year, researchers have reported dramatic complete remissions in relapsed[17,18], chemorefractory leukemia and metastatic melanoma[19-21], obtained with autologous peripheral blood T cells targeted to a defined antigen (CD19 and NY-ESO-1, respectively).

Rationale for a Genetic Approach:

Cell engineering can be used to redirect T cells toward tumor antigens and to enhance T cell function. One impetus for genetic T cell modification is the potential to enhance T cell survival and expansion and to offset T cell death, anergy, and immune suppression. The genetic targeting of T cells can also be refined to prevent undesired destruction of normal tissues.

Chimeric Antigen Receptors (CARs):

Tumor-specific T cells can be generated by the transfer of genes that encode CARs[22-27]. Second-generation CARs comprise a tumor antigen-binding domain fused to an intracellular signaling domain capable of activating T cells and a co-stimulatory domain designed to augment T cell potency and persistence[28]. CAR design can therefore reconcile antigen recognition with signal transduction, two functions that are physiologically borne by two separate complexes, the TCR heterodimer and the CD3 complex. The CAR's extracellular antigen-binding domain is usually derived from a murine monoclonal antibody (mAb) or from receptors or their ligands. Antigen recognition is therefore not MHC-restricted[29,30] and is therefore applicable to any patient expressing the target antigen, using the same CAR. Antigen binding by the CARs triggers phosphorylation of immunoreceptor tyrosine-based activation motifs (ITAMs) in the intracellular domain, initiating a signaling cascade required for cytolysis induction, cytokine secretion, and proliferation. Because MHC restriction of antigen recognition is bypassed, the function of CAR-targeted T cells is not affected by HLA downregulation or defects in the antigen-processing machinery.

T Cell Requirements for Expansion and Survival:

Proliferation of tumor-specific T cells is needed ex vivo and is arguably desirable in vivo. T cell proliferation must be accompanied by T cell survival to permit absolute T cell expansion and persistence. To proliferate in response to antigen, T cells must receive two signals. One is provided by TCR recognition of antigenic peptide/WIC complexes displayed on the surface of antigen-presenting cells (APCs)[26]. The other is provided by a T cell co-stimulatory receptor, such as the CD28 or 4-1BB receptors. Whereas the cytolytic activity of T cells does not require concomitant co-stimulation, there is a critical need for the provision of co-stimulatory signals to sustain the antitumor functions of adoptively transferred T cells, as previously demonstrated[24,28,31-33].

Immune Monitoring:

Lymphocytes are multifunctional “drugs” that exhibit dynamically evolving effects after infusion. Upon antigen encounter, tumor-specific T cells activate and/or release a variety of proteins that can trigger tumor killing, T cell proliferation, and recruitment or immunomodulation of other immune cells. Thus, measuring which proteins are secreted from which cells, in what quantity, and at what time point yields profound insights into why a particular patient is or is not responding and provides critical feedback for designing more-effective trials. These assay systems will permit direct and meaningful comparisons of clinical approaches and thus help design rational, next-generation therapeutic strategies.

For treatment, the amount administered is an amount effective in producing the desired effect. An effective amount can be provided in one or a series of administrations. An effective amount can be provided in a bolus or by continuous perfusion.

An “effective amount” (or, “therapeutically effective amount”) is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

For adoptive immunotherapy using antigen-specific T cells, cell doses in the range of about $10^6$ to about $10^{10}$ (e.g., about $10^9$) are typically infused. Upon administration of the immunoresponsive cells into the subject and subsequent differentiation, the immunoresponsive cells are induced that are specifically directed against one specific antigen (e.g., a G-protein coupled receptor (e.g., GPRC5D)). “Induction” of T cells can include inactivation of antigen-specific T cells such as by deletion or anergy. Inactivation is particularly useful to establish or reestablish tolerance such as in autoimmune disorders. The immunoresponsive cells of the presently disclosed subject matter can be administered by any methods known in the art, including, but not limited to, pleural administration, intravenous administration, subcutaneous administration, intranodal administration, intratumoral administration, intrathecal administration, intrapleural administration, intraperitoneal administration, and direct administration to the thymus. In certain embodiments, the immunoresponsive cells and the compositions comprising thereof are intravenously administered to the subject in need.

The presently disclosed subject matter provides various methods of using the immunoresponsive cells (e.g., T cells) expressing a G-protein coupled receptor (e.g., GPRC5D)-specific CAR. For example, the presently disclosed subject matter provides methods of reducing tumor burden in a subject. In one non-limiting example, the method of reducing tumor burden comprises administering an effective amount of the presently disclosed immunoresponsive cell to the subject, thereby inducing tumor cell death in the subject. The presently disclosed immunoresponsive cell can reduce the number of tumor cells, reduce tumor size, and/or eradicate the tumor in the subject. Non-limiting examples of suitable tumor include multiple myeloma Waldenstrom’s Macroglobulinemia. In certain embodiments, the tumor is multiple myeloma.

The presently disclosed subject matter also provides methods of increasing or lengthening survival of a subject having a neoplasia. In one non-limiting example, the method of increasing or lengthening survival of a subject having neoplasia comprises administering an effective amount of the presently disclosed immunoresponsive cell to the subject, thereby increasing or lengthening survival of the subject. The method can reduce or eradicate tumor burden in the subject. The presently disclosed subject matter further provides methods for treating or preventing a neoplasia in a subject, comprising administering the presently disclosed immunoresponsive cell to the subject.

As used herein, the term “neoplasia” refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

Cancers whose growth may be inhibited using the immunoresponsive cells of the presently disclosed subject matter comprise cancers typically responsive to immunotherapy. Non-limiting examples of cancers for treatment include multiple myeloma and Waldenstrom’s Macroglobulinemia. In certain embodiments, the cancer is multiple myeloma.

Additionally, the presently disclosed subject matter provides methods of increasing immune-activating cytokine production in response to a cancer cell in a subject. In one non-limiting example, the method comprises administering the presently disclosed immunoresponsive cell to the subject. The immune-activating cytokine can be granulocyte macrophage colony stimulating factor (GM-CSF), IFN-α, IFN-β, IFN-γ, TNF-α, IL-2, IL-3, IL-6, IL-11, IL-7, IL-12, IL-15, IL-21, interferon regulatory factor 7 (IRF7), and combinations thereof. In certain embodiments, the immunoresponsive cells including a G-protein coupled receptor (e.g., GPRC5D)-specific CAR of the presently disclosed subject matter increase the production of GM-CSF, IFN-γ, and/or TNF-α.

Suitable human subjects for therapy typically comprise two treatment groups that can be distinguished by clinical criteria. Subjects with “advanced disease” or “high tumor burden” are those who bear a clinically measurable tumor (e.g., multiple myeloma). A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in the presently disclosed subject matter is administered to these subjects to elicit an anti-tumor response, with the objective of palliating their condition. Ideally, reduction in tumor mass occurs as a result, but any clinical improvement constitutes a benefit. Clinical improvement comprises decreased risk or rate of progression or reduction in pathological consequences of the tumor (e.g., multiple myeloma).

A second group of suitable subjects is known in the art as the "adjuvant group." These are individuals who have had a history of neoplasia (e.g., multiple myeloma), but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor (e.g., multiple myeloma) has invaded neighboring tissues, or who show involvement of lymph nodes. Another group has a genetic predisposition to neoplasia (e.g., multiple myeloma) but has not yet evidenced clinical signs of neoplasia (e.g., multiple myeloma). For instance, women testing positive for a genetic mutation associated with breast cancer, but still of childbearing age, can wish to receive one or more of the antigen-binding fragments described herein in treatment prophylactically to prevent the occurrence of neoplasia until it is suitable to perform preventive surgery.

The subjects can have an advanced form of disease (e.g., multiple myeloma), in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Further modification can be introduced to the G-protein coupled receptor (e.g., GPRC5D)-specific CAR-expressing immunoresponsive cells (e.g., T cells) to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the CAR-expressing T cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T cell elimination by administering anti-EGFR monoclonal antibody (e.g., cetuximab). EGFRt can be covalently joined to the 3' terminus of the intracellular domain of the G-protein coupled receptor (e.g., GPRC5D)-specific CAR. The suicide gene can be included within the vector comprising nucleic acids encoding the presently disclosed G-protein coupled receptor (e.g., GPRC5D)-specific CARs. In this way, administration of a prodrug designed to activate the suicide gene (e.g., a prodrug (e.g., AP1903 that can activates iCasp-9) during malignant T-cell transformation (e.g., GVHD) triggers apoptosis in the suicide gene-activated CAR-expressing T cells.

IX. Kits

The presently disclosed subject matter provides kits for the treatment or prevention of a neoplasia (e.g., multiple myeloma). In certain embodiment, the kit comprises a therapeutic or prophylactic composition containing an effective amount of an immunoresponsive cell comprising a G-protein coupled receptor (e.g., GPRC5D)-specific CAR in unit dosage form. In particular embodiments, the cells further expresses at least one co-stimulatory ligand. In certain embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the immunoresponsive cell is provided together with instructions for administering the cell to a subject having or at risk of developing a neoplasia (e.g., multiple myeloma). The instructions will generally include information about the use of the composition for the treatment or prevention of a neoplasia (e.g., multiple myeloma). In other embodiments, the instructions include at least one of the following: description of the therapeutic agent; dosage schedule and administration for treatment or prevention of a neoplasia (e.g., multiple myeloma) or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1—GPRC5D Expression in Various Tissues

The Expression of human GPRC5D was evaluated in various malignant and normal tissues by investigating gene expression profiles in databases such as the cancer cell line encyclopedia and BioGPS. As shown in FIG. 2, human GPRC5D was highly expressed in multiple myeloma, but not in other malignant tissues. Normal expression appeared limited to plasma cells. Potential GPRC5D targeted CAR T cell eradication of this normal cell type may not have significant adverse effects based on inventors' patient experience with CD19 targeted CAR T cells. Any lack of physiologic antibody production can be addressed with intravenous immunoglobulin treatment.

Example 2—Construct of GPRC5D-Specific 28z CARs

Multiple unique fully human scFv's to GPRC5D were generated, and CARs based on these scFv's were generated. Multiple scFv's were identified by screening a fully human scFv phage library (>$6\times10^{10}$ scFv's) with 3T3 cells expressing GPRC5D. Four independent pannings with 12 different phage libraries were carried out against GPRC5D overexpressing 3T3 cells identifying 80 positive clones. 72 positive clones were identified out of 80 clones screened FACS; the positive clone rate was 90%. After sequencing, 32 unique and GPRC5D-3T3 positive binding clones were found out of 72 sequenced positive clones; the unique clone rate was 45%.

ET150-151 scFv (or "ET150-1 scFv"), ET150-152 scFv (or "ET150-2 scFv"), ET150-155 scFv (or "ET150-5 scFv"), ET150-158 (or "ET150-8 scFv")scFv, and ET150-168 scFv (or "ET150-18 scFv") were used to generate GPRC5D-targeted 28z CARs 2, 5, 8, and 18, respectively. These GPRC5D-targeted 28z CARs have similar structure, e.g., each has a transmembrane domain comprising a CD28 polypeptide, and an intracellular domain comprising a CD3ζ polypeptide and a co-stimulatory signaling region that comprises a CD28 polypeptide, as shown in FIG. 1. Each of these GPRC5D-targeted CARs were cloned into a retroviral vector. These viral vectors were then transduced into HEK 293galv9 viral packaging cells in order to generate a stable packaging line for generation of $CAR^+$ T cells.

Human T cells (unselected (CD4 and CD8) human T cells from a healthy donor) were transduced with each of these GPRC5D-targeted 28z CARs such that the T cells expressed these GPRC5D-targeted CARs.

Figure 3:
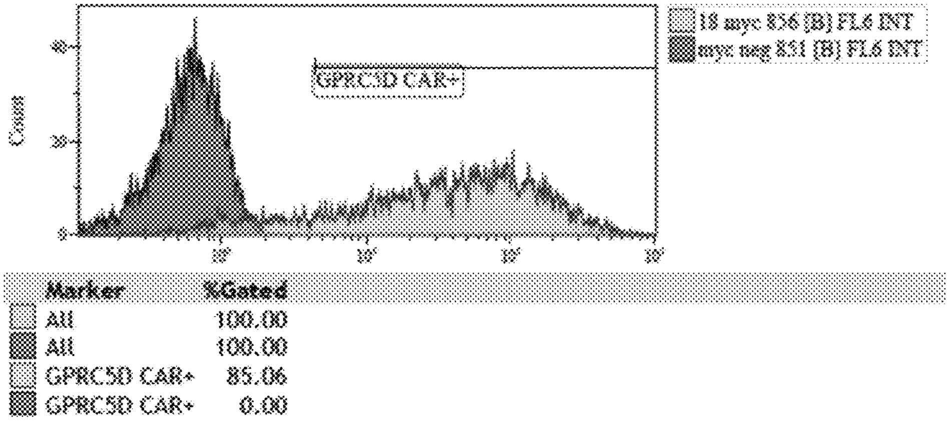
FIG. 3 depicts the expression of the presently disclosed GPRC5D CAR on human T cells.

The cell surface expression of GPRC5D-targeted 28z CAR18 on human T cells via binding human GPRC5D was assessed, and cell surface detection was validated by flow cytometry, as shown in FIG. 3.

Example 3—Activity of GPRC5D-Specific 28z CARs

Figure 4:
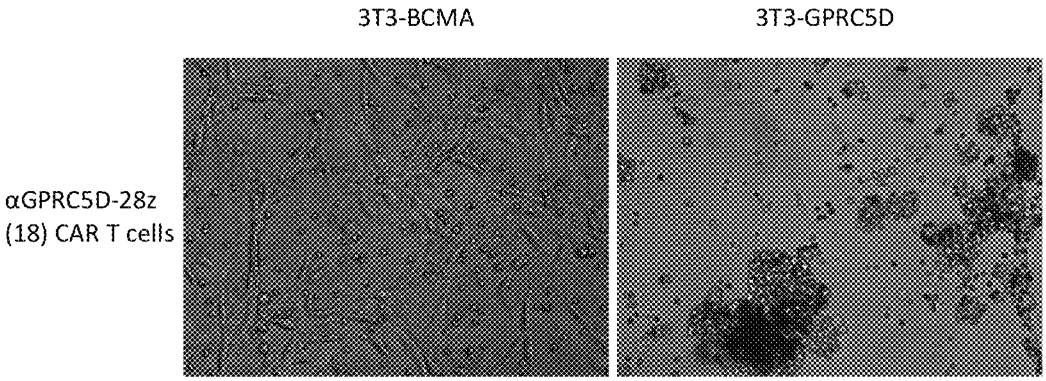
FIG. 4 depicts the killing activity of the presently disclosed GPRC5D for 3T3 cells overexpressing GPRC5D.
Figure 5:
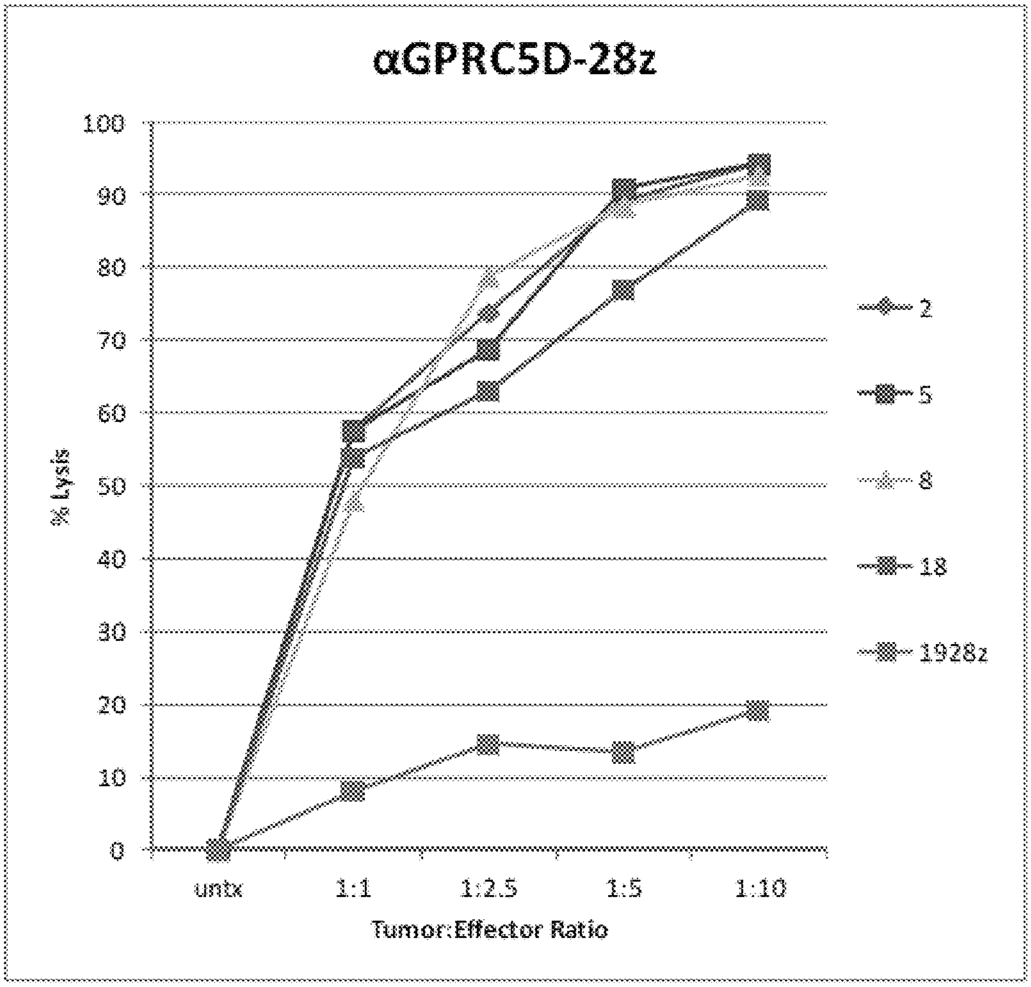
FIG. 5 depicts the killing activity of the presently disclosed GPRC5D for a human multiple myeloma cell line.

The anti-tumor activity of the presently disclosed GPRC5D-specific 28z CARs was evaluated. The in vitro data showed that the GPRC5D-specific CARs specifically killed GPRC5D presenting cells, including MM cell lines. For example, as shown in FIG. 4, the T cells expressing the GPRC5D-specific 28z CAR18 killed 3T3 cells overexpressing GPRC5D (but not control 3T3s overexpressing another antigen). As shown in FIG. 5, the T cells expressing the GPRC5D-specific 28z CARs 2, 5, 8, and 18 killed human MM cell lines.

Example 4—Screening Data for Anti-GPRC5D Antibodies

FACS Screening: FIG. 24 shows FACS analysis of GPRC5D-specific phage antibody clones (ET150-1, ET150-2, ET150-5, ET150-8, ET150-18). Phage clones were incubated with 3T3-GPRC5D cell line, then with anti-M13 mouse antibody. Finally APC-labeled anti-mouse IgG 2nd antibody was added to the reaction after washing again. The binding was measured by FACS and expressed as mean fluorescence intensity (MFI). Cells incubated with M13 K07 helper phage and cells only were used as negative controls.

Example 5—Construct of GPRC5D-Specific BBz CARs

Multiple unique fully human scFv's to GPRC5D were generated, and CARs based on these scFv's were generated as described in Example 2. ET150-151 scFv (or "ET150-1 scFv"), ET150-152 scFv (or "ET150-2 scFv"), ET150-155 scFv (or "ET150-5 scFv"), ET150-158 scFv (or "ET150-8 scFv"), and ET150-168 scFv (or "ET150-18 scFv") were used to generate GPRC5D-targeted BBz CARs 1, 2, 5, 8, and 18, respectively. These GPRC5D-targeted BBz CARs have similar structure, e.g., each has a transmembrane domain comprising a CD8a polypeptide, and an intracellular domain comprising a CD3ζ polypeptide and a co-stimulatory signaling region that comprises a 4-1BB polypeptide, as shown in FIG. 6. Each of these GPRC5D-targeted BBz CARs were cloned into an SFG retroviral vector, as shown in FIGS. 7-9, 26 and 27.

Example 6—Activity of GPRC5D-Targeted CAR T Cells

Figure 10:
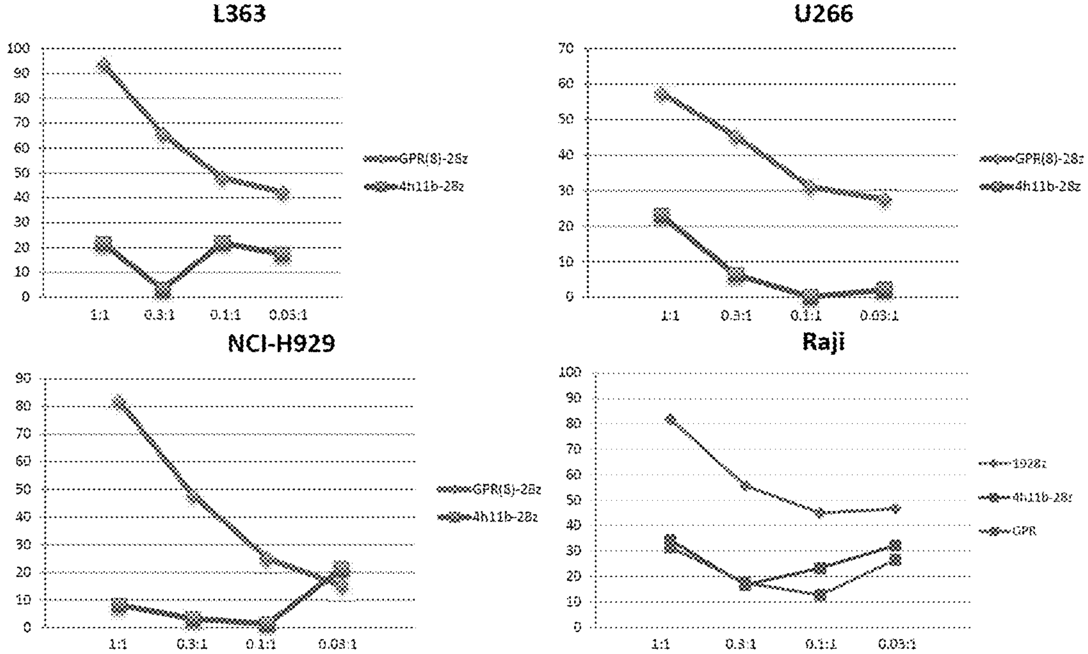
FIG. 10 depicts the cytotoxicity of GPRC5D targeted CAR T cells for human multiple myeloma cell lines.

As shown in FIG. 10, GPRC5D 28z CAR8 lysed human MM cell lines L363, NCL-H929, and U266, compared to irrelevantly targeted 4h11-28z MUC16 targeted CAR T cells. The cytotoxicity exhibited by observed GPRC5D 28z CAR8 was specific to GPRC5D, as it did not lyse GPRC5D negative CD19 positive Raji Burkett lymphoma cell line, as shown in FIG. 10.

Example 7—Induction of Cytokine Secretion by GPRC5D-Targeted CAR T Cells

Figure 11:
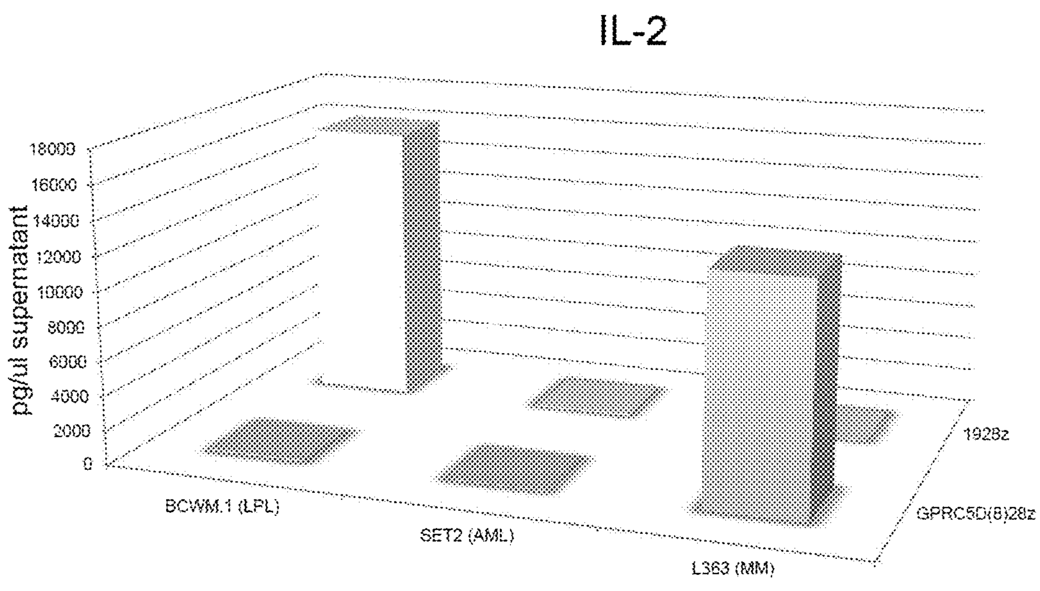
FIG. 11 depicts induction of cytokine secretion of GPRC5D targeted CAR T cells.

Co-culture of GPRC5D 28z CAR8 T cells specifically with MM cell line induced cytokine secretion profile consistent with T cell activation. FIG. 11 shows the IL-2 secretion after 24 h co-culture of CAR T cells with human tumor cell lines (E:T ratio 1:1). Only the lymphoplasmacytic lymphoma ($CD19^+$ $GPRC5D^-$) with CD19 targeted CAR T cells (positive control) and the MM cell line with the GPRC5D targeted 28z CAR8 T cells displayed increased cytokine production. IFNg, IL-6, TNFa, sCD40L, GM-CSF all had similar secretion profiles (data not shown).

Example 8—Anti-Tumor Activity of GPRC5D-Targeted CAR T Cells

Figure 12:
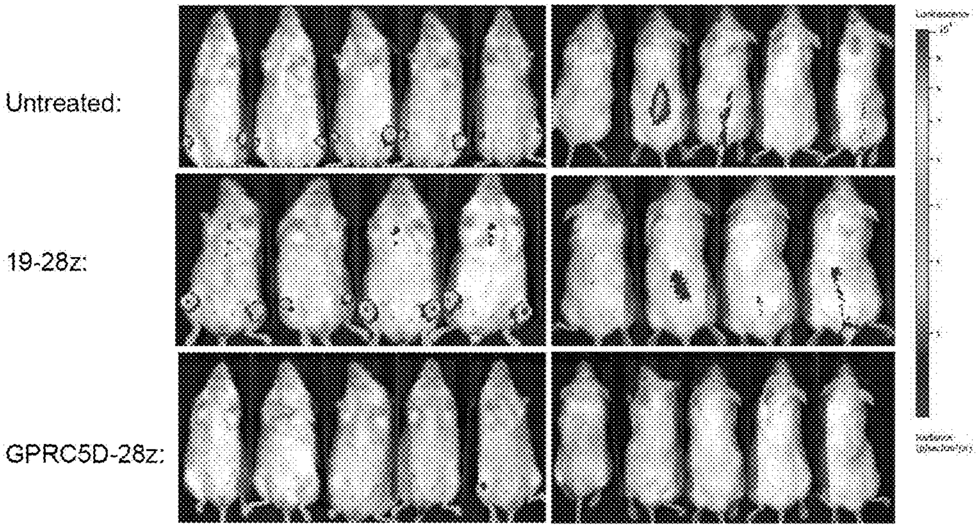
FIG. 12 depicts anti-tumor activity of GPRC5D targeted CAR T cells.

GPRC5D targeted 28z CAR18 T cells mediated an anti-myeloma immune response. $1\times10^7$ U266 human myeloma cell line cells were injected IV into NSG mice on day 0. On day 4 $1\times10^6$ GPRC5D targeted or CD19 targeted second generation CAR T cells were injected IV. Imaging on day 11 (day 7 s/p CAR T cell injection) shows that, unlike irrelevant (CD19) targeted CAR T cells; GPRC5D A targeted 28z CAR18 T cells can mediate an anti-tumor response. See FIG. 12.

Example 9—Activity of GPRC5D-Targeted CAR T Cells

The ability of GPRC5D targeted CAR T cells to specifically lyse human myeloma cell line (HMCL) was tested.

Figure 13A:
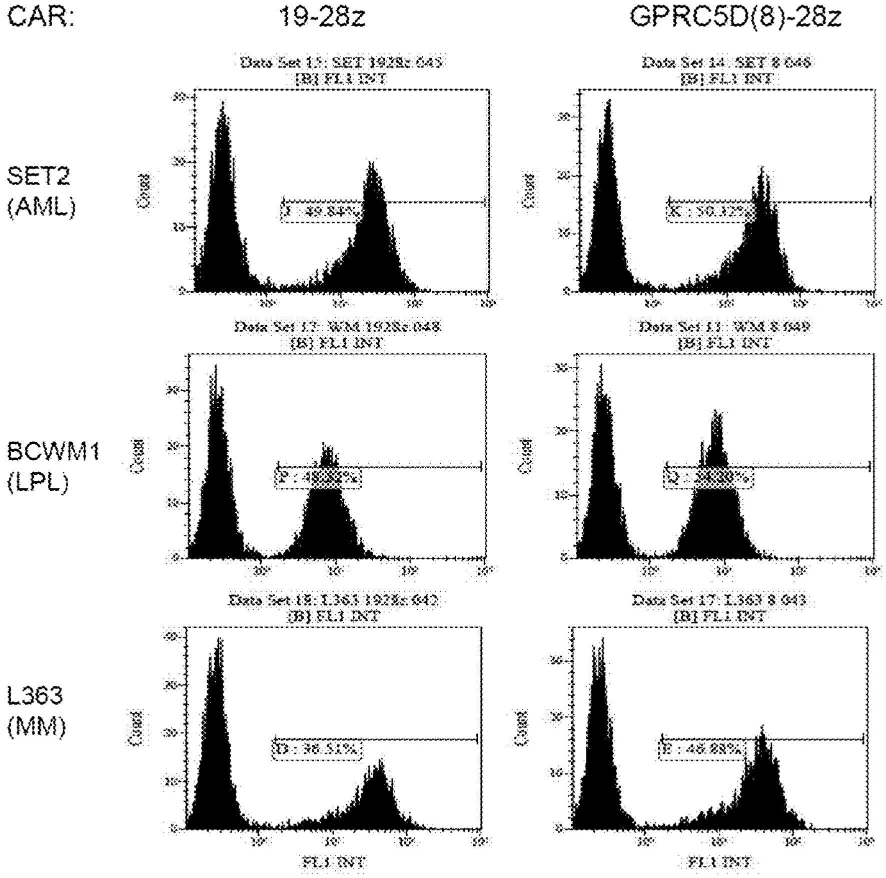
FIGS. 13A and 13B depict the killing activity of GPRC5D targeted CART cells. (A) Shows the percent of $GFP^+$ tumor line at time 0. (B) Shows the killing the percent of $GFP^+$ tumor line at time 36 hours.
Figure 13B:
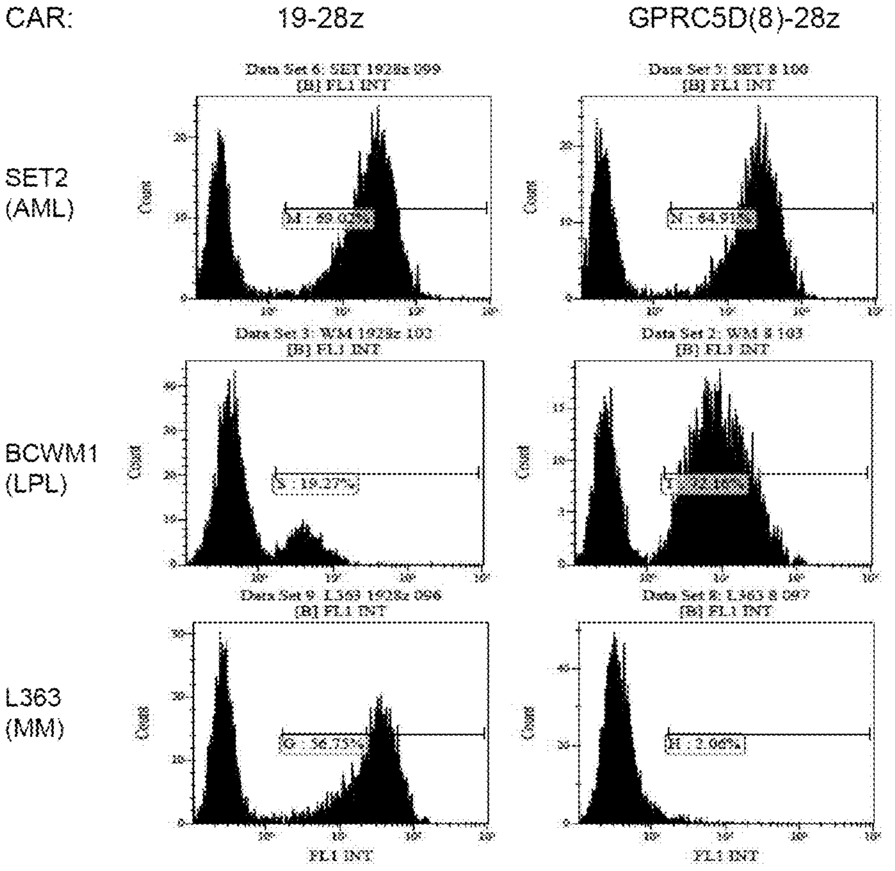

CD19 targeted CAR T cells or GPRC5D targeted 28z CAR8 T cells were incubated with GFP expressing tumor cell lines SET2 (Acute myeloid leukemia (AML), CD19-GPRC5D-); BCWM1 (Lymphoplasmacytic Lymphoma (LPL), CD19-GPRC5D-); L363 (Multiple Myeloma (MM), CD19-GPRC5D+). At time 0, the percent of $GFP^+$ tumor line is shown in FIG. 13A. At 36 h the positive control CD19 targeted CAR T cells have specifically killed the $GFP^+$ LPL line, and similarly the GPRC5D targeted 28z CAR8 T cells have specifically killed the $GFP^+$ MM line. See FIG. 13B.

Example 10—Epitope Mapping of Anti-GPRC5D Antibodies

Four anti-GPRC5D antibodies: ET150-2, ET150-5, ET150-8, and ET150-18 mlgG1. "mIgG1" used in all Examples represents that the variable region is fully human and the Fc part is mouse IgG1. See Table 37.

TABLE 37

| Name | Origin | Concentration | Location | Status |
|---|---|---|---|---|
| ET150-18 mIgG1 | mouse Fc | 1.1 mg/ml | +4° C./22 | ok |
| ET150-2 mIgG1 | mouse Fc | 0.66 mg/ml | +4° C./22 | ok |
| ET150-5 mIgG1 | mouse Fc | 1.9 mg/ml | +4° C./22 | ok |
| ET150-8 mIgG1 | mouse Fc | 2.9 mg/ml | +4° C./22 | ok |

The target protein is human GPRC5D having the amino acid sequence set forth in SEQ ID NO: 97. The N-terminal region of human GPRC5D has amino acids 1-27 of SEQ ID NO:97. The extracellular loop 1 (ECL1) region of human GPRC5D has amino acids 85-93 of SEQ ID NO:97. The extracellular loop 2 (ECL2) region of human GPRC5D has amino acids 145-167 of SEQ ID NO:97. The extracellular loop 3 (ECL3) region of human GPRC5D has amino acids 226-239 of SEQ ID NO:97.

Methods

Figure 14:
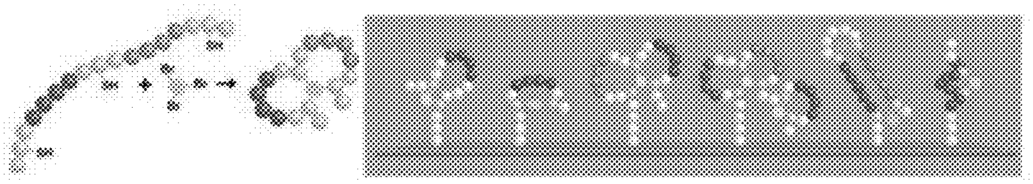
FIG. 14 illustrates the CLIPS technology. The CLIPS reaction takes place between bromo groups of the CLIPS scaffold and thiol sidechains of cysteines. The reaction is fast and specific under mild conditions. Using this elegant chemistry, native protein sequences are transformed into CLIPS constructs with a range of structures. From left to right: two different single T2 loops, T3 double loop, conjugated T2+T3 loops, stabilized beta sheet, and stabilized alpha helix (Timmerman et al., J. Mol. Recognit. 2007; 20: 283-29).

The principles of clips technology—CLIPS technology structurally fixes peptides into defined three-dimensional structures. This results in functional mimics of even the most complex binding sites. CLIPS technology is now routinely used to shape peptide libraries into single, double or triple looped structures as well as sheet- and helix-like folds (FIG. 14).

Figure 15:
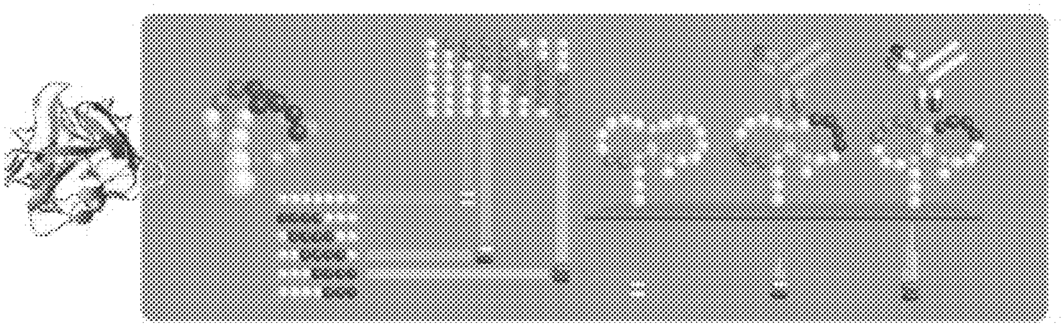
FIG. 15 illustrates combinatorial clips library screening. The target protein (left) containing a discontinuous conformational epitope is converted into a matrix library (middle).

Combinatorial clips library screening in detail—CLIPS library screening starts with the conversion of the target protein into a library of up to 10,000 overlapping peptide constructs, using a combinatorial matrix design. On a solid carrier, a matrix of linear peptides is synthesized, which are subsequently shaped into spatially defined CLIPS constructs (FIG. 15). Constructs representing both parts of the discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail.

Figures 17A, 17B, 17C, 17D:
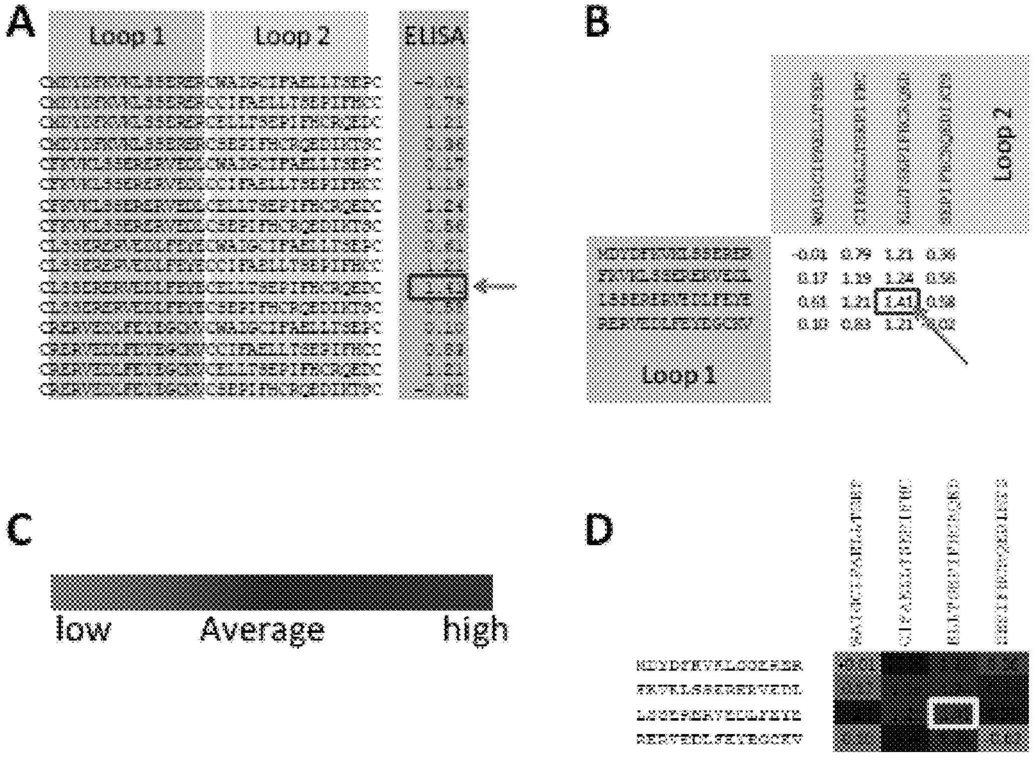

Heat map analysis—A heat map is a graphical representation of data where the values taken by a variable in a two-dimensional map are represented as colors. For double-looped CLIPS peptides, such a two-dimensional map can be derived from the independent sequences of the first and second loops. For example, the sequences of the 16 CLIPS peptides depicted in FIG. 17 are effectively permutations of 4 unique sub-sequences in loop 1 (colored in blue in FIG. 16) and 4 unique sub-sequences in loop 2 (colored in green in FIG. 16). Thus, the observed ELISA data (colored in red in FIG. 17A) can be plotted in a 4×4 matrix, where each X coordinate corresponds to the sequence of the first loop, and each Y coordinate corresponds to the sequence of the second loop. For instance, the ELISA value observed for CLIPS peptide CLSSERERVEDLFEYECELLTSEPIFHCRQEDC (indicated with an arrow in FIG. 4A) can be found at the third row, third column of FIG. 17B (indicated with an arrow and a red square). To further facilitate the visualization, ELISA values can be replaced with colors from a continuous gradient. In this case, extremely low values are colored in green, extremely high values are colored in red, and average values are colored in black (see FIG. 17C). For the aforementioned example, the average value is 0.71. When this color map is applied to the data matrix depicted in FIG. 17B, a color heat map is obtained (see FIG. 17D, the original data is still indicated for extra clarity).

Synthesis of peptides—To reconstruct epitopes of the target molecule a library of peptides was synthesized. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with Nhydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer). Synthesis of structural mimics was done using Pepscan's proprietary Chemically Linked Peptides on Scaffolds (CLIPS) technology. CLIPS technology allows to structure peptides into single loops, doubleloops, triple loops, sheet-like folds, helix-like folds and combinations thereof. CLIPS templates are coupled to cysteine residues. The side-chains of multiple cysteines in the peptides were coupled to one or two CLIPS templates. For example, a 0.5 mM solution of the P2 CLIPS (2,6-bis(bromomethyl)pyridine) was dissolved in ammonium bicarbonate (20 mM, pH 7.8)/acetonitrile (1:3(v/v)). This solution was added onto the peptide arrays. The CLIPS template bound to side-chains of two cysteines as present in the solid-phase bound peptides of the peptide-arrays (455 wells plate with 3 μl wells). The peptide arrays were gently shaken in the solution for 30 to 60 minutes while completely covered in solution. Finally, the peptide arrays were washed extensively with excess of $H_2O$ and sonicated in disrupt-buffer containing 1% SDS/0.1% beta-mercaptoethanol in PBS (pH 7.2) at 70° C. for 30 minutes, followed by sonication in $H_2O$ for another 45 minutes. The T3 CLIPS carrying peptides were made in a similar way but now with three cysteines.

ELISA Screening—The binding of antibody to each of the synthesized peptides was tested in a PEPSCAN-based ELISA. The peptide arrays were incubated with primary antibody solution (overnight at 4° C.). After washing, the peptide arrays were incubated with a 1/1000 dilution of an appropriate antibody peroxidase conjugate (SBA) for one hour at 25° C. After washing, the peroxidase substrate 2,2'-azino-di-3-ethylbenzthiazoline sulfonate (ABTS) and 2 μl/ml of 3 percent $H_2O_2$ were added. After one hour, the color development was measured. The color development was quantified with a charge coupled device (CCD)—camera and an image processing system.

Data processing—the values obtained from the CCD camera ranged from 0 to 3000 mAU, similar to a standard 96-well plate ELISA-reader. The results were quantified and stored into the Peplab database. Occasionally a well contained an air-bubble resulting in a false-positive value, the cards were manually inspected and any values caused by an air-bubble were scored as 0.

Synthesis quality control—To verify the quality of the synthesized peptides, a separate set of positive and negative control peptides was synthesized in parallel. These were screened with antibody 57.9 (ref. Posthumus et al., J. Virology, 1990, 64:3304-3309).

Results

Screening

Antibody binding depends on a combination of factors, including concentration of the antibody and the amounts and nature of competing proteins in the ELISA buffer. Also, the pre-coat conditions (the specific treatment of the peptide arrays prior to incubation with the experimental sample) affected binding. These details are summed up in Table 38. For the Pepscan Buffer and Preconditioning (SQ), the numbers indicate the relative amount of competing protein (a combination of horse serum and ovalbumin).

TABLE 38

| screening condition | | | |
|---|---|---|---|
| Label | Dilution | Sample buffer | Pre-conditioning |
| ET150-18 mIgG1 | 1 μg/ml | 1% SQ | 1% SQ |
| ET150-2 mIgG1 | 1 μg/ml | 10% SQ | 10% SQ |
| ET150-5 mIgG1 | 1 μg/ml | 10% SQ | 10% SQ |
| ET150-8 mIgG1 | 3 μg/ml | 10% SQ | 10% SQ |

Antibody ET150-2

When tested under moderate stringency conditions antibody ET150-2 avidly bound peptides from all sets (FIG. 18). Cumulative data analysis shows that the antibody recognize a discontinuous epitope composed of peptides stretches $_{16}$CDAEGPWGII$_{25}$ (N-term), $_{157}$MFVNMTPC$_{164}$ (ECL2) and $_{229}$PQFQRQPQW$_{237}$ (ECL3), where peptide stretches $_{16}$CDAEGPWGII$_{25}$ and $_{229}$PQFQRQPQW$_{237}$ alone suffice for binding.

Antibody ET150-5

When tested under high stringency conditions antibody ET150-5 avidly bound peptides from all sets (FIG. 19). Cumulative data analysis shows that the antibody recognizes a discontinuous epitope composed of peptide stretches $_{5}$CIESTGDYFLLCD$_{17}$ (N-term), $_{85}$NQQTAPVRYFL$_{95}$ (ECL1) and $_{157}$MFVNMTPC$_{164}$ (ECL2), where peptide stretch $_{5}$CIESTGDYFLCD$_{17}$ alone suffices for binding.

Antibody ET150-18

When tested under high stringency conditions antibody ET150-18 bound peptides from set 4 and set 7, containing structurally constrained peptides. No significant binding was recorded on sets containing linear peptides (FIG. 20). Cumulative data analysis shows that the antibody recognizes a discontinuous epitope composed of stretches $_{10}$GDYFLLCD$_{17}$ (N-term), $_{157}$MFVNMTPCQLN$_{167}$ (ECL2) and $_{227}$GNPQFQRQPQW$_{237}$ (ECL3). Peptide stretches $_{10}$GDYFLLCD$_{17}$ and $_{227}$GNPQFQRQPQW$_{237}$ represent the epitope's core, as both peptide stretches separately suffice for binding.

Antibody ET150-8

When tested under high stringency conditions antibody ET150-8 bound peptides from all sets, except for set 2 (FIG. 21). Cumulative data analysis shows that the antibody recognizes a discontinuous epitope composed of peptides stretches $_{15}$LCDAEGPWG$_{23}$ (N-term) and $_{230}$QFQRQPQWDDPVVC$_{243}$ (ECL3) where peptide stretch $_{15}$LCDAEGPWG$_{23}$ is the dominant part of the epitope, as it alone suffices for binding. Moreover, comparison of the results obtained on set 1 (linear) and set 4 (loop) shows that introduction of structural constrains to epitope mimics enhances binding of peptides, especially in case of peptides containing sequence $_{230}$QFQRQPQWDDPVVC$_{243}$.

Conclusions

All antibodies investigated recognized discontinuous epitopes, which were mapped using Pepscan arrays. Core tentative epitopes are listed in Table 39. All antibodies commonly recognized overlapping regions at the N-terminus of the protein in combination with regions from one or two ECLs. Two antibodies ET150-18 and ET150-8 showed a requirement for structural constraints to support antibody binding, suggesting that these two antibodies recognize not only discontinuous, but also conformational epitopes. Antibodies ET150-2 and ET150-5 did not show notable discrepancies in peptide binding between linear and looped peptides.

TABLE 39

| list of epitopes | | | | |
|---|---|---|---|---|
| Antibody | N-terminus | ECL1 | ECL2 | ECL3 |
| ET150-2 | $_{16}$CDAEGPWGII$_{25}$*) | — | $_{157}$MFVNMTPC$_{164}$ | $_{229}$PQFQRQFQW$_{237}$*) |
| ET150-5 | $_{5}$CIESTGDYFLLCD$_{17}$*) | $_{85}$NQQTAPVRYFL$_{95}$ | $_{157}$MFVNMTPC$_{164}$ | — |
| ET150-8 | $_{15}$LCDAEGPWG$_{23}$*) | — | — | $_{230}$QFQRQPQWDDPVVC$_{243}$ |
| ET150-18 | $_{10}$GDYFLLCD$_{17}$*) | — | $_{157}$MFVNMTPCQLN$_{167}$ | $_{227}$GNPQFQRQPQW$_{237}$*) |

*) dominant part

FIG. 22 is an illustration of the results of the study with respect to overall organization of GPCRs. As the N-terminus is highly flexible and unstructured, it likely transiently interacts with ECLs forming discontinuous immunodominant regions.

Differences and commonalities in peptide binding can be illustrated with a scatter plot analysis in FIG. 23. Data points in the top left and bottom right corners point to the differences in the binding. Despite significant epitope overlap, the fine specificities of epitopes of the individual antibodies differ to a large extent.

Example 11—Binding Affinity of Anti-GPRC5D Antibodies

FIG. 25 shows FACS analysis of GPRC5D-specific phage antibody clones (ET150-2, ET150-5, ET150-8, ET150-18). Each antibodies (ET150-2, ET150-5, ET150-8, ET150-18) were incubated with 3T3 or 3T3-GPRC5D cells at 10 or 1 ug/mL, then with anti-M13 mouse antibody. Finally PE-labeled anti-mouse IgG 2nd antibody was added to the reaction. The binding was measured by FACS and expressed as mean fluorescence intensity (MFI). Cells incubated with 2nd antibody alone, ET901 mIgG1 isotype control and cells only were used as negative controls.

Although the foregoing presently disclosed subject matter has been described in some detail by way of illustration and example for purposes of clarity of understanding, the descriptions and examples should not be construed as limiting the scope of the presently disclosed subject matter. The disclosures of all patent and scientific literature cited herein are expressly incorporated in their entirety by reference.

REFERENCES

1. Atamaniuk, J., et al. Overexpression of G protein-coupled receptor 5D in the bone marrow is associated with poor prognosis in patients with multiple myeloma. *European journal of clinical investigation* 42, 953-960 (2012).
2. Frigyesi, I., et al. Robust isolation of malignant plasma cells in multiple myeloma. *Blood* 123, 1336-1340 (2014).
3. Cohen, Y., Gutwein, O., Garach-Jehoshua, O., Bar-Haim, A. & Kornberg, A. GPRC5D is a promising marker for monitoring the tumor load and to target multiple myeloma cells. *Hematology* (*Amsterdam, Netherlands*) 18, 348-351 (2013).
4. Bam, R., et al. GPRC5D Is a Cell Surface Plasma Cell Marker Whose Expression Is High In Myeloma Cells and Reduced Following Coculture With Osteoclasts. *Blood* 122, 3099 (2013).
5. Brentjens, R. J., et al. Safety and persistence of adoptively transferred autologous CD19-targeted T cells in patients with relapsed or chemotherapy refractory B-cell leukemias. *Blood* 118, 4817-4828 (2011).
6. Brentjens, R. J., et al. Eradication of systemic B-cell tumors by genetically targeted human T lymphocytes co-stimulated by CD80 and interleukin-15. *Nature medicine* 9, 279-286 (2003).
7. Brentjens, R. J., et al. CD19-Targeted T Cells Rapidly Induce Molecular Remissions in Adults with Chemotherapy-Refractory Acute Lymphoblastic Leukemia. *Science translational medicine* 5, 177ra138 (2013).
8. Davila, M. L., et al. Efficacy and Toxicity Management of 19-28z CAR T Cell Therapy in B Cell Acute Lymphoblastic Leukemia. *Science translational medicine* 6, 224ra225 (2014).
9. Siegel, R., Naishadham, D. & Jemal, A. Cancer statistics, 2013. *CA: a cancer journal for clinicians* 63, 11-30 (2013).
10. Boyd, K. D., et al. The clinical impact and molecular biology of del(17p) in multiple myeloma treated with conventional or thalidomide-based therapy. *Genes, chromosomes & cancer* 50, 765-774 (2011).
11. Shaughnessy, J. D., Jr., et al. A validated gene expression model of high-risk multiple myeloma is defined by deregulated expression of genes mapping to chromosome 1. *Blood* 109, 2276-2284 (2007).
12. Gahrton, G., et al. Allogeneic bone marrow transplantation in multiple myeloma. European Group for Bone Marrow Transplantation. *The New England journal of medicine* 325, 1267-1273 (1991).
13. Pegram, H. J., et al. Tumor-targeted T cells modified to secrete IL-12 eradicate systemic tumors without need for prior conditioning. *Blood* 119, 4133-4141 (2012).
14. Sabrina Bertilaccio, M. T., et al. Low-Dose Lenalidomide Improves CAR-Based Immunotherapy In CLL By Reverting T-Cell Defects In Vivo. *Blood* 122, 4171 (2013).
15. Bataille, R., et al. The phenotype of normal, reactive and malignant plasma cells. Identification of "many and multiple myelomas" and of new targets for myeloma therapy. *Haematologica* 91, 1234-1240 (2006).
16. Morgan, R. A., et al. Case report of a serious adverse event following the administration of T cells transduced with a chimeric antigen receptor recognizing ERBB2. *Molecular therapy: the journal of the American Society of Gene Therapy* 18, 843-851 (2010).
17. Brentjens, R. J., et al. Safety and persistence of adoptively transferred autologous CD19-targeted T cells in patients with relapsed or chemotherapy refractory B-cell leukemias. *Blood* 118, 4817-4828 (2011).
18. Brentjens, R. J., et al. CD19-targeted T cells rapidly induce molecular remissions in adults with chemotherapy-refractory acute lymphoblastic leukemia. *Science translational medicine* 5, 177ra138 (2013).
19. Hunder, N. N., et al. Treatment of metastatic melanoma with autologous CD4+ T cells against NY-ESO-1. *N. Engl. J. Med.* 358, 2698-2703 (2008).
20. Rosenberg, S. A., Restifo, N. P., Yang, J. C., Morgan, R. A. & Dudley, M. E. Adoptive cell transfer: a clinical path to effective cancer immunotherapy. *Nat. Rev. Cancer* 8, 299-308 (2008).
21. Dudley, M. E., et al. Adoptive cell therapy for patients with metastatic melanoma: evaluation of intensive myeloablative chemoradiation preparative regimens. *J Clin Oncol* 26, 5233-5239 (2008).
22. Brentjens, R. J., et al. Genetically targeted T cells eradicate systemic acute lymphoblastic leukemia xenografts. *Clin. Cancer Res.* 13, 5426-5435 (2007).
23. Gade, T. P., et al. Targeted elimination of prostate cancer by genetically directed human T lymphocytes. *Cancer Res.* 65, 9080-9088 (2005).
24. Maher, J., Brentjens, R. J., Gunset, G., Riviere, I. & Sadelain, M. Human T-lymphocyte cytotoxicity and proliferation directed by a single chimeric TCRzeta/CD28 receptor. *Nat. Biotechnol.* 20, 70-75 (2002).
25. Kershaw, M. H., et al. Gene-engineered T cells as a superior adjuvant therapy for metastatic cancer. *J Immunol* 173, 2143-2150 (2004).
26. Sadelain, M., Brentjens, R. & Riviere, I. The promise and potential pitfalls of chimeric antigen receptors. *Curr Opin Immunol* (2009).
27. Hollyman, D., et al. Manufacturing validation of biologically functional T cells targeted to CD19 antigen for autologous adoptive cell therapy. *J Immunother* 32, 169-180 (2009).
28. Sadelain, M., Brentjens, R. & Riviere, I. The basic principles of chimeric antigen receptor design. *Cancer discovery* 3, 388-398 (2013).
29. Riviere, I., Sadelain, M. & Brentjens, R. J. Novel strategies for cancer therapy: the potential of genetically modified T lymphocytes. *Curr Hematol Rep* 3, 290-297 (2004).
30. Stephan, M. T., et al. T cell-encoded CD80 and 4-1BBL induce auto- and transco-stimulation, resulting in potent tumor rejection. *Nat. Med.* 13, 1440-1449 (2007).
31. Krause, A., et al. Antigen-dependent CD28 signaling selectively enhances survival and proliferation in genetically modified activated human primary T lymphocytes. *J Exp Med* 188, 619-626 (1998).
32. Gong, M. C., et al. Cancer patient T cells genetically targeted to prostate-specific membrane antigen specifically lyse prostate cancer cells and release cytokines in response to prostate-specific membrane antigen. *Neoplasia.* 1, 123-127 (1999).

33. Lyddane, C., et al. Cutting Edge: CD28 controls dominant regulatory T cell activity during active immunization. *J. Immunol.* 176, 3306-3310 (2006).

From the foregoing description, it will be apparent that variations and modifications may be made to the invention described herein to adopt it to various usages and conditions. Such embodiments are also within the scope of the following claims.

All patents and publications and sequences referred to by accession or reference number mentioned in this specification are herein incorporated by reference to the same extent as if each independent patent and publication and sequence was specifically and individually indicated to be incorporated by reference.

What is claimed is:

1. A chimeric antigen receptor (CAR), comprising an extracellular antigen-binding domain that binds to a G-protein coupled receptor family C group 5 member D (GPRC5D), a transmembrane domain, and an intracellular signaling domain, wherein the extracellular antigen-binding domain comprises a heavy chain variable region comprising a CDR1 comprising the amino acid sequence set forth in SEQ ID NO: 220, a CDR2 comprising the amino acid sequence set forth in SEQ ID NO:221 and a CDR3 comprising the amino acid sequence set forth in SEQ ID NO: 222; and a light chain variable region comprising a CDR1 comprising the amino acid sequence set forth in SEQ ID NO: 223, a CDR2 comprising the amino acid sequence set forth in SEQ ID NO:224 and a CDR3 comprising the amino acid sequence set forth in SEQ ID NO:225.

2. The CAR of claim 1, wherein the extracellular antigen-binding domain of the CAR binds to the GPRC5D with a binding affinity ($K_d$) of from about $1\times10^{-9}$ M to about $3\times10^{-6}$M.

3. The CAR of claim 1, wherein the GPRC5D is a human GPRC5D.

4. The CAR of claim 3, wherein the extracellular antigen-binding domain binds to the human GPRC5D with a binding affinity ($K_d$) of from about $1\times10^{-9}$ M to about $1\times10^{-8}$ M.

5. The CAR of claim 1, wherein the extracellular antigen-binding domain is a single-chain variable fragment (scFv).

6. The CAR of claim 5, wherein the extracellular antigen-binding domain is a human scFv.

7. The CAR of claim 1, wherein the extracellular antigen-binding domain is a Fab.

8. The CAR of claim 1, wherein the heavy chain variable region sequence comprises the amino acid sequence set forth in SEQ ID NO: 65.

9. The CAR of claim 1, wherein the light chain variable region sequence comprises the amino acid sequence set forth in SEQ ID NO: 66.

10. The CAR of claim 1, wherein:

the heavy chain variable region comprises an amino acid sequence that is at least about 90% homologous to the amino acid sequence set forth in SEQ ID NO:65, and the light chain variable region comprises an amino acid sequence that is at least about 90% homologous to the amino acid sequence set forth in SEQ ID NO:66.

11. The CAR of claim 10, wherein the extracellular antigen-binding domain is a single-chain variable fragment (scFv).

12. The CAR of claim 1, wherein:

the heavy chain variable region comprises the amino acid sequence set forth in SEQ ID NO:65, and the light chain variable region comprises the amino acid sequence set forth in SEQ ID NO:66.

13. The CAR of claim 12, wherein the extracellular antigen-binding domain is a single-chain variable fragment (scFv).

14. The CAR of claim 1, wherein the extracellular antigen-binding domain comprises a human variable region framework region.

15. The CAR of claim 5, wherein the scFv comprises the amino acid sequence set forth in SEQ ID NO: 116.

16. The CAR of claim 1, wherein the extracellular antigen-binding domain binds to at least one of:

an epitope region comprising amino acids 15-23 of SEQ ID NO:97 and an epitope region comprising amino acids 230-243 of SEQ ID NO:97.

17. The CAR of claim 1, wherein the transmembrane domain comprises a transmembrane domain of a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide that is not based on a protein associated with the immune response, or a combination thereof.

18. The CAR of claim 17, wherein the transmembrane domain comprises a transmembrane domain of a CD8 polypeptide or a CD28 polypeptide.

19. The CAR of claim 1, wherein the intracellular signaling domain comprises a signaling domain of a CD3ζ polypeptide.

20. The CAR of claim 19, wherein the intracellular signaling domain further comprises at least one co-stimulatory signaling region.

21. The CAR of claim 12, wherein the intracellular signaling domain comprises a signaling domain of a CD3ζ polypeptide.

22. The CAR of claim 21, wherein the intracellular signaling domain further comprises at least one co-stimulatory signaling region.

23. The CAR of claim 20, wherein the at least one co-stimulatory signaling region comprises an intracellular signaling region of a CD28 polypeptide, a 4-1BB polypeptide, an OX40 polypeptide, an ICOS polypeptide, a DAP-10 polypeptide, or a combination thereof.

24. The CAR of claim 23, wherein the at least one co-stimulatory signaling region comprises an intracellular signaling region of a CD28 polypeptide or a 4-1BB polypeptide.

25. The CAR of claim 22, wherein the at least one co-stimulatory signaling region comprises an intracellular signaling region of a CD28 polypeptide or a 4-1BB polypeptide.

26. The CAR of claim 20, wherein (a) the transmembrane domain comprises a transmembrane domain of a CD28 polypeptide, and the intracellular signaling domain comprises a signaling domain of a CD3ζ polypeptide and at least one co-stimulatory signaling region that comprises an intracellular signaling region of a CD28 polypeptide; or (b) the transmembrane domain comprises a transmembrane domain of a CD8 polypeptide, and the intracellular signaling domain comprises a signaling domain of a CD3ζ polypeptide and at least one co-stimulatory signaling region that comprises an intracellular signaling region of a 4-1BB polypeptide.

27. The CAR of claim 1, wherein (a) the transmembrane domain comprises a transmembrane domain of a CD28 polypeptide, and the intracellular signaling domain comprises a signaling domain of a CD3ζ polypeptide and at least one co-stimulatory signaling region that comprises an intracellular signaling region of a 4-1BB polypeptide.

28. The CAR of claim 27, wherein the extracellular antigen-binding domain is a single-chain variable fragment (scFv).

29. The CAR of claim 12, wherein (a) the transmembrane domain comprises a transmembrane domain of a CD28 polypeptide, and the intracellular signaling domain comprises a signaling domain of a CD3ζ polypeptide and at least one co-stimulatory signaling region that comprises an intracellular signaling region of a CD28 polypeptide; or (b) the transmembrane domain comprises a transmembrane domain of a CD8 polypeptide, and the intracellular signaling domain comprises a signaling domain of a CD3ζ polypeptide and at least one co-stimulatory signaling region that comprises an intracellular signaling region of a 4-1BB polypeptide.

30. The CAR of claim 29, wherein the extracellular antigen-binding domain is a single-chain variable fragment (scFv).

31. An immunoresponsive cell comprising the CAR of claim 1.

32. The immunoresponsive cell of claim 31, wherein the immunoresponsive cell is further transduced with (a) at least one co-stimulatory ligand such that the immunoresponsive cell expresses the at least one co-stimulatory ligand; and/or (b) at least one cytokine such that the immunoresponsive cell secretes the at least one cytokine.

33. The immunoresponsive cell of claim 31, wherein the immunoresponsive cell is selected from the group consisting of a T cell, a Natural Killer (NK) cell, a cytotoxic T lymphocyte (CTL), a regulatory T cell, a human embryonic stem cell, a lymphoid progenitor cell, a T cell-precursor cell, and a pluripotent stem cell from which lymphoid cells may be differentiated.

34. A T cell, wherein the T cell comprises the CAR of claim 1.

35. An immunoresponsive cell, wherein the immunoresponsive cell comprises the CAR of claim 27.

36. A T cell, wherein the T cell comprises the CAR of claim 27.

37. An immunoresponsive cell, wherein the immunoresponsive cell comprises the CAR of claim 29.

38. A T cell, wherein the T cell comprises the CAR of claim 29.

39. A composition comprising an effective amount of the immunoresponsive cells of claim 31.

40. A composition comprising an effective amount of the T cells of claim 34.

41. The composition of claim 39, which is a pharmaceutical composition that further comprises a pharmaceutically acceptable excipient.

42. A kit for treating a neoplasia, comprising the immunoresponsive cell of claim 31 and written instructions for using the immunoresponsive cells for treating a subject having a neoplasia selected from multiple myeloma and Waldenstrom's Macroglobulinemia.

43. The CAR of claim 26, wherein the extracellular antigen-binding domain is a single-chain variable fragment (scFv).

44. The CAR of claim 12, wherein the transmembrane domain comprises a transmembrane domain of a CD28 polypeptide, and the intracellular signaling domain comprises a signaling domain of a CD3 polypeptide and at least one co-stimulatory signaling region that comprises an intracellular signaling region of a 4-1BB polypeptide.

45. The CAR of claim 44, wherein the extracellular antigen-binding domain is a single-chain variable fragment (scFv).

46. An immunoresponsive cell, wherein the immunoresponsive cell comprises the CAR of claim 44.

47. A T cell, wherein the T cell comprises the CAR of claim 44.

48. A composition comprising an effective amount of the immunoresponsive cells of claim 46.

49. A composition comprising an effective amount of the T cells of claim 47.

* * * * *

SEQUENCE LISTING

```
<160> NUMBER OF SEQ ID NOS: 445

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ser Glu Leu Lys Lys Pro Gly Ala
1               5                   10                  15

Ser Val Arg Val Ser Cys Thr Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Val Ile Asn Pro Asn Ala Gly Ser Thr Arg Tyr Ala Gln Lys Phe
    50                  55                  60

Gln Gly Arg Val Thr Met Ser Thr Asp Thr Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Gly Met Tyr Arg Ser Leu Leu Phe Tyr Asp Pro Trp Gly Gln
            100                 105                 110

Gly Thr Leu Val Thr Val Ser Ser
        115                 120


<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Leu Thr Gln Pro Pro Ser Val Ser Ala Ala Pro Gly Gln
1               5                   10                  15

Lys Val Thr Ile Pro Cys Ser Gly Ser Arg Ser Asn Val Gly Asn Tyr
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Phe Cys Gly Thr Trp Asp Gly Ser Leu
                85                  90                  95

Ser Ala His Val Phe Gly Thr Gly Thr Lys Val Thr Val Leu Gly
            100                 105                 110
```

<210> SEQ ID NO 3
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 3
caggtgcagc tggtgcagtc tgggtctgag ttgaagaagc ctggggcctc agtcagagtc 60
tcctgcacgg cttctggata caccttcacc agttactata tgcactgggt gcgacaggcc 120
cctggacaag ggcttgagtg gatgggagta atcaacccta atgctggcag cacaagatac 180
gcacagaaat tccagggcag agtcaccatg agcactgaca cgtccacgag cacagcctac 240
atggacctga gcagtctgag atctgaggac acggccgtgt attactgtgc gcgcggtatg 300
taccgttctc tgctgttcta cgatccgtgg ggtcaaggta ctctggtgac cgtctcctca 360

<210> SEQ ID NO 4
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
cagtctgtgt tgacgcagcc gccctcagtg tctgcggccc caggacagaa ggtcaccatc 60
ccctgctctg gaagccgttc caacgttggg aattattatg tgtcctggta ccagcaactc 120
ccaggaacag cccccaaact cctcatttat gacaataata agcgaccctc agggattcct 180
gaccgattct ctggctccaa gtctggcacg tcagccaccc tgggcatcac cggactccag 240
actggggacg aggccgatta tttctgcgga acatgggatg gcagcctgag tgcccatgtc 300
ttcggaactg ggaccaaggt caccgtccta ggt 333

<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 5

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Ala Pro Gly Lys Gly Leu Glu Trp Val
35 40 45

Ser Ala Ile Ser Gly Ser Gly Asn Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Ser Val Arg Tyr Thr Asp Ile Trp Gly Gln Gly Thr Leu Val
100 105 110

Thr Val Ser Ser
115

<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 6

Asn Phe Met Leu Thr Gln Pro His Ser Val Ser Glu Ser Pro Gly Lys
1 5 10 15

Thr Val Ser Ile Ser Cys Thr Arg Thr Ser Gly Ala Ile Ala Gly Ala
20 25 30

Tyr Val Gln Trp Phe Gln Gln Arg Pro Gly Ser Ala Pro Thr Thr Val
35 40 45

Ile Tyr Asp Asp Asn Lys Arg Pro Ser Gly Val Pro Asp Arg Phe Ser
50 55 60

Gly Ser Ile Asp Lys Ser Ser Asn Ser Ala Ser Leu Thr Ile Ser Gly
65 70 75 80

Leu Lys Thr Glu Asp Glu Ala Asp Tyr Tyr Cys Gln Ser Tyr Asp Tyr
85 90 95

Asp Ser Ser Asn Val Leu Phe Gly Gly Gly Thr Lys Leu Thr Val Leu
100 105 110

Gly

<210> SEQ ID NO 7
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
gaggtgcagc tggtggagtc tgggggaggc ttggtacagc ctggggggtc cctgagactc 60
tcctgtgcag cctctggatt cacctttagc aactatgcca tgagttgggt ccgccaggct 120
ccagggaagg gactggagtg ggtctcagct attagtggta gtggtaacac atactacgca 180
gactccgtga agggccggtt caccatctcc agagacaatt ccaagaacac gctgtatctg 240
caaatgaaca gcctgagagc cgaggacacg gccgtatatt actgtgcgcg cggttctgtt 300
cgttacactg atatctgggg tcaaggtact ctggtgaccg tctcctca 348

<210> SEQ ID NO 8
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
aattttatgc tgactcagcc ccactcagtg tcggagtctc cggggaagac ggtaagcatc 60
tcctgcaccc gcaccagtgg cgccattgcc ggcgcctatg tgcagtggtt ccagcagcgc 120
ccgggcagtg cccccaccac tgtgatctat gacgataaca aaagaccctc tggggtccct 180
gatcggttct ctgggtccat cgacaagtcc tccaactctg cctccctcac catctctgga 240
ctgaagactg aggacgaggc tgactattat tgtcagtctt atgattatga tagcagcaat 300
gtgctattcg gcggagggac caagctgacc gtcctaggt 339

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Glu Val Gln Leu Val Gln Ser Gly Gly Gly Leu Val Gln Pro Gly Gly
1 5 10 15

Ser Leu Arg Leu Ser Cys Ala Thr Ser Gly Phe Thr Phe Asn Asn Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Ala Asp Ser Val
50 55 60

Arg Gly Arg Phe Thr Ile Ser Arg Asp Asn Ala Lys Asn Ser Leu Ser
65 70 75 80

Leu Gln Leu Asn Asn Leu Arg Ala Glu Asp Thr Ala Val Tyr Tyr Cys
85 90 95

Ala Arg Ser Met Ser Thr Ala Trp Gly Tyr Asp Glu Trp Gly Gln Gly
100 105 110

Thr Leu Val Thr Val Ser Ser
115

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Ala Asp Phe Ala Thr Tyr Tyr Cys Gln Gln Ser Tyr Ser Val Pro Tyr
85 90 95

Thr Phe Gly Gln Gly Thr Lys Leu Glu Ile Lys Arg
100 105

<210> SEQ ID NO 11
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
gaggtgcagc tggtgcagtc tgggggaggc ttggtccagc ctgggggtc cctgagactc 60 tcctgtgcaa cctctggatt cacctttaat aactattgga tgagttgggt ccgccaggct 120
ccagggaagg ggctggagtg ggtggccaac ataaagcaag atggaagtga gaaatactac 180
gcggactctg tgaggggccg attcaccatc tccagagaca acgccaagaa ctcactgtct 240
ctgcaattga acaacctgag agccgaggac acggccgtgt attactgtgc gcgctctatg 300
tctactgctt ggggttacga tgaatggggt caaggtactc tggtgaccgt ctcctca 357

<210> SEQ ID NO 12
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
gacatccagt tgacccagtc tccatcctcc ctgtctgcat ctgtcggaga cagagtcacc 60
atcacttgcc gggcaagtca gagcattagc agctatttaa attggtatca acagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gcagattttg caacttacta ctgtcaacag agttacagtg tcccgtacac ttttggccag 300
gggaccaagc tggagatcaa acgt 324

<210> SEQ ID NO 13
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Arg Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Ser Ser Arg Trp Gly Gly Trp Thr Gly Asp Tyr Trp Gly
100 105 110

Gln Gly Thr Leu Val Thr Val Ser Ser
115 120

<210> SEQ ID NO 14
<211> LENGTH: 111
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 14

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Phe Val Ser Trp Tyr Gln Gln His Pro Gly Lys Ala Pro Lys Val
35 40 45

Met Ile Tyr Asp Val Ser Lys Arg Pro Ser Gly Ile Ser Asn Arg Phe
50 55 60

Ser Gly Ser Lys Ser Gly Asn Thr Ala Ser Leu Thr Ile Ser Gly Leu
65 70 75 80

Gln Val Glu Asp Glu Ala Glu Tyr Tyr Cys Ser Ser Tyr Thr Ser Thr
85 90 95

Arg Thr Val Ile Phe Ala Gly Gly Thr Lys Val Thr Val Leu Gly
100 105 110

<210> SEQ ID NO 15
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
caggtgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaaggtac 180
gcacagaagt tccagggcag agtcaccatg accagggaca cgtcaacgag cacagtctac 240
atggagctga gcagcctgag atctgaggac acggccgtgt attactgtgc gcgcggttct 300
tctcgctggg gtggttggac tggtgattac tggggtcaag gtactctggt gaccgtctcc 360
tca 363

<210> SEQ ID NO 16
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16
caatctgccc tgactcagcc tgcctccgtg tctgggtctc ctggacagtc gatcaccatc 60
tcctgcactg gaaccagcag tgacgttggt ggttataact ttgtctcctg gtaccaacag 120
cacccaggca aagcccccaa agtcatgatt tatgatgtca gtaagcggcc ctcagggatt 180
tctaatcgct tctctggctc caagtctggc aacacggcct ccctgaccat ctctgggctc 240
caggttgagg acgaggctga atattactgc agctcatata caagcactag aactgtgata 300
ttcgccggag ggaccaaggt caccgtccta ggt 333

<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Glu Val Gln Leu Val Glu Thr Gly Gly Gly Leu Val Gln Pro Gly Gly
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Lys Ser Ser Lys Asp His Trp Gly Gln Gly Thr Leu
            100                 105                 110

Val Thr Val Ser Ser
        115
```

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (37)..(37)
<223> OTHER INFORMATION: Any amino acid

<400> SEQUENCE: 18

```
Gln Ser Val Leu Thr Gln Pro Pro Ser Leu Ser Gly Ala Pro Gly Gln
1               5                   10                  15

Arg Val Thr Ile Ser Cys Ser Gly Ser Arg Ser Asn Ile Gly Thr Asn
            20                  25                  30

Tyr Val Ser Trp Xaa Gln Gln Leu Pro Gly Thr Ala Pro Lys Leu Leu
        35                  40                  45

Ile Tyr Arg Asn His Gln Trp Pro Ser Gly Val Pro Asp Arg Phe Thr
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Asn Leu
                85                  90                  95

Ser Gly Val Val Phe Gly Gly Gly Thr Lys Leu Thr Val Leu Gly
            100                 105                 110
```

<210> SEQ ID NO 19
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
gaggtgcagc tggtggagac tgggggaggc ttggtacagc ctggggggtc cctgagactc     60
```

-continued

```
tcctgtgcag cctctggatc cacctttagc agctatgcca tgagctgggt ccgccaggct    120

ccagggaagg ggctggagtg ggtctcagct attagtggtc gtggtcgtag cacatactac    180

gcagactccg tgaagggccg gttcaccatc tccagagaca attccaagaa cacgctgtat    240

ctgcaaatga acagcctgag agccgaggac acggccgtat attactgtgc gcgctactac    300

aaatcttcta aagatcattg ggtcaaggt actctggtga ccgtctcctc a              351
```

```
<210> SEQ ID NO 20
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (109)..(109)
<223> OTHER INFORMATION: a, c, t, g, unknown or other

<400> SEQUENCE: 20

cagtctgtgt tgacgcagcc gccctcactg tctggggccc cagggcagag ggtcaccatc     60

tcttgttccg gaagcaggtc caacatcgga actaattatg tatcctggna ccagcaactc    120

ccaggaacgg cccccaaact cctcatctat aggaatcatc agtggccctc aggggtccct    180

gaccgattca ctggctccaa gtctggcacc tcagcctccc tggccatcag tgggctccgg    240

tccgaggatg aggctgatta ctactgtgca gcatgggatg acaatttgag tggtgtggtg    300

ttcggcggag ggaccaagct gaccgtccta ggt                                 333
```

```
<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Gln Arg Pro Gly Ala
1               5                   10                  15

Ser Val Arg Val Ser Cys Lys Ala Ile Ala Tyr Thr Phe Thr Asp Tyr
            20                  25                  30

Tyr Ile His Trp Val Arg Gln Ala Pro Gly Gln Gly Pro Glu Trp Met
        35                  40                  45

Gly Trp Ile Asn Pro Lys Ser Gly Arg Thr Gln Tyr Ala Pro Lys Phe
    50                  55                  60

Gln Asp Arg Val Thr Leu Ala Arg Glu Thr Pro Ile Ser Thr Ala Ser
65                  70                  75                  80

Met Glu Leu Arg Gly Leu Thr Ser Asp Asp Thr Ala Val Tyr Tyr Cys
                85                  90                  95

Ala Arg Val Tyr Gly Tyr Ser Arg Trp Ser Gly Phe Asp Leu Trp Gly
            100                 105                 110

Gln Gly Thr Leu Val Thr Val Ser Ser
        115                 120
```

```
<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 22

Gln Ala Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Tyr Val Tyr Trp Tyr Gln Gln Leu Pro Gly Thr Ala Pro Lys Leu Leu
35 40 45

Ile Tyr Arg Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Ala Ala Trp Asp Asp Ser Leu
85 90 95

Ser Gly Tyr Val Phe Gly Thr Gly Thr Lys Val Thr Val Leu Gly
100 105 110

<210> SEQ ID NO 23
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23
caggtccagc tggtgcagtc tggggctgag gtgcagaggc ctggggcctc agtgagggtc 60
tcctgcaagg ctattgcgta caccttcacc gactactata tccactgggt gcgacaggcc 120
cctggacaag ggcctgagtg gatggggtgg atcaacccta aaagtggtcg cacacagtat 180
gcaccgaagt ttcaagacag ggtcaccctg gccagggaga cgcccatcag cacagcctcc 240
atggagctgc gcggactgac atctgacgac acggccgtgt attactgtgc gcgcgtttac 300
ggttactctc gttggtctgg tttcgatctg tggggtcaag gtactctggt gaccgtctcc 360
tca 363

<210> SEQ ID NO 24
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24
caggctgtgc tgactcagcc accctcagcg tctgggaccc ccgggcagag ggtcaccatc 60
tcttgttctg gaagcagctc caacatcgga agtaattatg tatactggta ccagcagctc 120
ccaggaacgg cccccaaact cctcatctat aggaataatc agcggccctc aggggtccct 180
gaccgattct ctggctccaa gtctggcacc tcagcctccc tggccatcag tgggctccgg 240
tccgaggatg aggctgatta ttactgtgca gcatgggatg acagcctgag tggttatgtc 300
ttcggaactg ggaccaaggt caccgtccta ggt 333

<210> SEQ ID NO 25
<211> LENGTH: 124
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 25

```
Gln Val Gln Leu Val Gln Ser Gly Ala Glu Val Lys Gln Pro Gly Ala
1               5                   10                  15

Ser Val Lys Val Ser Cys Gln Ala Ser Gly Tyr Thr Phe Thr Thr Tyr
            20                  25                  30

Tyr Met His Trp Val Arg Gln Ala Pro Gly Gln Gly Leu Glu Trp Met
        35                  40                  45

Gly Ile Ile Asn Pro Asn Gly Gly Gly Thr Phe Tyr Ala Gln Lys Phe
    50                  55                  60

Gln Asp Arg Val Thr Met Thr Arg Asp Thr Ser Thr Gly Thr Val Tyr
65                  70                  75                  80

Met Glu Leu Ser Ser Leu Arg Ser Asp Asp Thr Ala Val Tyr Tyr Cys
                85                  90                  95

Ala Arg Gly His Lys Val Tyr Lys Ser His Pro Thr Gly Gly Tyr Asp
            100                 105                 110

Arg Trp Gly Gln Gly Thr Leu Val Thr Val Ser Ser
        115                 120
```

<210> SEQ ID NO 26
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Arg Asp Val Gly Gly Tyr
            20                  25                  30

Asn Tyr Val Ser Trp Tyr Gln Gln Tyr Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Asp Phe Gly Thr Gly Thr Lys Val Thr Val Leu Gly
            100                 105                 110
```

<210> SEQ ID NO 27
<211> LENGTH: 372
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27

```
caggtgcagc tggtgcaatc tggggctgag gtgaagcagc ctggggcctc agtgaaggtt     60

tcctgccagg catctggata caccttcacc acttattata tgcactgggt gcgacaggcc    120

cctggacaag ggcttgagtg gatgggaata atcaacccta atggtggtgg cacattctac    180

gcacagaagt tccaggacag agtcaccatg accagggaca cgtccacggg cacagtctac    240
```

atggaactga gcagcctgag atctgacgac actgccgtgt attactgtgc gcgcggtcat 300
aaagtttaca aatctcatcc gactggtggt tacgatcgtt ggggtcaagg tactctggtg 360
accgtctcct ca 372

<210> SEQ ID NO 28
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28
caatctgccc tgactcagcc tgcctccgtg tctgggtctc ctggacagtc gatcaccatc 60
tcctgcactg gaaccagccg tgacgttggt ggttataact atgtctcctg gtaccaacag 120
tacccaggca aagcccccaa actcatgatt tatgaggtca gtaagcggcc ctcaggggtt 180
tctaatcgct tctctggctc caagtctggc aacacggcct ccctgaccat ctctgggctc 240
caggctgagg acgaggctga ttattactgc agctcatata ccagtagcag cactttagac 300
ttcggaactg ggaccaaggt caccgtccta ggt 333

<210> SEQ ID NO 29
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Glu Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Lys Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser His Val Ala Trp Ser Leu Leu Asp Tyr Trp Gly Gln Gly
100 105 110

Thr Leu Val Thr Val Ser Ser
115

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Ser Tyr Glu Leu Thr Gln Pro Pro Ser Ala Ser Gly Thr Pro Gly Gln
1 5 10 15

```
Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu Gly
            100                 105                 110
```

<210> SEQ ID NO 31
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
gaggtccagc tggtgcagtc tggggctgag gtgaagaagc ctgggtcctc ggtgaaggtc     60

tcctgcaagg cttctggagg caccttcagc agctatgcta tcagctgggt gcgacaggcc    120

cctggacaag ggcttgagtg gatgggaggg attatcccta tctttggtac agcaaaatat    180

gcacagaagt tccagggcag agtcacgatt accgcggacg aatccacgag cacagcctac    240

atggagctga gcagcctgag atctgaggac acggccgtgt attactgtgc gcgctctcat    300

gttgcttggt ctctgctgga ttactggggt caaggtactc tggtgaccgt ctcctca       357
```

<210> SEQ ID NO 32
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
tcctatgagc tgactcagcc accctcagcg tctgggaccc ccgggcagag ggtcaccatc     60

tcttgttctg gaagcagctc caacatcgga agtaattatg tatcctggta ccagcagctc    120

ccaggaacgg cccccaaact cctcatctat aggaataatc agcggccctc aggggtccct    180

gaccgattct ctggctccaa gtctggcacc tcagcctccc tggccatcag tgggctccgg    240

tccgaggatg aggctgatta ttactgtgca gcatgggatg acagcctgag tggtgtggta    300

ttcggcggag ggaccaagct gaccgtccta ggt                                 333
```

<210> SEQ ID NO 33
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
            20                  25                  30

Ala Ile Ser Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gln Ser Tyr Lys Gly Ser Gln Ser Asp Ser Trp Gly Gln
            100                 105                 110

Gly Thr Leu Val Thr Val Ser Ser
        115                 120
```

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly
            100                 105                 110
```

<210> SEQ ID NO 35
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
caggtgcagc tggtgcagtc tggggctgag gtgaagaagc ctgggtcctc agtgaaggtc     60

tcctgcaagg cttctggagg caccttcagc agctatgcta tcagctgggt gcgacaggcc    120

cctggacaag ggcttgagtg gatgggatgg atgaacccta acagtggtaa cacaggctat    180

gcacagaagt tccagggcag agtcaccatg accaggaaca cctccataag cacagcctac    240

atggagctga gcagcctgag atctgaggac acggccgtgt attactgtgc gcgctaccag    300

tcttacaaag gttctcagtc tgattcttgg ggtcaaggta ctctggtgac cgtctcctca    360
```

<210> SEQ ID NO 36
<211> LENGTH: 333
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 36

cagtctgtgt tgacgcagcc accctcagcg tctgggaccc ccgggcagag ggtcaccatc     60

tcttgttctg gaagcagctc caacatcgga agtaattatg tatactggta ccagcagctc    120

ccaggaacgg cccccaaact cctcatctat aggaataatc agcggccctc aggggtccct    180

gaccgattct ctggctccaa gtctggcacc tcagcctccc tggccatcag tgggctccgg    240

tccgaggatg aggctgatta ttactgtgca gcatgggatg acagcctgag tggttgggtg    300

ttcggcggag ggaccaagct gaccgtccta ggt                                 333


<210> SEQ ID NO 37
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Lys Lys Trp Ser Gly Glu Lys Trp Arg Arg Glu
            100                 105                 110

Asn Phe Asp Tyr Trp Gly Gln Gly Thr Leu Val Thr Val Ser Ser
        115                 120                 125


<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80
```

Gln Ala Glu Asp Glu Ala Asp Tyr Tyr Cys Ser Ser Tyr Thr Arg Ser
85 90 95

Ser Thr Glu Val Phe Gly Gly Gly Thr Lys Leu Thr Val Leu Gly
100 105 110

<210> SEQ ID NO 39
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39
gaggtccagc tggtacagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc gcgcggtggt 300
tctaaaaaat ggtctggtga aaaatggcgt cgtgaaaact tcgattactg gggtcaaggt 360
actctggtga ccgtctcctc a 381

<210> SEQ ID NO 40
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40
caatctgccc tgactcagcc tgcctccgtg tctgggtctc ctggacagtc gatcaccatc 60
tcctgcactg gaaccagcag tgacgttggt ggttataact atgtctcctg gtaccaacag 120
cacccaggca aagcccccaa actcatgatt tatgatgtca gtaagcggcc ctcaggggtt 180
tctaatcgct tctctggctc caagtctggc aacacggcct ccctgaccat ctctgggctc 240
caggctgagg acgaggctga ttattactgc agctcatata caagaagcag cactgaggta 300
ttcggcggag ggaccaagct gaccgtccta ggt 333

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Gln Met Gln Leu Val Gln Ser Gly Ala Glu Val Lys Lys Pro Gly Ala
1 5 10 15

Ser Val Lys Val Ser Cys Lys Ala Ser Glu Tyr Thr Phe Thr Arg His
20 25 30

Ile Leu His Trp Val Arg Gln Ala Pro Gly Gln Ser Leu Glu Trp Met
35 40 45

Gly Trp Ile Asn Pro Gly Asn Gly Asn Thr Lys Tyr Ser Gln Lys Phe
50 55 60

Gln Val Arg Val Thr Phe Thr Arg Asp Thr Ser Ala Ser Thr Val Tyr 65 70 75 80

Met Glu Leu Ser Ser Leu Arg Ser Glu Asp Thr Ala Val Tyr Tyr Cys
85 90 95

Ala Arg Leu Pro Asp Gln Trp Gly Gln Gly Thr Leu Val Thr Val Ser
100 105 110

Ser

<210> SEQ ID NO 42
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Ser Tyr Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Arg Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Ala Ala Trp Asp Asp Ser Leu
85 90 95

Ser Gly Leu Phe Gly Thr Gly Thr Lys Val Thr Val Leu Gly
100 105 110

<210> SEQ ID NO 43
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43
cagatgcagc tggtgcagtc tggggctgag gtgaagaagc ctggggcctc agtgaaggtt 60
tcctgcaagg cttctgaata caccttcact aggcatattc tacattgggt gcgccaggct 120
cccggacaaa gccttgagtg gatgggatgg atcaacccag gcaatggtaa tacaaaatat 180
tcacagaagt tccaggtcag agtcaccttt accagggaca catccgcgag cacagtctat 240
atggagctga gcagcctgag atctgaagac acggccgtgt attactgtgc gcgcctgccg 300
gatcagtggg gtcaaggtac tctggtgacc gtctcctca 339

<210> SEQ ID NO 44
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44
tcctatgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat aggaataatc agcggccctc aggggtccct 180
gaccgattct ctggctccaa gtctggcacc tcagcctccc tggccatcag tgggctccgg 240
tccgaggatg aggctgatta ttactgtgca gcatgggatg acagcctgag tggtctcttc 300
ggaactggga ccaaggtcac cgtcctaggt 330

<210> SEQ ID NO 45
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

Glu Val Gln Leu Val Glu Ser Gly Gly Gly Val Val Arg Pro Gly Gly
1 5 10 15

Ser Leu Arg Leu Ser Cys Ala Ala Ser Gly Phe Thr Phe Gly Asp Tyr
20 25 30

Gly Met Ser Trp Val Arg Gln Ala Pro Gly Lys Gly Leu Glu Trp Val
35 40 45

Ser Gly Ile Asn Trp Asn Gly Gly Ser Thr Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Ser Lys Gln Asp Tyr Trp Gly Gln Gly Thr Leu Val Thr Val
100 105 110

Ser Ser

<210> SEQ ID NO 46
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 46

Gln Ser Ala Leu Thr Gln Pro Pro Ser Ala Ser Gly Ser Pro Gly Gln
1 5 10 15

Ser Val Thr Ile Ser Cys Thr Gly Thr Ser Arg Asp Ala Gly Gly Tyr
20 25 30

Asn Tyr Phe Ser Trp Tyr Gln Gln His Pro Gly Lys Ala Pro Lys Leu
35 40 45

Leu Ile Tyr Glu Val Thr Lys Arg Pro Ser Gly Val Pro Asp Arg Phe
50 55 60

Ser Gly Ser Lys Ser Gly Lys Thr Ala Ser Leu Thr Val Ser Gly Leu
65 70 75 80

Gln Ala Asp Asp Glu Ala Val Tyr Tyr Cys Ser Ser Tyr Gly Gly Ser
85 90 95

Asn Asn Phe Arg Val Phe Gly Gly Gly Thr Lys Leu Thr Val Leu Gly
100 105 110

<210> SEQ ID NO 47
<211> LENGTH: 342
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 47
gaggtgcagc tggtggagtc tgggggaggt gtggtacggc ctgggggtc cctgagactc 60 tcctgtgcag cctctggatt cacctttggt gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccgtat attactgtgc gcgctctaaa 300
caggattact ggggtcaagg tactctggtg accgtctcct ca 342

<210> SEQ ID NO 48
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48
cagtctgccc tgactcagcc tccctccgcg tccgggtctc ctggacagtc agtcaccatc 60
tcctgcactg gaaccagcag ggacgctggt ggttataatt atttctcctg gtaccaacaa 120
cacccaggca aagcccccaa actcctgatt tatgaggtca ctaagcggcc ctcaggggtc 180
cctgatcgct tctctggctc caagtctggc aagacggcct ccctgaccgt ctctgggctc 240
caggctgacg atgaggctgt atattactgc agctcatatg gaggcagcaa caactttcgg 300
gtgttcggcg gagggaccaa gctgaccgtc ctaggt 336

<210> SEQ ID NO 49
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

Glu Val Gln Leu Val Glu Thr Gly Gly Asn Leu Val Gln Pro Gly Ala
1 5 10 15

Ser Leu Arg Leu Ser Cys Ala Ala Ser Gly Phe Ser Phe Ser Gly Thr
20 25 30

Ala Met His Trp Val Arg Gln Ala Pro Gly Lys Gly Leu Glu Trp Val
35 40 45

Ser Thr Ile Ser Ser Thr Gly Arg Ser Thr Tyr Tyr Arg Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Gly Glu Asp Thr Ala Val Tyr Tyr Cys
85 90 95

Ala Arg Val Ser Phe Asp Tyr Trp Gly Gln Gly Thr Leu Val Thr Val
100 105 110

Ser Ser

<210> SEQ ID NO 50
<211> LENGTH: 113

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

Gln Ser Val Val Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly Ser Tyr Val Phe Gly Thr Gly Thr Lys Leu Thr Val Leu
100 105 110

Gly

<210> SEQ ID NO 51
<211> LENGTH: 342
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51
gaggtgcagc tggtggagac tgggggaaac ttggtacagc cgggggcgtc cctgagactc 60
tcctgtgcag cctctggatt cagctttagt ggcactgcca tgcactgggt ccgccaggct 120
ccagggaagg ggctggaatg ggtctcgact attagtagta ctgggcgtag cacatactac 180
agagactccg tgaagggccg gttcaccatc tccagagaca attccaagaa cacgctgtat 240
ctgcaaatga acagcctgag aggcgaggac acggccgtat attactgtgc gcgcgtttct 300
ttcgattact ggggtcaagg tactctggtg accgtctcct ca 342

<210> SEQ ID NO 52
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52
cagtctgtcg tgacgcagcc gccctcagtg tctggggccc cagggcagag ggtcaccatc 60
tcctgcactg ggagcagctc caacatcggg gcaggttatg atgtacactg gtaccagcag 120
cttccaggaa cagcccccaa actcctcatc tatggtaaca gcaatcggcc ctcaggggtc 180
cctgaccgat tctctggctc caagtctggc acctcagcct ccctggccat cactgggctc 240
caggctgagg atgaggctga ttattactgc cagtcctatg acagcagcct gagtggctcc 300
tacgtcttcg gaactgggac caagctgacc gtcctaggt 339

<210> SEQ ID NO 53

<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Glu Val Gln Leu Val Glu Ser Gly Gly Ala Phe Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Thr Ile Ser Gly Arg Gly Arg Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr His Ala Gly Ala Phe Asp Leu Trp Gly Gln Gly Thr
            100                 105                 110

Leu Val Thr Val Ser Ser
        115
```

<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Gln Ser Val Val Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu Gly
            100                 105                 110
```

<210> SEQ ID NO 55
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
gaggtgcagc tggtggagtc tgggggagcc tttgtacagc ctgggggggtc cctgagactc     60

tcctgtgcag cctctggatt cacctttagc agctatgcca tgacctgggt ccgccaggct    120
```

ccagggaagg gcctggaatg ggtctcgact attagtggtc gtggtcgtag cacattctac 180
gcagactccg tgaagggccg gtttaccatc tccagagaca attccaagaa cacgctatat 240
ctgcaaatga acagtctgag agccgaggac acggccgtat attactgtgc gcgctactac 300
catgctggtg ctttcgatct gtggggtcaa ggtactctgg tgaccgtctc ctca 354

<210> SEQ ID NO 56
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 56
cagtctgtcg tgacgcagcc tgcctccgtg tctgggtctc ctggacagtc gatcaccatc 60
tcctgcactg gaaccagcag tgacgttggt ggttataact atgtctcctg gtaccaacag 120
cacccaggca aagcccccaa actcatgatt tatgatgtca gtaagcggcc ctcaggggtt 180
tctaatcgct tctctggctc caagtctggc aacacggcct ccctgaccat ctctgggctc 240
caggctgagg acgaggctga ttattactgc agctcatata caagcagcag cactttggta 300
ttcggcggag ggaccaagct gaccgtccta ggt 333

<210> SEQ ID NO 57
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 57

Gln Met Gln Leu Val Gln Ser Gly Ala Glu Val Lys Lys Pro Gly Ala
1 5 10 15

Ser Val Lys Val Ser Cys Lys Ala Ser Gly Tyr Thr Phe Asn Arg Tyr
20 25 30

Ala Ile Thr Trp Val Arg Gln Ala Pro Gly Gln Gly Leu Glu Trp Met
35 40 45

Gly Trp Ile Ser Ala Tyr Asn Gly Asn Ser His Tyr Ala Gln Lys Leu
50 55 60

Gln Gly Arg Val Thr Met Thr Thr Asp Thr Ser Thr Gly Thr Ala Tyr
65 70 75 80

Met Glu Leu Arg Arg Leu Arg Ser Asp Asp Thr Ala Val Tyr Tyr Cys
85 90 95

Ala Arg Met Ala Tyr Asp Ser Trp Gly Gln Gly Thr Leu Val Thr Val
100 105 110

Ser Ser

<210> SEQ ID NO 58
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 58

Gln Ser Val Leu Thr Gln Pro Ala Ser Val Ser Gly Ser Pro Gly Gln
1 5 10 15

```
Ser Leu Thr Ile Ser Cys Thr Gly Thr Ser Asn Asp Val Gly Ala Tyr
            20                  25                  30

Lys Tyr Val Ser Trp Tyr Gln Gln Tyr Pro Gly Lys Ala Pro Lys Leu
        35                  40                  45

Ile Leu Tyr Asp Val Phe Lys Arg Pro Ser Gly Val Ser Asn Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Phe Ser Leu Thr Ser Ser
                85                  90                  95

Asn Thr Tyr Val Phe Gly Thr Gly Thr Lys Val Thr Val Leu Gly
            100                 105                 110


<210> SEQ ID NO 59
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

cagatgcagc tggtgcagtc tggagctgag gtgaagaagc ctggggcctc agtgaaggtc      60

tcctgcaagg cttctggtta cacctttaac agatatgcta tcacctgggt gcgacaggcc     120

cctggacaag gccttgagtg gatgggatgg atcagcgctt acaatggtaa ttcacactat     180

gcacagaagc tccagggcag agtcaccatg accacagaca catccacggg cacagcctat     240

atggagctga ggaggctgag atctgacgac acggccgtgt attactgtgc gcgcatggct     300

tacgattctt ggggtcaagg tactctggtg accgtctcct ca                        342


<210> SEQ ID NO 60
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

cagtctgtgt tgacgcagcc tgcctccgtg tctgggtctc ctggacagtc gctcaccatc      60

tcctgcactg gaaccagcaa tgacgttggt gcttataagt atgtctcctg gtatcaacag     120

tacccaggca aagcccccaa actcatactt tatgatgtct ttaagcggcc ctcaggggtc     180

tctaatcgct tctctggctc caagtctgac aacacggcct ccctgaccat ctctgggctc     240

caggctgagg acgaggctga ttattactgc ttctcactta caagcagtaa cacttatgtc     300

ttcggaactg ggaccaaggt caccgtccta ggt                                  333


<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Glu Ser Gly Gly Gly Leu Val Lys Pro Gly Gly
1               5                   10                  15
```

-continued

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Lys Ala Tyr Asp Gln Trp Gly Gln Gly Thr Leu
            100                 105                 110

Val Thr Val Ser Ser
        115

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Val Gly Gly Asn
            20                  25                  30

Tyr Val Phe Trp Tyr Gln Gln Val Pro Gly Ala Thr Pro Lys Leu Leu
        35                  40                  45

Ile Tyr Arg Ser Asn Gln Arg Pro Ser Gly Val Pro Asp Arg Phe Ala
    50                  55                  60

Gly Ser Lys Ser Gly Ser Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Phe Val Phe Gly Thr Gly Thr Lys Val Thr Val Leu Gly
            100                 105                 110

<210> SEQ ID NO 63
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gaggtgcagc tggtggagtc tgggggaggc ttggtcaagc ctggagggtc cctgagactc     60
tcctgtgcag cctctggatt caccttcagt gactactaca tgagctggat ccgccaggct    120
ccagggaagg ggctggagtg ggtttcatac attagtagta gtggtagtac catatactac    180
gcagactctg tgaagggccg attcaccatc tccagggaca acgccaagaa ctcactgtat    240
ctgcaaatga acagcctgag agccgaggac acggccgtat attactgtgc gcgcggttac    300
ggtaaagctt acgatcagtg gggtcaaggt actctggtga ccgtctcctc a             351

<210> SEQ ID NO 64
<211> LENGTH: 333

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 64
cagtctgtgt tgactcagcc accctcagcg tctgggaccc ccggacagag ggtcaccatc 60
tcttgttctg gaagcaggtc caacgtagga ggtaattatg tattttggta ccagcaagtc 120
cccggagcga cccccaaact cctcatctat aggagtaatc agcggccctc gggggtccct 180
gaccgattcg ctggctccaa gtctggctcc tcagcctccc tggccatcag tggactccgg 240
tccgaggatg aggctgatta ttactgtgca acatgggatg acagcctgag tggttttgtc 300
ttcggaactg ggaccaaggt caccgtccta ggt 333

<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

Gln Val Gln Leu Val Glu Ser Gly Gly Gly Leu Val His Pro Gly Gly
1 5 10 15

Ser Leu Arg Leu Ser Cys Ala Ala Ser Gly Phe Thr Phe Arg Ser His
20 25 30

Ser Met Asn Trp Val Arg Gln Ala Pro Gly Lys Gly Leu Glu Trp Val
35 40 45

Ser Ser Ile Ser Ser Asp Ser Thr Tyr Thr Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Ser Gly Gly Gln Trp Lys Tyr Tyr Asp Tyr Trp Gly Gln Gly
100 105 110

Thr Leu Val Thr Val Ser Ser
115

<210> SEQ ID NO 66
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 66

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu 65 70 75 80

Asp Glu Ala Asp Tyr Tyr Cys Asn Ser Arg Asp Ser Ser Gly Asn Pro
85 90 95

Pro Val Val Phe Gly Gly Gly Thr Lys Leu Thr Val Leu Gly
100 105 110

<210> SEQ ID NO 67
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67
caggtgcagc tggtggagtc tgggggaggc ctggtccacc ctgggggtc cctgagactc 60 tcctgtgcag cctctggatt caccttcaga agccatagca tgaactgggt ccgccaggct 120
ccagggaagg ggctggagtg ggtctcatcc attagtagtg atagtactta cacatactac 180
gcagactcag tgaagggccg attcaccatc tccagagaca acgccaagaa ctcactgtat 240
ctgcaaatga acagcctgag agccgaggac acggccgtat attactgtgc gcgctctggt 300
ggtcagtgga aatactacga ttactggggt caaggtactc tggtgaccgt ctcctca 357

<210> SEQ ID NO 68
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68
tcttctgagc tgactcagga ccctgctgtg tctgtggcct tgggacagac agtcaggatc 60
acatgccaag gagacagcct cagaagctat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcccgg gacagcagtg gtaacccccc tgtggtattc 300
ggcggaggga ccaagctgac cgtcctaggt 330

<210> SEQ ID NO 69
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Glu Val Gln Leu Val Glu Ser Gly Gly Gly Leu Ile Gln Pro Gly Gly
1 5 10 15

Ser Leu Arg Leu Ser Cys Ala Ala Ser Gly Phe Thr Phe Ser Asn Tyr
20 25 30

Ala Met Asn Trp Val Arg Gln Ala Pro Gly Lys Gly Leu Glu Trp Val
35 40 45

Ser Thr Ile Asn Gly Arg Gly Ser Ser Thr Ile Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Thr Tyr Tyr Cys
85 90 95

Ala Arg Tyr Ile Ser Arg Gly Leu Gly Asp Ser Trp Gly Gln Gly Thr
100 105 110

Leu Val Thr Val
115

<210> SEQ ID NO 70
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Gln Ser Val Val Thr Gln Pro Pro Ser Met Ser Ala Ala Pro Gly Gln
1 5 10 15

Gln Val Thr Ile Ser Cys Ser Gly Gly Asn Ser Asn Ile Glu Arg Asn
20 25 30

Tyr Val Ser Trp Tyr Leu Gln Leu Pro Gly Thr Ala Pro Lys Leu Val
35 40 45

Ile Phe Asp Asn Asp Arg Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asp Tyr Tyr Cys Gly Thr Trp Asp Ser Ser Leu
85 90 95

Arg Gly Trp Val Phe Gly Gly Gly Thr Lys Leu Thr Val Leu Gly
100 105 110

<210> SEQ ID NO 71
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71
gaggtgcagc tggtggagtc cgggggaggc ttgatacagc ctgggggtc cctgagactc 60 tcctgtgcag cctctggatt cacctttagc aactatgcca tgaactgggt ccgccaggct 120
ccagggaagg ggctggagtg ggtctcaact attaatggtc gtggtagtag tacaatctac 180
gcagactccg tgaagggccg gttcaccatc tccagagaca attccaagaa cacgctgtat 240
ctgcaaatga acagcctgag agccgaggac acagccacgt attactgtgc gcgctacatc 300
tctcgtggtc tgggtgattc ttggggtcaa ggtactctgg tgaccgtctc ctca 354

<210> SEQ ID NO 72
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72
cagtctgtcg tgacgcagcc gccctcaatg tctgcggccc caggacagca agtcaccatc 60
tcctgctctg gaggcaactc caacattgag agaaattatg tatcctggta cctccagctc 120
cctggaacag cccccaaact cgtcattttt gacaatgata ggcgaccctc agggattcct 180
gaccgattct ctggctccaa gtctggcacg tcagccaccc tgggcatcac cggactccag 240
actggggacg aggccgatta ttactgcgga acatgggata gcagcctgag aggttgggtg 300
ttcggcggag ggaccaagct gaccgtccta ggt 333

<210> SEQ ID NO 73
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 73

Gln Met Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Ala Gly Met Gly Met Asp Thr Trp Gly Gln Gly Thr Leu Val
100 105 110

Thr Val Ser Ser
115

<210> SEQ ID NO 74
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

Gln Ser Ala Leu Thr Gln Pro Pro Ser Ala Ser Gly Ser Pro Gly Gln
1 5 10 15

Ser Val Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Tyr Cys Ser Ser Tyr Ala Gly Ser
85 90 95

Asn Thr Leu Val Phe Gly Gly Gly Thr Lys Leu Thr Val Leu Gly
100 105 110

<210> SEQ ID NO 75
<211> LENGTH: 348

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 75
cagatgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc gcgcgctggt 300
atgggtatgg atacttgggg tcaaggtact ctggtgaccg tctcctca 348

<210> SEQ ID NO 76
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 76
cagtctgccc tgactcagcc tccctccgcg tccgggtctc ctggacagtc agtcaccatc 60
tcctgcactg gaaccagcag tgacgttggt ggttataact atgtctcctg gtaccaacag 120
cacccaggca aagcccccaa actcatgatt tatgaggtca gtaagcggcc ctcaggggtc 180
cctgatcgct tctctggctc caagtctggc aacacggcct ccctgaccgt ctctgggctc 240
caggctgagg atgaggctga ttattactgc agctcatatg caggcagcaa caccttggtg 300
ttcggcggag ggaccaagct gaccgtccta ggt 333

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 77

Gln Val Gln Leu Val Gln Ser Gly Ala Glu Val Lys Lys Pro Gly Ala
1 5 10 15

Ser Val Lys Val Ser Cys Arg Ala Ser Gly Tyr Thr Phe Thr Ala Tyr
20 25 30

Ser Leu His Trp Val Arg Gln Ala Pro Gly Gln Gly Leu Glu Trp Met
35 40 45

Gly Trp Ile Asn Pro Ser Ser Gly Gly Ala Val Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Gly Leu Arg Ser Asp Asp Thr Ala Val Tyr Tyr Cys
85 90 95

Ala Arg Asn Val Gly Gly Gln Ala Asp Asp Trp Gly Gln Gly Thr Leu
100 105 110

Val Thr Val Ser Ser
115

<210> SEQ ID NO 78
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 78

Gln Ser Ala Leu Thr Gln Pro Pro Ser Ala Ser Gly Ser Pro Gly Gln
1 5 10 15

Ser Val Thr Ile Ser Cys Thr Gly Thr Ser Ser Asp Ile Gly Gly Tyr
20 25 30

Asn Tyr Val Ser Trp Tyr Gln Gln His Pro Gly Lys Ala Pro Lys Leu
35 40 45

Met Ile Tyr Glu Val Asn Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Tyr Cys Ala Ser Phe Ala Gly Arg
85 90 95

Lys Thr Leu Val Phe Gly Gly Gly Thr Lys Leu Thr Val Leu Gly
100 105 110

<210> SEQ ID NO 79
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 79
caggtgcagc tggtgcagtc tggggctgag gtgaagaagc ctggggcctc agtgaaggtc 60
tcctgcaggg cttctggata caccttcacc gcctactctt tacactgggt gcgacaggcc 120
cctggacaag ggcttgagtg gatgggatgg atcaacccta gcagtggtgg cgcagtttat 180
gcacagaaat ttcagggtag ggtcaccatg accagggaca cgtccatcag cacagcctac 240
atggagctga gtggcctgag atctgacgac acggccgtgt attactgtgc gcgcaacgtt 300
ggtggtcagg ctgatgactg gggtcaaggt actctggtga ccgtctcctc a 351

<210> SEQ ID NO 80
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 80
caatctgccc tgactcagcc tccctccgcg tccgggtctc ctggacagtc agtcaccatc 60
tcctgcactg gaaccagcag tgacattggt ggttataact atgtctcctg gtaccaacag 120
cacccaggca aagcccccaa actcatgatt tatgaggtca ataagcggcc ctcaggggtc 180
cctgatcgct tctcgggctc caagtctggc aacacggcct ccctgaccgt ctctgggctc 240
caggctgagg atgaggctga ttattactgc gcctcatttg cgggcaggaa gacattggtc 300
ttcggcggag ggaccaagct gaccgtccta ggt 333

<210> SEQ ID NO 81

<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 81

Gln Val Gln Leu Val Gln Ser Gly Ala Glu Val Lys Lys Pro Gly Ala
1 5 10 15

Ser Val Lys Val Ser Cys Arg Ala Ser Gly Tyr Thr Phe Thr Ala Tyr
20 25 30

Ser Leu His Trp Val Arg Gln Ala Pro Gly Gln Gly Leu Glu Trp Met
35 40 45

Gly Trp Ile Asn Pro Ser Ser Gly Gly Ala Val Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Gly Leu Arg Ser Asp Asp Thr Ala Val Tyr Tyr Cys
85 90 95

Ala Arg Asn Val Gly Gly His Ala Asp Asp Trp Gly Gln Gly Thr Leu
100 105 110

Val Thr Val Ser Ser
115

<210> SEQ ID NO 82
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 82

Gln Ser Ala Leu Thr Gln Pro Pro Ser Ala Ser Gly Ser Pro Gly Gln
1 5 10 15

Ser Val Thr Ile Ser Cys Thr Gly Thr Ser Thr Asp Ile Gly Gly Tyr
20 25 30

Asn Tyr Val Ser Trp Tyr Gln His His Pro Ser Lys Ala Pro Lys Leu
35 40 45

Met Ile Tyr Glu Val Asn Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Tyr Cys Ala Ser Phe Ala Gly Arg
85 90 95

Lys Thr Leu Val Phe Gly Gly Gly Thr Lys Leu Thr Val Leu Gly
100 105 110

<210> SEQ ID NO 83
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 83
caggtgcagc tggtgcagtc tggggctgag gtgaaaaagc ctggggcctc agtgaaagtc 60
tcctgcaggg cttctggata caccttcacc gcctactctt tacactgggt gcgacaggcc 120

```
cctggacaag ggcttgagtg gatgggatgg atcaacccta gcagtggtgg cgcagtttat    180

gcacagaaat ttcagggtag ggtcaccatg accagggaca cgtccatcag cacagcctac    240

atggagctga gtggcctgag atctgacgac acggccgtgt attactgtgc gcgcaacgtt    300

ggtggtcacg ctgatgactg gggtcaaggt actctggtga ccgtctcctc a             351
```

<210> SEQ ID NO 84
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
caatctgccc tgactcagcc tccctccgcg tccgggtctc ctggacagtc agtcaccatc     60

tcctgcactg gaaccagcac tgacattggt ggttataact atgtctcctg gtaccaacac    120

cacccaagca aagcccccaa actcatgatt tatgaggtca ataagcggcc ctcaggggtc    180

cctgatcgct tctcgggctc caagtctggc aacacggcct ccctgaccgt ctctgggctc    240

caggctgagg atgaggctga ttattactgc gcctcatttg cgggcaggaa gacattggtc    300

ttcggcggag ggaccaagct gaccgtccta ggt                                 333
```

<210> SEQ ID NO 85
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Gln Val Gln Leu Val Gln Ser Gly Gly Glu Val Lys Lys Pro Gly Ala
1               5                   10                  15

Ser Val Lys Val Ser Cys Lys Ala Ser Gly Phe Thr Phe Asn Thr Tyr
            20                  25                  30

Gly Ile Ser Trp Val Arg Gln Ala Pro Gly Gln Gly Leu Glu Trp Met
        35                  40                  45

Gly Trp Ile Ser Ala Asn Asn Gly His Thr Lys Ser Ala Gln Arg Phe
    50                  55                  60

Gln Asp Arg Val Ala Met Ala Thr Asp Thr Ser Thr Ser Thr Ala Tyr
65                  70                  75                  80

Met Glu Leu Arg Ser Leu Lys Phe Asp Asp Thr Ala Val Tyr Tyr Cys
                85                  90                  95

Ala Arg Gly Gly Tyr His His Gln Met Gln Arg Tyr Tyr Lys Ala Thr
            100                 105                 110

Ser Val Tyr Ser Asp Tyr Trp Gly Gln Gly Thr Leu Val Thr Val Ser
        115                 120                 125

Ser
```

<210> SEQ ID NO 86
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly
            100                 105                 110
```

<210> SEQ ID NO 87
<211> LENGTH: 387
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
caggtccagc tggtgcagtc tggaggtgag gtgaagaagc ctggggcctc agtgaaggtc     60

tcctgcaagg cttctggttt cacctttaac acctatggca tcagttgggt gcgacaggcc    120

cctggacaag ggcttgagtg gatgggatgg atcagcgcta acaatggtca cacaaagtct    180

gcacagaggt tccaggacag agtcgccatg gccacagaca catccacgag cacggcctac    240

atggagctga ggagcctgaa atttgacgac acggccgtgt attactgtgc gcgcggtggt    300

taccatcatc agatgcagcg gtactacaaa gctacttctg tttactctga ttactggggt    360

caaggtactc tggtgaccgt ctcctca                                        387
```

<210> SEQ ID NO 88
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

```
cagtctgtcg tgacgcagcc gccctcagtg tctgcggccc caggacagaa ggtcaccatc     60

tcctgctctg gaagcagctc caacattggg aataattatg tatcctggta ccagcaactc    120

ccaggaacag cccccaaact cctcatttat gacaataata agcgaccctc agggattcct    180

gaccgattct ctggctccaa gtctggcacg tctgccaccc tgggcatcac cggactccag    240

actggggacg aggccgatta ttactgcgga acatgggata gcagcctgag tggtgtggta    300

ttcggcggag ggaccaagct gaccgtccta ggt                                 333
```

<210> SEQ ID NO 89
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

Gln Met Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Ser Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Ala Gly Met Gly Met Asp Thr Trp Gly Gln Gly Thr Leu Val
100 105 110

Thr Val Ser Ser
115

<210> SEQ ID NO 90
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

Gln Ser Ala Leu Thr Gln Pro Pro Ser Ala Ser Gly Ser Pro Gly Gln
1 5 10 15

Ser Val Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Tyr Cys Ser Ser Tyr Ala Gly Ser
85 90 95

Asn Thr Leu Val Phe Gly Gly Gly Thr Lys Leu Thr Val Leu Gly
100 105 110

<210> SEQ ID NO 91
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91
cagatgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag ctcaagctac 180
gcacagaagt tccagggcag agtcaccatg accagggaca cgtccacgag cacagtctac 240
atggagctga gcagcctgag atctgaggac acggccgtgt attactgtgc gcgcgctggt 300

-continued atgggtatgg atacttgggg tcaaggtact ctggtgaccg tctcctca 348

<210> SEQ ID NO 92
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92
cagtctgccc tgactcagcc tccctccgcg tccgggtctc ctggacagtc agtcaccatc 60
tcctgcactg gaaccagcag tgacgttggt ggttataact atgtctcctg gtaccaacag 120
cacccaggca aagcccccaa actcatgatt tatgaggtca gtaagcggcc ctcaggggtc 180
cctgatcgct tctctggctc caagtctggc aacacggcct ccctgaccgt ctctgggctc 240
caggctgagg atgaggctga ttattactgc agctcatatg caggcagcaa caccttggtg 300
ttcggcggag ggaccaagct gaccgtccta ggt 333

<210> SEQ ID NO 93
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp Val Ile Ser Gly Phe Asp Ser Trp Gly Gln Gly Thr Leu
100 105 110

Val Thr Val Ser Ser
115

<210> SEQ ID NO 94
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln Ser Pro Gly Lys Ala Pro Arg Leu
35 40 45

```
Met Ile Tyr Gly Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Val
                85                  90                  95

Asn Asn Leu Met Phe Gly Gly Gly Thr Lys Leu Thr Val Leu Gly
            100                 105                 110


<210> SEQ ID NO 95
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

caggtgcagc tggtgcaatc tggggctgag gtgaagaagc ctggggcctc agtgaaggtt      60

tcctgcaagg catctggata caccttcacc agctactata tgcactgggt gcgacaggcc     120

cctggacaag ggcttgagtg gatgggaata atcaacccta gtggtggtag cacaagctac     180

gcacagaagt tccagggcag agtcaccatg accagggaca cgtccacgag cacagtctac     240

atggagctga gcagcctgag atctgaggac actgccgtgt attactgtgc gcgcgacgtt     300

atctctggtt tcgattcttg gggtcaaggt actctggtga ccgtctcctc a              351


<210> SEQ ID NO 96
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

cagtctgccc tgactcagcc tgcctccgtg tctgggtctc ctggacagtc gatcaccatc      60

tcctgcactg gaaccagcag tgacgttggt ggttataact atgtctcctg gtaccaacaa     120

tccccaggca aagcccccag actcatgatt tatggggtca gtaagcggcc ctctggggtc     180

cctgatcgct tctctggctc caagtctggc aacacggcct ccctgaccgt ctctgggctc     240

caggctgaag atgaggctga ttattactgc agctcatatg caggcgtcaa caatttaatg     300

ttcggcggag ggaccaagct gaccgtccta ggt                                  333


<210> SEQ ID NO 97
<211> LENGTH: 345
<212> TYPE: PRT
<213> ORGANISM: Homo sapiens

<400> SEQUENCE: 97

Met Tyr Lys Asp Cys Ile Glu Ser Thr Gly Asp Tyr Phe Leu Leu Cys
1               5                   10                  15

Asp Ala Glu Gly Pro Trp Gly Ile Ile Leu Glu Ser Leu Ala Ile Leu
            20                  25                  30

Gly Ile Val Val Thr Ile Leu Leu Leu Leu Ala Phe Leu Phe Leu Met
        35                  40                  45

Arg Lys Ile Gln Asp Cys Ser Gln Trp Asn Val Leu Pro Thr Gln Leu
    50                  55                  60
```

```
Leu Phe Leu Leu Ser Val Leu Gly Leu Phe Gly Leu Ala Phe Ala Phe
65                  70                  75                  80

Ile Ile Glu Leu Asn Gln Gln Thr Ala Pro Val Arg Tyr Phe Leu Phe
                85                  90                  95

Gly Val Leu Phe Ala Leu Cys Phe Ser Cys Leu Leu Ala His Ala Ser
            100                 105                 110

Asn Leu Val Lys Leu Val Arg Gly Cys Val Ser Phe Ser Trp Thr Thr
        115                 120                 125

Ile Leu Cys Ile Ala Ile Gly Cys Ser Leu Leu Gln Ile Ile Ile Ala
    130                 135                 140

Thr Glu Tyr Val Thr Leu Ile Met Thr Arg Gly Met Met Phe Val Asn
145                 150                 155                 160

Met Thr Pro Cys Gln Leu Asn Val Asp Phe Val Val Leu Leu Val Tyr
                165                 170                 175

Val Leu Phe Leu Met Ala Leu Thr Phe Phe Val Ser Lys Ala Thr Phe
            180                 185                 190

Cys Gly Pro Cys Glu Asn Trp Lys Gln His Gly Arg Leu Ile Phe Ile
        195                 200                 205

Thr Val Leu Phe Ser Ile Ile Ile Trp Val Val Trp Ile Ser Met Leu
    210                 215                 220

Leu Arg Gly Asn Pro Gln Phe Gln Arg Gln Pro Gln Trp Asp Asp Pro
225                 230                 235                 240

Val Val Cys Ile Ala Leu Val Thr Asn Ala Trp Val Phe Leu Leu Leu
                245                 250                 255

Tyr Ile Val Pro Glu Leu Cys Ile Leu Tyr Arg Ser Cys Arg Gln Glu
            260                 265                 270

Cys Pro Leu Gln Gly Asn Ala Cys Pro Val Thr Ala Tyr Gln His Ser
        275                 280                 285

Phe Gln Val Glu Asn Gln Glu Leu Ser Arg Ala Arg Asp Ser Asp Gly
    290                 295                 300

Ala Glu Glu Asp Val Ala Leu Thr Ser Tyr Gly Thr Pro Ile Gln Pro
305                 310                 315                 320

Gln Thr Val Asp Pro Thr Gln Glu Cys Phe Ile Pro Gln Ala Lys Leu
                325                 330                 335

Ser Pro Gln Gln Asp Ala Gly Gly Val
            340                 345


<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Arg Gly Gly Gly Gly Ser Gly Gly Gly Gly Ser Gly Gly Gly Gly
1               5                   10                  15

Ser Leu Glu Met Ala
            20


<210> SEQ ID NO 99
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 99
tctagaggtg gtggtggtag cggcggcggc ggctctggtg gtggtggatc cctcgagatg 60
gcc 63

<210> SEQ ID NO 100
<211> LENGTH: 252
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 100

Gln Ser Val Leu Thr Gln Pro Pro Ser Val Ser Ala Ala Pro Gly Gln
1 5 10 15

Lys Val Thr Ile Pro Cys Ser Gly Ser Arg Ser Asn Val Gly Asn Tyr
20 25 30

Tyr Val Ser Trp Tyr Gln Gln Leu Pro Gly Thr Ala Pro Lys Leu Leu
35 40 45

Ile Tyr Asp Asn Asn Lys Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asp Tyr Phe Cys Gly Thr Trp Asp Gly Ser Leu
85 90 95

Ser Ala His Val Phe Gly Thr Gly Thr Lys Val Thr Val Leu Gly Ser
100 105 110

Arg Gly Gly Gly Gly Ser Gly Gly Gly Gly Ser Gly Gly Gly Gly Ser
115 120 125

Leu Glu Met Ala Gln Val Gln Leu Val Gln Ser Gly Ser Glu Leu Lys
130 135 140

Lys Pro Gly Ala Ser Val Arg Val Ser Cys Thr Ala Ser Gly Tyr Thr
145 150 155 160

Phe Thr Ser Tyr Tyr Met His Trp Val Arg Gln Ala Pro Gly Gln Gly
165 170 175

Leu Glu Trp Met Gly Val Ile Asn Pro Asn Ala Gly Ser Thr Arg Tyr
180 185 190

Ala Gln Lys Phe Gln Gly Arg Val Thr Met Ser Thr Asp Thr Ser Thr
195 200 205

Ser Thr Ala Tyr Met Asp Leu Ser Ser Leu Arg Ser Glu Asp Thr Ala
210 215 220

Val Tyr Tyr Cys Ala Arg Gly Met Tyr Arg Ser Leu Leu Phe Tyr Asp
225 230 235 240

Pro Trp Gly Gln Gly Thr Leu Val Thr Val Ser Ser
245 250

<210> SEQ ID NO 101
<211> LENGTH: 250
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 101

Asn Phe Met Leu Thr Gln Pro His Ser Val Ser Glu Ser Pro Gly Lys
1 5 10 15

Thr Val Ser Ile Ser Cys Thr Arg Thr Ser Gly Ala Ile Ala Gly Ala
20 25 30

Tyr Val Gln Trp Phe Gln Gln Arg Pro Gly Ser Ala Pro Thr Thr Val
35 40 45

Ile Tyr Asp Asp Asn Lys Arg Pro Ser Gly Val Pro Asp Arg Phe Ser
50 55 60

Gly Ser Ile Asp Lys Ser Ser Asn Ser Ala Ser Leu Thr Ile Ser Gly
65 70 75 80

Leu Lys Thr Glu Asp Glu Ala Asp Tyr Tyr Cys Gln Ser Tyr Asp Tyr
85 90 95

Asp Ser Ser Asn Val Leu Phe Gly Gly Gly Thr Lys Leu Thr Val Leu
100 105 110

Gly Ser Arg Gly Gly Gly Gly Ser Gly Gly Gly Gly Ser Gly Gly Gly
115 120 125

Gly Ser Leu Glu Met Ala Glu Val Gln Leu Val Glu Ser Gly Gly Gly
130 135 140

Leu Val Gln Pro Gly Gly Ser Leu Arg Leu Ser Cys Ala Ala Ser Gly
145 150 155 160

Phe Thr Phe Ser Asn Tyr Ala Met Ser Trp Val Arg Gln Ala Pro Gly
165 170 175

Lys Gly Leu Glu Trp Val Ser Ala Ile Ser Gly Ser Gly Asn Thr Tyr
180 185 190

Tyr Ala Asp Ser Val Lys Gly Arg Phe Thr Ile Ser Arg Asp Asn Ser
195 200 205

Lys Asn Thr Leu Tyr Leu Gln Met Asn Ser Leu Arg Ala Glu Asp Thr
210 215 220

Ala Val Tyr Tyr Cys Ala Arg Gly Ser Val Arg Tyr Thr Asp Ile Trp
225 230 235 240

Gly Gln Gly Thr Leu Val Thr Val Ser Ser
245 250

<210> SEQ ID NO 102
<211> LENGTH: 248
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 102

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Ala Asp Phe Ala Thr Tyr Tyr Cys Gln Gln Ser Tyr Ser Val Pro Tyr
85 90 95

Thr Phe Gly Gln Gly Thr Lys Leu Glu Ile Lys Arg Ser Arg Gly Gly
100 105 110

Gly Gly Ser Gly Gly Gly Gly Ser Gly Gly Gly Gly Ser Leu Glu Met

```
        115                 120                 125

Ala Glu Val Gln Leu Val Gln Ser Gly Gly Gly Leu Val Gln Pro Gly
    130                 135                 140

Gly Ser Leu Arg Leu Ser Cys Ala Thr Ser Gly Phe Thr Phe Asn Asn
145                 150                 155                 160

Tyr Trp Met Ser Trp Val Arg Gln Ala Pro Gly Lys Gly Leu Glu Trp
                165                 170                 175

Val Ala Asn Ile Lys Gln Asp Gly Ser Glu Lys Tyr Tyr Ala Asp Ser
            180                 185                 190

Val Arg Gly Arg Phe Thr Ile Ser Arg Asp Asn Ala Lys Asn Ser Leu
        195                 200                 205

Ser Leu Gln Leu Asn Asn Leu Arg Ala Glu Asp Thr Ala Val Tyr Tyr
    210                 215                 220

Cys Ala Arg Ser Met Ser Thr Ala Trp Gly Tyr Asp Glu Trp Gly Gln
225                 230                 235                 240

Gly Thr Leu Val Thr Val Ser Ser
                245


<210> SEQ ID NO 103
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Val
        35                  40                  45

Met Ile Tyr Asp Val Ser Lys Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Val Glu Asp Glu Ala Glu Tyr Tyr Cys Ser Ser Tyr Thr Ser Thr
                85                  90                  95

Arg Thr Val Ile Phe Ala Gly Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Thr Arg Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220
```

```
Val Tyr Tyr Cys Ala Arg Gly Ser Ser Arg Trp Gly Gly Trp Thr Gly
225                 230                 235                 240

Asp Tyr Trp Gly Gln Gly Thr Leu Val Thr Val Ser Ser
                245                 250


<210> SEQ ID NO 104
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Any amino acid

<400> SEQUENCE: 104

Gln Ser Val Leu Thr Gln Pro Pro Ser Leu Ser Gly Ala Pro Gly Gln
1               5                   10                  15

Arg Val Thr Ile Ser Cys Ser Gly Ser Arg Ser Asn Ile Gly Thr Asn
            20                  25                  30

Tyr Val Ser Trp Xaa Gln Gln Leu Pro Gly Thr Ala Pro Lys Leu Leu
        35                  40                  45

Ile Tyr Arg Asn His Gln Trp Pro Ser Gly Val Pro Asp Arg Phe Thr
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Asn Leu
                85                  90                  95

Ser Gly Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Glu Thr Gly Gly Gly Leu Val
    130                 135                 140

Gln Pro Gly Gly Ser Leu Arg Leu Ser Cys Ala Ala Ser Gly Ser Thr
145                 150                 155                 160

Phe Ser Ser Tyr Ala Met Ser Trp Val Arg Gln Ala Pro Gly Lys Gly
                165                 170                 175

Leu Glu Trp Val Ser Ala Ile Ser Gly Arg Gly Arg Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Tyr Tyr Lys Ser Ser Lys Asp His Trp Gly
225                 230                 235                 240

Gln Gly Thr Leu Val Thr Val Ser Ser
                245


<210> SEQ ID NO 105
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105
```

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Gln
    130                 135                 140

Arg Pro Gly Ala Ser Val Arg Val Ser Cys Lys Ala Ile Ala Tyr Thr
145                 150                 155                 160

Phe Thr Asp Tyr Tyr Ile His Trp Val Arg Gln Ala Pro Gly Gln Gly
                165                 170                 175

Pro Glu Trp Met Gly Trp Ile Asn Pro Lys Ser Gly Arg Thr Gln Tyr
            180                 185                 190

Ala Pro Lys Phe Gln Asp Arg Val Thr Leu Ala Arg Glu Thr Pro Ile
        195                 200                 205

Ser Thr Ala Ser Met Glu Leu Arg Gly Leu Thr Ser Asp Asp Thr Ala
    210                 215                 220

Val Tyr Tyr Cys Ala Arg Val Tyr Gly Tyr Ser Arg Trp Ser Gly Phe
225                 230                 235                 240

Asp Leu Trp Gly Gln Gly Thr Leu Val Thr Val Ser Ser
                245                 250


<210> SEQ ID NO 106
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Arg Asp Val Gly Gly Tyr
            20                  25                  30

Asn Tyr Val Ser Trp Tyr Gln Gln Tyr Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Asp Phe Gly Thr Gly Thr Lys Val Thr Val Leu Gly Ser
```

```
            100                 105                 110

Arg Gly Gly Gly Gly Ser Gly Gly Gly Gly Ser Gly Gly Gly Ser
        115                 120                 125

Leu Glu Met Ala Gln Val Gln Leu Val Gln Ser Gly Ala Glu Val Lys
    130                 135                 140

Gln Pro Gly Ala Ser Val Lys Val Ser Cys Gln Ala Ser Gly Tyr Thr
145                 150                 155                 160

Phe Thr Thr Tyr Tyr Met His Trp Val Arg Gln Ala Pro Gly Gln Gly
                165                 170                 175

Leu Glu Trp Met Gly Ile Ile Asn Pro Asn Gly Gly Gly Thr Phe Tyr
            180                 185                 190

Ala Gln Lys Phe Gln Asp Arg Val Thr Met Thr Arg Asp Thr Ser Thr
        195                 200                 205

Gly Thr Val Tyr Met Glu Leu Ser Ser Leu Arg Ser Asp Asp Thr Ala
    210                 215                 220

Val Tyr Tyr Cys Ala Arg Gly His Lys Val Tyr Lys Ser His Pro Thr
225                 230                 235                 240

Gly Gly Tyr Asp Arg Trp Gly Gln Gly Thr Leu Val Thr Val Ser Ser
                245                 250                 255


<210> SEQ ID NO 107
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Ser
        115                 120                 125

Leu Glu Met Ala Glu Val Gln Leu Val Gln Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Gly Ile Ile Pro Ile Phe Gly Thr Ala Lys Tyr
            180                 185                 190

Ala Gln Lys Phe Gln Gly Arg Val Thr Ile Thr Ala Asp Glu Ser Thr
        195                 200                 205
```

```
Ser Thr Ala Tyr Met Glu Leu Ser Ser Leu Arg Ser Glu Asp Thr Ala
    210                 215                 220

Val Tyr Tyr Cys Ala Arg Ser His Val Ala Trp Ser Leu Leu Asp Tyr
225                 230                 235                 240

Trp Gly Gln Gly Thr Leu Val Thr Val Ser Ser
                245                 250
```

<210> SEQ ID NO 108
<211> LENGTH: 252
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Trp Met Asn Pro Asn Ser Gly Asn Thr Gly Tyr
            180                 185                 190

Ala Gln Lys Phe Gln Gly Arg Val Thr Met Thr Arg Asn Thr Ser Ile
        195                 200                 205

Ser Thr Ala Tyr Met Glu Leu Ser Ser Leu Arg Ser Glu Asp Thr Ala
    210                 215                 220

Val Tyr Tyr Cys Ala Arg Tyr Gln Ser Tyr Lys Gly Ser Gln Ser Asp
225                 230                 235                 240

Ser Trp Gly Gln Gly Thr Leu Val Thr Val Ser Ser
                245                 250
```

<210> SEQ ID NO 109
<211> LENGTH: 259
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Arg Ser
85 90 95

Ser Thr Glu Val Phe Gly Gly Gly Thr Lys Leu Thr Val Leu Gly Ser
100 105 110

Arg Gly Gly Gly Gly Ser Gly Gly Gly Gly Ser Gly Gly Gly Gly Ser
115 120 125

Leu Glu Met Ala Glu Val Gln Leu Val Gln Ser Gly Ala Glu Val Lys
130 135 140

Lys Pro Gly Ala Ser Val Lys Val Ser Cys Lys Ala Ser Gly Tyr Thr
145 150 155 160

Phe Thr Ser Tyr Tyr Met His Trp Val Arg Gln Ala Pro Gly Gln Gly
165 170 175

Leu Glu Trp Met Gly Ile Ile Asn Pro Ser Gly Gly Ser Thr Ser Tyr
180 185 190

Ala Gln Lys Phe Gln Gly Arg Val Thr Met Thr Arg Asp Thr Ser Thr
195 200 205

Ser Thr Val Tyr Met Glu Leu Ser Ser Leu Arg Ser Glu Asp Thr Ala
210 215 220

Val Tyr Tyr Cys Ala Arg Gly Gly Ser Lys Lys Trp Ser Gly Glu Lys
225 230 235 240

Trp Arg Arg Glu Asn Phe Asp Tyr Trp Gly Gln Gly Thr Leu Val Thr
245 250 255

Val Ser Ser

<210> SEQ ID NO 110
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

Ser Tyr Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Arg Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Ala Ala Trp Asp Asp Ser Leu
85 90 95

-continued

Ser Gly Leu Phe Gly Thr Gly Thr Lys Val Thr Val Leu Gly Ser Arg
100 105 110

Gly Gly Gly Gly Ser Gly Gly Gly Gly Ser Gly Gly Gly Gly Ser Leu
115 120 125

Glu Met Ala Gln Met Gln Leu Val Gln Ser Gly Ala Glu Val Lys Lys
130 135 140

Pro Gly Ala Ser Val Lys Val Ser Cys Lys Ala Ser Glu Tyr Thr Phe
145 150 155 160

Thr Arg His Ile Leu His Trp Val Arg Gln Ala Pro Gly Gln Ser Leu
165 170 175

Glu Trp Met Gly Trp Ile Asn Pro Gly Asn Gly Asn Thr Lys Tyr Ser
180 185 190

Gln Lys Phe Gln Val Arg Val Thr Phe Thr Arg Asp Thr Ser Ala Ser
195 200 205

Thr Val Tyr Met Glu Leu Ser Ser Leu Arg Ser Glu Asp Thr Ala Val
210 215 220

Tyr Tyr Cys Ala Arg Leu Pro Asp Gln Trp Gly Gln Gly Thr Leu Val
225 230 235 240

Thr Val Ser Ser

<210> SEQ ID NO 111
<211> LENGTH: 247
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

Gln Ser Ala Leu Thr Gln Pro Pro Ser Ala Ser Gly Ser Pro Gly Gln
1 5 10 15

Ser Val Thr Ile Ser Cys Thr Gly Thr Ser Arg Asp Ala Gly Gly Tyr
20 25 30

Asn Tyr Phe Ser Trp Tyr Gln Gln His Pro Gly Lys Ala Pro Lys Leu
35 40 45

Leu Ile Tyr Glu Val Thr Lys Arg Pro Ser Gly Val Pro Asp Arg Phe
50 55 60

Ser Gly Ser Lys Ser Gly Lys Thr Ala Ser Leu Thr Val Ser Gly Leu
65 70 75 80

Gln Ala Asp Asp Glu Ala Val Tyr Tyr Cys Ser Ser Tyr Gly Gly Ser
85 90 95

Asn Asn Phe Arg Val Phe Gly Gly Gly Thr Lys Leu Thr Val Leu Gly
100 105 110

Ser Arg Gly Gly Gly Gly Ser Gly Gly Gly Gly Ser Gly Gly Gly Gly
115 120 125

Ser Leu Glu Met Ala Glu Val Gln Leu Val Glu Ser Gly Gly Gly Val
130 135 140

Val Arg Pro Gly Gly Ser Leu Arg Leu Ser Cys Ala Ala Ser Gly Phe
145 150 155 160

Thr Phe Gly Asp Tyr Gly Met Ser Trp Val Arg Gln Ala Pro Gly Lys
165 170 175

Gly Leu Glu Trp Val Ser Gly Ile Asn Trp Asn Gly Gly Ser Thr Gly
180 185 190

Tyr Ala Asp Ser Val Lys Gly Arg Phe Thr Ile Ser Arg Asp Asn Ala
195 200 205

Lys Asn Ser Leu Tyr Leu Gln Met Asn Ser Leu Arg Ala Glu Asp Thr
210 215 220

Ala Val Tyr Tyr Cys Ala Arg Ser Lys Gln Asp Tyr Trp Gly Gln Gly
225 230 235 240

Thr Leu Val Thr Val Ser Ser
245

<210> SEQ ID NO 112
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

Gln Ser Val Val Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly Ser Tyr Val Phe Gly Thr Gly Thr Lys Leu Thr Val Leu
100 105 110

Gly Ser Arg Gly Gly Gly Gly Ser Gly Gly Gly Gly Ser Gly Gly Gly
115 120 125

Gly Ser Leu Glu Met Ala Glu Val Gln Leu Val Glu Thr Gly Gly Asn
130 135 140

Leu Val Gln Pro Gly Ala Ser Leu Arg Leu Ser Cys Ala Ala Ser Gly
145 150 155 160

Phe Ser Phe Ser Gly Thr Ala Met His Trp Val Arg Gln Ala Pro Gly
165 170 175

Lys Gly Leu Glu Trp Val Ser Thr Ile Ser Ser Thr Gly Arg Ser Thr
180 185 190

Tyr Tyr Arg Asp Ser Val Lys Gly Arg Phe Thr Ile Ser Arg Asp Asn
195 200 205

Ser Lys Asn Thr Leu Tyr Leu Gln Met Asn Ser Leu Arg Gly Glu Asp
210 215 220

Thr Ala Val Tyr Tyr Cys Ala Arg Val Ser Phe Asp Tyr Trp Gly Gln
225 230 235 240

Gly Thr Leu Val Thr Val Ser Ser
245

<210> SEQ ID NO 113
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

```
Gln Ser Val Val Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Glu Ser Gly Gly Ala Phe Val
    130                 135                 140

Gln Pro Gly Gly Ser Leu Arg Leu Ser Cys Ala Ala Ser Gly Phe Thr
145                 150                 155                 160

Phe Ser Ser Tyr Ala Met Thr Trp Val Arg Gln Ala Pro Gly Lys Gly
                165                 170                 175

Leu Glu Trp Val Ser Thr Ile Ser Gly Arg Gly Arg Ser Thr Phe Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Tyr Tyr His Ala Gly Ala Phe Asp Leu Trp
225                 230                 235                 240

Gly Gln Gly Thr Leu Val Thr Val Ser Ser
                245                 250
```

<210> SEQ ID NO 114
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Gln Ser Val Leu Thr Gln Pro Ala Ser Val Ser Gly Ser Pro Gly Gln
1               5                   10                  15

Ser Leu Thr Ile Ser Cys Thr Gly Thr Ser Asn Asp Val Gly Ala Tyr
            20                  25                  30

Lys Tyr Val Ser Trp Tyr Gln Gln Tyr Pro Gly Lys Ala Pro Lys Leu
        35                  40                  45

Ile Leu Tyr Asp Val Phe Lys Arg Pro Ser Gly Val Ser Asn Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Phe Ser Leu Thr Ser Ser
                85                  90                  95

Asn Thr Tyr Val Phe Gly Thr Gly Thr Lys Val Thr Val Leu Gly Ser
            100                 105                 110
```

```
Arg Gly Gly Gly Gly Ser Gly Gly Gly Gly Ser Gly Gly Gly Gly Ser
        115                 120                 125

Leu Glu Met Ala Gln Met Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Asn Arg Tyr Ala Ile Thr Trp Val Arg Gln Ala Pro Gly Gln Gly
                165                 170                 175

Leu Glu Trp Met Gly Trp Ile Ser Ala Tyr Asn Gly Asn Ser His Tyr
            180                 185                 190

Ala Gln Lys Leu Gln Gly Arg Val Thr Met Thr Thr Asp Thr Ser Thr
        195                 200                 205

Gly Thr Ala Tyr Met Glu Leu Arg Arg Leu Arg Ser Asp Asp Thr Ala
    210                 215                 220

Val Tyr Tyr Cys Ala Arg Met Ala Tyr Asp Ser Trp Gly Gln Gly Thr
225                 230                 235                 240

Leu Val Thr Val Ser Ser
                245


<210> SEQ ID NO 115
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Val Gly Gly Asn
            20                  25                  30

Tyr Val Phe Trp Tyr Gln Gln Val Pro Gly Ala Thr Pro Lys Leu Leu
        35                  40                  45

Ile Tyr Arg Ser Asn Gln Arg Pro Ser Gly Val Pro Asp Arg Phe Ala
    50                  55                  60

Gly Ser Lys Ser Gly Ser Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Phe Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Glu Ser Gly Gly Gly Leu Val
    130                 135                 140

Lys Pro Gly Gly Ser Leu Arg Leu Ser Cys Ala Ala Ser Gly Phe Thr
145                 150                 155                 160

Phe Ser Asp Tyr Tyr Met Ser Trp Ile Arg Gln Ala Pro Gly Lys Gly
                165                 170                 175

Leu Glu Trp Val Ser Tyr Ile Ser Ser Ser Gly Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
```

```
    210                 215                 220

Val Tyr Tyr Cys Ala Arg Gly Tyr Gly Lys Ala Tyr Asp Gln Trp Gly
225                 230                 235                 240

Gln Gly Thr Leu Val Thr Val Ser Ser
                245


<210> SEQ ID NO 116
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Pro
                85                  90                  95

Pro Val Val Phe Gly Gly Gly Thr Lys Leu Thr Val Leu Gly Ser Arg
            100                 105                 110

Gly Gly Gly Gly Ser Gly Gly Gly Gly Ser Gly Gly Gly Gly Ser Leu
        115                 120                 125

Glu Met Ala Gln Val Gln Leu Val Glu Ser Gly Gly Gly Leu Val His
    130                 135                 140

Pro Gly Gly Ser Leu Arg Leu Ser Cys Ala Ala Ser Gly Phe Thr Phe
145                 150                 155                 160

Arg Ser His Ser Met Asn Trp Val Arg Gln Ala Pro Gly Lys Gly Leu
                165                 170                 175

Glu Trp Val Ser Ser Ile Ser Ser Asp Ser Thr Tyr Thr Tyr Tyr Ala
            180                 185                 190

Asp Ser Val Lys Gly Arg Phe Thr Ile Ser Arg Asp Asn Ala Lys Asn
        195                 200                 205

Ser Leu Tyr Leu Gln Met Asn Ser Leu Arg Ala Glu Asp Thr Ala Val
    210                 215                 220

Tyr Tyr Cys Ala Arg Ser Gly Gly Gln Trp Lys Tyr Tyr Asp Tyr Trp
225                 230                 235                 240

Gly Gln Gly Thr Leu Val Thr Val Ser Ser
                245                 250


<210> SEQ ID NO 117
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Ser Val Val Thr Gln Pro Pro Ser Met Ser Ala Ala Pro Gly Gln
```

```
1               5                   10                  15

Gln Val Thr Ile Ser Cys Ser Gly Gly Asn Ser Asn Ile Glu Arg Asn
            20                  25                  30

Tyr Val Ser Trp Tyr Leu Gln Leu Pro Gly Thr Ala Pro Lys Leu Val
        35                  40                  45

Ile Phe Asp Asn Asp Arg Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Arg Gly Trp Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Glu Ser Gly Gly Gly Leu Ile
    130                 135                 140

Gln Pro Gly Gly Ser Leu Arg Leu Ser Cys Ala Ala Ser Gly Phe Thr
145                 150                 155                 160

Phe Ser Asn Tyr Ala Met Asn Trp Val Arg Gln Ala Pro Gly Lys Gly
                165                 170                 175

Leu Glu Trp Val Ser Thr Ile Asn Gly Arg Gly Ser Ser Thr Ile Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Thr Tyr Tyr Cys Ala Arg Tyr Ile Ser Arg Gly Leu Gly Asp Ser Trp
225                 230                 235                 240

Gly Gln Gly Thr Leu Val Thr Val
                245


<210> SEQ ID NO 118
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr Leu Val Phe Gly Gly Gly Thr Lys Leu Thr Val Leu Gly Ser
            100                 105                 110
```

```
Arg Gly Gly Gly Gly Ser Gly Gly Gly Gly Ser Gly Gly Gly Gly Ser
        115                 120                 125

Leu Glu Met Ala Gln Met Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Thr Ser Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Arg Ala Gly Met Gly Met Asp Thr Trp Gly Gln
225                 230                 235                 240

Gly Thr Leu Val Thr Val Ser Ser
                245
```

<210> SEQ ID NO 119
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ala Ser Phe Ala Gly Arg
                85                  90                  95

Lys Thr Leu Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Lys Pro Gly Ala Ser Val Lys Val Ser Cys Arg Ala Ser Gly Tyr Thr
145                 150                 155                 160

Phe Thr Ala Tyr Ser Leu His Trp Val Arg Gln Ala Pro Gly Gln Gly
                165                 170                 175

Leu Glu Trp Met Gly Trp Ile Asn Pro Ser Ser Gly Gly Ala Val Tyr
            180                 185                 190

Ala Gln Lys Phe Gln Gly Arg Val Thr Met Thr Arg Asp Thr Ser Ile
        195                 200                 205

Ser Thr Ala Tyr Met Glu Leu Ser Gly Leu Arg Ser Asp Asp Thr Ala
    210                 215                 220
```

Val Tyr Tyr Cys Ala Arg Asn Val Gly Gly Gln Ala Asp Asp Trp Gly
225 230 235 240

Gln Gly Thr Leu Val Thr Val Ser Ser
245

<210> SEQ ID NO 120
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

Gln Ser Ala Leu Thr Gln Pro Pro Ser Ala Ser Gly Ser Pro Gly Gln
1 5 10 15

Ser Val Thr Ile Ser Cys Thr Gly Thr Ser Thr Asp Ile Gly Gly Tyr
20 25 30

Asn Tyr Val Ser Trp Tyr Gln His His Pro Ser Lys Ala Pro Lys Leu
35 40 45

Met Ile Tyr Glu Val Asn Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Tyr Cys Ala Ser Phe Ala Gly Arg
85 90 95

Lys Thr Leu Val Phe Gly Gly Gly Thr Lys Leu Thr Val Leu Gly Ser
100 105 110

Arg Gly Gly Gly Gly Ser Gly Gly Gly Gly Ser Gly Gly Gly Gly Ser
115 120 125

Leu Glu Met Ala Gln Val Gln Leu Val Gln Ser Gly Ala Glu Val Lys
130 135 140

Lys Pro Gly Ala Ser Val Lys Val Ser Cys Arg Ala Ser Gly Tyr Thr
145 150 155 160

Phe Thr Ala Tyr Ser Leu His Trp Val Arg Gln Ala Pro Gly Gln Gly
165 170 175

Leu Glu Trp Met Gly Trp Ile Asn Pro Ser Ser Gly Gly Ala Val Tyr
180 185 190

Ala Gln Lys Phe Gln Gly Arg Val Thr Met Thr Arg Asp Thr Ser Ile
195 200 205

Ser Thr Ala Tyr Met Glu Leu Ser Gly Leu Arg Ser Asp Asp Thr Ala
210 215 220

Val Tyr Tyr Cys Ala Arg Asn Val Gly Gly His Ala Asp Asp Trp Gly
225 230 235 240

Gln Gly Thr Leu Val Thr Val Ser Ser
245

<210> SEQ ID NO 121
<211> LENGTH: 261
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

Gln Ser Val Val Thr Gln Pro Pro Ser Val Ser Ala Ala Pro Gly Gln
1 5 10 15

Lys Val Thr Ile Ser Cys Ser Gly Ser Ser Ser Asn Ile Gly Asn Asn
20 25 30

Tyr Val Ser Trp Tyr Gln Gln Leu Pro Gly Thr Ala Pro Lys Leu Leu
35 40 45

Ile Tyr Asp Asn Asn Lys Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asp Tyr Tyr Cys Gly Thr Trp Asp Ser Ser Leu
85 90 95

Ser Gly Val Val Phe Gly Gly Gly Thr Lys Leu Thr Val Leu Gly Ser
100 105 110

Arg Gly Gly Gly Gly Ser Gly Gly Gly Gly Ser Gly Gly Gly Gly Ser
115 120 125

Leu Glu Met Ala Gln Val Gln Leu Val Gln Ser Gly Gly Glu Val Lys
130 135 140

Lys Pro Gly Ala Ser Val Lys Val Ser Cys Lys Ala Ser Gly Phe Thr
145 150 155 160

Phe Asn Thr Tyr Gly Ile Ser Trp Val Arg Gln Ala Pro Gly Gln Gly
165 170 175

Leu Glu Trp Met Gly Trp Ile Ser Ala Asn Asn Gly His Thr Lys Ser
180 185 190

Ala Gln Arg Phe Gln Asp Arg Val Ala Met Ala Thr Asp Thr Ser Thr
195 200 205

Ser Thr Ala Tyr Met Glu Leu Arg Ser Leu Lys Phe Asp Asp Thr Ala
210 215 220

Val Tyr Tyr Cys Ala Arg Gly Gly Tyr His His Gln Met Gln Arg Tyr
225 230 235 240

Tyr Lys Ala Thr Ser Val Tyr Ser Asp Tyr Trp Gly Gln Gly Thr Leu
245 250 255

Val Thr Val Ser Ser
260

<210> SEQ ID NO 122
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

Gln Ser Ala Leu Thr Gln Pro Pro Ser Ala Ser Gly Ser Pro Gly Gln
1 5 10 15

Ser Val Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Tyr Cys Ser Ser Tyr Ala Gly Ser
85 90 95

Asn Thr Leu Val Phe Gly Gly Gly Thr Lys Leu Thr Val Leu Gly Ser

```
            100                 105                 110

Arg Gly Gly Gly Gly Ser Gly Gly Gly Gly Ser Gly Gly Gly Gly Ser
        115                 120                 125

Leu Glu Met Ala Gln Met Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Ser Ser Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Arg Ala Gly Met Gly Met Asp Thr Trp Gly Gln
225                 230                 235                 240

Gly Thr Leu Val Thr Val Ser Ser
                245


<210> SEQ ID NO 123
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln Ser Pro Gly Lys Ala Pro Arg Leu
        35                  40                  45

Met Ile Tyr Gly Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Val
                85                  90                  95

Asn Asn Leu Met Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Thr Ser Tyr
            180                 185                 190

Ala Gln Lys Phe Gln Gly Arg Val Thr Met Thr Arg Asp Thr Ser Thr
        195                 200                 205
```

```
Ser Thr Val Tyr Met Glu Leu Ser Ser Leu Arg Ser Glu Asp Thr Ala
    210                 215                 220

Val Tyr Tyr Cys Ala Arg Asp Val Ile Ser Gly Phe Asp Ser Trp Gly
225                 230                 235                 240

Gln Gly Thr Leu Val Thr Val Ser Ser
                245


<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Tyr Thr Phe Thr Ser Tyr Tyr
1               5


<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Tyr Thr Phe Thr Ser Tyr Tyr
1               5


<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Arg Gly Met Tyr Arg Ser Leu Leu Phe Tyr Asp Pro
1               5                   10


<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Ser Asn Val Gly Asn Tyr Tyr
1               5


<210> SEQ ID NO 128
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Asp Asn Asn
1
```

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Gly Thr Trp Asp Gly Ser Leu Ser Ala His Val
1 5 10

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Gly Phe Thr Phe Ser Asn Tyr Ala
1 5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Ile Ser Gly Ser Gly Asn Thr
1 5

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Ala Arg Gly Ser Val Arg Tyr Thr Asp Ile
1 5 10

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Ser Gly Ala Ile Ala Gly Ala Tyr
1 5

<210> SEQ ID NO 134
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

Asp Asp Asn
1

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Gln Ser Tyr Asp Tyr Asp Ser Ser Asn Val Leu
1 5 10

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Gly Phe Thr Phe Asn Asn Tyr Trp
1 5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Ile Lys Gln Asp Gly Ser Glu Lys
1 5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Ala Arg Ser Met Ser Thr Ala Val
1 5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Gln Ser Ile Ser Ser Tyr
1 5

<210> SEQ ID NO 140
<211> LENGTH: 3
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 140

Ala Ala Ser
1

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Gln Gln Ser Tyr Ser Val Pro Tyr Thr
1 5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 142

Gly Tyr Thr Phe Thr Ser Tyr Tyr
1 5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Ile Asn Pro Ser Gly Gly Ser Thr
1 5

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 144

Ala Arg Gly Ser Ser Arg Trp Gly Gly Trp Thr Gly Asp Tyr
1 5 10

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 145

Ser Ser Asp Val Gly Gly Tyr Asn Phe
1 5

<210> SEQ ID NO 146
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Val Ser
1

<210> SEQ ID NO 147
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Ser Tyr Thr Ser Thr Arg Thr Val Ile Phe Ala Gly Gly Thr Lys
1               5                   10                  15

Val Thr Val Leu
            20

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Ser Thr Phe Ser Ser Tyr Ala
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Ser Gly Arg Gly Arg Ser Thr
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Arg Tyr Tyr Lys Ser Lys Asp His
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Arg Ser Asn Ile Gly Thr Asn Tyr
1 5

<210> SEQ ID NO 152
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Arg Asn His
1

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Ala Ala Trp Asp Asp Asn Leu Ser Gly Val Val
1 5 10

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Ala Tyr Thr Phe Thr Asp Tyr Tyr
1 5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Ile Asn Pro Lys Ser Gly Arg Thr
1 5

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Ala Arg Val Tyr Gly Tyr Ser Arg Trp Ser Gly Phe Asp Leu
1 5 10

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Ser Asn Ile Gly Ser Asn Tyr
1               5

<210> SEQ ID NO 158
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Arg Asn Asn
1

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Ala Trp Asp Asp Ser Leu Ser Gly Tyr Val
1               5                   10

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Tyr Thr Phe Thr Thr Tyr Tyr
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ile Asn Pro Asn Gly Gly Gly Thr
1               5

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Arg Gly His Lys Val Tyr Lys Ser His Pro Thr Gly Gly Tyr Asp
1 5 10 15

Arg

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Ser Arg Asp Val Gly Gly Tyr Asn Tyr
1 5

<210> SEQ ID NO 164
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Glu Val Ser
1

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Ser Ser Tyr Thr Ser Ser Ser Thr Leu Asp
1 5 10

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Gly Gly Thr Phe Ser Ser Tyr Ala
1 5

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Ile Ile Pro Ile Phe Gly Thr Ala
1 5

<210> SEQ ID NO 168

<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 168

Ala Arg Ser His Val Ala Trp Ser Leu Leu Asp Tyr
1 5 10

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 169

Ser Ser Asn Ile Gly Ser Asn Tyr
1 5

<210> SEQ ID NO 170
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 170

Arg Asn Asn
1

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 171

Ala Ala Trp Asp Asp Ser Leu Ser Gly Val Val
1 5 10

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 172

Gly Gly Thr Phe Ser Ser Tyr Ala
1 5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 173

Met Asn Pro Asn Ser Gly Asn Thr
1               5

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Arg Tyr Gln Ser Tyr Lys Gly Ser Gln Ser Asp Ser
1               5                   10

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Ser Asn Ile Gly Ser Asn Tyr
1               5

<210> SEQ ID NO 176
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Arg Asn Asn
1

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Ala Trp Asp Asp Ser Leu Ser Gly Trp Val
1               5                   10

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Tyr Thr Phe Thr Ser Tyr Tyr
1               5

<210> SEQ ID NO 179
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 179

Ile Asn Pro Ser Gly Gly Ser Thr
1               5

<210> SEQ ID NO 180
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Arg Gly Gly Ser Lys Lys Trp Ser Gly Glu Lys Trp Arg Arg Glu
1               5                   10                  15

Asn Phe Asp Tyr
            20

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Ser Asp Val Gly Gly Tyr Asn Tyr
1               5

<210> SEQ ID NO 182
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp Val Ser
1

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Ser Tyr Thr Arg Ser Ser Thr Glu Val
1               5                   10

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Glu Tyr Thr Phe Thr Arg His Ile 1 5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 185

Ile Asn Pro Gly Asn Gly Asn Thr
1 5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 186

Ala Arg Leu Pro Asp Gln
1 5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 187

Ser Ser Asn Ile Gly Ser Asn Thr
1 5

<210> SEQ ID NO 188
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 188

Arg Asn Asn
1

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 189

Ala Ala Trp Asp Asp Ser Leu Ser Gly Leu
1 5 10

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Gly Phe Thr Phe Gly Asp Tyr Gly
1 5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Ile Asn Trp Asn Gly Gly Ser Thr
1 5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Ala Arg Ser Lys Gln Asp Tyr
1 5

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Ser Arg Asp Ala Gly Gly Tyr Asn Tyr
1 5

<210> SEQ ID NO 194
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Glu Val Thr
1

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 195

Ser Ser Tyr Gly Gly Ser Asn Asn Phe Arg Val
1 5 10

<210> SEQ ID NO 196

<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Gly Phe Ser Phe Ser Gly Thr Ala
1 5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Ile Ser Ser Thr Gly Arg Ser Thr
1 5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Ala Arg Val Ser Phe Asp Tyr
1 5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Ser Ser Asn Ile Gly Ala Gly Tyr Asp
1 5

<210> SEQ ID NO 200
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 200

Gly Asn Ser
1

<210> SEQ ID NO 201
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Gln Ser Tyr Asp Ser Ser Leu Ser Gly Ser Tyr Val
1 5 10

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Gly Phe Thr Phe Ser Ser Tyr Ala
1 5

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Ile Ser Gly Arg Gly Arg Ser Thr
1 5

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Ala Arg Tyr Tyr His Ala Gly Ala Phe Asp Leu
1 5 10

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Ser Ser Asp Val Gly Gly Tyr Asn Tyr
1 5

<210> SEQ ID NO 206
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Asp Val Ser
1

<210> SEQ ID NO 207
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 207

Ser Ser Tyr Thr Ser Ser Ser Thr Leu Val
1               5                   10

<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Tyr Thr Phe Asn Arg Tyr Ala
1               5

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ile Ser Ala Tyr Asn Gly Asn Ser
1               5

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Arg Met Ala Tyr Asp Ser
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ser Asn Asp Val Gly Ala Tyr Lys Tyr
1               5

<210> SEQ ID NO 212
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asp Val Phe
1

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Phe Ser Leu Thr Ser Ser Asn Thr Tyr Val
1 5 10

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

Gly Phe Thr Phe Ser Asp Tyr Tyr
1 5

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Ile Ser Ser Ser Gly Ser Thr Ile
1 5

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Ala Arg Gly Tyr Gly Lys Ala Tyr Asp Gln
1 5 10

<210> SEQ ID NO 217
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Arg Ser Asn Val Gly Gly Asn Tyr
1 5

<210> SEQ ID NO 218
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Arg Ser Asn
1

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 219

Ala Thr Trp Asp Asp Ser Leu Ser Gly Phe Val
1 5 10

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 220

Gly Phe Thr Phe Arg Ser His Ser
1 5

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Ile Ser Ser Asp Ser Thr Tyr Thr
1 5

<210> SEQ ID NO 222
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

Ala Arg Ser Gly Gly Gln Trp Lys Tyr Tyr Asp Tyr
1 5 10

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 223

Ser Leu Arg Ser Tyr Tyr
1 5

<210> SEQ ID NO 224
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 224

Gly Lys Asn
1

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 225

Asn Ser Arg Asp Ser Ser Gly Asn Pro Pro Val Val
1 5 10

<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 226

Gly Phe Thr Phe Ser Asn Tyr Ala
1 5

<210> SEQ ID NO 227
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 227

Ile Asn Gly Arg Gly Ser Ser Thr
1 5

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 228

Ala Arg Tyr Ile Ser Arg Gly Leu Gly Asp Ser
1 5 10

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 229

Asn Ser Asn Ile Glu Arg Asn Tyr
1 5

<210> SEQ ID NO 230
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 230

Asp Asn Asp
1

<210> SEQ ID NO 231
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 231

Gly Thr Trp Asp Ser Ser Leu Arg Gly Trp Val
1 5 10

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 232

Gly Tyr Thr Phe Thr Ser Tyr Tyr
1 5

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 233

Ile Asn Pro Ser Gly Gly Ser Thr
1 5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 234

Ala Arg Ala Gly Met Gly Met Asp Thr
1 5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 235

Ser Ser Asp Val Gly Gly Tyr Asn Tyr
1 5

<210> SEQ ID NO 236
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 236

Glu Val Ser
1

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 237

Ser Ser Tyr Ala Gly Ser Asn Thr Leu Val
1 5 10

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 238

Gly Tyr Thr Phe Thr Ala Tyr Ser
1 5

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 239

Ile Asn Pro Ser Ser Gly Gly Ala
1 5

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 240

Ala Arg Asn Val Gly Gly Gln Ala Asp Asp
1 5 10

<210> SEQ ID NO 241
<211> LENGTH: 9
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 241

Ser Ser Asp Ile Gly Gly Tyr Asn Tyr
1 5

<210> SEQ ID NO 242
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 242

Glu Val Asn
1

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 243

Ala Ser Phe Ala Gly Arg Lys Thr Leu Val
1 5 10

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 244

Gly Tyr Thr Phe Thr Ala Tyr Ser
1 5

<210> SEQ ID NO 245
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 245

Ile Asn Pro Ser Ser Gly Gly Ala
1 5

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 246

Ala Arg Asn Val Gly Gly His Ala Asp Asp
1 5 10

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 247

Ser Thr Asp Ile Gly Gly Tyr Asn Tyr
1 5

<210> SEQ ID NO 248
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 248

Glu Val Asn
1

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 249

Ala Ser Phe Ala Gly Arg Lys Thr Leu Val
1 5 10

<210> SEQ ID NO 250
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 250

Gly Phe Thr Phe Asn Thr Tyr Gly
1 5

<210> SEQ ID NO 251
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 251

Ile Ser Ala Asn Asn Gly His Thr
1 5

<210> SEQ ID NO 252
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 252

Ala Arg Gly Gly Tyr His His Gln Met Gln Arg Tyr Tyr Lys Ala Thr
1 5 10 15

Ser Val Tyr Ser Asp Tyr
20

<210> SEQ ID NO 253
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 253

Ser Ser Asn Ile Gly Asn Asn Tyr
1 5

<210> SEQ ID NO 254
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 254

Asp Asn Asn
1

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 255

Gly Thr Trp Asp Ser Ser Leu Ser Gly Val Val
1 5 10

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 256

Gly Tyr Thr Phe Thr Ser Tyr Tyr
1 5

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Ile Asn Pro Ser Gly Gly Ser Ser
1 5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 258

Ala Arg Ala Gly Met Gly Met Asp Thr
1 5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 259

Ser Ser Asp Val Gly Gly Tyr Asn Tyr
1 5

<210> SEQ ID NO 260
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 260

Glu Val Ser
1

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 261

Ser Ser Tyr Ala Gly Ser Asn Thr Leu Val
1 5 10

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 262

Gly Tyr Thr Phe Thr Ser Tyr Tyr
1 5

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 263

Ile Asn Pro Ser Gly Gly Ser Thr
1 5

<210> SEQ ID NO 264
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 264

Ala Arg Asp Val Ile Ser Gly Phe Asp Ser
1 5 10

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 265

Ser Ser Asp Val Gly Gly Tyr Asn Tyr
1 5

<210> SEQ ID NO 266
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

Gly Val Ser
1

<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Ser Ser Tyr Ala Gly Val Asn Asn Leu Met
1 5 10

<210> SEQ ID NO 268
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

Met Ala Leu Pro Val Thr Ala Leu Leu Leu Pro Leu Ala Leu Leu Leu
1 5 10 15

His Ala Ala Arg
20

<210> SEQ ID NO 269
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 269
atggctctcc cagtgactgc cctactgctt cccctagcgc ttctcctgca tgcagctcgt 60

<210> SEQ ID NO 270
<211> LENGTH: 220
<212> TYPE: PRT
<213> ORGANISM: Homo sapiens

<400> SEQUENCE: 270

Met Leu Arg Leu Leu Leu Ala Leu Asn Leu Phe Pro Ser Ile Gln Val
1 5 10 15

Thr Gly Asn Lys Ile Leu Val Lys Gln Ser Pro Met Leu Val Ala Tyr
20 25 30

Asp Asn Ala Val Asn Leu Ser Cys Lys Tyr Ser Tyr Asn Leu Phe Ser
35 40 45

Arg Glu Phe Arg Ala Ser Leu His Lys Gly Leu Asp Ser Ala Val Glu
50 55 60

Val Cys Val Val Tyr Gly Asn Tyr Ser Gln Gln Leu Gln Val Tyr Ser
65 70 75 80

Lys Thr Gly Phe Asn Cys Asp Gly Lys Leu Gly Asn Glu Ser Val Thr
85 90 95

Phe Tyr Leu Gln Asn Leu Tyr Val Asn Gln Thr Asp Ile Tyr Phe Cys
100 105 110

Lys Ile Glu Val Met Tyr Pro Pro Pro Tyr Leu Asp Asn Glu Lys Ser
115 120 125

Asn Gly Thr Ile Ile His Val Lys Gly Lys His Leu Cys Pro Ser Pro
130 135 140

Leu Phe Pro Gly Pro Ser Lys Pro Phe Trp Val Leu Val Val Val Gly
145 150 155 160

Gly Val Leu Ala Cys Tyr Ser Leu Leu Val Thr Val Ala Phe Ile Ile
165 170 175

Phe Trp Val Arg Ser Lys Arg Ser Arg Leu Leu His Ser Asp Tyr Met
180 185 190

Asn Met Thr Pro Arg Arg Pro Gly Pro Thr Arg Lys His Tyr Gln Pro
195 200 205

Tyr Ala Pro Pro Arg Asp Phe Ala Ala Tyr Arg Ser
210 215 220

<210> SEQ ID NO 271
<211> LENGTH: 321
<212> TYPE: DNA
<213> ORGANISM: Homo sapiens

<400> SEQUENCE: 271
attgaagtta tgtatcctcc tccttaccta gacaatgaga agagcaatgg aaccattatc 60
catgtgaaag ggaaacacct ttgtccaagt cccctatttc ccggaccttc taagcccttt 120
tgggtgctgg tggtggttgg tggagtcctg gcttgctata gcttgctagt aacagtggcc 180
tttattattt tctgggtgag gagtaagagg agcaggctcc tgcacagtga ctacatgaac 240
atgactcccc gccgccccgg gcccacccgc aagcattacc agccctatgc cccaccacgc 300
gacttcgcag cctatcgctc c 321

<210> SEQ ID NO 272
<211> LENGTH: 163
<212> TYPE: PRT
<213> ORGANISM: Homo sapiens

<400> SEQUENCE: 272

Met Lys Trp Lys Ala Leu Phe Thr Ala Ala Ile Leu Gln Ala Gln Leu
1 5 10 15

Pro Ile Thr Glu Ala Gln Ser Phe Gly Leu Leu Asp Pro Lys Leu Cys
20 25 30

Tyr Leu Leu Asp Gly Ile Leu Phe Ile Tyr Gly Val Ile Leu Thr Ala
35 40 45

Leu Phe Leu Arg Val Lys Phe Ser Arg Ser Ala Asp Ala Pro Ala Tyr
50 55 60

Gln Gln Gly Gln Asn Gln Leu Tyr Asn Glu Leu Asn Leu Gly Arg Arg
65 70 75 80

Glu Glu Tyr Asp Val Leu Asp Lys Arg Arg Gly Arg Asp Pro Glu Met
85 90 95

Gly Gly Lys Pro Arg Arg Lys Asn Pro Gln Glu Gly Leu Tyr Asn Glu
100 105 110

Leu Gln Lys Asp Lys Met Ala Glu Ala Tyr Ser Glu Ile Gly Met Lys
115 120 125

Gly Glu Arg Arg Arg Gly Lys Gly His Asp Gly Leu Tyr Gln Gly Leu
130 135 140

Ser Thr Ala Thr Lys Asp Thr Tyr Asp Ala Leu His Met Gln Ala Leu
145 150 155 160

Pro Pro Arg

<210> SEQ ID NO 273
<211> LENGTH: 339
<212> TYPE: DNA
<213> ORGANISM: Homo sapiens

<400> SEQUENCE: 273
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgctaa 339

<210> SEQ ID NO 274
<211> LENGTH: 255
<212> TYPE: PRT
<213> ORGANISM: Homo sapiens

<400> SEQUENCE: 274

Met Gly Asn Ser Cys Tyr Asn Ile Val Ala Thr Leu Leu Leu Val Leu
1 5 10 15

Asn Phe Glu Arg Thr Arg Ser Leu Gln Asp Pro Cys Ser Asn Cys Pro
20 25 30

Ala Gly Thr Phe Cys Asp Asn Asn Arg Asn Gln Ile Cys Ser Pro Cys
35 40 45

```
Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 275
<211> LENGTH: 277
<212> TYPE: PRT
<213> ORGANISM: Homo sapiens

<400> SEQUENCE: 275

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
```

```
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275


<210> SEQ ID NO 276
<211> LENGTH: 199
<212> TYPE: PRT
<213> ORGANISM: Homo sapiens

<400> SEQUENCE: 276

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195


<210> SEQ ID NO 277
<211> LENGTH: 223
<212> TYPE: PRT
<213> ORGANISM: Homo sapiens

<400> SEQUENCE: 277

Met Ala Cys Leu Gly Phe Gln Arg His Lys Ala Gln Leu Asn Leu Ala
```

-continued

```
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 278
<211> LENGTH: 288
<212> TYPE: PRT
<213> ORGANISM: Homo sapiens

<400> SEQUENCE: 278

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160
```

```
Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285


<210> SEQ ID NO 279
<211> LENGTH: 525
<212> TYPE: PRT
<213> ORGANISM: Homo sapiens

<400> SEQUENCE: 279

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255
```

```
Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525


<210> SEQ ID NO 280
<211> LENGTH: 370
<212> TYPE: PRT
<213> ORGANISM: Homo sapiens

<400> SEQUENCE: 280

Met Leu Gly Gln Val Val Thr Leu Ile Leu Leu Leu Leu Leu Lys Val
1               5                   10                  15

Tyr Gln Gly Lys Gly Cys Gln Gly Ser Ala Asp His Val Val Ser Ile
            20                  25                  30

Ser Gly Val Pro Leu Gln Leu Gln Pro Asn Ser Ile Gln Thr Lys Val
        35                  40                  45

Asp Ser Ile Ala Trp Lys Lys Leu Leu Pro Ser Gln Asn Gly Phe His
    50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Leu Ile Lys Ala
                85                  90                  95

Ala Gln Gln Gln Asp Ser Gly Leu Tyr Cys Leu Glu Val Thr Ser Ile
```

```
            100                 105                 110

Ser Gly Lys Val Gln Thr Ala Thr Phe Gln Val Phe Val Phe Glu Ser
        115                 120                 125

Leu Leu Pro Asp Lys Val Glu Lys Pro Arg Leu Gln Gly Gln Gly Lys
    130                 135                 140

Ile Leu Asp Arg Gly Arg Cys Gln Val Ala Leu Ser Cys Leu Val Ser
145                 150                 155                 160

Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Glu Val Asp Ile Asn
            180                 185                 190

Gly Thr His Thr Tyr Thr Cys Asn Val Ser Asn Pro Val Ser Trp Glu
        195                 200                 205

Ser His Thr Leu Asn Leu Thr Gln Asp Cys Gln Asn Ala His Gln Glu
    210                 215                 220

Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
                245                 250                 255

Glu Lys Gln Ser Glu Thr Ser Pro Lys Glu Phe Leu Thr Ile Tyr Glu
            260                 265                 270

Asp Val Lys Asp Leu Lys Thr Arg Arg Asn His Glu Gln Glu Gln Thr
        275                 280                 285

Phe Pro Gly Gly Gly Ser Thr Ile Tyr Ser Met Ile Gln Ser Gln Ser
    290                 295                 300

Ser Ala Pro Thr Ser Gln Glu Pro Ala Tyr Thr Leu Tyr Ser Leu Ile
305                 310                 315                 320

Gln Pro Ser Arg Lys Ser Gly Ser Arg Lys Arg Asn His Ser Pro Ser
                325                 330                 335

Phe Asn Ser Thr Ile Tyr Glu Val Ile Gly Lys Ser Gln Pro Lys Ala
            340                 345                 350

Gln Asn Pro Ala Arg Leu Ser Arg Lys Glu Leu Glu Asn Phe Asp Val
        355                 360                 365

Tyr Ser
    370


<210> SEQ ID NO 281
<211> LENGTH: 289
<212> TYPE: PRT
<213> ORGANISM: Homo sapiens

<400> SEQUENCE: 281

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95
```

-continued

```
Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser


<210> SEQ ID NO 282
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Met Glu Thr Asp Thr Leu Leu Leu Trp Val Leu Leu Leu Trp Val Pro
1               5                   10                  15

Gly Ser Thr Gly
            20


<210> SEQ ID NO 283
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283

atggaaaccg acaccctgct gctgtgggtg ctgctgctgt gggtgccagg atccacagga     60


<210> SEQ ID NO 284
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284
```

Gly Gly Gly Gly Ser Gly Gly Gly Gly Ser Gly Gly Gly Gly Ser
1 5 10 15

<210> SEQ ID NO 285
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 285
ggtggaggtg gatcaggtgg aggtggatct ggtggaggtg gatct 45

<210> SEQ ID NO 286
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 286

Gly Gly Gly Gly Ser
1 5

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 287

Ser Gly Gly Ser Gly Gly Ser
1 5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 288

Gly Gly Gly Gly Ser Gly Gly Gly Ser
1 5

<210> SEQ ID NO 289
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 289

Gly Gly Gly Gly Ser Gly Gly Gly Gly Ser
1 5 10

<210> SEQ ID NO 290
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 290

Gly Gly Gly Gly Ser Gly Gly Gly Gly Ser Gly Gly Gly Gly Gly Gly
1 5 10 15

Gly Ser

<210> SEQ ID NO 291
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 291

Gly Gly Gly Gly Ser Gly Gly Gly Gly Ser Gly Gly Gly Gly Ser Gly
1 5 10 15

Gly Gly Gly Ser
20

<210> SEQ ID NO 292
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 292

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 293
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 293

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser
20 25 30

<210> SEQ ID NO 294
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 294

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser
35

<210> SEQ ID NO 295
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 295

Glu Pro Lys Ser Cys Asp Lys Thr His Thr Cys Pro Pro Cys Pro
1 5 10 15

<210> SEQ ID NO 296
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 296

Gly Gly Gly Gly Ser Gly Gly Gly Ser Glu Pro Lys Ser Cys Asp Lys
1 5 10 15

Thr His Thr Cys Pro Pro Cys Pro
20

<210> SEQ ID NO 297
<211> LENGTH: 62
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 297

Glu Leu Lys Thr Pro Leu Gly Asp Thr Thr His Thr Cys Pro Arg Cys
1 5 10 15

Pro Glu Pro Lys Ser Cys Asp Thr Pro Pro Pro Cys Pro Arg Cys Pro
20 25 30

Glu Pro Lys Ser Cys Asp Thr Pro Pro Pro Cys Pro Arg Cys Pro Glu
35 40 45

Pro Lys Ser Cys Asp Thr Pro Pro Pro Cys Pro Arg Cys Pro
50 55 60

<210> SEQ ID NO 298
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 298

Gly Ser Gly Ser Gly Ser
1 5

<210> SEQ ID NO 299
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 299

Ala Ala Ala
1

<210> SEQ ID NO 300
<211> LENGTH: 126
<212> TYPE: DNA
<213> ORGANISM: Homo sapiens

<400> SEQUENCE: 300
aaacggggca gaaagaagct cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 301
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 301

Met Lys Lys Thr Ala Ile Ala Ile Ala Val Ala Leu Ala Gly Phe Ala
1 5 10 15

Thr Val Ala Gln Ala Ala Glu Leu Gln Ser Ala Leu Thr Gln Pro Pro
20 25 30

Ser Ala Ser Gly Ser Pro Gly Gln Ser Val Thr Ile Ser Cys Thr Gly
35 40 45

Thr Ser Arg Asp Ala Gly Gly Tyr Asn Tyr Phe Ser Trp Tyr Gln Gln
50 55 60

His Pro Gly Lys Ala Pro Lys Leu Leu Ile Tyr Glu Val Thr Lys Arg
65 70 75 80

Pro Ser Gly Val Pro Asp Arg Phe Ser Gly Ser Lys Ser Gly Lys Thr
85 90 95

Ala Ser Leu Thr Val Ser Gly Leu Gln Ala Asp Asp Glu Ala Val Tyr
100 105 110

Tyr Cys Ser Ser Tyr Gly Gly Ser Asn Asn Phe Arg Val Phe Gly Gly
115 120 125

Gly Thr Lys Leu Thr Val Leu Gly Ser Arg Gly Gly Gly Gly Ser Gly
130 135 140

Gly Gly Gly Ser Gly Gly Gly Gly Ser Leu Glu Met Ala Glu Val Gln
145 150 155 160

Leu Val Glu Ser Gly Gly Gly Val Val Arg Pro Gly Gly Ser Leu Arg
165 170 175

Leu Ser Cys Ala Ala Ser Gly Phe Thr Phe Gly Asp Tyr Gly Met Ser
180 185 190

Trp Val Arg Gln Ala Pro Gly Lys Gly Leu Glu Trp Val Ser Gly Ile
195 200 205

Asn Trp Asn Gly Gly Ser Thr Gly Tyr Ala Asp Ser Val Lys Gly Arg
210 215 220

Phe Thr Ile Ser Arg Asp Asn Ala Lys Asn Ser Leu Tyr Leu Gln Met
225 230 235 240

Asn Ser Leu Arg Ala Glu Asp Thr Ala Val Tyr Tyr Cys Ala Arg Ser
245 250 255

Lys Gln Asp Tyr Trp Gly Gln Gly Thr Leu Val Thr Val Ser Ser
260 265 270

<210> SEQ ID NO 302
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 302

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Gly Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Gln Asp Tyr Trp Gly Gln Gly Thr Leu Val Thr Val
            100                 105                 110

Ser Ser
```

<210> SEQ ID NO 303
<211> LENGTH: 136
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 303

```
Met Lys Lys Thr Ala Ile Ala Ile Ala Val Ala Leu Ala Gly Phe Ala
1               5                   10                  15

Thr Val Ala Gln Ala Ala Glu Leu Gln Ser Ala Leu Thr Gln Pro Pro
            20                  25                  30

Ser Ala Ser Gly Ser Pro Gly Gln Ser Val Thr Ile Ser Cys Thr Gly
        35                  40                  45

Thr Ser Arg Asp Ala Gly Gly Tyr Asn Tyr Phe Ser Trp Tyr Gln Gln
    50                  55                  60

His Pro Gly Lys Ala Pro Lys Leu Leu Ile Tyr Glu Val Thr Lys Arg
65                  70                  75                  80

Pro Ser Gly Val Pro Asp Arg Phe Ser Gly Ser Lys Ser Gly Lys Thr
                85                  90                  95

Ala Ser Leu Thr Val Ser Gly Leu Gln Ala Asp Asp Glu Ala Val Tyr
            100                 105                 110

Tyr Cys Ser Ser Tyr Gly Gly Ser Asn Asn Phe Arg Val Phe Gly Gly
        115                 120                 125

Gly Thr Lys Leu Thr Val Leu Gly
    130                 135
```

<210> SEQ ID NO 304
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 304

Gly Phe Thr Phe Gly Asp Tyr Gly
1               5

<210> SEQ ID NO 305
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ile Asn Trp Asn Gly Gly Ser Thr
1               5

<210> SEQ ID NO 306
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ala Arg Ser Lys Gln Gly Tyr
1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ser Arg Asp Ala Gly Gly Tyr Asn Tyr
1               5

<210> SEQ ID NO 308
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Glu Val Thr
1

<210> SEQ ID NO 309
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ser Ser Tyr Gly Gly Ser Asn Asn Phe Arg Val
1               5                   10

<210> SEQ ID NO 310
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 310
gaggtgcagc tggtggagtc tgggggaggt gtggtacggc ctgggggggtc cctgagactc 60 tcctgtgcag cctctggatt cacctttggt gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccgtat attactgtgc gcgctctaaa 300
caggattact ggggtcaagg tactctggtg accgtctcct ca 342

<210> SEQ ID NO 311
<211> LENGTH: 408
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 311
atgaaaaaga cagctatcgc gattgcagtg gcactggctg gtttcgctac cgtggcccag 60
gcggccgagc tccagtctgc cctgactcag cctccctccg cgtccgggtc tcctggacag 120
tcagtcacca tctcctgcac tggaaccagc agggacgctg gtggttataa ttatttctcc 180
tggtaccaac aacacccagg caaagccccc aaactcctga tttatgaggt cactaagcgg 240
ccctcagggg tccctgatcg cttctctggc tccaagtctg gcaagacggc ctccctgacc 300
gtctctgggc tccaggctga cgatgaggct gtatattact gcagctcata tggaggcagc 360
aacaactttc gggtgttcgg cggagggacc aagctgaccg tcctaggt 408

<210> SEQ ID NO 312
<211> LENGTH: 813
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 312
atgaaaaaga cagctatcgc gattgcagtg gcactggctg gtttcgctac cgtggcccag 60
gcggccgagc tccagtctgc cctgactcag cctccctccg cgtccgggtc tcctggacag 120
tcagtcacca tctcctgcac tggaaccagc agggacgctg gtggttataa ttatttctcc 180
tggtaccaac aacacccagg caaagccccc aaactcctga tttatgaggt cactaagcgg 240
ccctcagggg tccctgatcg cttctctggc tccaagtctg gcaagacggc ctccctgacc 300
gtctctgggc tccaggctga cgatgaggct gtatattact gcagctcata tggaggcagc 360
aacaactttc gggtgttcgg cggagggacc aagctgaccg tcctaggttc tagaggtggt 420
ggtggtagcg gcggcggcgg ctctggtggt ggtggatccc tcgagatggc cgaggtgcag 480
ctggtggagt ctgggggagg tgtggtacgg cctgggggggt ccctgagact ctcctgtgca 540
gcctctggat tcacctttgg tgattatggc atgagctggg tccgccaagc tccagggaag 600
gggctggagt gggtctctgg tattaattgg aatggtggta gcacaggtta tgcagactct 660
gtgaagggcc gattcaccat ctccagagac aacgccaaga actccctgta tctgcaaatg 720
aacagtctga gagccgagga cacggccgta tattactgtg cgcgctctaa acaggattac 780
tggggtcaag gtactctggt gaccgtctcc tca 813

<210> SEQ ID NO 313
<211> LENGTH: 277
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 313

```
Met Lys Lys Thr Ala Ile Ala Ile Ala Val Ala Leu Ala Gly Phe Ala
1               5                   10                  15

Thr Val Ala Gln Ala Ala Glu Leu Ser Tyr Glu Leu Thr Gln Pro Pro
            20                  25                  30

Ser Ala Ser Gly Thr Pro Gly Gln Arg Val Ser Ile Ser Cys Ser Gly
        35                  40                  45

Ser Ser Ser Asn Ile Gly Ser Asn Thr Val Asn Trp Tyr Gln Gln Phe
    50                  55                  60

Pro Gly Thr Ala Pro Lys Leu Leu Ile His Ser Asn Asn Gln Arg Pro
65                  70                  75                  80

Ser Gly Val Pro Asp Arg Phe Ser Gly Ser Lys Ser Gly Thr Ser Ala
                85                  90                  95

Ser Leu Ala Ile Ser Gly Pro Gln Ser Glu Asp Glu Ala Asp Tyr Tyr
            100                 105                 110

Cys Ala Ala Trp Asp Asp Ser Val Asn Gly Tyr Val Phe Gly Thr Gly
        115                 120                 125

Thr Lys Val Thr Val Leu Gly Ser Arg Gly Gly Gly Gly Ser Gly Gly
    130                 135                 140

Gly Gly Ser Gly Gly Gly Gly Ser Leu Glu Met Ala Gln Leu Gln Leu
145                 150                 155                 160

Gln Glu Ser Gly Gly Gly Ser Val Gln Pro Gly Gly Ser Leu Arg Leu
                165                 170                 175

Ser Cys Ala Ala Ser Gly Phe Thr Phe Ser Asn Tyr Ala Met Ser Trp
            180                 185                 190

Val Arg Gln Ala Pro Gly Lys Gly Leu Glu Trp Val Ser Ala Ile Thr
        195                 200                 205

Asn Ser Gly Arg Ser Thr Tyr Tyr Ala Asp Ser Val Lys Gly Arg Phe
    210                 215                 220

Thr Ile Ser Arg Asp Asn Ser Lys Asn Thr Leu Ser Leu Gln Met Ser
225                 230                 235                 240

Ser Leu Arg Ala Glu Asp Thr Ala Val Tyr Tyr Cys Ala Arg Val Thr
                245                 250                 255

His Arg Arg Tyr Gly Ser Thr Phe Asp Ser Arg Gly Gln Gly Thr Leu
            260                 265                 270

Val Thr Val Ser Ser
        275
```

<210> SEQ ID NO 314
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 314

Gln Leu Gln Leu Gln Glu Ser Gly Gly Gly Ser Val Gln Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Ala Pro Gly Lys Gly Leu Glu Trp Val
35 40 45

Ser Ala Ile Thr Asn Ser Gly Arg Ser Thr Tyr Tyr Ala Asp Ser Val
50 55 60

Lys Gly Arg Phe Thr Ile Ser Arg Asp Asn Ser Lys Asn Thr Leu Ser
65 70 75 80

Leu Gln Met Ser Ser Leu Arg Ala Glu Asp Thr Ala Val Tyr Tyr Cys
85 90 95

Ala Arg Val Thr His Arg Arg Tyr Gly Ser Thr Phe Asp Ser Arg Gly
100 105 110

Gln Gly Thr Leu Val Thr Val Ser Ser
115 120

<210> SEQ ID NO 315
<211> LENGTH: 135
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 315

Met Lys Lys Thr Ala Ile Ala Ile Ala Val Ala Leu Ala Gly Phe Ala
1 5 10 15

Thr Val Ala Gln Ala Ala Glu Leu Ser Tyr Glu Leu Thr Gln Pro Pro
20 25 30

Ser Ala Ser Gly Thr Pro Gly Gln Arg Val Ser Ile Ser Cys Ser Gly
35 40 45

Ser Ser Ser Asn Ile Gly Ser Asn Thr Val Asn Trp Tyr Gln Gln Phe
50 55 60

Pro Gly Thr Ala Pro Lys Leu Leu Ile His Ser Asn Asn Gln Arg Pro
65 70 75 80

Ser Gly Val Pro Asp Arg Phe Ser Gly Ser Lys Ser Gly Thr Ser Ala
85 90 95

Ser Leu Ala Ile Ser Gly Pro Gln Ser Glu Asp Glu Ala Asp Tyr Tyr
100 105 110

Cys Ala Ala Trp Asp Asp Ser Val Asn Gly Tyr Val Phe Gly Thr Gly
115 120 125

Thr Lys Val Thr Val Leu Gly
130 135

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 316

Gly Phe Thr Phe Ser Asn Tyr Ala
1 5

```
<210> SEQ ID NO 317
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Ile Thr Asn Ser Gly Arg Ser Thr
1               5


<210> SEQ ID NO 318
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Ala Arg Val Thr His Arg Arg Tyr Gly Ser Thr Phe Asp Ser
1               5                   10


<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Ser Ser Asn Ile Gly Ser Asn Thr
1               5


<210> SEQ ID NO 320
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ser Asn Asn
1


<210> SEQ ID NO 321
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Ala Ala Trp Asp Asp Ser Val Asn Gly Tyr Val
1               5                   10


<210> SEQ ID NO 322
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 322
cagctgcagc tgcaggagtc gggggaggc tcggtacagc cgggggggtc tctgagactg 60
tcctgtgcag cctctggatt cacctttagc aactatgcca tgagctgggt ccgccaggct 120
ccagggaagg ggctggagtg ggtctcagct atcactaata gtggtcgtag tacatactac 180
gcagactccg tgaagggccg gttcaccatc tccagagaca attccaagaa cacgctgtct 240
ttgcaaatga gcagcctgag agccgaagac acggccgtgt attactgtgc gcgcgttact 300
catcgtcgtt acggttctac tttcgattct cggggtcaag gtactctggt gaccgtctcc 360
tcaactagtg gccaggccgg ccagc 385

<210> SEQ ID NO 323
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 323
atgaaaaaga cagctatcgc gattgcagtg gcactggctg gtttcgctac cgtggcccag 60
gcggccgagc tctcctatga gctgactcag ccaccctcag cgtctgggac ccccgggcag 120
agggtcagca tctcttgttc tggaagcagc tccaacatcg ggagtaatac tgtaaactgg 180
taccaacagt tccccggaac ggcccccaaa ctcctcatcc atagtaataa tcagcggccc 240
tcaggggtcc ctgaccgatt ctctggctcc aagtctggca cctcagcctc cctggccatc 300
agtgggcccc agtctgagga tgaggctgat tattactgtg cagcttggga tgacagtgtg 360
aatggttatg tcttcggaac tgggaccaag gtcaccgtcc taggt 405

<210> SEQ ID NO 324
<211> LENGTH: 831
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 324
atgaaaaaga cagctatcgc gattgcagtg gcactggctg gtttcgctac cgtggcccag 60
gcggccgagc tctcctatga gctgactcag ccaccctcag cgtctgggac ccccgggcag 120
agggtcagca tctcttgttc tggaagcagc tccaacatcg ggagtaatac tgtaaactgg 180
taccaacagt tccccggaac ggcccccaaa ctcctcatcc atagtaataa tcagcggccc 240
tcaggggtcc ctgaccgatt ctctggctcc aagtctggca cctcagcctc cctggccatc 300
agtgggcccc agtctgagga tgaggctgat tattactgtg cagcttggga tgacagtgtg 360
aatggttatg tcttcggaac tgggaccaag gtcaccgtcc taggttctag aggtggtggt 420
ggtagcggcg gcggcggctc tggtggtggt ggatccctcg agatggccca gctgcagctg 480
caggagtcgg ggggaggctc ggtacagccg ggggggtctc tgagactgtc ctgtgcagcc 540
tctggattca cctttagcaa ctatgccatg agctgggtcc gccaggctcc agggaagggg 600
ctggagtggg tctcagctat cactaatagt ggtcgtagta catactacgc agactccgtg 660
aagggccggt tcaccatctc cagagacaat tccaagaaca cgctgtcttt gcaaatgagc 720
agcctgagag ccgaagacac ggccgtgtat tactgtgcgc gcgttactca tcgtcgttac 780
ggttctactt tcgattctcg gggtcaaggt actctggtga ccgtctcctc a 831

<210> SEQ ID NO 325
<211> LENGTH: 276
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 325

Met Lys Lys Thr Ala Ile Ala Ile Ala Val Ala Leu Ala Gly Phe Ala
1 5 10 15

Thr Val Ala Gln Ala Ala Glu Leu Gln Pro Val Leu Thr Gln Pro Pro
20 25 30

Ser Ala Ser Gly Thr Pro Gly Gln Arg Val Thr Ile Ser Cys Ser Gly
35 40 45

Ser Ser Ser Asn Ile Gly Gly Asn Thr Val Ser Trp Tyr Gln Gln Val
50 55 60

Pro Gly Thr Ala Pro Arg Leu Leu Ile Phe Arg Asn Asn Gln Arg Pro
65 70 75 80

Pro Gly Val Pro Asp Arg Phe Ser Gly Ser Lys Ser Gly Thr Ser Ala
85 90 95

Ser Leu Ala Ile Ser Gly Leu Arg Ser Glu Asp Glu Ala Asp Tyr Tyr
100 105 110

Cys Ala Ala Trp Asp Ala Ser Arg Gln Gly Val Phe Gly Gly Gly Thr
115 120 125

Lys Leu Thr Val Leu Gly Ser Arg Gly Gly Gly Gly Ser Gly Gly Gly
130 135 140

Gly Ser Gly Gly Gly Gly Ser Leu Glu Met Ala Gln Val Gln Leu Val
145 150 155 160

Gln Ser Gly Ala Glu Val Lys Lys Pro Gly Ser Ser Val Lys Val Ser
165 170 175

Cys Lys Ala Ser Gly Gly Thr Phe Arg Ser Tyr Ala Ile Thr Trp Val
180 185 190

Arg Gln Ala Pro Gly Gln Gly Leu Glu Trp Met Gly Arg Ile Ile Pro
195 200 205

Met Leu Asp Ile Thr Asn Tyr Ala Gln Lys Phe Gln Gly Arg Val Thr
210 215 220

Ile Thr Ala Asp Lys Ser Thr Ser Thr Ala Tyr Met Glu Leu Ser Ser
225 230 235 240

Leu Arg Ser Glu Asp Thr Ala Val Tyr Tyr Cys Ala Arg Thr Tyr Ser
245 250 255

Arg Ser Pro Phe His Met Glu Asp Phe Trp Gly Gln Gly Thr Leu Val
260 265 270

Thr Val Ser Ser
275

<210> SEQ ID NO 326
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 326

Gln Val Gln Leu Val Gln Ser Gly Ala Glu Val Lys Lys Pro Gly Ser

```
1               5                   10                  15

Ser Val Lys Val Ser Cys Lys Ala Ser Gly Gly Thr Phe Arg Ser Tyr
            20                  25                  30

Ala Ile Thr Trp Val Arg Gln Ala Pro Gly Gln Gly Leu Glu Trp Met
        35                  40                  45

Gly Arg Ile Ile Pro Met Leu Asp Ile Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Tyr Ser Arg Ser Pro Phe His Met Glu Asp Phe Trp Gly
            100                 105                 110

Gln Gly Thr Leu Val Thr Val Ser Ser
        115                 120


<210> SEQ ID NO 327
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Met Lys Lys Thr Ala Ile Ala Ile Ala Val Ala Leu Ala Gly Phe Ala
1               5                   10                  15

Thr Val Ala Gln Ala Ala Glu Leu Gln Pro Val Leu Thr Gln Pro Pro
            20                  25                  30

Ser Ala Ser Gly Thr Pro Gly Gln Arg Val Thr Ile Ser Cys Ser Gly
        35                  40                  45

Ser Ser Ser Asn Ile Gly Gly Asn Thr Val Ser Trp Tyr Gln Gln Val
    50                  55                  60

Pro Gly Thr Ala Pro Arg Leu Leu Ile Phe Arg Asn Asn Gln Arg Pro
65                  70                  75                  80

Pro Gly Val Pro Asp Arg Phe Ser Gly Ser Lys Ser Gly Thr Ser Ala
                85                  90                  95

Ser Leu Ala Ile Ser Gly Leu Arg Ser Glu Asp Glu Ala Asp Tyr Tyr
            100                 105                 110

Cys Ala Ala Trp Asp Ala Ser Arg Gln Gly Val Phe Gly Gly Gly Thr
        115                 120                 125

Lys Leu Thr Val Leu Gly
    130


<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gly Gly Thr Phe Arg Ser Tyr Ala
1               5


<210> SEQ ID NO 329
<211> LENGTH: 8
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 329

Ile Ile Pro Met Leu Asp Ile Thr
1 5

<210> SEQ ID NO 330
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 330

Ala Arg Thr Tyr Ser Arg Ser Pro Phe His Met Glu Asp Phe
1 5 10

<210> SEQ ID NO 331
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 331

Ser Ser Asn Ile Gly Gly Asn Thr
1 5

<210> SEQ ID NO 332
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 332

Arg Asn Asn
1

<210> SEQ ID NO 333
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 333

Ala Ala Trp Asp Ala Ser Arg Gln Gly Val
1 5 10

<210> SEQ ID NO 334
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 334
caggtgcagc tggtgcagtc tggggctgag gtgaagaagc ctgggtcctc ggtgaaggtc 60

-continued

```
tcctgcaagg cttctggagg caccttccgc agctatgcta tcacctgggt gcgacaggcc    120

cctggacaag ggcttgagtg gatgggaagg atcatcccta tgcttgatat aacaaactac    180

gcacagaagt tccagggcag agtcacgatt accgcggaca aatccacgag cacagcctac    240

atggagctga gcagcctgag atctgaggac acggccgtgt attactgtgc gcgcacttac    300

tctcgttctc cgttccatat ggaagatttc tggggtcaag gtactctggt gaccgtctcc    360

tca                                                                  363
```

<210> SEQ ID NO 335
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 335

```
atgaaaaaga cagctatcgc gattgcagtg gcactggctg gtttcgctac cgtggcccag     60

gcggccgagc tccagcctgt gctgactcag ccaccctcag cgtctgggac ccccgggcag    120

agggtcacca tctcttgttc tggaagcagc tccaatatcg gaggtaacac tgtcagctgg    180

taccagcagg tcccaggaac ggcccccaga ctcctcattt ttaggaataa tcaacggccc    240

ccaggggtcc ctgaccgatt ctctggctcc aagtctggca cctcagcctc cctggccatc    300

agtgggctcc ggtctgagga tgaggctgat tattactgtg cagcatggga cgccagtcga    360

caaggggtgt tcggcggagg gaccaagctg accgtcctag gt                       402
```

<210> SEQ ID NO 336
<211> LENGTH: 828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 336

```
atgaaaaaga cagctatcgc gattgcagtg gcactggctg gtttcgctac cgtggcccag     60

gcggccgagc tccagcctgt gctgactcag ccaccctcag cgtctgggac ccccgggcag    120

agggtcacca tctcttgttc tggaagcagc tccaatatcg gaggtaacac tgtcagctgg    180

taccagcagg tcccaggaac ggcccccaga ctcctcattt ttaggaataa tcaacggccc    240

ccaggggtcc ctgaccgatt ctctggctcc aagtctggca cctcagcctc cctggccatc    300

agtgggctcc ggtctgagga tgaggctgat tattactgtg cagcatggga cgccagtcga    360

caaggggtgt tcggcggagg gaccaagctg accgtcctag gttctagagg tggtggtggt    420

agcggcggcg gcggctctgg tggtggtgga tccctcgaga tggcccaggt gcagctggtg    480

cagtctgggg ctgaggtgaa gaagcctggg tcctcggtga aggtctcctg caaggcttct    540

ggaggcacct tccgcagcta tgctatcacc tgggtgcgac aggcccctgg acaagggctt    600

gagtggatgg gaaggatcat ccctatgctt gatataacaa actacgcaca gaagttccag    660

ggcagagtca cgattaccgc ggacaaatcc acgagcacag cctacatgga gctgagcagc    720

ctgagatctg aggacacggc cgtgtattac tgtgcgcgca cttactctcg ttctccgttc    780

catatggaag atttctgggg tcaaggtact ctggtgaccg tctcctca                 828
```

<210> SEQ ID NO 337
<211> LENGTH: 270

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 337

Met Lys Lys Thr Ala Ile Ala Ile Ala Val Ala Leu Ala Gly Phe Ala
1 5 10 15

Thr Val Ala Gln Ala Ala Glu Leu Gln Ser Val Leu Thr Gln Pro Pro
20 25 30

Ser Ala Ser Gly Thr Pro Gly Gln Arg Val Thr Ile Ser Cys Ser Gly
35 40 45

Ser Ser Ser Asn Ile Gly Ser Asn Thr Val Asn Trp Tyr Gln Gln Leu
50 55 60

Pro Gly Thr Ala Pro Lys Leu Leu Ile Tyr Arg Asn Asn Gln Arg Pro
65 70 75 80

Ser Gly Val Pro Asp Arg Phe Ser Gly Ser Lys Ser Gly Thr Ser Ala
85 90 95

Ser Leu Ala Ile Ser Gly Leu Arg Ser Glu Asp Glu Ala Asp Tyr Tyr
100 105 110

Cys Ala Ala Trp Asp Asp Ser Leu Ser Gly Arg Val Phe Gly Gly Gly
115 120 125

Thr Lys Leu Thr Val Leu Gly Ser Arg Gly Gly Gly Gly Ser Gly Gly
130 135 140

Gly Gly Ser Gly Gly Gly Gly Ser Leu Glu Met Ala Glu Val Gln Leu
145 150 155 160

Val Glu Ser Gly Gly Gly Leu Val Gln Pro Gly Gly Ser Leu Arg Leu
165 170 175

Ser Cys Ala Ala Ser Gly Phe Thr Phe Ser Ser Tyr Ala Met Ser Trp
180 185 190

Val Arg Gln Ala Pro Gly Lys Gly Leu Glu Trp Val Ser Ala Ile Ser
195 200 205

Gly Ser Gly Gly Ser Thr Tyr Tyr Ala Asp Ser Val Lys Gly Arg Phe
210 215 220

Thr Ile Ser Arg Asp Asn Ala Lys Asn Thr Leu Tyr Leu Gln Met Asn
225 230 235 240

Ser Leu Arg Ala Glu Asp Thr Ala Val Tyr Tyr Cys Ala Arg Lys Tyr
245 250 255

Gln Asp Val Trp Gly Gln Gly Thr Leu Val Thr Val Ser Ser
260 265 270

<210> SEQ ID NO 338
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 338

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Arg Lys Tyr Gln Asp Val Trp Gly Gln Gly Thr Leu Val Thr Val
100 105 110

Ser Ser

<210> SEQ ID NO 339
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 339

Met Lys Lys Thr Ala Ile Ala Ile Ala Val Ala Leu Ala Gly Phe Ala
1 5 10 15

Thr Val Ala Gln Ala Ala Glu Leu Gln Ser Val Leu Thr Gln Pro Pro
20 25 30

Ser Ala Ser Gly Thr Pro Gly Gln Arg Val Thr Ile Ser Cys Ser Gly
35 40 45

Ser Ser Ser Asn Ile Gly Ser Asn Thr Val Asn Trp Tyr Gln Gln Leu
50 55 60

Pro Gly Thr Ala Pro Lys Leu Leu Ile Tyr Arg Asn Asn Gln Arg Pro
65 70 75 80

Ser Gly Val Pro Asp Arg Phe Ser Gly Ser Lys Ser Gly Thr Ser Ala
85 90 95

Ser Leu Ala Ile Ser Gly Leu Arg Ser Glu Asp Glu Ala Asp Tyr Tyr
100 105 110

Cys Ala Ala Trp Asp Asp Ser Leu Ser Gly Arg Val Phe Gly Gly Gly
115 120 125

Thr Lys Leu Thr Val Leu Gly
130 135

<210> SEQ ID NO 340
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 340

Gly Phe Thr Phe Ser Ser Tyr Ala
1 5

<210> SEQ ID NO 341
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Ile Ser Gly Ser Gly Gly Ser Thr
1 5

<210> SEQ ID NO 342
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 342

Ala Arg Lys Tyr Gln Asp Val
1 5

<210> SEQ ID NO 343
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 343

Ser Ser Asn Ile Gly Ser Asn Thr
1 5

<210> SEQ ID NO 344
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 344

Arg Asn Asn
1

<210> SEQ ID NO 345
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 345

Ala Ala Trp Asp Asp Ser Leu Ser Gly Arg Val
1 5 10

<210> SEQ ID NO 346
<211> LENGTH: 342
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 346
gaggtgcagc tggtggagtc tgggggaggc ttggtacagc ctgggggtc cctgagactc 60 tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca atgccaagaa cacgctgtat 240
ctgcaaatga acagcctgag agccgaggac acggccgtat attactgtgc gcgcaaatac 300
caggatgttt ggggtcaagg tactctggtg accgtctcct ca 342

<210> SEQ ID NO 347
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 347
atgaaaaaga cagctatcgc gattgcagtg gcactggctg gtttcgctac cgtggcccag     60
gcggccgagc tccagtctgt gctgacgcag ccgccctcag cgtctgggac ccccgggcag    120
agggtcacca tctcttgttc tggaagcagc tccaacatcg gaagtaatac tgtaaactgg    180
taccagcagc tcccaggaac ggcccccaaa ctcctcatct ataggaataa tcagcggccc    240
tcaggggtcc ctgaccgatt ctctggctcc aagtctggca cctcagcctc cctggccatc    300
agtgggctcc ggtccgagga tgaggctgat tattactgtg cagcatggga tgacagcctg    360
agtggtaggg tgttcggcgg agggaccaag ctgaccgtcc taggt                    405

<210> SEQ ID NO 348
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 348
atgaaaaaga cagctatcgc gattgcagtg gcactggctg gtttcgctac cgtggcccag     60
gcggccgagc tccagtctgt gctgacgcag ccgccctcag cgtctgggac ccccgggcag    120
agggtcacca tctcttgttc tggaagcagc tccaacatcg gaagtaatac tgtaaactgg    180
taccagcagc tcccaggaac ggcccccaaa ctcctcatct ataggaataa tcagcggccc    240
tcaggggtcc ctgaccgatt ctctggctcc aagtctggca cctcagcctc cctggccatc    300
agtgggctcc ggtccgagga tgaggctgat tattactgtg cagcatggga tgacagcctg    360
agtggtaggg tgttcggcgg agggaccaag ctgaccgtcc taggttctag aggtggtggt    420
ggtagcggcg gcggcggctc tggtggtggt ggatccctcg agatggccga ggtgcagctg    480
gtggagtctg ggggaggctt ggtacagcct ggggggtccc tgagactctc ctgtgcagcc    540
tctggattca cctttagcag ctatgccatg agctgggtcc gccaggctcc agggaagggg    600
ctggagtggg tctcagctat tagtggtagt ggtggtagca catactacgc agactccgtg    660
aagggccggt tcaccatctc cagagacaat gccaagaaca cgctgtatct gcaaatgaac    720
agcctgagag ccgaggacac ggccgtatat tactgtgcgc gcaaatacca ggatgtttgg    780
ggtcaaggta ctctggtgac cgtctcctca                                     810

<210> SEQ ID NO 349
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Met Lys Lys Thr Ala Ile Ala Ile Ala Val Ala Leu Ala Gly Phe Ala
1               5                   10                  15

-continued

Thr Val Ala Gln Ala Ala Glu Leu Gln Ser Val Leu Thr Gln Pro Pro
20 25 30

Ser Val Ser Gly Ala Pro Gly Gln Arg Val Thr Ile Ser Cys Thr Gly
35 40 45

Ser Ser Ser Asn Ile Gly Ala Gly Tyr Asp Val His Trp Tyr Gln Gln
50 55 60

Leu Pro Gly Arg Ala Pro Lys Leu Leu Ile Tyr Gly Asn Ser Asn Arg
65 70 75 80

Pro Ser Gly Val Pro Asp Arg Phe Ser Gly Ser Lys Ser Gly Thr Ser
85 90 95

Ala Ser Leu Ala Ile Thr Gly Leu Gln Ala Glu Asp Glu Ala Asp Tyr
100 105 110

Tyr Cys Gln Ser Tyr Asp Ser Ser Leu Arg Gly Tyr Val Phe Gly Thr
115 120 125

Gly Thr Lys Val Thr Val Leu Gly Ser Arg Gly Gly Gly Gly Ser Gly
130 135 140

Gly Gly Gly Ser Gly Gly Gly Gly Ser Leu Glu Met Ala Gln Val Gln
145 150 155 160

Leu Val Gln Ser Gly Gly Gly Val Val Gln Pro Gly Arg Ser Leu Arg
165 170 175

Leu Ser Cys Ala Ala Ser Gly Phe Ser Phe Ser Gly Thr Ala Met His
180 185 190

Trp Val Arg Gln Ala Pro Gly Lys Gly Leu Glu Trp Val Ser Thr Ile
195 200 205

Ser Ser Thr Gly Arg Ser Thr Tyr Tyr Arg Asp Ser Val Lys Gly Arg
210 215 220

Phe Thr Ile Ser Arg Asp Asn Ser Lys Asn Thr Leu Tyr Leu Gln Met
225 230 235 240

Asn Ser Leu Arg Gly Glu Asp Thr Ala Val Tyr Tyr Cys Ala Arg Pro
245 250 255

Val Ser Ser Met Thr Leu Ser Ile Gln Ser Asp Gly Trp Gly Gln Gly
260 265 270

Thr Leu Val Thr Val Ser Ser
275

<210> SEQ ID NO 350
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 350

Gln Val Gln Leu Val Gln Ser Gly Gly Gly Val Val Gln Pro Gly Arg
1 5 10 15

Ser Leu Arg Leu Ser Cys Ala Ala Ser Gly Phe Ser Phe Ser Gly Thr
20 25 30

Ala Met His Trp Val Arg Gln Ala Pro Gly Lys Gly Leu Glu Trp Val
35 40 45

Ser Thr Ile Ser Ser Thr Gly Arg Ser Thr Tyr Tyr Arg Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Gly Glu Asp Thr Ala Val Tyr Tyr Cys
85 90 95

```
Ala Arg Pro Val Ser Ser Met Thr Leu Ser Ile Gln Ser Asp Gly Trp
            100                 105                 110

Gly Gln Gly Thr Leu Val Thr Val Ser Ser
        115                 120


<210> SEQ ID NO 351
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Met Lys Lys Thr Ala Ile Ala Ile Ala Val Ala Leu Ala Gly Phe Ala
1               5                   10                  15

Thr Val Ala Gln Ala Ala Glu Leu Gln Ser Val Leu Thr Gln Pro Pro
            20                  25                  30

Ser Val Ser Gly Ala Pro Gly Gln Arg Val Thr Ile Ser Cys Thr Gly
        35                  40                  45

Ser Ser Ser Asn Ile Gly Ala Gly Tyr Asp Val His Trp Tyr Gln Gln
    50                  55                  60

Leu Pro Gly Arg Ala Pro Lys Leu Leu Ile Tyr Gly Asn Ser Asn Arg
65                  70                  75                  80

Pro Ser Gly Val Pro Asp Arg Phe Ser Gly Ser Lys Ser Gly Thr Ser
                85                  90                  95

Ala Ser Leu Ala Ile Thr Gly Leu Gln Ala Glu Asp Glu Ala Asp Tyr
            100                 105                 110

Tyr Cys Gln Ser Tyr Asp Ser Ser Leu Arg Gly Tyr Val Phe Gly Thr
        115                 120                 125

Gly Thr Lys Val Thr Val Leu Gly
    130                 135


<210> SEQ ID NO 352
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Gly Phe Ser Phe Ser Gly Thr Ala
1               5


<210> SEQ ID NO 353
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ile Ser Ser Thr Gly Arg Ser Thr
1               5


<210> SEQ ID NO 354
<211> LENGTH: 15
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 354

Ala Arg Pro Val Ser Ser Met Thr Leu Ser Ile Gln Ser Asp Gly
1 5 10 15

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 355

Ser Ser Asn Ile Gly Ala Gly Tyr Asp
1 5

<210> SEQ ID NO 356
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 356

Gly Asn Ser
1

<210> SEQ ID NO 357
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 357

Gln Ser Tyr Asp Ser Ser Leu Arg Gly Tyr Val
1 5 10

<210> SEQ ID NO 358
<211> LENGTH: 366
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 358
caggtgcagc tggtgcagtc tgggggaggc gtggtccagc ctgggaggtc cctgagactc 60
tcctgtgcag cctctggatt cagctttagt ggcactgcca tgcactgggt ccgccaggct 120
ccagggaagg ggctggaatg ggtctcgact attagtagta ctgggcgtag cacatactac 180
agagactccg tgaagggccg gttcaccatc tccagagaca attccaagaa cacgctgtat 240
ctgcaaatga acagcctgag aggcgaggac acggccgtat attactgtgc gcgcccggtt 300
tcttctatga ctctgtctat ccagtctgat ggttggggtc aaggtactct ggtgaccgtc 360
tcctca 366

<210> SEQ ID NO 359
<211> LENGTH: 408
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 359

```
atgaaaaaga cagctatcgc gattgcagtg gcactggctg gtttcgctac cgtggcccag     60

gcggccgagc tccagtctgt gttgacgcag ccgccctcag tgtctggggc cccagggcag    120

agggtcacca tctcctgcac tgggagcagc tccaacatcg gggcaggtta tgatgtacac    180

tggtaccagc agcttccagg aagagccccc aaactcctca tctatggtaa cagcaatcgg    240

ccctcagggg tccctgaccg attctctggc tccaagtctg gcacctcagc ctccctggcc    300

atcactgggc tccaggctga ggatgaggct gattattact gccagtccta tgacagcagc    360

ctgagaggtt atgtcttcgg aactgggacc aaggtcaccg tcctaggt                 408
```

<210> SEQ ID NO 360
<211> LENGTH: 837
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 360

```
atgaaaaaga cagctatcgc gattgcagtg gcactggctg gtttcgctac cgtggcccag     60

gcggccgagc tccagtctgt gttgacgcag ccgccctcag tgtctggggc cccagggcag    120

agggtcacca tctcctgcac tgggagcagc tccaacatcg gggcaggtta tgatgtacac    180

tggtaccagc agcttccagg aagagccccc aaactcctca tctatggtaa cagcaatcgg    240

ccctcagggg tccctgaccg attctctggc tccaagtctg gcacctcagc ctccctggcc    300

atcactgggc tccaggctga ggatgaggct gattattact gccagtccta tgacagcagc    360

ctgagaggtt atgtcttcgg aactgggacc aaggtcaccg tcctaggttc tagaggtggt    420

ggtggtagcg gcggcggcgg ctctggtggt ggtggatccc tcgagatggc ccaggtgcag    480

ctggtgcagt ctgggggagg cgtggtccag cctgggaggt ccctgagact ctcctgtgca    540

gcctctggat tcagctttag tggcactgcc atgcactggg tccgccaggc tccagggaag    600

gggctggaat gggtctcgac tattagtagt actgggcgta gcacatacta cagagactcc    660

gtgaagggcc ggttcaccat ctccagagac aattccaaga acacgctgta tctgcaaatg    720

aacagcctga gaggcgagga cacggccgta tattactgtg cgcgcccggt ttcttctatg    780

actctgtcta tccagtctga tggttggggt caaggtactc tggtgaccgt ctcctca       837
```

<210> SEQ ID NO 361
<211> LENGTH: 286
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 361

```
Met Lys Lys Thr Ala Ile Ala Ile Ala Val Ala Leu Ala Gly Phe Ala
1               5                   10                  15

Thr Val Ala Gln Ala Ala Glu Leu Gln Ser Val Val Thr Gln Pro Pro
            20                  25                  30

Ser Val Ser Ala Ala Pro Gly Gln Arg Val Thr Ile Ser Cys Ser Gly
        35                  40                  45
```

Gly Ser Ser Asn Ile Gly Asn Asn Tyr Val Ser Trp Phe Gln Gln Leu
50 55 60

Pro Arg Thr Ala Pro Lys Leu Leu Ile Tyr Asp Asn Asn Lys Arg Pro
65 70 75 80

Ser Gly Ile Pro Asp Arg Phe Ser Gly Ser Lys Ser Gly Thr Ser Ala
85 90 95

Ala Leu Asp Ile Thr Val Leu Gln Thr Gly Asp Glu Ala Asp Tyr Tyr
100 105 110

Cys Gly Thr Trp Asp Ser Ser Leu Arg Asn Trp Val Phe Gly Gly Gly
115 120 125

Thr Lys Leu Thr Val Leu Gly Ser Arg Gly Gly Gly Gly Ser Gly Gly
130 135 140

Gly Gly Ser Gly Gly Gly Gly Ser Leu Glu Met Ala Gln Met Gln Leu
145 150 155 160

Val Gln Ser Gly Ala Glu Val Lys Lys Pro Gly Ala Ser Val Lys Val
165 170 175

Ser Cys Lys Ala Ser Gly Tyr Thr Phe Thr Ser Tyr Tyr Met His Trp
180 185 190

Val Arg Gln Ala Pro Gly Gln Gly Leu Glu Trp Met Gly Ile Ile Asn
195 200 205

Pro Ser Gly Gly Ser Thr Ser Tyr Ala Gln Lys Phe Gln Gly Arg Val
210 215 220

Thr Met Thr Arg Asp Thr Ser Thr Ser Thr Val Tyr Met Glu Leu Ser
225 230 235 240

Ser Leu Arg Ser Glu Asp Thr Ala Val Tyr Tyr Cys Ala Arg Gly Gln
245 250 255

Lys Tyr His Ser Gln Tyr Ser Arg Gly Gly Thr Gly Gly Gly Met Thr
260 265 270

Gln Asp Met Trp Gly Gln Gly Thr Leu Val Thr Val Ser Ser
275 280 285

<210> SEQ ID NO 362
<211> LENGTH: 130
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 362

Gln Met Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Gln Lys Tyr His Ser Gln Tyr Ser Arg Gly Gly Thr Gly
100 105 110

Gly Gly Met Thr Gln Asp Met Trp Gly Gln Gly Thr Leu Val Thr Val 115 120 125

Ser Ser
130

<210> SEQ ID NO 363
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 363

Met Lys Lys Thr Ala Ile Ala Ile Ala Val Ala Leu Ala Gly Phe Ala
1 5 10 15

Thr Val Ala Gln Ala Ala Glu Leu Gln Ser Val Val Thr Gln Pro Pro
20 25 30

Ser Val Ser Ala Ala Pro Gly Gln Arg Val Thr Ile Ser Cys Ser Gly
35 40 45

Gly Ser Ser Asn Ile Gly Asn Asn Tyr Val Ser Trp Phe Gln Gln Leu
50 55 60

Pro Arg Thr Ala Pro Lys Leu Leu Ile Tyr Asp Asn Asn Lys Arg Pro
65 70 75 80

Ser Gly Ile Pro Asp Arg Phe Ser Gly Ser Lys Ser Gly Thr Ser Ala
85 90 95

Ala Leu Asp Ile Thr Val Leu Gln Thr Gly Asp Glu Ala Asp Tyr Tyr
100 105 110

Cys Gly Thr Trp Asp Ser Ser Leu Arg Asn Trp Val Phe Gly Gly Gly
115 120 125

Thr Lys Leu Thr Val Leu Gly
130 135

<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Gly Tyr Thr Phe Thr Ser Tyr Tyr
1 5

<210> SEQ ID NO 365
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 365

Ile Asn Pro Ser Gly Gly Ser Thr
1 5

<210> SEQ ID NO 366
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 366

Ala Arg Gly Gln Lys Tyr His Ser Gln Tyr Ser Arg Gly Gly Thr Gly
1 5 10 15

Gly Gly Met Thr Gln Asp Met
20

<210> SEQ ID NO 367
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 367

Ser Ser Asn Ile Gly Asn Asn Tyr
1 5

<210> SEQ ID NO 368
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 368

Asp Asn Asn
1

<210> SEQ ID NO 369
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 369

Gly Thr Trp Asp Ser Ser Leu Arg Asn Trp Val
1 5 10

<210> SEQ ID NO 370
<211> LENGTH: 390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 370
cagatgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaagctac 180
gcacaaaagt tccagggcag agtcaccatg accagggaca cgtccacgag cacagtctac 240
atggagctga gcagcctgag atctgaggac acggccgtgt attactgtgc gcgcggtcag 300
aaataccatt ctcagtactc tcgtggtggt actggtggtg gtatgactca ggatatgtgg 360
ggtcaaggta ctctggtgac cgtctcctca 390

<210> SEQ ID NO 371
<211> LENGTH: 405

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 371

```
atgaaaaaga cagctatcgc gattgcagtg gcactggctg gtttcgctac cgtggcccag     60

gcggccgagc tccagtctgt cgtgacgcag ccgccctctg tgtctgcggc cccaggacag    120

agggtcacca tctcctgctc tggaggtagt tccaacattg ggaataatta tgtttcctgg    180

ttccaacaac tcccacgaac agcccccaaa ctcctcattt atgacaataa taagcgaccc    240

tcagggattc ctgaccgatt ctctggctcc aagtctggca cgtcagccgc cctggacatc    300

accgttctcc agactgggga cgaggccgat tattactgcg gaacttggga tagcagcctg    360

agaaattggg tgttcggcgg agggaccaag ctgaccgtcc taggt                    405
```

<210> SEQ ID NO 372
<211> LENGTH: 858
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 372

```
atgaaaaaga cagctatcgc gattgcagtg gcactggctg gtttcgctac cgtggcccag     60

gcggccgagc tccagtctgt cgtgacgcag ccgccctctg tgtctgcggc cccaggacag    120

agggtcacca tctcctgctc tggaggtagt tccaacattg ggaataatta tgtttcctgg    180

ttccaacaac tcccacgaac agcccccaaa ctcctcattt atgacaataa taagcgaccc    240

tcagggattc ctgaccgatt ctctggctcc aagtctggca cgtcagccgc cctggacatc    300

accgttctcc agactgggga cgaggccgat tattactgcg gaacttggga tagcagcctg    360

agaaattggg tgttcggcgg agggaccaag ctgaccgtcc taggttctag aggtggtggt    420

ggtagcggcg gcggcggctc tggtggtggt ggatccctcg agatggccca gatgcagctg    480

gtgcagtctg gggctgaggt gaagaagcct ggggcctcag tgaaggtttc ctgcaaggca    540

tctggataca ccttcaccag ctactatatg cactgggtgc gacaggcccc tggacaaggg    600

cttgagtgga tgggaataat caaccctagt ggtggtagca caagctacgc acaaaagttc    660

cagggcagag tcaccatgac cagggacacg tccacgagca cagtctacat ggagctgagc    720

agcctgagat ctgaggacac ggccgtgtat tactgtgcgc gcggtcagaa ataccattct    780

cagtactctc gtggtggtac tggtggtggt atgactcagg atatgtgggg tcaaggtact    840

ctggtgaccg tctcctca                                                  858
```

<210> SEQ ID NO 373
<211> LENGTH: 273
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 373

```
Met Lys Lys Thr Ala Ile Ala Ile Ala Val Ala Leu Ala Gly Phe Ala
1               5                   10                  15

Thr Val Ala Gln Ala Ala Glu Leu Gln Ser Val Leu Thr Gln Pro Pro
            20                  25                  30
```

Ser Ala Ser Gly Ser Pro Gly Gln Ser Leu Thr Ile Ser Cys Thr Gly
35 40 45

Thr Ser Ser Asp Val Gly Gly Tyr Asn His Val Ser Trp Tyr Gln Gln
50 55 60

Tyr Pro Gly Lys Ala Pro Lys Leu Met Ile Tyr Glu Val Thr Lys Arg
65 70 75 80

Pro Ser Gly Val Pro Asp Arg Phe Ser Gly Ser Lys Ser Gly Asn Thr
85 90 95

Ala Ser Leu Thr Val Ser Gly Leu Gln Ala Glu Asp Glu Ala Asp Tyr
100 105 110

Tyr Cys Ser Ser Tyr Ala Gly Ser Ala His Trp Val Phe Gly Gly Gly
115 120 125

Thr Lys Leu Thr Val Leu Gly Ser Arg Gly Gly Gly Gly Ser Gly Gly
130 135 140

Gly Gly Ser Gly Gly Gly Gly Ser Leu Glu Met Ala Glu Val Gln Leu
145 150 155 160

Val Gln Ser Gly Ala Glu Val Lys Lys Pro Gly Ala Ser Val Lys Val
165 170 175

Ser Cys Lys Ala Ser Gly Tyr Thr Phe Ser Arg Tyr Tyr Ile His Trp
180 185 190

Val Arg Gln Ala Pro Gly Gln Gly Leu Glu Trp Met Gly Trp Met Asn
195 200 205

Pro Asn Ser Gly Asn Thr Gly Tyr Ala Gln Lys Phe Gln Gly Arg Val
210 215 220

Thr Met Thr Arg Asn Thr Ser Ile Ser Thr Ala Tyr Met Glu Leu Ser
225 230 235 240

Ser Leu Arg Ser Glu Asp Thr Ala Val Tyr Tyr Cys Ala Arg Gly Arg
245 250 255

Tyr His Val Ile Asp Tyr Trp Gly Gln Gly Thr Leu Val Thr Val Ser
260 265 270

Ser

<210> SEQ ID NO 374
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 374

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ser Arg Tyr
20 25 30

Tyr Ile His Trp Val Arg Gln Ala Pro Gly Gln Gly Leu Glu Trp Met
35 40 45

Gly Trp Met Asn Pro Asn Ser Gly Asn Thr Gly Tyr Ala Gln Lys Phe
50 55 60

Gln Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Gly Arg Tyr His Val Ile Asp Tyr Trp Gly Gln Gly Thr Leu
100 105 110

Val Thr Val Ser Ser
        115

<210> SEQ ID NO 375
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Met Lys Lys Thr Ala Ile Ala Ile Ala Val Ala Leu Ala Gly Phe Ala
1               5                   10                  15

Thr Val Ala Gln Ala Ala Glu Leu Gln Ser Val Leu Thr Gln Pro Pro
            20                  25                  30

Ser Ala Ser Gly Ser Pro Gly Gln Ser Leu Thr Ile Ser Cys Thr Gly
        35                  40                  45

Thr Ser Ser Asp Val Gly Gly Tyr Asn His Val Ser Trp Tyr Gln Gln
    50                  55                  60

Tyr Pro Gly Lys Ala Pro Lys Leu Met Ile Tyr Glu Val Thr Lys Arg
65                  70                  75                  80

Pro Ser Gly Val Pro Asp Arg Phe Ser Gly Ser Lys Ser Gly Asn Thr
                85                  90                  95

Ala Ser Leu Thr Val Ser Gly Leu Gln Ala Glu Asp Glu Ala Asp Tyr
            100                 105                 110

Tyr Cys Ser Ser Tyr Ala Gly Ser Ala His Trp Val Phe Gly Gly Gly
        115                 120                 125

Thr Lys Leu Thr Val Leu Gly
    130                 135

<210> SEQ ID NO 376
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gly Tyr Thr Phe Ser Arg Tyr Tyr
1               5

<210> SEQ ID NO 377
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Met Asn Pro Asn Ser Gly Asn Thr
1               5

<210> SEQ ID NO 378
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ala Arg Gly Arg Tyr His Val Ile Asp Tyr
1 5 10

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 379

Ser Ser Asp Val Gly Gly Tyr Asn His
1 5

<210> SEQ ID NO 380
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 380

Glu Val Thr
1

<210> SEQ ID NO 381
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 381

Ser Ser Tyr Ala Gly Ser Ala His Trp Val
1 5 10

<210> SEQ ID NO 382
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 382
gaggtccagc tggtgcagtc tggggctgag gtgaagaagc ctggggcctc agtgaaggtt 60
tcctgcaagg catctggata caccttcagc aggtactata tacactgggt gcgacaggcc 120
cctggacaag ggcttgagtg gatgggatgg atgaacccta acagtggtaa cacaggctat 180
gcacagaagt tccagggcag agtcaccatg accaggaaca cctccataag cacagcctac 240
atggagctga gcagcctgag atctgaggac acggccgtgt attactgtgc gcgcggtcgt 300
taccatgtta tcgattactg gggtcaaggt actctggtga ccgtctcctc a 351

<210> SEQ ID NO 383
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 383
atgaaaaaga cagctatcgc gattgcagtg gcactggctg gtttcgctac cgtggcccag 60
gcggccgagc tccagtctgt gttgactcag ccaccctccg cgtccgggtc tcctggacag 120
tcactcacca tctcctgcac tggaaccagc agtgacgttg gtggttataa ccatgtctcc 180
tggtaccaac agtacccagg caaagccccc aaactcatga tttatgaggt cactaagcgg 240
ccctcagggg tccctgatcg cttctctggc tccaagtctg gcaacacggc ctccctgacc 300
gtctctgggc tccaggctga ggatgaggct gattattact gcagctcata tgcaggcagc 360
gcccattggg tgttcggcgg agggaccaag ctgaccgtcc taggt 405

<210> SEQ ID NO 384
<211> LENGTH: 819
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 384
atgaaaaaga cagctatcgc gattgcagtg gcactggctg gtttcgctac cgtggcccag 60
gcggccgagc tccagtctgt gttgactcag ccaccctccg cgtccgggtc tcctggacag 120
tcactcacca tctcctgcac tggaaccagc agtgacgttg gtggttataa ccatgtctcc 180
tggtaccaac agtacccagg caaagccccc aaactcatga tttatgaggt cactaagcgg 240
ccctcagggg tccctgatcg cttctctggc tccaagtctg gcaacacggc ctccctgacc 300
gtctctgggc tccaggctga ggatgaggct gattattact gcagctcata tgcaggcagc 360
gcccattggg tgttcggcgg agggaccaag ctgaccgtcc taggttctag aggtggtggt 420
ggtagcggcg gcggcggctc tggtggtggt ggatccctcg agatggccga ggtccagctg 480
gtgcagtctg gggctgaggt gaagaagcct ggggcctcag tgaaggtttc ctgcaaggca 540
tctggataca ccttcagcag gtactatata cactgggtgc gacaggcccc tggacaaggg 600
cttgagtgga tgggatggat gaaccctaac agtggtaaca caggctatgc acagaagttc 660
cagggcagag tcaccatgac caggaacacc tccataagca cagcctacat ggagctgagc 720
agcctgagat ctgaggacac ggccgtgtat tactgtgcgc gcggtcgtta ccatgttatc 780
gattactggg gtcaaggtac tctggtgacc gtctcctca 819

<210> SEQ ID NO 385
<211> LENGTH: 269
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 385

Met Lys Lys Thr Ala Ile Ala Ile Ala Val Ala Leu Ala Gly Phe Ala
1 5 10 15

Thr Val Ala Gln Ala Ala Glu Leu Gln Ala Val Leu Thr Gln Pro Pro
20 25 30

Ser Ala Ser Gly Thr Pro Gly Gln Arg Val Thr Ile Ser Cys Ser Gly
35 40 45

Ser Ser Ser Asn Ile Gly Ser Asn Tyr Val Tyr Trp Tyr Gln Gln Leu
50 55 60

Pro Gly Thr Ala Pro Lys Leu Leu Ile Tyr Arg Asn Asn Gln Arg Pro

```
65                  70                  75                  80

Ser Gly Val Pro Asp Arg Phe Ser Gly Ser Lys Ser Gly Thr Ser Ala
                85                  90                  95

Ser Leu Ala Ile Ser Gly Leu Arg Ser Glu Asp Glu Ala Asp Tyr Tyr
            100                 105                 110

Cys Ala Ala Trp Asp Asp Ser Leu Ser Gly Arg Val Phe Gly Thr Gly
        115                 120                 125

Thr Lys Val Thr Val Leu Gly Ser Arg Gly Gly Gly Gly Ser Gly Gly
    130                 135                 140

Gly Gly Ser Gly Gly Gly Gly Ser Leu Glu Met Ala Gln Leu Gln Leu
145                 150                 155                 160

Val Gln Ser Gly Ala Glu Val Lys Lys Pro Gly Ser Ser Val Lys Val
                165                 170                 175

Ser Cys Lys Ala Ser Gly Tyr Thr Phe Asn Thr Tyr Tyr Leu His Trp
            180                 185                 190

Val Arg Gln Ala Pro Gly Gln Gly Leu Glu Trp Met Gly Arg Ile Asn
        195                 200                 205

Pro Asn Asn Gly Gly Thr Asn Tyr Ala Gln Lys Phe Gln Gly Arg Val
    210                 215                 220

Thr Met Thr Arg Asp Thr Ser Ile Asn Thr Ala Tyr Met Glu Leu Ser
225                 230                 235                 240

Arg Leu Arg Ser Asp Asp Thr Ala Val Tyr Tyr Cys Ala Arg Ser Tyr
                245                 250                 255

Asp Tyr Trp Gly Gln Gly Thr Leu Val Thr Val Ser Ser
            260                 265
```

<210> SEQ ID NO 386
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 386

```
Gln Leu Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Asn Thr Tyr
            20                  25                  30

Tyr Leu His Trp Val Arg Gln Ala Pro Gly Gln Gly Leu Glu Trp Met
        35                  40                  45

Gly Arg Ile Asn Pro Asn Asn Gly Gly Thr Asn Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Tyr Asp Tyr Trp Gly Gln Gly Thr Leu Val Thr Val Ser
            100                 105                 110

Ser
```

<210> SEQ ID NO 387
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 387

Met Lys Lys Thr Ala Ile Ala Ile Ala Val Ala Leu Ala Gly Phe Ala
1 5 10 15

Thr Val Ala Gln Ala Ala Glu Leu Gln Ala Val Leu Thr Gln Pro Pro
20 25 30

Ser Ala Ser Gly Thr Pro Gly Gln Arg Val Thr Ile Ser Cys Ser Gly
35 40 45

Ser Ser Ser Asn Ile Gly Ser Asn Tyr Val Tyr Trp Tyr Gln Gln Leu
50 55 60

Pro Gly Thr Ala Pro Lys Leu Leu Ile Tyr Arg Asn Asn Gln Arg Pro
65 70 75 80

Ser Gly Val Pro Asp Arg Phe Ser Gly Ser Lys Ser Gly Thr Ser Ala
85 90 95

Ser Leu Ala Ile Ser Gly Leu Arg Ser Glu Asp Glu Ala Asp Tyr Tyr
100 105 110

Cys Ala Ala Trp Asp Asp Ser Leu Ser Gly Arg Val Phe Gly Thr Gly
115 120 125

Thr Lys Val Thr Val Leu Gly
130 135

<210> SEQ ID NO 388
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 388

Gly Tyr Thr Phe Asn Thr Tyr Tyr
1 5

<210> SEQ ID NO 389
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 389

Ile Asn Pro Asn Asn Gly Gly Thr
1 5

<210> SEQ ID NO 390
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 390

Ala Arg Ser Tyr Asp Tyr
1 5

<210> SEQ ID NO 391
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 391

Ser Ser Asn Ile Gly Ser Asn Tyr
1               5

<210> SEQ ID NO 392
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Arg Asn Asn
1

<210> SEQ ID NO 393
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ala Ala Trp Asp Asp Ser Leu Ser Gly Arg Val
1               5                   10

<210> SEQ ID NO 394
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 394
cagctgcagc tggtgcaatc tggggctgag gtgaagaagc ctgggtcctc ggtgaaggtc     60
tcctgcaagg cttctggata caccttcaac acctactatc tgcactgggt acgacaggcc    120
cctggacaag ggcttgagtg gatgggacgg atcaacccta acaatggtgg cacaaactat    180
gcacagaagt ttcagggcag ggtcaccatg accagggaca cgtccatcaa cacagcctac    240
atggagctga gcaggctgag atctgacgac acggccgtgt attactgtgc gcgctcttac    300
gattactggg gtcaaggtac tctggtgacc gtctcctca                           339

<210> SEQ ID NO 395
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 395
atgaaaaaga cagctatcgc gattgcagtg gcactggctg gtttcgctac cgtggcccag     60
gcggccgagc tccaggctgt gctgactcag ccaccctcag cgtctgggac ccccgggcag    120
agggtcacca tctcttgttc tggaagcagc tccaacatcg gaagtaatta tgtatactgg    180
taccagcagc tcccaggaac ggcccccaaa ctcctcatct ataggaataa tcagcggccc    240
tcaggggtcc ctgaccgatt ctctggctcc aagtctggca cctcagcctc cctggccatc    300
agtgggctcc ggtccgagga tgaggctgat tattactgtg cagcatggga tgacagcctg 360
agtggtcggg tcttcggaac tgggaccaag gtcaccgtcc taggt 405

<210> SEQ ID NO 396
<211> LENGTH: 807
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 396
atgaaaaaga cagctatcgc gattgcagtg gcactggctg gtttcgctac cgtggcccag 60
gcggccgagc tccaggctgt gctgactcag ccaccctcag cgtctgggac ccccgggcag 120
agggtcacca tctcttgttc tggaagcagc tccaacatcg gaagtaatta tgtatactgg 180
taccagcagc tcccaggaac ggcccccaaa ctcctcatct ataggaataa tcagcggccc 240
tcaggggtcc ctgaccgatt ctctggctcc aagtctggca cctcagcctc cctggccatc 300
agtgggctcc ggtccgagga tgaggctgat tattactgtg cagcatggga tgacagcctg 360
agtggtcggg tcttcggaac tgggaccaag gtcaccgtcc taggttctag aggtggtggt 420
ggtagcggcg gcggcggctc tggtggtggt ggatccctcg agatggccca gctgcagctg 480
gtgcaatctg gggctgaggt gaagaagcct gggtcctcgg tgaaggtctc ctgcaaggct 540
tctggataca ccttcaacac ctactatctg cactgggtac gacaggcccc tggacaaggg 600
cttgagtgga tgggacggat caaccctaac aatggtggca caaactatgc acagaagttt 660
cagggcaggg tcaccatgac cagggacacg tccatcaaca cagcctacat ggagctgagc 720
aggctgagat ctgacgacac ggccgtgtat tactgtgcgc gctcttacga ttactggggt 780
caaggtactc tggtgaccgt ctcctca 807

<210> SEQ ID NO 397
<211> LENGTH: 1404
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 397
cagtctgtgt tgacgcagcc tgcctccgtg tctgggtctc ctggacagtc gctcaccatc 60
tcctgcactg gaaccagcaa tgacgttggt gcttataagt atgtctcctg gtatcaacag 120
tacccaggca aagcccccaa actcatactt tatgatgtct ttaagcggcc ctcaggggtc 180
tctaatcgct tctctggctc caagtctgac aacacggcct ccctgaccat ctctgggctc 240
caggctgagg acgaggctga ttattactgc ttctcactta caagcagtaa cacttatgtc 300
ttcggaactg ggaccaaggt caccgtccta ggttctagag gtggtggtgg tagcggcggc 360
ggcggctctg gtggtggtgg atccctcgag atggcccaga tgcagctggt gcagtctgga 420
gctgaggtga agaagcctgg ggcctcagtg aaggtctcct gcaaggcttc tggttacacc 480
tttaacagat atgctatcac ctgggtgcga caggcccctg gacaaggcct tgagtggatg 540
ggatggatca gcgcttacaa tggtaattca cactatgcac agaagctcca gggcagagtc 600
accatgacca cagacacatc cacgggcaca gcctatatgg agctgaggag gctgagatct 660
gacgacacgg ccgtgtatta ctgtgcgcgc atggcttacg attcttgggg tcaaggtact 720

```
ctggtgaccg tctcctcagc ggccgcaatt gaagttatgt atcctcctcc ttacctagac    780

aatgagaaga gcaatggaac cattatccat gtgaaaggga aacacctttg tccaagtccc    840

ctatttcccg gaccttctaa gcccttttgg gtgctggtgg tggttggtgg agtcctggct    900

tgctatagct tgctagtaac agtggccttt attattttct gggtgaggag taagaggagc    960

aggctcctgc acagtgacta catgaacatg actccccgcc gccccgggcc cacccgcaag   1020

cattaccagc cctatgcccc accacgcgac ttcgcagcct atcgctccag agtgaagttc   1080

agcaggagcg cagacgcccc cgcgtaccag cagggccaga accagctcta taacgagctc   1140

aatctaggac gaagagagga gtacgatgtt ttggacaaga gacgtggccg ggaccctgag   1200

atggggggaa agccgagaag gaagaaccct caggaaggcc tgtacaatga actgcagaaa   1260

gataagatgg cggaggccta cagtgagatt gggatgaaag gcgagcgccg gaggggcaag   1320

gggcacgatg gcctttacca gggtctcagt acagccacca aggacaccta cgacgccctt   1380

cacatgcagg ccctgccccc tcgc                                          1404


<210> SEQ ID NO 398
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 398

cagtctgtgt tgactcagcc accctcagcg tctgggaccc ccggacagag ggtcaccatc     60

tcttgttctg gaagcaggtc caacgtagga ggtaattatg tattttggta ccagcaagtc    120

cccggagcga cccccaaact cctcatctat aggagtaatc agcggccctc gggggtccct    180

gaccgattcg ctggctccaa gtctggctcc tcagcctccc tggccatcag tggactccgg    240

tccgaggatg aggctgatta ttactgtgca acatgggatg acagcctgag tggttttgtc    300

ttcggaactg ggaccaaggt caccgtccta ggttctagag gtggtggtgg tagcggcggc    360

ggcggctctg gtggtggtgg atccctcgag atggccgagg tgcagctggt ggagtctggg    420

ggaggcttgg tcaagcctgg agggtccctg agactctcct gtgcagcctc tggattcacc    480

ttcagtgact actacatgag ctggatccgc caggctccag ggaaggggct ggagtgggtt    540

tcatacatta gtagtagtgg tagtaccata tactacgcag actctgtgaa gggccgattc    600

accatctcca gggacaacgc caagaactca ctgtatctgc aaatgaacag cctgagagcc    660

gaggacacgg ccgtatatta ctgtgcgcgc ggttacggta aagcttacga tcagtggggt    720

caaggtactc tggtgaccgt ctcctcagcg gccgcaattg aagttatgta tcctcctcct    780

tacctagaca atgagaagag caatggaacc attatccatg tgaaagggaa acacctttgt    840

ccaagtcccc tatttcccgg accttctaag cccttttggg tgctggtggt ggttggtgga    900

gtcctggctt gctatagctt gctagtaaca gtggccttta ttattttctg ggtgaggagt    960

aagaggagca ggctcctgca cagtgactac atgaacatga ctccccgccg ccccgggccc   1020

acccgcaagc attaccagcc ctatgcccca ccacgcgact tcgcagccta tcgctccaga   1080

gtgaagttca gcaggagcgc agacgccccc gcgtaccagc agggccagaa ccagctctat   1140

aacgagctca atctaggacg aagagaggag tacgatgttt tggacaagag acgtggccgg   1200

gaccctgaga tggggggaaa gccgagaagg aagaaccctc aggaaggcct gtacaatgaa   1260

ctgcagaaag ataagatggc ggaggcctac agtgagattg ggatgaaagg cgagcgccgg   1320
```

aggggcaagg ggcacgatgg cctttaccag ggtctcagta cagccaccaa ggacacctac 1380
gacgcccttc acatgcaggc cctgcccccct cgc 1413

<210> SEQ ID NO 399
<211> LENGTH: 1416
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 399
tcttctgagc tgactcagga ccctgctgtg tctgtggcct tgggacagac agtcaggatc 60
acatgccaag gagacagcct cagaagctat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcccgg gacagcagtg gtaacccccc tgtggtattc 300
ggcggaggga ccaagctgac cgtcctaggt tctagaggtg gtggtggtag cggcggcggc 360
ggctctggtg gtggtggatc cctcgagatg gcccaggtgc agctggtgga gtctgggga 420 ggcctggtcc accctggggg gtccctgaga ctctcctgtg cagcctctgg attcaccttc 480
agaagccata gcatgaactg ggtccgccag gctccaggga aggggctgga gtgggtctca 540
tccattagta gtgatagtac ttacacatac tacgcagact cagtgaaggg ccgattcacc 600
atctccagag acaacgccaa gaactcactg tatctgcaaa tgaacagcct gagagccgag 660
gacacggccg tatattactg tgcgcgctct ggtggtcagt ggaaatacta cgattactgg 720
ggtcaaggta ctctggtgac cgtctcctca gcggccgcaa ttgaagttat gtatcctcct 780
ccttacctag acaatgagaa gagcaatgga accattatcc atgtgaaagg gaaacacctt 840
tgtccaagtc ccctatttcc cggaccttct aagccctttt gggtgctggt ggtggttggt 900
ggagtcctgg cttgctatag cttgctagta acagtggcct ttattatttt ctgggtgagg 960
agtaagagga gcaggctcct gcacagtgac tacatgaaca tgactccccg ccgccccggg 1020
cccacccgca agcattacca gccctatgcc ccaccacgcg acttcgcagc ctatcgctcc 1080
agagtgaagt tcagcaggag cgcagacgcc cccgcgtacc agcagggcca gaaccagctc 1140
tataacgagc tcaatctagg acgaagagag gagtacgatg ttttggacaa gagacgtggc 1200
cgggaccctg agatgggggg aaagccgaga aggaagaacc ctcaggaagg cctgtacaat 1260
gaactgcaga aagataagat ggcggaggcc tacagtgaga ttgggatgaa aggcgagcgc 1320
cggaggggca aggggcacga tggcctttac cagggtctca gtacagccac caaggacacc 1380
tacgacgccc ttcacatgca ggccctgccc cctcgc 1416

<210> SEQ ID NO 400
<211> LENGTH: 1416
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 400
cagtctgtcg tgacgcagcc gccctcaatg tctgcggccc caggacagca agtcaccatc 60
tcctgctctg gaggcaactc caacattgag agaaattatg tatcctggta cctccagctc 120
cctggaacag cccccaaact cgtcattttt gacaatgata ggcgaccctc agggattcct 180
gaccgattct ctggctccaa gtctggcacg tcagccaccc tgggcatcac cggactccag 240
actggggacg aggccgatta ttactgcgga acatgggata gcagcctgag aggttgggtg 300
ttcggcggag ggaccaagct gaccgtccta ggttctagag gtggtggtgg tagcggcggc 360
ggcggctctg gtggtggtgg atccctcgag atggccgagg tgcagctggt ggagtccggg 420
ggaggcttga tacagcctgg ggggtccctg agactctcct gtgcagcctc tggattcacc 480
tttagcaact atgccatgaa ctgggtccgc caggctccag ggaaggggct ggagtgggtc 540
tcaactatta atggtcgtgg tagtagtaca atctacgcag actccgtgaa gggccggttc 600
accatctcca gagacaattc caagaacacg ctgtatctgc aaatgaacag cctgagagcc 660
gaggacacag ccacgtatta ctgtgcgcgc tacatctctc gtggtctggg tgattcttgg 720
ggtcaaggta ctctggtgac cgtctcctca gcggccgcaa ttgaagttat gtatcctcct 780
ccttacctag acaatgagaa gagcaatgga accattatcc atgtgaaagg gaaacacctt 840
tgtccaagtc ccctatttcc cggaccttct aagccctttt gggtgctggt ggtggttggt 900
ggagtcctgg cttgctatag cttgctagta acagtggcct ttattatttt ctgggtgagg 960
agtaagagga gcaggctcct gcacagtgac tacatgaaca tgactccccg ccgccccggg 1020
cccacccgca agcattacca gccctatgcc ccaccacgcg acttcgcagc ctatcgctcc 1080
agagtgaagt tcagcaggag cgcagacgcc cccgcgtacc agcagggcca gaaccagctc 1140
tataacgagc tcaatctagg acgaagagag gagtacgatg ttttggacaa gagacgtggc 1200
cgggaccctg agatgggggg aaagccgaga aggaagaacc ctcaggaagg cctgtacaat 1260
gaactgcaga aagataagat ggcggaggcc tacagtgaga ttgggatgaa aggcgagcgc 1320
cggaggggca aggggcacga tggcctttac cagggtctca gtacagccac caaggacacc 1380
tacgacgccc ttcacatgca ggccctgccc cctcgc 1416

<210> SEQ ID NO 401
<211> LENGTH: 7689
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 401
ccggtgccgc caccatggaa accgacaccc tgctgctgtg ggtgctgctg ctgtgggtgc 60
caggatccac aggacagtct gtcgtgacgc agcctgcctc cgtgtctggg tctcctggac 120
agtcgatcac catctcctgc actggaacca gcagtgacgt tggtggttat aactatgtct 180
cctggtacca acagcaccca ggcaaagccc ccaaactcat gatttatgat gtcagtaagc 240
ggccctcagg ggtttctaat cgcttctctg gctccaagtc tggcaacacg gcctccctga 300
ccatctctgg gctccaggct gaggacgagg ctgattatta ctgcagctca tatacaagca 360
gcagcacttt ggtattcggc ggagggacca agctgaccgt cctaggttct agaggtggtg 420
gtggtagcgg cggcggcggc tctggtggtg gtggatccct cgagatggcc gaggtgcagc 480
tggtggagtc tgggggagcc tttgtacagc ctgggggggtc cctgagactc tcctgtgcag 540
cctctggatt cacctttagc agctatgcca tgacctgggt ccgccaggct ccagggaagg 600
gcctggaatg ggtctcgact attagtggtc gtggtcgtag cacattctac gcagactccg 660
tgaagggccg gtttaccatc tccagagaca attccaagaa cacgctatat ctgcaaatga 720
acagtctgag agccgaggac acggccgtat attactgtgc gcgctactac catgctggtg 780
ctttcgatct gtggggtcaa ggtactctgg tgaccgtctc ctcagaacaa aaactcatct 840
cagaagagga tctggcggcc gcacccacca cgacgccagc gccgcgacca ccaaccccgg 900
cgcccacgat cgcgtcgcag cccctgtccc tgcgcccaga ggcgtgccgg ccagcggcgg 960
ggggcgcagt gcacacgagg gggctggact tcgcctgtga tatctacatc tgggcgcccc 1020
tggccgggac ttgtggggtc cttctcctgt cactggttat caccctttac tgcaacaaac 1080
ggggcagaaa gaagctcctg tatatattca aacaaccatt tatgagacca gtacaaacta 1140
ctcaagagga agatggctgt agctgccgat ttccagaaga agaagaagga ggatgtgaac 1200
tgagagtgaa gttcagcagg agcgcagagc cccccgcgta ccagcagggc cagaaccagc 1260
tctataacga gctcaatcta ggacgaagag aggagtacga tgttttggac aagagacgtg 1320
gccgggaccc tgagatgggg ggaaagccga gaaggaagaa ccctcaggaa ggcctgtaca 1380
atgaactgca gaaagataag atggcggagg cctacagtga gattgggatg aaaggcgagc 1440
gccggagggg caaggggcac gatggccttt accagggtct cagtacagcc accaaggaca 1500
cctacgacgc ccttcacatg caggccctgc cccctcgcta acagccactc gaggatccgg 1560
attagtccaa tttgttaaag acaggatatc agtggtccag gctctagttt tgactcaaca 1620
atatcaccag ctgaagccta tagagtacga gccatagata aaataaaaga ttttatttag 1680
tctccagaaa aaggggggaa tgaaagaccc cacctgtagg tttggcaagc tagcttaagt 1740
aacgccattt tgcaaggcat ggaaaaatac ataactgaga atagagaagt tcagatcaag 1800
gtcaggaaca gatggaacag ctgaatatgg gccaaacagg atatctgtgg taagcagttc 1860
ctgccccggc tcagggccaa gaacagatgg aacagctgaa tatgggccaa acaggatatc 1920
tgtggtaagc agttcctgcc ccggctcagg gccaagaaca gatggtcccc agatgcggtc 1980
cagccctcag cagtttctag agaaccatca gatgtttcca gggtgcccca aggacctgaa 2040
atgaccctgt gccttatttg aactaaccaa tcagttcgct tctcgcttct gttcgcgcgc 2100
ttctgctccc cgagctcaat aaaagagccc acaacccctc actcggggcg ccagtcctcc 2160
gattgactga gtcgcccggg tacccgtgta tccaataaac cctcttgcag ttgcatccga 2220
cttgtggtct cgctgttcct tgggagggtc tcctctgagt gattgactac ccgtcagcgg 2280
gggtctttca cacatgcagc atgtatcaaa attaatttgg tttttttttct taagtattta 2340
cattaaatgg ccatagtact taaagttaca ttggcttcct tgaaataaac atggagtatt 2400
cagaatgtgt cataaatatt tctaatttta agatagtatc tccattggct ttctactttt 2460
tcttttattt ttttttgtcc tctgtcttcc atttgttgtt gttgttgttt gtttgtttgt 2520
ttgttggttg gttggttaat ttttttttaa agatcctaca ctatagttca agctagacta 2580
ttagctactc tgtaacccag ggtgaccttg aagtcatggg tagcctgctg ttttagcctt 2640
cccacatcta agattacagg tatgagctat catttttggt atattgattg attgattgat 2700
tgatgtgtgt gtgtgtgatt gtgtttgtgt gtgtgactgt gaaaatgtgt gtatgggtgt 2760
gtgtgaatgt gtgtatgtat gtgtgtgtgt gagtgtgtgt gtgtgtgtgt gcatgtgtgt 2820
gtgtgtgact gtgtctatgt gtatgactgt gtgtgtgtgt gtgtgtgtgt gtgtgtgtgt 2880
gtgtgtgtgt gtgttgtgaa aaaatattct atggtagtga gagccaacgc tccggctcag 2940
gtgtcaggtt ggtttttgag acagagtctt tcacttagct tggaattcac tggccgtcgt 3000
tttacaacgt cgtgactggg aaaaccctgg cgttacccaa cttaatcgcc ttgcagcaca 3060
tccccctttc gccagctggc gtaatagcga agaggcccgc accgatcgcc cttcccaaca 3120

-continued

```
gttgcgcagc ctgaatggcg aatggcgcct gatgcggtat tttctcctta cgcatctgtg   3180
cggtatttca caccgcatat ggtgcactct cagtacaatc tgctctgatg ccgcatagtt   3240
aagccagccc cgacacccgc caacacccgc tgacgcgccc tgacgggctt gtctgctccc   3300
ggcatccgct tacagacaag ctgtgaccgt ctccgggagc tgcatgtgtc agaggttttc   3360
accgtcatca ccgaaacgcg cgatgacgaa agggcctcgt gatacgccta tttttatagg   3420
ttaatgtcat gataataatg gtttcttaga cgtcaggtgg cacttttcgg ggaaatgtgc   3480
gcggaacccc tatttgttta tttttctaaa tacattcaaa tatgtatccg ctcatgagac   3540
aataaccctg ataaatgctt caataatatt gaaaaaggaa gagtatgagt attcaacatt   3600
tccgtgtcgc ccttattccc ttttttgcgg cattttgcct tcctgttttt gctcacccag   3660
aaacgctggt gaaagtaaaa gatgctgaag atcagttggg tgcacgagtg ggttacatcg   3720
aactggatct caacagcggt aagatccttg agagttttcg ccccgaagaa cgttttccaa   3780
tgatgagcac ttttaaagtt ctgctatgtg gcgcggtatt atcccgtatt gacgccgggc   3840
aagagcaact cggtcgccgc atacactatt ctcagaatga cttggttgag tactcaccag   3900
tcacagaaaa gcatcttacg gatggcatga cagtaagaga attatgcagt gctgccataa   3960
ccatgagtga taacactgcg gccaacttac ttctgacaac gatcggagga ccgaaggagc   4020
taaccgcttt tttgcacaac atgggggatc atgtaactcg ccttgatcgt tgggaaccgg   4080
agctgaatga agccatacca aacgacgagc gtgacaccac gatgcctgta gcaatggcaa   4140
caacgttgcg caaactatta actggcgaac tacttactct agcttcccgg caacaattaa   4200
tagactggat ggaggcggat aaagttgcag gaccacttct gcgctcggcc cttccggctg   4260
gctggtttat tgctgataaa tctggagccg gtgagcgtgg gtctcgcggt atcattgcag   4320
cactggggcc agatggtaag ccctcccgta tcgtagttat ctacacgacg gggagtcagg   4380
caactatgga tgaacgaaat agacagatcg ctgagatagg tgcctcactg attaagcatt   4440
ggtaactgtc agaccaagtt tactcatata tactttagat tgatttaaaa cttcattttt   4500
aatttaaaag gatctaggtg aagatccttt ttgataatct catgaccaaa atcccttaac   4560
gtgagttttc gttccactga gcgtcagacc ccgtagaaaa gatcaaagga tcttcttgag   4620
atcctttttt tctgcgcgta atctgctgct tgcaaacaaa aaaaccaccg ctaccagcgg   4680
tggtttgttt gccggatcaa gagctaccaa ctctttttcc gaaggtaact ggcttcagca   4740
gagcgcagat accaaatact gtccttctag tgtagccgta gttaggccac cacttcaaga   4800
actctgtagc accgcctaca tacctcgctc tgctaatcct gttaccagtg gctgctgcca   4860
gtggcgataa gtcgtgtctt accgggttgg actcaagacg atagttaccg gataaggcgc   4920
agcggtcggg ctgaacgggg ggttcgtgca cacagcccag cttggagcga acgacctaca   4980
ccgaactgag atacctacag cgtgagcatt gagaaagcgc cacgcttccc gaagggagaa   5040
aggcggacag gtatccggta agcggcaggg tcggaacagg agagcgcacg agggagcttc   5100
caggggggaaa cgcctggtat ctttatagtc ctgtcgggtt tcgccacctc tgacttgagc   5160
gtcgattttt gtgatgctcg tcaggggggc ggagcctatg gaaaaacgcc agcaacgcgg   5220
cctttttacg gttcctggcc ttttgctggc cttttgctca catgttcttt cctgcgttat   5280
cccctgattc tgtggataac cgtattaccg cctttgagtg agctgatacc gctcgccgca   5340
gccgaacgac cgagcgcagc gagtcagtga gcgaggaagc ggaagagcgc ccaatacgca   5400
aaccgcctct ccccgcgcgt tggccgattc attaatgcag ctggcacgac aggtttcccg   5460
actggaaagc gggcagtgag cgcaacgcaa ttaatgtgag ttagctcact cattaggcac   5520
```

```
cccaggcttt acactttatg cttccggctc gtatgttgtg tggaattgtg agcggataac   5580
aatttcacac aggaaacagc tatgaccatg attacgccaa gctttgctct taggagtttc   5640
ctaatacatc ccaaactcaa atatataaag catttgactt gttctatgcc ctagggggcg   5700
gggggaagct aagccagctt tttttaacat ttaaaatgtt aattccattt taaatgcaca   5760
gatgttttta tttcataagg gtttcaatgt gcatgaatgc tgcaatattc ctgttaccaa   5820
agctagtata aataaaaata gataaacgtg gaaattactt agagtttctg tcattaacgt   5880
ttccttcctc agttgacaac ataaatgcgc tgctgagcaa gccagtttgc atctgtcagg   5940
atcaatttcc cattatgcca gtcatattaa ttactagtca attagttgat ttttattttt   6000
gacatataca tgtgaatgaa agaccccacc tgtaggtttg gcaagctagc ttaagtaacg   6060
ccattttgca aggcatggaa aaatacataa ctgagaatag aaaagttcag atcaaggtca   6120
ggaacagatg gaacagctga atatgggcca aacaggatat ctgtggtaag cagttcctgc   6180
cccggctcag ggccaagaac agatggaaca gctgaatatg ggccaaacag gatatctgtg   6240
gtaagcagtt cctgccccgg ctcagggcca agaacagatg gtccccagat gcggtccagc   6300
cctcagcagt ttctagagaa ccatcagatg tttccagggt gccccaagga cctgaaatga   6360
ccctgtgcct tatttgaact aaccaatcag ttcgcttctc gcttctgttc gcgcgcttat   6420
gctccccgag ctcaataaaa gagcccacaa cccctcactc ggggcgccag tcctccgatt   6480
gactgagtcg cccgggtacc cgtgtatcca ataaaccctc ttgcagttgc atccgacttg   6540
tggtctcgct gttccttggg agggtctcct ctgagtgatt gactacccgt cagcgggggt   6600
ctttcatttg ggggctcgtc cgggatcggg agacccctgc ccagggacca ccgacccacc   6660
accgggaggt aagctggcca gcaacttatc tgtgtctgtc cgattgtcta gtgtctatga   6720
ctgattttat gcgcctgcgt cggtactagt tagctaacta gctctgtatc tggcggaccc   6780
gtggtggaac tgacgagttc ggaacacccg gccgcaaccc tgggagacgt cccagggact   6840
tcgggggccg tttttgtggc ccgacctgag tcctaaaatc ccgatcgttt aggactcttt   6900
ggtgcacccc ccttagagga gggatatgtg gttctggtag gagacgagaa cctaaaacag   6960
ttcccgcctc cgtctgaatt tttgctttcg gtttgggacc gaagccgcgc cgcgcgtctt   7020
gtctgctgca gcatcgttct gtgttgtctc tgtctgactg tgtttctgta tttgtctgaa   7080
aatatgggcc cgggctagac tgttaccact cccttaagtt tgaccttagg tcactggaaa   7140
gatgtcgagc ggatcgctca caaccagtcg gtagatgtca agaagagacg ttgggttacc   7200
ttctgctctg cagaatggcc aacctttaac gtcggatggc cgcgagacgg cacctttaac   7260
cgagacctca tcacccaggt taagatcaag gtcttttcac ctggcccgca tggacaccca   7320
gaccaggtcc cctacatcgt gacctgggaa gccttggctt ttgacccccc tccctgggtc   7380
aagccctttg tacaccctaa gcctccgcct cctcttcctc catccgcccc gtctctcccc   7440
cttgaacctc ctcgttcgac cccgcctcga tcctcccttt atccagccct cactccttct   7500
ctaggcgccc ccatatggcc atatgagatc ttatatgggg caccccccgcc ccttgtaaac   7560
ttccctgacc ctgacatgac aagagttact aacagcccct ctctccaagc tcacttacag   7620
gctctctact tagtccagca cgaagtctgg agacctctgg cggcagccta ccaagaacaa   7680
ctggaccga                                                           7689
```

<210> SEQ ID NO 402
<211> LENGTH: 7688
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 402

```
ccggtgccgc caccatggaa accgacaccc tgctgctgtg ggtgctgctg ctgtgggtgc     60
caggatccac aggacagtct gtgttgactc agccaccctc agcgtctggg acccccggac    120
agagggtcac catctcttgt tctggaagca ggtccaacgt aggaggtaat tatgtatttt    180
ggtaccagca agtccccgga gcgacccccca aactcctcat ctataggagt aatcagcggc    240
cctcgggggt ccctgaccga ttcgctggct ccaagtctgg ctcctcagcc tccctggcca    300
tcagtggact ccggtccgag gatgaggctg attattactg tgcaacatgg gatgacagcc    360
tgagtggttt tgtcttcgga actgggacca aggtcaccgt cctaggttct agaggtggtg    420
gtggtagcgg cggcggcggc tctggtggtg gtggatccct cgagatggcc gaggtgcagc    480
tggtggagtc tgggggaggc ttggtcaagc ctggagggtc cctgagactc tcctgtgcag    540
cctctggatt caccttcagt gactactaca tgagctggat ccgccaggct ccagggaagg    600
ggctggagtg ggtttcatac attagtagta gtggtagtac catatactac gcagactctg    660
tgaagggccg attcaccatc tcccagggac aacgccaaga actcactgta tctgcaaatg    720
aacagcctga gagccgagga cacggccgta tattactgtg cgcgcgggtt acggtaaagc    780
ttacgatcag tggggtcaag gtactctggt gaccgtctcc tcagaacaaa aactcatctc    840
agaagaggat ctggcggccg cacccaccac gacgccagcg ccgcgaccac caaccccggc    900
gcccacgatc gcgtcgcagc ccctgtccct gcgcccagag gcgtgccggc cagcggcggg    960
gggcgcagtg cacacgaggg ggctggactt cgcctgtgat atctacatct gggcgcccct   1020
ggccgggact tgtggggtcc ttctcctgtc actggttatc accctttact gcaacaaacg   1080
gggcagaaag aagctcctgt atatattcaa acaaccattt atgagaccag tacaaactac   1140
tcaagaggaa gatggctgta gctgccgatt tccagaagaa gaagaaggag gatgtgaact   1200
gagagtgaag ttcagcagga gcgcagagcc ccccgcgtac cagcagggcc agaaccagct   1260
ctataacgag ctcaatctag gacgaagaga ggagtacgat gttttggaca agagacgtgg   1320
ccgggaccct gagatggggg gaaagccgag aaggaagaac cctcaggaag gcctgtacaa   1380
tgaactgcag aaagataaga tggcggaggc ctacagtgag attgggatga aaggcgagcg   1440
ccggaggggc aaggggcacg atggccttta ccagggtctc agtacagcca ccaaggacac   1500
ctacgacgcc cttcacatgc aggccctgcc ccctcgctaa cagccactcg aggatccgga   1560
ttagtccaat ttgttaaaga caggatatca gtggtccagg ctctagtttt gactcaacaa   1620
tatcaccagc tgaagcctat agagtacgag ccatagataa aataaaagat tttatttagt   1680
ctccagaaaa aggggggaat gaaagacccc acctgtaggt ttggcaagct agcttaagta   1740
acgccatttt gcaaggcatg gaaaaataca taactgagaa tagagaagtt cagatcaagg   1800
tcaggaacag atggaacagc tgaatatggg ccaaacagga tatctgtggt aagcagttcc   1860
tgccccggct cagggccaag aacagatgga acagctgaat atgggccaaa caggatatct   1920
gtggtaagca gttcctgccc cggctcaggg ccaagaacag atggtcccca gatgcggtcc   1980
agccctcagc agtttctaga gaaccatcag atgtttccag ggtgccccaa ggacctgaaa   2040
tgaccctgtg ccttatttga actaaccaat cagttcgctt ctcgcttctg ttcgcgcgct   2100
tctgctcccc gagctcaata aaagagccca caacccctca ctcggggcgc cagtcctccg   2160
```

```
attgactgag tcgcccgggt acccgtgtat ccaataaacc ctcttgcagt tgcatccgac   2220
ttgtggtctc gctgttcctt gggagggtct cctctgagtg attgactacc cgtcagcggg   2280
ggtctttcac acatgcagca tgtatcaaaa ttaatttggt ttttttttctt aagtatttac   2340
attaaatggc catagtactt aaagttacat tggcttcctt gaaataaaca tggagtattc   2400
agaatgtgtc ataaatattt ctaattttaa gatagtatct ccattggctt tctacttttt   2460
cttttatttt tttttgtcct ctgtcttcca tttgttgttg ttgttgtttg tttgtttgtt   2520
tgttggttgg ttggttaatt tttttttaaa gatcctacac tatagttcaa gctagactat   2580
tagctactct gtaacccagg gtgaccttga agtcatgggt agcctgctgt tttagccttc   2640
ccacatctaa gattacaggt atgagctatc atttttggta tattgattga ttgattgatt   2700
gatgtgtgtg tgtgtgattg tgtttgtgtg tgtgactgtg aaaatgtgtg tatgggtgtg   2760
tgtgaatgtg tgtatgtatg tgtgtgtgtg agtgtgtgtg tgtgtgtgtg catgtgtgtg   2820
tgtgtgactg tgtctatgtg tatgactgtg tgtgtgtgtg tgtgtgtgtg tgtgtgtgtg   2880
tgtgtgtgtg tgttgtgaaa aaatattcta tggtagtgag agccaacgct ccggctcagg   2940
tgtcaggttg gtttttgaga cagagtcttt cacttagctt ggaattcact ggccgtcgtt   3000
ttacaacgtc gtgactggga aaaccctggc gttacccaac ttaatcgcct tgcagcacat   3060
ccccctttcg ccagctggcg taatagcgaa gaggcccgca ccgatcgccc ttcccaacag   3120
ttgcgcagcc tgaatggcga atggcgcctg atgcggtatt ttctccttac gcatctgtgc   3180
ggtatttcac accgcatatg gtgcactctc agtacaatct gctctgatgc cgcatagtta   3240
agccagcccc gacacccgcc aacacccgct gacgcgccct gacgggcttg tctgctcccg   3300
gcatccgctt acagacaagc tgtgaccgtc tccgggagct gcatgtgtca gaggttttca   3360
ccgtcatcac cgaaacgcgc gatgacgaaa gggcctcgtg atacgcctat ttttataggt   3420
taatgtcatg ataataatgg tttcttagac gtcaggtggc acttttcggg gaaatgtgcg   3480
cggaacccct atttgtttat ttttctaaat acattcaaat atgtatccgc tcatgagaca   3540
ataaccctga taaatgcttc aataatattg aaaaaggaag agtatgagta ttcaacattt   3600
ccgtgtcgcc cttattccct tttttgcggc attttgcctt cctgtttttg ctcacccaga   3660
aacgctggtg aaagtaaaag atgctgaaga tcagttgggt gcacgagtgg gttacatcga   3720
actggatctc aacagcggta agatccttga gagttttcgc cccgaagaac gttttccaat   3780
gatgagcact tttaaagttc tgctatgtgg cgcggtatta tcccgtattg acgccgggca   3840
agagcaactc ggtcgccgca tacactattc tcagaatgac ttggttgagt actcaccagt   3900
cacagaaaag catcttacgg atggcatgac agtaagagaa ttatgcagtg ctgccataac   3960
catgagtgat aacactgcgg ccaacttact tctgacaacg atcggaggac cgaaggagct   4020
aaccgctttt ttgcacaaca tgggggatca tgtaactcgc cttgatcgtt gggaaccgga   4080
gctgaatgaa gccataccaa acgacgagcg tgacaccacg atgcctgtag caatggcaac   4140
aacgttgcgc aaactattaa ctggcgaact acttactcta gcttcccggc aacaattaat   4200
agactggatg gaggcggata aagttgcagg accacttctg cgctcggccc ttccggctgg   4260
ctggtttatt gctgataaat ctggagccgg tgagcgtggg tctcgcggta tcattgcagc   4320
actggggcca gatggtaagc cctcccgtat cgtagttatc tacacgacgg ggagtcaggc   4380
aactatggat gaacgaaata gacagatcgc tgagataggt gcctcactga ttaagcattg   4440
gtaactgtca gaccaagttt actcatatat actttagatt gatttaaaac ttcattttta   4500
atttaaaagg atctaggtga agatcctttt tgataatctc atgaccaaaa tcccttaacg   4560
```

```
tgagttttcg ttccactgag cgtcagaccc cgtagaaaag atcaaaggat cttcttgaga   4620
tcctttttt ctgcgcgtaa tctgctgctt gcaaacaaaa aaaccaccgc taccagcggt   4680
ggtttgtttg ccggatcaag agctaccaac tctttttccg aaggtaactg gcttcagcag   4740
agcgcagata ccaaatactg tccttctagt gtagccgtag ttaggccacc acttcaagaa   4800
ctctgtagca ccgcctacat acctcgctct gctaatcctg ttaccagtgg ctgctgccag   4860
tggcgataag tcgtgtctta ccgggttgga ctcaagacga tagttaccgg ataaggcgca   4920
gcggtcgggc tgaacggggg gttcgtgcac acagcccagc ttggagcgaa cgacctacac   4980
cgaactgaga tacctacagc gtgagcattg agaaagcgcc acgcttcccg aagggagaaa   5040
ggcggacagg tatccggtaa gcggcagggt cggaacagga gagcgcacga gggagcttcc   5100
agggggaaac gcctggtatc tttatagtcc tgtcgggttt cgccacctct gacttgagcg   5160
tcgatttttg tgatgctcgt caggggggcg gagcctatgg aaaaacgcca gcaacgcggc   5220
ctttttacgg ttcctggcct tttgctggcc ttttgctcac atgttctttc ctgcgttatc   5280
ccctgattct gtggataacc gtattaccgc ctttgagtga gctgataccg ctcgccgcag   5340
ccgaacgacc gagcgcagcg agtcagtgag cgaggaagcg gaagagcgcc caatacgcaa   5400
accgcctctc cccgcgcgtt ggccgattca ttaatgcagc tggcacgaca ggtttcccga   5460
ctggaaagcg ggcagtgagc gcaacgcaat taatgtgagt tagctcactc attaggcacc   5520
ccaggcttta cactttatgc ttccggctcg tatgttgtgt ggaattgtga gcggataaca   5580
atttcacaca ggaaacagct atgaccatga ttacgccaag ctttgctctt aggagtttcc   5640
taatacatcc caaactcaaa tatataaagc atttgacttg ttctatgccc tagggggcgg   5700
ggggaagcta agccagcttt ttttaacatt taaaatgtta attccatttt aaatgcacag   5760
atgtttttat ttcataaggg tttcaatgtg catgaatgct gcaatattcc tgttaccaaa   5820
gctagtataa ataaaaatag ataaacgtgg aaattactta gagtttctgt cattaacgtt   5880
tccttcctca gttgacaaca taaatgcgct gctgagcaag ccagtttgca tctgtcagga   5940
tcaatttccc attatgccag tcatattaat tactagtcaa ttagttgatt tttattttg   6000
acatatacat gtgaatgaaa gaccccacct gtaggtttgg caagctagct taagtaacgc   6060
cattttgcaa ggcatggaaa aatacataac tgagaataga aaagttcaga tcaaggtcag   6120
gaacagatgg aacagctgaa tatgggccaa acaggatatc tgtggtaagc agttcctgcc   6180
ccggctcagg gccaagaaca gatggaacag ctgaatatgg gccaaacagg atatctgtgg   6240
taagcagttc ctgccccggc tcagggccaa gaacagatgg tccccagatg cggtccagcc   6300
ctcagcagtt tctagagaac catcagatgt ttccagggtg ccccaaggac ctgaaatgac   6360
cctgtgcctt atttgaacta accaatcagt tcgcttctcg cttctgttcg cgcgcttatg   6420
ctccccgagc tcaataaaag agcccacaac ccctcactcg gggcgccagt cctccgattg   6480
actgagtcgc ccgggtaccc gtgtatccaa taaaccctct tgcagttgca tccgacttgt   6540
ggtctcgctg ttccttggga gggtctcctc tgagtgattg actacccgtc agcgggggtc   6600
tttcatttgg gggctcgtcc gggatcggga gacccctgcc cagggaccac cgacccacca   6660
ccgggaggta agctggccag caacttatct gtgtctgtcc gattgtctag tgtctatgac   6720
tgattttatg cgcctgcgtc ggtactagtt agctaactag ctctgtatct ggcggacccg   6780
tggtggaact gacgagttcg gaacacccgg ccgcaaccct gggagacgtc ccagggactt   6840
cgggggccgt ttttgtggcc cgacctgagt cctaaaatcc cgatcgttta ggactctttg   6900
```

gtgcaccccc cttagaggag ggatatgtgg ttctggtagg agacgagaac ctaaaacagt 6960
tcccgcctcc gtctgaattt ttgctttcgg tttgggaccg aagccgcgcc gcgcgtcttg 7020
tctgctgcag catcgttctg tgttgtctct gtctgactgt gtttctgtat ttgtctgaaa 7080
atatgggccc gggctagact gttaccactc ccttaagttt gaccttaggt cactggaaag 7140
atgtcgagcg gatcgctcac aaccagtcgg tagatgtcaa gaagagacgt tgggttacct 7200
tctgctctgc agaatggcca acctttaacg tcggatggcc gcgagacggc acctttaacc 7260
gagacctcat cacccaggtt aagatcaagg tcttttcacc tggcccgcat ggacacccag 7320
accaggtccc ctacatcgtg acctgggaag ccttggcttt tgacccccct ccctgggtca 7380
agccctttgt acaccctaag cctccgcctc ctcttcctcc atccgccccg tctctccccc 7440
ttgaacctcc tcgttcgacc ccgcctcgat cctcccttta tccagccctc actccttctc 7500
taggcgcccc catatggcca tatgagatct tatatggggc acccccgccc cttgtaaact 7560
tccctgaccc tgacatgaca agagttacta acagcccctc tctccaagct cacttacagg 7620
ctctctactt agtccagcac gaagtctgga gacctctggc ggcagcctac caagaacaac 7680
tggaccga 7688

<210> SEQ ID NO 403
<211> LENGTH: 7689
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 403
ccggtgccgc caccatggaa accgacaccc tgctgctgtg ggtgctgctg ctgtgggtgc 60
caggatccac aggacagtct gtcgtgacgc agccgccctc aatgtctgcg gccccaggac 120
agcaagtcac catctcctgc tctggaggca actccaacat tgagagaaat tatgtatcct 180
ggtacctcca gctccctgga acagccccca aactcgtcat tttgacaat gataggcgac 240 cctcagggat tcctgaccga ttctctggct ccaagtctgg cacgtcagcc accctgggca 300
tcaccggact ccagactggg gacgaggccg attattactg cggaacatgg gatagcagcc 360
tgagaggttg ggtgttcggc ggagggacca agctgaccgt cctaggttct agaggtggtg 420
gtggtagcgg cggcggcggc tctggtggtg gtggatccct cgagatggcc gaggtgcagc 480
tggtggagtc cgggggaggc ttgatacagc ctggggggtc cctgagactc tcctgtgcag 540
cctctggatt cacctttagc aactatgcca tgaactgggt ccgccaggct ccagggaagg 600
ggctggagtg ggtctcaact attaatggtc gtggtagtag tacaatctac gcagactccg 660
tgaagggccg gttcaccatc tccagagaca attccaagaa cacgctgtat ctgcaaatga 720
acagcctgag agccgaggac acagccacgt attactgtgc gcgctacatc tctcgtggtc 780
tgggtgattc ttggggtcaa ggtactctgg tgaccgtctc ctcagaacaa aaactcatct 840
cagaggagga tctggcggcc gcacccacca cgacgccagc gccgcgacca ccaaccccgg 900
cgcccacgat cgcgtcgcag cccctgtccc tgcgcccaga ggcgtgccgg ccagcggcgg 960
ggggcgcagt gcacacgagg gggctggact tcgcctgtga tatctacatc tgggcgcccc 1020
tggccgggac ttgtggggtc cttctcctgt cactggttat caccctttac tgcaacaaac 1080
ggggcagaaa gaagctcctg tatatattca aacaaccatt tatgagacca gtacaaacta 1140
ctcaagagga agatggctgt agctgccgat ttccagaaga agaagaagga ggatgtgaac 1200

-continued

```
tgagagtgaa gttcagcagg agcgcagagc cccccgcgta ccagcagggc cagaaccagc   1260
tctataacga gctcaatcta ggacgaagag aggagtacga tgttttggac aagagacgtg   1320
gccgggaccc tgagatgggg ggaaagccga gaaggaagaa ccctcaggaa ggcctgtaca   1380
atgaactgca gaaagataag atggcggagg cctacagtga gattgggatg aaaggcgagc   1440
gccggagggg caaggggcac gatggccttt accagggtct cagtacagcc accaaggaca   1500
cctacgacgc ccttcacatg caggccctgc cccctcgcta acagccactc gaggatccgg   1560
attagtccaa tttgttaaag acaggatatc agtggtccag gctctagttt tgactcaaca   1620
atatcaccag ctgaagccta tagagtacga gccatagata aaataaaaga ttttatttag   1680
tctccagaaa aaggggggaa tgaaagaccc cacctgtagg tttggcaagc tagcttaagt   1740
aacgccattt tgcaaggcat ggaaaaatac ataactgaga atagagaagt tcagatcaag   1800
gtcaggaaca gatggaacag ctgaatatgg gccaaacagg atatctgtgg taagcagttc   1860
ctgccccggc tcagggccaa gaacagatgg aacagctgaa tatgggccaa acaggatatc   1920
tgtggtaagc agttcctgcc ccggctcagg gccaagaaca gatggtcccc agatgcggtc   1980
cagccctcag cagtttctag agaaccatca gatgtttcca gggtgcccca aggacctgaa   2040
atgaccctgt gccttatttg aactaaccaa tcagttcgct tctcgcttct gttcgcgcgc   2100
ttctgctccc cgagctcaat aaaagagccc acaacccctc actcggggcg ccagtcctcc   2160
gattgactga gtcgcccggg tacccgtgta tccaataaac cctcttgcag ttgcatccga   2220
cttgtggtct cgctgttcct tgggagggtc tcctctgagt gattgactac ccgtcagcgg   2280
gggtctttca cacatgcagc atgtatcaaa attaatttgg ttttttttct taagtattta   2340
cattaaatgg ccatagtact taaagttaca ttggcttcct tgaaataaac atggagtatt   2400
cagaatgtgt cataaatatt tctaatttta agatagtatc tccattggct ttctactttt   2460
tcttttattt ttttttgtcc tctgtcttcc atttgttgtt gttgttgttt gtttgtttgt   2520
ttgttggttg gttggttaat ttttttttaa agatcctaca ctatagttca agctagacta   2580
ttagctactc tgtaacccag ggtgaccttg aagtcatggg tagcctgctg ttttagcctt   2640
cccacatcta agattacagg tatgagctat catttttggt atattgattg attgattgat   2700
tgatgtgtgt gtgtgtgatt gtgtttgtgt gtgtgactgt gaaaatgtgt gtatgggtgt   2760
gtgtgaatgt gtgtatgtat gtgtgtgtgt gagtgtgtgt gtgtgtgtgt gcatgtgtgt   2820
gtgtgtgact gtgtctatgt gtatgactgt gtgtgtgtgt gtgtgtgtgt gtgtgtgtgt   2880
gtgtgtgtgt gtgttgtgaa aaaatattct atggtagtga gagccaacgc tccggctcag   2940
gtgtcaggtt ggtttttgag acagagtctt tcacttagct tggaattcac tggccgtcgt   3000
tttacaacgt cgtgactggg aaaaccctgg cgttacccaa cttaatcgcc ttgcagcaca   3060
tccccctttc gccagctggc gtaatagcga agaggcccgc accgatcgcc cttcccaaca   3120
gttgcgcagc ctgaatggcg aatggcgcct gatgcggtat tttctcctta cgcatctgtg   3180
cggtatttca caccgcatat ggtgcactct cagtacaatc tgctctgatg ccgcatagtt   3240
aagccagccc cgacacccgc caacacccgc tgacgcgccc tgacgggctt gtctgctccc   3300
ggcatccgct tacagacaag ctgtgaccgt ctccgggagc tgcatgtgtc agaggttttc   3360
accgtcatca ccgaaacgcg cgatgacgaa agggcctcgt gatacgccta tttttatagg   3420
ttaatgtcat gataataatg gtttcttaga cgtcaggtgg cacttttcgg ggaaatgtgc   3480
gcggaacccc tatttgttta tttttctaaa tacattcaaa tatgtatccg ctcatgagac   3540
aataaccctg ataaatgctt caataatatt gaaaaaggaa gagtatgagt attcaacatt   3600
```

-continued

```
tccgtgtcgc ccttattccc ttttttgcgg cattttgcct tcctgttttt gctcacccag   3660
aaacgctggt gaaagtaaaa gatgctgaag atcagttggg tgcacgagtg ggttacatcg   3720
aactggatct caacagcggt aagatccttg agagttttcg ccccgaagaa cgttttccaa   3780
tgatgagcac ttttaaagtt ctgctatgtg gcgcggtatt atcccgtatt gacgccgggc   3840
aagagcaact cggtcgccgc atacactatt ctcagaatga cttggttgag tactcaccag   3900
tcacagaaaa gcatcttacg gatggcatga cagtaagaga attatgcagt gctgccataa   3960
ccatgagtga taacactgcg gccaacttac ttctgacaac gatcggagga ccgaaggagc   4020
taaccgcttt tttgcacaac atgggggatc atgtaactcg ccttgatcgt tgggaaccgg   4080
agctgaatga agccatacca aacgacgagc gtgacaccac gatgcctgta gcaatggcaa   4140
caacgttgcg caaactatta actggcgaac tacttactct agcttcccgg caacaattaa   4200
tagactggat ggaggcggat aaagttgcag gaccacttct gcgctcggcc cttccggctg   4260
gctggtttat tgctgataaa tctggagccg gtgagcgtgg gtctcgcggt atcattgcag   4320
cactggggcc agatggtaag ccctcccgta tcgtagttat ctacacgacg gggagtcagg   4380
caactatgga tgaacgaaat agacagatcg ctgagatagg tgcctcactg attaagcatt   4440
ggtaactgtc agaccaagtt tactcatata tactttagat tgatttaaaa cttcattttt   4500
aatttaaaag gatctaggtg aagatccttt ttgataatct catgaccaaa atcccttaac   4560
gtgagttttc gttccactga gcgtcagacc ccgtagaaaa gatcaaagga tcttcttgag   4620
atcctttttt tctgcgcgta atctgctgct tgcaaacaaa aaaaccaccg ctaccagcgg   4680
tggtttgttt gccggatcaa gagctaccaa ctctttttcc gaaggtaact ggcttcagca   4740
gagcgcagat accaaatact gtccttctag tgtagccgta gttaggccac cacttcaaga   4800
actctgtagc accgcctaca tacctcgctc tgctaatcct gttaccagtg gctgctgcca   4860
gtggcgataa gtcgtgtctt accgggttgg actcaagacg atagttaccg gataaggcgc   4920
agcggtcggg ctgaacgggg ggttcgtgca cacagcccag cttggagcga acgacctaca   4980
ccgaactgag atacctacag cgtgagcatt gagaaagcgc cacgcttccc gaagggagaa   5040
aggcggacag gtatccggta agcggcaggg tcggaacagg agagcgcacg agggagcttc   5100
caggggggaaa cgcctggtat ctttatagtc ctgtcgggtt tcgccacctc tgacttgagc   5160
gtcgattttt gtgatgctcg tcaggggggc ggagcctatg gaaaaacgcc agcaacgcgg   5220
cctttttacg gttcctggcc ttttgctggc cttttgctca catgttcttt cctgcgttat   5280
cccctgattc tgtggataac cgtattaccg cctttgagtg agctgatacc gctcgccgca   5340
gccgaacgac cgagcgcagc gagtcagtga gcgaggaagc ggaagagcgc ccaatacgca   5400
aaccgcctct ccccgcgcgt tggccgattc attaatgcag ctggcacgac aggtttcccg   5460
actggaaagc gggcagtgag cgcaacgcaa ttaatgtgag ttagctcact cattaggcac   5520
cccaggcttt acactttatg cttccggctc gtatgttgtg tggaattgtg agcggataac   5580
aatttcacac aggaaacagc tatgaccatg attacgccaa gctttgctct taggagtttc   5640
ctaatacatc ccaaactcaa atatataaag catttgactt gttctatgcc ctagggggcg   5700
gggggaagct aagccagctt tttttaacat ttaaaatgtt aattccattt taaatgcaca   5760
gatgttttta tttcataagg gtttcaatgt gcatgaatgc tgcaatattc ctgttaccaa   5820
agctagtata aataaaaata gataaacgtg gaaattactt agagtttctg tcattaacgt   5880
ttccttcctc agttgacaac ataaatgcgc tgctgagcaa gccagtttgc atctgtcagg   5940
```

```
atcaatttcc cattatgcca gtcatattaa ttactagtca attagttgat ttttattttt   6000

gacatataca tgtgaatgaa agaccccacc tgtaggtttg gcaagctagc ttaagtaacg   6060

ccattttgca aggcatggaa aaatacataa ctgagaatag aaaagttcag atcaaggtca   6120

ggaacagatg gaacagctga atatgggcca aacaggatat ctgtggtaag cagttcctgc   6180

cccggctcag ggccaagaac agatggaaca gctgaatatg ggccaaacag gatatctgtg   6240

gtaagcagtt cctgccccgg ctcagggcca agaacagatg gtccccagat gcggtccagc   6300

cctcagcagt ttctagagaa ccatcagatg tttccagggt gccccaagga cctgaaatga   6360

ccctgtgcct tatttgaact aaccaatcag ttcgcttctc gcttctgttc gcgcgcttat   6420

gctccccgag ctcaataaaa gagcccacaa cccctcactc ggggcgccag tcctccgatt   6480

gactgagtcg cccgggtacc cgtgtatcca ataaaccctc ttgcagttgc atccgacttg   6540

tggtctcgct gttccttggg agggtctcct ctgagtgatt gactacccgt cagcgggggt   6600

ctttcatttg ggggctcgtc cgggatcggg agacccctgc ccagggacca ccgacccacc   6660

accgggaggt aagctggcca gcaacttatc tgtgtctgtc cgattgtcta gtgtctatga   6720

ctgattttat gcgcctgcgt cggtactagt tagctaacta gctctgtatc tggcggaccc   6780

gtggtggaac tgacgagttc ggaacacccg gccgcaaccc tgggagacgt cccagggact   6840

tcgggggccg tttttgtggc ccgacctgag tcctaaaatc ccgatcgttt aggactcttt   6900

ggtgcacccc ccttagagga gggatatgtg gttctggtag gagacgagaa cctaaaacag   6960

ttcccgcctc cgtctgaatt tttgctttcg gtttgggacc gaagccgcgc cgcgcgtctt   7020

gtctgctgca gcatcgttct gtgttgtctc tgtctgactg tgtttctgta tttgtctgaa   7080

aatatgggcc cgggctagac tgttaccact cccttaagtt tgaccttagg tcactggaaa   7140

gatgtcgagc ggatcgctca caaccagtcg gtagatgtca agaagagacg ttgggttacc   7200

ttctgctctg cagaatggcc aacctttaac gtcggatggc cgcgagacgg cacctttaac   7260

cgagacctca tcacccaggt taagatcaag gtcttttcac ctggcccgca tggacaccca   7320

gaccaggtcc cctacatcgt gacctgggaa gccttggctt ttgacccccc tccctgggtc   7380

aagccctttg tacaccctaa gcctccgcct cctcttcctc catccgcccc gtctctcccc   7440

cttgaacctc ctcgttcgac cccgcctcga tcctcccttt atccagccct cactccttct   7500

ctaggcgccc ccatatggcc atatgagatc ttatatgggg cacccccgcc ccttgtaaac   7560

ttccctgacc ctgacatgac aagagttact aacagcccct ctctccaagc tcacttacag   7620

gctctctact tagtccagca cgaagtctgg agacctctgg cggcagccta ccaagaacaa   7680

ctggaccga                                                           7689
```

<210> SEQ ID NO 404
<211> LENGTH: 235
<212> TYPE: PRT
<213> ORGANISM: Homo sapiens

<400> SEQUENCE: 404

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60
```

```
Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Cys
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235
```

<210> SEQ ID NO 405
<211> LENGTH: 213
<212> TYPE: DNA
<213> ORGANISM: Homo sapiens

<400> SEQUENCE: 405

```
cccaccacga cgccagcgcc gcgaccacca accccggcgc ccacgatcgc gtcgcagccc     60

ctgtccctgc gcccagaggc gtgccggcca gcggcggggg gcgcagtgca cacgaggggg    120

ctggacttcg cctgtgatat ctacatctgg gcgcccctgg ccgggacttg tggggtcctt    180

ctcctgtcac tggttatcac cctttactgc aac                                 213
```

<210> SEQ ID NO 406
<211> LENGTH: 1509
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 406

```
atggaaaccg acaccctgct gctgtgggtg ctgctgctgt gggtgccagg atccacagga     60

cagtctgtcg tgacgcagcc tgcctccgtg tctgggtctc ctggacagtc gatcaccatc    120

tcctgcactg gaaccagcag tgacgttggt ggttataact atgtctcctg gtaccaacag    180

cacccaggca aagcccccaa actcatgatt tatgatgtca gtaagcggcc ctcaggggtt    240

tctaatcgct tctctggctc caagtctggc aacacggcct ccctgaccat ctctgggctc    300

caggctgagg acgaggctga ttattactgc agctcatata caagcagcag cactttggta    360

ttcggcggag ggaccaagct gaccgtccta ggttctagag gtggtggtgg tagcggcggc    420

ggcggctctg gtggtggtgg atccctcgag atggccgagg tgcagctggt ggagtctggg    480

ggagcctttg tacagcctgg ggggtccctg agactctcct gtgcagcctc tggattcacc    540
```

-continued

```
tttagcagct atgccatgac ctgggtccgc caggctccag ggaagggcct ggaatgggtc    600

tcgactatta gtggtcgtgg tcgtagcaca ttctacgcag actccgtgaa gggccggttt    660

accatctcca gagacaattc caagaacacg ctatatctgc aaatgaacag tctgagagcc    720

gaggacacgg ccgtatatta ctgtgcgcgc tactaccatg ctggtgcttt cgatctgtgg    780

ggtcaaggta ctctggtgac cgtctcctca gaacaaaaac tcatctcaga agaggatctg    840

gcggccgcaa ttgaagttat gtatcctcct ccttacctag acaatgagaa gagcaatgga    900

accattatcc atgtgaaagg gaaacacctt tgtccaagtc ccctatttcc cggaccttct    960

aagccctttt gggtgctggt ggtggttggt ggagtcctgg cttgctatag cttgctagta   1020

acagtggcct ttattatttt ctgggtgagg agtaagagga gcaggctcct gcacagtgac   1080

tacatgaaca tgactccccg ccgccccggg cccacccgca agcattacca gccctatgcc   1140

ccaccacgcg acttcgcagc ctatcgctcc agagtgaagt tcagcaggag cgcagacgcc   1200

cccgcgtacc agcagggcca gaaccagctc tataacgagc tcaatctagg acgaagagag   1260

gagtacgatg ttttggacaa gagacgtggc cgggaccctg agatgggggg aaagccgaga   1320

aggaagaacc ctcaggaagg cctgtacaat gaactgcaga aagataagat ggcggaggcc   1380

tacagtgaga ttgggatgaa aggcgagcgc cggaggggca aggggcacga tggcctttac   1440

cagggtctca gtacagccac caaggacacc tacgacgccc ttcacatgca ggccctgccc   1500

cctcgctaa                                                           1509
```

<210> SEQ ID NO 407
<211> LENGTH: 7677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 407

```
ccggtgccgc caccatggaa accgacaccc tgctgctgtg ggtgctgctg ctgtgggtgc     60

caggatccac aggacagtct gtgttgacgc agcctgcctc cgtgtctggg tctcctggac    120

agtcgctcac catctcctgc actggaacca gcaatgacgt tggtgcttat aagtatgtct    180

cctggtatca acagtaccca ggcaaagccc ccaaactcat actttatgat gtctttaagc    240

ggccctcagg ggtctctaat cgcttctctg gctccaagtc tgacaacacg gcctccctga    300

ccatctctgg gctccaggct gaggacgagg ctgattatta ctgcttctca cttacaagca    360

gtaacactta tgtcttcgga actgggacca aggtcaccgt cctaggttct agaggtggtg    420

gtggtagcgg cggcggcggc tctggtggtg gtggatccct cgagatggcc cagatgcagc    480

tggtgcagtc tggagctgag gtgaagaagc ctggggcctc agtgaaggtc tcctgcaagg    540

cttctggtta cacctttaac agatatgcta tcacctgggt gcgacaggcc cctggacaag    600

gccttgagtg gatgggatgg atcagcgctt acaatggtaa ttcacactat gcacagaagc    660

tccagggcag agtcaccatg accacagaca catccacggg cacagcctat atggagctga    720

ggaggctgag atctgacgac acggccgtgt attactgtgc gcgcatggct tacgattctt    780

ggggtcaagg tactctggtg accgtctcct cagaacaaaa actcatctca gaagaggatc    840

tggcggccgc acccaccacg acgccagcgc cgcgaccacc aaccccggcg cccacgatcg    900

cgtcgcagcc cctgtccctg cgcccagagg cgtgccggcc agcggcgggg ggcgcagtgc    960

acacgagggg gctggacttc gcctgtgata tctacatctg ggcgcccctg gccgggactt   1020
```

```
gtggggtcct tctcctgtca ctggttatca ccctttactg caacaaacgg ggcagaaaga   1080
agctcctgta tatattcaaa caaccattta tgagaccagt acaaactact caagaggaag   1140
atggctgtag ctgccgattt ccagaagaag aagaaggagg atgtgaactg agagtgaagt   1200
tcagcaggag cgcagacgcc cccgcgtacc agcagggcca gaaccagctc tataacgagc   1260
tcaatctagg acgaagagag gagtacgatg ttttggacaa gagacgtggc cgggaccctg   1320
agatgggggg aaagccgaga aggaagaacc ctcaggaagg cctgtacaat gaactgcaga   1380
aagataagat ggcggaggcc tacagtgaga ttgggatgaa aggcgagcgc cggaggggca   1440
aggggcacga tggcctttac cagggtctca gtacagccac caaggacacc tacgacgccc   1500
ttcacatgca ggccctgccc cctcgctaac agccactcga ggatccggat tagtccaatt   1560
tgttaaagac aggatatcag tggtccaggc tctagttttg actcaacaat atcaccagct   1620
gaagcctata gagtacgagc catagataaa ataaaagatt ttatttagtc tccagaaaaa   1680
ggggggaatg aaagacccca cctgtaggtt tggcaagcta gcttaagtaa cgccattttg   1740
caaggcatgg aaaaatacat aactgagaat agagaagttc agatcaaggt caggaacaga   1800
tggaacagct gaatatgggc caaacaggat atctgtggta agcagttcct gccccggctc   1860
agggccaaga acagatggaa cagctgaata tgggccaaac aggatatctg tggtaagcag   1920
ttcctgcccc ggctcagggc caagaacaga tggtccccag atgcggtcca gccctcagca   1980
gtttctagag aaccatcaga tgtttccagg gtgccccaag gacctgaaat gaccctgtgc   2040
cttatttgaa ctaaccaatc agttcgcttc tcgcttctgt tcgcgcgctt ctgctccccg   2100
agctcaataa aagagcccac aacccctcac tcggggcgcc agtcctccga ttgactgagt   2160
cgcccgggta cccgtgtatc caataaaccc tcttgcagtt gcatccgact tgtggtctcg   2220
ctgttccttg ggagggtctc ctctgagtga ttgactaccc gtcagcgggg gtctttcaca   2280
catgcagcat gtatcaaaat taatttggtt tttttctta agtatttaca ttaaatggcc    2340
atagtactta aagttacatt ggcttccttg aaataaacat ggagtattca gaatgtgtca   2400
taaatatttc taattttaag atagtatctc cattggcttt ctactttttc ttttattttt   2460
ttttgtcctc tgtcttccat ttgttgttgt tgttgtttgt ttgtttgttt gttggttggt   2520
tggttaattt ttttttaaag atcctacact atagttcaag ctagactatt agctactctg   2580
taacccaggg tgaccttgaa gtcatgggta gcctgctgtt ttagccttcc cacatctaag   2640
attacaggta tgagctatca tttttggtat attgattgat tgattgattg atgtgtgtgt   2700
gtgtgattgt gtttgtgtgt gtgactgtga aaatgtgtgt atgggtgtgt gtgaatgtgt   2760
gtatgtatgt gtgtgtgtga gtgtgtgtgt gtgtgtgtgc atgtgtgtgt gtgtgactgt   2820
gtctatgtgt atgactgtgt gtgtgtgtgt gtgtgtgtgt gtgtgtgtgt gtgtgtgtgt   2880
gttgtgaaaa aatattctat ggtagtgaga gccaacgctc cggctcaggt gtcaggttgg   2940
tttttgagac agagtctttc acttagcttg gaattcactg gccgtcgttt tacaacgtcg   3000
tgactgggaa aaccctggcg ttacccaact taatcgcctt gcagcacatc cccctttcgc   3060
cagctggcgt aatagcgaag aggcccgcac cgatcgccct tcccaacagt tgcgcagcct   3120
gaatggcgaa tggcgcctga tgcggtattt tctccttacg catctgtgcg gtatttcaca   3180
ccgcatatgg tgcactctca gtacaatctg ctctgatgcc gcatagttaa gccagccccg   3240
acacccgcca acacccgctg acgcgccctg acgggcttgt ctgctcccgg catccgctta   3300
cagacaagct gtgaccgtct ccgggagctg catgtgtcag aggttttcac cgtcatcacc   3360
gaaacgcgcg atgacgaaag ggcctcgtga tacgcctatt tttataggtt aatgtcatga   3420
```

```
taataatggt ttcttagacg tcaggtggca cttttcgggg aaatgtgcgc ggaaccccta   3480
tttgtttatt tttctaaata cattcaaata tgtatccgct catgagacaa taaccctgat   3540
aaatgcttca ataatattga aaaaggaaga gtatgagtat tcaacatttc cgtgtcgccc   3600
ttattccctt ttttgcggca ttttgccttc ctgtttttgc tcacccagaa acgctggtga   3660
aagtaaaaga tgctgaagat cagttgggtg cacgagtggg ttacatcgaa ctggatctca   3720
acagcggtaa gatccttgag agttttcgcc ccgaagaacg ttttccaatg atgagcactt   3780
ttaaagttct gctatgtggc gcggtattat cccgtattga cgccgggcaa gagcaactcg   3840
gtcgccgcat acactattct cagaatgact tggttgagta ctcaccagtc acagaaaagc   3900
atcttacgga tggcatgaca gtaagagaat tatgcagtgc tgccataacc atgagtgata   3960
acactgcggc caacttactt ctgacaacga tcggaggacc gaaggagcta accgcttttt   4020
tgcacaacat gggggatcat gtaactcgcc ttgatcgttg ggaaccggag ctgaatgaag   4080
ccataccaaa cgacgagcgt gacaccacga tgcctgtagc aatggcaaca acgttgcgca   4140
aactattaac tggcgaacta cttactctag cttcccggca acaattaata gactggatgg   4200
aggcggataa agttgcagga ccacttctgc gctcggccct tccggctggc tggtttattg   4260
ctgataaatc tggagccggt gagcgtgggt ctcgcggtat cattgcagca ctggggccag   4320
atggtaagcc ctcccgtatc gtagttatct acacgacggg gagtcaggca actatggatg   4380
aacgaaatag acagatcgct gagataggtg cctcactgat taagcattgg taactgtcag   4440
accaagttta ctcatatata ctttagattg atttaaaact tcatttttaa tttaaaagga   4500
tctaggtgaa gatccttttt gataatctca tgaccaaaat cccttaacgt gagttttcgt   4560
tccactgagc gtcagacccc gtagaaaaga tcaaaggatc ttcttgagat cctttttttc   4620
tgcgcgtaat ctgctgcttg caaacaaaaa aaccaccgct accagcggtg gtttgtttgc   4680
cggatcaaga gctaccaact ctttttccga aggtaactgg cttcagcaga gcgcagatac   4740
caaatactgt ccttctagtg tagccgtagt taggccacca cttcaagaac tctgtagcac   4800
cgcctacata cctcgctctg ctaatcctgt taccagtggc tgctgccagt ggcgataagt   4860
cgtgtcttac cgggttggac tcaagacgat agttaccgga taaggcgcag cggtcgggct   4920
gaacgggggg ttcgtgcaca cagcccagct tggagcgaac gacctacacc gaactgagat   4980
acctacagcg tgagcattga gaaagcgcca cgcttcccga agggagaaag gcggacaggt   5040
atccggtaag cggcagggtc ggaacaggag agcgcacgag ggagcttcca gggggaaacg   5100
cctggtatct ttatagtcct gtcgggtttc gccacctctg acttgagcgt cgatttttgt   5160
gatgctcgtc aggggggcgg agcctatgga aaaacgccag caacgcggcc tttttacggt   5220
tcctggcctt ttgctggcct tttgctcaca tgttctttcc tgcgttatcc cctgattctg   5280
tggataaccg tattaccgcc tttgagtgag ctgataccgc tcgccgcagc cgaacgaccg   5340
agcgcagcga gtcagtgagc gaggaagcgg aagagcgccc aatacgcaaa ccgcctctcc   5400
ccgcgcgttg gccgattcat taatgcagct ggcacgacag gtttcccgac tggaaagcgg   5460
gcagtgagcg caacgcaatt aatgtgagtt agctcactca ttaggcaccc caggctttac   5520
actttatgct tccggctcgt atgttgtgtg gaattgtgag cggataacaa tttcacacag   5580
gaaacagcta tgaccatgat tacgccaagc tttgctctta ggagtttcct aatacatccc   5640
aaactcaaat atataaagca tttgacttgt tctatgccct agggggcggg gggaagctaa   5700
gccagctttt tttaacattt aaaatgttaa ttccatttta aatgcacaga tgttttttatt   5760
```

tcataagggt ttcaatgtgc atgaatgctg caatattcct gttaccaaag ctagtataaa 5820
taaaaataga taaacgtgga aattacttag agtttctgtc attaacgttt ccttcctcag 5880
ttgacaacat aaatgcgctg ctgagcaagc cagtttgcat ctgtcaggat caatttccca 5940
ttatgccagt catattaatt actagtcaat tagttgattt ttatttttga catatacatg 6000
tgaatgaaag accccacctg taggtttggc aagctagctt aagtaacgcc attttgcaag 6060
gcatggaaaa atacataact gagaatagaa aagttcagat caaggtcagg aacagatgga 6120
acagctgaat atgggccaaa caggatatct gtggtaagca gttcctgccc cggctcaggg 6180
ccaagaacag atggaacagc tgaatatggg ccaaacagga tatctgtggt aagcagttcc 6240
tgccccggct cagggccaag aacagatggt ccccagatgc ggtccagccc tcagcagttt 6300
ctagagaacc atcagatgtt tccagggtgc cccaaggacc tgaaatgacc ctgtgcctta 6360
tttgaactaa ccaatcagtt cgcttctcgc ttctgttcgc gcgcttatgc tccccgagct 6420
caataaaaga gcccacaacc cctcactcgg ggcgccagtc ctccgattga ctgagtcgcc 6480
cgggtacccg tgtatccaat aaaccctctt gcagttgcat ccgacttgtg gtctcgctgt 6540
tccttgggag ggtctcctct gagtgattga ctacccgtca gcgggggtct ttcatttggg 6600
ggctcgtccg ggatcgggag acccctgccc agggaccacc gacccaccac cgggaggtaa 6660
gctggccagc aacttatctg tgtctgtccg attgtctagt gtctatgact gattttatgc 6720
gcctgcgtcg gtactagtta gctaactagc tctgtatctg gcggacccgt ggtggaactg 6780
acgagttcgg aacacccggc cgcaaccctg ggagacgtcc cagggacttc gggggccgtt 6840
tttgtggccc gacctgagtc ctaaaatccc gatcgtttag gactctttgg tgcacccccc 6900
ttagaggagg gatatgtggt tctggtagga gacgagaacc taaaacagtt cccgcctccg 6960
tctgaatttt tgctttcggt ttgggaccga agccgcgccg cgcgtcttgt ctgctgcagc 7020
atcgttctgt gttgtctctg tctgactgtg tttctgtatt tgtctgaaaa tatgggcccg 7080
ggctagactg ttaccactcc cttaagtttg accttaggtc actggaaaga tgtcgagcgg 7140
atcgctcaca accagtcggt agatgtcaag aagagacgtt gggttacctt ctgctctgca 7200
gaatggccaa cctttaacgt cggatggccg cgagacggca cctttaaccg agacctcatc 7260
acccaggtta agatcaaggt cttttcacct ggcccgcatg gacacccaga ccaggtcccc 7320
tacatcgtga cctgggaagc cttggctttt gacccccctc cctgggtcaa gccctttgta 7380
caccctaagc ctccgcctcc tcttcctcca tccgccccgt ctctccccct tgaacctcct 7440
cgttcgaccc cgcctcgatc ctccctttat ccagccctca ctccttctct aggcgccccc 7500
atatggccat atgagatctt atatggggca cccccgcccc ttgtaaactt ccctgaccct 7560
gacatgacaa gagttactaa cagcccctct ctccaagctc acttacaggc tctctactta 7620
gtccagcacg aagtctggag acctctggcg gcagcctacc aagaacaact ggaccga 7677

<210> SEQ ID NO 408
<211> LENGTH: 7689
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 408
ccggtgccgc caccatggaa accgacaccc tgctgctgtg ggtgctgctg ctgtgggtgc 60
caggatccac aggatcttct gagctgactc aggaccctgc tgtgtctgtg gccttgggac 120

-continued

```
agacagtcag gatcacatgc caaggagaca gcctcagaag ctattatgca agctggtacc    180
agcagaagcc aggacaggcc cctgtacttg tcatctatgg taaaaacaac cggccctcag    240
ggatcccaga ccgattctct ggctccagct caggaaacac agcttccttg accatcactg    300
gggctcaggc ggaagatgag gctgactatt actgtaactc ccgggacagc agtggtaacc    360
cccctgtggt attcggcgga gggaccaagc tgaccgtcct aggttctaga ggtggtggtg    420
gtagcggcgg cggcggctct ggtggtggtg gatccctcga gatggcccag gtgcagctgg    480
tggagtctgg gggaggcctg gtccaccctg gggggtccct gagactctcc tgtgcagcct    540
ctggattcac cttcagaagc catagcatga actgggtccg ccaggctcca gggaaggggc    600
tggagtgggt ctcatccatt agtagtgata gtacttacac atactacgca gactcagtga    660
agggccgatt caccatctcc agagacaacg ccaagaactc actgtatctg caaatgaaca    720
gcctgagagc cgaggacacg gccgtatatt actgtgcgcg ctctggtggt cagtggaaat    780
actacgatta ctggggtcaa ggtactctgg tgaccgtctc ctcagaacaa aaactcatct    840
cagaagagga tctggcggcc gcacccacca cgacgccagc gccgcgacca ccaaccccgg    900
cgcccacgat cgcgtcgcag cccctgtccc tgcgcccaga ggcgtgccgg ccagcggcgg    960
ggggcgcagt gcacacgagg gggctggact tcgcctgtga tatctacatc tgggcgcccc   1020
tggccgggac ttgtggggtc cttctcctgt cactggttat caccctttac tgcaacaaac   1080
ggggcagaaa gaagctcctg tatatattca aacaaccatt tatgagacca gtacaaacta   1140
ctcaagagga agatggctgt agctgccgat ttccagaaga agaagaagga ggatgtgaac   1200
tgagagtgaa gttcagcagg agcgcagacg cccccgcgta ccagcagggc cagaaccagc   1260
tctataacga gctcaatcta ggacgaagag aggagtacga tgttttggac aagagacgtg   1320
gccgggaccc tgagatgggg ggaaagccga gaaggaagaa ccctcaggaa ggcctgtaca   1380
atgaactgca gaaagataag atggcggagg cctacagtga gattgggatg aaaggcgagc   1440
gccggagggg caaggggcac gatggccttt accagggtct cagtacagcc accaaggaca   1500
cctacgacgc ccttcacatg caggccctgc cccctcgcta acagccactc gaggatccgg   1560
attagtccaa tttgttaaag acaggatatc agtggtccag gctctagttt tgactcaaca   1620
atatcaccag ctgaagccta tagagtacga gccatagata aaataaaaga ttttatttag   1680
tctccagaaa aaggggggaa tgaaagaccc cacctgtagg tttggcaagc tagcttaagt   1740
aacgccattt tgcaaggcat ggaaaaatac ataactgaga atagagaagt tcagatcaag   1800
gtcaggaaca gatggaacag ctgaatatgg gccaaacagg atatctgtgg taagcagttc   1860
ctgccccggc tcagggccaa gaacagatgg aacagctgaa tatgggccaa acaggatatc   1920
tgtggtaagc agttcctgcc ccggctcagg gccaagaaca gatggtcccc agatgcggtc   1980
cagccctcag cagtttctag agaaccatca gatgtttcca gggtgcccca aggacctgaa   2040
atgaccctgt gccttatttg aactaaccaa tcagttcgct tctcgcttct gttcgcgcgc   2100
ttctgctccc cgagctcaat aaaagagccc acaacccctc actcggggcg ccagtcctcc   2160
gattgactga gtcgcccggg tacccgtgta tccaataaac cctcttgcag ttgcatccga   2220
cttgtggtct cgctgttcct tgggagggtc tcctctgagt gattgactac ccgtcagcgg   2280
gggtctttca cacatgcagc atgtatcaaa attaatttgg ttttttttct taagtattta   2340
cattaaatgg ccatagtact taaagttaca ttggcttcct tgaaataaac atggagtatt   2400
cagaatgtgt cataaatatt tctaatttta agatagtatc tccattggct ttctactttt   2460
tcttttattt ttttttgtcc tctgtcttcc atttgttgtt gttgttgttt gtttgtttgt   2520
```

-continued

```
ttgttggttg gttggttaat tttttttaa agatcctaca ctatagttca agctagacta   2580
ttagctactc tgtaacccag ggtgaccttg aagtcatggg tagcctgctg ttttagcctt   2640
cccacatcta agattacagg tatgagctat catttttggt atattgattg attgattgat   2700
tgatgtgtgt gtgtgtgatt gtgtttgtgt gtgtgactgt gaaaatgtgt gtatgggtgt   2760
gtgtgaatgt gtgtatgtat gtgtgtgtgt gagtgtgtgt gtgtgtgtgt gcatgtgtgt   2820
gtgtgtgact gtgtctatgt gtatgactgt gtgtgtgtgt gtgtgtgtgt gtgtgtgtgt   2880
gtgtgtgtgt gtgttgtgaa aaaatattct atggtagtga gagccaacgc tccggctcag   2940
gtgtcaggtt ggtttttgag acagagtctt tcacttagct tggaattcac tggccgtcgt   3000
tttacaacgt cgtgactggg aaaaccctgg cgttacccaa cttaatcgcc ttgcagcaca   3060
tccccctttc gccagctggc gtaatagcga agaggcccgc accgatcgcc cttcccaaca   3120
gttgcgcagc ctgaatggcg aatggcgcct gatgcggtat tttctcctta cgcatctgtg   3180
cggtatttca caccgcatat ggtgcactct cagtacaatc tgctctgatg ccgcatagtt   3240
aagccagccc cgacacccgc caacacccgc tgacgcgccc tgacgggctt gtctgctccc   3300
ggcatccgct tacagacaag ctgtgaccgt ctccgggagc tgcatgtgtc agaggttttc   3360
accgtcatca ccgaaacgcg cgatgacgaa agggcctcgt gatacgccta tttttatagg   3420
ttaatgtcat gataataatg gtttcttaga cgtcaggtgg cacttttcgg ggaaatgtgc   3480
gcggaacccc tatttgttta tttttctaaa tacattcaaa tatgtatccg ctcatgagac   3540
aataaccctg ataaatgctt caataatatt gaaaaaggaa gagtatgagt attcaacatt   3600
tccgtgtcgc ccttattccc ttttttgcgg cattttgcct tcctgttttt gctcacccag   3660
aaacgctggt gaaagtaaaa gatgctgaag atcagttggg tgcacgagtg ggttacatcg   3720
aactggatct caacagcggt aagatccttg agagttttcg ccccgaagaa cgttttccaa   3780
tgatgagcac ttttaaagtt ctgctatgtg gcgcggtatt atcccgtatt gacgccgggc   3840
aagagcaact cggtcgccgc atacactatt ctcagaatga cttggttgag tactcaccag   3900
tcacagaaaa gcatcttacg gatggcatga cagtaagaga attatgcagt gctgccataa   3960
ccatgagtga taacactgcg gccaacttac ttctgacaac gatcggagga ccgaaggagc   4020
taaccgcttt tttgcacaac atgggggatc atgtaactcg ccttgatcgt tgggaaccgg   4080
agctgaatga agccatacca aacgacgagc gtgacaccac gatgcctgta gcaatggcaa   4140
caacgttgcg caaactatta actggcgaac tacttactct agcttcccgg caacaattaa   4200
tagactggat ggaggcggat aaagttgcag gaccacttct gcgctcggcc cttccggctg   4260
gctggtttat tgctgataaa tctggagccg gtgagcgtgg gtctcgcggt atcattgcag   4320
cactggggcc agatggtaag ccctcccgta tcgtagttat ctacacgacg gggagtcagg   4380
caactatgga tgaacgaaat agacagatcg ctgagatagg tgcctcactg attaagcatt   4440
ggtaactgtc agaccaagtt tactcatata tactttagat tgatttaaaa cttcattttt   4500
aatttaaaag gatctaggtg aagatccttt ttgataatct catgaccaaa atcccttaac   4560
gtgagttttc gttccactga gcgtcagacc ccgtagaaaa gatcaaagga tcttcttgag   4620
atcctttttt tctgcgcgta atctgctgct tgcaaacaaa aaaaccaccg ctaccagcgg   4680
tggtttgttt gccggatcaa gagctaccaa ctctttttcc gaaggtaact ggcttcagca   4740
gagcgcagat accaaatact gtccttctag tgtagccgta gttaggccac cacttcaaga   4800
actctgtagc accgcctaca tacctcgctc tgctaatcct gttaccagtg gctgctgcca   4860
```

-continued

```
gtggcgataa gtcgtgtctt accgggttgg actcaagacg atagttaccg gataaggcgc   4920
agcggtcggg ctgaacgggg ggttcgtgca cacagcccag cttggagcga acgacctaca   4980
ccgaactgag atacctacag cgtgagcatt gagaaagcgc cacgcttccc gaagggagaa   5040
aggcggacag gtatccggta agcggcaggg tcggaacagg agagcgcacg agggagcttc   5100
cagggggaaa cgcctggtat ctttatagtc ctgtcgggtt tcgccacctc tgacttgagc   5160
gtcgattttt gtgatgctcg tcaggggggc ggagcctatg gaaaaacgcc agcaacgcgg   5220
cctttttacg gttcctggcc ttttgctggc cttttgctca catgttcttt cctgcgttat   5280
cccctgattc tgtggataac cgtattaccg cctttgagtg agctgatacc gctcgccgca   5340
gccgaacgac cgagcgcagc gagtcagtga gcgaggaagc ggaagagcgc ccaatacgca   5400
aaccgcctct ccccgcgcgt tggccgattc attaatgcag ctggcacgac aggtttcccg   5460
actggaaagc gggcagtgag cgcaacgcaa ttaatgtgag ttagctcact cattaggcac   5520
cccaggcttt acactttatg cttccggctc gtatgttgtg tggaattgtg agcggataac   5580
aatttcacac aggaaacagc tatgaccatg attacgccaa gctttgctct taggagtttc   5640
ctaatacatc ccaaactcaa atatataaag catttgactt gttctatgcc ctagggggcg   5700
gggggaagct aagccagctt tttttaacat ttaaaatgtt aattccattt taaatgcaca   5760
gatgttttta tttcataagg gtttcaatgt gcatgaatgc tgcaatattc ctgttaccaa   5820
agctagtata aataaaaata gataaacgtg gaaattactt agagtttctg tcattaacgt   5880
ttccttcctc agttgacaac ataaatgcgc tgctgagcaa gccagtttgc atctgtcagg   5940
atcaatttcc cattatgcca gtcatattaa ttactagtca attagttgat ttttattttt   6000
gacatataca tgtgaatgaa agaccccacc tgtaggtttg gcaagctagc ttaagtaacg   6060
ccattttgca aggcatggaa aaatacataa ctgagaatag aaaagttcag atcaaggtca   6120
ggaacagatg gaacagctga atatgggcca aacaggatat ctgtggtaag cagttcctgc   6180
cccggctcag ggccaagaac agatggaaca gctgaatatg ggccaaacag gatatctgtg   6240
gtaagcagtt cctgccccgg ctcagggcca agaacagatg gtccccagat gcggtccagc   6300
cctcagcagt ttctagagaa ccatcagatg tttccagggt gccccaagga cctgaaatga   6360
ccctgtgcct tatttgaact aaccaatcag ttcgcttctc gcttctgttc gcgcgcttat   6420
gctccccgag ctcaataaaa gagcccacaa cccctcactc ggggcgccag tcctccgatt   6480
gactgagtcg cccgggtacc cgtgtatcca ataaaccctc ttgcagttgc atccgacttg   6540
tggtctcgct gttccttggg agggtctcct ctgagtgatt gactacccgt cagcgggggt   6600
ctttcatttg ggggctcgtc cgggatcggg agacccctgc ccagggacca ccgacccacc   6660
accgggaggt aagctggcca gcaacttatc tgtgtctgtc cgattgtcta gtgtctatga   6720
ctgattttat gcgcctgcgt cggtactagt tagctaacta gctctgtatc tggcggaccc   6780
gtggtggaac tgacgagttc ggaacacccg gccgcaaccc tgggagacgt cccagggact   6840
tcgggggccg tttttgtggc ccgacctgag tcctaaaatc ccgatcgttt aggactcttt   6900
ggtgcacccc ccttagagga gggatatgtg gttctggtag gagacgagaa cctaaaacag   6960
ttcccgcctc cgtctgaatt tttgctttcg gtttgggacc gaagccgcgc cgcgcgtctt   7020
gtctgctgca gcatcgttct gtgttgtctc tgtctgactg tgtttctgta tttgtctgaa   7080
aatatgggcc cgggctagac tgttaccact cccttaagtt tgaccttagg tcactggaaa   7140
gatgtcgagc ggatcgctca caaccagtcg gtagatgtca agaagagacg ttgggttacc   7200
ttctgctctg cagaatggcc aacctttaac gtcggatggc cgcgagacgg cacctttaac   7260
```

-continued

```
cgagacctca tcacccaggt taagatcaag gtcttttcac ctggcccgca tggacaccca   7320

gaccaggtcc cctacatcgt gacctgggaa gccttggctt ttgacccccc tccctgggtc   7380

aagccctttg tacaccctaa gcctccgcct cctcttcctc catccgcccc gtctctcccc   7440

cttgaacctc ctcgttcgac cccgcctcga tcctcccttt atccagccct cactccttct   7500

ctaggcgccc ccatatggcc atatgagatc ttatatgggg cacccccgcc ccttgtaaac   7560

ttccctgacc ctgacatgac aagagttact aacagcccct ctctccaagc tcacttacag   7620

gctctctact tagtccagca cgaagtctgg agacctctgg cggcagccta ccaagaacaa   7680

ctggaccga                                                           7689
```

<210> SEQ ID NO 409
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 409

```
Thr Ser Gly Gln Ala Gly Gln His His His His His His Gly Ala Tyr
1               5                   10                  15

Pro Tyr Asp Val Pro Asp Tyr Ala Ser
            20                  25
```

<210> SEQ ID NO 410
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 410

```
actagtggcc aggccggcca gcaccatcac catcaccatg gcgcataccc gtacgacgtt     60

ccggactacg cttct                                                      75
```

<210> SEQ ID NO 411
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 411

```
Tyr Val Lys Met
1
```

<210> SEQ ID NO 412
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 412

```
Cys Leu Ser Ser Glu Arg Glu Arg Val Glu Asp Leu Phe Glu Tyr Glu
1               5                   10                  15

Cys Glu Leu Leu Thr Ser Glu Pro Ile Phe His Cys Arg Gln Glu Asp
            20                  25                  30
```

Cys

<210> SEQ ID NO 413
<211> LENGTH: 10
<212> TYPE: PRT
<213> ORGANISM: Homo sapiens

<400> SEQUENCE: 413

Cys Asp Ala Glu Gly Pro Trp Gly Ile Ile
1 5 10

<210> SEQ ID NO 414
<211> LENGTH: 8
<212> TYPE: PRT
<213> ORGANISM: Homo sapiens

<400> SEQUENCE: 414

Met Phe Val Asn Met Thr Pro Cys
1 5

<210> SEQ ID NO 415
<211> LENGTH: 9
<212> TYPE: PRT
<213> ORGANISM: Homo sapiens

<400> SEQUENCE: 415

Pro Gln Phe Gln Arg Gln Pro Gln Trp
1 5

<210> SEQ ID NO 416
<211> LENGTH: 13
<212> TYPE: PRT
<213> ORGANISM: Homo sapiens

<400> SEQUENCE: 416

Cys Ile Glu Ser Thr Gly Asp Tyr Phe Leu Leu Cys Asp
1 5 10

<210> SEQ ID NO 417
<211> LENGTH: 11
<212> TYPE: PRT
<213> ORGANISM: Homo sapiens

<400> SEQUENCE: 417

Asn Gln Gln Thr Ala Pro Val Arg Tyr Phe Leu
1 5 10

<210> SEQ ID NO 418
<211> LENGTH: 8
<212> TYPE: PRT
<213> ORGANISM: Homo sapiens

<400> SEQUENCE: 418

Gly Asp Tyr Phe Leu Leu Cys Asp
1 5

<210> SEQ ID NO 419
<211> LENGTH: 11
<212> TYPE: PRT
<213> ORGANISM: Homo sapiens

<400> SEQUENCE: 419

Met Phe Val Asn Met Thr Pro Cys Gln Leu Asn
1 5 10

<210> SEQ ID NO 420
<211> LENGTH: 11
<212> TYPE: PRT
<213> ORGANISM: Homo sapiens

<400> SEQUENCE: 420

Gly Asn Pro Gln Phe Gln Arg Gln Pro Gln Trp
1 5 10

<210> SEQ ID NO 421
<211> LENGTH: 9
<212> TYPE: PRT
<213> ORGANISM: Homo sapiens

<400> SEQUENCE: 421

Leu Cys Asp Ala Glu Gly Pro Trp Gly
1 5

<210> SEQ ID NO 422
<211> LENGTH: 14
<212> TYPE: PRT
<213> ORGANISM: Homo sapiens

<400> SEQUENCE: 422

Gln Phe Gln Arg Gln Pro Gln Trp Asp Asp Pro Val Val Cys
1 5 10

<210> SEQ ID NO 423
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 423

Cys Met Asp Tyr Asp Phe Lys Val Lys Leu Ser Ser Glu Arg Glu Arg
1 5 10 15

Cys Trp Ala Ile Gly Cys Ile Phe Ala Glu Leu Leu Thr Ser Glu Pro
20 25 30

Cys

<210> SEQ ID NO 424
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 424

Cys Met Asp Tyr Asp Phe Lys Val Lys Leu Ser Ser Glu Arg Glu Arg
1 5 10 15

Cys Cys Ile Phe Ala Glu Leu Leu Thr Ser Glu Pro Ile Phe His Cys
20 25 30

Cys

<210> SEQ ID NO 425
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 425

Cys Met Asp Tyr Asp Phe Lys Val Lys Leu Ser Ser Glu Arg Glu Arg
1 5 10 15

Cys Glu Leu Leu Thr Ser Glu Pro Ile Phe His Cys Arg Gln Glu Asp
20 25 30

Cys

<210> SEQ ID NO 426
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 426

Cys Met Asp Tyr Asp Phe Lys Val Lys Leu Ser Ser Glu Arg Glu Arg
1 5 10 15

Cys Ser Glu Pro Ile Phe His Cys Arg Gln Glu Asp Ile Lys Thr Ser
20 25 30

Cys

<210> SEQ ID NO 427
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 427

Cys Phe Lys Val Lys Leu Ser Ser Glu Arg Glu Arg Val Glu Asp Leu
1 5 10 15

Cys Trp Ala Ile Gly Cys Ile Phe Ala Glu Leu Leu Thr Ser Glu Pro
20 25 30

Cys

<210> SEQ ID NO 428
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 428

Cys Phe Lys Val Lys Leu Ser Ser Glu Arg Glu Arg Val Glu Asp Leu
1 5 10 15

Cys Cys Ile Phe Ala Glu Leu Leu Thr Ser Glu Pro Ile Phe His Cys
20 25 30

Cys

<210> SEQ ID NO 429
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 429

Cys Phe Lys Val Lys Leu Ser Ser Glu Arg Glu Arg Val Glu Asp Leu
1               5                   10                  15

Cys Glu Leu Leu Thr Ser Glu Pro Ile Phe His Cys Arg Gln Glu Asp
            20                  25                  30

Cys

<210> SEQ ID NO 430
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 430

Cys Phe Lys Val Lys Leu Ser Ser Glu Arg Glu Arg Val Glu Asp Leu
1               5                   10                  15

Cys Ser Glu Pro Ile Phe His Cys Arg Gln Glu Asp Ile Lys Thr Ser
            20                  25                  30

Cys

<210> SEQ ID NO 431
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 431

Cys Leu Ser Ser Glu Arg Glu Arg Val Glu Asp Leu Phe Glu Tyr Glu
1               5                   10                  15

Cys Trp Ala Ile Gly Cys Ile Phe Ala Glu Leu Leu Thr Ser Glu Pro
            20                  25                  30

Cys

<210> SEQ ID NO 432
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 432

Cys Leu Ser Ser Glu Arg Glu Arg Val Glu Asp Leu Phe Glu Tyr Glu
1               5                   10                  15

Cys Cys Ile Phe Ala Glu Leu Leu Thr Ser Glu Pro Ile Phe His Cys
            20                  25                  30

Cys

<210> SEQ ID NO 433
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 433

Cys Leu Ser Ser Glu Arg Glu Arg Val Glu Asp Leu Phe Glu Tyr Glu
1               5                   10                  15

Cys Ser Glu Pro Ile Phe His Cys Arg Gln Glu Asp Ile Lys Thr Ser
20 25 30

Cys

<210> SEQ ID NO 434
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 434

Cys Arg Glu Arg Val Glu Asp Leu Phe Glu Tyr Glu Gly Cys Lys Val
1 5 10 15

Cys Trp Ala Ile Gly Cys Ile Phe Ala Glu Leu Leu Thr Ser Glu Pro
20 25 30

Cys

<210> SEQ ID NO 435
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 435

Cys Arg Glu Arg Val Glu Asp Leu Phe Glu Tyr Glu Gly Cys Lys Val
1 5 10 15

Cys Cys Ile Phe Ala Glu Leu Leu Thr Ser Glu Pro Ile Phe His Cys
20 25 30

Cys

<210> SEQ ID NO 436
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 436

Cys Arg Glu Arg Val Glu Asp Leu Phe Glu Tyr Glu Gly Cys Lys Val
1 5 10 15

Cys Glu Leu Leu Thr Ser Glu Pro Ile Phe His Cys Arg Gln Glu Asp
20 25 30

Cys

<210> SEQ ID NO 437
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 437

Cys Arg Glu Arg Val Glu Asp Leu Phe Glu Tyr Glu Gly Cys Lys Val
1 5 10 15

Cys Ser Glu Pro Ile Phe His Cys Arg Gln Glu Asp Ile Lys Thr Ser
20 25 30

Cys

<210> SEQ ID NO 438
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 438

Met Asp Tyr Asp Phe Lys Val Lys Leu Ser Ser Glu Arg Glu Arg
1 5 10 15

<210> SEQ ID NO 439
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 439

Phe Lys Val Lys Leu Ser Ser Glu Arg Glu Arg Val Glu Asp Leu
1 5 10 15

<210> SEQ ID NO 440
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 440

Leu Ser Ser Glu Arg Glu Arg Val Glu Asp Leu Phe Glu Tyr Glu
1 5 10 15

<210> SEQ ID NO 441
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 441

Arg Glu Arg Val Glu Asp Leu Phe Glu Tyr Glu Gly Cys Lys Val
1 5 10 15

<210> SEQ ID NO 442
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 442

Trp Ala Ile Gly Cys Ile Phe Ala Glu Leu Leu Thr Ser Glu Pro
1 5 10 15

<210> SEQ ID NO 443
<211> LENGTH: 15
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 443

Cys Ile Phe Ala Glu Leu Leu Thr Ser Glu Pro Ile Phe His Cys
1               5                   10                  15


<210> SEQ ID NO 444
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Glu Leu Leu Thr Ser Glu Pro Ile Phe His Cys Arg Gln Glu Asp
1               5                   10                  15


<210> SEQ ID NO 445
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Ser Glu Pro Ile Phe His Cys Arg Gln Glu Asp Ile Lys Thr Ser
1               5                   10                  15
```